(12) United States Patent
Clube

(10) Patent No.: US 8,986,694 B1
(45) Date of Patent: Mar. 24, 2015

(54) TARGETING HUMAN NAV1.7 VARIANTS FOR TREATMENT OF PAIN

(71) Applicant: Kymab Limited, Cambridge (GB)

(72) Inventor: Jasper Rupert Clube, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 14/472,698

(22) Filed: Aug. 29, 2014

Related U.S. Application Data

(63) Continuation-in-part of application No. 14/331,730, filed on Jul. 15, 2014.

(51) Int. Cl.
*A61K 39/395* (2006.01)

(52) U.S. Cl.
USPC .................................... 424/146.1; 424/142.1

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. |
| 4,816,397 A | 3/1989 | Boss et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,677,425 A | 10/1997 | Bodmer et al. |
| 5,698,426 A | 12/1997 | Huse |
| 5,733,743 A | 3/1998 | Johnson et al. |
| 5,750,753 A | 5/1998 | Kimae et al. |
| 5,766,886 A | 6/1998 | Studnicka et al. |
| 5,770,429 A | 6/1998 | Lonberg et al. |
| 5,780,225 A | 7/1998 | Wigler et al. |
| 5,821,047 A | 10/1998 | Garrard et al. |
| 5,869,619 A | 2/1999 | Studnicka |
| 5,969,108 A | 10/1999 | McCafferty et al. |
| 6,331,415 B1 | 12/2001 | Cabilly et al. |
| 6,407,088 B1 | 6/2002 | Dong et al. |
| 6,548,507 B1 | 4/2003 | Bountra et al. |
| 6,599,906 B1 | 7/2003 | Ku et al. |
| 6,875,432 B2 | 4/2005 | Liu et al. |
| 7,029,895 B2 | 4/2006 | Glucksmann et al. |
| 7,129,338 B1 | 10/2006 | Otal et al. |
| 7,261,893 B2 | 8/2007 | Veldman et al. |
| 7,300,754 B2 | 11/2007 | Abi Fadel et al. |
| 7,368,531 B2 | 5/2008 | Rosen et al. |
| 7,411,051 B2 | 8/2008 | Rosen et al. |
| 7,456,187 B2 | 11/2008 | Ford et al. |
| 7,456,264 B2 | 11/2008 | Keler et al. |
| 7,482,147 B2 | 1/2009 | Glucksmann et al. |
| 7,521,541 B2 | 4/2009 | Eigenbrot et al. |
| 7,572,618 B2 | 8/2009 | Mintier et al. |
| 7,776,577 B2 | 8/2010 | Kapeller-Libermann et al. |
| 7,968,689 B2 | 6/2011 | Rosen et al. |
| 8,030,457 B2 | 10/2011 | Jackson et al. |
| 8,062,640 B2 | 11/2011 | Sleeman et al. |
| 8,080,243 B2 | 12/2011 | Liang et al. |
| 8,168,762 B2 | 5/2012 | Jackson et al. |
| 8,188,233 B2 | 5/2012 | Condra et al. |
| 8,188,234 B2 | 5/2012 | Condra et al. |
| 8,344,114 B2 | 1/2013 | Sparrow et al. |
| 8,357,371 B2 | 1/2013 | Sleeman et al. |
| 8,399,646 B2 | 3/2013 | Liang et al. |
| 8,420,098 B2 | 4/2013 | Camphausen et al. |
| 8,426,363 B2 | 4/2013 | Liang et al. |
| 8,486,647 B2 | 7/2013 | Haber et al. |
| 8,501,184 B2 | 8/2013 | Sleeman et al. |
| 8,530,414 B2 | 9/2013 | Davies et al. |
| 8,563,698 B2 | 10/2013 | Jackson et al. |
| 8,598,320 B2 | 12/2013 | Hedrick |
| 2002/0064555 A1 | 3/2002 | Chiang et al. |
| 2002/0045571 A1 | 4/2002 | Liu et al. |
| 2002/0081679 A1 | 6/2002 | Chiang et al. |
| 2003/0119038 A1 | 6/2003 | Bingham et al. |
| 2004/0009553 A1 | 1/2004 | Glucksmann et al. |
| 2004/0023243 A1 | 2/2004 | Henry et al. |
| 2004/0038242 A1 | 2/2004 | Edmonds et al. |
| 2004/0191265 A1 | 9/2004 | Schenerman et al. |
| 2004/0248177 A1 | 12/2004 | Abi Fadel et al. |
| 2005/0101529 A1 | 5/2005 | Yue et al. |

(Continued)

FOREIGN PATENT DOCUMENTS

| EP | 0438474 | 5/1996 |
|---|---|---|
| EP | 0463151 | 6/1996 |

(Continued)

OTHER PUBLICATIONS

Benn et al, Journal of the American College of Cardiology, vol. 55, No. 25, 2010, pp. 2833-2842.
Homer et al, Atherosclerosis, vol. 196, 2008, pp. 659-666.
Kotowski et al, The American Journal of Human Genetics, vol. 78, 2006, pp. 410-422.
Miyake et al, Atherosclerosis, vol. 196, 2008, pp. 29-36.
Abboud et al., "Proprotein convertase subtilisin/kexin type 9 (PCSK9) gene is a risk factor of large-vessel atherosclerosis stroke" PLoS One, 2(10):e1043, (2007).
Abifadel et al. "Mutations in PCSK9 cause autosomal dominant hypercholesterolemia" Nat. Genet. 34, 154-156 (2003).
Alborn et al., Serum proprotein convertase subtilisin kexin type 9 is correlated directly with serum LDL cholesterol:, Clin Chem, 53(10):1814-1819, (2007).

(Continued)

*Primary Examiner* — Sharon Wen
(74) *Attorney, Agent, or Firm* — Nixon Peabody LLP, David S. Resnick; Leena H. Karttunen Contarino; Nicole Kling

(57) ABSTRACT

The invention relates to human targets of interest (TOI), anti-TOI ligands, kits compositions and method.

28 Claims, 5 Drawing Sheets

(56) References Cited

U.S. PATENT DOCUMENTS

| | | |
|---|---|---|
| 2005/0118625 A1 | 6/2005 | Mounts |
| 2005/0147612 A1 | 7/2005 | Yayon et al. |
| 2005/0197285 A1 | 9/2005 | Rosen et al. |
| 2005/0271656 A1 | 12/2005 | Huang |
| 2006/0116508 A1 | 6/2006 | Glucksmann et al. |
| 2006/0147945 A1 | 7/2006 | Edmonds et al. |
| 2006/0223088 A1 | 10/2006 | Rosen et al. |
| 2006/0223090 A1 | 10/2006 | Rosen et al. |
| 2006/0246483 A1 | 11/2006 | Rosen et al. |
| 2007/0015696 A1 | 1/2007 | Rosen et al. |
| 2007/0037206 A1 | 2/2007 | Rosen et al. |
| 2007/0041963 A1 | 2/2007 | Rosen |
| 2007/0041972 A1 | 2/2007 | Rother et al. |
| 2007/0055056 A1 | 3/2007 | Rosen et al. |
| 2007/0082345 A1 | 4/2007 | Ota et al. |
| 2007/0224663 A1 | 9/2007 | Rosen et al. |
| 2008/0008697 A1 | 1/2008 | Mintier et al. |
| 2008/0103090 A1 | 5/2008 | Rosen et al. |
| 2008/0113930 A1 | 5/2008 | Tan et al. |
| 2009/0142352 A1 | 6/2009 | Jackson et al. |
| 2009/0232795 A1 | 9/2009 | Condra et al. |
| 2009/0246192 A1 | 10/2009 | Condra et al. |
| 2009/0269350 A1 | 10/2009 | Glucksmann et al. |
| 2009/0326202 A1 | 12/2009 | Jackson et al. |
| 2010/0040610 A1 | 2/2010 | Sitlani et al. |
| 2010/0040611 A1 | 2/2010 | Sparrow et al. |
| 2010/0041102 A1 | 2/2010 | Sitlani et al. |
| 2010/0068194 A1 | 3/2010 | Kim |
| 2010/0068199 A1 | 3/2010 | Liang et al. |
| 2010/0136028 A1 | 6/2010 | Sparrow et al. |
| 2010/0150937 A1 | 6/2010 | Sparrow et al. |
| 2010/0166768 A1 | 7/2010 | Sleeman et al. |
| 2010/0233177 A1 | 9/2010 | Yowe et al. |
| 2010/0291099 A1 | 11/2010 | Glucksmann et al. |
| 2010/0323359 A1 | 12/2010 | MacDonald et al. |
| 2011/0027287 A1 | 2/2011 | Jackson et al. |
| 2011/0033465 A1 | 2/2011 | Hedrick |
| 2011/0065902 A1 | 3/2011 | Sleeman et al. |
| 2011/0105726 A1 | 5/2011 | Rosen |
| 2011/0117011 A1 | 5/2011 | Jackson et al. |
| 2011/0135662 A1 | 6/2011 | Finney et al. |
| 2011/0142849 A1 | 6/2011 | Rue |
| 2011/0229489 A1 | 9/2011 | Pons et al. |
| 2011/0230392 A1 | 9/2011 | Chiang et al. |
| 2011/0256148 A1 | 10/2011 | Sleeman et al. |
| 2011/0307966 A1 | 12/2011 | MacDonald et al. |
| 2012/0014951 A1 | 1/2012 | Liang et al. |
| 2012/0015435 A1 | 1/2012 | Liang et al. |
| 2012/0020975 A1 | 1/2012 | Jackson et al. |
| 2012/0020976 A1 | 1/2012 | Jackson et al. |
| 2012/0027765 A1 | 2/2012 | Jackson et al. |
| 2012/0076799 A1 | 3/2012 | Sparrow et al. |
| 2012/0077964 A1 | 3/2012 | Sparrow et al. |
| 2012/0082679 A1 | 4/2012 | Sparrow et al. |
| 2012/0082680 A1 | 4/2012 | Sitlani et al. |
| 2012/0185956 A1 | 7/2012 | Gingras et al. |
| 2012/0195910 A1 | 8/2012 | Wu et al. |
| 2012/0208208 A1 | 8/2012 | Ni et al. |
| 2012/0208209 A1 | 8/2012 | Ichetovkin et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2012/0301461 A1 | 11/2012 | Condra et al. |
| 2013/0052201 A1 | 2/2013 | Jackson et al. |
| 2013/0058944 A1 | 3/2013 | Jackson et al. |
| 2013/0064825 A1 | 3/2013 | Chan et al. |
| 2013/0064834 A1 | 3/2013 | Sleeman et al. |
| 2013/0071379 A1 | 3/2013 | Condra et al. |
| 2013/0071405 A1 | 3/2013 | Davies et al. |
| 2013/0072665 A1 | 3/2013 | Jackson et al. |
| 2013/0079501 A1 | 3/2013 | Jackson et al. |
| 2013/0079502 A1 | 3/2013 | Jackson et al. |
| 2013/0085265 A1 | 4/2013 | Jackson et al. |
| 2013/0085266 A1 | 4/2013 | Sleeman et al. |
| 2013/0115171 A1 | 5/2013 | McDonough et al. |
| 2013/0115223 A1 | 5/2013 | Sparrow et al. |
| 2013/0189278 A1 | 7/2013 | Sitlani |
| 2013/0245235 A1 | 9/2013 | Jackson et al. |
| 2013/0273069 A1 | 10/2013 | Liang et al. |
| 2013/0310324 A1* | 11/2013 | Flinspach et al. ............ 514/18.3 |
| 2012/0321879 A1 | 12/2013 | Jackson et al. |
| 2014/0165219 A1 | 6/2014 | Leppert et al. |

FOREIGN PATENT DOCUMENTS

| | | |
|---|---|---|
| EP | 0546073 | 9/1997 |
| EP | 0996622 | 5/2000 |
| EP | 1067182 | 1/2001 |
| EP | 1514933 | 3/2005 |
| EP | 1 618 212 | 11/2007 |
| EP | 2481758 | 1/2012 |
| EP | 2650016 | 10/2013 |
| JP | 2005/130764 | 5/2005 |
| WO | 90/02809 | 3/1990 |
| WO | 91/09967 | 7/1991 |
| WO | 91/10737 | 7/1991 |
| WO | 92/01047 | 1/1992 |
| WO | 92/02551 | 2/1992 |
| WO | 92/18619 | 10/1992 |
| WO | 92/22583 | 12/1992 |
| WO | 93/11236 | 6/1993 |
| WO | 93/12227 | 6/1993 |
| WO | 95/15982 | 6/1995 |
| WO | 95/20401 | 8/1995 |
| WO | 97/49805 | 12/1997 |
| WO | 98/20734 | 5/1998 |
| WO | 98/24893 | 6/1998 |
| WO | 98/25971 | 6/1998 |
| WO | 99/03859 | 1/1999 |
| WO | 00/76310 | 12/2000 |
| WO | 01/31007 | 5/2001 |
| WO | 01/57081 | 8/2001 |
| WO | 01/98468 | 12/2001 |
| WO | 02/14358 | 2/2002 |
| WO | 02/46383 | 6/2002 |
| WO | 02/090526 | 11/2002 |
| WO | 02/102993 | 12/2002 |
| WO | 02/102994 | 12/2002 |
| WO | 03/048208 | 6/2003 |
| WO | 03/050531 | 6/2003 |
| WO | 2004/018649 | 3/2004 |
| WO | 2004/051268 | 6/2004 |
| WO | 2004/097047 | 11/2004 |
| WO | 2004/106377 | 12/2004 |
| WO | 2005/003169 | 1/2005 |
| WO | 2005/003170 | 1/2005 |
| WO | 2005/003171 | 1/2005 |
| WO | 2005/113605 | 12/2005 |
| WO | 2005/117984 | 12/2005 |
| WO | 2007023298 | 3/2007 |
| WO | 2007/041972 | 4/2007 |
| WO | 2007/109324 | 9/2007 |
| WO | 2007/128121 | 11/2007 |
| WO | 2008/038024 | 4/2008 |
| WO | 2008/057457 | 5/2008 |
| WO | 2008/057458 | 5/2008 |
| WO | 2008/057459 | 5/2008 |
| WO | 2008/063382 | 5/2008 |
| WO | 2008/086395 | 7/2008 |
| WO | 2008/090958 | 7/2008 |
| WO | 2008/109871 A2 | 9/2008 |
| WO | 2008/109871 A3 | 9/2008 |
| WO | 2008/125623 | 10/2008 |
| WO | 2008/133647 | 11/2008 |
| WO | 2009/026558 | 2/2009 |
| WO | 2009/033027 | 3/2009 |
| WO | 2009/055783 | 4/2009 |
| WO | 2008/109871 A8 | 7/2009 |
| WO | 2009/100297 | 8/2009 |
| WO | 2009/100318 | 8/2009 |
| WO | 2009/131740 | 10/2009 |
| WO | 2010/029513 | 3/2010 |

(56) References Cited

FOREIGN PATENT DOCUMENTS

| | | |
|---|---|---|
| WO | 2010/035012 | 4/2010 |
| WO | 2010/077854 | 8/2010 |
| WO | 2011/037791 | 3/2011 |
| WO | 2011/051351 | 5/2011 |
| WO | 2011/053665 | 5/2011 |
| WO | 2011/053743 | 5/2011 |
| WO | 2011/053759 | 5/2011 |
| WO | 2011/053783 | 5/2011 |
| WO | 2011051350 | 5/2011 |
| WO | 2011/072263 | 6/2011 |
| WO | 2011/111007 | 9/2011 |
| WO | 2012/054438 | 4/2012 |
| WO | 2012/088313 | 6/2012 |
| WO | 2012/101251 | 8/2012 |
| WO | 2012/101252 | 8/2012 |
| WO | 2012/101253 | 8/2012 |
| WO | 2012/109530 | 8/2012 |
| WO | 2012/154999 | 11/2012 |
| WO | 2012/168491 | 12/2012 |
| WO | 2012/170607 | 12/2012 |
| WO | 2012/177741 | 12/2012 |
| WO | 2013/008185 | 1/2013 |
| WO | 2013/016648 | 1/2013 |
| WO | 2013/039958 | 3/2013 |
| WO | 2013/039969 | 3/2013 |
| WO | 2013/041844 A2 | 3/2013 |
| WO | 2013/148284 | 10/2013 |
| WO | 2014/159595 | 10/2014 |

OTHER PUBLICATIONS

Allard et al., "Novel mutations of the PCSK9 gene cause variable phenotype of autosomal dominant hypercholesterolemia," Human mutation, 26(5), pp. 497, Nov. 2005.
Allard et al., "PC9, a new actor in autosomal dominant hypercholesterolemia," Current Genomics, 6(7), pp. 535-543, Nov. 2005.
Allard et al., Genetic heterogeneity of autosomal dominant hypercholesterolemia: PCSK9, a third genet involved in the disease:, Current Topics in Genetics, 1, pp. 103-112, 2005.
Anderson et al. Activation of the furin endoprotease is a multiple-step process: requirements for acidification and internal propeptide cleavage. EMBO J. 16, 1508-1518., 1997.
Attie et al., "Dual regulation of the LDL receptor—some clarity and new questions", Cell Metab., 1(5):290-292, (2005).
Attie et al., "The mystery of PCSK9", Aterioscler Thromb Vase Biol., 24(8):1337-1339, (2004).
Austin et al., "Genetic causes of monogenic heterozygous familial hypercholesterolemia: a HuGE prevalence review", American Journal of Epidemiology, 160 (5) pp. 407-420, 2004.
Barrios et al., "Length of the Antibody Heavy Chain Complementarity Determining Region 3 as a Specificity-Determining Factor," J. Mol. Recognit., 2004, pp. 332-338, vol. 17.
Basak, A., "Inhibitors of Proprotien Convertases", J Mol Med 83: pp. 844-855, 2005.
Bedi et al., "Inhibition of squalene synthase upregulates PCSK9 expression in rat liver", Arch Biochem Biophys., 470 (2):116-119, (2008).
Benjannet et al. (2006) "The Proprotein Convertase (PC) PCSK9 is Inactivated by Furin and/or PC5/6A," J. Biol. Chem. 281(41):30561-30572.
Benjannet et al. "NARC-1/PCSK9 and its natural mutants: zymogen cleavage and effects on the low density lipoprotein (LDL) receptor and LDL cholesterol." J Biol Chem, 2004, 279 (47): 48865-48875.
Berge et al. Missense mutations in the PCSK9 gene are associated with hypocholesterolemia and possibly increased response to statin therapy. Arterioscler. Thromb. Vasc. Biol. (2006) 26, 1094-1100.
Bingham et al. Proapoptotic Effects of NARC 1 (=PCSK9), the Gene Encoding a Novel Serine Proteinase. Cytometry Part A, 2006, 69A: 1123-1131.
Bottomley et al. Structural and biochemical characterization of the wild type PCSK9/EGF-AB complex and natural FH mutants. J Biol Chem Nov. 2008.

Brown, M.S. & Goldstein, J.L. Lowering LDL—not only how low, but how long? Science 311, 1721-1723 (2006).
Brunger et al., Crystallography & NMR System: A new software suite for macromolecular structure determination, Acta Crystallogr D Biol Crystallogr 54, 905-21 (1998).
Burnett et al. "New therapies for familial hypercholesterolemia" Expert Opin. Ther. Patents 16(3): 349-361, 2006.
Cameron et al. "Effect of mutations in the PCSK9 gene on the cell surface LDL receptors." Hum. Mol. Genet. 15, 1551-1558 (2006).
Cameron et al., "Berberine decreases PCSK9 expression in HepG2 cells", Atherosclerosis, 201(2):266-273, (2008).
Cameron et al., "Characterization of novel mutations in the catalytic domain of the PCSK9 gene", J Intern Med., 263 (4):420-431, (2008).
Cameron et al., "Investigations on the evolutionary conservation of PCSK9 reveal a functionally important protrusion," The FEBS Journal, pp. 1-13, 2008.
Campbell, Chapter 1, Monoclonal Antibody Technology, 1984 pp. 1-32, Elsevier Science Publishers B.V., The Netherlands.
Careskey et al., "Atorvastatin increases human serum levels of proprotein convertase subtilisin/kexin type 9", J Lipid Res., 49(2):394-398, (2008).
Casset et al., "A Peptide Mimetic of an Anti-CD4 Monoclonal Antibody by Rational Design," Biochemical and Biophysical Research Communications, 2003, vol. 307, pp. 198 205.
Cayman Chemical Company: "Material Safety Data Sheet PCSK9 (human) Polyclonal Antibody" Jul. 26, 2007, pp. 1-3.
Cayman Chemical Company: "Material Safety Data Sheet PCSK9 (murine) Polyclonal Antibody" Sep. 5, 2007, pp. 1-4.
Cayman Chemical Company: "Product information PCSK9 (murine) Polyclonal Antibody" Sep. 5, 2007, pp. 1-4.
Cayman Chemical Company: "Product information PCSK9 Polyclonal Antibody Catalog No. 10007185" Dec. 10, 2007, pp. 1-2.
Chamov and Ashkanazi, TIBTECH 14: 52-60, 1996 (entitled "Antibody Engineering at the Millennium").
Chan et al. (2009) "A Proprotein Convertase Subtilisin/Kexin Type 9 Neutralizing Antibody Reduced Serum Cholesterol in Mice and . . . ," Proc Natl Acad Sci USA 106(24):9820-9825.
Chen Bei et al. "Influence of histidine on the stability and physical properties of a fully human antibody in aqueous and solid forms" Pharmaceutical Research, Kluwer Academic Publishers, New York, NY vol. 20, No. 12, Dec. 1, 2003, pp. 1952-1960.
Chen et al., "Selection and Analysis of an Optimized Anti-VEGF Antibody: Crystal Structure of an Affinity Matured Fab in Complex with Antigen," J. Mol. Biol., 1999, vol. 293, pp. 865 881.
Chen et al., "A common PCSK9 haplotype, encompassing the E670G coding single nucleotide polymorphism, is a novel genetic marker for plasma low-density lipoprotein cholesterol levels and severity of coronary atherosclerosis", J Am Coll Cardiol. 45(10):1611-1619, (2005).
Cohen et al. Sequence variations in PCSK9, low LDL, and protection against coronary heart disease. N. Engl. J. Med. 354, 1264-1272 (2006).
Cohen et al., "Low LDL cholesterol in individuals of African descent resulting from frequent nonsense mutations in PCSK9", Nat Genet. 37(2):161-165, (2005), with Cohen et al., "Erratum: Low LDL cholesterol in African Americans resulting from frequent nonsense mutations in PCSK9," Nature Genetics, 37(3), pp. 328, 2005.
Colman (Research in Immunology, 1994. vol. 145, pp. 33-36).
Costet et al. Hepatic PCSK9 Expression Is Regulated by Nutritional Status via Insulin and Sterol Regulatory Element-binding Protein 1c. Journal of Biological Chemistry, Mar. 2006. 281(10): 6211-6218.
Costet et al., "PCSK9 and LDL cholesterol: unraveling the target to design the bullet", Trends Biochem Sci., 33(9):426-434, (2008).
Saito, Y. et al., "Sodium Channel Mutation in Irritable Bowel Syndrome: Evidence Ior an Ion C4 Channelopathy," Am. J. Physiol. Gatrointest. Liver Physiol., vol. 296, pp. G211-G218, 2009.
Babcook, J., et al., A Novel Strategy for generating Monoclonal Antibodies from Single, Isolated Lymphocytes Producing Antibodies of Defined Specificities, Proc. Natl. Acad. Sci. USA, vol. 93, No. 15, pp. 7843-7848, 1996.
Cummins, T. R., et al., "Eiectrophysiological Properties of Mutant Nav1.7 Sodium Channels in a Painful Inherited Neuropathy", The Journal of Neuroscience, 24(38), pp. 8232-8236, 2004.

(56) References Cited

OTHER PUBLICATIONS

De Genst, E., et al., "Molecular basis for the preferential cleft recognition by dromedary heavy-chain antibodies", PNAS, vol. 103, No. 12, pp. 4586-4591, 2006.
Gilly, et al., J. Neurosci., vol. 9, No. 4, pp. 1362-1374, 1989.
Gonoi, T., et al., "Voltage Clamp Analysis of Tetrodotoxin-sensitive and -insensitive Sodium Channels in Rat Muscle Cells Developing in Vitro1", J. Neurosci., vol. 5, No. 9, pp. 2559-2564, 1985.
Jones, S.W., "Sodium Currents in Dissociated Bull-Frog Sympathetic Neurones", J. Physiol., vol. 389, pp. 605-627, 1987.
Klionsky, L., et al., A Polyclonal Antibody to the Prepare Loop of Transient Receptor Potential Vanilloid Type1 Blocks Channel Activation, The Journal of Pharmacology and Experimental Therapeutics, vol. 319, No. 1, pp. 192-198, 2006.
Liu, J.L., et al., "Isolation of anti-toxin single domain antibodies from a semi-synthetic spiny dogfish shark display library", BMC Biotechnology, vol. 7:78, 2007.
Llinas, et al., "Eiectrophysiological properties of in vitro Purkinje cell dendrites in mammalian cerebellar slices", J. Physiol. (Land.), vol. 305, pp. 197-213, 1980.
Orlandi, et al., "Cloning immunoglobulin variable domains for expression by the polymerase chain reaction", PNAS USA, vol. 86, pp. 3833-3837, 1989.
Rasband, M.N., et al., "Distinct potassium channels on pain-sensing neurons", PNAS, vol. 98, No. 23, pp. 13373-13378, 2001.
Saerens, D., et al., Single Domain Antibodies Derived from Dromedary Lymph Node and Peripheral Blood Lymphocytes Sensing Conformational Variants of Prostate-specific Antigen, J. Bioi. Chem., vol. 279, No. 50, pp. 51965-51972, 2004.
Schmalhofer, W.A., et al., "ProTx-11, a Selective Inhibitor of Nav1.7 Sodium Channels, Blocks Action Potential Propagation in Nociceptors", Mol Pharmacal, vol. 74, pp. 1476-1484,2008.
Tao, M., et al., "The Differential Ability of Human IgG1 and IgG4 to Activate Complement Is Determined by the COOH-terminal Sequence of the CH2 Domain", J. Exp. Med, vol. 173, pp. 1 025-1028, 1991.
Tao, M., et al., "Structural Features of Human Immunoglobulin G that Determine Isotype-specific Differences in Complement Activation", J. Exp. Med, vol. 178, pp. 661-667, 1993.
Tickle, S., et al., "High-Throughput Screening for High Affinity Antibodies", Journal of the Association for Laboratory Automation, vol. 14, pp. 303-307, 2009.
Zucker, L.S., et al., "Chimeric Human-Mouse IgG Antibodies with Shuffled Constant Region Exons Demonstrate that Multiple Domains Contribute to in Vivo Half-Life", Cancer Research, vol. 58, pp. 3905-3908, 1998.
Lee et al, Cell 157, pp. 1-12, 2014.
de Haard, "Novel Strategies for Identification and Characterization of Human Antibodies Against Nav1.7 Ion Channel Target", Antibodies Against Membrane Protein Targets, 2013, pp. 1-31.
Piper et al., "The Crystal Structure of PCSK9: A Regulator of Plasma LDL-Cholesterol," Structure, 15, 1-8, pp. 545-552 (May 2007).
Pisciotta et al., "Additive effect of mutations in LDLR and PCSK9 genes on the phenotype of familial hypercholesterolemia," Atherosclerosis 186(2), pp. 433-440, Jun. 2006.
Poirier et al., "Implication of the proprotein convertase NARC-1/PCSK9 in the development of the nervous system", J Neurochem, 98(3):838-850, (2006).
Poirier et al., "The proprotein convertase PCSK9 induces the degradation of the low density lipoprotein receptor (LDLR) and its closest family members VLDLR and ApoER2", J Biol Chem., 283(4):2363-2372, (2008).
Polisecki et al., "Genetic variation a the PCSK9 locus moderately lowers low-density lipoprotein cholesterol levels, but does not significantly lower vascular disease risk in an elderly population", Atherosclerosis, 200(1): 95-101, (2008).
Qian et al*, "Secreted PCSK9 downregulates low density lipoprotein receptor through receptor-mediated endocytosis", J Lipid Res., 48(7):1488-1498, (2007).
Rader et al. "Monogenic hypercholesterolemia: New insights in pathogenesis and treatment", Journal of Clinical Investigation, 111 (12), pp. 1795-1803, 2003.
Rashid et al. (2005) "Decreased Plasma Cholesterol and Hypersensitivity to Statins in Mice Lacking PCSK9," Proc Natl Acad Sci USA 102(15):5374-5379.
Ratliff et al., "Transgenic Expression of CYP7A1 in LDL Receptor-Deficient Mice Blocks Diet-Induced Hypercholesterolemia," Journal of Lipid Research, 47, 2006, ;; 1513-1520.
Rawlings et al., (2006). MEROPS: the peptidase database. Nucleic Acids Res. 34, D270-D272.
RCSB Protein Data Bank: An Information Portal to Biological Macromolecular Structures. Search Results for keyword "pcsk9", search conducted Jan. 10, 2008. Website accessed at http://www.rcsb.org/pdb/home/home.do—Piper et al. "The Crystal Structure of Proprotein convertase subtilisin kexin type 9 (PCSK9)" (Released May 8, 2007)—Cunningham et al. "Crystal Structure of PCSK9" (Deposited Mar. 12, 2007, released Apr. 10, 2007)—Hampton et al. "The Crystal Structure of PCSK9 at 1.9 Angstroms Resolution Reveals Structure Homology to with resistin within the c thermainal domain" (PNAS 2007, 104:14604).
Rudenko et al., "Structure of the LDL Receptor Extracellular Domain at Endosomal pH," Science 298, 2353-8 (2002).
Rudikoff et al. "Single Amino Acid Substitution Altering Antigen Binding Specificity" Proc. Natl. Acad. Sci. 79: 1979-1983, 1982.
Sakai et al., (1998). Molecular identification of the sterol-regulated lumina! protease that cleaves SREBPs and controls lipid composition of animal cells. Mol. Cell 2, 505-514.
Saint-Jore et al. "Autosomal dominant type IIa hypercholesterolemia: Evaluation of the respective contributions of LDLR and APOB gene defects as well as a third major group of defects," European Journal of Human Genetics, 8(8), pp. 621-630, 2000.
"Sanofi and Regeneron Report Positive Preliminary Phase 2 Program Results for Anti-PCSK9 Antibody in Hypercholesterolemia," http://www.prnewswire.com/news-releases/sanofi-and-regeneron-report-positive-preliminary-phase-2-program-results-for-anti-pcsk9-antibody-in-hypercholesterolemia-133590188.html, PR Newswire, Nov. 10, 2011, pp. 1-3.
Schmidt et al. A Novel Splicing Variant of Proprotein Convertase Subtilisin/Kexin Type 9, DNA Cell Biol. Apr. 2008; 27(4):183-189.
Schmidt et al., "Secreted proprotein convertase subtilisin/kexin type 9 reduces both hepatic and extrahepatic low-density lipoprotein receptors in vivo", Biochem Biophys Res Commun., 370(4):634-640, (2008).
Schmidt et al., "A 15-ketosterol is a liver X receptor ligand that suppresses sterol-responsive element binding prSeidah et al., "The proprotein convertases and their implication in sterol and/or lipid metabolism", Biological Chemistry, 387(7), 871-877 (2006)otein-2 activity," Journal of Lipid Research, 47(5), May 2006, 1037-1044.
Seidah et al., (1999). Mammalian subtilisin/kexin isozyme SKI-1: a widely expressed proprotein convertase with a unique cleavage specificity and cellular localization. Proc. Natl. Acad. Sci. USA 96, 1321-1326.
Seidah et al., "The secretory proprotein convertase neural apoptosis-regulated convertase 1 (NARC-1): Liver regeneration and neuronal differentiation" PNAS 100: 928-933, 2003.
Seidah, N.G. and Pratt, A., "The proprotein convertases are potential targets in the treatment of dyslipidemia," J. Mol. Med., 95:685-696, Mar. 10, 2007.
Seidah et al., "The proprotein convertases in health and disease", Molecular & Cellular Proteomics, 2(9), Sep. 2003.
Shan et al., "PCSK9 binds to multiple receptors and can be functionally inhibited by an EGF-A peptide," Biochem. Biophys. Res. Commun., pp. 1-5 (2008).
Shioji et al., "Genetic variants in PCSK9 affect the cholesterol level in Japanese", Journal of Human Genetics, 49 (2) pp. 109-114, 2004.
Stahl, Neil, "Regeneron: Investor Day Early Clinical Development #1 REGN727: anti-PCSK9" Jul. 15, 2010: pp. 1-21.
Sun X-M et al, Evidence for effect of mutant PCSK9 on apoliprotein B secretion as the cause of unusually severe dominant hypercholesterolemia, Human Molecular Genetics 14: 1161-1169, 2005.

(56) References Cited

OTHER PUBLICATIONS

Tangrea et al., (2002). Solution structure of the pro-hormone convertase 1 pro-domain from Mus musculus. J. Mol. Biol. 320, 801-812.
Timms et al', "A mutation in PCSK9 causing autosomal-dominant hypercholesterolemia in a Utah pedigree", Hum Genet., 114(4):349-353, (2004).
Topol E.J., "Cholesterol, racial variation and targeted medicines," Nature Medicine, 11(2), pp. 122-123, Feb. 2005.
Topol et al., "Genetic susceptibility to myocardial infarction and coronary artery disease", Human Molecular Genetics, 15 (Rev. Issue 2), R117-R123, 2006.
Wosornu et al., "Genetic deficiency of proprotein convertase Subtilisin/Kexin 9: identification of a compound heterozygote with no PCSK9," Circulation, 114 (18, Suppl. S). Oct. 31, 2006.
Vajdos et al., "Comprehensive Functional Maps of the Antigen Binding Site of an Anti ErbB2 Antibody Obtained with Shotgun Scanning Mutagenesis," J. Mol. Biol., 2002, vol. 320, pp. 415 428.
Van Regenmortel et al., "Mapping Epitope Structure and Activity: From One-Dimensional Prediction to Four-Dimensional Description of Antigenic Specificity." Methods: A Companion to Methods in Enzymology 9 (1996): 465-472.
Varret et al. "A Third Major Locus for Autosomal Dominant Hypercholesterolema Maps to 1p34.1-p32" Am. J. Hum. Genet, 64:1378-1387, 1999.
Varret et al., "ARH and HCHOLA3: Two different genes at 1p both implicated in familial hypercholesterolemia," American Journal of Human Genetics, 71(4 Supplement), Oct. 2002 abstract 1597.
Varret et al., "Familial autosomal dominant hypercholesterolemia: Highly skewed contribution of mutations in the LDLR, APOB, FH3 and FH4 genes," Circulation, 106 (19 Supplement) Nov. 5, 2002 abstract 1461.
Wells, 1990, Biochemistry 29:8509-8517 (entitled "Additivity of mutational effects in proteins").
Yue et al., "The c.43_44insCTG variation in PCSK9 is associated with low plasma LDL-cholesterol in a Caucasian population," Human Mutation, 27(5), pp. 460-466, May 2006.
Wu et al., "Humanization of a Murine Monoclonal Antibody by Simultaneous Optimization of Framework and CDR Residues," J. Mol. Biol., 1999, vol. 294, pp. 151 162.
Zaid et al., "Proprotein convertase subtilisin/kexin type 9 (PCSK9): hepatocyte-specific low-density lipoprotein receptor degradation and critical role in mouse liver regeneration", Hepatology, 48(2):646-654, (2008).
Zhang et al. "Binding of PCSK9 to EGF-A Repeat of LDL Receptor Decreases Receptor Recycling and Increases Degradation," Journal of Biological Chemistry Apr. 23, 2007.
Zhang et al. "Structural requirements for PCSK9-mediated degradation of the low-density lipoprotein receptor." PNAS, Sep. 2, 2008, 105 (35): 13045-13050.
Zhang et al., "Binding of Proprotein Convertase Subtilisin/Kexin Type 9 to Epidermal Growth Factor-like Repeat A of Low Density Lipoprotein Receptor Decreases Receptor Recycling and Increases Degradation," Journal of Biological Chemistry, vol. 282, No. 25, pp. 18602-18612, Jun. 22, 2007.
Zhao et al., (2006). Molecular characterization of loss-of-function mutations in PCSK9 and identification of a compound heterozygote. Am. J. Hum. Genet. 79, 514-523.
Zhao et al., "Functional characterization of sequence variations in PCSK9," Circulation, 112 (17, Suppl. S.), Oct. 25, 2005.
Costet et al., "Proprotein Convertase Subtilisin Kexin type 9 is repressed by the peroxisome proliferator activated receptor alpha ligand fenofibric acid." Abstracts from Scientific Sessions 2006, 11-187. Basic Science.
Cunningham et al., "Structural and biophysical studies of PCSK9 and its mutants linked to familiar hypercholesterolemia," Nature Structural & Molecular Biology, vol. 14, No. 5, pp. 413-419 (May 2007).
Damgaard et al., "No genetic linkage or molecular evidence for involvement of the PCSK9, ARH or CYP7A1 genes in the Familial Hypercholesterolemia phenotype in a sample of Danish families without pathogenic mutations in the LDL receptor and apoB genes", Atherosclerosis 177 (2), pp. 415-422, 2004.
Davignon et al. "Erratum to NARC-1: A potential new target for drug therapy of hypercholesterolemia", Atherosclerosis, 176, pp. 429, 2004.
De Pascalis et al., "Grafting of 'Abbreviated' Complementarity Determining Regions Containing Specificity Determining Residues Essential for Ligand Contact to Engineer a Less Immunogenic Humanized Monoclonal Antibody," J. Immunol, 2002, vol. 169, pp. 3076-3084.
DEDoussis et al., "LDL-receptor mutations in Europe", Human Mutation, 24(6), pp. 443-459, 2004.
Ding et al., "Molecular population genetics of PCSK9: a signature of recent positive selection", Pharmacogenet Genomics. 18(3):169-179, (2008).
Dubuc et al. Statins upregulate PCSK9, the gene encoding the proprotein convertase neural apoptosis-regulated convertase-1 implicated in familial hypercholesterolemia. Arterioscler. Thromb. Vasc. Biol. 24, 1454-1459 (2004).
Duff et al. Antibody-mediated disruption of the interaction between PCSK9 and the low-density lipoprotein receptor. Biochemical Journal. Published online Feb. 5, 2009 as Manuscript BJ20082407.
EB 06682 Goat Anti-PCSK9 Antibody, Everest Biotech Online Catalogue, © 2007, auto-generated Sep. 7, 2007.
Ellis et al., "Engineered Anti-CD38 Monoclonal Antibodies for Immunotherapy of Multiple Myeloma." The Journal of Immunology 155 (1995): 925-937.
Evans et al., "The E670G SNP in the PCSK9 gene is associated with polygenic hypercholesterolemia in men but not in women", BMC Med Genet., 7:66, (2006).
Fan et al. "Self-Association of Human PCSK9 Correlates with Its LDLR-Degrading Activity", Biochemistry, 2008, 47:1631-1639.
Fisher et al., "Effects of pH and low density lipoprotein (LDL) on PCSK9-dependent LDL receptor regulation", J Biol Chem, 282(28):20502-20512, (2007).
Folsom et al., "Variation in PCSK9, low LDL cholesterol, and risk of peripheral arterial disease", Atherosclerosis, 202(1):211-215, (2009).
Fouchier et al., "PCSK9 mutations found in patients diagnosed with autosomal dominant hypercholesterolemia in the Netherlands", Circulation, 110 (17 Suppl. S) Oct. 26, 2004.
Fouchier et al., "Update of the molecular basis of familial hypercholesterolemia in The Netherlands," Human Mutation, 26(6), pp. 550-556, Dec. 2005.
Frank-Kamenetsky et al., "Therapeutic RNAi targeting PCSK9 acutely lowers plasma cholesterol in rodents and LDL cholesterol in nonhuman primates", Proc Natl Acad Sci., 105(33):11915-11920, (2008).
Fu et al. (2000). Folding pathway mediated by an intramolecular chaperone. The inhibitory and chaperone functions of the subtilisin propeptide are not obligatorily linked. J. Biol. Chem. 275, 16871-16878.
Goldstein et al. "Familial hypercholesterolemia" in The Metabolic & Molecular Bases of Inherited Disease (eds. Scriver, C.S. et al.) 2863-2913 (McGraw-Hill, New York, 2001).
Goldstein, J.L. & Brown, M.S. The cholesterol quartet. Science 292, 1310-1312 (2001).
Graadt Van Roggen et al., "FH Afrikaner-3 LDL receptor mutation results in defective LDL receptors and causes a mild form of familial hypercholesterolemia," Arteriosclerosis, Thrombosis, and Vascular Biology, 15(6), pp. 765-772, Jun. 1995.
Graadt Van Roggen et al., "Low density lipoprotein receptor founder mutations in Afrikaner familial hypercholesterolaemic patients: A comparison of two geographical areas," Human Genetics, 88(2), pp. 204-208, 1991.
Graham et al. Antisense inhibition of proprotein convertase subtilisin/kexin type 9 reduces serum LDL in hyperlipidemic mice. J Lipid Research 2007, 48:763-767.
Graham et al., "Genetic screening protocol for familial hypercholesterolemia which includes splicing defects gives an improved mutation detection rate," Atherosclerosis, 182(2), pp. 331-340, Oct. 2005.

(56) References Cited

OTHER PUBLICATIONS

Grefhorst et al., "Plasma PCSK9 preferentially reduces liver LDL receptors in mice", J Liped Res., 49(6):1303-1311, (2008).
Grozdanov et al. "Expression and localization of PCSK9 in rat hepatic cells" Biochemistry and Cell Biology, Feb. 2006, 84(1):80-92.
Grozdanov et al. "Expression of Pcsk9 in rat hepatic cells", FASEB Journal, 19(4, Suppl. S, Part 1, Mar. 4, 2005.
Hallman et al., "Relation of PCSK9 mutations to serum low-density lipoprotein cholesterol in childhood and adulthood (from the Bogalusa Heart Study)", Am J Cardiol., 100(1):69-72, (2007).
Hampton et al., "The self-inhibited structure of full-length PCSK9 at 1.9 A reveals structural homology with resistin within the C-terminal domain," Proc Nat Acad Sci USA, Sep. 2007, 104(37): 14604-14609.
Henrich et al. (2003). The crystal structure of the proprotein processing proteinase furin explains its stringent specificity. Nat Struct. Biol. 10, 520-526.
Henrich et al. (2005). Proprotein convertase models based on the crystal structures of furin and kexin: Explanation of their Specificity Journal of Molecular Biology vol. 345, Issue 2, Jan. 14, 2005, pp. 211-227.
Holla et al., "Degradation of the LDL receptors by PCSK9 is not mediated by a secreted protein acted upon by PCSK9 extracelluarly", BMC Cell Biol., 8:9, (2007).
Holla et al., "Low-density lipoprotein receptor activity in Epstein-Barr virus-transformed lymphocytes from heterozygotes for the D374Y mutation in the PCSK9 gene", Scand J Clin Lab., 66(4):317-328, (2006).
Hooper et al., "The C679X mutation in PCSK9 is present and lowers blood cholesterol in a Southern African population", Atherosclerosis, 193(2):445-448, (2007).
Horton et al., "Molecular biology of PCSK9: its role in LDL metabolism," Trends in Biochemical Sciences, 2006, vol. 32, No. 2, pp. 71-77.
Houghten et al., "Relative Importance of Position and Individual Amino Acid Residues in Peptide Antigen-Antibody Interactions: Implications in the Mechanism of Antigenic Drift and Antigenic Shift," New Approaches to Immunization, Vaccines 86, Cold Spring Harbor Laboratory, p. 21-25, 1986.
Human/Mouse Proprotein Convertase 9/PCSK9 Antibody, Monoclonal Rat IgG, Clone # 407119, Catalog Number: MAB3888. R & D Systems: Tools for Cell Biology ResearchTM Rev. Oct. 12, 2010 p. 1 of 1. Available for sale since Jun. 2007.
Human/Mouse Proprotein Convertase 9/PCSK9 Antibody, Monoclonal Rat IgG, Clone # 407119, Catalog Number: MAB38881. R & D Systems: Tools for Cell Biology ResearchTM Rev. Oct. 12, 2010 p. 1 of 1. Available for sale since Apr. 2008.
Human/Mouse Proprotein Convertase 9/PCSK9 Antibody, Monoclonal Rat IgG, Clone # 407119, Catalog Number: MAB38882. R & D Systems: Tools for Cell Biology ResearchTM Rev. Oct. 12, 2010 p. 1 of 1. Available for sale since Feb. 2009.
Human Proprotein Convertase 9/PCSK9 Antibody, Antigen Affinity-purified Polyclonal Sheep IgG, Catalog Number: AF3888. R & D Systems: Tools for Cell Biology ResearchTM Rev: Oct. 21, 2010 p. 1 of 1.
Ikemura et al., (1987). Requirement of pro-sequence for the production of active subtilisin E in *Escherichia coli*. J. Biol. Chem. 262, 7859-7864.
Jirholt et al., "How does mutant proprotein convertase neural apoptosis-regulated convertase 1 induce autosomal dominant hypercholersterolemia", Arteriosclerosis, Thrombosis and Vascular Biology, 24 (8) pp. 1334-1336, 2004.
Kala et al., "Phage Displayed Antibodies to Heat Stable Alkaline Phosphatase: Framework Region as a Determinant of Specificity," J. Biochem., 2002, pp. 535-541, vol. 132.
Kastelein et al., "What promise does PCSK9 hold?", J Am Coll Cardiol., 45(10):1620-1621, (2005).
Kathiresan et al., "A PCSK9 missense variant associated with a reduced risk of early-onset myocardial infarction", N Engl J Med., 358(21):2299-2300, (2008).
Kim et al. "Long-distance PCR-based screening for large rearrangements of the LDL receptor gene in Korean patients with familial hypercholesterolemia," Clinical Chemistry, 45(9), p. 1424-1430, 1999.
Alonso, A., et al., Subthreshold Na1-dependent theta-like rhythmicity in stellate cells of entorhinal cortex layer II, Nature, vol. 342,pp. 175-177,1989.
Anger, T., et al., "Medicinal chemistry of neuronal voltage-gated sodium channel blockers", J. Med. Chem., vol. 44, No. 2 pp. 115-137, 2001.
Bekele-Arcuri, Z. et al., "Generation and Characterization of Subtype-specific Monoclonal Antibodies to K+ Channel a- and 13-subunit Polypeptides," Neuropharmacology, vol. 35, No. 7, pp. 851-865, 1996.
Benes, J., et al., "Anticonvulsant and sodium channel-blocking properties of novel 10,11-dihydro-5H-dibenz[b,f] azepine-5-carboxamide derivatives", J. Med. Chem., vol. 42, pp. 2582-2587, 1999.
Black, J.A., et al., "Multiple Sodium Channel Isoforms and Mitogens-Activated Protein Kinases Are Present in Painful Human Neromas", American Neurological Association, vol. 64, pp. 664-653, 2008.
Bossu, J.L., et al., "Patch-clamp study of the tetrodotoxin-resistant sodium current in group C sensory neurons", Neuroscience Letters, vol. 51, pp. 241-246 1984.
Chioni, A-M. et al., "A Novel Polyclonal antibody Specific lor the Nav 1.5 Voltage-Gated Na+ Channel 'Neonatal' Splice Form," Journal of Neuroscience Methods, vol. 147, pp. 88-98, 2005.
Cox, J.J et al., "An SCN9A channelopathy causes congenital inability to experience pain", Nature, vol. 444, No. 7121, pp. 894-898, 2006.
Dellemijn, Paul, "Are opioids effective in relieving neuropathic pain?", International Association for the Study of Pain, vol. 80, No. 3, pp. 453-462, 1999.
Dib-Hajj, et al., "Genetics and molecular pathophysiology of Na(v)1.7-related pain syndromes", Advances in Genetics, vol. 63, pp. 85-110, 2008.
Dib-Hajj, et al., "Voltage-gated sodium channels: therapeutic targets for pain", American Academy of Pain Medicine, vol. 10, No. 7, pp. 1260-1269, 2009.
Doyle, D.A., et al., "The Structure of the Potassium Channel, Molecular Basis of K+ Conduction and Selectivity", Science, vol. 280, No. 5360. pp. 69-77, 1998.
Dworkin, R. H., "An overview of neuropathic pain: syndromes, symptoms, signs, and several mechanisms", The Clinical Journal of Pain, vol. 18, pp. 343-349, 2002.
Frampton, J.E., et al., "Pregabalin: in the treatment of painful diabetic peripheral neuropathy", vol. 64, No. 24, pp. 2813-2820, 2004.
French et al., "A thresfold sodiumchannell in pyramidal cells in rat hippocampus", Neuroscience Letters, 56:289-294, 1985.
Gilly et al., "Threshold channels—a novel type of sodium channel in squid giant axon", Nature. May 31-Jun. 6, 1984;309(5967):448-50.
Goldberg et al., "Loss-of-function mutations in the Nav1.7 gene underlie congenital indifference to pain in multiple human populations", Clin Genet. Apr. 2007;71(4):311-9.
Gross et al., "Aryl sulfonamido tetralin inhibitors of the Kv1.5 ion channel", Bioorg Med Chem Lett. Jun. 1, 2009;19(11):3063-6.
Hoyt et al., "Benzazepinone Nav1.7 blockers: potential treatments for neuropathic pain", Bioorg Med Chem Lett. Nov. 15, 2007;17(22):6172-7.
Ikeda et al., "Na+ and Ca2+ currents of acutely isolated adult rat nodose ganglion cells", J Neurophysiol. Mar. 1986;55(3):527-39.
Jiang et al., "The principle of gating charge movement in a voltage-dependent K+ channel", Nature. May 1, 2003;423(6935):42-8.
Kostyuk et al., "Ionic currents in the somatic membrane of rat dorsal root ganglion neurons-I. Sodium currents", Neuroscience. 1981;6(12):2423-30.
Long et al., "Crystal structure of a mammalian voltage-dependent Shaker family K+ channel", Science. Aug. 5, 2005;309(5736):897-903.
McGowan et al., "A peripherally acting Na(v)1.7 sodium channel blocker reverses hyperalgesia and allodynia on rat models of inflammatory and neuropathic pain", Anesth Analg. Sep. 2009;109(3):951-8.

(56) References Cited

OTHER PUBLICATIONS

Meiri et al., "Monoclonal antibodies associated with sodium channel block nerve impulse and stain nodes of Ranvier", Brain Res. Sep. 17, 1984;310(1):168-73.
Meiri et al., "Detection of cell surface sodium channels by monoclonal antibodies—could the channels become exposed to the external surface and 'down regulated' by binding to antibodies?", Brain Res. Mar. 12, 1986;368(1):188-92.
Namaka et al., "A treatment algorithm for neuropathic pain", Clin Ther. Jul. 2004;26(7):951-79.
Ranouf et al, http://www.jci.org/articles/view/43158; 2010, pp. 1-23.
Renfrey et al, "The painful reality", Nat Rev Drug Discov. Mar. 2003;2(3):175-6.
Tarwana et al., "Blockers of voltage-gated sodium channels for the treatment of central nervous system diseases", Recent Pat CNS Drug Discov. Jan. 2007;2(1):57-78.
Weiss, R.E., et al, "Functional differences between two classes of sodium channels in developing rat skeletal muscle", Science, vol. 233, pp. 361-364, 1986.
Yang, J., et al., "3-(4-Phenoxyphenyl)pyrazoles: A Novel Class of Sodium Channel Blockers", J. Med. Chem., vol. 47, No. 6, pp. 1547-1552, 2004.
Toledo-Aral, et al. (1997), PNAS 94:1527-1532.
Drenth et al. (2001 ), Am. J. Hum. Genet. 68:1277-1282.
Nassar et al. (2004), PNAS 101 :12706-12711.
Dib-Hajj et al, Review, 2007, vol. 30, No. 11, pp. 555-563.
Reimann et al, PNAS, 2010, vol. 107, No. 11, pp. 5148-5153.
Abifadel et al, Human Mutation, vol. 30, No. 4, pp. 520-529, 2009.
Aung, et al, Lipids in Health and Disease, vol. 10, No. 5, pp. 1-15, 2001.
Slimani, et al, J Mol Neurosci, Mar. 6, 2014, [Epub ahead of print], DOI 10.1007/s12031-014-0238-2.
Yende et al., "Genetic polymorphisms that predict outcome and need for treatment in cardiovascular disease," Current Opinion in Critical Care 12(5), pp. 420-425, Oct. 2006.
Davignon et al., "Narc-1: A Potential New Target for Drug Therapy of Hypercholesterolemia," XIIIth International Symposium on Atherosclerosis, Sep. 28-Oct. 2, 2003, Kyoto, Japan, pp. 182-183.
Akers Michael J. et al., "Formulation Development of Protein Dosage Forms" Pharmaceutical Biotechnology, Kluwer, Dordrecht, NL, vol. 14, Jan. 1, 2002, pp. 47-127.
CCP4. The CCP4 suite: programs for protein crystallography. Acta Crystallogr D. Biol Crystallogr 50, 760-3 (1994).
Bansal et al., "Cord blood lipoproteins and prenatal influences," Current Opinion in Lipidology, 16(4), pp. 400-408, Aug. 2005.
Jeon, H. & Blacklow, S.C. Structure and physiologic function of the low-density lipoprotein receptor. Annu. Rev. Biochem. 74, 535-562 (2005).
Seidah et al., "The proprotein convertases and their implication in sterol and/or lipid metabolism", Biological Chemistry, 387(7), 871-877 (2006).
Shen, et al., "The molecular genetics of coronary artery disease and myocardial infarction", Acute Coronary Syndromes, 6 (4), pp. 129-141, 2004.
Shibata, et al, "No genetic association between PCSK9 polymorphisms and Alzheimer's disease and plasma cholesterol level in Japanese patients", Psychiatric Genetics, 2005, vol. 15, pp. 239.
Tall, "Protease variants, LDL, and coronary heart disease," New England Journal of Medicine, 354(12), pp. 1310-1312, Mar. 23, 2006.
Villeger, et al., "Familial hypercholesterolemia: 30 years after Brown and Goldstein", Recent Research Developments in Human Genetics, 1(pt.1), pp. 35-51, 2002.
Mayne et al, Lipids in Health and Disease, vol. 12, No. 70, pp. 1-11, 2013.
Knappik et al., "Fully Synthetic Human Combinatorial Antibody Libraries (HuCAL) Based on Modular Consensus Frameworks and CDRs Randomized with Trinucleotides." J Mol. Bio1.296 (2000): 57-86.
Kotowski et al, A spectrum of PCSK9 alleles contributes to plasma levels of low-density lipoprotein cholesterol., Am. J. Hum. Genet. 2006;78:410-422.
Kotowski et al., "Multiple sequence variations in PCSK9 contribute to decreased plasma levels of LDL cholesterol," Circulation, 112 (17, Suppl. S), Oct. 25 2005. Abstract No. 1766.
Kotze et al., "Familial hypercholesterolemia: Potential diagnostic value of mutation screening in a pediatric population of South Africa," Clinical Genetics, 54(1), pp. 74-78, Jul. 1998.
Kourimate et al', "Dual mechanisms for the fibrate-mediated repression of proprotein convertase subtilisin/kexin type 9", J Biol Chem., 283(15):9666-9673, (2008).
Kwon et al. "Molecular basis for LDL receptor recognition by PSK9". PNAS Feb. 12, 2008, 105(6):1820-1825.
Lagace et al. (2006) "Secreted PCSK9 Decreases the Number of LDL Receptors in Hepatocytes and in Livers of Parabiotic Mice," J. Clin. Invest. 116(11):2995-3005.
Lalanne et al., "Wild-type PCSK9 inhibits LDL clearance but does not affect apoB-containing lipoprotein production in mouse and cultured cells", J Lipid Res., 46(6):1312-1319, (2005).
Lambert et al. PCSK9: a promising therapeutic target for dyslipidemias? Trends Endocrinol. Metab. 17, 79-81 (2006).
Lambert et al., "Fasting induces hyperlipidemia in mice overexpressing proprotein convertase subtilisin kexin type 9: lack of modulation of very-low density lipoprotein hepatic output by the low-density lipoprotein receptor", Endocrinology, 147(10):4985-4995, (2006).
Lambert et al., "Molecular basis of PCSK9 function", Atherosclerosis, 203(1):1-7, (2009).
Lambert et al., "Plasma PCSK9 concentrations correlate with LDL and total cholesterol in diabetic patients and are decreased by fenofibrate treatment", Clin Chem., 54(6):1038-1045, (2008).
Lambert et al., "Unravelling the functional significance of PCSK9", Curr Opin Lipidol., 18(3):304-309, (2007).
Lamminmaki et al., "Crystal Structure of a Recombinant Anti-estradiol Fab Fragment in Complex with 1713-Estradiol," The Journal of Biological Chemistry, vol. 276 (39), Sep. 28, 2001, pp. 36687 36694.
Langhi et al., "Activation of the farnesoid X receptor represses PCSK9 expression in human hepatocytes", FEBS Lett., 582(6):949-955, (2008).
Lederman et al., Molecular Immunology 28: 1171-1181, 1991.
Leren et al., "Mutations in the PCSK9 gene in Norwegian subjects with autosomal dominant hypercholesterolemia", Clin Genet., 65(5):419-422, (2004).
Li et al., "Secreted PCSK9 promotes LDL receptor degradation independently of proteolytic activity," Biochem J. 406, 203-207 (2007).
Li et al., PNAS 77: 3211-3214, 1980.
Lopez et al., "Inhibition of PCSK9 as a novel strategy for the treatment of hypercholesterolemia", Drug News Perspect., 21(6):323-330, (2008).
Lopez et al., "PCSK9: an enigmatic process", Biochim Biophys Acta., 1781(4):184-191, (2008).
Ma et al., "Functional Characterization of Novel Genes Regulated in a Cell Culture Model of Neuronal Apoptosis," Neuroscience 2002 Abstract, Nov. 5, 2002, p. 1.
MacCallum, et al. (Journal of Molecular Biology, 1996. vol. 262, pp. 732-745).
Marais et al., "The diagnosis and management of familial hypercholesterolaemia," European Review for Medical and Pharmacological Sciences, 9(3), pp. 141-149, May 2005.
Maxwell et al., "Overexpression of Pcsk9 leads to the formation of an LDLR-Pcsk9 complex and acceleration of LDLR degredation", Circulation, 110 (17 Suppl. S) Oct. 26, 2004. Abstract No. 1171.
Maxwell et al. "Adenoviral-mediated expression of PCSK9 in mice results in a low-desnity lipoprotein receptor knockout phenotype", Proc Natl Acad Sci USA, May 2004, 101(18): 7100-7105.
Maxwell et al. "Novel putative SREBP and LXR target genes identified by microarray analysis in liver of cholesterol-fed mice" Journal of Lipid Research, vol. 14, 2109-2119, 2003.
Maxwell et al. "Overexpression of PCSK9 accelerates the degradation of the LDLR in a post-endoplasmic reticulum compartment" Proc. Natl. Acad. Sci. USA (2005) 102, 2069-2074.

(56) References Cited

OTHER PUBLICATIONS

Maxwell, K.N. & Breslow, J.L. Proprotein convertase subtilisin kexin 9: the third locus implicated in autosomal dominant hypercholesterolemia. Curr. Opin. Lipidol. 16, 167-172 (2005).

Mayne et al., "Plasma PCSK9 levels are significantly modified by statins and fibrates in humans", Lipids Health Dis., 7:22, (2008).

Mayne et al., "Plasma PCSK9 Levels Correlate with Cholesterol in Men but not in Women." Biochemical and Biophysical Research Communications (BBRC) 361 (2007): 451-456.

Mbikay et al., "Of PCSK9, cholesterol homeostasis and parasitic infections: possible survival benefits of loss-of-function PCSK9 genetic polymorphisms", Med Hypotheses, 69(5):1010-1017, (2007).

McNutt, M.C. et al. Antagonism of secreted PCSK9 increases low density lipoprotein receptor expression in HepG2 cells—2009—Journal of Biological Chemistry, 284: 10561-10570.

McNutt et al., "Catalytic Activity Is Not Required for Secreted PCSK9 to Reduce Low Density Lipoprotein Receptors in HepG2 Cells," Journal of Biological Chemistry, vol. 282, No. 29, pp. 20799-20803 (Jul. 20, 2007).

Mendez et al., Nature Genetics, 15:146-156 (1997).

Naoumova et al., "Severe hypercholesterolemia in four British families with the D374Y mutation in the PCSK9 gene: Long-term follow-up and treatment response," Arteriosclerosis, Thrombosis, and Vascular Biology, 25(12), pp. 2654-2660, Dec. 2005.

Nassoury et al. "The Cellular Trafficking of the Secretory Proprotein Convertase PCSK9 and Its Dependence on the LDLR", Traffic, 2007, 8: 718-732.

Naureckiene et al. "Functional Characterization of Narc1, a Novel Proteinase Related to Proteinase K", Arch Biochem Biophys. Dec. 1, 2003;420(1):55-67.

Ngo et al., 1994, The Protein Folding Problem and Tertiary Structure Prediction, pp. 492-495.

Ni Yan G et al. A PCSK9 C-terminal Domain Binding Fab Inhibits PCSK9 Internalization and Restores LDL-uptake: Circulation, vol. 120 No. 18 Suppl 2, Nov. 2009, p. S477. Abstract No. 1318.

Otwinowski et al., Multiparametric scaling of diffraction intensities, Acta Crystallogr A 59, 228-34 (2003).

Ouguerram et al, Apolipoprotein B100 metabolism in autosomal-dominant hypercholesterolemia related to mutations in PCSK9, Arterioscler thromb Vasc Biol. 24: 1448-1453, 2004.

Padlan et al., "Structure of an Antibody-Antigen Complex: Crystal Structure of the HyHEL 10 Fab Lysozyme Complex," Proc. Natl. Acad. Sci., vol. 86, Aug. 1989, pp. 5938 5942.

Pandit et al., "Functional analysis of sites within PCSK9 responsible for hypercholesterolemia", J Lipid Res., 49(6):1333-1343, (2008).

Parhofer et al., "What we have learned about VLDL and LDL metabolism from human kinetics studies", Journal of Lipid Research, 47(8), pp. 1620-1630, 2006.

Park et al., (2004). Post-transcriptional regulation of low density lipoprotein receptor protein by proprotein convertase subtilisin/kexin type 9a in mouse liver. J. Biol. Chem. 279, 50630-50638.

Paul, Fundamental Immunology, 3rd Edition, 1993, pp. 292-295, under the heading "Fv Structure and Diversity in Three Dimensions".

Peterson et al., "PCSK9 function and physiology", J Lipid Res., 49(7):1595-1599, (2008).

Piatesi et al., Immunological Optimizatino of a Generic Hydrophobic Pocket for High Affinity Hapten Binding and Diels-Alder Activicy, ChemBio Chem, Apr. 2004, pp. 460-466, vol. 5(4).

\* cited by examiner

AFR sub-populations
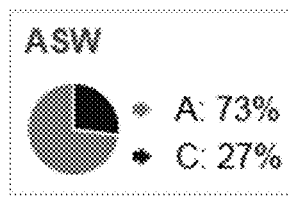 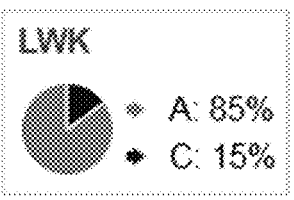 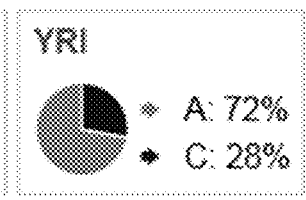
Variants:   f, c, m, e, h, p, q        f, c, m, e, h         f, c, m, e, h
EUR sub-populations
 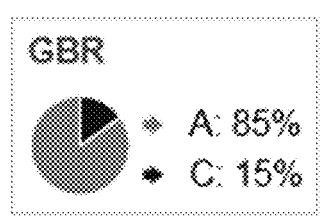
Variants:        f, c, p, aj              f, c, p
Figure 2

Non-Synonymous FW1 residue change to Valine due to rs56069819 SNP is underlined)

E V Q L <u>V</u> E S G G G L V Q P G G S L R
L S C A A S G F T F S S Y A M S W V R
Q A P G K G L E W V S A I S G S G G S
T Y Y A D S V K G R F T I S R D N S K
N T L Y L Q M N S L R A E D T A V Y Y
C A K

VH3-23*04

(rs56069819 SNP is underlined)

gag gtg cag ctg <u>g</u>tg gag tct ggg gga ggc ttg gta cag cct ggg
ggg tcc ctg aga ctc tcc tgt gca gcc tct gga ttc acc ttt agc agc tat
gcc atg agc tgg gtc cgc cag gct cca ggg aag ggg ctg gag tgg
gtc tca gct att agt ggt agt ggt ggt agc aca tac tac gca gac tcc
gtg aag ggc cgg ttc acc atc tcc aga gac aat tcc aag aac acg ctg
tat ctg caa atg aac agc ctg aga gcc gag gac acg gcc gta tat tac
tgt gcg aaa ga FW1 Encoded by VH3-23*04

SEQUENCE LISTING

<160> NUMBER OF SEQ ID NOS: 126

<210> SEQ ID NO 1
<211> LENGTH: 692
<212> TYPE: PRT
<213> ORGANISM: Homo sapiens

<400> SEQUENCE: 1

Met Gly Thr Val Ser Ser Arg Arg Ser Trp Trp Pro Leu Pro Leu Leu
1               5                   10                  15

```
Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430
```

```
Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
450                 455                 460

Ser Gly Pro Thr Arg Met Ala Thr Ala Ile Ala Arg Cys Ala Pro Asp
465                 470                 475                 480

Glu Glu Leu Leu Ser Cys Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
            530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
            610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
            675                 680                 685

Gln Glu Leu Gln
    690

<210> SEQ ID NO 2
<211> LENGTH: 662
<212> TYPE: PRT
<213> ORGANISM: Homo sapiens

<400> SEQUENCE: 2

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110
```

```
Ile Glu Glu Asp Ser Ser Val Phe Ala Gln Ser Ile Pro Trp Asn Leu
            115                 120                 125

Glu Arg Ile Thr Pro Pro Arg Tyr Arg Ala Asp Glu Tyr Gln Pro Pro
        130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

Met Leu Ser Ala Glu Pro Glu Leu Thr Leu Ala Glu Leu Arg Gln Arg
    370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Ile Ala Arg Cys Ala
        435                 440                 445

Pro Asp Glu Glu Leu Leu Ser Cys Ser Ser Phe Ser Arg Ser Gly Lys
    450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525
```

-continued

```
Leu Thr Gly Cys Ser Ser His Trp Glu Val Glu Asp Leu Gly Thr His
            530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660
```

<210> SEQ ID NO 3
<211> LENGTH: 540
<212> TYPE: PRT
<213> ORGANISM: Homo sapiens

<400> SEQUENCE: 3

```
Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
                20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
        50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
210                 215                 220

Thr Cys Phe Val Ser Gln Ser Gly Thr Ser Gln Ala Ala Ala His Val
225                 230                 235                 240
```

```
Ala Gly Ile Ala Ala Met Met Leu Ser Ala Glu Pro Glu Leu Thr Leu
            245                 250                 255

Ala Glu Leu Arg Gln Arg Leu Ile His Phe Ser Ala Lys Asp Val Ile
        260                 265                 270

Asn Glu Ala Trp Phe Pro Glu Asp Gln Arg Val Leu Thr Pro Asn Leu
            275                 280                 285

Val Ala Ala Leu Pro Pro Ser Thr His Gly Ala Gly Trp Gln Leu Phe
        290                 295                 300

Cys Arg Thr Val Trp Ser Ala His Ser Gly Pro Thr Arg Met Ala Thr
305                 310                 315                 320

Ala Ile Ala Arg Cys Ala Pro Asp Glu Glu Leu Leu Ser Cys Ser Ser
            325                 330                 335

Phe Ser Arg Ser Gly Lys Arg Arg Gly Glu Arg Met Glu Ala Gln Gly
        340                 345                 350

Gly Lys Leu Val Cys Arg Ala His Asn Ala Phe Gly Gly Glu Gly Val
        355                 360                 365

Tyr Ala Ile Ala Arg Cys Cys Leu Leu Pro Gln Ala Asn Cys Ser Val
        370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
            405                 410                 415

Glu Asp Leu Gly Thr His Lys Pro Pro Val Leu Arg Pro Arg Gly Gln
        420                 425                 430

Pro Asn Gln Cys Val Gly His Arg Glu Ala Ser Ile His Ala Ser Cys
        435                 440                 445

Cys His Ala Pro Gly Leu Glu Cys Lys Val Lys Glu His Gly Ile Pro
450                 455                 460

Ala Pro Gln Glu Gln Val Thr Val Ala Cys Glu Glu Gly Trp Thr Leu
465                 470                 475                 480

Thr Gly Cys Ser Ala Leu Pro Gly Thr Ser His Val Leu Gly Ala Tyr
            485                 490                 495

Ala Val Asp Asn Thr Cys Val Val Arg Ser Arg Asp Val Ser Thr Thr
            500                 505                 510

Gly Ser Thr Ser Glu Glu Ala Val Thr Ala Val Ala Ile Cys Cys Arg
        515                 520                 525

Ser Arg His Leu Ala Gln Ala Ser Gln Glu Leu Gln
        530                 535                 540

<210> SEQ ID NO 4
<211> LENGTH: 692
<212> TYPE: PRT
<213> ORGANISM: Homo sapiens

<400> SEQUENCE: 4

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
```

```
               65                  70                  75                  80
Val Leu Lys Glu Glu Thr His Leu Ser Gln Ser Glu Arg Thr Ala Arg
                    85                  90                  95

Arg Leu Gln Ala Gln Ala Arg Arg Gly Tyr Leu Thr Lys Ile Leu
                100                 105                 110

His Val Phe His Gly Leu Leu Pro Gly Phe Leu Val Lys Met Ser Gly
                115                 120                 125

Asp Leu Leu Glu Leu Ala Leu Lys Leu Pro His Val Asp Tyr Ile Glu
                130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
                195                 200                 205

Pro Glu Glu Asp Gly Thr Arg Phe His Arg Gln Ala Ser Lys Cys Asp
                210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
                275                 280                 285

Leu Ala Gly Gly Tyr Ser Arg Val Leu Asn Ala Ala Cys Gln Arg Leu
                290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
                355                 360                 365

Ile Gly Ala Ser Ser Asp Cys Ser Thr Cys Phe Val Ser Gln Ser Gly
                370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
                435                 440                 445

His Gly Ala Gly Trp Gln Leu Phe Cys Arg Thr Val Trp Ser Ala His
                450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495
```

```
Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 5
<211> LENGTH: 662
<212> TYPE: PRT
<213> ORGANISM: Homo sapiens

<400> SEQUENCE: 5

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
```

-continued

```
                165                 170                 175
Asn Val Pro Glu Glu Asp Gly Thr Arg Phe His Arg Gln Ala Ser Lys
            180                 185                 190
Cys Asp Ser His Gly Thr His Leu Ala Gly Val Val Ser Gly Arg Asp
            195                 200                 205
Ala Gly Val Ala Lys Gly Ala Ser Met Arg Ser Leu Arg Val Leu Asn
            210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
            245                 250                 255
Leu Pro Leu Ala Gly Gly Tyr Ser Arg Val Leu Asn Ala Ala Cys Gln
            260                 265                 270
Arg Leu Ala Arg Ala Gly Val Val Leu Val Thr Ala Ala Gly Asn Phe
            275                 280                 285
Arg Asp Asp Ala Cys Leu Tyr Ser Pro Ala Ser Ala Pro Glu Val Ile
            290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
            325                 330                 335
Asp Ile Ile Gly Ala Ser Ser Asp Cys Ser Thr Cys Phe Val Ser Gln
            340                 345                 350
Ser Gly Thr Ser Gln Ala Ala Ala His Val Ala Gly Ile Ala Ala Met
            355                 360                 365
Met Leu Ser Ala Glu Pro Glu Leu Thr Leu Ala Glu Leu Arg Gln Arg
            370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Ala Leu Pro Pro
            405                 410                 415
Ser Thr His Gly Ala Gly Trp Gln Leu Phe Cys Arg Thr Val Trp Ser
            420                 425                 430
Ala His Ser Gly Pro Thr Arg Met Ala Thr Ala Val Ala Arg Cys Ala
            435                 440                 445
Pro Asp Glu Glu Leu Leu Ser Cys Ser Ser Phe Ser Arg Ser Gly Lys
            450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
            485                 490                 495
Cys Leu Leu Pro Gln Ala Asn Cys Ser Val His Thr Ala Pro Pro Ala
            500                 505                 510
Glu Ala Ser Met Gly Thr Arg Val His Cys His Gln Gln Gly His Val
            515                 520                 525
Leu Thr Gly Cys Ser Ser His Trp Glu Val Glu Asp Leu Gly Thr His
            530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys Cys His Ala Pro Gly Leu
            565                 570                 575
Glu Cys Lys Val Lys Glu His Gly Ile Pro Ala Pro Gln Glu Gln Val
            580                 585                 590
```

```
Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
        610                 615                 620

Val Val Arg Ser Arg Asp Val Ser Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 6
<211> LENGTH: 540
<212> TYPE: PRT
<213> ORGANISM: Homo sapiens

<400> SEQUENCE: 6

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
            20                  25                  30

Leu Asp Thr Ser Ile Gln Ser Asp His Arg Glu Ile Glu Gly Arg Val
        35                  40                  45

Met Val Thr Asp Phe Glu Asn Val Pro Glu Glu Asp Gly Thr Arg Phe
    50                  55                  60

His Arg Gln Ala Ser Lys Cys Asp Ser His Gly Thr His Leu Ala Gly
65              70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
    130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260                 265                 270

Asn Glu Ala Trp Phe Pro Glu Asp Gln Arg Val Leu Thr Pro Asn Leu
        275                 280                 285

Val Ala Ala Leu Pro Pro Ser Thr His Gly Ala Gly Trp Gln Leu Phe
```

```
                290                 295                 300
Cys Arg Thr Val Trp Ser Ala His Ser Gly Pro Thr Arg Met Ala Thr
305                 310                 315                 320

Ala Val Ala Arg Cys Ala Pro Asp Glu Glu Leu Leu Ser Cys Ser Ser
                325                 330                 335

Phe Ser Arg Ser Gly Lys Arg Arg Gly Glu Arg Met Glu Ala Gln Gly
                340                 345                 350

Gly Lys Leu Val Cys Arg Ala His Asn Ala Phe Gly Gly Glu Gly Val
                355                 360                 365

Tyr Ala Ile Ala Arg Cys Cys Leu Leu Pro Gln Ala Asn Cys Ser Val
                370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                405                 410                 415

Glu Asp Leu Gly Thr His Lys Pro Pro Val Leu Arg Pro Arg Gly Gln
                420                 425                 430

Pro Asn Gln Cys Val Gly His Arg Glu Ala Ser Ile His Ala Ser Cys
                435                 440                 445

Cys His Ala Pro Gly Leu Glu Cys Lys Val Lys Glu His Gly Ile Pro
                450                 455                 460

Ala Pro Gln Glu Gln Val Thr Val Ala Cys Glu Glu Gly Trp Thr Leu
465                 470                 475                 480

Thr Gly Cys Ser Ala Leu Pro Gly Thr Ser His Val Leu Gly Ala Tyr
                485                 490                 495

Ala Val Asp Asn Thr Cys Val Val Arg Ser Arg Asp Val Ser Thr Thr
                500                 505                 510

Gly Ser Thr Ser Glu Glu Ala Val Thr Ala Val Ala Ile Cys Cys Arg
                515                 520                 525

Ser Arg His Leu Ala Gln Ala Ser Gln Glu Leu Gln
                530                 535                 540

<210> SEQ ID NO 7
<211> LENGTH: 692
<212> TYPE: PRT
<213> ORGANISM: Homo sapiens

<400> SEQUENCE: 7

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
                35                  40                  45

Glu Asp Gly Leu Ala Glu Ala Pro Glu His Gly Thr Thr Ala Thr Phe
                50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
                115                 120                 125
```

```
Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
                195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
```

```
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
                580                 585                 590
Glu Ala Ser Ile His Ala Ser Cys His Ala Pro Gly Leu Glu Cys
                595                 600                 605
Lys Val Lys Glu His Gly Ile Pro Ala Pro Gln Glu Gln Val Thr Val
                610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Gly Ala Val
                660                 665                 670
Thr Ala Val Ala Ile Cys Cys Arg Ser Arg His Leu Ala Gln Ala Ser
                675                 680                 685
Gln Glu Leu Gln
        690

<210> SEQ ID NO 8
<211> LENGTH: 662
<212> TYPE: PRT
<213> ORGANISM: Homo sapiens

<400> SEQUENCE: 8

Gln Glu Asp Glu Asp Gly Asp Tyr Glu Glu Leu Val Leu Ala Leu Arg
1               5                   10                  15
Ser Glu Glu Asp Gly Leu Ala Glu Ala Pro Glu His Gly Thr Thr Ala
                20                  25                  30
Thr Phe His Arg Cys Ala Lys Asp Pro Trp Arg Leu Pro Gly Thr Tyr
            35                  40                  45
Val Val Val Leu Lys Glu Glu Thr His Leu Ser Gln Ser Glu Arg Thr
50                  55                  60
Ala Arg Arg Leu Gln Ala Gln Ala Ala Arg Arg Gly Tyr Leu Thr Lys
65                  70                  75                  80
Ile Leu His Val Phe His Gly Leu Leu Pro Gly Phe Leu Val Lys Met
                85                  90                  95
Ser Gly Asp Leu Leu Glu Leu Ala Leu Lys Leu Pro His Val Asp Tyr
                100                 105                 110
Ile Glu Glu Asp Ser Ser Val Phe Ala Gln Ser Ile Pro Trp Asn Leu
            115                 120                 125
Glu Arg Ile Thr Pro Pro Arg Tyr Arg Ala Asp Glu Tyr Gln Pro Pro
        130                 135                 140
Asp Gly Gly Ser Leu Val Glu Val Tyr Leu Leu Asp Thr Ser Ile Gln
145                 150                 155                 160
Ser Asp His Arg Glu Ile Glu Gly Arg Val Met Val Thr Asp Phe Glu
                165                 170                 175
Asn Val Pro Glu Glu Asp Gly Thr Arg Phe His Arg Gln Ala Ser Lys
                180                 185                 190
Cys Asp Ser His Gly Thr His Leu Ala Gly Val Val Ser Gly Arg Asp
            195                 200                 205
Ala Gly Val Ala Lys Gly Ala Ser Met Arg Ser Leu Arg Val Leu Asn
        210                 215                 220
```

-continued

```
Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Ile Ala Arg Cys Ala
        435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gly His Val
        515                 520                 525

Leu Thr Gly Cys Ser Ser His Trp Glu Val Glu Asp Leu Gly Thr His
530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
```

-continued

Ala Ser Gln Glu Leu Gln
          660

<210> SEQ ID NO 9
<211> LENGTH: 540
<212> TYPE: PRT
<213> ORGANISM: Homo sapiens

<400> SEQUENCE: 9

Ser Ile Pro Trp Asn Leu Glu Arg Ile Thr Pro Arg Tyr Arg Ala
1               5                   10                  15

Asp Glu Tyr Gln Pro Pro Asp Gly Gly Ser Leu Val Glu Val Tyr Leu
                20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
        50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
    130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260                 265                 270

Asn Glu Ala Trp Phe Pro Glu Asp Gln Arg Val Leu Thr Pro Asn Leu
        275                 280                 285

Val Ala Ala Leu Pro Pro Ser Thr His Gly Ala Gly Trp Gln Leu Phe
    290                 295                 300

Cys Arg Thr Val Trp Ser Ala His Ser Gly Pro Thr Arg Met Ala Thr
305                 310                 315                 320

Ala Ile Ala Arg Cys Ala Pro Asp Glu Glu Leu Leu Ser Cys Ser Ser
                325                 330                 335

Phe Ser Arg Ser Gly Lys Arg Arg Gly Glu Arg Met Glu Ala Gln Gly
            340                 345                 350

```
Gly Lys Leu Val Cys Arg Ala His Asn Ala Phe Gly Glu Gly Val
            355                 360                 365

Tyr Ala Ile Ala Arg Cys Cys Leu Leu Pro Gln Ala Asn Cys Ser Val
        370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                405                 410                 415

Glu Asp Leu Gly Thr His Lys Pro Val Leu Arg Pro Arg Gly Gln
            420                 425                 430

Pro Asn Gln Cys Val Gly His Arg Glu Ala Ser Ile His Ala Ser Cys
        435                 440                 445

Cys His Ala Pro Gly Leu Glu Cys Lys Val Lys Glu His Gly Ile Pro
    450                 455                 460

Ala Pro Gln Glu Gln Val Thr Val Ala Cys Glu Gly Trp Thr Leu
465                 470                 475                 480

Thr Gly Cys Ser Ala Leu Pro Gly Thr Ser His Val Leu Gly Ala Tyr
                485                 490                 495

Ala Val Asp Asn Thr Cys Val Val Arg Ser Arg Asp Val Ser Thr Thr
            500                 505                 510

Gly Ser Thr Ser Glu Gly Ala Val Thr Ala Val Ala Ile Cys Cys Arg
        515                 520                 525

Ser Arg His Leu Ala Gln Ala Ser Gln Glu Leu Gln
    530                 535                 540

<210> SEQ ID NO 10
<211> LENGTH: 692
<212> TYPE: PRT
<213> ORGANISM: Homo sapiens

<400> SEQUENCE: 10

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190
```

```
His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
            290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
            450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605
```

-continued

```
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
            645                 650                 655
Arg Ser Arg Asp Val Ser Thr Thr Gly Ser Thr Ser Glu Gly Ala Val
        660                 665                 670
Thr Ala Val Ala Ile Cys Cys Arg Ser Arg His Leu Ala Gln Ala Ser
            675                 680                 685
Gln Glu Leu Gln
    690

<210> SEQ ID NO 11
<211> LENGTH: 662
<212> TYPE: PRT
<213> ORGANISM: Homo sapiens

<400> SEQUENCE: 11

Gln Glu Asp Glu Asp Gly Asp Tyr Glu Glu Leu Val Leu Ala Leu Arg
1               5                   10                  15
Ser Glu Glu Asp Gly Leu Ala Glu Ala Pro Glu His Gly Thr Thr Ala
            20                  25                  30
Thr Phe His Arg Cys Ala Lys Asp Pro Trp Arg Leu Pro Gly Thr Tyr
        35                  40                  45
Val Val Val Leu Lys Glu Glu Thr His Leu Ser Gln Ser Glu Arg Thr
    50                  55                  60
Ala Arg Arg Leu Gln Ala Gln Ala Ala Arg Arg Gly Tyr Leu Thr Lys
65                  70                  75                  80
Ile Leu His Val Phe His Gly Leu Leu Pro Gly Phe Leu Val Lys Met
                85                  90                  95
Ser Gly Asp Leu Leu Glu Leu Ala Leu Lys Leu Pro His Val Asp Tyr
            100                 105                 110
Ile Glu Glu Asp Ser Ser Val Phe Ala Gln Ser Ile Pro Trp Asn Leu
        115                 120                 125
Glu Arg Ile Thr Pro Pro Arg Tyr Arg Ala Asp Glu Tyr Gln Pro Pro
    130                 135                 140
Asp Gly Gly Ser Leu Val Glu Val Tyr Leu Leu Asp Thr Ser Ile Gln
145                 150                 155                 160
Ser Asp His Arg Glu Ile Glu Gly Arg Val Met Val Thr Asp Phe Glu
                165                 170                 175
Asn Val Pro Glu Glu Asp Gly Thr Arg Phe His Arg Gln Ala Ser Lys
            180                 185                 190
Cys Asp Ser His Gly Thr His Leu Ala Gly Val Val Ser Gly Arg Asp
        195                 200                 205
Ala Gly Val Ala Lys Gly Ala Ser Met Arg Ser Leu Arg Val Leu Asn
    210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
                245                 250                 255
Leu Pro Leu Ala Gly Gly Tyr Ser Arg Val Leu Asn Ala Ala Cys Gln
            260                 265                 270
Arg Leu Ala Arg Ala Gly Val Val Leu Val Thr Ala Ala Gly Asn Phe
        275                 280                 285
```

Arg Asp Asp Ala Cys Leu Tyr Ser Pro Ala Ser Ala Pro Glu Val Ile
          290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
                340                 345                 350

Ser Gly Thr Ser Gln Ala Ala Ala His Val Ala Gly Ile Ala Ala Met
            355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
                420                 425                 430

Ala His Ser Gly Pro Thr Arg Met Ala Thr Ala Val Ala Arg Cys Ala
            435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
                500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
                580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 12
<211> LENGTH: 540
<212> TYPE: PRT
<213> ORGANISM: Homo sapiens

```
<400> SEQUENCE: 12

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
            20                  25                  30

Leu Asp Thr Ser Ile Gln Ser Asp His Arg Glu Ile Glu Gly Arg Val
        35                  40                  45

Met Val Thr Asp Phe Glu Asn Val Pro Glu Glu Asp Gly Thr Arg Phe
    50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Tyr Ser Arg Val
    130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260                 265                 270

Asn Glu Ala Trp Phe Pro Glu Asp Gln Arg Val Leu Thr Pro Asn Leu
        275                 280                 285

Val Ala Ala Leu Pro Pro Ser Thr His Gly Ala Gly Trp Gln Leu Phe
    290                 295                 300

Cys Arg Thr Val Trp Ser Ala His Ser Gly Pro Thr Arg Met Ala Thr
305                 310                 315                 320

Ala Val Ala Arg Cys Ala Pro Asp Glu Glu Leu Leu Ser Cys Ser Ser
                325                 330                 335

Phe Ser Arg Ser Gly Lys Arg Arg Gly Glu Arg Met Glu Ala Gln Gly
            340                 345                 350

Gly Lys Leu Val Cys Arg Ala His Asn Ala Phe Gly Gly Glu Gly Val
        355                 360                 365

Tyr Ala Ile Ala Arg Cys Cys Leu Leu Pro Gln Ala Asn Cys Ser Val
    370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                405                 410                 415
```

```
Glu Asp Leu Gly Thr His Lys Pro Pro Val Leu Arg Pro Arg Gly Gln
            420                 425                 430

Pro Asn Gln Cys Val Gly His Arg Glu Ala Ser Ile His Ala Ser Cys
            435                 440                 445

Cys His Ala Pro Gly Leu Glu Cys Lys Val Lys Glu His Gly Ile Pro
            450                 455                 460

Ala Pro Gln Glu Gln Val Thr Val Ala Cys Glu Glu Gly Trp Thr Leu
465                 470                 475                 480

Thr Gly Cys Ser Ala Leu Pro Gly Thr Ser His Val Leu Gly Ala Tyr
            485                 490                 495

Ala Val Asp Asn Thr Cys Val Val Arg Ser Arg Asp Val Ser Thr Thr
            500                 505                 510

Gly Ser Thr Ser Glu Gly Ala Val Thr Ala Val Ala Ile Cys Cys Arg
            515                 520                 525

Ser Arg His Leu Ala Gln Ala Ser Gln Glu Leu Gln
            530                 535                 540

<210> SEQ ID NO 13
<211> LENGTH: 692
<212> TYPE: PRT
<213> ORGANISM: Homo sapiens

<400> SEQUENCE: 13

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
            35                  40                  45

Glu Asp Gly Leu Val Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
            85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
            130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
            210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
```

-continued

```
                245                 250                 255
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Leu Leu Pro
        275                 280                 285
Leu Ala Gly Gly Tyr Ser Arg Val Leu Asn Ala Ala Cys Gln Arg Leu
        290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
            340                 345                 350
Thr Asn Phe Gly Arg Cys Val Asp Leu Phe Ala Pro Gly Glu Asp Ile
        355                 360                 365
Ile Gly Ala Ser Ser Asp Cys Ser Thr Cys Phe Val Ser Gln Ser Gly
        370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
            420                 425                 430
Gln Arg Val Leu Thr Pro Asn Leu Val Ala Ala Leu Pro Pro Ser Thr
        435                 440                 445
His Gly Ala Gly Trp Gln Leu Phe Cys Arg Thr Val Trp Ser Ala His
        450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
            500                 505                 510
Asn Ala Phe Gly Gly Glu Gly Val Tyr Ala Ile Ala Arg Cys Cys Leu
        515                 520                 525
Leu Pro Gln Ala Asn Cys Ser Val His Thr Ala Pro Pro Ala Glu Ala
        530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
        595                 600                 605
Lys Val Lys Glu His Gly Ile Pro Ala Pro Gln Glu Gln Val Thr Val
        610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Glu Ala Val
            660                 665                 670
```

```
Thr Ala Val Ala Ile Cys Cys Arg Ser Arg His Leu Ala Gln Ala Ser
            675                 680                 685

Gln Glu Leu Gln
    690

<210> SEQ ID NO 14
<211> LENGTH: 662
<212> TYPE: PRT
<213> ORGANISM: Homo sapiens

<400> SEQUENCE: 14

Gln Glu Asp Glu Asp Gly Asp Tyr Glu Glu Leu Val Leu Ala Leu Arg
1               5                   10                  15

Ser Glu Glu Asp Gly Leu Val Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
```

```
            340                 345                 350
Ser Gly Thr Ser Gln Ala Ala His Val Ala Gly Ile Ala Ala Met
        355                 360                 365

Met Leu Ser Ala Glu Pro Glu Leu Thr Leu Ala Glu Leu Arg Gln Arg
    370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
        435                 440                 445

Pro Asp Glu Glu Leu Leu Ser Cys Ser Ser Phe Ser Arg Ser Gly Lys
    450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525

Leu Thr Gly Cys Ser Ser His Trp Glu Val Glu Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 15
<211> LENGTH: 692
<212> TYPE: PRT
<213> ORGANISM: Homo sapiens

<400> SEQUENCE: 15

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45
```

```
Glu Asp Gly Leu Ala Glu Ala Pro Glu His Gly Thr Thr Ala Thr Phe
 50                  55                  60

His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
                115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
                195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
                275                 280                 285

Leu Ala Gly Gly Tyr Ser Arg Val Leu Asn Ala Ala Cys Gln Arg Leu
                290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
                355                 360                 365

Ile Gly Ala Ser Ser Asp Cys Ser Thr Cys Phe Val Ser Gln Ser Gly
                370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Thr Leu Pro Pro Ser Thr
                435                 440                 445

His Gly Ala Gly Trp Gln Leu Phe Cys Arg Thr Val Trp Ser Ala His
450                 455                 460

Ser Gly Pro Thr Arg Met Ala Thr Ala Ile Ala Arg Cys Ala Pro Asp
```

```
             465                 470                 475                 480
        Glu Glu Leu Leu Ser Cys Ser Ser Phe Ser Arg Ser Gly Lys Arg Arg
                        485                 490                 495
        Gly Glu Arg Met Glu Ala Gln Gly Gly Lys Leu Val Cys Arg Ala His
                        500                 505                 510
        Asn Ala Phe Gly Gly Glu Gly Val Tyr Ala Ile Ala Arg Cys Cys Leu
                        515                 520                 525
        Leu Pro Gln Ala Asn Cys Ser Val His Thr Ala Pro Pro Ala Glu Ala
                        530                 535                 540
        Ser Met Gly Thr Arg Val His Cys His Gln Gln Gly His Val Leu Thr
        545                 550                 555                 560
        Gly Cys Ser Ser His Trp Glu Val Glu Asp Leu Gly Thr His Lys Pro
                        565                 570                 575
        Pro Val Leu Arg Pro Arg Gly Gln Pro Asn Gln Cys Val Gly His Arg
                        580                 585                 590
        Glu Ala Ser Ile His Ala Ser Cys Cys His Ala Pro Gly Leu Glu Cys
                        595                 600                 605
        Lys Val Lys Glu His Gly Ile Pro Ala Pro Gln Glu Gln Val Thr Val
                        610                 615                 620
        Ala Cys Glu Glu Gly Trp Thr Leu Thr Gly Cys Ser Ala Leu Pro Gly
        625                 630                 635                 640
        Thr Ser His Val Leu Gly Ala Tyr Ala Val Asp Asn Thr Cys Val Val
                        645                 650                 655
        Arg Ser Arg Asp Val Ser Thr Thr Gly Ser Thr Ser Glu Glu Ala Val
                        660                 665                 670
        Thr Ala Val Ala Ile Cys Cys Arg Ser Arg His Leu Ala Gln Ala Ser
                        675                 680                 685
        Gln Glu Leu Gln
                690

<210> SEQ ID NO 16
<211> LENGTH: 662
<212> TYPE: PRT
<213> ORGANISM: Homo sapiens

<400> SEQUENCE: 16

Gln Glu Asp Glu Asp Gly Asp Tyr Glu Glu Leu Val Leu Ala Leu Arg
        1               5                   10                  15
        Ser Glu Glu Asp Gly Leu Ala Glu Ala Pro Glu His Gly Thr Thr Ala
                        20                  25                  30
        Thr Phe His Arg Cys Ala Lys Asp Pro Trp Arg Leu Pro Gly Thr Tyr
                        35                  40                  45
        Val Val Val Leu Lys Glu Glu Thr His Leu Ser Gln Ser Glu Arg Thr
                        50                  55                  60
        Ala Arg Arg Leu Gln Ala Gln Ala Ala Arg Arg Gly Tyr Leu Thr Lys
        65                  70                  75                  80
        Ile Leu His Val Phe His Gly Leu Leu Pro Gly Phe Leu Val Lys Met
                        85                  90                  95
        Ser Gly Asp Leu Leu Glu Leu Ala Leu Lys Leu Pro His Val Asp Tyr
                        100                 105                 110
        Ile Glu Glu Asp Ser Ser Val Phe Ala Gln Ser Ile Pro Trp Asn Leu
                        115                 120                 125
        Glu Arg Ile Thr Pro Pro Arg Tyr Arg Ala Asp Glu Tyr Gln Pro Pro
                        130                 135                 140
```

-continued

```
Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
195                 200                 205

Ala Gly Val Ala Lys Gly Ala Ser Met Arg Ser Leu Arg Val Leu Asn
        210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Thr Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Ile Ala Arg Cys Ala
        435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525

Leu Thr Gly Cys Ser Ser His Trp Glu Val Glu Asp Leu Gly Thr His
530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
```

-continued

```
                    565                 570                 575
Glu Cys Lys Val Lys Glu His Gly Ile Pro Ala Pro Gln Glu Gln Val
                580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
        610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
                660

<210> SEQ ID NO 17
<211> LENGTH: 540
<212> TYPE: PRT
<213> ORGANISM: Homo sapiens

<400> SEQUENCE: 17

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
                20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
        50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
                100                 105                 110

Leu Ile Gly Leu Glu Phe Ile Arg Lys Ser Gln Leu Val Gln Pro Val
            115                 120                 125

Gly Pro Leu Val Val Leu Leu Pro Leu Ala Gly Gly Tyr Ser Arg Val
        130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
                180                 185                 190

Pro Val Thr Leu Gly Thr Leu Gly Thr Asn Phe Gly Arg Cys Val Asp
            195                 200                 205

Leu Phe Ala Pro Gly Glu Asp Ile Ile Gly Ala Ser Ser Asp Cys Ser
        210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
                260                 265                 270
```

```
Asn Glu Ala Trp Phe Pro Glu Asp Gln Arg Val Leu Thr Pro Asn Leu
            275                 280                 285

Val Ala Thr Leu Pro Pro Ser Thr His Gly Ala Gly Trp Gln Leu Phe
    290                 295                 300

Cys Arg Thr Val Trp Ser Ala His Ser Gly Pro Thr Arg Met Ala Thr
305                 310                 315                 320

Ala Ile Ala Arg Cys Ala Pro Asp Glu Glu Leu Leu Ser Cys Ser Ser
                325                 330                 335

Phe Ser Arg Ser Gly Lys Arg Arg Glu Arg Met Glu Ala Gln Gly
            340                 345                 350

Gly Lys Leu Val Cys Arg Ala His Asn Ala Phe Gly Gly Glu Gly Val
        355                 360                 365

Tyr Ala Ile Ala Arg Cys Cys Leu Leu Pro Gln Ala Asn Cys Ser Val
    370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                405                 410                 415

Glu Asp Leu Gly Thr His Lys Pro Pro Val Leu Arg Pro Arg Gly Gln
            420                 425                 430

Pro Asn Gln Cys Val Gly His Arg Glu Ala Ser Ile His Ala Ser Cys
        435                 440                 445

Cys His Ala Pro Gly Leu Glu Cys Lys Val Lys Glu His Gly Ile Pro
    450                 455                 460

Ala Pro Gln Glu Gln Val Thr Val Ala Cys Glu Glu Gly Trp Thr Leu
465                 470                 475                 480

Thr Gly Cys Ser Ala Leu Pro Gly Thr Ser His Val Leu Gly Ala Tyr
                485                 490                 495

Ala Val Asp Asn Thr Cys Val Val Arg Ser Arg Asp Val Ser Thr Thr
            500                 505                 510

Gly Ser Thr Ser Glu Glu Ala Val Thr Ala Val Ala Ile Cys Cys Arg
        515                 520                 525

Ser Arg His Leu Ala Gln Ala Ser Gln Glu Leu Gln
    530                 535                 540

<210> SEQ ID NO 18
<211> LENGTH: 692
<212> TYPE: PRT
<213> ORGANISM: Homo sapiens

<400> SEQUENCE: 18

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110
```

```
His Val Phe His Gly Leu Leu Pro Gly Phe Leu Val Lys Met Ser Gly
    115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
        370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Ser Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
        450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
            515                 520                 525
```

```
Leu Pro Gln Ala Asn Cys Ser Val His Thr Ala Pro Pro Ala Glu Ala
        530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
                595                 600                 605

Lys Val Lys Glu His Gly Ile Pro Ala Pro Gln Glu Gln Val Thr Val
            610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
            675                 680                 685

Gln Glu Leu Gln
    690

<210> SEQ ID NO 19
<211> LENGTH: 662
<212> TYPE: PRT
<213> ORGANISM: Homo sapiens

<400> SEQUENCE: 19

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205
```

```
Ala Gly Val Ala Lys Gly Ala Ser Met Arg Ser Leu Arg Val Leu Asn
    210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
                245                 250                 255
Leu Pro Leu Ala Gly Gly Tyr Ser Arg Val Leu Asn Ala Ala Cys Gln
            260                 265                 270
Arg Leu Ala Arg Ala Gly Val Val Val Thr Ala Ala Gly Asn Phe
            275                 280                 285
Arg Asp Asp Ala Cys Leu Tyr Ser Pro Ala Ser Ala Pro Glu Val Ile
    290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                325                 330                 335
Asp Ile Ile Gly Ala Ser Ser Asp Cys Ser Thr Cys Phe Val Ser Gln
            340                 345                 350
Ser Gly Thr Ser Gln Ala Ala His Val Ala Gly Ile Ala Ala Met
            355                 360                 365
Met Leu Ser Ala Glu Pro Glu Leu Thr Leu Ala Glu Leu Arg Gln Arg
370                 375                 380
Leu Ile His Phe Ser Ala Lys Asp Val Ile Ser Glu Ala Trp Phe Pro
385                 390                 395                 400
Glu Asp Gln Arg Val Leu Thr Pro Asn Leu Val Ala Ala Leu Pro Pro
                405                 410                 415
Ser Thr His Gly Ala Gly Trp Gln Leu Phe Cys Arg Thr Val Trp Ser
            420                 425                 430
Ala His Ser Gly Pro Thr Arg Met Ala Thr Ala Val Ala Arg Cys Ala
            435                 440                 445
Pro Asp Glu Glu Leu Leu Ser Cys Ser Ser Phe Ser Arg Ser Gly Lys
    450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                485                 490                 495
Cys Leu Leu Pro Gln Ala Asn Cys Ser Val His Thr Ala Pro Pro Ala
            500                 505                 510
Glu Ala Ser Met Gly Thr Arg Val His Cys His Gln Gly His Val
            515                 520                 525
Leu Thr Gly Cys Ser Ser His Trp Glu Val Glu Asp Leu Gly Thr His
530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys His Ala Pro Gly Leu
                565                 570                 575
Glu Cys Lys Val Lys Glu His Gly Ile Pro Ala Pro Gln Glu Gln Val
            580                 585                 590
Thr Val Ala Cys Glu Glu Gly Trp Thr Leu Thr Gly Cys Ser Ala Leu
            595                 600                 605
Pro Gly Thr Ser His Val Leu Gly Ala Tyr Ala Val Asp Asn Thr Cys
    610                 615                 620
```

-continued

```
Val Val Arg Ser Arg Asp Val Ser Thr Thr Gly Ser Thr Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 20
<211> LENGTH: 540
<212> TYPE: PRT
<213> ORGANISM: Homo sapiens

<400> SEQUENCE: 20

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
                20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
        50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
    130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260                 265                 270

Ser Glu Ala Trp Phe Pro Glu Asp Gln Arg Val Leu Thr Pro Asn Leu
        275                 280                 285

Val Ala Ala Leu Pro Pro Ser Thr His Gly Ala Gly Trp Gln Leu Phe
    290                 295                 300

Cys Arg Thr Val Trp Ser Ala His Ser Gly Pro Thr Arg Met Ala Thr
305                 310                 315                 320

Ala Val Ala Arg Cys Ala Pro Asp Glu Glu Leu Leu Ser Cys Ser Ser
                325                 330                 335
```

```
Phe Ser Arg Ser Gly Lys Arg Arg Gly Glu Arg Met Glu Ala Gln Gly
            340                 345                 350

Gly Lys Leu Val Cys Arg Ala His Asn Ala Phe Gly Gly Glu Gly Val
            355                 360                 365

Tyr Ala Ile Ala Arg Cys Cys Leu Leu Pro Gln Ala Asn Cys Ser Val
370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
            405                 410                 415

Glu Asp Leu Gly Thr His Lys Pro Val Leu Arg Pro Arg Gly Gln
            420                 425                 430

Pro Asn Gln Cys Val Gly His Arg Glu Ala Ser Ile His Ala Ser Cys
            435                 440                 445

Cys His Ala Pro Gly Leu Glu Cys Lys Val Lys Glu His Gly Ile Pro
    450                 455                 460

Ala Pro Gln Glu Gln Val Thr Val Ala Cys Glu Gly Trp Thr Leu
465                 470                 475                 480

Thr Gly Cys Ser Ala Leu Pro Gly Thr Ser His Val Leu Gly Ala Tyr
            485                 490                 495

Ala Val Asp Asn Thr Cys Val Val Arg Ser Arg Asp Val Ser Thr Thr
            500                 505                 510

Gly Ser Thr Ser Glu Glu Ala Val Thr Ala Val Ala Ile Cys Cys Arg
            515                 520                 525

Ser Arg His Leu Ala Gln Ala Ser Gln Glu Leu Gln
            530                 535                 540

<210> SEQ ID NO 21
<211> LENGTH: 692
<212> TYPE: PRT
<213> ORGANISM: Homo sapiens

<400> SEQUENCE: 21

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
```

```
                165                 170                 175
Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Thr Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590
```

```
Glu Ala Ser Ile His Ala Ser Cys Cys His Ala Pro Gly Leu Glu Cys
            595                 600                 605

Lys Val Lys Glu His Gly Ile Pro Ala Pro Pro Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
            645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
            675                 680                 685

Gln Glu Leu Gln
    690

<210> SEQ ID NO 22
<211> LENGTH: 662
<212> TYPE: PRT
<213> ORGANISM: Homo sapiens

<400> SEQUENCE: 22

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
```

```
            260                 265                 270
Arg Leu Ala Arg Ala Gly Val Val Leu Val Thr Ala Ala Gly Asn Phe
            275                 280                 285
Arg Asp Asp Ala Cys Leu Tyr Ser Pro Ala Ser Ala Pro Glu Val Ile
            290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                325                 330                 335
Asp Ile Ile Gly Ala Ser Ser Asp Cys Ser Thr Cys Phe Val Ser Gln
            340                 345                 350
Ser Gly Thr Ser Gln Ala Ala His Val Ala Gly Ile Ala Ala Met
            355                 360                 365
Met Leu Ser Ala Glu Pro Glu Leu Thr Leu Ala Glu Leu Arg Gln Arg
            370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Thr Leu Pro Pro
                405                 410                 415
Ser Thr His Gly Ala Gly Trp Gln Leu Phe Cys Arg Thr Val Trp Ser
            420                 425                 430
Ala His Ser Gly Pro Thr Arg Met Ala Thr Ala Ile Ala Arg Cys Ala
            435                 440                 445
Pro Asp Glu Glu Leu Leu Ser Cys Ser Ser Phe Ser Arg Ser Gly Lys
450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                485                 490                 495
Cys Leu Leu Pro Gln Ala Asn Cys Ser Val His Thr Ala Pro Pro Ala
            500                 505                 510
Glu Ala Ser Met Gly Thr Arg Val His Cys His Gln Gln Gly His Val
            515                 520                 525
Leu Thr Gly Cys Ser Ser His Trp Glu Val Glu Asp Leu Gly Thr His
530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys Cys His Ala Pro Gly Leu
                565                 570                 575
Glu Cys Lys Val Lys Glu His Gly Ile Pro Ala Pro Glu Gln Val
            580                 585                 590
Thr Val Ala Cys Glu Glu Gly Trp Thr Leu Thr Gly Cys Ser Ala Leu
            595                 600                 605
Pro Gly Thr Ser His Val Leu Gly Ala Tyr Ala Val Asp Asn Thr Cys
            610                 615                 620
Val Val Arg Ser Arg Asp Val Ser Thr Thr Gly Ser Thr Ser Glu Glu
625                 630                 635                 640
Ala Val Thr Ala Val Ala Ile Cys Cys Arg Ser Arg His Leu Ala Gln
                645                 650                 655
Ala Ser Gln Glu Leu Gln
            660

<210> SEQ ID NO 23
```

-continued

```
<211> LENGTH: 540
<212> TYPE: PRT
<213> ORGANISM: Homo sapiens

<400> SEQUENCE: 23
```

| | | | | | | | | | | | | | | |
|---|---|---|---|---|---|---|---|---|---|---|---|---|---|---|
|Ser|Ile|Pro|Trp|Asn|Leu|Glu|Arg|Ile|Thr|Pro|Pro|Arg|Tyr|Arg|Ala
1| | | |5| | | | |10| | | | |15|
|Asp|Glu|Tyr|Gln|Pro|Pro|Asp|Gly|Gly|Ser|Leu|Val|Glu|Val|Tyr|Leu
| | |20| | | | |25| | | | |30| | |
|Leu|Asp|Thr|Ser|Ile|Gln|Ser|Asp|His|Arg|Glu|Ile|Glu|Gly|Arg|Val
| | |35| | | | |40| | | | |45| | |
|Met|Val|Thr|Asp|Phe|Glu|Asn|Val|Pro|Glu|Glu|Asp|Gly|Thr|Arg|Phe
50| | | | |55| | | | |60| | | | | |
|His|Arg|Gln|Ala|Ser|Lys|Cys|Asp|Ser|His|Gly|Thr|His|Leu|Ala|Gly
65| | | | |70| | | | |75| | | | |80|
|Val|Val|Ser|Gly|Arg|Asp|Ala|Gly|Val|Ala|Lys|Gly|Ala|Ser|Met|Arg
| | | | |85| | | | |90| | | | |95| |
|Ser|Leu|Arg|Val|Leu|Asn|Cys|Gln|Gly|Lys|Gly|Thr|Val|Ser|Gly|Thr
| | | |100| | | | |105| | | | |110| | |
|Leu|Ile|Gly|Leu|Glu|Phe|Ile|Arg|Lys|Ser|Gln|Leu|Val|Gln|Pro|Val
| | | |115| | | | |120| | | | |125| | |
|Gly|Pro|Leu|Val|Val|Leu|Leu|Pro|Leu|Ala|Gly|Gly|Tyr|Ser|Arg|Val
| | |130| | | | |135| | | | |140| | | |
|Leu|Asn|Ala|Ala|Cys|Gln|Arg|Leu|Ala|Arg|Ala|Gly|Val|Val|Leu|Val
145| | | | |150| | | | |155| | | | |160|
|Thr|Ala|Ala|Gly|Asn|Phe|Arg|Asp|Asp|Ala|Cys|Leu|Tyr|Ser|Pro|Ala
| | | | |165| | | | |170| | | | |175| |
|Ser|Ala|Pro|Glu|Val|Ile|Thr|Val|Gly|Ala|Thr|Asn|Ala|Gln|Asp|Gln
| | | |180| | | | |185| | | | |190| | |
|Pro|Val|Thr|Leu|Gly|Thr|Leu|Gly|Thr|Asn|Phe|Gly|Arg|Cys|Val|Asp
| | |195| | | | |200| | | | |205| | | |
|Leu|Phe|Ala|Pro|Gly|Glu|Asp|Ile|Ile|Gly|Ala|Ser|Ser|Asp|Cys|Ser
| |210| | | | |215| | | | |220| | | | |
|Thr|Cys|Phe|Val|Ser|Gln|Ser|Gly|Thr|Ser|Gln|Ala|Ala|Ala|His|Val
225| | | | |230| | | | |235| | | | |240| |
|Ala|Gly|Ile|Ala|Ala|Met|Met|Leu|Ser|Ala|Glu|Pro|Glu|Leu|Thr|Leu
| | | | |245| | | | |250| | | | |255| |
|Ala|Glu|Leu|Arg|Gln|Arg|Leu|Ile|His|Phe|Ser|Ala|Lys|Asp|Val|Ile
| | | |260| | | | |265| | | | |270| | |
|Asn|Glu|Ala|Trp|Phe|Pro|Glu|Asp|Gln|Arg|Val|Leu|Thr|Pro|Asn|Leu
| | |275| | | | |280| | | | |285| | | |
|Val|Ala|Thr|Leu|Pro|Pro|Ser|Thr|His|Gly|Ala|Gly|Trp|Gln|Leu|Phe
| |290| | | | |295| | | | |300| | | | |
|Cys|Arg|Thr|Val|Trp|Ser|Ala|His|Ser|Gly|Pro|Thr|Arg|Met|Ala|Thr
305| | | | |310| | | | |315| | | | |320|
|Ala|Ile|Ala|Arg|Cys|Ala|Pro|Asp|Glu|Glu|Leu|Leu|Ser|Cys|Ser|Ser
| | | | |325| | | | |330| | | | |335| |
|Phe|Ser|Arg|Ser|Gly|Lys|Arg|Gly|Glu|Arg|Met|Glu|Ala|Gln|Gly|Gly
| | | |340| | | | |345| | | | |350| | |
|Gly|Lys|Leu|Val|Cys|Arg|Ala|His|Asn|Ala|Phe|Gly|Gly|Glu|Gly|Val
| | | |355| | | | |360| | | | |365| | |
|Tyr|Ala|Ile|Ala|Arg|Cys|Cys|Leu|Leu|Pro|Gln|Ala|Asn|Cys|Ser|Val
| |370| | | | |375| | | | |380| | | | |
|His|Thr|Ala|Pro|Pro|Ala|Glu|Ala|Ser|Met|Gly|Thr|Arg|Val|His|Cys

```
            385                 390                 395                 400
His Gln Gln Gly His Val Leu Thr Gly Cys Ser Ser His Trp Glu Val
                405                 410                 415

Glu Asp Leu Gly Thr His Lys Pro Pro Val Leu Arg Pro Arg Gly Gln
                420                 425                 430

Pro Asn Gln Cys Val Gly His Arg Glu Ala Ser Ile His Ala Ser Cys
                435                 440                 445

Cys His Ala Pro Gly Leu Glu Cys Lys Val Lys Glu His Gly Ile Pro
                450                 455                 460

Ala Pro Pro Glu Gln Val Thr Val Ala Cys Glu Gly Trp Thr Leu
465                 470                 475                 480

Thr Gly Cys Ser Ala Leu Pro Gly Thr Ser His Val Leu Gly Ala Tyr
                485                 490                 495

Ala Val Asp Asn Thr Cys Val Val Arg Ser Arg Asp Val Ser Thr Thr
                500                 505                 510

Gly Ser Thr Ser Glu Glu Ala Val Thr Ala Val Ala Ile Cys Cys Arg
                515                 520                 525

Ser Arg His Leu Ala Gln Ala Ser Gln Glu Leu Gln
                530                 535                 540

<210> SEQ ID NO 24
<211> LENGTH: 692
<212> TYPE: PRT
<213> ORGANISM: Homo sapiens

<400> SEQUENCE: 24

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Leu Ser Glu
                35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
                115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
                195                 200                 205

Pro Glu Glu Asp Gly Thr Arg Phe His Arg Gln Ala Ser Lys Cys Asp
210                 215                 220
```

-continued

```
Ser His Gly Thr His Leu Ala Gly Val Val Ser Gly Arg Asp Ala Gly
225                 230                 235                 240
Val Ala Lys Gly Ala Ser Met Arg Ser Leu Arg Val Leu Asn Cys Gln
            245                 250                 255
Gly Lys Gly Thr Val Ser Gly Thr Leu Ile Gly Leu Glu Phe Ile Arg
        260                 265                 270
Lys Ser Gln Leu Val Gln Pro Val Gly Pro Leu Val Leu Leu Pro
    275                 280                 285
Leu Ala Gly Gly Tyr Ser Arg Val Leu Asn Ala Ala Cys Gln Arg Leu
290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
            340                 345                 350
Thr Asn Phe Gly Arg Cys Val Asp Leu Phe Ala Pro Gly Glu Asp Ile
        355                 360                 365
Ile Gly Ala Ser Ser Asp Cys Ser Thr Cys Phe Val Ser Gln Ser Gly
    370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
            420                 425                 430
Gln Arg Val Leu Thr Pro Asn Leu Val Ala Ala Leu Pro Pro Ser Thr
        435                 440                 445
His Gly Ala Gly Trp Gln Leu Phe Cys Arg Thr Val Trp Ser Ala His
    450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
            500                 505                 510
Asn Ala Phe Gly Gly Glu Gly Val Tyr Ala Ile Ala Arg Cys Cys Leu
        515                 520                 525
Leu Pro Gln Ala Asn Cys Ser Val His Thr Ala Pro Pro Ala Glu Ala
    530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
        595                 600                 605
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
```

```
                         645                 650                 655
Arg Ser Arg Asp Val Ser Thr Thr Gly Ser Thr Ser Glu Glu Ala Val
            660                 665                 670
Thr Ala Val Ala Ile Cys Cys Arg Ser Arg His Leu Ala Gln Ala Ser
            675                 680                 685
Gln Glu Leu Gln
    690

<210> SEQ ID NO 25
<211> LENGTH: 662
<212> TYPE: PRT
<213> ORGANISM: Homo sapiens

<400> SEQUENCE: 25

Gln Glu Asp Glu Asp Gly Asp Tyr Glu Glu Leu Val Leu Ala Leu Leu
1               5                  10                  15
Ser Glu Glu Asp Gly Leu Ala Glu Ala Pro Glu His Gly Thr Thr Ala
            20                  25                  30
Thr Phe His Arg Cys Ala Lys Asp Pro Trp Arg Leu Pro Gly Thr Tyr
        35                  40                  45
Val Val Leu Lys Glu Thr His Leu Ser Gln Ser Glu Arg Thr
50                  55                  60
Ala Arg Arg Leu Gln Ala Gln Ala Arg Arg Gly Tyr Leu Thr Lys
65                  70                  75                  80
Ile Leu His Val Phe His Gly Leu Leu Pro Gly Phe Leu Val Lys Met
                85                  90                  95
Ser Gly Asp Leu Leu Glu Leu Ala Leu Lys Leu Pro His Val Asp Tyr
            100                 105                 110
Ile Glu Glu Asp Ser Ser Val Phe Ala Gln Ser Ile Pro Trp Asn Leu
        115                 120                 125
Glu Arg Ile Thr Pro Pro Arg Tyr Arg Ala Asp Glu Tyr Gln Pro Pro
130                 135                 140
Asp Gly Gly Ser Leu Val Glu Val Tyr Leu Leu Asp Thr Ser Ile Gln
145                 150                 155                 160
Ser Asp His Arg Glu Ile Glu Gly Arg Val Met Val Thr Asp Phe Glu
                165                 170                 175
Asn Val Pro Glu Glu Asp Gly Thr Arg Phe His Arg Gln Ala Ser Lys
            180                 185                 190
Cys Asp Ser His Gly Thr His Leu Ala Gly Val Val Ser Gly Arg Asp
        195                 200                 205
Ala Gly Val Ala Lys Gly Ala Ser Met Arg Ser Leu Arg Val Leu Asn
    210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
                245                 250                 255
Leu Pro Leu Ala Gly Gly Tyr Ser Arg Val Leu Asn Ala Ala Cys Gln
            260                 265                 270
Arg Leu Ala Arg Ala Gly Val Val Leu Val Thr Ala Ala Gly Asn Phe
        275                 280                 285
Arg Asp Asp Ala Cys Leu Tyr Ser Pro Ala Ser Ala Pro Glu Val Ile
    290                 295                 300
Thr Val Gly Ala Thr Asn Ala Gln Asp Gln Pro Val Thr Leu Gly Thr
305                 310                 315                 320
```

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala His Val Ala Gly Ile Ala Ala Met
        355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
        435                 440                 445

Pro Asp Glu Glu Leu Leu Ser Cys Ser Ser Phe Ser Arg Ser Gly Lys
    450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525

Leu Thr Gly Cys Ser Ser His Trp Glu Val Glu Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 26
<211> LENGTH: 692
<212> TYPE: PRT
<213> ORGANISM: Homo sapiens

<400> SEQUENCE: 26

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

-continued

```
Asp Glu Asp Gly Asp Tyr Glu Leu Val Leu Ala Leu Arg Ser Glu
         35                  40                  45

Glu Asp Gly Leu Val Glu Ala Pro Glu His Gly Thr Thr Ala Thr Phe
 50                  55                  60

His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
                115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
                195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
                275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
                355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
                435                 440                 445
```

-continued

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
        690

<210> SEQ ID NO 27
<211> LENGTH: 662
<212> TYPE: PRT
<213> ORGANISM: Homo sapiens

<400> SEQUENCE: 27

Gln Glu Asp Glu Asp Gly Asp Tyr Glu Glu Leu Val Leu Ala Leu Arg
1               5                   10                  15

Ser Glu Glu Asp Gly Leu Val Glu Ala Pro Glu His Gly Thr Thr Ala
                20                  25                  30

Thr Phe His Arg Cys Ala Lys Asp Pro Trp Arg Leu Pro Gly Thr Tyr
            35                  40                  45

Val Val Val Leu Lys Glu Glu Thr His Leu Ser Gln Ser Glu Arg Thr
        50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

-continued

```
Glu Arg Ile Thr Pro Pro Arg Tyr Arg Ala Asp Glu Tyr Gln Pro Pro
        130                 135                 140
Asp Gly Gly Ser Leu Val Glu Val Tyr Leu Leu Asp Thr Ser Ile Gln
145                 150                 155                 160
Ser Asp His Arg Glu Ile Glu Gly Arg Val Met Val Thr Asp Phe Glu
                165                 170                 175
Asn Val Pro Glu Glu Asp Gly Thr Arg Phe His Arg Gln Ala Ser Lys
            180                 185                 190
Cys Asp Ser His Gly Thr His Leu Ala Gly Val Val Ser Gly Arg Asp
        195                 200                 205
Ala Gly Val Ala Lys Gly Ala Ser Met Arg Ser Leu Arg Val Leu Asn
    210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
                245                 250                 255
Leu Pro Leu Ala Gly Gly Tyr Ser Arg Val Leu Asn Ala Ala Cys Gln
            260                 265                 270
Arg Leu Ala Arg Ala Gly Val Val Leu Val Thr Ala Ala Gly Asn Phe
        275                 280                 285
Arg Asp Asp Ala Cys Leu Tyr Ser Pro Ala Ser Ala Pro Glu Val Ile
    290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                325                 330                 335
Asp Ile Ile Gly Ala Ser Ser Asp Cys Ser Thr Cys Phe Val Ser Gln
            340                 345                 350
Ser Gly Thr Ser Gln Ala Ala Ala His Val Ala Gly Ile Ala Ala Met
        355                 360                 365
Met Leu Ser Ala Glu Pro Glu Leu Thr Leu Ala Glu Leu Arg Gln Arg
    370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Ala Leu Pro Pro
                405                 410                 415
Ser Thr His Gly Ala Gly Trp Gln Leu Phe Cys Arg Thr Val Trp Ser
            420                 425                 430
Ala His Ser Gly Pro Thr Arg Met Ala Thr Ala Ile Ala Arg Cys Ala
        435                 440                 445
Pro Asp Glu Glu Leu Leu Ser Cys Ser Ser Phe Ser Arg Ser Gly Lys
    450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                485                 490                 495
Cys Leu Leu Pro Gln Ala Asn Cys Ser Val His Thr Ala Pro Pro Ala
            500                 505                 510
Glu Ala Ser Met Gly Thr Arg Val His Cys His Gln Gln Gly His Val
        515                 520                 525
Leu Thr Gly Cys Ser Ser His Trp Glu Val Glu Asp Leu Gly Thr His
    530                 535                 540
```

```
Lys Pro Pro Val Leu Arg Pro Arg Gly Gln Pro Asn Gln Cys Val Gly
545                 550                 555                 560
His Arg Glu Ala Ser Ile His Ala Ser Cys Cys His Ala Pro Gly Leu
                565                 570                 575
Glu Cys Lys Val Lys Glu His Gly Ile Pro Ala Pro Gln Glu Gln Val
            580                 585                 590
Thr Val Ala Cys Glu Glu Gly Trp Thr Leu Thr Gly Cys Ser Ala Leu
        595                 600                 605
Pro Gly Thr Ser His Val Leu Gly Ala Tyr Ala Val Asp Asn Thr Cys
    610                 615                 620
Val Val Arg Ser Arg Asp Val Ser Thr Thr Gly Ser Thr Ser Glu Gly
625                 630                 635                 640
Ala Val Thr Ala Val Ala Ile Cys Cys Arg Ser Arg His Leu Ala Gln
                645                 650                 655
Ala Ser Gln Glu Leu Gln
            660
```

<210> SEQ ID NO 28
<211> LENGTH: 2080
<212> TYPE: DNA
<213> ORGANISM: Homo sapiens

<400> SEQUENCE: 28

| | | | | | |
|---|---|---|---|---|---|
| atgggcaccg | tcagctccag | gcggtcctgg | tggccgctgc | cactgctgct | gctgctgctg | 60 |
| ctgctcctgg | gtcccgcggg | cgcccgtgcg | caggaggacg | aggacggcga | ctacgaggag | 120 |
| ctggtgctag | ccttgcgttc | cgaggaggac | ggcctggccg | aagcacccga | gcacggaacc | 180 |
| acagccacct | ccaccgcctg | cgccaaggat | ccgtggaggt | tgcctggcac | ctacgtggtg | 240 |
| gtgctgaagg | aggagaccca | cctctcgcag | tcagagcgca | ctgcccgccg | cctgcaggcc | 300 |
| caggctgccc | gccggggata | cctcaccaag | atcctgcatg | tcttccatgg | ccttcttcct | 360 |
| ggcttcctgt | gaagatgag | tggcgacctg | ctggagctgg | ccttgaagtt | gccccatgtc | 420 |
| gactacatcg | aggaggactc | ctctgtcttt | gcccagagca | tcccgtggaa | cctggagcgg | 480 |
| attccccctc | cacggtaccg | ggcggatgaa | taccagcccc | ccgacggagg | cagcctggtg | 540 |
| gaggtgtatc | tcctagacac | cagcatacag | agtgaccacc | gggaaatcga | gggcagggtc | 600 |
| atggtcaccg | acttcgagaa | tgtgcccgag | gaggacggga | cccgcttcca | cagacaggcc | 660 |
| agcaagtgtg | acagtcatgg | cacccacctg | gcaggggtgg | tcagcggccg | ggatgccggc | 720 |
| gtggccaagg | gtgccagcat | gcgcagcctg | cgcgtgctca | actgccaagg | aagggcacg | 780 |
| gttagcggca | ccctcatagg | cctggagttt | attcggaaaa | gccagctggt | ccagcctgtg | 840 |
| gggccactgg | tggtgctgct | gcccctggcg | ggtgggtaca | gccgcgtcct | caacgccgcc | 900 |
| tgccagcgcc | tggcgagggc | tggggtcgtg | ctggtcaccg | ctgccggcaa | cttccgggac | 960 |
| gatgcctgcc | tctactcccc | agcctcagct | cccgaggtca | tcacagttgg | gccaccaat | 1020 |
| gcccaagacc | agccggtgac | cctggggact | ttggggacca | actttggccg | ctgtgtggac | 1080 |
| ctctttgccc | caggggagga | catcattggt | gcctccagcg | actgcagcac | ctgctttgtg | 1140 |
| tcacagagtg | ggacatcaca | ggctgctgcc | acgtggctg | gcattgcagc | catgatgctg | 1200 |
| tctgccgagc | cggagctcac | cctggccgag | ttgaggcaga | actgatcca | cttctctgcc | 1260 |
| aaagatgtca | tcaatgaggc | ctggttccct | gaggaccagc | gggtactgac | ccccaacctg | 1320 |
| gtggccgccc | tgcccccag | cacccatggg | gcaggttggc | agctgttttg | caggactgta | 1380 |
| tggtcagcac | actcggggcc | tacacggatg | ccacagccca | tcgcccgctg | cgccccagat | 1440 |

-continued

```
gaggagctgc tgagctgctc cagtttctcc aggagtggga agcggcgggg cgagcgcatg    1500
gaggcccaag ggggcaagct ggtctgccgg gcccacaacg cttttggggg tgagggtgtc    1560
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacaggagg ccagcatcca cgcttcctgc     1800
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctgggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccagtgac                          2080
```

<210> SEQ ID NO 29
<211> LENGTH: 2080
<212> TYPE: DNA
<213> ORGANISM: Homo sapiens

<400> SEQUENCE: 29

```
atgggcaccg tcagctccag gcggtcctgg tggccgctgc cactgctgct gctgctgctg     60
ctgctcctgg gtcccgcggg cgcccgtgcg caggaggacg aggacggcga ctacgaggag    120
ctggtgctag ccttgcgttc cgaggaggac ggcctggccg aagcacccga gcacggaacc    180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg cagggggtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaagacc agccgtgac cctggggact ttggggacca ctttggccg ctgtgtggac    1080 ctctttgccc caggggagga catcattggt gcctccagcg actgcagcac ctgctttgtg    1140
tcacagagtg gacatcaca ggctgctgcc cacgtggctg gcattgcagc catgatgctg   1200 tctgccagc cggagctcac cctggccgag ttgaggcaga actgatcca cttctctgcc     1260 aaagatgtca tcaatgaggc ctggttccct gaggaccagc gggtactgac ccccaacctg    1320
gtggccgccc tgcccccag cacccatggg gcaggttggc agctgttttg caggactgta    1380
tggtcagcac actcggggcc tacacggatg gccacagccg tcgcccgctg cgccccagat    1440
```

| | |
|---|---:|
| gaggagctgc tgagctgctc cagtttctcc aggagtggga agcggcgggg cgagcgcatg | 1500 |
| gaggcccaag ggggcaagct ggtctgccgg gcccacaacg cttttggggg tgagggtgtc | 1560 |
| tacgccattg ccaggtgctg cctgctaccc caggccaact gcagcgtcca cacagctcca | 1620 |
| ccagctgagg ccagcatggg gacccgtgtc cactgccacc aacagggcca cgtcctcaca | 1680 |
| ggctgcagct cccactggga ggtggaggac cttggcaccc acaagccgcc tgtgctgagg | 1740 |
| ccacgaggtc agcccaacca gtgcgtgggc cacaggagg ccagcatcca cgcttcctgc | 1800 |
| tgccatgccc caggtctgga atgcaaagtc aaggagcatg gaatcccggc ccctcaggag | 1860 |
| caggtgaccg tggcctgcga ggagggctgg accctgactg gctgcagtgc cctccctggg | 1920 |
| acctcccacg tcctgggggc ctacgccgta gacaaacacgt gtgtagtcag gagccgggac | 1980 |
| gtcagcacta caggcagcac cagcgaagag gccgtgacag ccgttgccat ctgctgccgg | 2040 |
| agccggcacc tggcgcaggc ctcccaggag ctccagtgac | 2080 |

<210> SEQ ID NO 30
<211> LENGTH: 2080
<212> TYPE: DNA
<213> ORGANISM: Homo sapiens

<400> SEQUENCE: 30

| | |
|---|---:|
| atgggcaccg tcagctccag gcggtcctgg tggccgctgc cactgctgct gctgctgctg | 60 |
| ctgctcctgg gtcccgcggg cgccgtgcg caggaggacg aggacggcga ctacgaggag | 120 |
| ctggtgctag ccttgcgttc gaggaggac ggcctggccg aagcacccga gcacggaacc | 180 |
| acagccacct tccaccgctg cgccaaggat ccgtggaggt tgcctggcac ctacgtggtg | 240 |
| gtgctgaagg aggagaccca cctctcgcag tcagagcgca ctgcccgccg cctgcaggcc | 300 |
| caggctgccc gccggggata cctcaccaag atcctgcatg tcttccatgg ccttcttcct | 360 |
| ggcttcctgg tgaagatgag tggcgacctg ctggagctgg ccttgaagtt gccccatgtc | 420 |
| gactacatcg aggaggactc ctctgtcttt gcccagagca tcccgtggaa cctggagcgg | 480 |
| attacccctc cacggtaccg ggcggatgaa taccagcccc ccgacggagg cagcctggtg | 540 |
| gaggtgtatc tcctagacac cagcatacag agtgaccacc gggaaatcga gggcagggtc | 600 |
| atggtcaccg acttcgagaa tgtgcccgag gaggacggga cccgcttcca cagacaggcc | 660 |
| agcaagtgtg acagtcatgg cacccacctg gcaggggtgg tcagcggccg ggatgccggc | 720 |
| gtggccaagg gtgccagcat gcgcagcctg cgcgtgctca actgccaagg gaagggcacg | 780 |
| gttagcggca ccctcatagg cctggagttt attcggaaaa gccagctggt ccagcctgtg | 840 |
| gggccactgg tggtgctgct gcccctggcg ggtgggtaca gccgcgtcct caacgccgcc | 900 |
| tgccagcgcc tggcgagggc tggggtcgtg ctggtcaccg ctgccggcaa cttccgggac | 960 |
| gatgcctgcc tctactcccc agcctcagct cccgaggtca tcacagttgg ggccaccaat | 1020 |
| gcccaagacc agccggtgac cctgggggact ttggggacca ctttggccg ctgtgtggac | 1080 |
| ctctttgccc caggggagga catcattggt gcctccagcg actgcagcac ctgctttgtg | 1140 |
| tcacagagtg ggacatcaca ggctgctgcc cacgtggctg gcattgcagc catgatgctg | 1200 |
| tctgccgagc ggagctcac cctggccgag ttgaggcaga actgatcca cttctctgcc | 1260 |
| aaagatgtca tcaatgaggc ctggttccct gaggaccagc gggtactgac ccccaacctg | 1320 |
| gtggccgccc tgccccccag cacccatggg gcaggttggc agctgttttg caggactgta | 1380 |
| tggtcagcac actcggggcc tacacggatg gccacagcca tcgcccgctg cgccccagat | 1440 |
| gaggagctgc tgagctgctc cagtttctcc aggagtggga agcggcgggg cgagcgcatg | 1500 |

-continued

```
gaggcccaag ggggcaagct ggtctgccgg gcccacaacg cttttggggg tgagggtgtc    1560
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacagggagg ccagcatcca cgcttcctgc    1800
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctggggc ctacgccgta gacaacacgt gtgtagtcag gagccgggac    1980
gtcagcacta caggcagcac cagcgaaggg gccgtgacag ccgttgccat ctgctgccgg    2040
agccggcacc tggcgcaggc ctcccaggag ctccagtgac                          2080
```

<210> SEQ ID NO 31
<211> LENGTH: 2080
<212> TYPE: DNA
<213> ORGANISM: Homo sapiens

<400> SEQUENCE: 31

```
atgggcaccg tcagctccag gcggtcctgg tggccgctgc cactgctgct gctgctgctg    60
ctgctcctgg gtcccgcggg cgcccgtgcg caggaggacg aggacggcga ctacgaggag    120
ctggtgctag ccttgcgttc cgaggaggac ggcctggccg aagcacccga gcacggaacc    180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attccccctc cacggtaccg gcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg aagggcacg    780 gttagcggca ccctcatagg cctggagttt attcggaaaa gccagctggt ccagcctgtg    840
gggccactgg tggtgctgct gccccctggcg ggtgggtaca ccgcgtcct caacgccgcc    900 tgccagcgcc tggcgagggc tggggtcgtg ctggtcaccg ctgccggcaa cttccgggac    960
gatgcctgcc tctactcccc agcctcagct cccgaggtca tcacagttgg ggccaccaat    1020
gcccaagacc agccggtgac cctggggact ttggggacca actttggccg ctgtgtggac    1080
ctctttgccc caggggagga catcattggt gcctccagcg actgcagcac ctgctttgtg    1140
tcacagagtg ggacatcaca ggctgctgcc cacgtggctg gcattgcagc catgatgctg    1200
tctgccgagc cggagctcac cctggccgag ttgaggcaga gactgatcca cttctctgcc    1260
aaagatgtca tcaatgaggc ctggttccct gaggaccagg ggtactgac ccccaacctg    1320 gtggccgccc tgcccccag cacccatggg gcaggttggc agctgttttg caggactgta    1380
tggtcagcac actcggggcc tacacggatg ccacagccg tcgcccgctg cgccccagat    1440
gaggagctgc tgagctgctc cagtttctcc aggagtggga agcggcgggg cgagcgcatg    1500
```

| | |
|---|---|
| gaggcccaag ggggcaagct ggtctgccgg gcccacaacg cttttggggg tgagggtgtc | 1560 |
| tacgccattg ccaggtgctg cctgctaccc caggccaact gcagcgtcca cacagctcca | 1620 |
| ccagctgagg ccagcatggg gacccgtgtc cactgccacc aacagggcca cgtcctcaca | 1680 |
| ggctgcagct cccactggga ggtggaggac cttggcaccc acaagccgcc tgtgctgagg | 1740 |
| ccacgaggtc agcccaacca gtgcgtgggc cacagggagg ccagcatcca cgcttcctgc | 1800 |
| tgccatgccc caggtctgga atgcaaagtc aaggagcatg gaatcccggc ccctcaggag | 1860 |
| caggtgaccg tggcctgcga ggagggctgg accctgactg gctgcagtgc cctccctggg | 1920 |
| acctcccacg tcctgggggc ctacgccgta gacaacacgt gtgtagtcag gagccgggac | 1980 |
| gtcagcacta caggcagcac cagcgaaggg gccgtgacag ccgttgccat ctgctgccgg | 2040 |
| agccggcacc tggcgcaggc ctcccaggag ctccagtgac | 2080 |

<210> SEQ ID NO 32
<211> LENGTH: 2080
<212> TYPE: DNA
<213> ORGANISM: Homo sapiens

<400> SEQUENCE: 32

| | |
|---|---|
| atgggcaccg tcagctccag gcggtcctgg tggccgctgc cactgctgct gctgctgctg | 60 |
| ctgctcctgg gtcccgcggg cgcccgtgcg caggaggacg aggacggcga ctacgaggag | 120 |
| ctggtgctag ccttgcgttc cgaggaggac ggcctggtcg aagcacccga gcacggaacc | 180 |
| acagccacct ccaccgctg cgccaaggat ccgtggaggt tgcctggcac ctacgtggtg | 240 |
| gtgctgaagg aggagaccca cctctcgcag tcagagcgca ctgcccgccg cctgcaggcc | 300 |
| caggctgccc gccggggata cctcaccaag atcctgcatg tcttccatgg ccttcttcct | 360 |
| ggcttcctgg tgaagatgag tggcgacctg ctggagctgg ccttgaagtt gccccatgtc | 420 |
| gactacatcg aggaggactc ctctgtcttt gcccagagca tcccgtggaa cctggagcgg | 480 |
| attacccctc cacggtaccg ggcggatgaa taccagcccc ccgacggagg cagcctggtg | 540 |
| gaggtgtatc tcctagacac cagcatacag agtgaccacc gggaaatcga gggcagggtc | 600 |
| atggtcaccg acttcgagaa tgtgcccgag gaggacgggg cccgcttcca cagacaggcc | 660 |
| agcaagtgtg acagtcatgg caccccacctg gcaggggtgg tcagcggccg ggatgccggc | 720 |
| gtggccaagg gtgccagcat gcgcagcctg cgcgtgctca actgccaagg gaagggcacg | 780 |
| gttagcggca ccctcatagg cctggagttt attcggaaaa gccagctggt ccagcctgtg | 840 |
| gggccactgg tggtgctgct gccctggcg ggtgggtaca gccgcgtcct caacgccgcc | 900 |
| tgccagcgcc tggcgagggc tggggtcgtg ctggtcaccg ctgccggcaa cttccgggac | 960 |
| gatgcctgcc tctactcccc agcctcagct cccgaggtca tcacagttgg gccaccaat | 1020 |
| gcccaagacc agccggtgac cctggggact ttggggacca actttggccg ctgtgtggac | 1080 |
| ctctttgccc caggggagga catcattggt gcctccagcg actgcagcac ctgctttgtg | 1140 |
| tcacagagtg ggacatcaca ggctgctgcc acgtgctg gcattgcagc catgatgctg | 1200 |
| tctgccgagc cggagctcac cctggccgag ttgaggcaga actgatcca cttctctgcc | 1260 |
| aaagatgtca tcaatgaggc ctggttccct gaggaccagg gggtactgac ccccaacctg | 1320 |
| gtggccgccc tgcccccag cacccatggg gcaggttggc agctgttttg caggactgta | 1380 |
| tggtcagcac actcggggcc tacacggatg ccacagccg tcgcccgctg cgccccagat | 1440 |
| gaggagctgc tgagctgctc cagtttctcc aggagtggga agcggcgggg cgagcgcatg | 1500 |
| gaggcccaag ggggcaagct ggtctgccgg gcccacaacg cttttggggg tgagggtgtc | 1560 |

-continued

```
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacaggagg  ccagcatcca cgcttcctgc    1800
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctgggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccagtgac                          2080
```

```
<210> SEQ ID NO 33
<211> LENGTH: 2080
<212> TYPE: DNA
<213> ORGANISM: Homo sapiens

<400> SEQUENCE: 33
```

```
atgggcaccg tcagctccag gcggtcctgg tggccgctgc cactgctgct gctgctgctg     60
ctgctcctgg gtcccgcggg cgcccgtgcg caggaggacg aggacggcga ctacgaggag    120
ctggtgctag ccttgcgttc cgaggaggac ggcctggccg aagcacccga gcacggaacc    180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg caccccacctg gcaggggtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctgggc ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaagacc agccggtgac cctggggact ttggggacca ctttggccg  ctgtgtggac   1080 ctctttgccc caggggagga catcattggt gcctccagcg actgcagcac ctgctttgtg   1140
tcacagagtg ggacatcaca ggctgctgcc cacgtggctg gcattgcagc catgatgctg   1200
tctgccgagc cggagctcac cctggccgag ttgaggcaga actgatcca  cttctctgcc   1260 aaagatgtca tcaatgaggc ctggttccct gaggaccagc gggtactgac ccccaacctg   1320
gtggccaccc tgcccccag cacccatggg gcaggttggc agctgttttg caggactgta   1380
tggtcagcac actcggggcc tacacggatg gccacagcca tcgcccgctg cgccccagat   1440
gaggagctgc tgagctgctc cagtttctcc aggagtggga gcggcgggg  cgagcgcatg   1500 gaggcccaag ggggcaagct ggtctgccgg gcccacaacg cttttggggg tgagggtgtc   1560
```

```
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacaggagg ccagcatcca cgcttcctgc     1800
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctgggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccagtgac                          2080

<210> SEQ ID NO 34
<211> LENGTH: 2080
<212> TYPE: DNA
<213> ORGANISM: Homo sapiens

<400> SEQUENCE: 34
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgttc gaggaggac ggcctggccg aagcacccga gcacggaacc      180
acagccacct tccaccgctg cgccaaggat ccgtggaggt tgcctggcac ctacgtggtg     240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480 attcccctc cacggtaccg ggcggatgaa taccagcccc ccgacggagg cagcctggtg     540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg cagggtggt cagcggccg ggatgccggc      720 gtggccaagg gtgccagcat cgcagcctg cgcgtgctca actgccaagg gaagggcacg    780
gttagcggca ccctcatagg cctggagttt attcggaaaa gccagctggt ccagcctgtg    840
gggccactgg tggtgctgct gccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaagacc agccggtgac cctggggact tggggacca actttggccg ctgtgtggac    1080 ctcttttgccc caggggagga catcattggt gcctccagcg actgcagcac tgctttgtg     1140 tcacagagtg ggacatcaca ggctgctgcc cacgtggctg gcattgcagc catgatgctg   1200
tctgccgagc cggagctcac cctggccgag ttgaggcaga gactgatcca cttctctgcc    1260
aaagatgtca tcagtgaggc ctggttccct gaggaccagc gggtactgac ccccaacctg    1320
gtggccgccc tgccccccag cacccatggg gcaggttggc agctgttttg caggactgta   1380
tggtcagcac actcggggcc tacacggatg ccacagccg tcgcccgctg cgccccagat    1440
gaggagctgc tgagctgctc cagtttctcc aggagtggga agcggcgggg cgagcgcatg   1500
gaggcccaag gggcaagct ggtctgccgg gcccacaacg cttttggggg tgagggtgtc     1560
tacgccattg ccaggtgctg cctgctaccc caggccaact gcagcgtcca cacagctcca    1620
```

```
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacagggagg ccagcatcca cgcttcctgc    1800
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccagtgac                          2080
```

<210> SEQ ID NO 35
<211> LENGTH: 2080
<212> TYPE: DNA
<213> ORGANISM: Homo sapiens

<400> SEQUENCE: 35

```
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgttc cgaggaggac ggcctggccg aagcacccga gcacggaacc     180
acagccacct tccaccgctg cgccaaggat ccgtggaggt tgcctggcac ctacgtggtg     240
gtgctgaagg aggagaccca cctctcgcag tcagagcgca ctgcccgccg cctgcaggcc     300
caggctgccc ccgggggata cctcaccaag atcctgcatg tcttccatgg ccttcttcct     360
ggcttcctgg tgaagatgag tggcgacctg ctggagctgg ccttgaagtt gccccatgtc     420
gactacatcg aggaggactc ctctgtcttt gcccagagca tcccgtggaa cctggagcgg     480
attccccctc cacggtaccg gcggatgaa taccagcccc ccgacggagg cagcctggtg     540
gaggtgtatc tcctagacac cagcatacag agtgaccacc gggaaatcga gggcagggtc     600
atggtcaccg acttcgagaa tgtgcccgag gaggacggga cccgcttcca cagacaggcc     660
agcaagtgtg acagtcatgg cacccacctg caggggtgg tcagcggccg ggatgccggc     720
gtggccaagg gtgccagcat gcgcagcctg cgcgtgctca actgccaagg gaagggcacg     780
gttagcggca ccctcatagg cctggagttt attcggaaaa gccagctggt ccagcctgtg     840
gggccactgg tggtgctgct gccccctggcg ggtgggtaca gccgcgtcct caacgccgcc     900
tgccagcgcc tggcgagggc tggggtcgtg ctggtcaccg ctgccggcaa cttccgggac     960
gatgcctgcc tctactcccc agcctcagct cccgaggtca tcacagttgg ggccaccaat    1020
gcccaagacc agccggtgac cctggggact ttggggacca actttggccg ctgtgtggac    1080
ctctttgccc caggggagga catcattggt gcctccagcg actgcagcac ctgctttgtg    1140
tcacagagtg ggacatcaca ggctgctgcc cacgtggctg gcattgcagc catgatgctg    1200
tctgccgagc ggagctcac cctggccgag ttgaggcaga actgatcca cttctctgcc    1260 aaagatgtca tcaatgaggc ctggttccct gaggaccagc gggtactgac ccccaacctg    1320
gtggccaccc tgcccccccag cacccatggg gcaggttggc agctgttttg caggactgta    1380
tggtcagcac actcggggcc tacacggatg ccacagccca tcgcccgctg cgccccagat    1440
gaggagctgc tgagctgctc cagttttctcc aggagtggga agcggcgggg cgagcgcatg    1500
gaggcccaag ggggcaagct ggtctgccgg gcccacaacg cttttggggg tgagggtgtc    1560
tacgccattg ccaggtgctg cctgctaccc caggccaact gcagcgtcca cacagctcca    1620
```

| | |
|---|---|
| ccagctgagg ccagcatggg gacccgtgtc cactgccacc aacagggcca cgtcctcaca | 1680 |
| ggctgcagct cccactggga ggtggaggac cttggcaccc acaagccgcc tgtgctgagg | 1740 |
| ccacgaggtc agcccaacca gtgcgtgggc cacagggagg ccagcatcca cgcttcctgc | 1800 |
| tgccatgccc caggtctgga atgcaaagtc aaggagcatg gaatcccggc ccctccggag | 1860 |
| caggtgaccg tggcctgcga ggagggctgg accctgactg gctgcagtgc cctccctggg | 1920 |
| acctcccacg tcctggggc ctacgccgta gacaacacgt gtgtagtcag gagccgggac | 1980 |
| gtcagcacta caggcagcac cagcgaagag gccgtgacag ccgttgccat ctgctgccgg | 2040 |
| agccggcacc tggcgcaggc ctcccaggag ctccagtgac | 2080 |

<210> SEQ ID NO 36
<211> LENGTH: 2080
<212> TYPE: DNA
<213> ORGANISM: Homo sapiens
<400> SEQUENCE: 36

| | |
|---|---|
| atgggcaccg tcagctccag gcggtcctgg tggccgctgc cactgctgct gctgctgctg | 60 |
| ctgctcctgg gtcccgcggg cgcccgtgcg caggaggacg aggacggcga ctacgaggag | 120 |
| ctggtgctag ccttgctttc cgaggaggac ggcctggccg aagcacccga gcacggaacc | 180 |
| acagccacct tccaccgctg cgccaaggat ccgtggaggt tgcctggcac ctacgtggtg | 240 |
| gtgctgaagg aggagaccca cctctcgcag tcagagcgca ctgcccgccg cctgcaggcc | 300 |
| caggctgccc gccggggata cctcaccaag atcctgcatg tcttccatgg ccttcttcct | 360 |
| ggcttcctgt gaagatgag tggcgacctg ctggagctgg ccttgaagtt gccccatgtc | 420 |
| gactacatcg aggaggactc ctctgtcttt gcccagagca tcccgtggaa cctggagcgg | 480 |
| attccccctc cacggtaccg ggcggatgaa taccagcccc ccgacggagg cagcctggtg | 540 |
| gaggtgtatc tcctagacac cagcatacag agtgaccacc gggaaatcga gggcagggtc | 600 |
| atggtcaccg acttcgagaa tgtgcccgag gaggacggga cccgcttcca cagacaggcc | 660 |
| agcaagtgtg acagtcatgg caccccacctg gcagggggtgg tcagcggccg ggatgccggc | 720 |
| gtggccaagg gtgccagcat gcgcagcctg cgcgtgctca actgccaagg gaagggcacg | 780 |
| gttagcggca ccctcatagg cctggagttt attcggaaaa gccagctggt ccagcctgtg | 840 |
| gggccactgg tggtgctgct gccctggccg ggtgggtaca ccgcgtcct caacgccgcc | 900 |
| tgccagcgcc tggcgagggc tggggtcgtg ctggtcaccg ctgccggcaa cttccgggac | 960 |
| gatgcctgcc tctactcccc agcctcagct cccgaggtca tcacagttgg gccaccaat | 1020 |
| gcccaagacc agccggtgac cctggggact ttggggacca actttggccg ctgtgtggac | 1080 |
| ctctttgccc cagggagga catcattggt gcctccagcg actgcagcac ctgctttgtg | 1140 |
| tcacagagtg ggacatcaca ggctgctgcc cacgtggctg gcattgcagc catgatgctg | 1200 |
| tctgccgagc cggagctcac cctggccgag ttgaggcaga gactgatcca cttctctgcc | 1260 |
| aaagatgtca tcaatgaggc ctggttccct gaggaccagc gggtactgac ccccaacctg | 1320 |
| gtggccgccc tgccccccag cacccatggg gcaggttggc agctgttttg caggactgta | 1380 |
| tggtcagcac actcggggcc tacacggatg ccacagccg tcgcccgctg cgccccagat | 1440 |
| gaggagctgc tgagctgctc cagtttctcc aggagtggga gcggcgggg cgagcgcatg | 1500 |
| gaggcccaag gggcaagct ggtctgccgg gcccacaacg cttttggggg tgagggtgtc | 1560 |
| tacgccattg ccaggtgctg cctgctaccc caggccaact gcagcgtcca cacagctcca | 1620 |
| ccagctgagg ccagcatggg gacccgtgtc cactgccacc aacagggcca cgtcctcaca | 1680 |

| | |
|---|---|
| ggctgcagct cccactggga ggtggaggac cttggcaccc acaagccgcc tgtgctgagg | 1740 |
| ccacgaggtc agcccaacca gtgcgtgggc cacaggagg ccagcatcca cgcttcctgc | 1800 |
| tgccatgccc caggtctgga atgcaaagtc aaggagcatg gaatcccggc ccctcaggag | 1860 |
| caggtgaccg tggcctgcga ggagggctgg accctgactg gctgcagtgc cctccctggg | 1920 |
| acctcccacg tcctgggggc ctacgccgta gacaacacgt gtgtagtcag gagccgggac | 1980 |
| gtcagcacta caggcagcac cagcgaagag gccgtgacag ccgttgccat ctgctgccgg | 2040 |
| agccggcacc tggcgcaggc ctcccaggag ctccagtgac | 2080 |

<210> SEQ ID NO 37
<211> LENGTH: 2080
<212> TYPE: DNA
<213> ORGANISM: Homo sapiens

<400> SEQUENCE: 37

| | |
|---|---|
| atgggcaccg tcagctccag gcggtcctgg tggccgctgc cactgctgct gctgctgctg | 60 |
| ctgctcctgg gtcccgcggg cgcccgtgcg caggaggacg aggacggcga ctacgaggag | 120 |
| ctggtgctag ccttgcgttc cgaggaggac ggcctggtcg aagcacccga gcacggaacc | 180 |
| acagccacct tccaccgctg cgccaaggat ccgtggaggt tgcctggcac ctacgtggtg | 240 |
| gtgctgaagg aggagaccca cctctcgcag tcagagcgca ctgcccgccg cctgcaggcc | 300 |
| caggctgccc gccggggata cctcaccaag atcctgcatg tcttccatgg ccttcttcct | 360 |
| ggcttcctgg tgaagatgag tggcgacctg ctggagctgg ccttgaagtt gccccatgtc | 420 |
| gactacatcg aggaggactc ctctgtcttt gcccagagca tcccgtggaa cctggagcgg | 480 |
| attcccctc cacggtaccg ggcggatgaa taccagcccc ccgacggagg cagcctggtg | 540 |
| gaggtgtatc tcctagacac cagcatacag agtgaccacc gggaaatcga gggcagggtc | 600 |
| atggtcaccg acttcgagaa tgtgcccgag gaggacggga cccgcttcca cagacaggcc | 660 |
| agcaagtgtg acagtcatgg cacccacctg gcaggggtgg tcagcggccg ggatgccggc | 720 |
| gtggccaagg gtgccagcat gcgcagcctg cgcgtgctca actgccaagg gaagggcacg | 780 |
| gttagcggca ccctcatagg cctggagttt attcggaaaa gccagctggt ccagcctgtg | 840 |
| gggccactgg tggtgctgct gccccctggcg ggtgggtaca gccgcgtcct caacgccgcc | 900 |
| tgccagcgcc tggcgagggc tggggtcgtg ctggtcaccg ctgccggcaa cttccgggac | 960 |
| gatgcctgcc tctactcccc agcctcagct cccgaggtca tcacagttgg ggccaccaat | 1020 |
| gcccaagacc agccggtgac cctggggact ttggggacca actttggccg ctgtgtggac | 1080 |
| ctctttgccc caggggagga catcattggt gcctccagcg actgcagcac ctgctttgtg | 1140 |
| tcacagagtg ggacatcaca ggctgctgcc cacgtgctg gcattgcagc catgatgctg | 1200 |
| tctgccgagc cggagctcac cctggccgag ttgaggcaga actgatcca cttctctgcc | 1260 |
| aaagatgtca tcaatgaggc ctggttccct gaggaccagc gggtactgac ccccaacctg | 1320 |
| gtggccgccc tgcccccag cacccatggg gcaggttggc agctgttttg caggactgta | 1380 |
| tggtcagcac actcggggcc tacacggatg ccacagcca tcgcccgctg cgccccagat | 1440 |
| gaggagctgc tgagctgctc cagtttctcc aggagtggga gcggcggggg cgagcgcatg | 1500 |
| gaggcccaag ggggcaagct ggtctgccgg gcccacaacg cttttggggg tgagggtgtc | 1560 |
| tacgccattg ccaggtgctg cctgctaccc caggccaact gcagcgtcca cagctcca | 1620 |
| ccagctgagg ccagcatggg gaccccgtgtc cactgccacc aacagggcca cgtcctcaca | 1680 |

```
ggctgcagct cccactggga ggtggaggac cttggcaccc acaagccgcc tgtgctgagg    1740
ccacgaggtc agcccaacca gtgcgtgggc cacagggagg ccagcatcca cgcttcctgc    1800
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctgggggc ctacgccgta gacaacacgt gtgtagtcag gagccgggac    1980
gtcagcacta caggcagcac cagcgaaggg gccgtgacag ccgttgccat ctgctgccgg    2040
agccggcacc tggcgcaggc ctcccaggag ctccagtgac                          2080

<210> SEQ ID NO 38
<211> LENGTH: 98
<212> TYPE: PRT
<213> ORGANISM: Homo sapiens

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 39
<211> LENGTH: 296
<212> TYPE: DNA
<213> ORGANISM: Homo sapiens
<220> FEATURE:
<221> NAME/KEY: CDS
<222> LOCATION: (1)..(294)

<400> SEQUENCE: 39 gag gtg cag ctg gtg gag tct ggg gga ggc ttg gta cag cct ggg ggg     48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat     96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc    144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg    192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt    288
Leu Gln Met Asn Ser Leu Arg Ala Glu Asp Thr Ala Val Tyr Tyr Cys
                85                  90                  95 gcg aaa ga                                                          296
Ala Lys
```

<210> SEQ ID NO 40
<211> LENGTH: 25
<212> TYPE: PRT
<213> ORGANISM: Homo sapiens

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 41
<211> LENGTH: 990
<212> TYPE: DNA
<213> ORGANISM: Homo sapiens

<400> SEQUENCE: 41

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggaggga gcagtacaac     540
agcacgtacc gggtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                      990
```

<210> SEQ ID NO 42
<211> LENGTH: 330
<212> TYPE: PRT
<213> ORGANISM: Homo sapiens

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 43
<211> LENGTH: 978
<212> TYPE: DNA
<213> ORGANISM: Homo sapiens

<400> SEQUENCE: 43
gcctccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660

```
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac ctcccatgct ggactccgac    840
ggctccttct cctctacag caagctcacc gtggacaaga gcaggtggca gcaggggaac     900
gtcttctcat gctccgtgat gcatgaggct ctgcacaacc actacacgca gaagagcctc    960
tccctgtctc cgggtaaa                                                  978

<210> SEQ ID NO 44
<211> LENGTH: 326
<212> TYPE: PRT
<213> ORGANISM: Homo sapiens

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

Ser Leu Ser Pro Gly Lys
            325

<210> SEQ ID NO 45
<211> LENGTH: 296
<212> TYPE: DNA
<213> ORGANISM: Homo sapiens

<400> SEQUENCE: 45
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagaga       296

<210> SEQ ID NO 46
<211> LENGTH: 98
<212> TYPE: PRT
<213> ORGANISM: Homo sapiens

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 47
<211> LENGTH: 296
<212> TYPE: DNA
<213> ORGANISM: Homo sapiens

<400> SEQUENCE: 47
caggtgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag ggcttgagtg gatgggaata atcaaccctag tggtggtag cacaagctac   180 gcacagaagt tccagggcag agtcaccatg accagggaca cgtccacgag cacagtctac   240
atggagctga gcagcctgag atctgaggac acggccgtgt attactgtgc gagaga       296

<210> SEQ ID NO 48
<211> LENGTH: 98
<212> TYPE: PRT
<213> ORGANISM: Homo sapiens

<400> SEQUENCE: 48

Gln Val Gln Leu Val Gln Ser Gly Ala Glu Val Lys Lys Pro Gly Ala
1               5                   10                  15

| | | | | | | | | | | | |
|---|---|---|---|---|---|---|---|---|---|---|---|
|Ser|Val|Lys|Val|Ser|Cys|Lys|Ala|Ser|Gly|Tyr|Thr|Phe|Thr|Ser|Tyr|
| | | |20| | | |25| | | |30|

Tyr Met His Trp Val Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 49
<211> LENGTH: 321
<212> TYPE: DNA
<213> ORGANISM: Homo sapiens

<400> SEQUENCE: 49
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg t                                              321

<210> SEQ ID NO 50
<211> LENGTH: 107
<212> TYPE: PRT
<213> ORGANISM: Homo sapiens

<400> SEQUENCE: 50

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 51
<211> LENGTH: 318
<212> TYPE: DNA
<213> ORGANISM: Homo sapiens

<400> SEQUENCE: 51
ggtcagccca aggctgcccc ctcggtcact ctgttcccgc cctcctctga ggagcttcaa     60
gccaacaagg ccacactggt gtgtctcata agtgacttct acccgggagc cgtgacagtg    120
gcttggaaag cagatagcag ccccgtcaag gcgggagtgg agaccaccac accctccaaa    180

```
caaagcaaca acaagtacgc ggccagcagc tatctgagcc tgacgcctga gcagtggaag    240
tcccacagaa gctacagctg ccaggtcacg catgaaggga gcaccgtgga aagacagtg    300 gcccctacag aatgttca                                                 318
```

<210> SEQ ID NO 52
<211> LENGTH: 106
<212> TYPE: PRT
<213> ORGANISM: Homo sapiens

<400> SEQUENCE: 52

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 53
<211> LENGTH: 365
<212> TYPE: DNA
<213> ORGANISM: Homo sapiens

<400> SEQUENCE: 53

```
atggtgttgc agacccaggt cttcatttct ctgttgctct ggatctctgg tgcctacggg     60
gacatcgtga tgacccagtc tccagactcc ctggctgtgt ctctgggcga gagggccacc    120
atcaactgca gtccagcca gagtgtttta tacagctcca acaataagaa ctacttagct    180
tggtaccagc agaaaccagg acagcctcct aagctgctca tttactgggc atctacccgg    240
gaatccgggg tccctgaccg attcagtggc agcgggtctg ggacagattt cactctcacc    300
atcagcagcc tgcaggctga agatgtggca gtttattact gtcagcaata ttatagtact    360
cctcc                                                               365
```

<210> SEQ ID NO 54
<211> LENGTH: 101
<212> TYPE: PRT
<213> ORGANISM: Homo sapiens

<400> SEQUENCE: 54

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
```

```
            65                  70                  75                  80
Ile Ser Ser Leu Gln Ala Glu Asp Val Ala Val Tyr Tyr Cys Gln Gln
                    85                  90                  95

Tyr Tyr Ser Thr Pro
            100

<210> SEQ ID NO 55
<211> LENGTH: 654
<212> TYPE: DNA
<213> ORGANISM: Homo sapiens

<400> SEQUENCE: 55
atggacatga gggtccccgc tcagctcctg gggcttctgc tgctctggct cccagcaggt      60
gccagatgtg ccatccagtt gacccagtct ccatcctccc tgtctgcatc tgtaggagac     120
agagtcacca tcacttgccg ggcaagtcag ggcattagca gtgctttagc ctggtatcag     180
cagaaaccag ggaaagctcc taagctcctg atctatgatg cctccagttt ggaaagtggg     240
gtcccatcaa ggttcagcgg cagtggatct gggacagatt tcactctcac catcagcagc     300
ctgcagcctg aagattttgc aacttattac tgtcaacagt ttaatagtta ccctcagtgc     360
cagatgtgcc atccagttga cccagtctcc atcctccctg tctgcatctg taggagacag     420
agtcaccatc acttgccggg caagtcaggg cattagcagt gctttagcct ggtatcagca     480
gaaaccaggg aaagctccta agctcctgat ctatgatgcc tccagtttgg aaagtggggt     540
cccatcaagg ttcagcggca gtggatctgg gacagatttc actctcacca tcagcagcct     600
gcagcctgaa gattttgcaa cttattactg tcaacagttt aatagttacc ctca           654

<210> SEQ ID NO 56

<400> SEQUENCE: 56

000

<210> SEQ ID NO 57
<211> LENGTH: 39
<212> TYPE: DNA
<213> ORGANISM: Homo sapiens

<400> SEQUENCE: 57
tgtacacttt tggccagggg accaagctgg agatcaaac                             39

<210> SEQ ID NO 58
<211> LENGTH: 12
<212> TYPE: PRT
<213> ORGANISM: Homo sapiens

<400> SEQUENCE: 58

Tyr Thr Phe Gly Gln Gly Thr Lys Leu Glu Ile Lys
1               5                   10

<210> SEQ ID NO 59
<211> LENGTH: 38
<212> TYPE: DNA
<213> ORGANISM: Homo sapiens

<400> SEQUENCE: 59
tgtggtattc ggcggaggga ccaagctgac cgtcctag                              38

<210> SEQ ID NO 60
<211> LENGTH: 12
```

```
<212> TYPE: PRT
<213> ORGANISM: Homo sapiens

<400> SEQUENCE: 60

Val Val Phe Gly Gly Gly Thr Lys Leu Thr Val Leu
1               5                   10

<210> SEQ ID NO 61
<211> LENGTH: 329
<212> TYPE: PRT
<213> ORGANISM: Homo sapiens

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 62
<211> LENGTH: 107
<212> TYPE: PRT
<213> ORGANISM: Homo sapiens

<400> SEQUENCE: 62

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 63
<211> LENGTH: 326
<212> TYPE: PRT
<213> ORGANISM: Homo sapiens

<400> SEQUENCE: 63

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 64
<211> LENGTH: 105
<212> TYPE: PRT
<213> ORGANISM: Homo sapiens

<400> SEQUENCE: 64

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 65
<211> LENGTH: 326
<212> TYPE: PRT
<213> ORGANISM: Homo sapiens

<400> SEQUENCE: 65

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 66
<211> LENGTH: 107
<212> TYPE: PRT
<213> ORGANISM: Homo sapiens

<400> SEQUENCE: 66

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 67
<211> LENGTH: 825
<212> TYPE: PRT
<213> ORGANISM: Homo sapiens

<400> SEQUENCE: 67
```

-continued

```
Met Gly Trp Leu Cys Ser Gly Leu Leu Phe Pro Val Ser Cys Leu Val
1               5                   10                  15
Leu Leu Gln Val Ala Ser Ser Gly Asn Met Lys Val Leu Gln Glu Pro
            20                  25                  30
Thr Cys Val Ser Asp Tyr Met Ser Ile Ser Thr Cys Glu Trp Lys Met
            35                  40                  45
Asn Gly Pro Thr Asn Cys Ser Thr Glu Leu Arg Leu Leu Tyr Gln Leu
50                      55                  60
Val Phe Leu Leu Ser Glu Ala His Thr Cys Ile Pro Glu Asn Asn Gly
65                  70                  75                  80
Gly Ala Gly Cys Val Cys His Leu Leu Met Asp Asp Val Val Ser Ala
                85                  90                  95
Asp Asn Tyr Thr Leu Asp Leu Trp Ala Gly Gln Gln Leu Leu Trp Lys
            100                 105                 110
Gly Ser Phe Lys Pro Ser Glu His Val Lys Pro Arg Ala Pro Gly Asn
            115                 120                 125
Leu Thr Val His Thr Asn Val Ser Asp Thr Leu Leu Leu Thr Trp Ser
            130                 135                 140
Asn Pro Tyr Pro Pro Asp Asn Tyr Leu Tyr Asn His Leu Thr Tyr Ala
145                 150                 155                 160
Val Asn Ile Trp Ser Glu Asn Asp Pro Ala Asp Phe Arg Ile Tyr Asn
                165                 170                 175
Val Thr Tyr Leu Glu Pro Ser Leu Arg Ile Ala Ala Ser Thr Leu Lys
            180                 185                 190
Ser Gly Ile Ser Tyr Arg Ala Arg Val Arg Ala Trp Ala Gln Cys Tyr
            195                 200                 205
Asn Thr Thr Trp Ser Glu Trp Ser Pro Ser Thr Lys Trp His Asn Ser
210                 215                 220
Tyr Arg Glu Pro Phe Glu Gln His Leu Leu Leu Gly Val Ser Val Ser
225                 230                 235                 240
Cys Ile Val Ile Leu Ala Val Cys Leu Leu Cys Tyr Val Ser Ile Thr
                245                 250                 255
Lys Ile Lys Lys Glu Trp Trp Asp Gln Ile Pro Asn Pro Ala Arg Ser
            260                 265                 270
Arg Leu Val Ala Ile Ile Ile Gln Asp Ala Gln Gly Ser Gln Trp Glu
    275                 280                 285
Lys Arg Ser Arg Gly Gln Glu Pro Ala Lys Cys Pro His Trp Lys Asn
        290                 295                 300
Cys Leu Thr Lys Leu Leu Pro Cys Phe Leu Glu His Asn Met Lys Arg
305                 310                 315                 320
Asp Glu Asp Pro His Lys Ala Ala Lys Glu Met Pro Phe Gln Gly Ser
                325                 330                 335
Gly Lys Ser Ala Trp Cys Pro Val Glu Ile Ser Lys Thr Val Leu Trp
            340                 345                 350
Pro Glu Ser Ile Ser Val Val Arg Cys Val Glu Leu Phe Glu Ala Pro
            355                 360                 365
Val Glu Cys Glu Glu Glu Glu Val Glu Glu Glu Lys Gly Ser Phe
370                 375                 380
Cys Ala Ser Pro Glu Ser Ser Arg Asp Asp Phe Gln Glu Gly Arg Glu
385                 390                 395                 400
Gly Ile Val Ala Arg Leu Thr Glu Ser Leu Phe Leu Asp Leu Leu Gly
                405                 410                 415
Glu Glu Asn Gly Gly Phe Cys Gln Gln Asp Met Gly Glu Ser Cys Leu
```

```
                420                 425                 430
Leu Pro Pro Ser Gly Ser Thr Ser Ala His Met Pro Trp Asp Glu Phe
            435                 440                 445
Pro Ser Ala Gly Pro Lys Glu Ala Pro Pro Trp Gly Lys Glu Gln Pro
        450                 455                 460
Leu His Leu Glu Pro Ser Pro Pro Ala Ser Pro Thr Gln Ser Pro Asp
465                 470                 475                 480
Asn Leu Thr Cys Thr Glu Thr Pro Leu Val Ile Ala Gly Asn Pro Ala
                485                 490                 495
Tyr Arg Ser Phe Ser Asn Ser Leu Ser Gln Ser Pro Cys Pro Arg Glu
            500                 505                 510
Leu Gly Pro Asp Pro Leu Leu Ala Arg His Leu Glu Glu Val Glu Pro
        515                 520                 525
Glu Met Pro Cys Val Pro Gln Leu Ser Glu Pro Thr Thr Val Pro Gln
    530                 535                 540
Pro Glu Pro Glu Thr Trp Glu Gln Ile Leu Arg Arg Asn Val Leu Gln
545                 550                 555                 560
His Gly Ala Ala Ala Pro Val Ser Ala Pro Thr Ser Gly Tyr Gln
                565                 570                 575
Glu Phe Val His Ala Val Glu Gln Gly Gly Thr Gln Ala Ser Ala Val
            580                 585                 590
Val Gly Leu Gly Pro Pro Gly Glu Ala Gly Tyr Lys Ala Phe Ser Ser
        595                 600                 605
Leu Leu Ala Ser Ser Ala Val Ser Pro Glu Lys Cys Gly Phe Gly Ala
    610                 615                 620
Ser Ser Gly Glu Glu Gly Tyr Lys Pro Phe Gln Asp Leu Ile Pro Gly
625                 630                 635                 640
Cys Pro Gly Asp Pro Ala Pro Val Pro Val Pro Leu Phe Thr Phe Gly
                645                 650                 655
Leu Asp Arg Glu Pro Pro Arg Ser Pro Gln Ser Ser His Leu Pro Ser
            660                 665                 670
Ser Ser Pro Glu His Leu Gly Leu Glu Pro Gly Glu Lys Val Glu Asp
        675                 680                 685
Met Pro Lys Pro Pro Leu Pro Gln Glu Gln Ala Thr Asp Pro Leu Val
    690                 695                 700
Asp Ser Leu Gly Ser Gly Ile Val Tyr Ser Ala Leu Thr Cys His Leu
705                 710                 715                 720
Cys Gly His Leu Lys Gln Cys His Gly Gln Glu Asp Gly Gly Gln Thr
                725                 730                 735
Pro Val Met Ala Ser Pro Cys Cys Gly Cys Cys Cys Gly Asp Arg Ser
            740                 745                 750
Ser Pro Pro Thr Thr Pro Leu Arg Ala Pro Asp Pro Ser Pro Gly Gly
        755                 760                 765
Val Pro Leu Glu Ala Ser Leu Cys Pro Ala Ser Leu Ala Pro Ser Gly
    770                 775                 780
Ile Ser Glu Lys Ser Lys Ser Ser Ser Phe His Pro Ala Pro Gly
785                 790                 795                 800
Asn Ala Gln Ser Ser Ser Gln Thr Pro Lys Ile Val Asn Phe Val Ser
                805                 810                 815
Val Gly Pro Thr Tyr Met Arg Val Ser
            820                 825

<210> SEQ ID NO 68
```

<211> LENGTH: 2478
<212> TYPE: DNA
<213> ORGANISM: Homo sapiens

<400> SEQUENCE: 68

| | | | | | |
|---|---|---|---|---|---|
| atggggtggc | tttgctctgg | gctcctgttc | cctgtgagct | gcctggtcct | gctgcaggtg | 60 |
| gcaagctctg | ggaacatgaa | ggtcttgcag | gagcccacct | gcgtctccga | ctacatgagc | 120 |
| atctctactt | gcgagtggaa | gatgaatggt | cccaccaatt | gcagcaccga | gctccgcctg | 180 |
| ttgtaccagc | tggttttcct | gctctccgaa | gcccacacgt | gtatccctga | aacaacgga | 240 |
| ggcgcgggt | gcgtgtgcca | cctgctcatg | gatgacgtgg | tcagtgcgga | taactataca | 300 |
| ctggacctgt | gggctgggca | gcagctgctg | tggaagggct | ccttcaagcc | cagcgagcat | 360 |
| gtgaaaccca | gggccccagg | aaacctgaca | gttcacacca | tgtctccga | cactctgctg | 420 |
| ctgacctgga | gcaacccgta | tcccctgac | aattacctgt | ataatcatct | cacctatgca | 480 |
| gtcaacattt | ggagtgaaaa | cgacccggca | gatttcagaa | tctataacgt | gacctaccta | 540 |
| gaaccctccc | tccgcatcgc | agccagcacc | ctgaagtctg | ggatttccta | cagggcacgg | 600 |
| gtgagggcct | gggctcagtg | ctataacacc | acctggagtg | agtggagccc | cagcaccaag | 660 |
| tggcacaact | cctacaggga | gccccttcgag | cagcacctcc | tgctgggcgt | cagcgtttcc | 720 |
| tgcattgtca | tcctggccgt | ctgcctgttg | tgctatgtca | gcatcaccaa | gattaagaaa | 780 |
| gaatggtggg | atcagattcc | caacccagcc | cgcagccgcc | tcgtggctat | aataatccag | 840 |
| gatgctcagg | ggtcacagtg | ggagaagcgg | tcccgaggcc | aggaaccagc | caagtgccca | 900 |
| cactggaaga | attgtcttac | caagctcttg | ccctgttttc | tggagcacaa | catgaaaagg | 960 |
| gatgaagatc | ctcacaaggc | tgccaaagag | atgcctttcc | agggctctgg | aaaatcagca | 1020 |
| tggtgcccag | tggagatcag | caagacagtc | ctctggccag | agagcatcag | cgtggtgcga | 1080 |
| tgtgtggagt | tgtttgaggc | cccggtggag | tgtgaggagg | aggaggaggt | agaggaagaa | 1140 |
| aaagggagct | tctgtgcatc | gcctgagagc | agcaggatg | acttccagga | gggaagggag | 1200 |
| ggcattgtgg | cccggctaac | agagagcctg | ttcctggacc | tgctcggaga | ggagaatggg | 1260 |
| ggcttttgcc | agcaggacat | gggggagtca | tgccttcttc | caccttcggg | aagtacgagt | 1320 |
| gctcacatgc | cctgggatga | gttcccaagt | gcagggccca | aggaggcacc | tcctggggc | 1380 |
| aaggagcagc | ctctccacct | ggagccaagt | cctcctgcca | gcccgaccca | gagtccagac | 1440 |
| aacctgactt | gcacagagac | gccctcgtc | atcgcaggca | accctgctta | ccgcagcttc | 1500 |
| agcaactccc | tgagccagtc | accgtgtccc | agagagctgg | gtccagaccc | actgctggcc | 1560 |
| agacacctgg | aggaagtaga | acccgagatg | ccctgtgtcc | cccagctctc | tgagccaacc | 1620 |
| actgtgcccc | aacctgagcc | agaaacctgg | gagcagatcc | tccgccgaaa | tgtcctccag | 1680 |
| catgggcag | ctgcagcccc | cgtctcggcc | ccaccagtg | gctatcagga | gtttgtacat | 1740 |
| gcggtggagc | agggtggcac | ccaggccagt | gcggtggtgg | gcttgggtcc | cccaggagag | 1800 |
| gctggttaca | aggccttctc | aagcctgctt | gccagcagtg | ctgtgtcccc | agaaaatgt | 1860 |
| gggtttgggg | ctagcagtgg | ggaagagggg | tataagcctt | tccaagacct | cattcctggc | 1920 |
| tgccctgggg | accctgcccc | agtccctgtc | cccttgttca | cctttggact | ggacagggag | 1980 |
| ccacctcgca | gtccgcagag | ctcacatctc | ccaagcagct | cccagagca | cctgggtctg | 2040 |
| gagccggggc | aaaaggtaga | ggacatgcca | aagcccccac | ttcccagga | gcaggccaca | 2100 |
| gaccccttg | tggacagcct | gggcagtggc | attgtctact | cagcccttac | ctgccacctg | 2160 |
| tgcggccacc | tgaaacagtg | tcatggccag | gaggatggtg | gccagacccc | tgtcatggcc | 2220 |

```
agtccttgct gtggctgctg ctgtggagac aggtcctcgc ccccctacaac cccccctgagg    2280 gccccagacc cctctccagg tggggttcca ctggaggcca gtctgtgtcc ggcctccctg     2340
gcaccctcgg gcatctcaga gaagagtaaa tcctcatcat ccttccatcc tgccctggc      2400 aatgctcaga gctcaagcca gaccccccaaa atcgtgaact tgtctccgt gggacccaca    2460 tacatgaggg tctcttag                                                    2478
```

<210> SEQ ID NO 69
<211> LENGTH: 125
<212> TYPE: PRT
<213> ORGANISM: Homo sapiens

<400> SEQUENCE: 69

```
Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser
        115                 120                 125
```

<210> SEQ ID NO 70
<211> LENGTH: 112
<212> TYPE: PRT
<213> ORGANISM: Homo sapiens

<400> SEQUENCE: 70

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 71
<211> LENGTH: 451
<212> TYPE: PRT
<213> ORGANISM: Homo sapiens

<400> SEQUENCE: 71

```
Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415
```

```
Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly
    450

<210> SEQ ID NO 72
<211> LENGTH: 214
<212> TYPE: PRT
<213> ORGANISM: Homo sapiens

<400> SEQUENCE: 72

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe
    210

<210> SEQ ID NO 73
<211> LENGTH: 327
<212> TYPE: PRT
<213> ORGANISM: Homo sapiens

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 74
<211> LENGTH: 984
<212> TYPE: DNA
<213> ORGANISM: Homo sapiens

<400> SEQUENCE: 74
gcttccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
```

```
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggctc accgtggaca agagcaggtg gcaggagggg    900
aatgtcttct catgctccgt gatgcatgag gctctgcaca accactacac acagaagagc    960
ctctccctgt ctctgggtaa atga                                           984
```

```
<210> SEQ ID NO 75
<211> LENGTH: 1988
<212> TYPE: PRT
<213> ORGANISM: Homo sapiens

<400> SEQUENCE: 75
```

| | | | | | | | | | | | | | | |
|---|---|---|---|---|---|---|---|---|---|---|---|---|---|---|
| Met | Ala | Met | Leu | Pro | Pro | Gly | Pro | Gln | Ser | Phe | Val | His | Phe | Thr |
| 1 | | | | 5 | | | | | 10 | | | | | 15 |
| Lys | Gln | Ser | Leu | Ala | Leu | Ile | Glu | Gln | Arg | Ile | Ala | Glu | Arg | Lys | Ser |
| | | | 20 | | | | | 25 | | | | | 30 | | |
| Lys | Glu | Pro | Lys | Glu | Glu | Lys | Lys | Asp | Asp | Asp | Glu | Glu | Ala | Pro | Lys |
| | | 35 | | | | | 40 | | | | | 45 | | | |
| Pro | Ser | Ser | Asp | Leu | Glu | Ala | Gly | Lys | Gln | Leu | Pro | Phe | Ile | Tyr | Gly |
| 50 | | | | | 55 | | | | | 60 | | | | | |
| Asp | Ile | Pro | Pro | Gly | Met | Val | Ser | Glu | Pro | Leu | Glu | Asp | Leu | Asp | Pro |
| 65 | | | | 70 | | | | | 75 | | | | | 80 | |
| Tyr | Tyr | Ala | Asp | Lys | Lys | Thr | Phe | Ile | Val | Leu | Asn | Lys | Gly | Lys | Thr |
| | | | | 85 | | | | | 90 | | | | | 95 | |
| Ile | Phe | Arg | Phe | Asn | Ala | Thr | Pro | Ala | Leu | Tyr | Met | Leu | Ser | Pro | Phe |
| | | | 100 | | | | | 105 | | | | | 110 | | |
| Ser | Pro | Leu | Arg | Arg | Ile | Ser | Ile | Lys | Ile | Leu | Val | His | Ser | Leu | Phe |
| | | 115 | | | | | 120 | | | | | 125 | | | |
| Ser | Met | Leu | Ile | Met | Cys | Thr | Ile | Leu | Thr | Asn | Cys | Ile | Phe | Met | Thr |
| | 130 | | | | | 135 | | | | | 140 | | | | |
| Met | Asn | Asn | Pro | Pro | Asp | Trp | Thr | Lys | Asn | Val | Glu | Tyr | Thr | Phe | Thr |
| 145 | | | | | 150 | | | | | 155 | | | | | 160 |
| Gly | Ile | Tyr | Thr | Phe | Glu | Ser | Leu | Val | Lys | Ile | Leu | Ala | Arg | Gly | Phe |
| | | | | 165 | | | | | 170 | | | | | 175 | |
| Cys | Val | Gly | Glu | Phe | Thr | Phe | Leu | Arg | Asp | Pro | Trp | Asn | Trp | Leu | Asp |
| | | | 180 | | | | | 185 | | | | | 190 | | |
| Phe | Val | Val | Ile | Val | Phe | Ala | Tyr | Leu | Thr | Glu | Phe | Val | Asn | Leu | Gly |
| | | 195 | | | | | 200 | | | | | 205 | | | |
| Asn | Val | Ser | Ala | Leu | Arg | Thr | Phe | Arg | Val | Leu | Arg | Ala | Leu | Lys | Thr |
| | 210 | | | | | 215 | | | | | 220 | | | | |
| Ile | Ser | Val | Ile | Pro | Gly | Leu | Lys | Thr | Ile | Val | Gly | Ala | Leu | Ile | Gln |
| 225 | | | | | 230 | | | | | 235 | | | | | 240 |
| Ser | Val | Lys | Lys | Leu | Ser | Asp | Val | Met | Ile | Leu | Thr | Val | Phe | Cys | Leu |
| | | | | 245 | | | | | 250 | | | | | 255 | |
| Ser | Val | Phe | Ala | Leu | Ile | Gly | Leu | Gln | Leu | Phe | Met | Gly | Asn | Leu | Lys |
| | | | 260 | | | | | 265 | | | | | 270 | | |
| His | Lys | Cys | Phe | Arg | Asn | Ser | Leu | Glu | Asn | Asn | Glu | Thr | Leu | Glu | Ser |
| | | 275 | | | | | 280 | | | | | 285 | | | |
| Ile | Met | Asn | Thr | Leu | Glu | Ser | Glu | Glu | Asp | Phe | Arg | Lys | Tyr | Phe | Tyr |
| | 290 | | | | | 295 | | | | | 300 | | | | |

```
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
            325                 330                 335
Pro Asp Tyr Gly Tyr Thr Ser Phe Asp Thr Phe Ser Trp Ala Phe Leu
                340                 345                 350
Ala Leu Phe Arg Leu Met Thr Gln Asp Tyr Trp Glu Asn Leu Tyr Gln
            355                 360                 365
Gln Thr Leu Arg Ala Ala Gly Lys Thr Tyr Met Ile Phe Phe Val Val
        370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Glu Tyr Thr
        435                 440                 445
Ser Ile Arg Arg Ser Arg Ile Met Gly Leu Ser Glu Ser Ser Ser Glu
450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
        515                 520                 525
Leu Ser Thr Pro Asn Gln Ser Pro Leu Ser Ile Arg Gly Ser Leu Phe
530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
610                 615                 620
Asn Gly Val Val Ser Leu Val Asp Gly Arg Ser Ala Leu Met Leu Pro
625                 630                 635                 640
Asn Gly Gln Leu Leu Pro Glu Val Ile Ile Asp Lys Ala Thr Ser Asp
                645                 650                 655
Asp Ser Gly Thr Thr Asn Gln Ile His Lys Lys Arg Arg Cys Ser Ser
            660                 665                 670
Tyr Leu Leu Ser Glu Asp Met Leu Asn Asp Pro Asn Leu Arg Gln Arg
        675                 680                 685
Ala Met Ser Arg Ala Ser Ile Leu Thr Asn Thr Val Glu Glu Leu Glu
        690                 695                 700
Glu Ser Arg Gln Lys Cys Pro Pro Trp Trp Tyr Arg Phe Ala His Lys
705                 710                 715                 720
Phe Leu Ile Trp Asn Cys Ser Pro Tyr Trp Ile Lys Phe Lys Lys Cys
```

```
                     725                 730                 735
Ile Tyr Phe Ile Val Met Asp Pro Phe Val Asp Leu Ala Ile Thr Ile
                740                 745                 750

Cys Ile Val Leu Asn Thr Leu Phe Met Ala Met Glu His His Pro Met
            755                 760                 765

Thr Glu Glu Phe Lys Asn Val Leu Ala Ile Gly Asn Leu Val Phe Thr
770                 775                 780

Gly Ile Phe Ala Ala Glu Met Val Leu Lys Leu Ile Ala Met Asp Pro
785                 790                 795                 800

Tyr Glu Tyr Phe Gln Val Gly Trp Asn Ile Phe Asp Ser Leu Ile Val
                805                 810                 815

Thr Leu Ser Leu Val Glu Leu Phe Leu Ala Asp Val Glu Gly Leu Ser
            820                 825                 830

Val Leu Arg Ser Phe Arg Leu Leu Arg Val Phe Lys Leu Ala Lys Ser
        835                 840                 845

Trp Pro Thr Leu Asn Met Leu Ile Lys Ile Ile Gly Asn Ser Val Gly
850                 855                 860

Ala Leu Gly Asn Leu Thr Leu Val Leu Ala Ile Ile Val Phe Ile Phe
865                 870                 875                 880

Ala Val Val Gly Met Gln Leu Phe Gly Lys Ser Tyr Lys Glu Cys Val
                885                 890                 895

Cys Lys Ile Asn Asp Asp Cys Thr Leu Pro Arg Trp His Met Asn Asp
            900                 905                 910

Phe Phe His Ser Phe Leu Ile Val Phe Arg Val Leu Cys Gly Glu Trp
        915                 920                 925

Ile Glu Thr Met Trp Asp Cys Met Glu Val Ala Gly Gln Ala Met Cys
930                 935                 940

Leu Ile Val Tyr Met Met Val Met Val Ile Gly Asn Leu Val Val Leu
945                 950                 955                 960

Asn Leu Phe Leu Ala Leu Leu Leu Ser Ser Phe Ser Ser Asp Asn Leu
                965                 970                 975

Thr Ala Ile Glu Glu Asp Pro Asp Ala Asn Asn Leu Gln Ile Ala Val
            980                 985                 990

Thr Arg Ile Lys Lys Gly Ile Asn Tyr Val Lys Gln Thr Leu Arg Glu
        995                1000                1005

Phe Ile Leu Lys Ala Phe Ser Lys Lys Pro Lys Ile Ser Arg Glu
1010                1015                1020

Ile Arg Gln Ala Glu Asp Leu Asn Thr Lys Lys Glu Asn Tyr Ile
   1025                1030                1035

Ser Asn His Thr Leu Ala Glu Met Ser Lys Gly His Asn Phe Leu
1040                1045                1050

Lys Glu Lys Asp Lys Ile Ser Gly Phe Gly Ser Ser Val Asp Lys
1055                1060                1065

His Leu Met Glu Asp Ser Asp Gly Gln Ser Phe Ile His Asn Pro
1070                1075                1080

Ser Leu Thr Val Thr Val Pro Ile Ala Pro Gly Glu Ser Asp Leu
1085                1090                1095

Glu Asn Met Asn Ala Glu Leu Ser Ser Asp Ser Asp Ser Glu
1100                1105                1110

Tyr Ser Lys Val Arg Leu Asn Arg Ser Ser Ser Ser Glu Cys Ser
1115                1120                1125

Thr Val Asp Asn Pro Leu Pro Gly Glu Gly Glu Glu Ala Glu Ala
1130                1135                1140
```

-continued

```
Glu Pro Met Asn Ser Asp Glu Pro Ala Cys Phe Thr Asp Gly
    1145                1150            1155

Cys Val Trp Arg Phe Ser Cys Cys Gln Val Asn Ile Glu Ser Gly
    1160                1165            1170

Lys Gly Lys Ile Trp Trp Asn Ile Arg Lys Thr Cys Tyr Lys Ile
    1175                1180            1185

Val Glu His Ser Trp Phe Glu Ser Phe Ile Val Leu Met Ile Leu
    1190                1195            1200

Leu Ser Ser Gly Ala Leu Ala Phe Glu Asp Ile Tyr Ile Glu Arg
    1205                1210            1215

Lys Lys Thr Ile Lys Ile Ile Leu Glu Tyr Ala Asp Lys Ile Phe
    1220                1225            1230

Thr Tyr Ile Phe Ile Leu Glu Met Leu Leu Lys Trp Ile Ala Tyr
    1235                1240            1245

Gly Tyr Lys Thr Tyr Phe Thr Asn Ala Trp Cys Trp Leu Asp Phe
    1250                1255            1260

Leu Ile Val Asp Val Ser Leu Val Thr Leu Val Ala Asn Thr Leu
    1265                1270            1275

Gly Tyr Ser Asp Leu Gly Pro Ile Lys Ser Leu Arg Thr Leu Arg
    1280                1285            1290

Ala Leu Arg Pro Leu Arg Ala Leu Ser Arg Phe Glu Gly Met Arg
    1295                1300            1305

Val Val Val Asn Ala Leu Ile Gly Ala Ile Pro Ser Ile Met Asn
    1310                1315            1320

Val Leu Leu Val Cys Leu Ile Phe Trp Leu Ile Phe Ser Ile Met
    1325                1330            1335

Gly Val Asn Leu Phe Ala Gly Lys Phe Tyr Glu Cys Ile Asn Thr
    1340                1345            1350

Thr Asp Gly Ser Arg Phe Pro Ala Ser Gln Val Pro Asn Arg Ser
    1355                1360            1365

Glu Cys Phe Ala Leu Met Asn Val Ser Gln Asn Val Arg Trp Lys
    1370                1375            1380

Asn Leu Lys Val Asn Phe Asp Asn Val Gly Leu Gly Tyr Leu Ser
    1385                1390            1395

Leu Leu Gln Val Ala Thr Phe Lys Gly Trp Thr Ile Ile Met Tyr
    1400                1405            1410

Ala Ala Val Asp Ser Val Asn Val Asp Lys Gln Pro Lys Tyr Glu
    1415                1420            1425

Tyr Ser Leu Tyr Met Tyr Ile Tyr Phe Val Val Phe Ile Ile Phe
    1430                1435            1440

Gly Ser Phe Phe Thr Leu Asn Leu Phe Ile Gly Val Ile Ile Asp
    1445                1450            1455

Asn Phe Asn Gln Gln Lys Lys Lys Leu Gly Gly Gln Asp Ile Phe
    1460                1465            1470

Met Thr Glu Glu Gln Lys Lys Tyr Tyr Asn Ala Met Lys Lys Leu
    1475                1480            1485

Gly Ser Lys Lys Pro Gln Lys Pro Ile Pro Arg Pro Gly Asn Lys
    1490                1495            1500

Ile Gln Gly Cys Ile Phe Asp Leu Val Thr Asn Gln Ala Phe Asp
    1505                1510            1515

Ile Ser Ile Met Val Leu Ile Cys Leu Asn Met Val Thr Met Met
    1520                1525            1530
```

-continued

| | | | | | | | | | | | |
|---|---|---|---|---|---|---|---|---|---|---|---|
| Val | Glu | Lys | Glu | Gly | Gln | Ser | Gln | His | Met | Thr | Glu | Val | Leu | Tyr |
| 1535 | | | | | 1540 | | | | | 1545 | | | | |

Val Glu Lys Glu Gly Gln Ser Gln His Met Thr Glu Val Leu Tyr
1535                1540                1545

Trp Ile Asn Val Val Phe Ile Ile Leu Phe Thr Gly Glu Cys Val
1550                1555                1560

Leu Lys Leu Ile Ser Leu Arg His Tyr Tyr Phe Thr Val Gly Trp
1565                1570                1575

Asn Ile Phe Asp Phe Val Val Ile Ile Ser Ile Val Gly Met
1580                1585                1590

Phe Leu Ala Asp Leu Ile Glu Thr Tyr Phe Val Ser Pro Thr Leu
1595                1600                1605

Phe Arg Val Ile Arg Leu Ala Arg Ile Gly Arg Ile Leu Arg Leu
1610                1615                1620

Val Lys Gly Ala Lys Gly Ile Arg Thr Leu Leu Phe Ala Leu Met
1625                1630                1635

Met Ser Leu Pro Ala Leu Phe Asn Ile Gly Leu Leu Leu Phe Leu
1640                1645                1650

Val Met Phe Ile Tyr Ala Ile Phe Gly Met Ser Asn Phe Ala Tyr
1655                1660                1665

Val Lys Lys Glu Asp Gly Ile Asn Asp Met Phe Asn Phe Glu Thr
1670                1675                1680

Phe Gly Asn Ser Met Ile Cys Leu Phe Gln Ile Thr Thr Ser Ala
1685                1690                1695

Gly Trp Asp Gly Leu Leu Ala Pro Ile Leu Asn Ser Lys Pro Pro
1700                1705                1710

Asp Cys Asp Pro Lys Lys Val His Pro Gly Ser Ser Val Glu Gly
1715                1720                1725

Asp Cys Gly Asn Pro Ser Val Gly Ile Phe Tyr Phe Val Ser Tyr
1730                1735                1740

Ile Ile Ile Ser Phe Leu Val Val Val Asn Met Tyr Ile Ala Val
1745                1750                1755

Ile Leu Glu Asn Phe Ser Val Ala Thr Glu Glu Ser Thr Glu Pro
1760                1765                1770

Leu Ser Glu Asp Asp Phe Glu Met Phe Tyr Glu Val Trp Glu Lys
1775                1780                1785

Phe Asp Pro Asp Ala Thr Gln Phe Ile Glu Phe Ser Lys Leu Ser
1790                1795                1800

Asp Phe Ala Ala Ala Leu Asp Pro Pro Leu Leu Ile Ala Lys Pro
1805                1810                1815

Asn Lys Val Gln Leu Ile Ala Met Asp Leu Pro Met Val Ser Gly
1820                1825                1830

Asp Arg Ile His Cys Leu Asp Ile Leu Phe Ala Phe Thr Lys Arg
1835                1840                1845

Val Leu Gly Glu Ser Gly Glu Met Asp Ser Leu Arg Ser Gln Met
1850                1855                1860

Glu Glu Arg Phe Met Ser Ala Asn Pro Ser Lys Val Ser Tyr Glu
1865                1870                1875

Pro Ile Thr Thr Thr Leu Lys Arg Lys Gln Glu Asp Val Ser Ala
1880                1885                1890

Thr Val Ile Gln Arg Ala Tyr Arg Arg Tyr Arg Leu Arg Gln Asn
1895                1900                1905

Val Lys Asn Ile Ser Ser Ile Tyr Ile Lys Asp Gly Asp Arg Asp
1910                1915                1920

Asp Asp Leu Leu Asn Lys Lys Asp Met Ala Phe Asp Asn Val Asn

-continued

```
         1925              1930             1935
Glu Asn Ser Ser Pro Glu Lys Thr Asp Ala Thr Ser Ser Thr Thr
        1940             1945             1950

Ser Pro Pro Ser Tyr Asp Ser Val Thr Lys Pro Asp Lys Glu Lys
        1955             1960             1965

Tyr Glu Gln Asp Arg Thr Glu Lys Glu Asp Lys Gly Lys Asp Ser
        1970             1975             1980

Lys Glu Ser Lys Lys
        1985

<210> SEQ ID NO 76
<211> LENGTH: 5965
<212> TYPE: DNA
<213> ORGANISM: Homo sapiens

<400> SEQUENCE: 76
```

| | | | | | |
|---|---|---|---|---|---|
| atggcaatgt | tgcctccccc | aggacctcag | agctttgtcc | atttcacaaa | acagtctctt     60 |
| gccctcattg | aacaacgcat | tgctgaaaga | aaatcaaagg | aacccaaaga | agaaaagaaa    120 |
| gatgatgatg | aagaagcccc | aaagccaagc | agtgacttgg | aagctggcaa | acagctgccc    180 |
| ttcatctatg | gggacattcc | tcccggcatg | tgtcagagc | ccctggagga | cttgacccc     240 |
| tactatgcag | acaaaaagac | tttcatagta | ttgaacaaag | ggaaaacaat | cttccgtttc    300 |
| aatgccacac | ctgctttata | tatgctttct | cctttcagtc | tctaagaag | aatatctatt    360 |
| aagattttag | tacactcctt | attcagcatg | ctcatcatgt | gcactattct | gacaaactgc    420 |
| atatttatga | ccatgaataa | cccaccggac | tggaccaaaa | atgtcgagta | cacttttact    480 |
| ggaatatata | cttttgaatc | acttgtaaaa | atccttgcaa | gaggcttctg | tgtaggagaa    540 |
| ttcacttttc | ttcgtgaccc | gtggaactgg | ctggattttg | tcgtcattgt | ttttgcgtat    600 |
| ttaacagaat | ttgtaaacct | aggcaatgtt | tcagctcttc | gaactttcag | agtattgaga    660 |
| gctttgaaaa | ctatttctgt | aatcccaggc | ctgaagacaa | ttgtagggc | tttgatccag    720 |
| tcagtgaaga | agctttctga | tgtcatgatc | ctgactgtgt | tctgtctgag | tgtgtttgca    780 |
| ctaattggac | tacagctgtt | catgggaaac | ctgaagcata | aatgttttcg | aaattcactt    840 |
| gaaaataatg | aaacattaga | aagcataatg | aatacccta | gagtgaaga | agactttaga    900 |
| aaatatttt | attacttgga | aggatccaaa | gatgctctcc | tttgtggttt | cagcacagat    960 |
| tcaggtcagt | gtccagaggg | gtacacctgt | gtgaaaattg | gcagaaaccc | tgattatggc   1020 |
| tacacgagct | ttgacacttt | cagctgggcc | ttcttagcct | tgtttaggct | aatgaccca   1080 |
| gattactggg | aaaaccttta | ccaacagacg | ctgcgtgctg | ctggcaaaac | ctacatgatc   1140 |
| ttctttgtcg | tagtgatttt | cctgggctcc | ttttatctaa | taaacttgat | cctggctgtg   1200 |
| gttgccatgg | catatgaaga | acagaaccag | gcaaacattg | aagaagctaa | acagaaagaa   1260 |
| ttagaatttc | aacagatgtt | agaccgtctt | aaaaaagagc | aagaagaagc | tgaggcaatt   1320 |
| gcagcggcag | cggctgaata | tacaagtatt | aggagaagca | gaattatggg | cctctcagag   1380 |
| agttcttctg | aaacatccaa | actgagctct | aaaagtgcta | agaaagaag | aacagaagaa   1440 |
| agaaaaagaa | tcaaaagaag | ctctccagtg | gagaggaaaa | gggagatgct | gagaaattgt   1500 |
| cgaaatcaga | atcagaggac | agcatcagaa | gaaaagttt | ccaccttggt | gtcgaagggc   1560 |
| ataggcgagc | acatgaaaag | aggttgtcta | cccccaatca | gtcaccactc | agcattcgtg   1620 |
| gctccttgtt | ttctgcaagg | cgaagcagca | gaacaagtct | ttttagtttc | aaaggcagag   1680 |
| gaagagatat | aggatctgag | actgaatttg | ccgatgatga | gcacagcatt | tttggagaca   1740 |

```
atgagagcag aaggggctca ctgtttgtgc cccacagacc ccaggagcga cgcagcagta   1800
acatcagcca agccagtagg tccccaccaa tgctgccggt gaacgggaaa atgcacagtg   1860
ctgtggactg caacggtgtg gtctccctgg ttgatggacg ctcagccctc atgctcccca   1920
atggacagct tctgccagag gtgataatag ataaggcaac ttctgatgac agcggcacga   1980
ccaatcaaat acacaagaaa aggcgttgta gttcctatct cctttcagag gatatgctga   2040
atgatcccaa cctcagacag agagcaatga gtagagcaag catattaaca aacactgtgg   2100
aagaacttga agagtccaga caaaaatgtc caccttggtg gtacagattt gcacacaaat   2160
tcttgatctg gaattgctct ccatattgga taaaattcaa aaagtgtatc tattttattg   2220
taatggatcc ttttgtagat cttgcaatta ccatttgcat agttttaaac acattattta   2280
tggctatgga acaccaccca atgactgagg aattcaaaaa tgtactgcta taggaaattt   2340
ggtctttact ggaatctttg cagctgaaat ggtattaaaa ctgattgcca tggatccata   2400
tgagtatttc caagtaggct ggaatatttt tgacagcctt attgtgactt taagtttagt   2460
ggagctcttt ctagcagatg tggaaggatt gtcagttctg cgatcattca gactgctccg   2520
agtcttcaag ttggcaaaat cctggccaac attgaacatg ctgattaaga tcattggtaa   2580
ctcagtaggg gctctaggta acctcacctt agtgttggcc atcatcgtct tcatttttgc   2640
tgtggtcggc atgcagctct ttggtaagag ctacaaagaa tgtgtctgca agatcaatga   2700
tgactgtacg ctcccacggt ggcacatgaa cgacttcttc cactccttcc tgattgtgtt   2760
ccgcgtgctg tgtggagagt ggatagagac catgtgggac tgtatggagg tcgctggtca   2820
agctatgtgc cttattgttt acatgatggt catggtcatt ggaaacctgg tggtcctaaa   2880
cctatttctg gccttattat tgagctcatt tagttcagac aatcttacag caattgaaga   2940
agaccctgat gcaaacaacc tccagattgc agtgactaga attaaaaagg gaataaatta   3000
tgtgaaacaa accttacgtg aatttattct aaaagcattt tccaaaaagc caaagatttc   3060
cagggagata agacaagcag aagatctgaa tactaagaag gaaaactata tttctaacca   3120
tacacttgct gaaatgagca aaggtcacaa tttcctcaag gaaaaagata aaatcagtgg   3180
ttttggaagc agcgtggaca acacttgat ggaagacagt gatggtcaat catttattca   3240
caatcccagc ctcacagtga cagtgccaat tgcacctggg gaatccgatt tggaaaatat   3300
gaatgctgag gaacttagca gtgattcgga tagtgaatac agcaaagtga gattaaaccg   3360
gtcaagctcc tcagagtgca gcacagttga taaccctttg cctggagaag gagaagaagc   3420
agaggctgaa cctatgaatt ccgatgagcc agaggcctgt ttcacagatg ttgtgtatg   3480
gaggttctca tgctgccaag ttaacataga gtcaggaaaa ggaaaaatct ggtggaacat   3540
caggaaaacc tgctacaaga ttgttgaaca cagttggttt gaaagcttca ttgtcctcat   3600
gatcctgctc agcagtggtg ccctggcttt tgaagatatt tatattgaaa ggaaaaagac   3660
cattaagatt atcctggagt atgcagacaa gatcttcact tacatcttca ttctggaaat   3720
gcttctaaaa tggatagcat atggttataa aacatatttc accaatgcct ggtgttggct   3780
ggatttccta attgttgatg tttctttggt tactttagtg gcaaacactc ttggctactc   3840
agatcttggc cccattaaat cccttcggac actgagagct ttaagacctc taagagcctt   3900
atctagattt gaaggaatga gggtcgttgt gaatgcactc ataggagcaa ttccttccat   3960
catgaatgtg ctacttgtgt gtcttatatt ctggctgata ttcagcatca tgggagtaaa   4020
tttgtttgct ggcaagttct atgagtgtat taacaccaca gatggggtcac ggtttcctgc   4080
```

```
aagtcaagtt ccaaatcgtt ccgaatgttt tgcccttatg aatgttagtc aaaatgtgcg    4140
atggaaaaac ctgaaagtga actttgataa tgtcggactt ggttacctat ctctgcttca    4200
agttgcaact tttaagggat ggacgattat tatgtatgca gcagtggatt ctgttaatgt    4260
agacaagcag cccaaatatg aatatagcct ctacatgtat atttattttg tcgtctttat    4320
catctttggg tcattcttca cttttgaactt gttcattggt gtcatcatag ataatttcaa    4380
ccaacagaaa aagaagcttg gaggtcaaga catctttatg acagaagaac agaagaaata    4440
ctataatgca atgaaaaagc tggggtccaa gaagccacaa aagccaattc ctcgaccagg    4500
gaacaaaatc caaggatgta tatttgacct agtgacaaat caagcctttg atattagtat    4560
catggttctt atctgtctca acatggtaac catgatggta gaaaaggagg gtcaaagtca    4620
acatatgact gaagttttat attggataaa tgtggttttt ataatccttt tcactggaga    4680
atgtgtgcta aaactgatct ccctcagaca ctactacttc actgtaggat ggaatatttt    4740
tgattttgtg gttgtgatta tctccattgt aggtatgttt ctagctgatt tgattgaaac    4800
gtattttgtg tcccctaccc tgttccgagt gatccgtctt gccaggattg gccgaatcct    4860
acgtctagtc aaaggagcaa aggggatccg cacgctgctc tttgctttga tgatgtccct    4920
tcctgcgttg tttaacatcg gcctcctgct cttcctggtc atgttcatct acgccatctt    4980
tggaatgtcc aactttgcct atgttaaaaa ggaagatgga attaatgaca tgttcaattt    5040
tgagaccttt ggcaacagta tgatttgcct gttccaaatt acaacctctg ctggctggga    5100
tggattgcta gcacctattc ttaacagtaa gccacccgac tgtgacccaa aaaagttca    5160 tcctggaagt tcagttgaag gagactgtgg taacccatct gttggaatat tctactttgt    5220
tagttatatc atcatatcct tcctggttgt ggtgaacatg tacattgcag tcatactgga    5280
gaattttagt gttgccactg aagaaagtac tgaacctctg agtgaggatg actttgagat    5340
gttctatgag gtttgggaga gtttgatcc cgatgcgacc cagtttatag agttctctaa    5400
actctctgat tttgcagctg ccctggatcc tcctcttctc atagcaaaac ccaacaaagt    5460
ccagctcatt gccatggatc tgcccatggt tagtggtgac cggatccatt gtcttgacat    5520
cttatttgct tttacaaagc gtgttttggg tgagagtggg gagatggatt ctcttcgttc    5580
acagatggaa gaaaggttca tgtctgcaaa tccttccaaa gtgtcctatg aacccatcac    5640
aaccacacta aaacgaaaac aagaggatgt gtctgctact gtcattcagc gtgcttatag    5700
acgttaccgc ttaaggcaaa atgtcaaaaa tatatcaagt atatacataa aagatggaga    5760
cagagatgat gatttactca ataaaaaaga tatggctttt gataatgtta atgagaactc    5820
aagtccagaa aaaacagatg ccacttcatc caccacctct ccaccttcat atgatagtgt    5880
aacaaagcca gacaaagaga aatatgaaca agacagaaca gaaaaggaag acaaagggaa    5940
agacagcaag gaaagcaaaa aatag                                          5965
```

<210> SEQ ID NO 77

<400> SEQUENCE: 77

000

<210> SEQ ID NO 78
<211> LENGTH: 468
<212> TYPE: PRT
<213> ORGANISM: Homo sapiens

<400> SEQUENCE: 78

```
Met Leu Ala Val Gly Cys Ala Leu Leu Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
            130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
            210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
            355                 360                 365

Val Ala Gly Gly Ser Leu Ala Phe Gly Thr Leu Leu Cys Ile Ala Ile
            370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
```

```
            420                 425                 430
Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
            450                 455                 460

Phe Phe Pro Arg
465

<210> SEQ ID NO 79
<211> LENGTH: 1407
<212> TYPE: DNA
<213> ORGANISM: Homo sapiens

<400> SEQUENCE: 79
atgctggccg tcggctgcgc gctgctggct gccctgctgg ccgcgccggg agcggcgctg      60
gccccaaggc gctgccctgc gcaggaggtg gcgagaggcg tgctgaccag tctgccagga     120
gacagcgtga ctctgacctg cccgggggta gagccgaaga caatgccac tgttcactgg      180 gtgctcagga agccggctgc aggctcccac cccagcagat gggctggcat gggaaggagg     240
ctgctgctga ggtcggtgca gctccacgac tctggaaaact attcatgcta ccgggccggc    300
cgcccagctg ggactgtgca cttgctggtg gatgttcccc ccgaggagcc ccagctctcc     360
tgcttccgga gagccccct cagcaatgtt gtttgtgagt gggtcctcg gagcacccca      420 tccctgacga caaaggctgt gctcttggtg aggaagtttc agaacagtcc ggccgaagac     480
ttccaggagc cgtgccagta ttcccaggag tcccagaagt tctcctgcca gttagcagtc     540
ccggagggag acagctcttt ctacatagtg tccatgtgcg tcgccagtag tgtcgggagc     600
aagttcagca aaactcaaac ctttcagggt tgtggaatct gcagcctga tccgcctgcc     660 aacatcacag tcactgccgt ggccagaaac ccccgctggc tcagtgtcac ctggcaagac     720
ccccactcct ggaactcatc tttctacaga ctacggtttg agctcagata tcgggctgaa     780
cggtcaaaga cattcacaac atggatggtc aaggacctcc agcatcactg tgtcatccac     840
gacgcctgga gcggcctgag gcacgtggtg cagcttcgtg cccaggagga gttcgggcaa     900
ggcgagtgga gcgagtggag cccggaggcc atgggcacgc cttggacaga atccaggagt     960
cctccagctg agaacgaggt gtccacccc atgcaggcac ttactactaa taaagacgat     1020
gataatattc tcttcagaga ttctgcaaat gcgacaagcc tcccagtgca agattcttct    1080
tcagtaccac tgcccacatt cctggttgct ggagggagcc tggccttcgg aacgctcctc    1140
tgcattgcca ttgttctgag gttcaagaag acgtggaagc tgcgggctct gaaggaaggc    1200
aagacaagca tgcatccgcc gtactctttg gggcagctgg tcccggagag gcctcgaccc    1260 acccagtgc ttgttcctct catctcccca ccggtgtccc cagcagcct ggggtctgac     1320 aatacctcga gccacaaccg accagatgcc agggacccac ggagccctta tgacatcagc    1380
aatacagact acttcttccc cagatag                                        1407

<210> SEQ ID NO 80
<211> LENGTH: 990
<212> TYPE: DNA
<213> ORGANISM: Homo sapiens

<400> SEQUENCE: 80
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
```

```
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 81
<211> LENGTH: 330
<212> TYPE: PRT
<213> ORGANISM: Homo sapiens

<400> SEQUENCE: 81

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 82
<211> LENGTH: 978
<212> TYPE: DNA
<213> ORGANISM: Homo sapiens

<400> SEQUENCE: 82
gcctccacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                   978

<210> SEQ ID NO 83
<211> LENGTH: 326
<212> TYPE: PRT
<213> ORGANISM: Homo sapiens

<400> SEQUENCE: 83

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
             50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 84
<211> LENGTH: 298
<212> TYPE: DNA
<213> ORGANISM: Homo sapiens

<400> SEQUENCE: 84
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtag cataggctat   180
gcggactctg tgaagggccg attcaccatc tccagagaca cgccaagaa ctccctgtat   240 ctgcaaatga acagtctgag agctgaggac acggccttgt attactgtgc aaaagata    298

<210> SEQ ID NO 85
<211> LENGTH: 99
<212> TYPE: PRT
<213> ORGANISM: Homo sapiens
```

<400> SEQUENCE: 85

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 86
<211> LENGTH: 296
<212> TYPE: DNA
<213> ORGANISM: Homo sapiens

<400> SEQUENCE: 86
gaggtgcagc tggtggagtc tgggggaggc ttggtccagc ctggggggtc cctgagactc     60
tcctgtgcag cctctggatt cacctttagt agctattgga tgagctgggt ccgccaggct    120
ccagggaagg ggctggagtg ggtggccaac ataaagcaag atggaagtga aaatactat     180 gtggactctg tgaagggccg attcaccatc tccagagaca cgccaagaa ctcactgtat     240 ctgcaaatga acagcctgag agccgaggac acggctgtgt attactgtgc gagaga        296

<210> SEQ ID NO 87
<211> LENGTH: 98
<212> TYPE: PRT
<213> ORGANISM: Homo sapiens

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 88
<211> LENGTH: 50
<212> TYPE: DNA
<213> ORGANISM: Homo sapiens

<400> SEQUENCE: 88
tgatgctttt gatatctggg gccaagggac aatggtcacc gtctcttcag                50

<210> SEQ ID NO 89
<211> LENGTH: 16
<212> TYPE: PRT
<213> ORGANISM: Homo sapiens

<400> SEQUENCE: 89

Asp Ala Phe Asp Ile Trp Gly Gln Gly Thr Met Val Thr Val Ser Ser
1               5                   10                  15

<210> SEQ ID NO 90
<211> LENGTH: 63
<212> TYPE: DNA
<213> ORGANISM: Homo sapiens

<400> SEQUENCE: 90
attactacta ctactacggt atggacgtct gggggcaagg gaccacggtc accgtctcct    60
cag                                                                 63

<210> SEQ ID NO 91
<211> LENGTH: 20
<212> TYPE: PRT
<213> ORGANISM: Homo sapiens

<400> SEQUENCE: 91

Tyr Tyr Tyr Tyr Tyr Gly Met Asp Val Trp Gly Gln Gly Thr Thr Val
1               5                   10                  15

Thr Val Ser Ser
            20

<210> SEQ ID NO 92
<211> LENGTH: 321
<212> TYPE: DNA
<213> ORGANISM: Homo sapiens

<400> SEQUENCE: 92
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321

<210> SEQ ID NO 93
<211> LENGTH: 107
<212> TYPE: PRT
<213> ORGANISM: Homo sapiens

<400> SEQUENCE: 93

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 94
<211> LENGTH: 312
<212> TYPE: DNA
<213> ORGANISM: Homo sapiens

<400> SEQUENCE: 94
cccaaggcca accccacggt cactctgttc ccgccctcct ctgaggagct ccaagccaac      60
aaggccacac tagtgtgtct gatcagtgac ttctacccgg agctgtgaca gtggcttgg     120 aaggcagatg gcagccccgt caaggcggga gtggagacga ccaaaccctc caaacagagc    180
aacaacaagt acgcggccag cagctacctg agcctgacgc cgagcagtg gaagtcccac     240 agaagctaca gctgccaggt cacgcatgaa gggagcaccg tggagaagac agtggcccct   300
acagaatgtt ca                                                          312

<210> SEQ ID NO 95
<211> LENGTH: 104
<212> TYPE: PRT
<213> ORGANISM: Homo sapiens

<400> SEQUENCE: 95

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 96
<211> LENGTH: 287
<212> TYPE: DNA
<213> ORGANISM: Homo sapiens

<400> SEQUENCE: 96
gacatccaga tgacccagtc tccatcttcc gtgtctgcat ctgtaggaga cagagtcacc      60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat tcactctca ccatcagcag cctgcagcct     240
gaagattttg caacttacta ttgtcaacag gctaacagtt tccctcc                 287

<210> SEQ ID NO 97
<211> LENGTH: 95
<212> TYPE: PRT
<213> ORGANISM: Homo sapiens
```

<400> SEQUENCE: 97

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 98
<211> LENGTH: 287
<212> TYPE: DNA
<213> ORGANISM: Homo sapiens

<400> SEQUENCE: 98
gaaattgtgt tgacacagtc tccagccacc ctgtctttgt ctccagggga aagagccacc    60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagcaact ggcctcc                287

<210> SEQ ID NO 99
<211> LENGTH: 95
<212> TYPE: PRT
<213> ORGANISM: Homo sapiens

<400> SEQUENCE: 99

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 100
<211> LENGTH: 39
<212> TYPE: DNA
<213> ORGANISM: Homo sapiens

<400> SEQUENCE: 100
tgtacacttt tggccagggg accaagctgg agatcaaac                           39

<210> SEQ ID NO 101
<211> LENGTH: 12
<212> TYPE: PRT

```
<213> ORGANISM: Homo sapiens

<400> SEQUENCE: 101

Tyr Thr Phe Gly Gln Gly Thr Lys Leu Glu Ile Lys
1               5                   10

<210> SEQ ID NO 102
<211> LENGTH: 38
<212> TYPE: DNA
<213> ORGANISM: Homo sapiens

<400> SEQUENCE: 102
gctcactttc ggcggaggga ccaaggtgga gatcaaac                              38

<210> SEQ ID NO 103
<211> LENGTH: 12
<212> TYPE: PRT
<213> ORGANISM: Homo sapiens

<400> SEQUENCE: 103

Leu Thr Phe Gly Gly Gly Thr Lys Val Glu Ile Lys
1               5                   10

<210> SEQ ID NO 104
<211> LENGTH: 446
<212> TYPE: PRT
<213> ORGANISM: Homo sapiens

<400> SEQUENCE: 104

Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
```

```
                    225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Thr Tyr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 105
<211> LENGTH: 214
<212> TYPE: PRT
<213> ORGANISM: Homo sapiens

<400> SEQUENCE: 105

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 106
<211> LENGTH: 449
<212> TYPE: PRT
<213> ORGANISM: Homo sapiens

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Phe
            20                  25                  30

Ala Met Ser Trp Val Arg Gln Ala Pro Gly Lys Gly Leu Glu Trp Val
        35                  40                  45

Ala Lys Ile Ser Pro Gly Gly Ser Trp Thr Tyr Tyr Ser Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Trp Gly Tyr Tyr Ala Leu Asp Ile Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

-continued

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 107
<211> LENGTH: 213
<212> TYPE: PRT
<213> ORGANISM: Homo sapiens

<400> SEQUENCE: 107

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ile Ser Val Ser Tyr Met
            20                  25                  30

Tyr Trp Tyr Gln Gln Lys Pro Gly Gln Ala Pro Arg Leu Leu Ile Tyr
        35                  40                  45

Asp Met Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Met Gln Trp Ser Gly Tyr Pro Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 108

```
<211> LENGTH: 24
<212> TYPE: DNA
<213> ORGANISM: Homo sapiens

<400> SEQUENCE: 108
ggattcacct ttgatgatta tgcc                                          24

<210> SEQ ID NO 109
<211> LENGTH: 8
<212> TYPE: PRT
<213> ORGANISM: Homo sapiens

<400> SEQUENCE: 109

Gly Phe Thr Phe Asp Asp Tyr Ala
1               5

<210> SEQ ID NO 110
<211> LENGTH: 114
<212> TYPE: DNA
<213> ORGANISM: Homo sapiens

<400> SEQUENCE: 110
ggctatgcgg actctgtgaa gggccgattc accatctcca gagacaacgc caagaactcc    60
ctgtatctgc aaatgaacag tctgagagct gaggacacgg ccttgtatta ctgt         114

<210> SEQ ID NO 111
<211> LENGTH: 38
<212> TYPE: PRT
<213> ORGANISM: Homo sapiens

<400> SEQUENCE: 111

Gly Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Leu Tyr Tyr Cys
        35

<210> SEQ ID NO 112
<211> LENGTH: 23
<212> TYPE: DNA
<213> ORGANISM: Homo sapiens

<400> SEQUENCE: 112
cagcagcgta gcaactggcc tcc                                           23

<210> SEQ ID NO 113
<211> LENGTH: 7
<212> TYPE: PRT
<213> ORGANISM: Homo sapiens

<400> SEQUENCE: 113

Gln Gln Arg Ser Asn Trp Pro
1               5

<210> SEQ ID NO 114
<211> LENGTH: 108
<212> TYPE: DNA
<213> ORGANISM: Homo sapiens

<400> SEQUENCE: 114
aacagggcca ctggcatccc agccaggttc agtggcagtg ggtctgggac agacttcact    60
```
ctcaccatca gcagcctaga gcctgaagat tttgcagttt attactgt                 108

<210> SEQ ID NO 115
<211> LENGTH: 36
<212> TYPE: PRT
<213> ORGANISM: Homo sapiens

<400> SEQUENCE: 115

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Val Tyr Tyr Cys
        35

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Val Phe Ala Gln Ser Ile Pro
1               5

<210> SEQ ID NO 117
<211> LENGTH: 296
<212> TYPE: DNA
<213> ORGANISM: Homo sapiens
<220> FEATURE:
<221> NAME/KEY: CDS
<222> LOCATION: (1)..(294)

<400> SEQUENCE: 117 gag gtg cag ctg ttg gag tct ggg gga ggc ttg gta cag cct ggg ggg        48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat        96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc       144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg       192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt       288
Leu Gln Met Asn Ser Leu Arg Ala Glu Asp Thr Ala Val Tyr Tyr Cys
                85                  90                  95 gcg aaa ga                                                             296
Ala Lys <210> SEQ ID NO 118
<211> LENGTH: 98
<212> TYPE: PRT
<213> ORGANISM: Homo sapiens

<400> SEQUENCE: 118

| | | | | | | | | | | | | |
|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
| | | | 35 | | | | | 40 | | | | | 45 | | |

| Ser | Ala | Ile | Ser | Gly | Ser | Gly | Gly | Ser | Thr | Tyr | Tyr | Ala | Asp | Ser | Val |
| | | 50 | | | | | 55 | | | | | 60 | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

Ala Lys

<210> SEQ ID NO 119
<211> LENGTH: 294
<212> TYPE: DNA
<213> ORGANISM: Homo sapiens
<220> FEATURE:
<221> NAME/KEY: CDS
<222> LOCATION: (1)..(294)

<400> SEQUENCE: 119

| gag | gtg | cag | ctg | ttg | gag | tct | ggg | gga | ggc | ttg | gta | cag | cct | ggg | ggg | 48 |
|---|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly | |
| 1 | | | | 5 | | | | | 10 | | | | | 15 | | |

| tcc | ctg | aga | ctc | tcc | tgt | gca | gcc | tct | gga | ttc | acc | ttt | agc | agc | tat | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |

| gcc | atg | agc | tgg | gtc | cgc | cag | gct | cca | ggg | aag | ggg | ctg | gag | tgg | gtc | 144 |
|---|---|---|---|---|---|---|---|---|---|---|---|---|---|---|---|---|
| Ala | Met | Ser | Trp | Val | Arg | Gln | Ala | Pro | Gly | Lys | Gly | Leu | Glu | Trp | Val | |
| | | | 35 | | | | | 40 | | | | | 45 | | | |

| tca | gct | att | agt | ggt | agt | ggt | ggt | agc | aca | tac | tac | gca | gac | tcc | gtg | 192 |
|---|---|---|---|---|---|---|---|---|---|---|---|---|---|---|---|---|
| Ser | Ala | Ile | Ser | Gly | Ser | Gly | Gly | Ser | Thr | Tyr | Tyr | Ala | Asp | Ser | Val | |
| | | 50 | | | | | 55 | | | | | 60 | | | | |

| aag | ggc | cgg | ttc | acc | atc | tcc | aga | gac | aat | tcc | aag | aac | acg | ctg | tat | 240 |
|---|---|---|---|---|---|---|---|---|---|---|---|---|---|---|---|---|
| Lys | Gly | Arg | Phe | Thr | Ile | Ser | Arg | Asp | Asn | Ser | Lys | Asn | Thr | Leu | Tyr | |
| 65 | | | | | 70 | | | | | 75 | | | | | 80 | |

| ctg | caa | atg | aac | agc | ctg | aga | gcc | gag | gac | acg | gcc | gta | tat | tac | tgt | 288 |
|---|---|---|---|---|---|---|---|---|---|---|---|---|---|---|---|---|
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |

| gcg | aaa | | | | | | | | | | | | | | | 294 |
|---|---|---|---|---|---|---|---|---|---|---|---|---|---|---|---|---|
| Ala | Lys | | | | | | | | | | | | | | | |

<210> SEQ ID NO 120
<211> LENGTH: 296
<212> TYPE: DNA
<213> ORGANISM: Homo sapiens
<220> FEATURE:
<221> NAME/KEY: CDS
<222> LOCATION: (1)..(294)

<400> SEQUENCE: 120

| gag | gtg | cag | ctg | ttg | gag | tct | ggg | gga | ggc | ttg | gta | cag | cct | ggg | ggg | 48 |
|---|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly | |
| 1 | | | | 5 | | | | | 10 | | | | | 15 | | |

| tcc | ctg | aga | ctc | tcc | tgt | gca | gcc | tct | gga | ttc | acc | ttt | agc | agc | tat | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |

| gcc | atg | agc | tgg | gtc | cgc | cag | gct | cca | ggg | aag | ggg | ctg | gag | tgg | gtc | 144 |
|---|---|---|---|---|---|---|---|---|---|---|---|---|---|---|---|---|
| Ala | Met | Ser | Trp | Val | Arg | Gln | Ala | Pro | Gly | Lys | Gly | Leu | Glu | Trp | Val | |

```
               35                  40                  45
tca gct att agt ggt agt ggt ggt agc aca tac tac gga gac tcc gtg    192
Ser Ala Ile Ser Gly Ser Gly Gly Ser Thr Tyr Tyr Gly Asp Ser Val
 50                  55                  60 aag ggc cgg ttc acc atc tca aga gac aat tcc aag aac acg ctg tat    240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gcc gta tat tac tgt    288
Leu Gln Met Asn Ser Leu Arg Ala Glu Asp Thr Ala Val Tyr Tyr Cys
                 85                  90                  95 gcg aaa ga                                                          296
Ala Lys

<210> SEQ ID NO 121
<211> LENGTH: 98
<212> TYPE: PRT
<213> ORGANISM: Homo sapiens

<400> SEQUENCE: 121

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 122
<211> LENGTH: 294
<212> TYPE: DNA
<213> ORGANISM: Homo sapiens
<220> FEATURE:
<221> NAME/KEY: CDS
<222> LOCATION: (1)..(294)

<400> SEQUENCE: 122 gag gtg cag ctg ttg gag tct ggg gga ggc ttg gta cag cct ggg ggg     48
Glu Val Gln Leu Leu Glu Ser Gly Gly Gly Leu Val Gln Pro Gly Gly
  1               5                  10                  15 tcc ctg aga ctc tcc tgt gca gcc tct gga ttc acc ttt agc agc tat     96
Ser Leu Arg Leu Ser Cys Ala Ala Ser Gly Phe Thr Phe Ser Ser Tyr
             20                  25                  30 gcc atg agc tgg gtc cgc cag gct cca ggg aag ggg ctg gag tgg gtc    144
Ala Met Ser Trp Val Arg Gln Ala Pro Gly Lys Gly Leu Glu Trp Val
         35                  40                  45 tca gtt att tat agc ggt ggt agt agc aca tac tat gca gac tcc gtg    192
Ser Val Ile Tyr Ser Gly Gly Ser Ser Thr Tyr Tyr Ala Asp Ser Val
 50                  55                  60 aag ggc cgg ttc acc atc tcc aga gat aat tcc aag aac acg ctg tat    240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gcc gta tat tac tgt    288
Leu Gln Met Asn Ser Leu Arg Ala Glu Asp Thr Ala Val Tyr Tyr Cys
                 85                  90                  95
```

```
gcg aaa                                                                                          294
Ala Lys <210> SEQ ID NO 123
<211> LENGTH: 98
<212> TYPE: PRT
<213> ORGANISM: Homo sapiens

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 124
<211> LENGTH: 296
<212> TYPE: DNA
<213> ORGANISM: Homo sapiens
<220> FEATURE:
<221> NAME/KEY: CDS
<222> LOCATION: (1)..(294)

<400> SEQUENCE: 124 gag gtg cag ctg ttg gag tct ggg gga ggc ttg gta cag cct ggg ggg         48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat         96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc        144
Ala Met Ser Trp Val Arg Gln Ala Pro Gly Lys Gly Leu Glu Trp Val
        35                  40                  45 tca gtt att tat agc ggt ggt agt agc aca tac tat gca gac tcc gtg        192
Ser Val Ile Tyr Ser Gly Gly Ser Ser Thr Tyr Tyr Ala Asp Ser Val
    50                  55                  60 aag ggc cgg ttc acc atc tcc aga gat aat tcc aag aac acg ctg tat        240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt        288
Leu Gln Met Asn Ser Leu Arg Ala Glu Asp Thr Ala Val Tyr Tyr Cys
                85                  90                  95 gcg aaa ga                                                              296
Ala Lys <210> SEQ ID NO 125
<211> LENGTH: 294
<212> TYPE: DNA
<213> ORGANISM: Homo sapiens
<220> FEATURE:
<221> NAME/KEY: CDS
<222> LOCATION: (1)..(294)
```

```
<400> SEQUENCE: 125 gag gtg cag ctg ttg gag tct ggg gga ggc ttg gta cag cct ggg ggg       48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45 tca gct att tat agc agt ggt agt agc aca tac tat gca gac tcc gtg      192
Ser Ala Ile Tyr Ser Ser Gly Ser Ser Thr Tyr Tyr Ala Asp Ser Val
    50                  55                  60 aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt      288
Leu Gln Met Asn Ser Leu Arg Ala Glu Asp Thr Ala Val Tyr Tyr Cys
                85                  90                  95 gcg aaa                                                              294
Ala Lys <210> SEQ ID NO 126
<211> LENGTH: 98
<212> TYPE: PRT
<213> ORGANISM: Homo sapiens

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Tyr Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

TARGETING HUMAN NAV1.7 VARIANTS FOR TREATMENT OF PAIN

CROSS-REFERENCE TO RELATED APPLICATIONS

This application is a continuation-in-part of U.S. application Ser. No. 14/331,730 filed Jul. 15, 2014, the entire content of which is incorporated by reference.

SEQUENCE LISTING

The instant application contains a Sequence Listing which has been submitted electronically in ASCII format and is hereby incorporated by reference in its entirety. Said ASCII copy, created on Aug. 28, 2014, is named 069496-082415-CIP_SL.txt and is 308,554 bytes in size.

TECHNICAL FIELD

The technology described herein relates to ligands, e.g., antibodies for the treatment of disease.

BACKGROUND

It is recognized that individual humans differ in their sequence and recently several individuals have had their genomes sequenced, for instance James Watson and Craig Venter. Comparison of the genome sequence of individuals has revealed differences in their sequences in both coding and non-coding parts of the genome. Some of these variations in humans are significant and contribute to phenotypic differences between individuals. In extreme cases these will result in genetic disease. The 1000 Genomes Project has the objective of cataloguing sequences in the human genome, involving sequencing the genomes of a very large sampling of individuals from diverse art-recognized human ethnic populations.

SUMMARY

Through the application of human genetic variation analysis and rationally-designed sequence selection the present invention provides for improved human patient diagnosis and therapy. Importantly, the invention enables tailored medicines that address individual human patient genotypes or phenotypes.

The inventor's analysis of large numbers of naturally-occurring genomic human TOI sequences reveals that there is significant variation across diverse human populations and provides for the ability for correlation between individual human patients and tailored medical and diagnostic approaches addressing the target. The technical applications of these findings, as per the present invention, thus contribute to better treatment, prophylaxis and diagnosis in humans and provides for patient benefit by enabling personalized medicines and therapies. This provides advantages of better prescribing, less wastage of medications and improved chances of drug efficacy and better diagnosis in patients.

Furthermore, the inventor surprisingly realised that some rarer natural forms, although present in humans at much lower frequencies than the common form, nevertheless are represented in multiple and ethnically-diverse human populations and usually with many human examples per represented ethnic population. Thus, the inventor realised that targeting such rarer forms would provide for effective treatment, prophylaxis or diagnosis across many human ethnic populations, thereby extending the utility of the present invention and better serving patients in those populations.

With this, the inventor realised that there is significant industrial and medical application for the invention in terms of guiding the choice of an anti-TOI ligand for administration to human patients for therapy and/or prophylaxis of TOI-mediated or associated diseases and conditions. In this way, the patient receives drugs and ligands that are tailored to their needs—as determined by the patient's genetic or phenotypic makeup. Hand-in-hand with this, the invention provides for the genotyping and/or phenotyping of patients in connection with such treatment, thereby allowing a proper match of drug to patient. This increases the chances of medical efficacy, reduces the likelihood of inferior treatment using drugs or ligands that are not matched to the patient (eg, poor efficacy and/or side-effects) and avoids pharmaceutical mis-prescription and waste.

To this end, the invention provides:—

In a First Configuration

A method of treating or preventing a disease or condition in a human, wherein the disease or condition is mediated by a Target of Interest (TOI), wherein the TOI is present in humans as different polymorphic variants, the method comprising a. Administering to the human an anti-TOI ligand to target a TOI variant in the human and treat or prevent said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%;
wherein
    b. Before step (a) said human has been or is genotyped as positive for said nucleotide sequence or phenotyped as positive for said TOI variant.

In a Second Configuration

A method of treating or preventing a disease or condition in a human, wherein the disease or condition is mediated by a Target of Interest (TOI), wherein the TOI is present in humans as different polymorphic variants, the method comprising a. Administering to the human an anti-TOI ligand to target a TOI variant in the human and treat or prevent said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%; wherein
    b. before step (a) the ligand has been or is determined as capable of binding to said TOI variant.

In a Third Configuration

A method of treating or preventing a disease or condition in a human, wherein the disease or condition is mediated by a Target of Interest (TOI), wherein the TOI is present in humans as different polymorphic variants, the method comprising a. Administering to the human an anti-TOI ligand to target a TOI variant in the human and treat or prevent said disease or condition, wherein the TOI in said human is a variant encoded by a nucleotide sequence having a cumulative human allele frequency of more than 50% and/or having a total human genotype frequency of more than 50%; wherein
    b. Before step (a) said human has been or is genotyped as negative for a variant nucleotide sequence having a cumulative human allele frequency of less than 50% and/or having a total human genotype frequency of less than 50%; or phenotyped as negative for a TOI variant encoded by a nucleotide sequence having a cumulative human allele frequency of less than 50% and/or having a total human genotype frequency of less than 50%.

In a Fourth Configuration

An anti-human TOI ligand for use in a method of treating and/or preventing a TOI-mediated disease or condition in a human, wherein the TOI is present in humans as different polymorphic variants and wherein the genome of said human comprises a TOI nucleotide sequence having a cumulative human allele frequency of less than 50% and/or a total human genotype frequency of less than 50%, the method comprising administering the ligand to the human.

In a Fifth Configuration

A ligand that binds a human TOI comprising an amino acid sequence encoded by a TOI nucleotide sequence having a cumulative human allele frequency of less than 50% and/or a total human genotype frequency of less than 50%, for use in a method comprising the step of using the ligand to target said TOI in a human to treat and/or prevent a disease or condition mediated by TOI, the method comprising administering the ligand to the human.

In a Sixth Configuration

A pharmaceutical composition or kit for treating or preventing a condition or disease mediated by a TOI.

In a Seventh Configuration

A method of producing an anti-human TOI antibody binding site, the method comprising obtaining a plurality of anti-TOI antibody binding sites, screening the antibody binding sites for binding to a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody binding site that binds in the screening step.

In a Eighth Configuration

A method of producing an anti-human TOI antibody, the method comprising immunising a non-human vertebrate (eg, a mouse or a rat) with a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody that binds a TOI comprising an amino acid sequence encoded by a TOI nucleotide sequence having a cumulative human allele frequency of less than 50% and/or a total human genotype frequency of less than 50%, and optionally producing a TOI-binding fragment or derivative of the isolated antibody.

In a Ninth Configuration

A kit for TOI genotyping a human, wherein the kit comprises a nucleic acid comprising a nucleotide sequence that specifically hybridises to a TOI nucleotide sequence selected having a cumulative human allele frequency of less than 50% and/or a total human genotype frequency of less than 50% or an RNA transcript thereof; and/or the nucleic acid comprises a nucleotide sequence that comprises at least 10 contiguous nucleotides of a TOI nucleotide sequence having a cumulative human allele frequency of less than 50% and/or a total human genotype frequency of less than 50% or is an antisense sequence thereof.

In a Tenth Configuration

Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for treating and/or preventing a TOI-mediated disease or condition in a human whose genome comprises a TOI nucleotide sequence having a cumulative human allele frequency of less than 50% and/or having a total human genotype frequency of less than 50%.

In a Eleventh Configuration

Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for targeting said TOI in a human to treat and/or prevent a disease or condition mediated by TOI.

In a Twelfth Configuration

A method of targeting a TOI for treating and/or preventing a TOI-mediated disease or condition in a human, the method comprising administering an anti-TOI ligand to a human comprising a TOI nucleotide sequence selected having a cumulative human allele frequency of less than 50% and/or a total human genotype frequency of less than 50%, whereby a TOI encoded by said nucleotide sequence is targeted.

In a Thirteenth Configuration

A method of TOI genotyping a nucleic acid sample of a human, the method comprising identifying in the sample the presence of a TOI nucleotide sequence having a cumulative human allele frequency of less than 50% and/or having a total human genotype frequency of less than 50%.

In a Fourteenth Configuration

A method of TOI typing a protein sample of a human, the method comprising identifying in the sample the presence of a TOI amino acid sequence encoded by a TOI nucleotide sequence having a cumulative human allele frequency of less than 50% and/or having a total human genotype frequency of less than 50%.

In an example, the TOI is a human TOI selected from the group consisting of PCSK9, VEGF-A and IL6 receptor.

A Fifteenth Configuration provides a ligand, method, use, kit or composition of the invention, wherein (i) the ligand (eg, antibody or fragment) comprises
   (a) a variable domain that is encoded by a human V region nucleotide sequence, wherein the V nucleotide sequence is derived from recombination of human VH, D and JH gene segments or human VL and JL gene segments; or
   (b) a constant region domain encoded by a C region gene segment;
   Wherein a first gene segment of said gene segments of (a), or said C region gene segment of (b) comprises a first single nucleotide polymorphism (SNP) encoding a first amino acid polymorphism; and
(ii) the genome of said human comprises said first SNP or wherein said human expresses (a') an antibody variable domain comprising said first amino acid polymorphism or (b') an antibody constant domain comprising said first amino acid polymorphism.

A Sixteenth Configuration provides the ligand, method, use, kit or composition of the invention, wherein the ligand comprises or consists of an antibody or fragment that comprises a human antibody variable domain derived from the recombination of a human V gene segment and a human J gene segment (and optionally a human D gene segment when the variable domains are VH domains); and wherein the genome of the human comprises said human V gene segment and/or the human expresses antibodies comprising antibody variable domains derived from the recombination of said human V gene segment and a human J gene segment (and optionally a human D gene segment).

A Sixteenth Configuration provides the ligand, method, use, kit or composition of the invention, wherein the ligand (eg, comprising or consisting of an antibody or fragment or an Fc-fused human PCSK9 receptor) comprises a human heavy chain constant domain encoded by a first constant region nucleotide sequence; and wherein the genome of the human comprises a heavy chain constant region nucleotide sequence that is identical to said first constant region nucleotide sequence and/or the human expresses antibodies comprising said human constant domain.

A Seventeenth Configuration provides the ligand, method, use, kit or composition of the invention, wherein the ligand (eg, comprising or consisting of an antibody or fragment or an Fc-fused TOI receptor) comprises a human gamma-1 heavy chain constant region that comprises an Asp corresponding to position 204 of SEQ ID NO: 42 or a Leu corresponding to position 206 of SEQ ID NO: 42 and wherein the genome of the human comprises a gamma-1 heavy chain constant region nucleotide sequence that encodes such an Asp or Leu or the human expresses antibodies comprising human gamma-1 constant regions comprising such an Asp or Leu.

A Eighteenth Configuration provides the ligand, method, use, kit or composition of the invention, wherein the ligand (eg, comprising or consisting of an antibody or fragment or an Fc-fused TOI receptor) comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44; and wherein the genome of the human comprises a gamma-2 heavy chain constant region nucleotide sequence that encodes such a selected amino acid or the human expresses antibodies comprising human gamma-2 constant regions comprising such a selected amino acid.

A Ninteenth Configuration provides the ligand, method, use, kit or composition of the invention, wherein the ligand (eg, comprising or consisting of an antibody or fragment or an Fc-fused TOI receptor) comprises a human kappa light chain constant region that comprises a Val corresponding to position 84 of SEQ ID NO: 50 or a Cys corresponding to position 87 of SEQ ID NO: 50; and wherein the genome of the human comprises a kappa light chain constant region nucleotide sequence that encodes such a Val or Cys or the human expresses antibodies comprising human kappa light chain constant regions comprising such a Val or Cys.

A Twentieth Configuration provides the ligand, method, use, kit or composition of the invention, wherein the ligand comprises or consists of an antibody or fragment, wherein the antibody or fragment comprises a VH domain that is derived from the recombination of a human VH gene segment, a human D gene segment and a human JH gene segment, wherein the VH gene segment is selected from the group consisting of (i) IGHV1-18*01 and the genome of the human comprises a human IGHV1-18*01 nucleotide sequence or the human expresses antibodies comprising variable domains derived from the recombination of human IGHV1-18*01; or (ii) IGVH1-46*01 and the genome of the human comprises a human IGHV1-46*01 nucleotide sequence or the human expresses antibodies comprising variable domains derived from the recombination of human IGHV1-46*01.

A Twenty-First Configuration provides the ligand, method, use, kit or composition of the invention, wherein the ligand comprises or consists of an antibody or fragment, wherein the antibody or fragment comprises a VL domain that is derived from the recombination of a human VL gene segment and a human JL gene segment, wherein the VL gene segment is selected from the group consisting of (i) IGKV4-1*01 and the genome of the human comprises a human IGKV4-1*01 nucleotide sequence or the human expresses antibodies comprising variable domains derived from the recombination of human IGKV4-1*01; (ii) IGLV2-14*01 and the genome of the human comprises a human IGLV2-14*01 nucleotide sequence or the human expresses antibodies comprising variable domains derived from the recombination of human IGLV2-14*01; or (iii) IGKV1-13*02 and the genome of the human comprises a human IGKV1-13*02 nucleotide sequence or the human expresses antibodies comprising variable domains derived from the recombination of human IGKV1-13*02.

A Twenty-Second Configuration provides a method of treating or reducing the risk of an IL4Ra-mediated disease or condition in a human in need thereof, the method comprising administering to said human a ligand (eg, an antibody or antibody fragment) that specifically binds a human IL4RA protein that comprises a mutation selected from the group consisting of I75V, E400A, C431R, S503P, Q576R and S752A in SEQ ID NO: 67. As explained further below, these amino acid variations are found in naturally-occurring IL-4Ra variants in humans found in many populations. Said human comprises a nucleotide sequence encoding said IL4RA protein comprising said mutation selected from the group consisting of I75V, E400A, C431R, S503P, Q576R and S752A in SEQ ID NO: 67.

A Twenty-Third Configuration provides a ligand (eg, an antibody or antibody fragment) for treating or reducing the risk of an IL4Ra-mediated disease or condition in a human in need thereof, the method comprising administering to said human said ligand, wherein the ligand specifically binds a human IL4RA protein that comprises a mutation selected from the group consisting of I75V, E400A, C431R, S503P, Q576R and S752A in SEQ ID NO: 67. Said human comprises a nucleotide sequence encoding said IL4RA protein comprising said mutation selected from the group consisting of I75V, E400A, C431R, S503P, Q576R and S752A in SEQ ID NO: 67.

A Twenty-Fourth Configuration provides provides a method of targeting IL4Ra in a human, the method comprising administering to said human a ligand (eg, an antibody or antibody fragment) that specifically binds a human IL4RA protein that comprises a mutation selected from the group consisting of I75V, E400A, C431R, S503P, Q576R and S752A in SEQ ID NO: 67. Said human comprises a nucleotide sequence encoding said IL4RA protein comprising said mutation selected from the group consisting of I75V, E400A, C431R, S503P, Q576R and S752A in SEQ ID NO: 67. In an example, the human is suffering from or at risk of an IL4Ra-mediated disease or condition. In an example, the method treats or reduces the risk of an IL4Ra-mediated disease or condition in the human.

A Twenty-Fifth Configuration provides a ligand (eg, an antibody or antibody fragment) for targeting IL4Ra in a human, the method comprising administering to said human said ligand, wherein the ligand specifically binds a human IL4RA protein that comprises a mutation selected from the group consisting of I75V, E400A, C431R, S503P, Q576R and S752A in SEQ ID NO: 67. Said human comprises a nucleotide sequence encoding said IL4RA protein comprising said mutation selected from the group consisting of I75V, E400A, C431R, S503P, Q576R and S752A in SEQ ID NO: 67. In an example, the human is suffering from or at risk of an IL4Ra-mediated disease or condition. In an example, the method treats or reduces the risk of an IL4Ra-mediated disease or condition in the human.

In an embodiment of any of the 21-25$^{th}$ configurations, (i) the antibody or fragment comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and wherein (ii) said human comprises a nucleotide sequence encoding said IL4RA protein comprising said mutation selected from the group consisting of I75V, E400A, C431R, S503P, Q576R and S752A in SEQ ID NO: 67.

Additionally or alternatively, in an embodiment of any of the 21-25$^{th}$ configurations, (i) the antibody or fragment comprises a human gamma-4 heavy chain constant region that comprises a Leu at position 189 shown in SEQ ID NO: 73 or an Arg at position 289 shown in SEQ ID NO: 73 and wherein said human comprises an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and wherein (ii) said human comprises a nucleotide sequence encoding said IL4RA protein comprising said mutation selected from the group consisting of I75V, E400A, C431R, S503P, Q576R and S752A in SEQ ID NO: 67.

Examples of any configuration or relating to any TOI are as follows:—

(i) wherein the ligand comprises a VH domain derived from the recombination of a human VH segment (eg, human VH3-23*04), a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40.

(ii) wherein the ligand comprises a VH domain derived from the recombination of human VH segment IGHV3-7*01, a human D gene segment and a human JH segment, and wherein said human comprises a IGHV3-7*01 VH gene segment or the human expresses VH domains derived from the recombination of human VH segment IGHV3-7*01, a human D gene segment and a human JH segment.

(iii) wherein the ligand comprises a Vκ domain derived from the recombination of human Vκ segment IGKV1-12*01 and a human Jκ segment, and wherein said human comprises a IGKV1-12*01 Vκ gene segment or the human expresses Vκ domains derived from the recombination of human Vκ segment IGKV1-12*01 and a human Jκ segment.

(iv) wherein the ligand comprises a Vκ domain derived from the recombination of a human Vκ segment and a human Jκ segment, the human Vκ segment encoding (i) a CDR3 comprising a Pro at position 7 shown in SEQ ID NO: 36 and wherein said human comprises a Vκ gene segment encoding a CDR3 comprising a Pro at position 7 shown in SEQ ID NO: 36, or the human expresses Vκ domains that comprise a CDR3 comprising a Pro at position 7 shown in SEQ ID NO: 36; or (ii) a FW3 comprising a Ser at position 15 shown in SEQ ID NO: 38 and wherein said human comprises a Vκ gene segment encoding a FW3 comprising a Ser at position 15 shown in SEQ ID NO: 38 or the human expresses Vκ domains that comprise a FW3 comprising a Ser at position 15 shown in SEQ ID NO: 38.

(v) wherein the ligand comprises a human gamma-1 heavy chain constant region that comprises an Asp at position 204 shown in SEQ ID NO: 4 or a Leu at position 206 shown in SEQ ID NO: 4 and wherein said human comprises (i) an IGHG1*01 human heavy chain constant region gene segment, or the human expresses antibodies comprising human gamma-1 heavy chain constant regions comprising an Asp at position 204 shown in SEQ ID NO: 4 or a Leu at position 206 shown in SEQ ID NO: 4.

(vi) wherein the ligand comprises a human gamma-2 heavy chain constant region that comprises an amino acid selected from the group consisting of a Pro at position 72 shown in SEQ ID NO: 6, an Asn at position 75 shown in SEQ ID NO: 6, a Phe at position 76 shown in SEQ ID NO: 6, a Val at position 161 shown in SEQ ID NO: 6 and an Ala at position 257 shown in SEQ ID NO: 6 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 6, Asn at position 75 shown in SEQ ID NO: 6, Phe at position 76 shown in SEQ ID NO: 6, Val at position 161 shown in SEQ ID NO: 6 or Ala at position 257 shown in SEQ ID NO: 6.

(vii) wherein the ligand comprises a human kappa chain constant region that comprises a Val at position 84 shown in SEQ ID NO: 16 or a Cys at position 87 shown in SEQ ID NO: 16 and wherein said human comprises (i) an IGKC1*01 human heavy chain constant region gene segment, or the human expresses antibodies comprising human kappa chain constant regions comprising a Val corresponding to position 84 shown in SEQ ID NO: 16 or a Cys at position 87 shown in SEQ ID NO: 16 and (ii) a nucleotide sequence encoding said Nav1.7 protein comprising said Asp358Ala or Val385Ile in SEQ ID NO: 1.

(viii) wherein the ligand comprises a human IGLC1*01 lambda chain constant region and wherein said human comprises (i) a human IGLC1*01 lambda chain constant region gene segment, or the human expresses antibodies comprising human IGLC1*01 lambda chain constant regions.

(ix) wherein the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73.

(x) wherein the ligand comprises a human gamma-3 heavy chain constant region encoded by a first human IGHG3 (eg, IGHG3*01) constant region gene segment and wherein said human comprises (i) said first constant region gene segment (eg, an IGHG3*01), or the human expresses antibodies comprising human gamma-3 heavy chain constant regions encoded by said first human IGHG3 (eg, IGHG3*01) constant region gene segment.

(xi) wherein the ligand comprises a human epsilon heavy chain constant region encoded by a first human epsilon heavy chain constant region gene segment and wherein said human comprises (i) said first constant region gene segment, or the human expresses antibodies comprising human epsilon heavy chain constant regions encoded by said first constant region gene segment.

(xii) wherein the ligand comprises a human mu heavy chain constant region encoded by a first human mu heavy chain constant region gene segment and wherein said human comprises (i) said first constant region gene segment, or the human expresses antibodies comprising human mu heavy chain constant regions encoded by said first constant region gene segment.

(xiii) wherein the ligand comprises a human alpha heavy chain constant region encoded by a first human alpha heavy chain constant region gene segment and wherein said human comprises (i) said first constant region gene segment, or the human expresses antibodies comprising human alpha heavy chain constant regions encoded by said first constant region gene segment.

(xiv) wherein the ligand comprises a human delta heavy chain constant region encoded by a first human delta heavy chain constant region gene segment and wherein said human comprises (i) said first constant region gene segment, or the human expresses antibodies comprising human delta heavy chain constant regions encoded by said first constant region gene segment.

(xv) wherein the ligand comprises a human kappa light chain constant region encoded by a first human kappa light chain constant region gene segment and wherein said human comprises (i) said first constant region gene segment, or the human expresses antibodies comprising human kappa light chain constant regions encoded by said first constant region gene segment.

(xvi) wherein the ligand comprises a human lambda light chain constant region encoded by a first human lambda light chain constant region gene segment and wherein said human comprises (i) said first constant region gene segment, or the human expresses antibodies comprising human lambda light chain constant regions encoded by said first constant region gene segment.

A Twenty-sixth configuration provides a method of treating or reducing the risk of a Nav1.7-mediated disease or condition in a human in need thereof, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;

wherein (i) the ligand comprises a human gamma-2 heavy chain constant region that comprises an amino acid selected from the group consisting of a Pro at position 72 shown in SEQ ID NO: 6, an Asn at position 75 shown in SEQ ID NO: 6, a Phe at position 76 shown in SEQ ID NO: 6, a Val at position 161 shown in SEQ ID NO: 6 and an Ala at position 257 shown in SEQ ID NO: 6 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 6, Asn at position 75 shown in SEQ ID NO: 6, Phe at position 76 shown in SEQ ID NO: 6, Val at position 161 shown in SEQ ID NO: 6 or Ala at position 257 shown in SEQ ID NO: 6; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In some embodiments, said amino acid is selected from the group consisting of any one of 136I, 216S, 241T, 395K, 848T, 858H, 858F, 863P and 1449V; optionally wherein said disease or condition is a pain disease or condition. In some embodiments, said amino acid is selected from the group consisting of 996C, 1298F, 1298D, 1299F, 1461T, 1462V, 1464I and 1627K; optionally wherein said disease or condition is a pain disease or condition. In some embodiments, said amino acid is selected from the group consisting of 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K) and 1689X (wherein X is an amino acid other than W); optionally wherein said disease or condition is a pain disease or condition. In some embodiments, the constant region gene segment comprised by said human is a germline gene segment.

In some embodiments, the method further comprises, before said administering, selecting a human comprising said nucleotide sequence of (ii).

In some embodiments, the human has been determined to comprise the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In some embodiments, the method further comprises the step of determining that the human comprises (a) the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or (b) an Nav1.7 protein comprising said mutation said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein the determining step is performed before administration of the antibody to the human. In some embodiments, the step of determining comprises assaying a biological sample from the human for a nucleotide sequence encoding a Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G. In some embodiments, the assaying comprises contacting the biological sample with at least one oligonucleotide probe comprising a sequence of at least 10 contiguous nucleotides of a nucleotide sequence encoding an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G or comprising an antisense sequence of said contiguous nucleotides, wherein said sequence of contiguous nucleotides comprises a nucleotide sequence encoding said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, thereby forming a complex when at least one nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G is present; and detecting the presence or absence of the complex, wherein detecting the presence of the complex determines that the human comprises the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G. In some embodiments, the assaying comprises nucleic acid amplification and optionally one or more methods selected from sequencing, next generation sequencing, nucleic acid hybridization, and allele-specific amplification and/or wherein the assaying is performed in a multiplex format.

In some embodiments, said biological sample comprises serum, blood, faeces, tissue, a cell, urine and/or saliva of said human.

In some embodiments, said human is indicated as heterozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein said human is further indicated as comprising the nucleotide sequence of SEQ ID NO: 76, or said human is indicated as homozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In some embodiments, said human is or has been further determined to be substantially resistant to a pain or itching treatment. In some embodiments, said human is receiving or has received a pain or anti-itching treatment or has reduced responsiveness to a pain or itching treatment. In some embodiments, said disease or condition is a pain or itching disease or condition. In some embodiments, said disease or condition is a channelopathy or associated with a channelopathy; or is selected from the group consisting of primary erythermalgia (PE), paroxysmal extreme pain disorder (PEPD) and channelopathy-associated insensitivity to pain (CIP). In some embodiments, said human has been diagnosed with a pain or itching disease or condition.

In some embodiments, said ligand fragment treats or reduces the risk in said human of a pain or itching disease or condition.

In some embodiments, the nucleotide sequence comprises one or more SNPs selected from the group consisting of rs6746030, rs3750904, rs58022607, rs4369876, rs13402180 and rs12478318.

In some embodiments, said ligand (eg, antibody or antibody fragment) is administered by inhaled, intravenous or subcutaneous administration and/or is comprised in an inhalable or injectable preparation.

In some embodiments, the human gamma-2 heavy chain constant region of the ligand comprises IGHG2*01 amino acid sequence or an ADCC inactivated version thereof.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 2 depicts the cumulative allele frequency distribution across the 1000 Genomes Project databse of human VH3-23 alleles comprising SNP rs56069819 (such alleles denoted "C" and the most frequent allele (which does not comprise this SNP) denoted "A"). The figure shows that VH3-23 alleles comprising SNP rs56069819 are present at a cumulative frequency of 11% across all human ethnic populations taken as a whole, whereas in certain specific human ethnic sub-populations (ASW, LWK, YRI, CEU and GBR) such alleles are present at an above-average cumulative frequency. Indicated in the figure are those human PCSK9 variant forms (marked "Variants") that are found in the various sub-populations with above-average occurrence of human VH3-23 alleles comprising SNP rs56069819.

FIG. 3 depicts frameworks and CDRs encoded by VH3-23*04 as obtained from the IMGT database (available on the World Wide Web at www.IMGT.org). FIG. 3 discloses the nucleotide sequences as SEQ ID NOS 117, 117, 117, 119, 119, 119, 120, 122, 124, 39 and 125, respectively, in order of appearance. FIG. 3 discloses the coded amino acid sequences as SEQ ID NOS 118, 118, 118, 118, 118, 118, 121, 123, 123, 38 and 126, respectively, in order of appearance.

FIG. 4 depicts sequences of VH3-23*04. The portion of VH3-23*04 comprising the FW1 residue change of rs56069819 (SEQ ID NO: 38). The portion of the nucleic acid sequence encoding rs56069819 is depicted (SEQ ID NO: 39). The FW1 encoded by VH3-23*04 is depicted (SEQ ID NO: 40).

DETAILED DESCRIPTION

Figure 1:
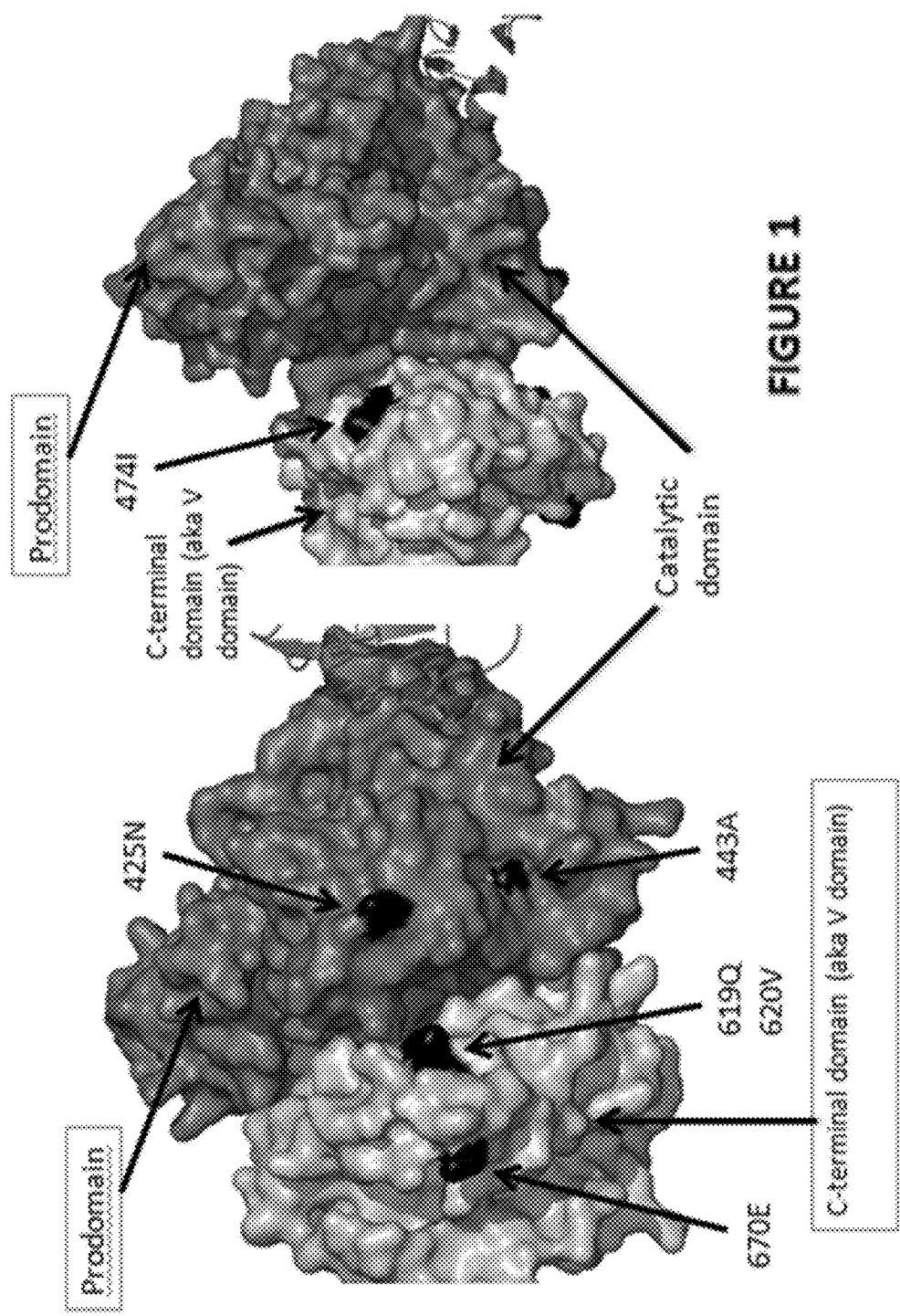
FIG. 1 shows in silico modeling of PCSK9 surface variant residues.

The skilled person will know that SNPs or other changes that translate into amino acid variation can cause variability in conformation or activity of human targets to be addressed. This has spawned great interest in personalized medicine where genotyping and knowledge of protein and nucleotide variability is used to tailor medicines and diagnosis of patients more effectively. The present invention provides for tailored pharmaceuticals and testing that specifically addresses rarer variant forms of a human target of interest (TOI).

The present invention harnesses the power of human genetic variation analysis and rationally-designed sequence selection. The technical applications of these approaches, as per the present invention, contribute to better treatment, prophylaxis and diagnosis in humans and provides for patient benefit by providing choice and enabling personalized medicines and therapies. This provides advantages of better prescribing, less wastage of medications and improved chances of drug efficacy and better diagnosis in patients.

As sources of genomic sequence variation data, the skilled person will be aware of the available databases and resources (including updates thereof) provided by the following:—

1. HapMap (The International HapMap Consortium. 2003; available on the World Wide Web at hapmap.ncbi.nlm.nih.gov/index.html.en). The HapMap Project is an international project that aims to compare the genetic sequences of different individuals to identify chromosomal regions containing shared genetic variants. The HapMap www site provides tools to identify chromosomal regions and the variant therein, with options to drill down to population level frequency data.
2. 1000 Genomes Project (The 1000 Genomes Project Consortium 2010; available on the World Wide Web at 1000genomes.org/). This resource provides complete genomic sequence for at least 2500 unidentified individuals from one of 25 distinct population groups.
3. Japanese SNP Database (H. Haga et al. 2002; available on the World Wide Web at snp.ims.u-tokyo.ac.jp/index.html). Based on a study identifying 190,562 human genetic variants.

The present invention involves the identification and cataloguing of naturally-occurring human genomic target sequence variants, including those found to be relatively low-frequency or rare variants that segregate with specific human ethnic populations and in many individual humans.

An aspect of the invention is based on rational design of sequence selection addressing the desirability to tailor medicaments and diagnostics to rarer, but yet still significant groups of human individuals that suffer from, or have the potential to suffer from (ie, who are at risk of), a disease or condition mediated or associated with the target of interest. In devising this rational design of the present aspect of the invention, the inventor included considerations of the spread of prevalence of naturally-occurring target variant sequences across multiple, diverse human ethnic populations, as well as the importance of addressing such populations where many individuals are likely to display a genotype and/or phenotype of one or more of the variants being analysed. As part of this design, the inventor saw the importance of adopting the art-recognised classifications of human ethnic populations, and in this respect the inventor based the analysis and design on the recognised human ethnic populations adopted by the 1000 Genomes Project, since this is a resource that is, and will continue to be, widely adopted by the scientific and medical community.

Thus, in this aspect of the invention, the inventor designed the following variant sequence selection criteria, these being criteria that the inventor realised would provide for useful medical drugs and diagnostics to tailored need in the human population.

Selection Criteria

Three or four of the following:—

Naturally-occurring human target variant sequences having a cumulative human allele frequency of 35% or less;

Naturally-occurring human target variant sequences having a total human genotype frequency of 40% or less;

Naturally-occurring human target variant sequences found in many different human ethnic populations (using the standard categorisation of the 1000 Genomes Project; see Table 4 below); and Naturally-occurring human target variant sequences found in many individuals distributed across such many different ethnic populations.

The inventor's selection included, as a consideration, selection for nucleotide variation that produced amino acid variation in corresponding TOI forms (ie, non-synonymous variations), as opposed to silent variations that do not alter amino acid residues in the target protein.

In an embodiment, the cumulative human allele frequency is 30, 25, 20, 15, 10 or 5% or less, eg, in the range from 1 to 20% or 1 to 15% or 1 to 10%.

In an embodiment, the total human genotype frequency is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

In an embodiment, the naturally-occurring human target variant sequences are found in at least 9, 10, 11, 12, 13, 14, 15, 16, 17, 18, 19 or 20 different human ethnic populations (using the standard categorisation of the 1000 Genomes Project).

In an embodiment, the naturally-occurring human target variant sequences are found in at least 20, 25, 30, 35, 40, 45, 50, 55, 60, 65, 70, 75, 80, 85, 90, 95, 100, 105, 110, 115, 120, 130, 140 or 150 individuals distributed across such many different ethnic populations.

In an example, the following criteria are applied:—

Naturally-occurring human target variant sequences having a cumulative human allele frequency of 15% or less;

Naturally-occurring human target variant sequences having a total human genotype frequency of 20% or less;

Naturally-occurring human target variant sequences found in at least 5 different human ethnic populations (using the standard categorisation of the 1000 Genomes Project); and Naturally-occurring human target variant sequences found in many individuals distributed across such many different ethnic populations.

In an example, the criteria are applied with reference to one or more human genomic sequence databases as described herein. For example, the criteria are those as applied to the 1000 Genomes database.

For example in any aspect example, embodiment or configuration of the invention, the 1000 Genomes database release 13. For example, the 1000 Genomes database in its most recent version as at 1 Oct. 2013.

Optionally, further sequence analysis and 3D in silico modelling (eg, see FIG. 1) can also be used as an additional selection criterion: variants whose variant amino acid residues (versus the most common form of human TOI) are surface-exposed on the target are desirable for selection, since the inventor saw these as contributing to determining the topography of the target and potentially contributing to how and where ligand binding on the target occurs.

The following bioinformatics protocol is envisaged to identify human sequences for use in the present invention:

(a) Identify a genomic region containing a target sequence of interest ('target genomic region') and calculate the genomic coordinates, using coordinates that match the sequence assembly build used by either the 1000 Genomes Project or International HapMap project (or another selected human gene database of choice).

(b) Identify genomic variants mapped to the genomic region previously identified in (a). Retrieve allele frequencies for variants for each super population and preferably sub-population where such data is available. The VWC tools for the 1000 Genomes Project can be used for this step.

(c) Filter list of genomic variants from target genomic region to contain only variants classed as either 'non-synonymous' single nucleotide polymorphisms (SNPs) or genomic 'insertions or delections' (indels). Filter further to include those that are present in exonic sequences only. "Non-synonymous" refers to nucleotide variation that produces amino acid variation (ie, excluding silent mutations).

(d) Correlate population frequency data for each of the identified variants for each of the super populations (for example 'European Ancestry', 'East Asian ancestry', 'West African ancestry', 'Americas', and 'South Asian ancestry') to identify those variants that segregate with less than two super-populations. Further correlate all identified variants with each of the sub-populations (for example, 'European ancestry' super-population might be subdivided into groups such as 'CEU—Utah residents with Northern or Western European ancestry', 'TSI Toscani in Italia' and 'British from England and Scotland') and produce a second score for rarity of variants within a super-population.

(e) Collect one or more sequences that show segregation to specific sub-populations for use in the present invention, eg, according to selection criteria as described herein.

Human Populations

Optionally the ethnic populations are selected from those identified in the 1000 Genomes Project database. In this respect, see Table 4 which provides details of the ethnic populations on which the 1000 Genomes Project database is based.

N A Rosenberg et al (Science 20 Dec. 2002: vol. 298 no. 5602 2342-2343) studied the genetic structure of human populations of differing geographical ancestry. In total, 52 populations were sampled, these being populations with:

African Ancestry (Mbuti Pygmies, Biaka Pygmies, San peoples, and speakers of Niger-Kordofanian languages (Bantu, Yoruba or Mandenka populations), Eurasian Ancestry (European ancestry (Orcadian, Adygel, Basque, French, Russians, Italians, Sardinian, Tuscan), Middle Eastern ancestry (Mozabite, Bedouin, Druze, Palestinians), Central/South Asian ancestry (Balochl, Brahul, Makrani, Sindhi, Pathan, Burusho, Hazara, Uygur, Kalash)), East Asian ancestry (Han, Dal, Daur, Hezhen, Lahu, Miao, Oroqen, She, Tujia, Tu, Xibo, Yi, Mongola, Naxi, Cambodian, Japanese, Yakut),
Oceanic ancestry (Melanesian, Papuan); or Americas Ancestry (Karitiana, Surui, Colombian, Maya, Pima).

The International HapMap Project, Nature, 2003 Dec. 18; 426(6968):789-96, discloses that goal of the HapMap Project: to determine the common patterns of DNA sequence variation in the human genome by determining the genotypes of one million or more sequence variants, their frequencies and the degree of association between them in DNA samples from populations with ancestry from parts of Africa, Asia and Europe. The relevant human populations of differing geographical ancestry include Yoruba, Japanese, Chinese, Northern European and Western European populations. More specifically:—

Utah population with Northern or Western European ancestry (samples collected in 1980 by the Centre d'Etude du Polymorphisme Humain (CEPH));
population with ancestry of Yoruba people from Ibadan, Nigeria;
population with Japanese ancestry; and
population with ancestry of Han Chinese from China.

The authors, citing earlier publications, suggest that ancestral geography is a reasonable basis for sampling human populations.

A suitable sample of human populations used in the present invention is as follows:—

(a) European ancestry
(b) Northern European ancestry; Western European ancestry; Toscani ancestry; British ancestry, Finnish ancestry or Iberian ancestry.
(c) More specifically, population of Utah residents with Northern and/or Western European ancestry; Toscani population in Italia; British population in England and/or Scotland; Finnish population in Finland; or Iberian population in Spain.
(a) East Asian ancestry
(b) Japanese ancestry; Chinese ancestry or Vietnamese ancestry.
(c) More specifically, Japanese population in Toyko, Japan; Han Chinese population in Beijing, China; Chinese Dai population in Xishuangbanna; Kinh population in Ho Chi Minh City, Vietnam; or Chinese population in Denver, Colo., USA.
(a) West African ancestry
(b) Yoruba ancestry; Luhya ancestry; Gambian ancestry; or Malawian ancestry.
(c) More specifically, Yoruba population in Ibadan, Nigeria; Luhya population in Webuye, Kenya; Gambian population in Western Division, The Gambia; or Malawian population in Blantyre, Malawi.
(a) Population of The Americas
(b) Native American ancestry; Afro-Caribbean ancestry; Mexican ancestry; Puerto Rican ancestry; Columbian ancestry; or Peruvian ancestry.
(c) More specifically, population of African Ancestry in Southwest US; population of African American in Jackson, Miss.; population of African Caribbean in Barbados; population of Mexican Ancestry in Los Angeles, Calif.; population of Puerto Rican in Puerto Rico; population of Colombian in Medellin, Colombia; or population of Peruvian in Lima, Peru.

(a) South Asian ancestry
(b) Ahom ancestry; Kayadtha ancestry; Reddy ancestry; Maratha; or Punjabi ancestry.
(c) More specifically, Ahom population in the State of Assam, India; Kayadtha population in Calcutta, India; Reddy population in Hyderabad, India; Maratha population in Bombay, India; or Punjabi population in Lahore, Pakistan.

In any configuration of the invention, in one embodiment, each human population is selected from a population marked "(a)" above.

In any configuration of the invention, in another embodiment, each human population is selected from a population marked "(b)" above.

In any configuration of the invention, in another embodiment, each human population is selected from a population marked "(c)" above.

In one embodiment the ethnic populations are selected from the group consisting of an ethnic population with European ancestry, an ethnic population with East Asian, an ethnic population with West African ancestry, an ethnic population with Americas ancestry and an ethnic population with South Asian ancestry.

In one embodiment the ethnic populations are selected from the group consisting of an ethnic population with Northern European ancestry; or an ethnic population with Western European ancestry; or an ethnic population with Toscani ancestry; or an ethnic population with British ancestry; or an ethnic population with Icelandic ancestry; or an ethnic population with Finnish ancestry; or an ethnic population with Iberian ancestry; or an ethnic population with Japanese ancestry; or an ethnic population with Chinese ancestry; or an ethnic population Vietnamese ancestry; or an ethnic population with Yoruba ancestry; or an ethnic population with Luhya ancestry; or an ethnic population with Gambian ancestry; or an ethnic population with Malawian ancestry; or an ethnic population with Native American ancestry; or an ethnic population with Afro-Caribbean ancestry; or an ethnic population with Mexican ancestry; or an ethnic population with Puerto Rican ancestry; or an ethnic population with Columbian ancestry; or an ethnic population with Peruvian ancestry; or an ethnic population with Ahom ancestry; or an ethnic population with Kayadtha ancestry; or an ethnic population with Reddy ancestry; or an ethnic population with Maratha; or an ethnic population with Punjabi ancestry.

Anti-Target Ligands

The invention provides useful anti-target ligands for addressing humans suffering from or likely to suffer from a disease or condition mediated or associated with the TOI. For example, the ligand specifically binds to the TOI variant as per the invention. The ligand may inhibit or antagonise the activity of the target, eg, the ligand neutralises the target. The skilled person will be familiar with neutralising ligands in general, such as antibodies or antibody fragments, and can readily test suitable ligands for specific binding and/or neutralisation of a target in vitro or in an in vivo assay.

An antibody "fragment" comprises a portion of an intact antibody, preferably the antigen binding and/or the variable region of the intact antibody. Examples of antibody fragments include dAb, Fab, Fab', F(ab')2 and Fv fragments; diabodies; linear antibodies; single-chain antibody molecules and multispecific antibodies formed from antibody fragments.

In an embodiment, the ligand of the invention is or comprises an antibody or antibody fragment, for example an antibody or fragment comprising human variable regions (and optionally also human constant regions). Anti-TOI or TOI-binding or targeting antibodies and fragments can be prepared according to any known method, eg, using transgenic mice (eg, the Kymouse™ or Velocimouse™, or Omnimouse™, Xenomouse™, HuMab Mouse™ or MeMo Mouse™), rats (eg, the Omnirat™), camelids, sharks, rabbits, chickens or other non-human animals immunised with the TOI followed optionally by humanisation of the constant regions and/or variable regions to produce human or humanised antibodies. In an example, display technologies can be used, such as yeast, phage or ribosome display, as will be apparent to the skilled person. Standard affinity maturation, eg, using a display technology, can be performed in a further step after isolation of an antibody lead from a transgenic animal, phage display library or other library. Representative examples of suitable technologies are described in US20120093818 (Amgen, Inc), which is incorporated herein by reference, eg, the methods set out in paragraphs [0309] to [0346]. Although this is with reference to PCSK9, the antibody-generating methods can be applied to other TOIs as per the broadest scopes of the present invention.

Generally, a VELOCIMMUNE™ or other mouse or rat can be challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimaeric antibodies or the variable domains of the light and heavy chains may be isolated directly from antigen-specific lymphocytes.

Initially, high affinity chimaeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4 (for example, SEQ ID NO: 751, 752,753 in US2011/0065902, which sequences are incorporated herein by reference for use in the ligands of the present invention). While the constant region selected may vary according to specific use, high affinity antigen-binding and target specificity characteristics reside in the variable region.

In an example, the ligand of the invention is or comprises a nucleic acid, eg, RNA, eg, siRNA that hybridises under stringent condition to the TOI variant sequence, eg, hybridises a nucleotide sequence comprising one or more nucleotides that are variant (versus the most common TOI sequence, eg, with reference to the 1000 Genomes Project database).

Target binding ability, specificity and affinity (Kd, $K_{off}$ and/or $K_{on}$) can be determined by any routine method in the art, eg, by surface plasmon resonance (SPR). The term "Kd", as used herein, is intended to refer to the equilibrium dissociation constant of a particular antibody-antigen interaction.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the ligand (eg, antibody) is determined using SPR by
1. Coupling anti-mouse (or other relevant human, rat or non-human vertebrate antibody constant region species-matched) IgG (eg, Biacore™ BR-1008-38) to a biosensor chip (eg, GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH11.7. This removes the captured antibody and allows the surface to be used for another interaction. The binding data can be fitted to 1:1 model inherent using standard techniques, eg, using a model inherent to the ProteOn XPR36™ analysis software.

In an example, the ligand of the invention is contained in a medical container, eg, a vial, syringe, IV container or an injection device (eg, an intraocular or intravitreal injection device). In an example, the ligand is in vitro, eg, in a sterile container. In an example, the invention provides a kit comprising the ligand of the invention, packaging and instructions for use in treating or preventing or diagnosing in a human a disease or condition mediated by the TOI. In an example, the instructions indicate that the human should be genotyped for a TOI variant sequence of the invention before administering the ligand to the human. In an example, the instructions indicate that the human should be phenotyped for a TOI variant of the invention before administering the ligand to the human. In an example, the human is of Chinese (eg, Han) ethnicity and the instructions are in Chinese (eg, Mandarin). In an example, the instructions comprise directions to administer alirocumab or evolocumab to said human.

The invention relates to the concepts set out in the following clauses.

Clause 1 A method of treating or preventing a disease or condition in a human, wherein the disease or condition is mediated by a Target of Interest (TOI), wherein the TOI is present in humans as different polymorphic variants, the method comprising
a. Administering to the human an anti-TOI ligand to target a TOI variant in the human and treat or prevent (eg, by at least 40, 50, 60, 70, 80, 90 or 95%) said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%;

wherein
  Before step (a) said human has been or is genotyped as positive for said nucleotide sequence or phenotyped as positive for said TOI variant, or the method comprises before step (a) genotyping the human as positive for said nucleotide sequence or phenotyping the human as positive for said TOI variant.

In any aspect, configuration, example, embodiment, clause or concept herein, frequencies may be determined using bioinformatics.

In any aspect, configuration, example, embodiment, clause or concept herein, frequencies may be determined by reference to a database comprising at least 1000 or 2000 human sequences.

In any aspect, configuration, example, embodiment, clause or concept herein "heterozygous human genotype frequency" means the cumulative frequency of all genotypes in the sample or database or in humans having one occurrence of the rare variant allele and one occurrence of another allele (heterozygous state), eg, genotype in 1000 Genomes database.

In any aspect, configuration, example, embodiment, clause or concept herein "homozygous human genotype frequency" means the cumulative frequency of two occurrences of the variant allele (homozygous state), eg, genotype in 1000 Genomes Project database.

In any aspect, configuration, example, embodiment, clause or concept herein "total human genotype frequency" means the total of heterozygous plus homozygous human genotype frequencies.

In any aspect, configuration, example, embodiment, clause or concept herein "cumulative human allele frequency" refers to the total of all occurrences of the variant allele in the sample or database or in humans, eg, in the 1000 Genomes Project database.

Clause 2: The method of clause 1, wherein before step (a) the ligand has been or is determined as being capable of binding to said TOI variant, eg, with an affinity (Kd) disclosed below.

In an example, the ligand is (or has been determined as) a neutraliser of the TOI. In an example, determination is carried out in a human (eg, in a clinical trial). In an example, determination is carried out in a non-human, eg, in a mouse, rat, rabbit, pig, dog, sheep or non-human primate (eg, Cynomolgous monkey, rhesus monkey or baboon).

Clause 3: A method of treating or preventing a disease or condition in a human, wherein the disease or condition is mediated by a Target of Interest (TOI), wherein the TOI is present in humans as different polymorphic variants, the method comprising
  a. Administering to the human an anti-TOI ligand to target a TOI variant in the human and treat or prevent (eg, by at least 40, 50, 60, 70, 80, 90 or 95%) said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%; wherein
  b. Before step (a) the ligand has been or is determined as capable of binding to said TOI variant, eg, with an affinity (Kd) disclosed below.

In an example, the ligand is (or has been determined as) a neutraliser of the TOI. In an example, determination is carried out in a human (eg, in a clinical trial). In an example, determination is carried out in a non-human, eg, in a mouse, rat, rabbit, pig, dog, sheep or non-human primate (eg, Cynomolgous monkey, rhesus monkey or baboon).

Clause 4: The method of clause 3, wherein the genome of said human comprises a nucleotide sequence encoding said TOI variant; and before step (a) said nucleotide sequence has been or is determined as having a cumulative human allele frequency of less than 50% and/or having a total human genotype frequency of less than 50%.

The TOI variant is not the most frequent.

Clause 5: The method of clause 3 or 4, wherein said human has been or is genotyped as positive for said variant nucleotide sequence before step (a), or the method comprises genotyping the human as positive for said variant nucleotide sequence before step (a).

Clause 6: The method of any preceding clause, wherein the human has been or is phenotyped as positive for said TOI variant before step (a), or the method comprises phenotyping the human as positive for said variant nucleotide sequence before step (a).

Clause 7: The method of any preceding clause, wherein said frequency is less than 10 or 15% (eg, from 1 to 10%).

In an embodiment, the cumulative human allele frequency is 30, 25, 20, 15, 10 or 5% or less, eg, in the range from 1 to 20% or 1 to 15% or 1 to 10%.

In an embodiment, the total human genotype frequency is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

Clause 8: The method of any preceding clause, wherein the ligand is capable of binding to two or more different TOI variants, each being encoded by a nucleotide sequence having a cumulative human allele frequency of less than 50% (eg, from 1 to 10%) and/or having a total human genotype frequency of less than 50% (eg, from 1 to 20%).

In an embodiment, the cumulative human allele frequency of each TOI variant is 30, 25, 20, 15, 10 or 5% or less, eg, in the range from 1 to 20% or 1 to 15% or 1 to 10%.

In an embodiment, the total human genotype frequency of each TOI variant is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

Clause 9: A method of treating or preventing a disease or condition in a human, wherein the disease or condition is mediated by a Target of Interest (TOI), wherein the TOI is present in humans as different polymorphic variants, the method comprising
  a. Administering to the human an anti-TOI ligand to target a TOI variant in the human and treat or prevent (eg, by at least 40, 50, 60, 70, 80, 90 or 95%) said disease or condition, wherein the TOI in said human is a variant encoded by a nucleotide sequence having a cumulative human allele frequency of more than 50% (eg, the highest frequency) and/or having a total human genotype frequency of more than 50% (eg, the highest frequency); wherein
  b. Before step (a) said human has been or is genotyped as negative for a variant nucleotide sequence having a cumulative human allele frequency of less than 50% and/or having a total human genotype frequency of less than 50%; or phenotyped as negative for a TOI variant encoded by a nucleotide sequence having a cumulative human allele frequency of less than 50% and/or having a total human genotype frequency of less than 50%;
  or
    Before step (a) said the method comprises genotyping the human as negative for a variant nucleotide sequence having a cumulative human allele frequency of less than 50% and/or having a total human genotype frequency of less than 50%; or phenotyping the human as negative for a TOI variant encoded by a nucleotide sequence having a cumulative human allele frequency of less than 50% and/or having a total human genotype frequency of less than 50%.

In an embodiment, in (a) the cumulative human allele frequency is 55, 60, 65, 70, 75, 80, 85 or 90 or more but less than 95, 96, 97, 98, 99 or 100% (eg, in the range from 51 to 80%).

In an embodiment, in (a) the total human genotype frequency is 55, 60, 65, 70, 75, 80, 85 or 90 or more but less than 95, 96, 97, 98, 99 or 100% (eg, in the range from 51 to 80%).

In an embodiment, in (b) the cumulative human allele frequency is 30, 25, 20, 15, 10 or 5% or less, eg, in the range from 1 to 20% or 1 to 15% or 1 to 10%.

In an embodiment, in (b) the total human genotype frequency is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

Clause 10: The method of clause 9, wherein before step (a), the human has been or is phenotyped as positive for the most frequent TOI variant or genotyped for the nucleotide sequence thereof.

In an embodiment, before step (a) the human has been or is genotyped as positive for TOI variant nucleotide sequence having a cumulative human allele frequency of 55, 60, 65, 70, 75, 80, 85 or 90 or more but less than 95, 96, 97, 98, 99 or 100% (eg, in the range from 51 to 80%) or phenotyped for the TOI variant thereof.

In an embodiment, before step (a) the human has been or is genotyped as positive for TOI variant nucleotide sequence having a total human genotype frequency of 55, 60, 65, 70, 75, 80, 85 or 90 or more but less than 95, 96, 97, 98, 99 or 100% (eg, in the range from 51 to 80%) or phenotyped for the TOI variant thereof.

Clause 11: The method of clause 9 or 10, wherein before step (a) the ligand has been or is determined as being capable of binding to the most frequent TOI variant.

Clause 12: The method of clause 9, 10 or 11, wherein before step (a) the ligand has been or is determined as being substantially incapable of neutralising or inhibiting said TOI variant recited in step (b).

By "substantially incapable or neutralising or inhibiting" is meant: Neutralisation or inhibition less than 50, 25, 10, 5 or 0.5% inhibition or neutralisation of the most frequent TOI variant.

Clause 13: The method of any one of clauses 9 to 12, wherein the ligand is capable of binding to the most frequent TOI variant.

Clause 14: The method of any one of clauses 9 to 13, wherein the ligand is capable of binding to two or more different TOI variants, each being encoded by a nucleotide sequence having a cumulative human allele frequency of more than 50%.

In an embodiment, each TOI variant is encoded by a nucleotide sequence having a cumulative human allele frequency of 55, 60, 65, 70, 75, 80, 85 or 90 or more but less than 95, 96, 97, 98, 99 or 100% (eg, in the range from 51 to 80%).

In an embodiment, each TOI variant is encoded by a nucleotide sequence having a total human genotype frequency of 55, 60, 65, 70, 75, 80, 85 or 90 or more but less than 95, 96, 97, 98, 99 or 100% (eg, in the range from 51 to 80%).

Clause 15: The method of any preceding clause, wherein said variant nucleotide sequence recited in step (a) has been or is determined as being present in at least 2 different human ethnic populations, eg, at least 2, 3, 4, 5, 6, 7, 8 or 9 different human ethnic populations in Table 4.

Clause 16: The method of any preceding clause, wherein said human frequency is the frequency in a database of naturally-occurring sequences sampled from at least 15, 20 or 25 different human ethnic populations and comprising at least 1000 sequences. In an embodiment, the database is the 1000 Genomes Project database as described herein.

Clause 17: An anti-human TOI ligand for use in a method of treating and/or preventing a TOI-mediated disease or condition in a human, wherein the TOI is present in humans as different polymorphic variants and wherein the genome of said human comprises a TOI nucleotide sequence having a cumulative human allele frequency of less than 50% and/or a total human genotype frequency of less than 50%, the method comprising administering the ligand to the human.

In the alternative, clause 17 provides an anti-human TOI ligand for use in a method according to any one of clauses 1 to 16, the method comprising administering the ligand to the human.

In an embodiment, the cumulative human allele frequency is 30, 25, 20, 15, 10 or 5% or less, eg, in the range from 1 to 20% or 1 to 15% or 1 to 10%.

In an embodiment, the total human genotype frequency is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

Clause 18: The ligand of clause 17, wherein the ligand has been or is determined as capable of binding the human TOI encoded by said nucleotide sequence.

In the alternative, clause 18 provides a ligand that binds a human TOI comprising an amino acid sequence encoded by a TOI nucleotide sequence having a cumulative human allele frequency of less than 50% and/or a total human genotype frequency of less than 50%, for use in a method comprising the step of using the ligand to target said TOI in a human to treat and/or prevent a disease or condition mediated by TOI, the method comprising administering the ligand to the human.

Clause 19: A ligand that binds a human TOI comprising an amino acid sequence encoded by a TOI nucleotide sequence having a cumulative human allele frequency of less than 50% and/or a total human genotype frequency of less than 50%, for use in a method according to any one of clauses 1 to 16, the method comprising administering the ligand to the human.

Clause 20: The ligand of any one of clauses 17 to 19, wherein the human has been or is genotyped as positive for said TOI nucleotide sequence having a cumulative human allele frequency of less than 50%.

The ligand of any one of clauses 17 to 19, wherein the human has been or is genotyped as positive for said TOI nucleotide sequence having a total human genotype frequency of less than 50%.

Clause 21: The ligand of any one of clauses 17 to 20, wherein the human has been or is phenotyped as positive for a TOI encoded by a nucleotide sequence having a cumulative human allele frequency of less than 50% and/or having a total human genotype frequency of less than 50%.

Clause 22: The ligand of any one of clauses 17 to 21, wherein the human has been or is genotyped as heterozygous for a TOI nucleotide sequence having a cumulative human allele frequency of less than 50% and/or having a total human genotype frequency of less than 50%; optionally wherein the human has been or is genotyped as comprising a TOI nucleotide sequence having a cumulative human allele frequency of less than 50% and a TOI nucleotide sequence having a cumulative human allele frequency of more than 50% (eg, having the highest cumulative human allele frequency) and/ or having a total human genotype frequency of more than 50% (eg, having the highest total human genotype frequency).

Clause 23: The ligand of any one of clauses 17 to 22, wherein the genome of the human has been or is genotyped as homozygous for a TOI nucleotide sequence having a cumulative human allele frequency of less than 50% and/or having a total human genotype frequency of less than 50%.

Clause 24: The ligand of any one of clauses 17 to 23, wherein the ligand comprises an antibody binding site that binds a human TOI comprising an amino acid sequence encoded by a TOI nucleotide sequence having a cumulative human allele frequency of less than 50% and/or having a total human genotype frequency of less than 50%; and optionally has been or is determined as capable of such binding.

Clause 25: The ligand of clause 24, wherein the ligand is an antibody or antibody fragment.

Clause 26: The ligand of any one of clauses 17 to 23, wherein the ligand comprises a nucleotide sequence that specifically hybridises to a TOI nucleotide sequence having a cumulative human allele frequency of less than 50% and/or having a total human genotype frequency of less than 50% or an RNA transcript thereof; and/or the ligand comprises a nucleotide sequence that comprises at least 10 contiguous nucleotides of a nucleotide sequence having a cumulative human allele frequency of less than 50% and/or having a total human genotype frequency of less than 50% or is an antisense sequence thereof.

In an embodiment, the ligand comprises a nucleotide sequence that comprises at least 10, 11, 12, 13, 14, 15, 20, 25, 30, 35, 40, 45, 50 or 100 contiguous nucleotides of a nucleotide sequence having a cumulative human allele frequency of less than 50% and/or having a total human genotype frequency of less than 50% or is an antisense sequence thereof.

Clause 27: The ligand of any one of clauses 17 to 26, wherein the genome of said human comprises a nucleotide sequence having a cumulative human allele frequency of less than 50% and the sequence is found in at least 2 different ethnic populations (eg, found in at least 9, 10, 11, 12, 13, 14, 15, 16, 17, 18, 19 or 20 different human ethnic populations (for example as per the populations in Table 4)). In an example, numbers are with reference to the 1000 Genomes Project database.

The ligand of any one of clauses 17 to 26, wherein the genome of said human comprises a nucleotide sequence having a cumulative human allele frequency of less than 50% and the sequence is found in at least 20 individuals distributed across at least 2 said different ethnic populations (eg, found in at least in at least 20, 25, 30, 35, 40, 45, 50, 55, 60, 65, 70, 75, 80, 85, 90, 95, 100, 105, 110, 115, 120, 130, 140 or 150 individuals distributed across such many different ethnic populations). In an example, numbers are with reference to the 1000 Genomes Project database.

Clause 28: A pharmaceutical composition or kit for treating or preventing a condition or disease mediated by a TOI as recited in any preceding clause, the composition or kit comprising a ligand of any one of clauses 17 to 27; and optionally in combination with a label or instructions for use to treat and/or prevent said disease or condition in a human; optionally wherein the label or instructions comprise a marketing authorisation number (eg, an FDA or EMA authorisation number); optionally wherein the kit comprises an injection pen or IV container that comprises the ligand.

In an example, the label or instructions cover or describe use for a human comprising a TOI variant encoded by a nucleotide sequence as recited in clause 17.

Clause 29: A method of producing an anti-human TOI antibody binding site, the method comprising obtaining a plurality of anti-TOI antibody binding sites, screening the antibody binding sites for binding to a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody binding site that binds in the screening step.

In an embodiment of any aspect herein, the antibody, fragment or binding site is recombinant.

In the alternative, clause 29 provides: A method of producing an anti-human TOI antibody, the method comprising immunising a non-human vertebrate (eg, a mouse or a rat) with a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody that binds a TOI comprising an amino acid sequence encoded by a TOI nucleotide sequence having a cumulative human allele frequency of less than 50% and/or a total human genotype frequency of less than 50%, and optionally producing a TOI-binding fragment or derivative of the isolated antibody.

The term "isolated" with reference to a ligand, antibody or protein, for example in any aspect, configuration, example or embodiment, means that a subject ligand, antibody, protein etc (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated" ligand, antibody, protein etc constitutes at least about 5%, at least about 10%, at least about 25%, or at least about 50% of a given sample. Genomic DNA, cDNA, mRNA or other RNA, of synthetic origin, or any combination thereof can encode such an isolated ligand, antibody protein etc. Preferably, the isolated ligand, antibody protein etc is substantially free from proteins or polypeptides or other contaminants that are found in its natural environment that would interfere with its therapeutic, diagnostic, prophylactic, research or other use.

For example, an "isolated" antibody is one that has been identified, separated and/or recovered from a component of its production environment (eg, naturally or recombinantly). Preferably, the isolated polypeptide is free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

Immunoconjugates

The invention encompasses the ligand (eg, antibody) conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081.

Bispecifics

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The human anti-TOI (eg, anti-PCSK9) mAbs can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Clause 30: The method of clause 29, comprising the step of obtaining a nucleic acid encoding the antibody, fragment, derivative or binding site and optionally inserting the nucleic acid in an expression vector.

Clause 31: A kit for TOI genotyping a human, wherein the kit comprises a nucleic acid comprising a nucleotide sequence that specifically hybridises to a TOI nucleotide sequence selected having a cumulative human allele frequency of less than 50% and/or a total human genotype frequency of less than 50% or an RNA transcript thereof; and/or the nucleic acid comprises a nucleotide sequence that comprises at least 10 (eg, at least 10, 11, 12, 13, 14, 15, 20, 25, 30, 35, 40, 45, 50 or 100) contiguous nucleotides of a TOI nucleotide sequence having a cumulative human allele frequency of less than 50% and/or a total human genotype frequency of less than 50% or is an antisense sequence thereof.

For example, the nucleic acid hybridises to a region immediately flanking a nucleotide that is variant compared to the corresponding nucleotide of the TOI nucleotide sequence having the highest cumulative human allele frequency and/or the highest total human genotype frequency. In an example, the nucleic acid hybridises to at two or more such variant nucleotides.

Specific hybridisation is under stringent conditions, as will be apparent to the skilled person, eg, conditions of 5×SSC, 5×Denhardt's reagent, and 0.5% SDS at 65° C.

Clause 32: A kit for TOI genotyping or phenotyping a human, wherein the kit comprises a ligand according to any one of clauses 17 to 27 or an antibody, fragment or derivative produced by the method of any one of clauses 29 to 31.

For example, the ligand specifically binds to an epitope comprising an amino acid that is variant compared to the corresponding amino acid of the TOI encoded by a nucleotide sequence having the highest cumulative human allele frequency and/or the highest total human genotype frequency. In an example, the ligand specifically binds to an epitope comprising two or more such variant amino acids. In an example, specific binding means binding with an affinity (Kd) of 1 mM, 100 nM, 10 nM or 1 nM or less, eg, as determined by SPR.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Clause 33: Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for treating and/or preventing a TOI-mediated disease or condition in a human whose genome comprises a TOI nucleotide sequence having a cumulative human allele frequency of less than 50% and/or having a total human genotype frequency of less than 50%.

Clause 34: Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for targeting said TOI in a human to treat and/or prevent a disease or condition mediated by TOI.

The use of clause 33 or 34, wherein the ligand, human, disease or condition is according to any one of clauses 1 to 27.

Clause 35: A method of targeting a TOI for treating and/or preventing a TOI-mediated disease or condition in a human, the method comprising administering an anti-TOI ligand to a human comprising a TOI nucleotide sequence selected having a cumulative human allele frequency of less than 50% and/or a total human genotype frequency of less than 50%, whereby a TOI encoded by said nucleotide sequence is targeted.

Clause 36: The method of clause 35, wherein the method comprises targeting a human TOI comprising an amino acid sequence with said ligand to treat and/or prevent said disease or condition in said human, wherein said amino acid sequence is encoded by a nucleotide sequence having a cumulative human allele frequency of less than 50% and/or a total human genotype frequency of less than 50%.

Clause 37: A method of TOI genotyping a nucleic acid sample of a human, the method comprising identifying in the sample the presence of a TOI nucleotide sequence having a cumulative human allele frequency of less than 50% and/or having a total human genotype frequency of less than 50%.

In an example, the method comprises obtaining a TOI nucleic acid sample from the human and then carrying out the identifying step.

Clause 38: A method of TOI typing a protein sample of a human, the method comprising identifying in the sample the presence of a TOI amino acid sequence encoded by a TOI nucleotide sequence having a cumulative human allele frequency of less than 50% and/or having a total human genotype frequency of less than 50%.

In an example, the method comprises obtaining a TOI protein sample from the human and then carrying out the identifying step.

Clause 39: The method of clause 37 or 38, comprising obtaining a sample of serum, blood, faeces, hair, urine or saliva from a human, whereby the nucleic acid or protein sample is obtained for use in the step of identifying said sequence.

Clause 40: The method of any one of clauses 37 to 39, comprising using a ligand according to any one of clauses 17 to 27 to carry out said identifying step.

Clause 41: A diagnostic kit comprising a ligand that is capable of binding a human TOI comprising an amino acid sequence encoded by a TOI nucleotide sequence having a cumulative human allele frequency of less than 50% and/or a total human genotype frequency of less than 50% and instructions for carrying out the method of clause 38 or 39.

Clause 42: A diagnostic kit comprising a nucleic acid probe comprising a nucleotide sequence that specifically hybridises a TOI nucleotide sequence having a cumulative human allele frequency of less than 50% and/or a total human genotype frequency of less than 50% or an RNA transcript thereof and instructions for carrying out the method of clause 38 or 39.

Clause 43: The method, ligand, composition, kit or use of any preceding clause, wherein the TOI is encoded by a nucleotide sequence having a cumulative human allele frequency from 1 to 10% and/or a total human genotype frequency from 1 to about 15% or from 1 to 15%.

Clause 44: The method, ligand, composition, kit or use of any preceding clause wherein the TOI is a human TOI selected from Table 5; optionally for treating and/or preventing a corresponding disease or condition as set out in Table 5.

For example, the TOI is human PCSK9, eg, a mature, cleaved, autocatalysed or active PCSK9. In an example, the disease is a cardiovascular disease such as hyperlipidaemia.

Ligands of the invention are useful, for instance, in specific binding assays, for genotyping or phenotyping humans, affinity purification of the TOI and in screening assays to identify other antagonists of TOI activity. Some of the ligands of the invention are useful for inhibiting binding of TOI to a congnate human receptor or protein, or inhibiting TOI-mediated activities.

The invention encompasses anti-TOI (eg, PCSK9) antibody ligands having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In an example, the invention features a pharmaceutical composition comprising a ligand of the invention, wherein the ligand is or comprises a recombinant human antibody or fragment thereof which specifically binds the TOI (eg, a rare variant as described herein) and a pharmaceutically acceptable carrier. In one embodiment, the invention features a composition which is a combination of an antibody ligand or antigen-binding fragment of an antibody of the invention, and a second therapeutic agent. The second therapeutic agent may be any of an anti-inflammatory agent, an anti-angiogenesis agent, a painkiller, a diuretic, a chemotherapeutic agent, an anti-neoplastic agent, a vasodilator, a vasoconstrictor, a statin, a beta blocker, a nutrient, an adjuvant, an anti-obesity agent and an anti-diabetes agent.

"Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to an carrier, excipient, or adjuvant that can be administered to a subject, together with an agent, e.g., any antibody or antibody chain described herein, and which does not destroy the pharmacological activity thereof and is nontoxic when administered in doses sufficient to deliver a therapeutic amount of the agent.

In an example, the invention features a method for inhibiting TOI activity using the anti-TOI ligand of the invention (eg, an antibody or antigen-binding portion of the antibody of the invention), wherein the therapeutic method comprises administering a therapeutically effective amount of a pharmaceutical composition comprising the ligand. The disorder treated is any disease or condition which is improved, ameliorated, inhibited or prevented by removal, inhibition or reduction of TOI activity.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The term "specifically binds," or the like, means that a ligand, eg, an antibody or antigen-binding fragment thereof, forms a complex with an antigen that is relatively stable under physiologic conditions. Specific binding can be characterized by an equilibrium dissociation constant of at least about $1 \times 10^{-6}$ M or less (e.g., a smaller KD denotes a tighter binding). Methods for determining whether two molecules specifically bind are well known in the art and include, for example, equilibrium dialysis, surface plasmon resonance, and the like. An isolated antibody that specifically binds a human TOI may, however, exhibit cross-reactivity to other antigens such as a TOI molecule from another species. Moreover, multi-specific antibodies (e.g., bispecifics) that bind to human TOI and one or more additional antigens are nonetheless considered antibodies that "specifically bind" TOI, as used herein.

Genotyping & Phenotyping

The skilled person will be familiar with techniques that can be used for accurate genotyping and application to the invention. These include the following.

1 Hybridization-based methods
1.1 Dynamic allele-specific hybridization
1.2 Molecular beacons
1.3 SNP microarrays
2 Enzyme-based methods
2.1 Restriction fragment length polymorphism
2.2 PCR-based methods
2.3 Flap endonuclease
2.4 Primer extension
2.5 5'-nuclease
2.6 Oligonucleotide Ligation Assay
3 Other post-amplification methods based on physical properties of DNA
3.1 Single strand conformation polymorphism
3.2 Temperature gradient gel electrophoresis
3.3 Denaturing high performance liquid chromatography
3.4 High-resolution melting of the entire amplicon
3.5 Use of DNA mismatch-binding proteins
3.6 SNPlex (SNPlex™ is a proprietary genotyping platform sold by Applied Biosystems).

Next-generation sequencing technologies such as pyrosequencing is also useful.

Reference is also made to GB2444410A and the genotyping method disclosed therein, which is incorporated herein by reference in its entirety.

Miniaturized assays, such as microarrays with oligonucleotide reagents immobilized on small surfaces, are frequently proposed for large-scale mutation analysis and high-throughput genotyping (Large-scale identification, mapping, and genotyping of single-nucleotide polymorphisms in the human genome (Wang D G, Fan J B, Siao C J, Berno A, Young P, Sapolsky R, Ghandour G, Perkins N, Winchester E, Spencer J, Kruglyak L, Stein L, Hsie L, Topalogou T, Hubbell E, Robinson E, Mittmann M, Morris M S, Shen N, Kilburn D, Rioux J, Nusbaum C, Rozen S, Hudson T J, Lipshutz R, Chee M, Lander E S, Science. 1998 May 15; 280 (5366):1077-82). Other high-throughput methods discriminate alleles by differential hybridization, primer extension, ligation and cleavage of an allele-specific probe (Review Accessing genetic variation: genotyping single nucleotide polymorphisms, Syvinen A C, Nat Rev Genet. 2001 December; 2 (12):930-42; Review Techniques patents for SNP genotyping, Twyman R M, Primrose S B, Pharmacogenomics. 2003 January; 4(1): 67-79).

An approach for a fully automated, large-scale SNP analysis is the 'homogeneous' assay, i.e. a single-phase assay without separation steps, permitting continual monitoring during amplification. The TaqMan™ assay (Applied Biosystems), originally designed for quantitative real-time PCR, is a homogeneous, single-step assay also used in determination of mutation status of DNA (see, eg, A. A. Komar (ed.), Single Nucleotide Polymorphisms, Methods in Molecular Biology 578, DOI 10.1007/978-1-60327-411-1_19, Humana Press, a part of Springer Science+Business Media, LLC; and Single Nucleotide Polymorphisms, Methods in Molecular Biology™ Volume 578, 2009, pp 293-306, The TaqMan Method for SNP Genotyping, Gong-Qing Shen et al). The TaqMan SNP Genotyping Assay exploits the 5'-exonuclease activity of AmpliTaq Gold™ DNA polymerase to cleave a doubly labeled probe hybridized to the SNP-containing sequence of ssDNA. Cleavage separates a 5'-fluorophore from a 3'-quencher leading to detectable fluorescent signal. The use of two allele-specific probes carrying different fluorophores permits SNP determination in the same tube without any post-PCR processing. Genotype is determined from the ratio of intensities of the two fluorescent probes at the end of amplification. Thus, rather than taking advantage of the full set of real-time PCR data as in quantitative studies, only end-point data are used.

TaqMan SNP genotyping in a high-throughput, automated manner is facilitated by the use of validated Pre-made TaqMan Genotyping assays, but Custom TaqMan Assays may also be used (High-throughput genotyping with single nucleotide polymorphisms, Ranade K, Chang M S, Ting C T, Pei D, Hsiao C F, Olivier M, Pesich R, Hebert J, Chen Y D, Dzau V J, Curb D, Olshen R, Risch N, Cox D R, Botstein D, Genome Res. 2001 July; 11 (7):1262-8; Assessment of two flexible and compatible SNP genotyping platforms: TaqMan SNP Genotyping Assays and the SNPlex Genotyping System, De la Vega F M, Lazaruk K D, Rhodes M D, Wenz M H, Mutat Res. 2005 Jun. 3; 573 (1-2):111-35). The results of the assay can be automatically determined by genotyping software provided with real-time thermal cyclers (e.g. IQ software of Bio-Rad, Sequence Detection Software of Applied Biosystems).

Single nucleotide polymorphisms (SNPs) can be determined using TaqMan™ real-time PCR assays (Applied Biosystems) and commercial software that assigns genotypes based on reporter probe signals at the end of amplification. An algorithm for automatic genotype caling of SNPs using the full course of TaqMan real-time data is available for use (A. Callegaro et al, Nucleic Acids Res. 2006; 34 (7): e56, Published online 2006 Apr. 14. doi: 10.1093/nar/gk1185, PMCID: PMC1440877). The algorithm is unique in that it classifies samples according to the behavior of blanks (no DNA samples), which cluster with heterozygous samples. This method of classification eliminates the need for positive controls and permits accurate genotyping even in the absence of a genotype class, for example when one allele is rare.

The skilled person will be familiar with techniques that can be used for accurate phenotyping and application to the invention. These include the use of amino acid sequencing of isolated target protein and comparison of sequences from different variants (eg, with the most common variant). An antibody that specifically and selectively binds in the area of a SNP under stringent conditions can also be used to identify a particular variant. In another method, the genotype is determined and a corresponding amino acid sequence (phenotype) determined, eg, by in silico translation.

Therapeutic Administration and Formulations

The invention provides therapeutic compositions comprising the anti-TOI ligand, eg, antibodies or antigen-binding fragments thereof, of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTINT™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the ligand, eg, antibody, of the present invention is used for treating various conditions and diseases associated with the TOI in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the ligand or pharmaceutical composition of the invention, for example a ligand provided by e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The ligand or composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The ligand or pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the ligand or pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a ligand or pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the ligand(s). Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Exemplary TOIs

For example in any configuration, aspect, concept, example or configuration of the invention, the or each TOI is selected from the group consisting of ABCF1; ACVR1; ACVR1B; ACVR2; ACVR2B; ACVRL1; ADORA2A; Aggrecan; AGR2; AICDA; AW1; AIG1; AKAP1; AKAP2; AIYIH; amyloid-beta; AMHR2; ANGPT1; ANGPT2; ANGPTL3; ANGPTL4; ANPEP; APC; APOC1; AR; Axl; AZGP1 (zinc-a-glycoprotein); B7.1; B7.2; BAD; BAFF; BAG1; BAI1; BCL2; BCL6; BDNF; BLNK; BLR1 (MDR15); BlyS; BMP1; BMP2; BMP3B (GDF1O); BMP4; BMP6; BMP8; BMPR1A; BMPR1B; BMPR2; BPAG1 (plectin); BRCA1; Cl9orflO (IL27w); C3; C4A; C5; C5R1; CANT1; CASP1; CASP4; CAV1; CB1; CCBP2 (D6/JAB61); CCL1 (1-309); CCL11 (eotaxin); CCL13 (MCP-4); CCL15 (MIP-id); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2 I eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3);

CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD7; CD164; CD19; CD1C; CD2O; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CD96; CD207; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKNIC; CDKN2A (p16INK4a); CDKN2B; CDKN2C; CDKN3; CEBPB; CELSR3; CER1; CHGA; CHGB; Chitinase; CHRNG; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CRLF2; CSF2 (GM-CSF); CSF3 (GCSF); CTLA4; CTNNB1 (b-catenin); CTSB (cathepsin B); CX3CL1 (SCYDi); CX3CR1 (V28); CXCR6; CXCL1 (GRO1); CXCL10 (IP-10); CXCL11 (1-TAC/IP-9); CXCL12 (SDF1); CXCL13; CXCL14; CXCL16; CXCL2 (GRO2); CXCL3 (GRO3); CXCL5 (ENA-78 ILIX); CXCL6 (GCP-2); CXCL9 (MIG); CXCR3 (GPR9/CKR-L2); CXCR4; CXCR6 (TYMSTR ISTRL33 I Bonzo); CYB5; CYC1; CYSLTR1; DAB21P; DAND5; DES; DKFZp451J0118; DNCL1; DPP4; E2F1; ECGF1; EDG1; EFNAI; EFNA3; EFNB2; EGF; EGFR; ELAC2; ENG; ENO1; ENO2; ENO3; EphA4; EPHB4; EPO; ERBB2 (Her-2); EREG; ERK8; ESR1; ESR2; F3 (TF); FADD; FasL; FASN; FCER1A; FCER2; FCGR3A; FCRL4; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRT1 (fibronectin); FLT1; FOS; FOSL1 (FRA-1); FY (DARC); GABRP (GABAa); GAGEB1; GAGEC1; Galectin-3; GALNAC4S-65T; GATA3; GDF5; GFI1; GGT1; GHR; GM-CSF; GNAS1; GNRH1; GPR2 (CCR1O); GPR31; GPR44; GPR81 (FKSG8O); GPR87; GPR137c; GRCC10 (C10); GRP; GSN (Gelsolin); GSTP1; HAVCR1; HAVCR2; HDAC4; EDAC5; HDAC7A; HDAC9; hepcidin; hemojuvelin; HGF; HIF1A; HIP1; histamine and histamine receptors; HLA-A; HLA-DRA; HM74; HMOX1; HUMCYT2A; ICEBERG; ICOS; 1D2; IFN-a; IFNA1; IFNA2; IFNA4; IFNA5; IFNA6; IFNA7; IFNB1; IFN-gamma; TFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; 1L18; IL18BP; IL18R1; IL18RAP; 1L19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; 1L2; 1L20; 1L20RA; 1L21R; 1L22; 1L22R; 1L22RA2; 1L23; 1L24; 1L25; 1L26; 1L27; 1L28A; 1L28B; 1L29; IL2RA; IL2RB; IL2RG; 1L3; 1L30; IL3RA; 1L4; IL4R; 1L5; IL5RA; 1L6; IL6 receptor; IL6ST (glycoprotein 130); 1L7; TL7R; 1L8; IL8RA; IL8RB; IL8RB; 1L9; IL9R; ILK; INHA; INHBA; INSL3; INSL4; IRAK1; IRAK2; ITGA1; ITGA2; 1TGA3; ITGA6 (a6 integrin); ITGAV; ITGB3; ITGB4 (b 4 integrin); JAG1; JAK1; JAK3; JUN; K6HF; KAI1; KDR; MTLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAG3; LAMA5; LEP (leptin); LIGHT; Lingo-p75; Lingo-Troy; LPS; LRP5; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MK167 (Ki-67); MMP2; MMP9; MS4A1; MSMB; MT3 (metallothionectin-ifi); MTSS 1; MUC 1 (mucin); MYC; MYD88; NCK2; neurocan; $Na_v1.7$; $Na_v1.8$; NFKB1; NFKB2; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPG; OPRD1; OX40L; OX40; P2RX7; PAP; PART1; PATE; PAWR; PCA3; PCNA; PCSK9; PD-1, PD-L1; PDGFA; PDGFB; PECAM1; PF4 (CXCL4); PGF; PGR; phosphacan; PIAS2; Placental Growth Factor (P1GF); PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; ROR1; S100A2; SCGBiD2 (lipophilin B); SCGB2A1 (mammaglobin 2); SCGB2A2 (mammaglobin 1); SCYE1 (endothelial Monocyte-activating cytokine); SDF2; SERPINA1; SERPINIA3; SERPINB5 (maspin); SERPINE1 (PAT-i); SERPINF1; SHBG; SLA2; SLC2A2; SLC33A1; SLC43A1; SLIT2; SPP1; SPRR1B (Spri); ST6GAL1; STAB1; STAT6; STEAP; STEAP2; TB4R2; TBX21; TCP1O; TDGF1; TEK; TGFA; TGFB1; TGFB1I1; TGFB2; TGFB3; TGFBI; TGFBR1; TGFBR2; TGFBR3; TH1L; THBS1 (thrombospondin-1); THBS2; THBS4; THPO; TIE (Tie-i); TIM3; TMP3; tissue factor; TLR1O; TLR2; TLR3; TLR4; TLR5; TLR6; TLR7; TLR8; TLR9; TMPRSS6; TNF; TNF-a; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSF1O (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (0X40 ligand); TNFSF5 (CD4O ligand); TNFSF6 (FasL); TNFSF7 (CD27 ligand); TNFSF8 (CD3O ligand); TNFSF9 (4-1BB ligand); TOLLIP; Toll-like receptors; TOP2A (topoisomerase lia); TP53; TPM1; TPM2; TRADD; TRAF1; TRAF2; TRAF3; TRAF4; TRAF5; TRAF6; TRAIL; TREM1; TREM2; TRPC6; TSLP; TWEAK; VEGFA; VEGFB; VEGFC; versican; VHL C5; VLA-4; Wnt7A; XCL1 (lymphotactin); XCL2 (SCM-1b); XCR1 (GPR5/CCXCR1); YY1; and ZFPM2.

In an example, the TOI is a human TOI selected from Table 5.

In an example, the TOI is OX40 ligand.
In an example, the TOI is OX40.
In an example, the TOI is PCSK9.
In an example, the TOI is IL6 receptor (IL-6R).
In an example, the TOI is LIGHT.
In an example, the TOI is VEGF-A.
In an example, the TOI is TNF alpha.
In an example, the TOI is P1GF.
In an example, the TOI is IGF1R.
In an example, the TOI is OPG.
In an example, the TOI is ICOS
In an example, the TOI is NGF.
In an example, the TOI is BMP6.
In an example, the TOI is ferroportin.
In an example, the TOI is TMPRSS6.
In an example, the TOI is hemojuvelin.
In an example, the TOI is VEGF receptor.
In an example, the TOI is PDGF receptor.

In an example, the TOI is stem cell factor receptor.
In an example, the TOI is hepcidin.
In an example, the TOI is IL-4 receptor alpha.
In an example, the TOI is sclerostin.
In an example, the TOI is IL-13 receptor.
In an example, the TOI is CD7.
In an example, the TOI is delta-like ligand-4 (Dll4).
In an example, the TOI is HGF.
In an example, the TOI is angiopoietin-2 (Ang2).
In an example, the TOI is GDF8.
In an example, the TOI is ERBB3.
In an example, the TOI is IL-17 receptor.
In an example, the TOI is CD40.
In an example, the TOI is CD40 ligand.
In an example, the TOI is EGFR.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", or "reduction" are all used herein to mean a decrease by a statistically significant amount. In some embodiments, "reduce," "reduction" or "decrease" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" does not encompass a complete reduction as compared to a reference level. A decrease can be preferably down to a level accepted as within the range of normal for an individual without a given disorder. However, for example, for the purposes of lowering or reducing cholesterol level, for example, a reduction by about 5-10 points can be considered a "decrease" or "reduction."

In certain aspects of all embodiments of the invention, the term "inhibition" is used. Inhibition refers and refers to decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more including 100% inhibition as compared to a reference level. "Complete inhibition" refers to a 100% inhibition as compared to a reference level.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. For the removal of doubt, "substantially" can refer to at least a 90% extent or degree of a characteristic or property of interest, e.g. at least 90%, at least 92%, at least 95%, at least 98%, at least 99% or greater.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. In some embodiments, the subject is a mammal, e.g., a primate, e.g., a human. The terms, "individual," "patient" and "subject" are used interchangeably herein. In some embodiments, the subject can be a non-human vertebrate, e.g. a primate, a rodent, a mouse, a rat, a pig, a sheep, a zebrafish, a frog, etc.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or condition, e.g., a cardiovascular condition. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" or "human in need" of treatment for a particular condition can be a subject having that condition, such as increased cholesterol levels, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids with natural amino acids. When referring to "modified polypeptides" one refers to polypeptides that include modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins with the specified sequence. One can also use peptide homologs, peptide orthologs, peptide paralogs, peptide fragments and other equivalents, variants, fragments, and analogs of the peptides as these terms are understood by one of ordinary skill in the art.

As used herein, the term "nucleic acid" or "nucleic acid sequence" refers to any molecule, preferably a polymeric molecule, incorporating units of ribonucleic acid, deoxyribonucleic acid. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA. In some aspects one can also use analogs of nucleic acids.

As used herein, the term "nucleic acid probe" refers to an isolated oligonucleotide molecule having a nucleic acid sequence which can hybridize to a target nucleic acid sequence, e.g. specifically hybridize to the target sequence. In some embodiments, a nucleic acid probe can further comprise a detectable label. In some embodiments, a nucleic acid probe can be attached to a solid surface. In some embodiments, a nucleic acid from is from about 5 nt to about 100 nt in length.

As used herein, the term "siRNA" refers to a nucleic acid that forms an RNA molecule comprising two individual strands of RNA which are substantially complementary to each other. Typically, the siRNA is at least about 15-40 nucleotides in length (e.g., each complementary sequence of the double stranded siRNA is about 15-40 nucleotides in length, and the double stranded siRNA is about 15-40 base pairs in length, preferably about 19-25 base nucleotides, e.g., 19, 20, 21, 22, 23, 24, or 25 nucleotides in length). In some embodiments, a siRNA can be blunt-ended. In some embodiments, a siRNA can comprise a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. The siRNA molecules can also comprise a 3' hydroxyl group. In some embodiments, the siRNA can comprise a 5' phosphate group. A siRNA has the ability to reduce or inhibit expression of a gene or target RNA when the siRNA is present or expressed in the same cell as the target gene, e.g. the target RNA. siRNA-dependent post-transcriptional silencing of gene expression involves cutting the target RNA molecule at a site guided by the siRNA.

As used herein, "PCSK9" or "proprotein convertase subtilisin/kexin type 9" refers to a serine protease involved in regulating the levels of the low density lipoprotein receptor (LDLR) protein (Horton et al., 2007; Seidah and Prat, 2007). PCSK9 has been shown to directly interact with the LDLR protein, be endocytosed along with the LDLR, and co-immunofluoresce with the LDLR throughout the endosomal pathway (Lagace et al., 2006). PCSK9 is a prohormone-proprotein convertase in the subtilisin (S8) family of serine proteases (Seidah et al., 2003). The sequence of PCSK9 for a variety of species is known, e.g., human PCSK9 (NCBI Gene ID No: 255738). Nucleotide and polypeptide sequences for a number of PCSK9 isoforms are provided herein, e.g., SEQ ID NOs: 1-37.

PCSK9 exists as both a pro-form and a mature form. Autocatalysis of the PCSK9 proform occurs between Gln152 and Ser153 (VFAQ|SIP (SEQ ID NO: 116)) (Naureckiene et al., 2003), and has been shown to be required for its secretion from cells (Seidah et al., 2003). The inactive form prior to this cleavage can be referred to herein as the "inactive", "pro-form", or "unprocessed" form of PCSK9. The C-terminal fragment generated by the autocatalysis event can be referred to herein as the "mature," "cleaved", "processed" or "active" PCSK9. Examples of pro-form and mature PCSK9 isoforms are provided herein, see, e.g. SEQ ID NOs: 1-27.

As used herein, the "catalytic domain" of PCSK9 refers to the portion of a PCSK9 polypeptide corresponding to positions 153 to 449 of PCSK9, e.g. of SEQ ID NO: 1. As used herein, the "C-terminal domain" of PCSK9 refers to the portion of a PCSK9 polypeptide corresponding to positions 450-692 of PCSK9, e.g., of SEQ ID NO: 1.

As used herein, a disease or condition "mediated by PCSK9" refers to a disease or condition which is caused by or characterized by a change in PCSK9, e.g. a change in expression level, a change in activity, and/or the presence of a variant or mutation of PCSK9. Non-limiting examples of such diseases or conditions can include, for example, a lipid disorder, hyperlipoproteinemia, hyperlipidemia; dyslipidemia; hypercholesterolemia, a heart attack, a stroke, coronary heart disease, atherosclerosis, peripheral vascular disease, claudication, type II diabetes, high blood pressure, and a cardiovascular disease or condition. In an example, the disease or condition is an inflammatory or autoimmune disease or condition. Methods of identifying and/or diagnosing such diseases and conditions are well known to medical practitioners of ordinary skill.

A subject at risk of having or developing a disease or condition mediated by PCSK9 can be a subject exhibiting one or more signs or symptoms of such a disease or condition or having one or more risk factors for such a disease or condition, e.g. being overweight, having elevated cholesterol level, comprising one or more genetic polymorphisms known to predispose to the disease or condition, e.g., elevated cholesterol level, such as having a mutation in the LDLR (encoding low-density lipoprotein receptor) or APOB (encoding apolipoprotein B) or in the PCSK9 gene and/or having a family history of such a disease or condition.

As used herein, "ligand" refers to a molecule which can bind, e.g., specifically bind, to a second molecule or receptor. In some embodiments, a ligand can be, e.g., an antibody, antibody fragment, antibody portion, and/or affibody.

The term "variant" as used herein refers to a peptide or nucleic acid that differs from the polypeptide or nucleic acid (eg, the most common one in humans, eg, most frequent in a database as disclosed herein, such as the 1000 Genomes Project database) by one or more amino acid or nucleic acid deletions, additions, yet retains one or more specific functions or biological activities of the naturally occurring molecule. Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

Variants of PCSK9 are provided elsewhere herein. Variants of PCSK9 can include the forms described herein as a, f, c, r, p, m, e h, aj, and q. Sequences of these variants are provided herein, see, e.g, SEQ ID NOs: 1-27 and in Table 1, 2 or 6.

In some aspects, one can use "synthetic variants", "recombinant variants", or "chemically modified" polynucleotide variants or polypeptide variants isolated or generated using methods well known in the art. "Modified variants" can include conservative or non-conservative amino acid changes, as described below. Polynucleotide changes can result in amino acid substitutions, additions, deletions, fusions and truncations in the polypeptide encoded by the reference sequence. Some aspects use include insertion variants, deletion variants or substituted variants with substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine.

"Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the blood brain barrier (BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol. Biol, 1999, 217, 721-739 and Taylor et al, J. Theor. Biol. 119 (1986); 205-218 and S. French and B. Robson, J. Mol. Evol. 19 (1983) 171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria. Antibodies can be humanized using routine technology.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody fragment" refers to a polypeptide that includes at least one immunoglobulin variable domain or immunoglobulin variable domain sequence and which specifically binds a given antigen. An antibody fragment can comprise an antibody or a polypeptide comprising an antigen-binding domain of an antibody. In some embodiments, an antibody fragment can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody fragment" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26 (3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). VH refers to the variable domain of the heavy chain. VL refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) or according to IMGT nomenclature.

D domain or region refers to the diversity domain or region of an antibody chain. J domain or region refers to the joining domain or region of an antibody chain.

An antibody "gene segment", e.g. a VH gene segment, D gene segment, or JH gene segment refers to oligonucleotide having a nucleic acid sequence that encodes that portion of an antibody, e.g. a VH gene segment is an oligonucleotide comprising a nucleic acid sequence that encodes a polypeptide VH domain.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, IMGT or Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "antibody binding site" refers to a polypeptide or domain that comprises one or more CDRs of an antibody and is capable of binding an antigen. For example, the polypeptide comprises a CDR3 (eg, HCDR3). For example the polypeptide comprises CDRs 1 and 2 (eg, HCDR1 and 2) or CDRs 1-3 of a variable domain of an antibody (eg, HCDRs1-3). In an example, the antibody binding site is provided by a single variable domain (eg, a VH or VL domain). In another example, the binding site comprises a VH/VL pair or two or more of such pairs.

As used herein, the term "specific binding" refers to a chemical interaction between two molecules, compounds, cells and/or particles wherein the first entity binds to the second, target entity with greater specificity and affinity than it binds to a third entity which is a non-target. For example, in an diagnostic test the specific binding of a ligand can distinguish between two variant PCSK9 proteins as described herein. In some embodiments, specific binding can refer to an affinity of the first entity for the second target entity which is at least 10 times, at least 50 times, at least 100 times, at least 500 times, at least 1000 times or greater than the affinity for the third nontarget entity. In the context of oligonucleotide strands which interact via hybridization, specific binding can be "specific hybridization."

Additionally, and as described herein, a recombinant human(ized) antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a target molecule.

The term "immunizing" refers to the step or steps of administering one or more antigens to an animal so that antibodies can be raised in the animal Generally, immunizing comprises injecting the antigen or antigens into the animal. Immunization can involve one or more administrations of the antigen or antigens. Suitable methods are prime-boost and RIMMS procedures as known to the skilled person in the art.

As used herein, an "affibody" refers to a relatively small synthetic protein molecule that has high binding affinity for a target protein (e.g. for PCSK9 or a variant therefor). Affibodies are composed of a three-helix bundle domain derived from the IgG-binding domain of staphylococcal protein A. The protein domain consists of a 58 amino acid sequence, with 13 randomized amino acids affording a range of affibody variants. Despite being significantly smaller than an antibody (an affibody weighs about 6 kDa while an antibody commonly weighs about 150 kDa), an affibody molecule works like an antibody since its binding site is approximately equivalent in surface area to the binding site of an antibody.

Figure 3:
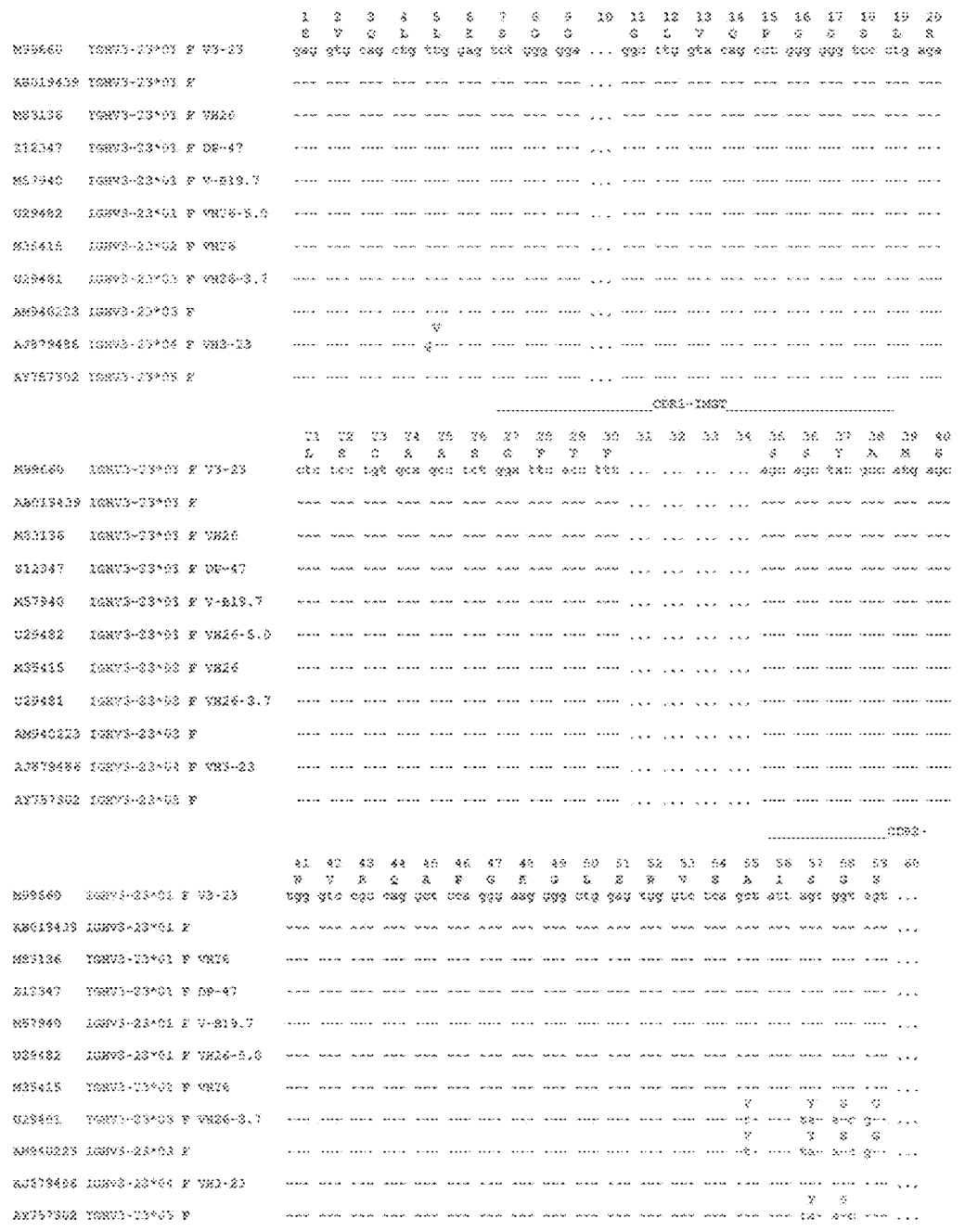
Figure 3:
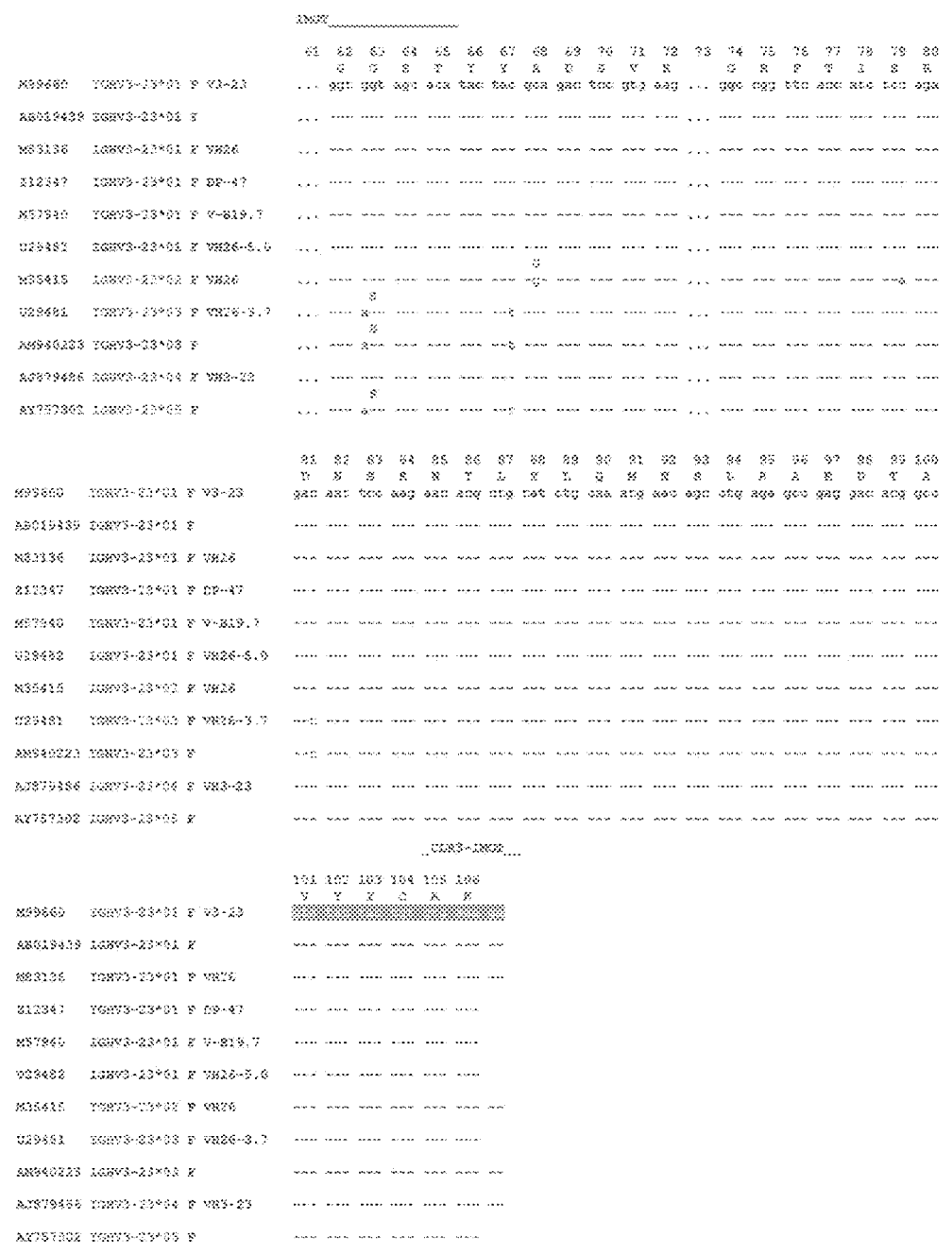

As used herein, "VH3-23*04" refers to a human VH domain variant comprising the polypeptide sequence of SEQ ID NO: 38. As opposed to the reference sequence, VH3-23*04 has a valine residue instead of a leucine residue (see FIGS. 3 and 4; L24V, numbering including signal sequence; valine at position 5 shown in FIG. 4) as a result of the presence of the rs56069819 SNP in the nucleic acid sequence encoding the VH domain. As used herein, "rs56069819" refers to a mutation or variant in a VH gene segment from adenosine to cytosine (or thymine to guanine, depending upon the strand of DNA which is being read), resulting in the VH domain encoding VH3-23*04. Rs56069819 is depicted in FIG. 4 and SEQ ID NO: 39, which demonstrate the T→G mutation (it is noted that the dbSNP entry for RS5606819 depicts the other strand, which comprises the A→C mutation). Further description of VH3-23*04 can be found, e.g., in US Patent Publication 2013/0071405; which is incorporated by reference herein in its entirety.

As used herein, "determine" or "determining" refers to ascertaining, e.g., by a quantitative or qualitative analysis. As used herein, "has been determined" can refer to ascertaining on the basis of previously obtained information or simultaneously obtained information.

In some aspects of all embodiments of the invention selecting can include automation such as a computer implemented software program that upon input of the relevant data such as ethnicity or a panel of SNP data can make the determination based on the instructions set forth herein.

As used herein, "assaying" refers to assessing, evaluating, quantifying, measuring, or characterizing an analyte, e.g., measuring the level of an analyte in a sample, identifying an analyte, or detecting the presence or absence of an analyte in a sample. In some embodiments, assaying refers to detecting a presence or absence of the analyte of interest. In some embodiments, assaying refers to quantifying an amount of an analyte, e.g., providing a measure of concentration or degree of analyte abundance. In some embodiments, assaying refers to enumerating the number of molecules of analyte present in a sample and/or specimen, e.g., to determine an analyte copy number.

As used herein "multiplex" refers to the carrying out of a method or process simultaneously and in the same reaction vessel on two or more, typically three or more, different target sequences, e.g. on two or more isoforms of PCSK9, or PCSK9 and an additional target. A multiplex analysis typically includes analysis of 10-50; 10-100; 10-1000, 10-5000, 10-10000 reactions in a multiplex format, such as a multiwall, an array, or a multichannel reaction.

Often the analysis or multiplex analysis is also automated using robotics and typically software executed by a computer and may include a robotic handling of samples, automatic or robotic selection of positive or negative results, assaying for presence of absence of a target, such as a nucleic acid polymorphism or a protein variant.

The term "biological sample" or "test sample" as used herein denotes a sample taken or isolated from a biological organism, e.g., a sample from a subject. Exemplary biological samples include, but are not limited to, a biofluid sample; serum; plasma; urine; saliva; hair, epithelial cells, skin, a tumor biopsy and/or tissue sample etc. The term also includes a mixture of the above-mentioned samples. The term "test sample" or "biological sample" also includes untreated or pretreated (or pre-processed) biological samples. For the analysis of nucleic acids, the biological sample should typically comprise at least one cell comprising nucleic acids.

The test sample can be obtained by removing a sample of cells from a subject, but can also be accomplished by using previously isolated cells (e.g. isolated at a prior time point and isolated by the same or another person). In addition, the test sample can be freshly collected or a previously collected, refrigerated, frozen or otherwise preserved sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

As used herein, "genotyping" refers to a process of determining the specific allelic composition of a cell and/or subject at one or more position within the genome, e.g. by determining the nucleic acid sequence at that position. Genotyping refers to a nucleic acid analysis and/or analysis at the nucleic acid level. As used herein, "phenotyping" refers a process of determining the identity and/or composition of an expression product of a cell and/or subject, e.g. by determining the polypeptide sequence of an expression product. Phenotyping refers to a protein analysis and/or analysis at the protein level.

As used herein, the term "nucleic acid amplification" refers to the production of additional copies of a nucleic acid sequence and is typically carried out using polymerase chain reaction (PCR) or ligase chain reaction (LCR) technologies well known in the art (Dieffenbach, C. W. and G. S. Dveksler (1995) PCR Primer, a Laboratory Manual, Cold Spring Harbor Press, Plainview, N.Y.). Other methods for amplification are also contemplated in aspects of the invention.

The term "allele-specific amplification" refers to a reaction (e.g., PCR reaction) in which at least one of the primers (e.g., allele-specific primer) is chosen from a polymorphic area of gene (e.g., single nucleotide polymorphism), with the polymorphism located at or near the primer's 3'-end. A mismatched primer will not initiate amplification, whereas a matched primer will initiate amplification. The appearance of an amplification product is indicative of the presence of the polymorphism.

As used herein, "sequencing" refers to the determination of the exact order of nucleotide bases in a strand of DNA (deoxyribonucleic acid) or RNA (ribonucleic acid) or the exact order of amino acids residues or peptides in a protein. Nucleic acid sequencing can be done using Sanger sequencing or next-generation high-throughput sequencing.

As used herein "next-generation sequencing" refers to oligonucleotide sequencing technologies that have the capacity to sequence oligonucleotides at speeds above those possible with conventional sequencing methods (e.g. Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyro-sequencing (454 Life Sciences/Roche Diagnostics); solid-phase, reversible dye-terminator sequencing (Solexa/Illumina): SOLiD technology (Applied Biosystems); Ion semiconductor sequencing (ION Torrent); DNA nanoball sequencing (Complete Genomics); and technologies available from Pacific Biosciences, Intelligen Bio-systems, Oxford Nanopore Technologies, and Helicos Biosciences. Next-generation sequencing technologies and the constraints and design parameters of associated sequencing primers are well known in the art (see, e.g. Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; Zhang et al., "The impact of next-generation sequencing on genomics", J Genet Genomics, 2011, 38 (3):95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. No. 7,282,337; U.S. Pat. No. 7,279,563; U.S. Pat. No. 7,226,720; U.S. Pat. No. 7,220,549; U.S. Pat. No. 7,169,560; U.S. Pat. No. 6,818,395; U.S. Pat. No. 6,911,345; US Pub. Nos. 2006/0252077; 2007/0070349; and 20070070349; which are incorporated by reference herein in their entireties).

As used herein, "nucleic acid hybridization" refers to the pairing of complementary RNA and DNA strands as well as the pairing of complementary DNA single strands. In some embodiments, nucleic acid hybridization can refer to a method of determining a nucleic acid sequence and/or identity by hybridizing a nucleic acid sample with a probe, e.g. Northern or Southern blot analysis or microarray analysis.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). For treatment to be effective a complete cure is not contemplated. The method can in certain aspects include cure as well.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

Multiple compositions can be administered separately or simultaneously. Separate administration refers to the two compositions being administered at different times, e.g. at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g. less than 10 or less than 5 minutes apart. Compositions administered simultaneously can, in some aspects, be administered as a mixture, with or without similar or different time release mechanism for each of the components.

As used herein, "contacting" refers to any suitable means for delivering, or exposing, an agent to at least one complex, enzyme, or cell. Exemplary delivery methods include, but are not limited to, direct delivery to cell culture medium, perfusion, injection, or other delivery method well known to one skilled in the art.

As used herein, "obtain" refers to any method of acquiring, securing, procuring, or coming into the possession of, e.g. a sample. Obtaining a biological sample from a subject can comprise physical removing a sample from a subject (e.g. drawing blood or taking a hair or saliva sample) without or without active participation from the subject; receiving a sample from a subject (e.g. the subject collects a saliva or hair sample themselves and provides it, e.g. in a container provided for the purpose); or procuring a sample from a storage facility, medical facility, or medical provider. Obtain from the human or subject, refers to an active step of, e.g., drawing blood or taking a tissue or cell sample.

As used herein, "cholesterol level" refers to a level of one or more of total cholesterol, LDL cholesterol, HDL cholesterol, and/or triglycerides. Cholesterol levels can be the level of cholesterol in the blood of a subject.

As used herein in reference to cholesterol levels, "maintain" refers to preventing the level from worsening (e.g. increasing). In some embodiments, maintaining a particular level refers to a process that results in the cholesterol level not increasing by more than 10% over time. Maintaining may also refer to maintaining a previously achieved level. For example, if a human has received statin treatment, one can maintain the cholesterol level achieved using the statin treatment.

In some embodiments, the subject treated according to the methods described herein has previously had their cholesterol level reduced. As used herein, "previously reduced" indicates that at a prior point in time, the subject experienced a decrease in cholesterol levels. The decrease can be due to administration of a pharmaceutical composition (e.g. administration of a composition as described herein or another composition, e.g. a statin) or due to another cause, e.g. a change in diet and/or exercise.

An existing treatment for high cholesterol levels is the administration of a statin. As referred to herein, a "statin" (also known as HMG-CoA reductase inhibitors) are inhibitors of the enzyme HMG-coA reductase, which mediates cholesterol production in the liver. Statins, by competitively binding HMG-CoA reductase, prevent the binding of HMG- CoA to the enzyme and thereby inhibit the activity of the reductase (e.g. the production of mevalonate). Non-limiting examples of statins can include atorvastatin (LIPITOR™), fluvastatin (LESCOL™), lovastatin (MEVACOR™, ALTOCOR™), pitavastatin (LIVALO™), pravastatin (PRAVACHOL™), rosuvastatin (CRESTOR™), and simvastatin (ZOCOR™). Statins can be administered in combination with other agents, e.g. the combination of ezetimibe and simvastatin.

Some subjects are, or become, resistant to statin treatment. As used herein, "resistant to statin treatment" or "reduced responsiveness to statin treatment" refers to a subject exhibiting a statistically significantly lower response to the administration of a statin as compared to a reference level. The reference level can be, e.g., the average response for a population of subjects or the level of the individual subject at an earlier date. A response to statin treatment is readily measured by one of skill in the art, e.g., measurement of cholesterol levels, changes in cholesterol levels, and/or HMG-CoA reductase activity.

As used herein, the term "detectable label" refers to a molecule or moiety that can be detected, e.g. measured and/or determined to be present or absent. Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detectable label can be a fluorescent compound. When the fluorescently label is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrahodimine isothiocynate (TRITC)), biotin, phycoerythrin, AMCA, CyDyes™, 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use as a detectable label can include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylenediaminetetraacetic acid (EDTA).

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g, the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g., the blood in a vein. A common, but non-limiting example of an injection device is a needle and syringe.

As used herein, a "buffer" refers to a chemical agent that is able to absorb a certain quantity of acid or base without undergoing a strong variation in pH.

As used herein, "packaging" refers to how the components are organized and/or restrained into a unit fit for distribution and/or use. Packaging can include, e.g., boxes, bags, syringes, ampoules, vials, tubes, clamshell packaging, barriers and/or containers to maintain sterility, labeling, etc.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

As used herein, a "solid surface" refers to an object suitable for the attachment of biomolecules. Non-limiting examples of a solid surface can include a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid surface can include many different materials including, but not limited to, polymers, plastics, resins, polysaccharides, silicon or silica based materials, carbon, metals, inorganic glasses, and membranes.

As used herein, "classification" of a subject, e.g., classification of the subject's ancestry refers to determining if the subject has biological ancestors who originated in a particular geographical area, and are therefore likely to have particular genetic variants found in the populations which have historically occupied that area. Classification can comprise, e.g. obtaining information on the subject's family, interviewing the subject or a family member regarding their biological family's ancestry, and/or genetic testing. Classification can be on the basis used for the 1000 Genomes Project, as will be familiar to the skilled person in the art. In some embodiments, the subject can be classified as being of a particular ancestry if at least the subject's genome comprises a substantial number of different alleles in common with other humans of that ancestry (eg, determined by reference to the 1000 Genomes Project database), for example, at least 10, 20, 30, 40, 50 or 100 or more alleles in common. Abbreviations for particular ancestral groups are provided in Table 4.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

It will be understood that particular configurations, aspects, examples, clauses and embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples.

Some embodiments of the technology described herein can be defined according to any of the following numbered paragraphs:

1. A method of treating or preventing a disease or condition in a human, wherein the disease or condition is mediated by a Target of Interest (TOI), wherein the TOI is present in humans as different polymorphic variants, the method comprising
   a. selecting a human that is positive for the TOI polymorphic variant, wherein the TOI in said human is encoded by a nucleotide sequence comprising an allele having a cumulative human allele frequency of less than 50% and/or wherein the TOI in said human is encoded by a nucleotide sequence comprising an allele having total human genotype frequency of less than 50%; and
   b. administering to the human an anti-TOI ligand to target the TOI in the human to treat or prevent said disease or condition.

In an alternative where the TOI is human PCSK9, paragraph 1 provides:—
   A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation as defined herein (eg, I474V or E670G) in SEQ ID NO: 1, wherein the antibody comprises a VH domain derived from the recombination of a human VH segment, a human D gene segment and a human JH segment, the human VH segment encoding a valine at the amino acid corresponding to position 5 of SEQ ID NO: 40 and wherein said human comprises (i) a VH gene segment encoding the framework 1 of SEQ ID NO: 40 and (ii) a nucleotide sequence encoding a proprotein convertase subtilisin/kexin type 9 (PCSK9) that comprises a C-terminal domain comprising said mutation in SEQ ID NO: 1.

In an alternative where the TOI is human PCSK9, paragraph 1 provides:—
   A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation as defined herein (eg, I474V or E670G) in SEQ ID NO: 1, wherein the antibody comprises a VL domain derived from the recombination of a human VL segment and a human JL segment, the human VL segment is a Vλ or Vκ disclosed herein and wherein said human comprises (i) said VL gene segment and (ii) a nucleotide sequence encoding a proprotein convertase subtilisin/kexin type 9 (PCSK9) that comprises a C-terminal domain comprising said mutation in SEQ ID NO: 1.

In an alternative where the TOI is human PCSK9, paragraph 1 provides:—

A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation as defined herein (eg, I474V or E670G) in SEQ ID NO: 1, wherein the antibody comprises a C domain encoded by a human CH, Cλ or Cκ gene segment disclosed herein and wherein said human comprises (i) said C gene segment and (ii) a nucleotide sequence encoding a proprotein convertase subtilisin/kexin type 9 (PCSK9) that comprises a C-terminal domain comprising said mutation in SEQ ID NO: 1.

2. The method of paragraph 1, wherein before step (a) the ligand has been or is determined as being capable of specifically binding to said TOI variant.

3. The method of paragraph 1 or 2, comprising determining that the human is positive for the TOI polymorphic variant, optionally wherein the step of determining comprises determining that the human is positive for a nucleotide variant encoding said TOI variant.

4. The method of paragraph 3, wherein the step of determining comprises assaying a biological sample obtained from said human for a nucleotide polymorphism encoding said TOI polymorphic variant.

5. The method of paragraph 3 or 4, wherein the step of determining comprises assaying a biological sample obtained from said human for a protein corresponding to the TOI polymorphic variant.

6. The method of any preceding paragraph, wherein said frequency is less than 15%.

7. The method of any preceding paragraph, wherein said frequency is less than 10%.

8. The method of any preceding paragraph, wherein the ligand is capable of specifically binding to two or more different TOI variants, each being encoded by a nucleotide sequence comprising an allele having a cumulative human allele frequency of less than 50% and/or having a total human genotype frequency of less than 50%.

9. A method of treating or preventing a disease or condition in a human, wherein the disease or condition is mediated by a Target of Interest (TOI), wherein the TOI is present in humans as different polymorphic variants, the method comprising
a. selecting a human that is negative for a variant nucleotide sequence comprising an allele having a cumulative human allele frequency of less than 50% and/or having a total human genotype frequency of less than 50%; or that the human is negative for a TOI variant encoded by a nucleotide sequence comprising the allele having a cumulative human allele frequency of less than 50% and/or having a total human genotype frequency of less than 50%; and
b. administering to the human an anti-TOI ligand to target the TOI variant in the human and treat or prevent said disease or condition, wherein the TOI in said human is a variant encoded by a nucleotide sequence comprising an allele having a cumulative human allele frequency of more than 50% and/or having a total human genotype frequency of more than 50%.

10. The method of paragraph 9, comprising determining that the human is positive for the TOI polymorphic variant, optionally wherein the determining comprises that the human has been or is phenotyped as positive for the most frequent TOI variant or genotyped for the nucleotide sequence thereof.

11. The method of paragraph 10, wherein determining comprises assaying for the nucleotide sequence to determine the presence of said allele.

12. The method of paragraph 11, wherein the assaying comprises nucleic acid amplification.

13. The method of paragraph 11 or 12, wherein the assaying comprises hybridization, sequencing, or next generation sequencing.

14. The method of any of paragraphs 11-13, further comprising the step of obtaining a biological sample from the human.

15. The method of any one of paragraphs 9-14, wherein the ligand has been or is determined as being capable of specifically binding to the most frequent TOI variant.

16. The method of any one of paragraphs 9-15, wherein the ligand has been or is determined as being substantially incapable of neutralising or inhibiting said TOI variant.

17. The method of any one of paragraphs 9-16, wherein the ligand is capable of specifically binding to the most frequent TOI variant.

18. The method of any one of paragraphs 9-17, wherein the ligand is capable of specifically binding to two or more different TOI variants, each being encoded by a nucleotide sequence comprising an allele having a cumulative human allele frequency of more than 50%.

19. The method of any preceding paragraph, wherein said TOI polymorphic variant has been or is determined as being present in at least two different human ethnic populations.

20. The method of any preceding paragraph, wherein said cumulative human allele frequency is the frequency in a database of naturally-occurring sequences sampled from at least 15 different human ethnic populations and comprising at least 1000 sequences.

21. The method of any of the preceding paragraphs, wherein the ligand is an antibody, antibody fragment or an affibody.

22. The method of any of the preceding paragraphs, wherein the ligand comprises a nucleotide sequence that specifically hybridises to a TOI nucleotide sequence comprising an allele having a cumulative human allele frequency of less than 50% and/or having a total human genotype frequency of less than 50% or an RNA transcript thereof; and/or the ligand comprises a nucleotide sequence that comprises at least 10 contiguous nucleotides of a nucleotide sequence having a cumulative human allele frequency of less than 50% and/or having a total human genotype frequency of less than 50% or is an antisense sequence thereof.

23. The method of any of the preceding paragraphs, wherein the genome of said human comprises an allele having a cumulative human allele frequency of less than 50% and the allele is found in at least 2 different ethnic populations.

24. A composition comprising a ligand capable of binding a target of interest encoded by a nucleotide sequence comprising an allele having a cumulative human allele frequency of less than 50% and the allele is found in at least 2 different ethnic populations and optionally a pharmaceutically acceptable carrier and optionally a label or instructions for use to treat and/or prevent said disease or condition in a human; optionally wherein the label or instructions comprise a marketing authorisation number issued by a regulatory authority.
25. A kit for treating or preventing a condition or disease mediated by a target of interest as recited in any preceding paragraph, the kit comprising a ligand capable of specifically binding a target of interest encoded by a nucleotide sequence comprising an allele having a cumulative human allele frequency of less than 50% and the allele is found in at least 2 different ethnic populations; and optionally in combination with a label or instructions for use to treat and/or prevent said disease or condition in a human; optionally wherein the label or instructions comprise a marketing authorisation number issued by a regulatory agency; optionally wherein the kit comprises an injection pen or IV container that comprises the ligand.
26. The composition of paragraph 24 or the kit of paragraph 25, wherein the regulatory agency is FDA or EMA.
27. A method of producing an anti-human TOI antibody binding site, the method comprising obtaining a plurality of anti-TOI antibody binding sites, screening the antibody binding sites for binding to a TOI comprising an amino acid sequence encoded by a nucleotide sequence comprising an allele having a cumulative human allele frequency of less than 50% and/or a total human genotype frequency of less than 50%, or to a peptide thereof that comprises an amino acid variation from the corresponding sequence encoded by the TOI-encoding nucleotide sequence comprising an allele having the highest cumulative human allele frequency and/or the highest total human genotype frequency, and isolating an antibody binding site that binds in the screening step.
28. A method of producing an anti-human TOI antibody, the method comprising immunising a non-human vertebrate with a TOI comprising an amino acid sequence encoded by a nucleotide sequence comprising an allele having a cumulative human allele frequency of less than 50% and/or a total human genotype frequency of less than 50%, or to a peptide thereof that comprises an amino acid variation from the corresponding sequence encoded by the TOI-encoding nucleotide sequence comprising an allele having the highest cumulative human allele frequency and/or the highest total human genotype frequency, and isolating an antibody that binds a TOI comprising an amino acid sequence encoded by a TOI nucleotide sequence comprising an allele having a cumulative human allele frequency of less than 50% and/or a total human genotype frequency of less than 50%, and optionally producing a TOI-binding fragment or derivative of the isolated antibody.
29. The method of paragraph 28, wherein the non-human vertebrate is a mouse or a rat.
30. The method of paragraph 29 or 30, comprising the step of obtaining a nucleic acid encoding the antibody, fragment, derivative or binding site and optionally inserting the nucleic acid in an expression vector.
31. A kit for TOI genotyping a human, wherein the kit comprises a nucleic acid comprising a nucleotide sequence that specifically hybridises to a TOI nucleotide sequence selected having a cumulative human allele frequency of less than 50% and/or a total human genotype frequency of less than 50% or an RNA transcript thereof; and/or the nucleic acid comprises a nucleotide sequence that comprises at least 10 contiguous nucleotides of a TOI nucleotide sequence having a cumulative human allele frequency of less than 50% and/or a total human genotype frequency of less than 50% or is an antisense sequence thereof.
32. A kit for TOI genotyping or phenotyping a human, wherein the kit comprises a ligand capable of binding a target of interest encoded by a nucleotide sequence comprising an allele having a cumulative human allele frequency of less than 50% or an antibody, fragment or derivative produced by the method of any one of paragraphs 28 to 30.
33. The kit of paragraph 32, wherein the allele is found in at least 2 different ethnic populations.
34. Use of an anti-TOI ligand that specifically binds a human TOI comprising an amino acid sequence encoded by a TOI nucleotide sequence having a cumulative human allele frequency of less than 50% and/or a total human genotype frequency of less than 50%, in the manufacture of a medicament for treating and/or preventing a TOI-mediated disease or condition in a human whose genome comprises a TOI nucleotide sequence having a cumulative human allele frequency of less than 50% and/or having a total human genotype frequency of less than 50%.
35. Use of an anti-TOI ligand that specifically binds a human TOI comprising an amino acid sequence encoded by a TOI nucleotide sequence having a cumulative human allele frequency of less than 50% and/or a total human genotype frequency of less than 50%, in the manufacture of a medicament for targeting said TOI in a human to treat and/or prevent a disease or condition mediated by TOI.
36. A method of targeting a Target of Interest (TOI) for treating and/or preventing a TOI-mediated disease or condition in a human, the method comprising administering an anti-TOI ligand to a human comprising a TOI nucleotide sequence comprising an allele selected as having a cumulative human allele frequency of less than 50% and/or a total human genotype frequency of less than 50%, whereby a TOI encoded by said nucleotide sequence is targeted.
37. The method of paragraph 36, wherein the method comprises targeting a human TOI comprising an amino acid sequence with said ligand to treat and/or prevent said disease or condition in said human, wherein said amino acid sequence is encoded by a nucleotide sequence comprising an allele having a cumulative human allele frequency of less than 50% and/or a total human genotype frequency of less than 50%.
38. A method of Target of Interest (TOI) genotyping a nucleic acid sample of a human, the method comprising assaying in the sample the presence of a TOI nucleotide sequence comprising an allele having a cumulative human allele frequency of less than 50% and/or having a total human genotype frequency of less than 50%.
39. A method of Target of Interest (TOI) typing a protein sample of a human, the method comprising assaying the sample the presence of a TOI amino acid sequence encoded by a TOI nucleotide sequence comprising an allele having a cumulative human allele frequency of less than 50% and/or having a total human genotype frequency of less than 50%.
40. The method of paragraph 38 or 39, comprising obtaining a sample of serum, blood, faeces, hair, urine or saliva from a human, whereby the nucleic acid or protein sample is obtained for use in the step of assaying said sequence.
41. The method of any one of paragraphs 38-40, comprising using a ligand capable of targeting a nucleic acid sequence comprising an allele having a cumulative human allele frequency of less than 50% and/or having a total human genotype frequency of less than 50% or a ligand capable of specifically binding the TOI encoded by said nucleic acid sequence to carry out said identifying step.

42. A diagnostic kit comprising a ligand that is capable of binding a human Target of Interest (TOI) comprising an amino acid sequence encoded by a TOI nucleotide sequence comprising an allele having a cumulative human allele frequency of less than 50% and/or a total human genotype frequency of less than 50% and instructions for carrying out the method of any one of paragraphs 38-41.

43. The diagnostic kit wherein the ligand is selected from an antibody, antibody fragment, antibody portion, affybody, oligonucleotide, modified oligonucleotide, antisense oligonucleotide, siRNA, and microRNA.

44. A diagnostic kit comprising a nucleic acid probe comprising a nucleotide sequence that specifically hybridises a Target of Interest (TOI) nucleotide sequence comprising an allele having a cumulative human allele frequency of less than 50% and/or a total human genotype frequency of less than 50% or an RNA transcript thereof and instructions for carrying out the method of paragraph 38 or 39.

45. The method, ligand, composition, kit or use of any preceding paragraph, wherein the TOI is encoded by a nucleotide sequence having a cumulative human allele frequency from 1 to 10% and/or a total human genotype frequency from 1 to about 15% or from 1 to 15%.

46. The method, ligand, composition, kit or use of any preceding paragraph wherein the TOI is a human TOI selected from Table 5; optionally for treating and/or preventing a corresponding disease or condition as set out in Table 5.

47. A method of treating or preventing a disease or condition in a human, wherein the disease or condition is mediated by a Target of Interest (TOI), wherein the TOI is present in humans as different polymorphic variants, the method comprising administering to the human determined to be positive for the TOI polymorphic variant, wherein the TOI in said human is encoded by a nucleotide sequence comprising an allele having a cumulative human allele frequency of less than 50% and/or wherein the TOI in said human is encoded by a nucleotide sequence comprising an allele having total human genotype frequency of less than 50% an anti-TOI ligand to target the TOI in the human to treat or prevent said disease or condition.

48. The method of paragraph 47, wherein the anti-TOI ligand is selected from an antibody, an antibody portion, an antibody fragment, an affibody, an antisense oligonucleotide, an siRNA, and a microRNA.

Additional Tailoring of Ligands to Genotype and/or Phenotype of the Human Patient As described herein, the present invention contemplates ligands (eg, antibodies and fragments) whose binding site specificities have been matched to one or more variant human TOIs (eg, PCSK9 or IL6R). Additionally or alternatively (and as further illustrated in the non-limiting Examples below), an optional aspect of the invention provides for matching of other features of the ligand to the patient's genotype or phenotype. In this respect, for example, the invention includes the ability to match amino acid sequence variation in a human patient to one or more ligand sequences or domains outside of the binding sites. For example, where the ligand comprises or consists of a human TOI-binding antibody or an anti-human TOI receptor Fc fusion, this aspect of the invention provides for more tailored matching of one or more constant region domains (eg, the Fc) to the patient genotype or phenotype. Additionally or alternatively, it is contemplated that sequence variation in the binding site can be similarly matched to the patient's genotype or phenotype. The present inventor has done this by considering the SNP occurrences in sequences encoding one or more parts of the ligand, eg, SNP occurrences in one, more or all of the gene segments from which the variable domain(s) and/or constant region domain(s) are derived. The inventor realised that it would be desirable to match the ligand to one or more corresponding variant SNPs found in the patient to be treated therapeutically and/or prophylactically. Matching could involve designing the ligand specifically for a patient of known phenotype and/or genotype, or matching could involve choosing a ligand by determining that there is correspondence between variation in the patient's phenotype or genotype with the variation in the ligand amino acid and/or corresponding nucleotides.

A key consideration for the inventor was the desire to promote compatibility of the ligand with the patient's body, and in particular, the possible patient immune system responses to administered ligands. For example, it has been observed that human patients receiving human or humanised antibody drugs may mount an immune response against the incoming antibody (a so-called HAHA response) which results in the patient producing anti-drug antibodies as a result of the patient's immune system recognising the drug as foreign. For example, studies have suggested that some patients receiving HUMIRA™ (adalimumab), currently the biggest selling antibody medicine, mount a HAHA immune response against the medicine, and this may impact treatment adversely. Reference is made to JAMA. 2011; 305 (14):1460-1468. doi:10.1001/jama.2011.406: "Development of Antidrug Antibodies Against Adalimumab and Association With Disease Activity and Treatment Failure During Long-term Follow-up", G M Bartelds et al. The authors concluded that results of this study showed that development of antidrug antibodies was associated with a negative outcome of adalimumab treatment in human RA patients. It was reported that not only did patients with anti-adalimumab antibodies discontinue treatment more often and earlier than patients without anti-adalimumab antibodies, they also had a higher disease activity during treatment and only rarely came into remission. In addition, reportedly the data showed that two-thirds of the anti-adalimumab antibody-positive patients developed these antibodies in the first 28 weeks of treatment and that the presence of anti-adalimumab antibodies substantially influenced serum adalimumab concentrations.

This HAHA theme is, therefore, a significant concern and this has been considered by the regulatory authorities. For example, the European Medicines Agency (EMA) has issued a "Guideline on immunogenicity assessment of monoclonal antibodies intended for in vivo clinical use" (available on the world wide web at ema.europa.eu/docs/en_GB/document_library/Scientific_guideline/2012/06/WC500128688.pdf; EMA/CHMP/BMWP/86289/2010, addendum to EMEA/CHMP/BMWP/14327/2006), which came into force on 1 Dec. 2012. As such, it is good practice for researchers to identify and assess risk of anti-antibody drug occurrence and effects.

The present aspect of the invention, by more closely tailoring the ligand itself (as well as its specificity) to the patient, helps to address these considerations when designing and administering anti-human TOI medicines for treating and/or preventing human TOI-related diseases and conditions.

The inventor also considered the desirability to tailor the variation in the ligand constant region (eg, for an antibody or Fc-containing ligand), mindful that then the constant region being administered to the patient would be tuned to the various components, such as patient's Fc receptors, that would interact with the constant region in the patient. Good Fc/Fc receptor interactions can be important for drug recycling (via the FcRn) to provide for useful half-lives in vivo or for use in cell killing, eg, for cancer indications. In this way it is possible, therefore, to tune the effector function of the constant region (eg, Fc) to the patient more closely, to promote efficacy. For example, more efficacious drugs are desirable for better patient treatment and may provide the possibility of lowered dosing and/or dosing frequencies.

Thus, in examples of this aspect, the invention provides the following (set out as clauses):—

1. The ligand, method, use, kit or composition of the invention, wherein
    (i) the ligand (eg, antibody or fragment) comprises
        (c) a variable domain that is encoded by a human V region nucleotide sequence, wherein the V nucleotide sequence is derived from recombination of human VH, D and JH gene segments or human VL and JL gene segments; or
        (d) a constant region domain encoded by a C region gene segment;
        Wherein a first gene segment of said gene segments of (a), or said C region gene segment of (b) comprises a first single nucleotide polymorphism (SNP) encoding a first amino acid polymorphism; and
    (ii) the genome of said human comprises said first SNP or wherein said human expresses (a') an antibody variable domain comprising said first amino acid polymorphism or (b') an antibody constant domain comprising said first amino acid polymorphism.
2. The ligand, method, use, kit or composition of clause 1, wherein blood of said human comprises substantially no antibodies that specifically bind to the domain comprising said first amino acid polymorphism as determined in an in vitro binding assay.
3. The ligand, method, use, kit or composition of clause 2, wherein SPR is used to carry out said assay.
    In an alternative, ELISA is used.
4. The ligand, method, use, kit or composition of any one of clauses 1 to 3, wherein the genome of said human comprises said first gene segment (when (a) applies) or said C region gene segment (when (b) applies).
5. The ligand, method, use, kit or composition of any one of clauses 1 to 4, wherein said first segment or a second segment of said segments of (a), or said C region gene segment of (b), comprises a second SNP encoding a second amino acid polymorphism; and wherein the genome of said human comprises said second SNP or wherein said human expresses (a'') an antibody variable domain comprising said second amino acid polymorphism or (b'') an antibody constant region domain comprising said first and second amino acid polymorphisms.
6. The ligand, method, use, kit or composition of clause 5, wherein said human expresses an antibody variable domain comprising said first and second amino acid polymorphisms.
7. The ligand, method, use, kit or composition of clause 5 or 6, wherein the first and second SNPs of said genome are comprised by the same antibody gene segment.
    For example, the first and second SNPs of the genome are comprised by an IGHG1*01 gene segment and said first segment of (a) is an IGHG1*01 gene segment.
    For example, the first and second SNPs of the genome are comprised by an IGHG2*01 gene segment and said first segment of (a) is an IGHG2*01 gene segment.
8. The ligand, method, use, kit or composition of any one of clauses 1 to 7, wherein each SNP is a variable region gene segment SNP.
9. The ligand, method, use, kit or composition of any one of clauses 1 to 7, wherein each SNP is a constant region gene segment SNP, eg each SNP is a gamma-1 constant region gene segment SNP, or a gamma-2 constant region gene segment SNP, or a gamma-3 constant region gene segment SNP or a gamma-4 constant region gene segment SNP.
10. The ligand, method, use, kit or composition of clause 9, wherein the first SNP is a CH1, CH2, CH3 or CH4 gene segment SNP and/or the second SNP is a CH1, CH2, CH3 or CH4 gene segment SNP.
11. The ligand, method, use, kit or composition of any one of clauses 1 to 8, wherein each SNP is a variable domain SNP, eg, a VH domain SNP, or a Vκ domain SNP, or a Vλ SNP.
12. The ligand, method, use, kit or composition of any one of clauses 1 to 11, wherein said constant region domain of (b) is comprised by an antibody Fc region.
13. The ligand, method, use, kit or composition of any one of clauses 1 to 12, wherein the ligand (eg, antibody or fragment) has been determined to specifically bind one or more human TOI variants as disclosed herein, for example, with a KD of 1 nM or less (eg, 100 or 10 pM or less) as determined by SPR.
14. The ligand, method, use, kit or composition of the invention (eg, according to any one of clauses 1 to 13), wherein the ligand comprises or consists of an antibody or fragment that comprises a human antibody variable domain derived from the recombination of a human V gene segment and a human J gene segment (and optionally a human D gene segment when the variable domains are VH domains); and wherein the genome of the human comprises said human V gene segment and/or the human expresses antibodies comprising antibody variable domains derived from the recombination of said human V gene segment and a human J gene segment (and optionally a human D gene segment).
    In an example, the V gene segment is any of the V gene segments disclosed in WO2013041844, a 1000 Genomes database and/or www.imgt.org, the disclosures of which (including disclosure relating to sequence) is explicitly incorporated herein by reference for use in the present invention.
15. The ligand, method, use, kit or composition of the invention (eg, according to any one of clauses 1 to 14), wherein the ligand (eg, comprising or consisting of an antibody or fragment or an Fc-fused human TOI receptor) comprises a human heavy chain constant domain encoded by a first constant region nucleotide sequence; and wherein the genome of the human comprises a heavy chain constant region nucleotide sequence that is identical to said first constant region nucleotide sequence and/or the human expresses antibodies comprising said human constant domain.
16. The ligand, method, use, kit or composition of the invention (eg, according to any one of clauses 1 to 15), wherein the ligand (eg, comprising or consisting of an antibody or fragment or an Fc-fused human TOI receptor) comprises a human gamma heavy chain CH1 domain encoded by a CH1 nucleotide sequence; and wherein the genome of the human comprises a gamma heavy chain constant region nucleotide sequence that is identical to said CH1 nucleotide sequence and/or the human expresses antibodies comprising said human gamma CH1 domain.
17. The ligand, method, use, kit or composition of the invention (eg, according to any one of clauses 1 to 16), wherein the ligand (eg, comprising or consisting of an antibody or fragment or an Fc-fused human TOI receptor) comprises a human gamma heavy chain CH2 domain encoded by a CH2 nucleotide sequence; and wherein the genome of the human comprises a gamma heavy chain constant region nucleotide sequence that is identical to said CH2 nucleotide sequence and/or the human expresses antibodies comprising said human gamma CH2 domain.

18. The ligand, method, use, kit or composition of the invention (eg, according to any one of clauses 1 to 17), wherein the ligand (eg, comprising or consisting of an antibody or fragment or an Fc-fused human TOI receptor) comprises a human gamma heavy chain CH3 domain encoded by a CH3 nucleotide sequence; and wherein the genome of the human comprises a gamma heavy chain constant region nucleotide sequence that is identical to said CH3 nucleotide sequence and/or the human expresses antibodies comprising said human gamma CH3 domain.

19. The ligand, method, use, kit or composition of the invention (eg, according to any one of clauses 1 to 18), wherein the ligand (eg, comprising or consisting of an antibody or fragment or an Fc-fused human TOI receptor) comprises a human gamma heavy chain CH4 domain encoded by a CH4 nucleotide sequence; and wherein the genome of the human comprises a gamma heavy chain constant region nucleotide sequence that is identical to said CH4 nucleotide sequence and/or the human expresses antibodies comprising said human gamma CH4 domain.

20. The ligand, method, use, kit or composition of the invention (eg, according to any one of clauses 1 to 19), wherein the ligand (eg, comprising or consisting of an antibody or fragment or an Fc-fused human TOI receptor) comprises a human gamma heavy chain Fc region encoded by a Fc nucleotide sequence; and wherein the genome of the human comprises a gamma heavy chain constant region nucleotide sequence that is identical to said Fc nucleotide sequence and/or the human expresses antibodies comprising said human gamma Fc region.

21. The ligand, method, use, kit or composition of any one of clauses 16 to 20, wherein said human gamma heavy chain is a human gamma-1 heavy chain.

22. The ligand, method, use, kit or composition of any one of clauses 16 to 20, wherein said human gamma heavy chain is a human gamma-2 heavy chain.

23. The ligand, method, use, kit or composition of any one of clauses 16 to 20, wherein ligand comprises a human IGHG1*01 gamma-1 heavy chain constant region.

24. The ligand, method, use, kit or composition of any one of clauses 16 to 20, wherein ligand comprises a human IGHG2*01 gamma-1 heavy chain constant region.

25. The ligand, method, use, kit or composition of any one of clauses 15 to 24, wherein the human has been or is genotyped as positive for said heavy chain constant region nucleotide sequence.

26. The ligand, method, use, kit or composition of clause 23, wherein the human has been or is genotyped as positive for human IGHG1*01 nucleotide sequence.

27. The ligand, method, use, kit or composition of clause 24, wherein the human has been or is genotyped as positive for human IGHG2*01 nucleotide sequence.

28. The ligand, method, use, kit or composition of any one of clauses 16 to 24, wherein the human has been or is phenotyped as positive for said gamma heavy chain constant domain, CH1, CH2, CH3, CH4 or Fc.

29. The ligand, method, use, kit or composition of clause 28, (i) when dependent from clause 23, wherein the human has been or is phenotyped as positive for a human IGHG1*01 gamma heavy chain constant domain, CH1, CH2, CH3, CH4 or Fc or (ii) when dependent from clause 24, wherein the human has been phenotyped as positive for a human IGHG2*01 gamma heavy chain constant domain, CH1, CH2, CH3, CH4 or Fc.

30. The method or use of any one of clauses 16 to 24 and 26 to 29, comprising genotyping the human as positive for said gamma heavy chain constant region nucleotide sequence, eg, positive for said gamma heavy chain constant domain, CH1, CH2, CH3, CH4 or Fc nucleotide sequence; positive for said human IGHG1*01 gamma heavy chain constant region, CH1, CH2, CH3, CH4 or Fc nucleotide sequence; or positive for said human IGHG2*01 gamma heavy chain constant region, CH1, CH2, CH3, CH4 or Fc nucleotide sequence.

31. The method or use of any one of clauses 16 to 24 and 26 to 30, comprising phenotyping the human as positive for said gamma heavy chain constant region, eg, positive for said gamma heavy chain constant domain, CH1, CH2, CH3, CH4 or Fc; positive for said human IGHG1*01 gamma heavy chain constant domain, CH1, CH2, CH3, CH4 or Fc; or positive for said human IGHG2*01 gamma heavy chain constant domain, CH1, CH2, CH3, CH4 or Fc.

Examples of Tailored Ligands

The inventor analysed amino acid variability and distribution amongst large representative human samples. The result of the analysis for example antibody gene segments is shown in Table 9.

In a first example, the inventor identified the possibility of addressing the rarer IGH-gamma-1 SNPs 204D (observed cumulative frequency of 0.296) and 206L (observed cumulative frequency of 0.283) individually or in combination. These residues are part of the CH3 domain, and as such they form part of antibody Fc regions. Thus, matching of these CH3 variations with the patient is especially beneficial for reasons as discussed above. Thus, this example provides aspects set out in the following clauses.

32. The ligand, method, use, kit or composition of the invention (eg, according to any one of clauses 1 to 31), wherein the ligand (eg, comprising or consisting of an antibody or fragment or an Fc-fused TOI receptor) comprises a human gamma-1 heavy chain constant region that comprises an Asp corresponding to position 204 of SEQ ID NO: 42 or a Leu corresponding to position 206 of SEQ ID NO: 42 and wherein the genome of the human comprises a gamma-1 heavy chain constant region nucleotide sequence that encodes such an Asp or Leu or the human expresses antibodies comprising human gamma-1 constant regions comprising such an Asp or Leu.

The skilled person will be familiar with techniques for determining genome sequences of a human, eg, by using a sample containing genomic DNA and/or RNA, sequencing and comparing using bioinformatics or other computer tools to compare the sampled sequence with sequences of human alleles (eg, as shown in the IMGT, 100 genomes or other database as disclosed herein). In an example, the sample is a blood or saliva or cheek swab sample.

33. The ligand, method, use, kit or composition of clause 32, wherein the ligand comprises a human gamma-1 heavy chain constant region that comprises an Asp corresponding to position 204 of SEQ ID NO: 42 and a Leu corresponding to position 206 of SEQ ID NO: 42.

34. The ligand, method, use, kit or composition of clause 32 or 33, wherein the genome of the human comprises a gamma-1 heavy chain constant region nucleotide sequence that encodes such an Asp and Leu or the human expresses antibodies comprising human gamma-1 constant regions comprising such an Asp and Leu.

35. The ligand, method, use, kit or composition of clause 32, 33 or 34, wherein the ligand comprises a human IGHG1*01 gamma-1 heavy chain constant region, eg, an Fc, CH1, CH2 and/or CH3 domain encoded by human IGHG1*01.

36. The ligand, method, use, kit or composition of any one of clauses 32 to 35, wherein the genome of the human comprises a human IGHG1*01 nucleotide sequence or the human expresses antibodies comprising human constant domains encoded by a human IGHG1*01 nucleotide sequence.

37. The ligand, method, use, kit or composition of any one of clauses 32 to 36, wherein the ligand comprises a hinge region encoded by human IGHG1*01.

38. The ligand, method, use, kit or composition of any one of clauses 32 to 37, wherein the ligand comprises or consists of an antibody, wherein the antibody comprises heavy chains that comprise SEQ ID NO: 61.

39. The ligand, method, use, kit or composition of any one of clauses 32 to 38, wherein the human is of European ancestry.

As shown in Table 9, 204D and 206L are found in such humans.

40. The ligand, method, use, kit or composition of any one of clauses 32 to 39, wherein the human has been or is genotyped as positive for said Asp and/or Leu.

41. The ligand, method, use, kit or composition of any one of clauses 32 to 40, wherein the human has been or is genotyped as positive for human IGHG1*01.

42. The ligand, method, use, kit or composition of any one of clauses 32 to 41, wherein the human has been or is phenotyped as positive for a human IGHG1*01 CH3.

43. The method or use of any one of clauses 32 to 42, comprising selecting a said human whose genome comprises a codon(s) encoding said Asp and/or Leu; comprises human IGHG1*01; or comprises a human IGHG1*01 CH3.

44. The method or use of any one of clauses 32 to 43, comprising selecting a said human whose phenotype comprises said Asp and/or Leu; a human IGHG1*01 region; or a human IGHG1*01 CH3.

44a. The ligand, method, use, kit or composition of any one of clauses 32 to 44, wherein the human expresses antibodies comprising human gamma-1 constant regions comprising such an Asp and Leu.

In a second example, the inventor identified the possibility of addressing IGH-gamma-2 SNPs. This included consideration of Fc region variation—in this respect, the inventor focused on positions 161 and 257 which are in the Fc region. Thus, this example provides aspects set out in the following clauses.

45. The ligand, method, use, kit or composition of the invention (eg, according to any one of clauses 1 to 31), wherein the ligand (eg, comprising or consisting of an antibody or fragment or an Fc-fused TOI receptor) comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44; and wherein the genome of the human comprises a gamma-2 heavy chain constant region nucleotide sequence that encodes such a selected amino acid or the human expresses antibodies comprising human gamma-2 constant regions comprising such a selected amino acid.

46. The ligand, method, use, kit or composition of clause 45, wherein the ligand comprises a human gamma-2 heavy chain constant region that comprises (i) a Pro corresponding to position 72 of SEQ ID NO: 44, an Asn corresponding to position 75 of SEQ ID NO: 44, a Phe corresponding to position 76 of SEQ ID NO: 44 and optionally (ii) a Val corresponding to position 161 of SEQ ID NO: 44 and/or an Ala corresponding to position 257 of SEQ ID NO: 44; and wherein the genome of the human comprises a gamma-2 heavy chain constant region nucleotide sequence that encodes such amino acids of (i) or the human expresses antibodies comprising human gamma-2 constant regions comprising such amino acids of (i).

This example focuses on CH1 variation.

47. The ligand, method, use, kit or composition of clause 45 or 46, wherein the ligand comprises a human gamma-2 heavy chain constant region that comprises (i) a Val corresponding to position 161 of SEQ ID NO: 44 and an Ala corresponding to position 257 of SEQ ID NO: 44 and optionally (ii) an amino acid selected from the group consisting of a Pro corresponding to position 72 of SEQ ID NO: 44, an Asn corresponding to position 75 of SEQ ID NO: 44 and a Phe corresponding to position 76 of SEQ ID NO: 44; and wherein the genome of the human comprises a gamma-2 heavy chain constant region nucleotide sequence that encodes such amino acids of (i) or the human expresses antibodies comprising human gamma-2 constant regions comprising such amino acids of (i).

This example focuses on Fc variation.

48. The ligand, method, use, kit or composition of any one of clauses 45 to 47, wherein the ligand comprises a human IGHG2*01 gamma-2 heavy chain constant region, eg, an Fc, CH1, CH2 and/or CH3 domain encoded by human IGHG2*01.

49. The ligand, method, use, kit or composition of any one of clauses 45 to 48, wherein the genome of the human comprises a human IGHG2*01 nucleotide sequence or the human expresses antibodies comprising human constant domains encoded by a human IGHG2*01 nucleotide sequence.

50. The ligand, method, use, kit or composition of any one of clauses 45 to 49, wherein the ligand comprises a hinge region encoded by human IGHG2*01.

51. The ligand, method, use, kit or composition of any one of clauses 45 to 50, wherein the ligand comprises or consists of an antibody, wherein the antibody comprises heavy chains that comprise SEQ ID NO: 63 or 65.

52. The ligand, method, use, kit or composition of any one of clauses 45 to 51, wherein the human is of European, African American, or European American ancestry.

53. The ligand, method, use, kit or composition of any one of clauses 45 to 52, wherein the human has been or is genotyped as positive for one, more or all of said Pro, Asn, Phe, Val and Ala.

54. The ligand, method, use, kit or composition of any one of clauses 45 to 53, wherein the human has been or is genotyped as positive for human IGHG2*01.

55. The ligand, method, use, kit or composition of any one of clauses 45 to 54, wherein the human has been or is phenotyped as positive for a human IGHG2*01 CH1.

56. The ligand, method, use, kit or composition of any one of clauses 45 to 55, wherein the human has been or is phenotyped as positive for a human IGHG2*01 CH2.

57. The ligand, method, use, kit or composition of any one of clauses 45 to 56, wherein the human has been or is phenotyped as positive for a human IGHG2*01 CH3.

58. The method or use of any one of clauses 45 to 57, comprising selecting a said human whose genome comprises a codon(s) encoding one, more or all of said Pro, Asn, Phe, Val and Ala; comprises human IGHG2*01; or comprises a human IGHG2*01 CH1, CH2 and/or CH3.

59. The method or use of any one of clauses 45 to 58, comprising selecting a said human whose phenotype comprises one, more or all of said Pro, Asn, Phe, Val and Ala; a human IGHG2*01 region; or a human IGHG2*01 CH1, CH2 and/or CH3.

60. The ligand, method, use, kit or composition of any one of clauses 45 to 59, wherein the human expresses antibodies comprising human gamma-2 constant regions comprising such a Pro, Asn, Phe, Val and Ala.

In a third example, the inventor addressed human kappa constant region variation. Thus, the present aspect of the invention also provides the following.

61. The ligand, method, use, kit or composition of the invention (eg, according to any one of clauses 1 to 60), wherein the ligand (eg, comprising or consisting of an antibody or fragment or an Fc-fused TOI receptor) comprises a human kappa light chain constant region that comprises a Val corresponding to position 84 of SEQ ID NO: 50 or a Cys corresponding to position 87 of SEQ ID NO: 50; and wherein the genome of the human comprises a kappa light chain constant region nucleotide sequence that encodes such a Val or Cys or the human expresses antibodies comprising human kappa light chain constant regions comprising such a Val or Cys.

62. The ligand, method, use, kit or composition of clause 61, wherein the ligand comprises a human kappa light chain constant region that comprises a Val corresponding to position 84 of SEQ ID NO: 50 and a Cys corresponding to position 87 of SEQ ID NO: 50.

63. The ligand, method, use, kit or composition of clause 61 or 62, wherein the genome of the human comprises a kappa light chain constant region nucleotide sequence that encodes such a Val and Cys or the human expresses antibodies comprising human kappa constant regions comprising such a Val and Cys.

64. The ligand, method, use, kit or composition of any one of clauses 61 to 63, wherein the antibody or fragment comprises a human IGKC*01 kappa light chain constant region.

65. The ligand, method, use, kit or composition of any one of clauses 61 to 64, wherein the ligand comprises or consists of an antibody, wherein the antibody comprises light chains that comprise SEQ ID NO: 62 or 66.

66. The ligand, method, use, kit or composition of any one of clauses 61 to 65, wherein the ligand comprises or consists of an antibody, wherein the antibody comprises a light chain variable domain derived from recombination of a human Vκ gene segment and a human Jκ gene segment, wherein the Jκ gene segment is IGKJ2*01 (SEQ ID NO: 57).

67. The ligand, method, use, kit or composition of any one of clauses 61 to 66, wherein the human has been or is phenotyped as positive for said Val and/or Cys.

68. The ligand, method, use, kit or composition of any one of clauses 61 to 67, wherein the human has been or is genotyped as positive for human IGKC*01.

69. The ligand, method, use, kit or composition of any one of clauses 61 to 68, wherein the human has been or is phenotyped as positive for a human IGKC*01 domain.

70. The method or use of any one of clauses 61 to 69, comprising selecting a said human whose genome comprises a codon(s) encoding said Val and/or Cys; or comprises human IGKC*01.

71. The method or use of any one of clauses 61 to 70, comprising selecting a said human whose phenotype comprises such a Val and/or Cys; or comprises a human IGKC*01 domain.

72. The ligand, method, use, kit or composition of any one of clauses 61 to 71, wherein the human expresses antibodies comprising human kappa constant domains comprising such a Val and Cys, eg, expresses human IGKC*01 constant domains.

In a fourth example, the inventor addressed human lambda constant region variation. Thus, this example provides aspects set out in the following clauses.

73. The ligand, method, use, kit or composition of the invention (eg, according to any one of clauses 1 to 60), wherein the ligand (eg, comprising or consisting of an antibody or fragment or an Fc-fused TOI receptor) comprises a human IGLC2*01 light chain constant region; and wherein the genome of the human comprises a human IGLC2*01 nucleotide sequence or the human expresses antibodies comprising human light chain IGLC2*01 constant regions.

74. The ligand, method, use, kit or composition of clause 73, wherein the antibody comprises light chains that comprise SEQ ID NO: 64.

75. The ligand, method, use, kit or composition of clause 73 or 74, wherein the human has been or is genotyped as positive for human IGLC2*01.

76. The ligand, method, use, kit or composition of any one of clauses 73 to 75, wherein the human has been or is phenotyped as positive for a human IGLC2*01 domain.

77. The method or use of any one of clauses 73 to 76, comprising selecting a said human whose genome comprises human IGLC2*01.

78. The method or use of any one of clauses 73 to 77, comprising selecting a said human whose phenotype comprises a human IGLC2*01 domain.

79. The ligand, method, use, kit or composition of any one of clauses 73 to 78, wherein the human expresses antibodies comprising human lambda IGLC2*01 constant domains.

In a fifth example, the inventor addressed human heavy chain variable region variation. Thus, this example provides aspects set out in the following clauses.

80. The ligand, method, use, kit or composition of the invention (eg, according to any one of clauses 1 to 79), wherein the ligand comprises or consists of an antibody or fragment, wherein the antibody or fragment comprises a VH domain that is derived from the recombination of a human VH gene segment, a human D gene segment and a human JH gene segment, wherein the VH gene segment is selected from the group consisting of (i) IGHV1-18*01 and the genome of the human comprises a human IGHV1-18*01 nucleotide sequence or the human expresses antibodies comprising variable domains derived from the recombination of human IGHV1-18*01; or (ii) IGVH1-46*01 and the genome of the human comprises a human IGHV1-46*01 nucleotide sequence or the human expresses antibodies comprising variable domains derived from the recombination of human IGHV1-46*01.

81. The ligand, method, use, kit or composition of clause 80, wherein the antibody or fragment comprises a one more or all of a CH1 domain, CH2 domain, CH3 domain, hinge or Fc encoded by human IGHG2*01.

82. The ligand, method, use, kit or composition of clause 80 or 81, wherein the antibody or fragment comprises heavy chains that comprise SEQ ID NO: 63 or 65.

83. The ligand, method, use, kit or composition of any one of clauses 80 to 82, wherein the human has been or is genotyped as positive for said selected VH gene segment, positive for human IGHV1-18*01 or IGVH1-46*01.

84. The method or use of any of clauses 80 to 83, comprising genotyping the human as positive for said selected VH gene segment, eg, positive for human IGHV1-18*01 or IGVH1-46*01.

In a sixth example, the inventor addressed human light chain variable region variation. Thus, this example provides aspects set out in the following clauses.

85. The ligand, method, use, kit or composition of the invention (eg, according to any one of clauses 1 to 84), wherein the ligand comprises or consists of an antibody or fragment, wherein the antibody or fragment comprises a VL domain that is derived from the recombination of a human VL gene segment and a human JL gene segment, wherein the VL gene segment is selected from the group consisting of (i) IGKV4-1*01 and the genome of the human comprises a human IGKV4-1*01 nucleotide sequence or the human expresses antibodies comprising variable domains derived from the recombination of human IGKV4-1*01; (ii) IGLV2-14*01 and the genome of the human comprises a human IGLV2-14*01 nucleotide sequence or the human expresses antibodies comprising variable domains derived from the recombination of human IGLV2-14*01; or (iii) IGKV1-13*02 and the genome of the human comprises a human IGKV1-13*02 nucleotide sequence or the human expresses antibodies comprising variable domains derived from the recombination of human IGKV1-13*02.
86. The ligand, method, use, kit or composition of clause 85, wherein the antibody comprises light chains that comprise SEQ ID NO: 62, 64 or 66.
87. The ligand, method, use, kit or composition of clause 85 or 86, wherein the antibody or fragment comprises a light chain variable domain derived from recombination of a human Vκ gene segment and a human Jκ gene segment, wherein the Jκ gene segment is IGKJ2*01 (SEQ ID NO: 57; wherein (i) or (iii) applies.
88. The ligand, method, use, kit or composition of any one of clauses 85 to 87, wherein the human has been or is genotyped as positive for said selected VL gene segment, eg, positive for human IGKV4-1*01, IGLV2-14*01 or IGKV1-13*02.
89. The method or use of clause 88, comprising genotyping the human as positive for said selected VL gene segment, eg, genotyping the human as positive for human IGKV4-1*01, IGLV2-14*01 or IGKV1-13*02.
90. The ligand, method, use, kit or composition of any one of clauses 1 to 89, wherein the ligand (eg, antibody or fragment) binds said human TOI with a dissociation constant (Kd) of 1 nM or less as determined by SPR, (eg, 100, 10 or 1 pM or less).

In a specific embodiment, the ligand, antibody or fragment of present invention comprises an Fc region, wherein the Fc region comprises at least one non-native amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241R. 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non-native amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

In an example the ligand, antibody or fragment comprises one or more human binding sites that specifically bind the TOI (eg, PCSK9, IL4Ra, IL6R, VEGFA or Nav1.7). In an embodiment, the binding sites comprise or consist of human antibody variable domains or human receptors for the TOI (eg, Human receptor binding sites for VEGFA). Furthermore, the ligand, antibody or fragment can be optionally fully human (eg, comprising human constant regions, eg, human Fc regions with or without human CL regions). In an example, the ligand is aflibercept, alirocumab, sarilumab or dupilumab. Fully human ligands maximise compatibility with the human patient when used in the context of the invention wherein the V and/or C regions are tailored to the human genotype and/or phenotype as per the description herein.

Some embodiments of the technology described herein can be defined according to any of the following numbered paragraphs:

1. A method of treating or preventing a disease or condition in a human, wherein the disease or condition is mediated by a Target of Interest (TOI), wherein the TOI is present in humans as different polymorphic variants, the method comprising
   a. Administering to the human an anti-TOI ligand to target a TOI variant in the human and treat or prevent said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%;
   wherein
   b. Before step (a) said human has been or is genotyped as positive for said nucleotide sequence or phenotyped as positive for said TOI variant.
2. The method of paragraph 1, wherein before step (a) the ligand has been or is determined as being capable of binding to said TOI variant.
3. A method of treating or preventing a disease or condition in a human, wherein the disease or condition is mediated by a Target of Interest (TOI), wherein the TOI is present in humans as different polymorphic variants, the method comprising
   a. Administering to the human an anti-TOI ligand to target a TOI variant in the human and treat or prevent said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%;
   wherein
   b. Before step (a) the ligand has been or is determined as capable of binding to said TOI variant.
4. The method of paragraph 3, wherein the genome of said human comprises a nucleotide sequence encoding said TOI variant; and before step (a) said nucleotide sequence has been or is determined as having a cumulative human allele frequency of less than 50% and/or having a total human genotype frequency of less than 50%.

5. The method of paragraph 3 or 4, wherein said human has been or is genotyped as positive for said variant nucleotide sequence before step (a).
6. The method of any preceding paragraph, wherein the human has been or is phenotyped as positive for said TOI variant before step (a).
7. The method of any preceding paragraph, wherein said frequency is less than 10 or 15%.
8. The method of any preceding paragraph, wherein the ligand is capable of binding to two or more different TOI variants, each being encoded by a nucleotide sequence having a cumulative human allele frequency of less than 50% and/or having a total human genotype frequency of less than 50%.
9. A method of treating or preventing a disease or condition in a human, wherein the disease or condition is mediated by a Target of Interest (TOI), wherein the TOI is present in humans as different polymorphic variants, the method comprising
    a. Administering to the human an anti-TOI ligand to target a TOI variant in the human and treat or prevent said disease or condition, wherein the TOI in said human is a variant encoded by a nucleotide sequence having a cumulative human allele frequency of more than 50% and/or having a total human genotype frequency of more than 50%;
    wherein
    b. Before step (a) said human has been or is genotyped as negative for a variant nucleotide sequence having a cumulative human allele frequency of less than 50% and/or having a total human genotype frequency of less than 50%; or phenotyped as negative for a TOI variant encoded by a nucleotide sequence having a cumulative human allele frequency of less than 50% and/or having a total human genotype frequency of less than 50%.
10. The method of paragraph 9, wherein before step (a), the human has been or is phenotyped as positive for the most frequent TOI variant or genotyped for the nucleotide sequence thereof.
11. The method of paragraph 9 or 10, wherein before step (a) the ligand has been or is determined as being capable of binding to the most frequent TOI variant.
12. The method of paragraph 9, 10 or 11, wherein before step (a) the ligand has been or is determined as being substantially incapable of neutralising or inhibiting said TOI variant recited in step (b).
13. The method of any one of paragraphs 9 to 12, wherein the ligand is capable of binding to the most frequent TOI variant.
14. The method of any one of paragraphs 9 to 13, wherein the ligand is capable of binding to two or more different TOI variants, each being encoded by a nucleotide sequence having a cumulative human allele frequency of more than 50%.
15. The method of any preceding paragraph, wherein said variant nucleotide sequence recited in step (a) has been or is determined as being present in at least 2 different human ethnic populations.
16. The method of any preceding paragraph, wherein said human frequency is the frequency in a database of naturally-occurring sequences sampled from at least 15 different human ethnic populations and comprising at least 1000 sequences.
17. An anti-human TOI ligand for use in a method of treating and/or preventing a TOI-mediated disease or condition in a human, wherein the TOI is present in humans as different polymorphic variants and wherein the genome of said human comprises a TOI nucleotide sequence having a cumulative human allele frequency of less than 50% and/or a total human genotype frequency of less than 50%, the method comprising administering the ligand to the human.
18. The ligand of paragraph 17, wherein the ligand has been or is determined as capable of binding the human TOI encoded by said nucleotide sequence.
19. A ligand that binds a human TOI comprising an amino acid sequence encoded by a TOI nucleotide sequence having a cumulative human allele frequency of less than 50% and/or a total human genotype frequency of less than 50%, for use in a method comprising the step of using the ligand to target said TOI in a human to treat and/or prevent a disease or condition mediated by TOI, the method comprising administering the ligand to the human.
20. The ligand of any one of paragraphs 17 to 19, wherein the human has been or is genotyped as positive for said TOI nucleotide sequence having a cumulative human allele frequency of less than 50%.
    The ligand of any one of paragraphs 17 to 19, wherein the human has been or is genotyped as positive for said TOI nucleotide sequence having a total human genotype frequency of less than 50%.
21. The ligand of any one of paragraphs 17 to 20, wherein the human has been or is phenotyped as positive for a TOI encoded by a nucleotide sequence having a cumulative human allele frequency of less than 50% and/or having a total human genotype frequency of less than 50%.
22. The ligand of any one of paragraphs 17 to 21, wherein the human has been or is genotyped as heterozygous for a TOI nucleotide sequence having a cumulative human allele frequency of less than 50% and/or having a total human genotype frequency of less than 50%; optionally wherein the human has been or is genotyped as comprising a TOI nucleotide sequence having a cumulative human allele frequency of less than 50% and a TOI nucleotide sequence having a cumulative human allele frequency of more than 50% and/or having a total human genotype frequency of more than 50%.
23. The ligand of any one of paragraphs 17 to 22, wherein the genome of the human has been or is genotyped as homozygous for a TOI nucleotide sequence having a cumulative human allele frequency of less than 50% and/or having a total human genotype frequency of less than 50%.
24. The ligand of any one of paragraphs 17 to 23, wherein the ligand comprises an antibody binding site that binds a human TOI comprising an amino acid sequence encoded by a TOI nucleotide sequence having a cumulative human allele frequency of less than 50% and/or having a total human genotype frequency of less than 50%; and optionally has been or is determined as capable of such binding.
25. The ligand of paragraph 24, wherein the ligand is an antibody or antibody fragment.
26. The ligand of any one of paragraphs 17 to 23, wherein the ligand comprises a nucleotide sequence that specifically hybridises to a TOI nucleotide sequence having a cumulative human allele frequency of less than 50% and/or having a total human genotype frequency of less than 50% or an RNA transcript thereof; and/or the ligand comprises a nucleotide sequence that comprises at least 10 contiguous nucleotides of a nucleotide sequence having a cumulative human allele frequency of less than 50% and/or having a total human genotype frequency of less than 50% or is an antisense sequence thereof.

27. The ligand of any one of paragraphs 17 to 26, wherein the genome of said human comprises a nucleotide sequence having a cumulative human allele frequency of less than 50% and the sequence is found in at least 2 different ethnic populations.

28. A pharmaceutical composition or kit for treating or preventing a condition or disease mediated by a TOI as recited in any preceding paragraph, the composition or kit comprising a ligand of any one of paragraphs 17 to 27; and optionally in combination with a label or instructions for use to treat and/or prevent said disease or condition in a human; optionally wherein the label or instructions comprise a marketing authorisation number (eg, an FDA or EMA authorisation number); optionally wherein the kit comprises an injection pen or IV container that comprises the ligand.

29. A method of producing an anti-human TOI antibody binding site, the method comprising obtaining a plurality of anti-TOI antibody binding sites, screening the antibody binding sites for binding to a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody binding site that binds in the screening step.

30. A method of producing an anti-human TOI antibody, the method comprising immunising a non-human vertebrate (eg, a mouse or a rat) with a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody that binds a TOI comprising an amino acid sequence encoded by a TOI nucleotide sequence having a cumulative human allele frequency of less than 50% and/or a total human genotype frequency of less than 50%, and optionally producing a TOI-binding fragment or derivative of the isolated antibody.

31. The method of paragraph 29 or 30, comprising the step of obtaining a nucleic acid encoding the antibody, fragment, derivative or binding site and optionally inserting the nucleic acid in an expression vector.

32. A kit for TOI genotyping a human, wherein the kit comprises a nucleic acid comprising a nucleotide sequence that specifically hybridises to a TOI nucleotide sequence selected having a cumulative human allele frequency of less than 50% and/or a total human genotype frequency of less than 50% or an RNA transcript thereof; and/or the nucleic acid comprises a nucleotide sequence that comprises at least 10 contiguous nucleotides of a TOI nucleotide sequence having a cumulative human allele frequency of less than 50% and/or a total human genotype frequency of less than 50% or is an antisense sequence thereof.

33. A kit for TOI genotyping or phenotyping a human, wherein the kit comprises a ligand according to any one of paragraphs 17 to 27 or an antibody, fragment or derivative produced by the method of any one of paragraphs 29 to 31.

34. Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for treating and/or preventing a TOI-mediated disease or condition in a human whose genome comprises a TOI nucleotide sequence having a cumulative human allele frequency of less than 50% and/or having a total human genotype frequency of less than 50%.

35. Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for targeting said TOI in a human to treat and/or prevent a disease or condition mediated by TOI.

36. A method of targeting a TOI for treating and/or preventing a TOI-mediated disease or condition in a human, the method comprising administering an anti-TOI ligand to a human comprising a TOI nucleotide sequence selected having a cumulative human allele frequency of less than 50% and/or a total human genotype frequency of less than 50%, whereby a TOI encoded by said nucleotide sequence is targeted.

37. The method of paragraph 36, wherein the method comprises targeting a human TOI comprising an amino acid sequence with said ligand to treat and/or prevent said disease or condition in said human, wherein said amino acid sequence is encoded by a nucleotide sequence having a cumulative human allele frequency of less than 50% and/or a total human genotype frequency of less than 50%.

38. A method of TOI genotyping a nucleic acid sample of a human, the method comprising identifying in the sample the presence of a TOI nucleotide sequence having a cumulative human allele frequency of less than 50% and/or having a total human genotype frequency of less than 50%.

39. A method of TOI typing a protein sample of a human, the method comprising identifying in the sample the presence of a TOI amino acid sequence encoded by a TOI nucleotide sequence having a cumulative human allele frequency of less than 50% and/or having a total human genotype frequency of less than 50%.

40. The method of paragraph 38 or 39, comprising obtaining a sample of serum, blood, faeces, hair, urine or saliva from a human, whereby the nucleic acid or protein sample is obtained for use in the step of identifying said sequence.

41. The method of any one of paragraphs 38 to 40, comprising using a ligand according to any one of paragraphs 17 to 27 to carry out said identifying step.

42. A diagnostic kit comprising a ligand that is capable of binding a human TOI comprising an amino acid sequence encoded by a TOI nucleotide sequence having a cumulative human allele frequency of less than 50% and/or a total human genotype frequency of less than 50% and instructions for carrying out the method of paragraph 38 or 39.

43. A diagnostic kit comprising a nucleic acid probe comprising a nucleotide sequence that specifically hybridises a TOI nucleotide sequence having a cumulative human allele frequency of less than 50% and/or a total human genotype frequency of less than 50% or an RNA transcript thereof and instructions for carrying out the method of paragraph 38 or 39.

44. The method, ligand, composition, kit or use of any preceding paragraph, wherein the TOI is encoded by a nucleotide sequence having a cumulative human allele frequency from 1 to 10% and/or a total human genotype frequency from 1 to about 15% or from 1 to 15%.

45. The method, ligand, composition, kit or use of any preceding paragraph wherein the TOI is a human TOI selected from Table 5; optionally for treating and/or preventing a corresponding disease or condition as set out in table 5.

46. The ligand, method, use, kit or composition of any preceding paragraph, wherein
    (i) the ligand (eg, antibody or fragment) comprises
        (e) a variable domain that is encoded by a human V region nucleotide sequence, wherein the V nucleotide sequence is derived from recombination of human VH, D and JH gene segments or human VL and JL gene segments; or
        (f) a constant region domain encoded by a C region gene segment; Wherein a first gene segment of said gene segments of (a), or said C region gene segment of (b) comprises a first single nucleotide polymorphism (SNP) encoding a first amino acid polymorphism; and
    (ii) the genome of said human comprises said first SNP or wherein said human expresses (a') an antibody variable domain comprising said first amino acid polymorphism or (b') an antibody constant domain comprising said first amino acid polymorphism.

47. The ligand, method, use, kit or composition of paragraph 46, wherein blood of said human comprises substantially no antibodies that specifically bind to the domain comprising said first amino acid polymorphism as determined in an in vitro binding assay.

48. The ligand, method, use, kit or composition of paragraph 47, wherein SPR is used to carry out said assay.

49. The ligand, method, use, kit or composition of any one of paragraphs 46 to 48, wherein the genome of said human comprises said first gene segment (when (a) applies) or said C region gene segment (when (b) applies).

50. The ligand, method, use, kit or composition of any one of paragraphs 46 to 49, wherein said first segment or a second segment of said segments of (a), or said C region gene segment of (b), comprises a second SNP encoding a second amino acid polymorphism; and wherein the genome of said human comprises said second SNP or wherein said human expresses (a'') an antibody variable domain comprising said second amino acid polymorphism or (b'') an antibody constant region domain comprising said first and second amino acid polymorphisms.

51. The ligand, method, use, kit or composition of paragraph 50, wherein said human expresses an antibody variable domain comprising said first and second amino acid polymorphisms.

52. The ligand, method, use, kit or composition of paragraph 50 or 51, wherein the first and second SNPs of said genome are comprised by the same antibody gene segment.

53. The ligand, method, use, kit or composition of any one of paragraphs 46 to 52, wherein each SNP is a variable region gene segment SNP.

54. The ligand, method, use, kit or composition of any one of paragraphs 46 to 52, wherein each SNP is a constant region gene segment SNP, eg each SNP is a gamma-1 constant region gene segment SNP, or a gamma-2 constant region gene segment SNP, or a gamma-3 constant region gene segment SNP or a gamma-4 constant region gene segment SNP.

55. The ligand, method, use, kit or composition of paragraph 54, wherein the first SNP is a CH1, CH2, CH3 or CH4 gene segment SNP and/or the second SNP is a CH1, CH2, CH3 or CH4 gene segment SNP.

56. The ligand, method, use, kit or composition of any one of paragraphs 46 to 53, wherein each SNP is a variable domain SNP, eg, a VH domain SNP, or a Vκ domain SNP, or a Vλ SNP.

57. The ligand, method, use, kit or composition of any one of paragraphs 46 to 56, wherein said constant region domain of (b) is comprised by an antibody Fc region.

58. The ligand, method, use, kit or composition of any one of paragraphs 46 to 57, wherein the ligand (eg, antibody or fragment) has been determined to specifically bind one or more human TOI variants as disclosed herein, for example, with a KD of 1 nM or less (eg, 100 or 10 pM or less) as determined by SPR.

59. The ligand, method, use, kit or composition of any preceding paragraph (eg, according to any one of paragraphs 46 to 58), wherein the ligand comprises or consists of an antibody or fragment that comprises a human antibody variable domain derived from the recombination of a human V gene segment and a human J gene segment (and optionally a human D gene segment when the variable domains are VH domains); and wherein the genome of the human comprises said human V gene segment and/or the human expresses antibodies comprising antibody variable domains derived from the recombination of said human V gene segment and a human J gene segment (and optionally a human D gene segment).

60. The ligand, method, use, kit or composition of any preceding paragraph (eg, according to any one of paragraphs 46 to 59), wherein the ligand (eg, comprising or consisting of an antibody or fragment or an Fc-fused human TOI receptor) comprises a human heavy chain constant domain encoded by a first constant region nucleotide sequence; and wherein the genome of the human comprises a heavy chain constant region nucleotide sequence that is identical to said first constant region nucleotide sequence and/or the human expresses antibodies comprising said human constant domain.

61. The ligand, method, use, kit or composition of any preceding paragraph (eg, according to any one of paragraphs 46 to 60), wherein the ligand (eg, comprising or consisting of an antibody or fragment or an Fc-fused human TOI receptor) comprises a human gamma heavy chain CH1 domain encoded by a CH1 nucleotide sequence; and wherein the genome of the human comprises a gamma heavy chain constant region nucleotide sequence that is identical to said CH1 nucleotide sequence and/or the human expresses antibodies comprising said human gamma CH1 domain.

62. The ligand, method, use, kit or composition of any preceding paragraph (eg, according to any one of paragraphs 46 to 61), wherein the ligand (eg, comprising or consisting of an antibody or fragment or an Fc-fused human TOI receptor) comprises a human gamma heavy chain CH2 domain encoded by a CH2 nucleotide sequence; and wherein the genome of the human comprises a gamma heavy chain constant region nucleotide sequence that is identical to said CH2 nucleotide sequence and/or the human expresses antibodies comprising said human gamma CH2 domain.

63. The ligand, method, use, kit or composition of any preceding paragraph (eg, according to any one of paragraphs 46 to 62), wherein, wherein the ligand (eg, comprising or consisting of an antibody or fragment or an Fc-fused human TOI receptor) comprises a human gamma heavy chain CH3 domain encoded by a CH3 nucleotide sequence; and wherein the genome of the human comprises a gamma heavy chain constant region nucleotide sequence that is identical to said CH3 nucleotide sequence and/or the human expresses antibodies comprising said human gamma CH3 domain.

64. The ligand, method, use, kit or composition of any preceding paragraph (eg, according to any one of paragraphs 46 to 63), wherein the ligand (eg, comprising or consisting of an antibody or fragment or an Fc-fused human TOI receptor) comprises a human gamma heavy chain CH4 domain encoded by a CH4 nucleotide sequence; and wherein the genome of the human comprises a gamma heavy chain constant region nucleotide sequence that is identical to said CH4 nucleotide sequence and/or the human expresses antibodies comprising said human gamma CH4 domain.

65. The ligand, method, use, kit or composition of any preceding paragraph (eg, according to any one of paragraphs 46 to 64), wherein the ligand (eg, comprising or consisting of an antibody or fragment or an Fc-fused human TOI receptor) comprises a human gamma heavy chain Fc region encoded by a Fc nucleotide sequence; and wherein the genome of the human comprises a gamma heavy chain constant region nucleotide sequence that is identical to said Fc nucleotide sequence and/or the human expresses antibodies comprising said human gamma Fc region.

66. The ligand, method, use, kit or composition of any one of paragraphs 61 to 65, wherein said human gamma heavy chain is a human gamma-1 heavy chain.

67. The ligand, method, use, kit or composition of any one of paragraphs 61 to 65, wherein said human gamma heavy chain is a human gamma-2 heavy chain.

68. The ligand, method, use, kit or composition of any one of paragraphs 61 to 65, wherein ligand comprises a human IGHG1*01 gamma-1 heavy chain constant region.

69. The ligand, method, use, kit or composition of any one of paragraphs 61 to 65, wherein ligand comprises a human IGHG2*01 gamma-1 heavy chain constant region.

70. The ligand, method, use, kit or composition of any one of paragraphs 60 to 69, wherein the human has been or is genotyped as positive for said heavy chain constant region nucleotide sequence.

71. The ligand, method, use, kit or composition of paragraph 68, wherein the human has been or is genotyped as positive for human IGHG1*01 nucleotide sequence.

72. The ligand, method, use, kit or composition of paragraph 69, wherein the human has been or is genotyped as positive for human IGHG2*01 nucleotide sequence.

73. The ligand, method, use, kit or composition of any one of paragraphs 61 to 69, wherein the human has been or is phenotyped as positive for said gamma heavy chain constant domain, CH1, CH2, CH3, CH4 or Fc.

74. The ligand, method, use, kit or composition of paragraph 63, (i) when dependent from clause 23, wherein the human has been or is phenotyped as positive for a human IGHG1*01 gamma heavy chain constant domain, CH1, CH2, CH3, CH4 or Fc or (ii) when dependent from clause 24, wherein the human has been phenotyped as positive for a human IGHG2*01 gamma heavy chain constant domain, CH1, CH2, CH3, CH4 or Fc.

75. The method or use of any one of paragraphs 61 to 69 and 71 to 74, comprising genotyping the human as positive for said gamma heavy chain constant region nucleotide sequence, eg, positive for said gamma heavy chain constant domain, CH1, CH2, CH3, CH4 or Fc nucleotide sequence; positive for said human IGHG1*01 gamma heavy chain constant region, CH1, CH2, CH3, CH4 or Fc nucleotide sequence; or positive for said human IGHG2*01 gamma heavy chain constant region, CH1, CH2, CH3, CH4 or Fc nucleotide sequence.

76. The method or use of any one of paragraphs 61 to 69 and 71 to 75, comprising phenotyping the human as positive for said gamma heavy chain constant region, eg, positive for said gamma heavy chain constant domain, CH1, CH2, CH3, CH4 or Fc; positive for said human IGHG1*01 gamma heavy chain constant domain, CH1, CH2, CH3, CH4 or Fc; or positive for said human IGHG2*01 gamma heavy chain constant domain, CH1, CH2, CH3, CH4 or Fc.

77. The ligand, method, use, kit or composition of any preceding paragraph (eg, according to any one of clauses 46 to 76), wherein the ligand (eg, comprising or consisting of an antibody or fragment or an Fc-fused TOI receptor) comprises a human gamma-1 heavy chain constant region that comprises an Asp corresponding to position 204 of SEQ ID NO: 42 or a Leu corresponding to position 206 of SEQ ID NO: 42 and wherein the genome of the human comprises a gamma-1 heavy chain constant region nucleotide sequence that encodes such an Asp or Leu or the human expresses antibodies comprising human gamma-1 constant regions comprising such an Asp or Leu.

78. The ligand, method, use, kit or composition of paragraph 77, wherein the ligand comprises a human gamma-1 heavy chain constant region that comprises an Asp corresponding to position 204 of SEQ ID NO: 42 and a Leu corresponding to position 206 of SEQ ID NO: 42.

79. The ligand, method, use, kit or composition of paragraph 77 or 78, wherein the genome of the human comprises a gamma-1 heavy chain constant region nucleotide sequence that encodes such an Asp and Leu or the human expresses antibodies comprising human gamma-1 constant regions comprising such an Asp and Leu.

80. The ligand, method, use, kit or composition of paragraph 77, 78 or 79, wherein the ligand comprises a human IGHG1*01 gamma-1 heavy chain constant region, eg, an Fc, CH1, CH2 and/or CH3 domain encoded by human IGHG1*01.

81. The ligand, method, use, kit or composition of any one of paragraphs 77 to 80, wherein the genome of the human comprises a human IGHG1*01 nucleotide sequence or the human expresses antibodies comprising human constant domains encoded by a human IGHG1*01 nucleotide sequence.

82. The ligand, method, use, kit or composition of any one of paragraphs 77 to 81, wherein the ligand comprises a hinge region encoded by human IGHG1*01.

83. The ligand, method, use, kit or composition of any one of paragraphs 77 to 82, wherein the ligand comprises or consists of an antibody, wherein the antibody comprises heavy chains that comprise SEQ ID NO: 61.

84. The ligand, method, use, kit or composition of any one of paragraphs 77 to 83, wherein the human is of European ancestry.

85. The ligand, method, use, kit or composition of any one of paragraphs 77 to 84, wherein the human has been or is genotyped as positive for said Asp and/or Leu.

86. The ligand, method, use, kit or composition of any one of paragraphs 77 to 85, wherein the human has been or is genotyped as positive for human IGHG1*01.

87. The ligand, method, use, kit or composition of any one of paragraphs 77 to 86, wherein the human has been or is phenotyped as positive for a human IGHG1*01 CH3.

88. The method or use of any one of paragraphs 77 to 87, comprising selecting a said human whose genome comprises a codon(s) encoding said Asp and/or Leu; comprises human IGHG1*01; or comprises a human IGHG1*01 CH3.

89. The method or use of any one of paragraphs 77 to 88, comprising selecting a said human whose phenotype comprises said Asp and/or Leu; a human IGHG1*01 region; or a human IGHG1*01 CH3.

90. The ligand, method, use, kit or composition of any preceding paragraph, wherein the ligand (eg, comprising or consisting of an antibody or fragment or an Fc-fused TOI receptor) comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44; and wherein the genome of the human comprises a gamma-2 heavy chain constant region nucleotide sequence that encodes such a selected amino acid or the human expresses antibodies comprising human gamma-2 constant regions comprising such a selected amino acid.

91. The ligand, method, use, kit or composition of paragraph 90, wherein the ligand comprises a human gamma-2 heavy chain constant region that comprises (i) a Pro corresponding to position 72 of SEQ ID NO: 44, an Asn corresponding to position 75 of SEQ ID NO: 44, a Phe corresponding to position 76 of SEQ ID NO: 44 and optionally (ii) a Val corresponding to position 161 of SEQ ID NO: 44 and/or an Ala corresponding to position 257 of SEQ ID NO: 44; and wherein the genome of the human comprises a gamma-2 heavy chain constant region nucleotide sequence that encodes such amino acids of (i) or the human expresses antibodies comprising human gamma-2 constant regions comprising such amino acids of (i).

92. The ligand, method, use, kit or composition of paragraph 90 or 91, wherein the ligand comprises a human gamma-2 heavy chain constant region that comprises (i) a Val corresponding to position 161 of SEQ ID NO: 44 and an Ala corresponding to position 257 of SEQ ID NO: 44 and optionally (ii) an amino acid selected from the group consisting of a Pro corresponding to position 72 of SEQ ID NO: 44, an Asn corresponding to position 75 of SEQ ID NO: 44 and a Phe corresponding to position 76 of SEQ ID NO: 44; and wherein the genome of the human comprises a gamma-2 heavy chain constant region nucleotide sequence that encodes such amino acids of (i) or the human expresses antibodies comprising human gamma-2 constant regions comprising such amino acids of (i).

93. The ligand, method, use, kit or composition of any one of paragraph 90 to 92, wherein the ligand comprises a human IGHG2*01 gamma-2 heavy chain constant region, eg, an Fc, CH1, CH2 and/or CH3 domain encoded by human IGHG2*01.

94. The ligand, method, use, kit or composition of any one of paragraphs 90 to 93, wherein the genome of the human comprises a human IGHG2*01 nucleotide sequence or the human expresses antibodies comprising human constant domains encoded by a human IGHG2*01 nucleotide sequence.

95. The ligand, method, use, kit or composition of any one of paragraphs 90 to 94, wherein the ligand comprises a hinge region encoded by human IGHG2*01.

96. The ligand, method, use, kit or composition of any one of paragraphs 90 to 95, wherein the ligand comprises or consists of an antibody, wherein the antibody comprises heavy chains that comprise SEQ ID NO: 63 or 65.

97. The ligand, method, use, kit or composition of any one of paragraphs 90 to 96, wherein the human is of European, African American, or European American ancestry.

98. The ligand, method, use, kit or composition of any one of paragraphs 90 to 97, wherein the human has been or is genotyped as positive for one, more or all of said Pro, Asn, Phe, Val and Ala.

99. The ligand, method, use, kit or composition of any one of paragraphs 90 to 98, wherein the human has been or is genotyped as positive for human IGHG2*01.

100. The ligand, method, use, kit or composition of any one of paragraphs 90 to 99, wherein the human has been or is phenotyped as positive for a human IGHG2*01 CH1.

101. The ligand, method, use, kit or composition of any one of paragraphs 90 to 100, wherein the human has been or is phenotyped as positive for a human IGHG2*01 CH2.

102. The ligand, method, use, kit or composition of any one of paragraphs 90 to 101, wherein the human has been or is phenotyped as positive for a human IGHG2*01 CH3.

103. The method or use of any one of paragraphs 90 to 102, comprising selecting a said human whose genome comprises a codon(s) encoding one, more or all of said Pro, Asn, Phe, Val and Ala; comprises human IGHG2*01; or comprises a human IGHG2*01 CH1, CH2 and/or CH3.

104. The method or use of any one of paragraphs 90 to 103, comprising selecting a said human whose phenotype comprises one, more or all of said Pro, Asn, Phe, Val and Ala; a human IGHG2*01 region; or a human IGHG2*01 CH1, CH2 and/or CH3.

105. The ligand, method, use, kit or composition of any one of paragraphs 90 to 104, wherein the human expresses antibodies comprising human gamma-2 constant regions comprising such a Pro, Asn, Phe, Val and Ala.

106. The ligand, method, use, kit or composition of any preceding paragraph, wherein the ligand (eg, comprising or consisting of an antibody or fragment or an Fc-fused TOI receptor) comprises a human kappa light chain constant region that comprises a Val corresponding to position 84 of SEQ ID NO: 50 or a Cys corresponding to position 87 of SEQ ID NO: 50; and wherein the genome of the human comprises a kappa light chain constant region nucleotide sequence that encodes such a Val or Cys or the human expresses antibodies comprising human kappa light chain constant regions comprising such a Val or Cys.

107. The ligand, method, use, kit or composition of paragraph 106, wherein the ligand comprises a human kappa light chain constant region that comprises a Val corresponding to position 84 of SEQ ID NO: 50 and a Cys corresponding to position 87 of SEQ ID NO: 50.

108. The ligand, method, use, kit or composition of paragraph 106 or 107, wherein the genome of the human comprises a kappa light chain constant region nucleotide sequence that encodes such a Val and Cys or the human expresses antibodies comprising human kappa constant regions comprising such a Val and Cys.

109. The ligand, method, use, kit or composition of any one of paragraphs 106 to 108, wherein the antibody or fragment comprises a human IGKC*01 kappa light chain constant region.

110. The ligand, method, use, kit or composition of any one of paragraphs 106 to 109, wherein the ligand comprises or consists of an antibody, wherein the antibody comprises light chains that comprise SEQ ID NO: 62 or 66.

111. The ligand, method, use, kit or composition of any one of paragraphs 106 to 110, wherein the ligand comprises or consists of an antibody, wherein the antibody comprises a light chain variable domain derived from recombination of a human Vκ gene segment and a human Jκ gene segment, wherein the Jκ gene segment is IGKJ2*01 (SEQ ID NO: 57).
112. The ligand, method, use, kit or composition of any one of paragraphs 106 to 111, wherein the human has been or is phenotyped as positive for said Val and/or Cys.
113. The ligand, method, use, kit or composition of any one of paragraphs 106 to 112, wherein the human has been or is genotyped as positive for human IGKC*01.
114. The ligand, method, use, kit or composition of any one of paragraphs 106 to 113, wherein the human has been or is phenotyped as positive for a human IGKC*01 domain.
115. The method or use of any one of paragraphs 106 to 114, comprising selecting a said human whose genome comprises a codon(s) encoding said Val and/or Cys; or comprises human IGKC*01.
116. The method or use of any one of paragraphs 106 to 115, comprising selecting a said human whose phenotype comprises such a Val and/or Cys; or comprises a human IGKC*01 domain.
117. The ligand, method, use, kit or composition of any one of paragraphs 106 to 116, wherein the human expresses antibodies comprising human kappa constant domains comprising such a Val and Cys, eg, expresses human IGKC*01 constant domains.
118. The ligand, method, use, kit or composition of any preceding paragraph, wherein the ligand (eg, comprising or consisting of an antibody or fragment or an Fc-fused TOI receptor) comprises a human IGLC2*01 light chain constant region; and wherein the genome of the human comprises a human IGLC2*01 nucleotide sequence or the human expresses antibodies comprising human light chain IGLC2*01 constant regions.
119. The ligand, method, use, kit or composition of paragraph 118, wherein the antibody comprises light chains that comprise SEQ ID NO: 64.
120. The ligand, method, use, kit or composition of paragraph 118 or 119, wherein the human has been or is genotyped as positive for human IGLC2*01.
121. The ligand, method, use, kit or composition of any one of paragraphs 118 to 120, wherein the human has been or is phenotyped as positive for a human IGLC2*01 domain.
122. The method or use of any one of paragraphs 118 to 212, comprising selecting a said human whose genome comprises human IGLC2*01.
123. The method or use of any one of clauses 73 to 77, comprising selecting a said human whose phenotype comprises a human IGLC2*01 domain.
124. The ligand, method, use, kit or composition of any one of paragraphs 108 to 123, wherein the human expresses antibodies comprising human lambda IGLC2*01 constant domains.
125. The ligand, method, use, kit or composition of any preceding paragraph, wherein the ligand comprises or consists of an antibody or fragment, wherein the antibody or fragment comprises a VH domain that is derived from the recombination of a human VH gene segment, a human D gene segment and a human JH gene segment, wherein the VH gene segment is selected from the group consisting of (i) IGHV1-18*01 and the genome of the human comprises a human IGHV1-18*01 nucleotide sequence or the human expresses antibodies comprising variable domains derived from the recombination of human IGHV1-18*01; or (ii) IGVH1-46*01 and the genome of the human comprises a human IGHV1-46*01 nucleotide sequence or the human expresses antibodies comprising variable domains derived from the recombination of human IGHV1-46*01.
126. The ligand, method, use, kit or composition of paragraph 125, wherein the antibody or fragment comprises a one more or all of a CH1 domain, CH2 domain, CH3 domain, hinge or Fc encoded by human IGHG2*01.
127. The ligand, method, use, kit or composition of paragraph 125 or 126, wherein the antibody or fragment comprises heavy chains that comprise SEQ ID NO: 63 or 65.
128. The ligand, method, use, kit or composition of any one of paragraphs 125 to 127, wherein the human has been or is genotyped as positive for said selected VH gene segment, positive for human IGHV1-18*01 or IGVH1-46*01.
129. The method or use of any of paragraphs 125 to 128, comprising genotyping the human as positive for said selected VH gene segment, eg, positive for human IGHV1-18*01 or IGVH1-46*01.
130. The ligand, method, use, kit or composition any preceding paragraph, wherein the ligand comprises or consists of an antibody or fragment, wherein the antibody or fragment comprises a VL domain that is derived from the recombination of a human VL gene segment and a human JL gene segment, wherein the VL gene segment is selected from the group consisting of (i) IGKV4-1*01 and the genome of the human comprises a human IGKV4-1*01 nucleotide sequence or the human expresses antibodies comprising variable domains derived from the recombination of human IGKV4-1*01; (ii) IGLV2-14*01 and the genome of the human comprises a human IGLV2-14*01 nucleotide sequence or the human expresses antibodies comprising variable domains derived from the recombination of human IGLV2-14*01; or (iii) IGKV1-13*02 and the genome of the human comprises a human IGKV1-13*02 nucleotide sequence or the human expresses antibodies comprising variable domains derived from the recombination of human IGKV1-13*02.
131. The ligand, method, use, kit or composition of paragraph 130, wherein the antibody comprises light chains that comprise SEQ ID NO: 62, 64 or 66.
132. The ligand, method, use, kit or composition of paragraph 130 or 131, wherein the antibody or fragment comprises a light chain variable domain derived from recombination of a human Vi gene segment and a human Jκ gene segment, wherein the Jκ gene segment is IGKJ2*01 (SEQ ID NO: 57; wherein (i) or (iii) applies.
133. The ligand, method, use, kit or composition of any one of paragraphs 130 to 132, wherein the human has been or is genotyped as positive for said selected VL gene segment, eg, positive for human IGKV4-1*01, IGLV2-14*01 or IGKV1-13*02.
134. The method or use of paragraph 133, comprising genotyping the human as positive for said selected VL gene segment, eg, genotyping the human as positive for human IGKV4-1*01, IGLV2-14*01 or IGKV1-13*02.
135. The ligand, method, use, kit or composition of any preceding paragraph, wherein the ligand (eg, antibody or fragment) binds said human TOI with a dissociation constant (Kd) of 1 nM or less as determined by SPR, (eg, 100, 10 or 1 pM or less).
136. The ligand, method, use, kit or composition of any preceding paragraph, wherein the TOI is human PCSK9 or human IL-6R.

EXAMPLES

Example 1

Rare PCSK9 Variants

Proprotein convertase subtilisin kexin type 9 (PCSK9) is a serine protease involved in regulating the levels of the low density lipoprotein receptor (LDLR) protein (Horton et al., 2007; Seidah and Prat, 2007). In vitro experiments have shown that adding PCSK9 to HepG2 cells lowers the levels of cell surface LDLR (Benjannet et al., 2004; Lagace et al., 2006; Maxwell et al., 2005; Park et al., 2004). Experiments with mice have shown that increasing PCSK9 protein levels decreases levels of LDLR protein in the liver (Benjannet et al., 2004; Lagace et al., 2006; Maxwell et al., 2005; Park et al., 2004), while PCSK9 knockout mice have increased levels of LDLR in the liver (Rashid et al., 2005). Additionally, various human PCSK9 mutations that result in either increased or decreased levels of plasma LDL have been identified (Kotowski et al., 2006; Zhao et al., 2006). PCSK9 has been shown to directly interact with the LDLR protein, be endocytosed along with the LDLR, and co-immunofluoresce with the LDLR throughout the endosomal pathway (Lagace et al., 2006).

PCSK9 is a prohormone-proprotein convertase in the subtilisin (S8) family of serine proteases (Seidah et al., 2003). Humans have nine prohormone-proprotein convertases that can be divided between the S8A and S8B subfamilies (Rawlings et al., 2006). Furin, PC1/PC3, PC2, PACE4, PC4, PC5/PC6 and PC7/PC8/LPC/SPC7 are classified in subfamily S8B. Crystal and NMR structures of different domains from mouse furin and PC1 reveal subtilisin-like pro- and catalytic domains, and a P domain directly C-terminal to the catalytic domain (Henrich et al., 2003; Tangrea et al., 2002). Based on the amino acid sequence similarity within this subfamily, all seven members are predicted to have similar structures (Henrich et al., 2005). SKI-1/S1P and PCSK9 are classified in subfamily S8A. Sequence comparisons with these proteins also suggest the presence of subtilisin-like pro- and catalytic domains (Sakai et al., 1998; Seidah et al., 2003; Seidah et al., 1999). In these proteins the amino acid sequence C-terminal to the catalytic domain is more variable and does not suggest the presence of a P domain.

Prohormone-proprotein convertases are expressed as zymogens and they mature through a multi step process. The function of the pro-domain in this process is two-fold. The pro-domain first acts as a chaperone and is required for proper folding of the catalytic domain (Ikemura et al., 1987). Once the catalytic domain is folded, autocatalysis occurs between the pro-domain and catalytic domain. Following this initial cleavage reaction, the pro-domain remains bound to the catalytic domain where it then acts as an inhibitor of catalytic activity (Fu et al., 2000). When conditions are correct, maturation proceeds with a second autocatalytic event at a site within the pro-domain (Anderson et al., 1997). After this second cleavage event occurs the pro-domain and catalytic domain dissociate, giving rise to an active protease.

Autocatalysis of the PCSK9 zymogen occurs between Gln152 and Ser153 (VFAQ|SIP (SEQ ID NO: 116)) (Naureckiene et al., 2003), and has been shown to be required for its secretion from cells (Seidah et al., 2003). A second autocatalytic event at a site within PCSK9's pro-domain has not been observed. Purified PCSK9 is made up of two species that can be separated by non-reducing SDS-PAGE; the pro-domain at 17 Kd, and the catalytic plus C-terminal domains at 65 Kd. PCSK9 has not been isolated without its inhibitory pro-domain, and measurements of PCSK9's catalytic activity have been variable (Naureckiene et al., 2003; Seidah et al., 2003).

In certain embodiments, a PCSK9 polypeptide includes terminal residues, such as, but not limited to, leader sequence residues, targeting residues, amino terminal methionine residues, lysine residues, tag residues and/or fusion protein residues. "PCSK9" has also been referred to as FH3, NARC1, HCHOLA3, proprotein convertase subtilisin/kexin type 9, and neural apoptosis regulated convertase 1. The PCSK9 gene encodes a proprotein convertase protein that belongs to the proteinase K subfamily of the secretory subtilase family. The term "PCSK9" denotes both the proprotein and the product generated following autocatalysis of the proprotein. When only the autocatalyzed product is being referred to (such as for an antigen binding protein or ligand that binds to the cleaved PCSK9), the protein can be referred to as the "mature," "cleaved", "processed" or "active" PCSK9. When only the inactive form is being referred to, the protein can be referred to as the "inactive", "pro-form", or "unprocessed" form of PCSK9. The term PCSK9 also encompasses PCSK9 molecules incorporating post-translational modifications of the PCSK9 amino acid sequence, such as PCSK9 sequences that have been glycosylated, PCSK9 sequences from which its signal sequence has been cleaved, PCSK9 sequence from which its pro domain has been cleaved from the catalytic domain but not separated from the catalytic domain (see, e.g., FIGS. 1A and 1B of US20120093818A1; which is incorporated by reference herein in its entirety).

The present invention provides anti-PCSK9 ligands; and PCSK9-binding or targeting ligands as described herein. The ligands have a variety of utilities. Some of the ligands, for instance, are useful in specific binding assays, for genotyping or phenotyping humans, affinity purification of PCSK9, in particular human PCSK9 or its ligands and in screening assays to identify other antagonists of PCSK9 activity. Some of the ligands of the invention are useful for inhibiting binding of PCSK9 to LDLR, or inhibiting PCSK9-mediated activities.

Anti-PCSK9 ligands (eg, antibodies and anti-sense RNA) have been developed based on targeting and neutralising so-called "wild-type" human PCSK9, which is a commonly-occurring form (see, eg, US20120093818A1 and US20110065902A1; each of which is incorporated by reference herein in its entirety). While such therapies are useful for human patients harbouring this form of human PCSK9, the inventor considered it useful to investigate the possibility of targeting much rarer—but still naturally-occurring—forms of PCSK9 amongst human populations. In this way, the inventor arrived at insight into the natural occurrences and distributions of rarer human PCSK9 forms that can serve as useful targets (at the protein or nucleic acid level) for human treatment, prophylaxis and diagnosis pertinent to diseases and conditions mediated or associated with PCSK9 activity. This particularly provides for tailored therapies, prophylaxis and diagnosis in humans that are devoid of the common PCSK9 gene or protein (ie, the form a or a' as used in US20120093818A1 and US20110065902A1 to generate antibodies).

The skilled person will know that SNPs or other changes that translate into amino acid variation can cause variability in activity and/or conformation of human targets to be addressed. This has spawned great interest in personalized medicine where genotyping and knowledge of protein and nucleotide variability is used to more effectively tailor medicines and diagnosis of patients. The invention, therefore, provides for tailored pharmaceuticals and testing that specifically addresses rarer PCSK9 polymorphic variant forms. Such forms or "alleles" (at the nucleotide level), in many of the examples determined by the inventor, comprise multiple changes at the nucleotide and amino acid levels from the corresponding common form nucleotide and amino acids sequences, ie, there are multiple non-synonymous changes at the nucleotide level that translate into multiple corresponding changes in the protein target in humans.

Furthermore, the inventor surprisingly realised that the rarer natural forms, although present in humans at much lower frequencies than the common form, nevertheless are represented in multiple and ethnically-diverse human populations and usually with many human examples per represented ethnic population. Thus, the inventor realised that targeting such rarer forms would provide for effective treatment, prophylaxis or diagnosis across many human ethnic populations, thereby extending the utility of the present invention.

With this realisation, the inventor realised that there is significant industrial and medical application for the invention in terms of guiding the choice of anti-PCSK9 ligand for administration to human patients for therapy and/or prophylaxis of PCSK9-mediated or associated diseases or conditions. In this way, the patient receives drugs and ligands that are tailored to their needs—as determined by the patient's genetic or phenotypic makeup. Hand-in-hand with this, the invention provides for the genotyping and/or phenotyping of patients in connection with such treatment, thereby allowing a proper match of drug to patient. This increases the chances of medical efficacy, reduces the likelihood of inferior treatment using drugs or ligands that are not matched to the patient (eg, poor efficacy and/or side-effects) and avoids pharmaceutical mis-prescription and waste.

In developing this thinking, the present inventor decided to determine a set of human PCSK9 variants on the basis of the following criteria, these being criteria that the inventor realised would provide for useful medical drugs and diagnostics to tailored need in the human population. The inventor selected variants having at least 3 of the 4 following criteria:—

PCSK9 variants having a cumulative human allele frequency in the range from 1 to 10%;

PCSK9 variants having a total human genotype frequency in the range from 1 to about 15%;

PCSK9 variants found in many different human ethnic populations (using the standard categorisation of the 1000 Genomes Project, which is an accepted standard in the art; see Table 4 below); and PCSK9 variants found in many individuals distributed across such many different ethnic populations.

On the basis of these criteria, the inventor identified the variants listed in Table 1 below (excluding form a).

The inventor's selection included, as a consideration, selection for nucleotide variation that produced amino acid variation in corresponding PCSK9 forms (ie, non-synonymous variations), as opposed to silent variations that do not alter amino acid residues in the target protein.

TABLE 1

Human PCSK9 variants distributed over several human ethnic populations & having a total human genotype frequency in the range of 1 to about 15%
(a) Amino acid variability, population distributions and frequencies

| Form a | 46R | 53A | 425N | 443A | 474I | 619Q | 670E | ASW, YRI, GBR, TSI, CLM, CHB, LWK, CHS, MXL, JPT, PUR, IBS, FIN, CEU | 939 | 14 | 0.3951 | 0.4506 (0.8457) Hom Freq[4] | 0.64815 |
|---|---|---|---|---|---|---|---|---|---|---|---|---|---|
| Variant | | Amino Acid Position & Variation | | | | | | Human | No. | No. Unique | Het | (Het + Hom | Cum |
| Form | 46L | 53V | 425S | 443T | 474V | 619P | 670G | Populations | Individs[1] | Pops[2] | Freq[3] | freq[5]) | Freq[6] |
| f | | | | | x | | | ASW, YRI, GBR, TSI, CLM, LWK, MXL, JPT, PUR, IBS, FIN, CEU | 180 | 12 | 0.153 | 0.009 (0.162) | 0.0855 |
| c | | | | | | | x | ASW, YRI, GBR, TSI, CLM, CHB, LWK, CHS, JPT, PUR, FIN, CEU | 153 | 12 | 0.1296 | 0.0081 (0.1377) | 0.0729 |
| r | | | | | x | | x | | | | 0.0234 | 0.009 (0.0324) | 0.0292 |
| p | | x | | | x | | | ASW, GBR, TSI, CLM, JPT, PUR, IBS, FIN, CEU, | 49 | 9 | 0.0441 | (0.0441) | 0.0221 |
| m | | | | x | | | | LWK, ASW, YRI, CLM | 29 | 4 | 0.0225 | (0.0225) | 0.0149 |
| e | | | x | | x | | | LWK, ASW, YRI | 15 | 3 | 0.0135 | (0.0135) | 0.0068 |
| h | | | | x | | x | | LWK, ASW, YRI | 10 | 3 | 0.009 | (0.009) | 0.0045 |
| aj | X | | | | x | | | PUR, TSI, FIN, CEU | 9 | 4 | 0.0081 | (0.0081) | 0.0041 |
| q | | x | | | | | x | CHS, ASW, JPT, PUR, CHB | 7 | 5 | 0.0063 | (0.0063) | 0.0032 |

Table Footnotes:

"x" in a box indicates that the amino acid for the variant form is different from the amino acid at that position in form a, the variant amino acid being shown in "Amino Acid Position & Variation" of the table and the form a amino acid being shown in the first row of the table; amino acids at all other positions of each variant form are identical to those found in form a. Amino acid numbering is per the numbering shown for the pro-form in Table 2 below.

1. Number of individuals in 1000 Genomes database found to have the allele;

2. Number of unique human ethnic populations in 1000 Genomes database in which the allele was found to occur;

3. Heterozygous human genotype frequency, ie, cumulative frequency of all genotypes having one occurrence of the variant allele and one occurrence of another allele (heterozygous state), eg, ac genotype in 1000 Genomes database;

4. Homozygous human genotype frequency, ie, cumulative frequency of two occurrences of the variant allele (homozygous state), eg, cc genotype in 1000 Genomes database; and 5. Total human genotype frequency, ie, total of heterozygous plus homozygous human genotype frequencies.

6. Cumulative human allele frequency of all occurrences of the variant allele in 1000 Genomes database.

Form a' is identical to form a with the exception that form a' has a glycine (G) at position 620 (see US20120093818 (Amgen, Inc)); form a has E at this position.

| (b) Nucleotide Sequence Variations of Selected Alleles | | | | | | |
|---|---|---|---|---|---|---|
| Allele a Variant | G | C | A | G | A | A | A |
| | Nucleotide Position[1] | | | | | | |
| Allele | 1:55505647 | 1:55505668 | 1:55523802 | 1:55523855 | 1:55524237 | 1:55527222 | 1:55529187 |
| | Non-Synonymous Nucleotide Variation[2] | | | | | | |
| | T | T | G | A | G | C | G |
| | Variant ID[3] | | | | | | |
| | rs11591147 | rs11583680 | rs28362261 | rs28362263 | rs562556 | rs28362277 | rs505151 |
| | Corresponding Amino Acid Variation | | | | | | |
| | 46L | 53V | 425S | 443T | 474V | 619P | 670G |
| f |  |  |  |  | X |  |  |
| c |  |  |  |  |  |  | X |
| r |  |  |  |  | X |  | X |
| P |  | X |  |  | X |  |  |
| m |  |  |  | X |  |  |  |
| e |  | X |  |  | X |  |  |
| h |  |  |  | X |  | X |  |
| aj | X |  |  |  | X |  |  |
| q |  | X |  |  |  |  | X |

"x" in a box indicates that a variant allele comprises the non-synonymous nucleotide variation indicated in the 5th row.

Table Footnotes:

1. Notation is chromosome number (all positions are on human chromosome 1):coordinate number (Ensembl release 73 - Sep. 2013, Genome assembly: GRCh37 (GCA_000001405.13));
2. Nucleotide change (compared to allele a nucleotide shown in first row) giving rise to an amino acid change in the variant form (compared to amino acid of allele a); and
3. NCBI dbSNP reference number (NCBI dbSNP Build 138 released on Apr. 25, 2013).

TABLE 2

Sequences (a) Human PCSK9 Form a Amino Acid Sequence (SEQ ID NO: 1) - "Pro-form" with Signal Sequence 46       53

*MGTVSSRRSWWPLPLLLLLLLLLLGPAGARA*QEDEDGDYEELVLALRSEEDGLAEAPEHGTTATFHRCAKDP

WRLPGTYVVVLKEETHLSQSERTARRLQAQAARRGYLTKILHVFHGLLPGFLVKMSGDLLELALKLPH

VDYIEEDSSVFAQsipwnleritppryradeyqppdggslvevylldtsiqsdhreiegrvmvtdfenvpeedgtrfhrqaskcdshg thlagvvsgrdagvakgasmrslrvlncqgkgtvsgtligleflrksqlvqpvgplvvllplaggysrvlnaacqrlaragvvlvtaagnfrddacly spasapevitvgatnaqdqpvtlgtlgtnfgrcvdlfapgediigassdcstcfvsqsgtsqaaahvagiaammlsaepeltlaelrqrlihfsak 425           443                                 474 dvineawfpedqrvltpnlvaalppsthGAGWQLFCRTVWSAHSGPTRMATAIARCAPDEELLSCSSFSRSGKRRGERM

EAQGGKLVCRAHNAFGGEGVYAIARCCLLPQANCSVHTAPPAEASMGTRVHCHQQGHVLTGCSSHWEVEDLGT 619 620

HKPPVLRPRGQPNQCVGHREASIHASCCHAPGLECKVKEHGIPAPQEQVTVACEEGWTLTGCSALPGTSHVLGAY

670

AVDNTCVVRSRDVSTTGSTSEEAVTAVAICCRSRHLAQASQELQ

*Italics* = signal sequence 1-30

`Courier` = pro peptide 31-152 lower case = catalytic domain 153-449
UPPER CASE = C-terminal domain 450-692
Underlined = residues changed from allele a in other sequences (aa residue number shown)
The pro-form is the sequence from amino acid number 31 to (and including) amino acid number 692 of SEQ ID NO: 1.
The mature form is the sequence from amino acid number 153 to (and including) amino acid number 692 of SEQ ID NO: 1.
(b) Human PCSK9 Form a Amino Acid Sequence (SEQ ID NO: 3) - "Mature-form"
(Numbering and notation as per SEQ ID NO: 1 above has been retained)

TABLE 2-continued

Sequences sipwnleritppryradeyqppdggslvevylldtsiqsdhreiegrvmvtdfenvpeedgtrfhrqaskcdshg thlagvvsgrdagvakgasmrslrvlncqgkgtvsgtliglefirksqlvqpvgplvvllplaggysrvlnaacqrlaragvvlvtaagnfrddacly spasapevitvgatnaqdqpvtlgtlgtnfgrcvdlfapgediigassdcstcfvsqsgtsqaaahvagiaammlsaepeltlaelrqrlihfsak 425          443                    474
dvineawfpedqrvltpnlvaalppsthGAGWQLFCRTVWSAHSGPTRMATAIARCAPDEELLSCSSFSRSGKRRGERM

EAQGGKLVCRAHNAFGGEGVYAIARCCLLPQANCSVHTAPPAEASMGTRVHCHQQGHVLTGCSSHWEVEDLGT 619 620
HKPPVLRPRGQPNQCVGHREASIHASCCHAPGLECKVKEHGIPAPQEQVTVACEEGWTLTGCSALPGTSHVLGAY

670
AVDNTCVVRSRDVSTTGSTSEEAVTAVAICCRSRHLAQASQELQ (c) Human PCSK9 Allele a Nucleotide Sequence (SEQ ID NO: 28) - Encoding "Pro-form" Plus Signal Sequence

ATGGGCACCGTCAGCTCCAGGCGGTCCTGGTGGCCGCTGCCACTGCTGCTGCTGCTGCTGCTCCTGGGTC

R45L CGT to CTT
*CCGCGGGCGCCCGTGCGC*CAGGAGGACGAGGACGGCGACTACGAGGAGCTGGTGCTAGCCTTGCGTTCCG

A53V GCC to GTC
AGGAGGACGGCCTGGCCGAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCGACCTGCTGGAGCTGGCCTTGAAGTTGCCC

CATGTCGACTACATCGAGGAGGACTCCTCTGTCTTTGCCCAGagcatcccgtggaacctggagcggattcccctcca cggtaccggcggatgaataccagcccccgacggaggcagcctggtggaggtgtatctcctagacaccagcatacagagtgaccaccgggaa atcgagggcagggtcatggtcaccgacttcgagaatgtgcccgaggaggacgggacccgcttccacagacaggccagcaagtgtgacagtcat ggcacccacctggcaggggtggtcagcggccgggatgccggcgtggccaagggtgccagcatgcgcagcctgcgcgtgctcaactgccaaggg aagggcacggttagcggcaccctcataggcctggagtttattcggaaaagccagctggtccagcctgtggggccactggtggtgctgctgcccct ggcgggtgggtacagccgcgtcctcaacgccgcctgccagcgcctggcgagggctggggtcgtgctggtcaccgctgccggcaacttccgggac gatgcctgcctctactcccagcctcagctcccgaggtcatcacagttggggccaccaatgcccaagaccagccggtgaccctggggactttggg gaccaactttggccgctgtgtggacctctttgccccaggggaggacatcattggtgcctccagcgactgcagcacctgctttgtgtcacagagtgg gacatcacaggctgctgcccacgtggctggcattgcagccatgatgctgtctgccgagccggagctcaccctggccgagttgaggcagagactg N425S AAT to AGT                            A443T GCC to ACC
atccacttctctgccaaagatgtcatcaatgaggcctggttccctgaggaccagcgggtactgaccccaacctggtggccgccctgccccccag cacccatGGGGCAGGTTGGCAGCTGTTTTGCAGGACTGTATGGTCAGCACACTCGGGGCCTACACGGATGGCC I474V ATC to GTC
ACAGCCATCGCCCGCTGCGCCCCAGATGAGGAGCTGCTGAGCTGCTCCAGTTTCTCCAGGAGTGGGAAGCGG

CGGGGCGAGCGCATGGAGGCCCAAGGGGGCAAGCTGGTCTGCCGGGCCCACAACGCTTTTGGGGGTGAGG

GTGTCTACGCCATTGCCAGGTGCTGCCTGCTATCCCCAGGCCAACTGCAGCGTCCACACAGCTCCACCAGCTGA

GGCCAGCATGGGGACCCGTGTCCACTGCCACCAACAGGGCCACGTCCTCACAGGCTGCAGCTCCCACTGGGA

GGTGGAGGACCTTGGCACCCACAAGCCGCCTGTGCTGAGGCCACGAGGTCAGCCCAACCAGTGCGTGGGCC

TABLE 2-continued

Sequences

ACAGGGAGGCCAGCATCCACGCTTCCTGCTGCCATGCCCCAGGTCTGGAATGCAAAGTCAAGGAGCATGGAA

Q619P CAG to CCG E620G GAG to GGG
TCCCGGCCCCTCAGGAGCAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTGTAGTCAGGAGCCGGGACGTCAGCA

E670G GAG to GGG
CTACAGGCAGCACCAGCGAAGAGGCCGTGACAGCCGTTGCCATCTGCTGCCGGAGCCGGCACCTGGCGCAG

GCCTCCCAGGAGCTCCAGTGAC

*Italics* = nucleotide sequence encoding signal sequence (nucleotides 1-90)

Courier = nucleotide sequence encoding pro peptide (nucleotides 91-456)

lower case = nucleotide sequence encoding catalytic domain (nucleotides 457-1346)
UPPER CASE = nucleotide sequence encoding C-terminal domain (nucleotides 1347-2076)
Underlined = allelic variations from allele a in other sequences (aa residue number changes and codon changes shown)
The pro-form is encoded by nucleotide sequence from nucleotide 91 to (and including) nucleotide 2076.
The mature form is encoded by nucleotide sequence from nucleotide 457 to (and including) nucleotide 2076.

Variant Allele Nucleotide Sequences
Thus,
(i) The nucleotide sequence of allele f is identical to SEQ ID NO: 28 except that the nucleotide sequence of allele f comprises a GTC codon instead of an ATC codon at the position labelled "I474V" in SEQ ID NO: 28;
(ii) The nucleotide sequence of allele c is identical to SEQ ID NO: 28 except that the nucleotide sequence of allele c comprises a GGG codon instead of an GAG codon at the position labelled "E670G" in SEQ ID NO: 28;
(iii) The nucleotide sequence of allele r is identical to SEQ ID NO: 28 except that the nucleotide sequence of allele r comprises a GTC codon instead of an ATC codon at the position labelled "I474V" in SEQ ID NO: 28; and a GGG codon instead of an GAG codon at the position labelled "E670G" in SEQ ID NO: 28;
(iv) The nucleotide sequence of allele p is identical to SEQ ID NO: 28 except that the nucleotide sequence of allele p comprises a GTC codon instead of a GCC codon at the position labelled "A53V" in SEQ ID NO: 28; and a GTC codon instead of an ATC codon at the position labelled "I474V" in SEQ ID NO: 28;
(v) The nucleotide sequence of allele m is identical to SEQ ID NO: 28 except that the nucleotide sequence of allele m comprises a ACC codon instead of a GCC codon at the position labelled "A443T" in SEQ ID NO: 28;
(vi) The nucleotide sequence of allele e is identical to SEQ ID NO: 28 except that the nucleotide sequence of allele e comprises a AGT codon instead of an AAT codon at the position labelled "N425S" in SEQ ID NO: 28; and a GTC codon instead of an ATC codon at the position labelled "I474V" in SEQ ID NO: 28;
(vii) The nucleotide sequence of allele h is identical to SEQ ID NO: 28 except that the nucleotide sequence of allele h comprises a ACC codon instead of a GCC codon at the position labelled "A443T" in SEQ ID NO: 28; and a CCG codon instead of a CAG codon at the position labelled "Q619P" in SEQ ID NO: 28;
(viii) The nucleotide sequence of allele aj is identical to SEQ ID NO: 28 except that the nucleotide sequence of allele aj comprises a CTT codon instead of an CGT codon at the position labelled "R46L" in SEQ ID NO: 28; and a GTC codon instead of an ATC codon at the position labelled "I474V" in SEQ ID NO: 28; and
(ix) The nucleotide sequence of allele q is identical to SEQ ID NO: 28 except that the nucleotide sequence of allele q comprises a GTC codon instead of a GCC codon at the position labelled "A53V" in SEQ ID NO: 28; and a GGG codon instead of an GAG codon at the position labelled "E670G" in SEQ ID NO: 28.

Variant Pro-Form Amino Acid Sequences
(Numbering is as per SEQ ID NO: 1 recited above)
(A) The amino acid sequence of form f is identical to the amino acid sequence from amino acid number 31 to (and including) amino acid number 692 of SEQ ID NO: 1 except that the amino acid sequence of form f comprises a valine at position 474;
(B) The amino acid sequence of form c is identical to the amino acid sequence from amino acid number 31 to (and including) amino acid number 692 of SEQ ID NO: 1 except that the amino acid sequence of form c comprises a glycine at position 670;
(C) The amino acid sequence of form r is identical to the amino acid sequence from amino acid number 31 to (and including) amino acid number 692 of SEQ ID NO: 1 except that the amino acid sequence of form r comprises a valine at position 474 and a glycine at position 670;
(D) The amino acid sequence of form p is identical the amino acid sequence from amino acid number 31 to (and including) amino acid number 692 of SEQ ID NO: 1 except that the amino acid sequence of form p comprises a valine at position 53 and a valine at position 474;
(E) The amino acid sequence of form m is identical to the amino acid sequence from amino acid number 31 to (and including) amino acid number 692 of SEQ ID NO: 1 except that the amino acid sequence of form m comprises a threonine at position 443;
(F) The amino acid sequence of form e is identical to the amino acid sequence from amino acid number 31 to (and including) amino acid number 692 of SEQ ID NO: 1 except that the amino acid sequence of form e comprises a serine at position 425 and a valine at position 474;
(G) The amino acid sequence of form h is identical to the amino acid sequence from amino acid number 31 to (and including) amino acid number 692 of SEQ ID NO: 1 except that the amino acid sequence of form h comprises a threonine at position 443 and a proline at position 619;

(H) The amino acid sequence of form aj is identical to the amino acid sequence from amino acid number 31 to (and including) amino acid number 692 of SEQ ID NO: 1 except that the amino acid sequence of form aj comprises a leucine at position 46 and a valine at position 474; and (I) The amino acid sequence of form q is identical to the amino acid sequence from amino acid number 31 to (and including) amino acid number 692 of SEQ ID NO: 1 except that the amino acid sequence of form q comprises a valine at position 53 and a glycine at position 670.

Variant Mature Form Amino Acid Sequences (Numbering is as per SEQ ID NO: 1 recited above)

(A') The amino acid sequence of form f is identical to SEQ ID NO: 2 except that the amino acid sequence of form f comprises a valine at position 474;

(B') The amino acid sequence of form c is identical to SEQ ID NO: 2 except that the amino acid sequence of form c comprises a glycine at position 670;

(C') The amino acid sequence of form r is identical to SEQ ID NO: 2 except that the amino acid sequence of form r comprises a valine at position 474 and a glycine at position 670;

(D') The amino acid sequence of form p is identical to SEQ ID NO: 2 except that the amino acid sequence of form p comprises a valine at position 474;

(E') The amino acid sequence of form m is identical to SEQ ID NO: 2 except that the amino acid sequence of form m comprises a threonine at position 443;

(F') The amino acid sequence of form e is identical to SEQ ID NO: 2 except that the amino acid sequence of form e comprises a serine at position 425 and a valine at position 474;

(G') The amino acid sequence of form h is identical to SEQ ID NO: 2 except that the amino acid sequence of form h comprises a threonine at position 443 and a proline at position 619;

(H') The amino acid sequence of form aj is identical to SEQ ID NO: 2 except that the amino acid sequence of form aj comprises valine at position 474; and (I') The amino acid sequence of form q is identical to SEQ ID NO: 2 except that the amino acid sequence of form q comprises a glycine at position 670.

The mature form of p is identical to the mature form off and aj.

The mature form of c is identical to the mature form of q.

Further sequence analysis and 3D in silico modelling (see FIG. 1) revealed that selected variants also fulfilled the following selection criteria:—

- PCSK9 variants whose variant amino acid residues (versus the common form of human PCSK9) are found in the mature form of the target (ie, outside the pro-domain); and
- PCSK9 variants whose variant amino acid residues (versus the common form of human PCSK9) are surface-exposed on the target, which the inventor saw as contributing to determining the topography of the target and potentially contributing to how and where ligand binding on the target occurs.

As shown in FIG. 1, identified positions 425, 443, 474, 619 and 670 (found in the selected variants of the invention) are all surface-exposed and outside of the pro-domain. Variant positions 425 and 443 are surface-exposed on the catalytic domain, while variant positions 474, 619 and 670 are surface-exposed on the C-terminal domain.

In a first example, the invention addresses the need to treat humans having naturally-occurring rarer natural PCSK9 alleles, genotypes and phenotypes (rarer protein forms). In this respect, the invention provides the following aspects:

In a First Aspect:

An anti-human PCSK9 ligand for use in a method of treating and/or preventing a PCSK9-mediated disease or condition in a human whose genome comprises a nucleotide sequence selected from the group consisting of SEQ ID NOs: 29-37, wherein the method comprises administering the ligand to the human.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.

In an example, the nucleotide sequence is SEQ ID NO: 30.

In an example, the nucleotide sequence is SEQ ID NO: 31.

In an example, the nucleotide sequence is SEQ ID NO: 32.

In an example, the nucleotide sequence is SEQ ID NO: 33.

In an example, the nucleotide sequence is SEQ ID NO: 34.

In an example, the nucleotide sequence is SEQ ID NO: 35.

In an example, the nucleotide sequence is SEQ ID NO: 36.

In an example, the nucleotide sequence is SEQ ID NO: 37.

In a Second Aspect:

The ligand of aspect 1, wherein the ligand has been or is determined as capable of binding a human PCSK9 selected from the group consisting forms f, c, r, p, m, e, h, aj and q.

In an example of any aspect, the ligand binds (or has been determined to bind) two, three, four or more human PCSK9 selected from the group consisting forms f, c, r, p, m, e, h, aj and q.

In an example of any aspect, the ligand comprises a protein domain that specifically binds to PCSK9, eg, a human PCSK9 selected from the group consisting forms f, c, r, p, m, e, h, aj and q.

The term "specifically binds," or the like, means that a ligand, eg, an antibody or antigen-binding fragment thereof, forms a complex with an antigen that is relatively stable under physiologic conditions. Specific binding can be characterized by an equilibrium dissociation constant of at least about $1\times10^{-6}$ M or less (e.g., a smaller KD denotes a tighter binding). Methods for determining whether two molecules specifically bind are well known in the art and include, for example, equilibrium dialysis, surface plasmon resonance, and the like. An isolated antibody that specifically binds a human PCSK9 may, however, exhibit cross-reactivity to other antigens such as a PCSK9 molecule from another specie. Moreover, multi-specific antibodies (e.g., bispecifics) that bind to human PCSK9 and one or more additional antigens are nonetheless considered antibodies that "specifically bind" PCSK9, as used herein.

In an example of any aspect, the ligand comprises or consists of a protein that mimics the EGFA domain of the LDL receptor and specifically binds to PCSK9, eg, a human PCSK9 selected from the group consisting forms f, c, r, p, m, e, h, aj and q.

In an example of any aspect, the ligand antagonises PCSK9, eg, a human PCSK9 selected from the group consisting forms f, c, r, p, m, e, h, aj and q.

In an example of any aspect, the method comprises (before administering the ligand) the step of determining that the ligand is capable of binding a human PCSK9 selected from the group consisting forms f, c, r, p, m, e, h, aj and q.

In an example of any aspect, binding is determined by SPR. In an example of any aspect, binding is determined by ELISA.

In an example of any aspect, said forms are the mature forms.

In an example of any aspect, said forms are the pro-forms.

In a Third Aspect:

A ligand that binds a human PCSK9 comprising an amino acid sequence selected from the group consisting of SEQ ID NOs: 4-27 for use in a method comprising the step of using the ligand to target said PCSK9 in a human to treat and/or prevent a disease or condition mediated by PCSK9, the method comprising administering the ligand to the human.

In an example, the disease or condition is mediated by a human PCSK9 comprising an amino acid sequence selected from the group consisting of SEQ ID NOs: 4-27.

In an example, the amino acid sequence selected from the group consisting of SEQ ID NOs: 4-23, 26 and 27; or selected from the group consisting of SEQ ID NOs: 4-14 and 18-27; or selected from the group consisting of SEQ ID NOs: 4-14, 18-23, 26 and 27. These are naturally-occurring sequences that do not comprise 46L and which meet the criteria set out above. These groups comprise variants that are associated with elevated LDL-C.

In an example, the amino acid sequence is SEQ ID NO: 18, 19 or 20, that comprises a 425S, which is associated with elevated LDL-C (Pisciotta et al 2006).

In an example, the amino acid sequence selected from the group consisting of SEQ ID NOs: 10, 11, 12, 26 and 27, that comprise 670G which is a marker for severity of coronary atherosclerosis (Chen et al 2005).

In an example, the amino acid sequence selected from the group consisting of SEQ ID NOs: 10-14 and 18-27; or selected from the group consisting of SEQ ID NOs: 10-14, 18-23, 26 and 27. These are sequences that have a naturally-occurring combination of differences from SEQ ID NOs: 1-3 (form a) and which meet the criteria set out above.

In an example, the amino acid sequence is SEQ ID NO: 4.
In an example, the amino acid sequence is SEQ ID NO: 5.
In an example, the amino acid sequence is SEQ ID NO: 6.
In an example, the amino acid sequence is SEQ ID NO: 7.
In an example, the amino acid sequence is SEQ ID NO: 8.
In an example, the amino acid sequence is SEQ ID NO: 9.
In an example, the amino acid sequence is SEQ ID NO: 10.
In an example, the amino acid sequence is SEQ ID NO: 11.
In an example, the amino acid sequence is SEQ ID NO: 12.
In an example, the amino acid sequence is SEQ ID NO: 13.
In an example, the amino acid sequence is SEQ ID NO: 14.
In an example, the amino acid sequence is SEQ ID NO: 15.
In an example, the amino acid sequence is SEQ ID NO: 16.
In an example, the amino acid sequence is SEQ ID NO: 17.
In an example, the amino acid sequence is SEQ ID NO: 18.
In an example, the amino acid sequence is SEQ ID NO: 19.
In an example, the amino acid sequence is SEQ ID NO: 20.
In an example, the amino acid sequence is SEQ ID NO: 21.
In an example, the amino acid sequence is SEQ ID NO: 22.
In an example, the amino acid sequence is SEQ ID NO: 23.
In an example, the amino acid sequence is SEQ ID NO: 24.
In an example, the amino acid sequence is SEQ ID NO: 25.
In an example, the amino acid sequence is SEQ ID NO: 26.
In an example, the amino acid sequence is SEQ ID NO: 27.

In a Fourth Aspect: The ligand of aspect 3, wherein the genome of the human comprises a nucleotide sequence selected from the group consisting of SEQ ID NOs: 29-37.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33
In an example, the nucleotide sequence is SEQ ID NO: 34
In an example, the nucleotide sequence is SEQ ID NO: 35.
In an example, the nucleotide sequence is SEQ ID NO: 36.
In an example, the nucleotide sequence is SEQ ID NO: 37.

In a Fifth Aspect:

The ligand of any preceding aspect, wherein the human has been or is genotyped as positive for a nucleotide sequence selected from the group consisting of SEQ ID NOs: 29-37 or at least the catalytic domain- or C-terminal domain-encoding sequence thereof.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Sixth Aspect:

The ligand of any preceding aspect, wherein the human has been or is phenotyped as positive for a human PCSK9 selected from the group consisting of forms f, c, r, p, m, e, h, aj and q or at least the catalytic or C-terminal domain thereof.

In an example, said forms are the mature forms.
In an example, said forms are the pro-forms.

In a Seventh Aspect:

The ligand of any preceding aspect, wherein the method comprises genotyping the human as positive for a nucleotide sequence selected from the group consisting of SEQ ID NOs: 29-37 or at least the catalytic domain- or C-terminal domain-encoding sequence thereof.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In an Eighth Aspect:

The ligand of any preceding aspect, wherein the method comprises phenotyping the human has positive for a human PCSK9 selected from the group consisting of forms f, c, r, p, m, e, h, aj and q or at least the catalytic or C-terminal domain thereof.

In an example, said forms are the mature forms.
In an example, said forms are the pro-forms.

In a Ninth Aspect:

The ligand of any preceding aspect, wherein the human has been or is genotyped as heterozygous for a nucleotide sequence selected from the group consisting of SEQ ID NOs: 29-37 or at least the catalytic domain- or C-terminal domain-encoding sequence thereof; optionally wherein the human has been or is genotyped as comprising the nucleotide sequence of SEQ ID NO: 28 or at least the catalytic domain- or C-terminal domain-encoding sequence thereof and a nucleotide sequence selected from the group consisting of SEQ ID NOs: 29-37 or at least the catalytic domain- or C-terminal domain-encoding sequence thereof.

"Heterozygous" here means that in the human's genotype one allele comprises a nucleotide sequence selected from the group consisting of SEQ ID NOs: 29-37 or at least the catalytic domain- or C-terminal domain-encoding sequence thereof and other allele can be any PCSK9 (eg, form a, a' or an allele comprising a nucleotide sequence selected from the group consisting of SEQ ID NOs: 29-37 or at least the catalytic domain- or C-terminal domain-encoding sequence thereof).

In an example, the method comprises (before administering the ligand) genotyping the human as heterozygous for a nucleotide sequence selected from the group consisting of SEQ ID NOs: 29-37 or at least the catalytic domain- or C-terminal domain-encoding sequence thereof; optionally also genotyping the human as comprising the nucleotide sequence of SEQ ID NO: 28 or at least the catalytic domain- or C-terminal domain-encoding sequence thereof and a nucleotide sequence selected from the group consisting of SEQ ID NOs: 29-37 or at least the catalytic domain- or C-terminal domain-encoding sequence thereof.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37.

These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Tenth Aspect:

The ligand of any one of aspects 1 to 9, wherein the genome of the human has been or is genotyped as homozygous for a nucleotide sequence selected from the group consisting of SEQ ID NOs: 29-37 or at least the catalytic domain- or C-terminal domain-encoding sequence thereof.

"Homozygous" here means that in the human's genotype each allele comprises the same nucleotide sequence selected from the group consisting of SEQ ID NOs: 29-37 or at least the catalytic domain- or C-terminal domain-encoding sequence thereof.

In an example, the method comprises genotyping the human as homozygous for a nucleotide sequence selected from the group consisting of SEQ ID NOs: 29-37 or at least the catalytic domain- or C-terminal domain-encoding sequence thereof.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In an Eleventh Aspect:

The ligand of any preceding aspect, wherein the ligand comprises an antibody binding site that binds a human PCSK9 comprising an amino acid sequence selected from the group consisting of SEQ ID NOs: 4-27 and optionally has been or is determined as capable of such binding.

In an example, the method comprises (before administering the ligand) the step of determining that the ligand is capable of binding to said human PCSK9.

In an example, the binding is specific binding. In an example, the ligand binds (or has been determined as binding) to the PCSK9 with an affinity (Kd) of 1 mM, 100 nM, 10 nM or 1 nM or less. In an embodiment, the affinity is no less than 10, 100 or 1000 fM.

In an example, binding or affinity is determined by SPR or ELISA.

In an example, the disease or condition is mediated by a human PCSK9 comprising an amino acid sequence selected from the group consisting of SEQ ID NOs: 4-27.

In an example, the amino acid sequence selected from the group consisting of SEQ ID NOs: 4-23, 26 and 27; or selected from the group consisting of SEQ ID NOs: 4-14 and 18-27; or selected from the group consisting of SEQ ID NOs: 4-14, 18-23, 26 and 27. These are naturally-occurring sequences that do not comprise 46L and which meet the criteria set out above. These groups comprise variants that are associated with elevated LDL-C.

In an example, the amino acid sequence is SEQ ID NO: 18, 19 or 20, that comprises a 425S, which is associated with elevated LDL-C (Pisciotta et al 2006).

In an example, the amino acid sequence selected from the group consisting of SEQ ID NOs: 10, 11, 12, 26 and 27, that comprise 670G which is a marker for severity of coronary atherosclerosis (Chen et al 2005).

In an example, the amino acid sequence selected from the group consisting of SEQ ID NOs: 10-14 and 18-27; or selected from the group consisting of SEQ ID NOs: 10-14, 18-23, 26 and 27. These are sequences that have a naturally-occurring combination of differences from SEQ ID NOs: 1-3 (form a) and which meet the criteria set out above In an example, the amino acid sequence is SEQ ID NO: 4.
In an example, the amino acid sequence is SEQ ID NO: 5.
In an example, the amino acid sequence is SEQ ID NO: 6.
In an example, the amino acid sequence is SEQ ID NO: 7.
In an example, the amino acid sequence is SEQ ID NO: 8.
In an example, the amino acid sequence is SEQ ID NO: 9.
In an example, the amino acid sequence is SEQ ID NO: 10.
In an example, the amino acid sequence is SEQ ID NO: 11.
In an example, the amino acid sequence is SEQ ID NO: 12.
In an example, the amino acid sequence is SEQ ID NO: 13.
In an example, the amino acid sequence is SEQ ID NO: 14.
In an example, the amino acid sequence is SEQ ID NO: 15.
In an example, the amino acid sequence is SEQ ID NO: 16.
In an example, the amino acid sequence is SEQ ID NO: 17.
In an example, the amino acid sequence is SEQ ID NO: 18.
In an example, the amino acid sequence is SEQ ID NO: 19.
In an example, the amino acid sequence is SEQ ID NO: 20.
In an example, the amino acid sequence is SEQ ID NO: 21.
In an example, the amino acid sequence is SEQ ID NO: 22.
In an example, the amino acid sequence is SEQ ID NO: 23.
In an example, the amino acid sequence is SEQ ID NO: 24.
In an example, the amino acid sequence is SEQ ID NO: 25.
In an example, the amino acid sequence is SEQ ID NO: 26.
In an example, the amino acid sequence is SEQ ID NO: 27.

In a Twelfth Aspect:

The ligand of aspect 11, wherein the ligand is an antibody or antibody fragment. For example, the antibody or antibody fragment is a PCSK9 antagonist, eg, neutralises PCSK9.

Examples of such antibodies are disclosed, for instance, in WO 2008/057457, WO2008/057458, WO 2008/057459, WO 2008/063382, WO 2008/133647, WO 2009/100297, WO 2009/100318, WO 2011/037791, WO 2011/053759, WO 2011/053783, WO 2008/125623, WO 2011/072263, WO 2009/055783, WO 2010/029513, WO 2011/111007, WO 2010/077854, the disclosures and sequences of such antibodies being incorporated herein for use in the invention in their entireties by reference. One specific example is AMG 145 (Amgen), LY3015014 (Eli Lilly) or alirocumab. Advantageously, the ligand is or comprises alirocumab. Alternatively, the ligand is or comprises evolocumab.

In an example, the ligand is SAR236553/REGN727 (Sanofi Aventis/Regeneron) or a PCSK9-binding derivative thereof.

In an example, the ligand comprises or consists of a neutralizing antibody that binds to the PCSK9, wherein the antibody binds to PCSK9 and reduces the likelihood that PCSK9 binds to LDLR.

The ligand of aspect 11, wherein the ligand is a PCSK9 antagonist, eg, neutralises PCSK9.

In an example of any aspect of the invention, the ligand comprises or consists a ligand selected from evolocumab, 1D05-IgG2 (Merck & Co.), ALN-PCS02 (Alnylam), RN316 (Pfizer-Rinat), LY3015014 (Eli Lilly) and alirocumab (SAR236553/REGN727; Sanofi Aventis/Regeneron).

In Thirteenth Aspect:

The ligand of any one of aspects 1 to 10, wherein (i) the ligand comprises a sequence of contiguous nucleotides that specifically hybridises to a nucleotide sequence selected from the group consisting of SEQ ID NOs: 29-37 or at least the catalytic domain- or C-terminal domain-encoding sequence thereof, or specifically hybridises to an antisense sequence or an RNA transcript of said sequence, wherein said sequence of contiguous nucleotides hybridises to at least one nucleotide present in said selected sequence which is not present in SEQ ID NO: 28 or hybridises to an antisense sequence or an RNA transcript thereof respectively; and/or (ii) the ligand comprises a sequence of at least 10 contiguous nucleotides of a nucleotide sequence selected from the group consisting of SEQ ID NOs: 29-37 or is an antisense sequence or RNA version of said contiguous nucleotides, wherein said sequence of contiguous nucleotides comprises at least one nucleotide present in said selected sequence which is not present in SEQ ID NO: 28.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In an embodiment, the ligand comprises at least 10, 11, 12, 13, 14, 15, 20, 25, 30, 35, 40, 45, 50 or 100 contiguous nucleotides of said nucleotide sequence.

In a Fourteenth Aspect:

The ligand of any preceding aspect, wherein said disease or condition is hyperlipidaemia, hypercholesterolaemia (eg, familial hypercholesterolaemia), heart attack, stroke, coronary heart disease, atherosclerosis or a cardiovascular disease or condition.

The ligand of any preceding aspect, wherein the disease or condition is hypercholesterolemia, hyperlipidemia, hypercholesterolemia, dyslipidemia, cholestatic liver disease, nephrotic syndrome, hypothyroidism, obesity, atherosclerosis or a cardiovascular disease.

In an example, said disease or condition is hypercholesterolaemia. The term "hypercholesterolaemia," as used herein, refers to a condition in which cholesterol levels are elevated above a desired level. In some embodiments, this denotes that serum cholesterol levels are elevated. In some embodiments, the desired level takes into account various "risk factors" that are known to one of skill in the art (and are described or referenced in US20120093818).

The ligand of any preceding aspect, wherein the human is identified as heterozygous for Familial Hypercholesterolemia, statin intolerant, statin uncontrolled, or at risk for developing hypercholesterolemia, dyslipidemia, cholestatic liver disease, nephrotic syndrome, hypothyroidism, obesity, atherosclerosis or a cardiovascular disease.

In a Fifteenth Aspect:

The ligand of any preceding aspect, wherein said disease or condition is associated with elevated LDL cholesterol.

Cholesterol levels are measured in milligrams (mg) of cholesterol per deciliter (dL) of blood in the United States and some other countries. Canada and most European countries measure cholesterol in millimoles (mmol) per liter (L) of blood. Below are general guideline ideal ranges and elevated ranges.

| Total cholesterol (U.S. and some other countries) | Total cholesterol* (Canada and most of Europe) | |
|---|---|---|
| Below 200 mg/dL | Below 5.2 mmol/L | Ideal |
| 200-239 mg/dL | 5.2-6.2 mmol/L | Borderline high |
| 240 mg/dL and above | Above 6.2 mmol/L | High |
| LDL cholesterol (U.S. and some other countries) | LDL cholesterol* (Canada and most of Europe) | |
| 100-129 mg/dL | 2.6-3.3 mmol/L | Ideal |
| 130-159 mg/dL | 3.4-4.1 mmol/L | Borderline high |
| 160-189 mg/dL | 4.1-4.9 mmol/L | High |
| 190 mg/dL and above | Above 4.9 mmol/L | Very high |

*Canadian and European guidelines differ slightly from U.S. guidelines. These conversions are based on U.S. guidelines.

Elevated LDL cholesterol is, therefore, 160 mg/dL or above (4.1 mmol/L or above).

In a Sixteenth Aspect:

The ligand of any preceding aspect, wherein the ligand inhibits human PCSK9 binding to human LDL receptor and optionally has been or is determined as capable of such inhibition.

In an example, the method comprises (before administering the ligand) determining that the ligand is capable of such inhibition.

Inhibition determination is eg, inhibition in a blood or serum sample, at rtp, at ph7, at 37 degrees centigrade and/or under the physiological conditions of a human body.

In a Seventeeth Aspect:

The ligand of any preceding aspect, wherein the human is resistant or substantially resistant to statin (eg, avorstatin and/or fluvastatin) treatment of said disease or condition.

In an Eighteenth Aspect:

The ligand of any preceding aspect, wherein the ligand is for treating and/or preventing a PCSK9-mediated disease or condition in a human
(i) whose genome comprises SEQ ID NO: 29 and wherein the human is of ASW, YRI, GBR, TSI, CLM, LWK, MXL, JPT, PUR, IBS, FIN or CEU ancestry; or
(ii) whose genome comprises SEQ ID NO: 30 and wherein the human is of ASW, YRI, GBR, TSI, CLM, CHB, LWK, CHS, JPT, PUR, FIN or CEU ancestry; or (iii) whose genome comprises SEQ ID NO: 32 and wherein the human is of ASW, GBR, TSI, CLM, JPT, PUR, IBS, FIN or CEU ancestry; or
(iv) whose genome comprises SEQ ID NO: 33 and wherein the human is of LWK, ASW, YRI or CLM ancestry; or
(v) whose genome comprises SEQ ID NO: 34 and wherein the human is of LWK, ASW or YRI ancestry; or
(vi) whose genome comprises SEQ ID NO: 35 and wherein the human is of PUR, TSI, FIN or CEU ancestry; or
(vii) whose genome comprises SEQ ID NO: 36 and wherein the human is of LWK, ASW or YRI ancestry; or
(viii) whose genome comprises SEQ ID NO: 37 and wherein the human is of CHS, ASW, JPT, PUR or CHB ancestry.

In a Ninteenth Aspect:
The ligand of any preceding aspect, wherein the ligand is for treating and/or preventing a PCSK9-mediated disease or condition in a human
(i) that expresses PCSK9 form f and wherein the human is of ASW, YRI, GBR, TSI, CLM, LWK, MXL, JPT, PUR, IBS, FIN or CEU ancestry; or
(ii) that expresses PCSK9 form c and wherein the human is of ASW, YRI, GBR, TSI, CLM, CHB, LWK, CHS, JPT, PUR, FIN or CEU ancestry; or
(iii) that expresses PCSK9 form p and wherein the human is of ASW, GBR, TSI, CLM, JPT, PUR, IBS, FIN or CEU ancestry; or
(iv) that expresses PCSK9 form m and wherein the human is of LWK, ASW, YRI or CLM ancestry; or
(v) that expresses PCSK9 form e and wherein the human is of LWK, ASW or YRI ancestry; or
(vi) that expresses PCSK9 form h and wherein the human is of PUR, TSI, FIN or CEU ancestry; or
(vii) that expresses PCSK9 form aj and wherein the human is of LWK, ASW or YRI ancestry; or
(viii) that expresses PCSK9 form q and wherein the human is of CHS, ASW, JPT, PUR or CHB ancestry.

In an example, said forms are the mature forms.
In an example, said forms are the pro-forms.

In a Twentieth Aspect:
A pharmaceutical composition or kit for treating and/or preventing a PCSK9-mediated condition or disease (eg, as recited in aspect 14 or 15), the composition or kit comprising a ligand of any preceding aspect and optionally a statin (eg, cerovastatin, atorvastatin, simvastatin, pitavastin, rosuvastatin, fluvastatin, lovastatin or pravastatin); and optionally in combination with a label or instructions for use to treat and/or prevent said disease or condition in a human (eg, covering treatment of a human as recited in aspect 18 or 19); optionally wherein the label or instructions comprise a marketing authorisation number (eg, an FDA or EMA authorisation number); optionally wherein the label or instructions comprise directions to administer alirocumab or evolocumab to said human; optionally wherein the kit comprises an IV or injection device that comprises the ligand (and, eg, also a statin).

In a Twenty-First Aspect:
A method of producing an anti-human PCSK9 antibody binding site, the method comprising obtaining a plurality of anti-PCSK9 antibody binding sites, screening the antibody binding sites for binding to a human PCSK9 selected from the group consisting of forms f, c, r, p, m, e, h, aj and q or a catalytic or C-terminal domain or a peptide thereof that comprises amino acid variation from the corresponding sequence of SEQ ID NO: 1, 2 or 3 and isolating an antibody binding site that binds in the screening step, and optionally producing a form f, c, r, p, m, e, h, aj or q PCSK9-binding fragment or derivative of the isolated antibody.

In an example, said forms are the mature forms.
In an example, said forms are the pro-forms.

In an example of this and the next aspect, the plurality of binding sites comprises or consists of a plurality of 4-chain antibodies or fragments thereof, eg, dAbs, Fabs or scFvs. Suitable methods for producing pluralities of binding sites for screening include phage display (producing a phage display library of antibody binding sites), ribosome display (producing a ribosome display library of antibody binding sites), yeast display (producing a yeast display library of antibody binding sites), or immunisation of a non-human vertebrate (eg, a rodent, eg, a mouse or rat, eg, a Velocimouse™, Kymouse™, Xenomouse™, Aliva Mouse™, HuMab Mouse™, Omnimouse™, Omnirat™ or MeMo Mouse™) with a PCSK9 epitope and isolation of a repertoire of antibody-producing cells (eg, a B-cell, plasma cell or plasmablast repertoire) and/or a repertoire of isolated antibodies.

In an example, the method comprises selecting one or more antibody binding sites that each specifically binds to a human PCSK9 epitope comprising amino acid variation from the corresponding sequence of SEQ ID NO: 1, 2 or 3.

In a Twenty-Second Aspect:
A method of producing an anti-human PCSK9 antibody, the method comprising immunising a non-human vertebrate (eg, a mouse or a rat) with a human PCSK9 comprising an amino acid sequence selected from the group consisting of the amino acid sequences of forms f, c, r, p, m, e, h, aj and q or a catalytic or C-terminal domain or a peptide thereof that comprises amino acid variation from the corresponding sequence of SEQ ID NO: 1, 2 or 3 and isolating an antibody that binds a human PCSK9 comprising selected from the group consisting of forms f, c, r, p, m, e, h, aj and q or a catalytic or C-terminal domain or a peptide thereof that comprises amino acid variation from the corresponding sequence of SEQ ID NO: 1, 2 or 3, and optionally producing a form f, c, r, p, m, e, h, aj or q PCSK9-binding fragment or derivative of the isolated antibody.

In an example, said forms are the mature forms.
In an example, said forms are the pro-forms.

In a Twenty-Third Aspect:
The method of aspect 21 or 22, comprising the step of obtaining a nucleic acid encoding the antibody, fragment, derivative or binding site and optionally inserting the nucleic acid in an expression vector.

For example, the method comprises isolating a cell (eg, B-cell, plasmablast, plasma cell or memory cell) comprising the nucleic acid, wherein the cell is obtained from a non-human vertebrate that has been immunised with the PCSK9 epitope.

In a Twenty-Fourth Aspect:
A kit for PCSK9 genotyping a human, wherein the kit comprises a nucleic acid (i) comprising a sequence of 10 or more (eg, 10, 15, 20, 30, 40, 50, 60, 70, 80, 90, 100 or more) contiguous nucleotides that specifically hybridises to a nucleotide sequence selected from the group consisting of SEQ ID NOs: 29-37 or at least the catalytic domain- or C-terminal domain-encoding sequence thereof, or specifically hybridises to an antisense sequence or an RNA transcript of said sequence, wherein said sequence of contiguous nucleotides hybridises to at least one nucleotide present in said selected sequence which is not present in SEQ ID NO: 28 or hybridises to an antisense sequence or an RNA transcript thereof; and/or (ii) comprising a sequence of at least 10 or more (eg, 10, 15, 20, 30, 40, 50, 60, 70, 80, 90, 100 or more) nucleotides of a nucleotide sequence selected from the group consisting of SEQ ID NOs: 29-37 or comprising an antisense sequence or RNA version of said contiguous nucleotides, wherein said sequence of contiguous nucleotides comprises at least one nucleotide present in said selected sequence which is not present in SEQ ID NO: 28.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Twenty-Fifth Aspect:

A kit for PCSK9 genotyping or phenotyping a human, wherein the kit comprises a ligand according to any one of aspects 1 to 19 or an antibody, fragment or derivative produced by the method of any one of aspects 21 to 23.

In a Twenty-Sixth Aspect:

Use of an anti-PCSK9 ligand that binds a human PCSK9 selected from the group consisting of forms f, c, r, p, m, e, h, aj and q in the manufacture of a medicament for treating and/or preventing a PCSK9-mediated disease or condition in a human whose genome comprises a nucleotide sequence selected from the group consisting of SEQ ID NOs: 29-37, optionally for treating and/or preventing a PCSK9-mediated disease or condition in a human as recited in aspect 18 or 19.

In an example, said forms are the mature forms.
In an example, said forms are the pro-forms.

In a Twenty-Seventh Aspect:

Use of an anti-PCSK9 ligand that binds a human PCSK9 selected from the group consisting of forms f, c, r, p, m, e, h, aj and q in the manufacture of a medicament for targeting said PCSK9 in a human to treat and/or prevent a disease or condition mediated by PCSK9, optionally for targeting PCSK9 in a human as recited in aspect 18 or 19.

In an example, said forms are the mature forms.
In an example, said forms are the pro-forms.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

The ligand can be any anti-PCSK9 ligand disclosed herein.

In a Twenty-Eight Aspect:

The use of aspect 26 or 27, wherein the ligand, human, disease or condition is according to any one of aspects 1 to 19.

In a Twenty-Ninth Aspect:

A method of targeting a PCSK9 for treating and/or preventing a PCSK9-mediated disease or condition in a human, the method comprising administering an anti-PCSK9 ligand to a human comprising a nucleotide sequence selected from the group consisting SEQ ID NOs: 29-37, whereby a PCSK9 encoded by said nucleotide sequence is targeted.

The ligand can be any anti-PCSK9 ligand disclosed herein.

In a Thirtieth Aspect:

The method of aspect 29, wherein the method comprises targeting a human PCSK9 selected from the group consisting of forms f, c, r, p, m, e, h, aj and q with said ligand to treat and/or prevent said disease or condition in said human.

In an example, said forms are the mature forms.
In an example, said forms are the pro-forms.

In a Thirty-First Aspect:

A method of treating and/or preventing a disease or condition mediated by PCSK9 in a human, the method comprising targeting a human PCSK9 selected from the group consisting of forms f, c, r, p, m, e, h, aj and q by administering to the human a ligand that binds said PCSK9 thereby treating and/or preventing said disease or condition in the human.

In an example, said forms are the mature forms.
In an example, said forms are the pro-forms.

The ligand can be any anti-PCSK9 ligand disclosed herein.

In a Thirty-Second Aspect:

The method of aspect 31, wherein the genome of the human comprises a nucleotide sequence selected from the group consisting of SEQ ID NOs: 29-37.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Thirty-Third Aspect:
The method of any one of aspects 29 to 32, wherein the human has been or is genotyped as positive for a nucleotide sequence selected from the group consisting of SEQ ID NOs: 29-37 or the catalytic- or C-terminal domain-encoding sequence thereof.

In a Thirty-Fourth Aspect:
The method of any one of aspects 29 to 33, wherein the human has been or is phenotyped as positive for a human PCSK9 selected from the group consisting of forms f, c, r, p, m, e, h, aj and q.

In an example, said forms are the mature forms.
In an example, said forms are the pro-forms.

In a Thirty-Fifth Aspect:
The method of any one of aspects 29 to 34, wherein the method comprises genotyping the human as positive for a nucleotide sequence selected from the group consisting of SEQ ID NOs: 29-37 or the catalytic- or C-terminal domain-encoding sequence thereof.

In a Thirty-Sixth Aspect:
The method of any one of aspects 29 to 35, wherein the method comprises phenotyping the human as positive for a human PCSK9 sequence selected from the group consisting of forms f, c, r, p, m, e, h, aj and q.

In an example, said forms are the mature forms.
In an example, said forms are the pro-forms.

In a Thirty-Seventh Aspect:
The method of any one of aspects 29 to 36, wherein the human has been or is genotyped as heterozygous for a nucleotide sequence selected from the group consisting of SEQ ID NOs: 29-37 or the catalytic- or C-terminal domain-encoding sequence thereof; optionally wherein the human has been or is genotyped as comprising the nucleotide sequence of SEQ ID NO: 28 or the catalytic- or C-terminal domain-encoding sequence thereof and a nucleotide sequence selected from the group consisting of SEQ ID NOs: 29-37 or the catalytic- or C-terminal domain-encoding sequence thereof.

In a Thirty-Eighth Aspect:
The method of any one of aspects 29 to 37, wherein the genome of the human has been or is genotyped as homozygous for a nucleotide sequence selected from the group consisting of SEQ ID NOs: 29-37 or the catalytic- or C-terminal domain-encoding sequence thereof.

In a Thirty-Ninth Aspect:
The method of any one of aspects 29 to 38, wherein the method comprises genotyping the human for a nucleotide sequence selected from the group consisting of SEQ ID NOs: 29-37 or the catalytic- or C-terminal domain-encoding sequence thereof before administering the ligand to the human, wherein the ligand is determined to be capable of binding to a PCSK9 encoded by said selected sequence.

In a Fortieth Aspect:
The method of any one of aspects 29 to 39, wherein the ligand, human, disease or condition is according to any one of aspects 1 to 19.

In a Forty-First Aspect:
A method according to any one of aspects 29 to 40 for treating and/or preventing a condition or disease as recited in aspect 14 or 15, the method comprising administering said ligand and a statin (eg, cerovastatin, atorvastatin, simvastatin, pitavastin, rosuvastatin, fluvastatin, lovastatin or pravastatin) to the human.

In a Forty-Second Aspect:
The method of aspect 41, wherein the ligand and statin are administered separately.

In a Forty-Third Aspect:
The method of aspect 41, wherein the ligand and statin are administered simultaneously.

In a Forty-Fourth Aspect:
The method of any one of aspects 29 to 43, wherein the ligand is administered by subcutaneous injection.

In a Forty-Fifth Aspect:
A method of PCSK9 genotyping a nucleic acid sample of a human, the method comprising identifying in the sample the presence of a nucleotide sequence selected from the group consisting of SEQ ID NOs: 29-37 or the catalytic- or C-terminal domain-encoding sequence thereof.

In a Forty-Sixth Aspect:
A method of PCSK9 typing a protein sample of a human, the method comprising identifying in the sample the presence of a human PCSK9 selected from the group consisting of forms f, c, r, p, m, e, h, aj and q.

In an example, said forms are the mature forms.
In an example, said forms are the pro-forms.

In a Forty-Seventh Aspect:
The method of aspect 45 or 46, comprising obtaining a sample of serum, blood, faeces, hair, tissue, cells, urine or saliva from a human, whereby the nucleic acid or protein sample is obtained and used in the step of identifying said sequence.

In a Forty-eighth Aspect:
The method of any one of aspects 45 to 47, comprising using a ligand according to any one of aspects 1 to 19 to carry out said identifying step.

In a Forty-ninth Aspect:
A method of treating and/or preventing in a human patient a cardiovascular disease or condition, or a disease or condition that is associated with elevated LDL cholesterol (eg, hypercholesterolaemia), wherein the patient is receiving or has previously received statin treatment for said disease or condition, the method comprising typing the patient using a method of any one of aspects 45 to 48 and administering a ligand according to one of aspects 1 to 19 whereby the human is treated or said disease or condition is prevented; optionally also reducing or stopping statin treatment.

In an example, said reducing or stopping comprises reducing the dose and/or dosing frequency of statin.

In a Fiftieth Aspect:
A diagnostic, therapeutic or prophylactic kit comprising a ligand that is capable of binding to or has been or is determined as capable of binding to an amino acid sequence selected from SEQ ID NOs: 4-27 and instructions for carrying out the method of any one of aspects 46 to 49 and/or a label or instructions indicating or covering administration of the ligand to a human as defined in any one of aspects 1 to 19.

In a Fifty-First Aspect:

A diagnostic, therapeutic or prophylactic kit comprising a nucleic acid probe comprising a nucleotide sequence that specifically hybridises to a nucleotide sequence selected from the group consisting of SEQ ID NOs: 29-37 or an antisense sequence or RNA transcript thereof and instructions for carrying out the method of aspect 45, 47 or 48.

In examples of the present invention, the ligand specifically binds to human PCSK9, eg, one or more of the rare PCSK9 variants disclosed herein (eg, one, two, three, more or all mature forms f, c, r, p, m, e, h, aj and q) and optionally also the a and/or a'form. For example, the ligand specifically binds to mature form f and/or c as well as form a. Determination of such binding can be performed by any antibody binding test as known in the art, eg, by surface plasmon resonance. Binding to each such form is, for example, respectively with a Kd of at least 1 mM, 100 nM, 1 nM, 100 pM, 10 pM or 1 pM.

In an example, the ligand binds form a and a PCSK9 selected from the group consisting of forms f, c, r, p, m, e, h, aj and q, wherein the ligand binding to said selected form is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form f wherein the ligand binding to form f is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form c, wherein the ligand binding to form c is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form r, wherein the ligand binding to form r is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form p, wherein the ligand binding to form p is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form m, wherein the ligand binding to form m is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form e, wherein the ligand binding to form e is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form h, wherein the ligand binding to form h is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form aj, wherein the ligand binding to form aj is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form q, wherein the ligand binding to form q is with a Kd (determined by SPR) that is at least 60, 70, 80, 90 or 95% of the Kd for binding to form a. In an embodiment, both forms are mature forms. In an embodiment, both forms are pro-forms.

In examples of the present invention, the ligand neutralises human PCSK9, eg, one or more of the rare PCSK9 variants disclosed herein (eg, one, two, three, more or all mature forms f, c, r, p, m, e, h, aj and q) and optionally also the a and/or a'form. For example, the ligand neutralises mature form f and/or c as well as form a. Determination of neutralisation can be performed, for example, by any neutralisation assay method disclosed in US20120093818A1 (Amgen, Inc) or US20110065902A1 (Regeneron Pharmaceuticals, Inc). Ligands of the invention that bind or target PCSK9 are useful, for example, for therapeutic and prophylactic applications disclosed in US20120093818A1 and US20110065902A1, these specific disclosures being incorporated herein by reference for use in the present invention and for possible inclusion in claims herein.

In embodiments where the ligand is used for therapeutic applications, an antigen binding protein can inhibit, interfere with or modulate one or more biological activities of a PCSK9 (eg, one or more of the rare variants disclosed herein and optionally also the a and/or a'form). In one embodiment, ligand binds specifically to human PCSK9 (eg, one or more of the rare variants disclosed herein and optionally also the a and/or a'form) and/or substantially inhibits binding of human PCSK9 (eg, said one or more of the rare variants disclosed herein and optionally also the a and/or a'form) to LDLR by at least 20%, eg, 20%-40%, 40-60%, 60-80%, 80-85%, or more (for example, by measuring binding in an in vitro competitive binding assay). In an example, the ligand is an antibody.

In an embodiment, the ligand has a Kd of less (binding more tightly) than $10^{-7}$, $10^{-8}$, $10^{-9}$, $10^{-10}$, $10^{-11}$, $10^{-12}$, $10^{-13}$ M for binding to one, two or more of the rare variants disclosed herein and optionally also the a and/or a'form. In an example, Kd is determined using SPR.

In an embodiment, the ligand has an IC50 for blocking the binding of LDLR to one or more of the rare PCSK9 variants disclosed herein (and optionally also the a and/or a'form) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

In an embodiment, the ligand has an IC50 for blocking the binding of LDLR to the a and/or a'form of PCSK9 that is no more than 1000, 100, 90, 80, 70, 60, 50, 40, 30, 20 or 10-fold more (ie, more inhibitory) than the IC50 for blocking the binding of LDLR to one or more of the rare PCSK9 variants disclosed herein (eg, one or more PCSK9 proteins comprising a sequence selected from SEQ ID NOs: 4 to 27). Additionally or alternatively, for example, the ligand has an IC50 for blocking the binding of LDLR to (i) the a and/or a'form of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, eg, in the range of 1 mM to 1 pM (eg, 1 mM to 100 pM; 10 nM to 100 pM; 1 nM to 10 pM; or 100 pM to 1 pM) and (ii) one or more PCSK9 proteins comprising a sequence selected from SEQ ID NOs: 4 to 27 of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, eg, in the range of 1 mM to 1 pM (eg, 1 mM to 100 pM; 10 nM to 100 pM; 1 nM to 10 pM; or 100 pM to 1 pM).

In an embodiment, the ligand binds to the a and/or a' form of PCSK9 with a binding affinity (Kd) that is greater than up to 10%, greater than up to 20%, greater than up to 40%, greater than up to 50%, greater than up to 55%, greater than up to 60%, greater than up to 65%, greater than up to 70%, greater than up to 75%, greater than up to 80%, greater than up to 85%, greater than up to 90%, greater than up to 95% or greater than up to 100% (ie, is double) relative to binding to a PCSK9 comprising a sequence selected from SEQ ID NOs: 4 to 27. Such binding measurements can be made using a variety of binding assays known in the art, eg, using surface plasmon resonance (SPR), such as by Biacore™ or using the ProteOn XPR36™ (Bio-Rad®), or using KinExA® (Sapidyne Instruments, Inc).

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the ligand which is an antibody is determined using SPR by 1. Coupling anti-mouse (or other relevant vertebrate) IgG (eg, Biacore BR-1008-38) to a biosensor chip (eg, GLM chip) such as by primary amine coupling;
2. Exposing the anti-mouse IgG (vertebrate antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH11.7. This removes the captured antibody and allows the surface to be used for another interaction. The binding data can be fitted to 1:1 model inherent using standard techniques, eg, using a model inherent to the ProteOn XPR36™ analysis software.

In an embodiment, assaying or testing of a ligand of the invention is carried out at or substantially at pH7 (eg, for in vitro tests and assays) and at or substantially at rtp.

One example of an IgG2 heavy chain constant domain of an anti-PCSK9 antibody of the present invention has the amino acid sequence as shown in SEQ ID NO: 154, FIG. 3KK of US20120093818A1, which sequence is incorporated herein by reference.

One example of an IgG4 heavy chain constant domain of an anti-PCSK9 antibody of the present invention has the amino acid sequence as shown in SEQ ID NO: 155, FIG. 3KK of US20120093818A1, which sequence is incorporated herein by reference.

One example of a kappa light chain constant domain of an anti-PCSK9 antibody has the amino acid sequence as shown in SEQ ID NO: 157, FIG. 3KK which sequence is incorporated herein by reference.

One example of a lambda light chain constant domain of an anti-PCSK9 antibody has the amino acid sequence as shown in SEQ ID NO: 156, FIG. 3KK of US20120093818A1, which sequence is incorporated herein by reference.

In examples of the present invention, the ligand binds mature PCSK9, eg, a mature form of one or more of the rare variants disclosed herein and optionally also the a and/or a' form.

In examples of the present invention, the ligand binds the catalytic domain of PCSK9, eg, of a mature form of one or more of the rare variants disclosed herein and optionally also the a and/or a' form.

In examples of the present invention, the ligand binds the prodomain of PCSK9, eg, of a mature form of one or more of the rare variants disclosed herein and optionally also the a and/or a' form.

In some embodiments, the ligand binds to the V domain of PCSK9, eg, of a mature form of one or more of the rare variants disclosed herein and optionally also the a and/or a' form. In some embodiments, the ligand binds to the V domain of PCSK9 (eg, of a mature form of one or more of the rare variants disclosed herein and optionally also the a and/or a'form) and prevents (or reduces, eg, by at least 10%) PCSK9 from binding to LDLR. In some embodiments, the ligand binds to the V domain of PCSK9 (eg, of a mature form of one or more of the rare variants disclosed herein and optionally also the a and/or a' form), and while it does not prevent (or reduce) the binding of PCSK9 to LDLR, the ligand prevents or reduces (eg, by at least 10%) the adverse activities mediated through PCSK9 on LDLR.

In examples of the present invention, the ligand is or comprises a fully human antibody. In an example, the ligand comprises human variable regions or humanised variable regions.

In an example, the ligand of the invention specifically binds to an epitope of a human PCSK9 selected from the group consisting of forms f, c, r, p, m, e, h, aj and q, wherein the epitope comprises at least one amino acid that is not found in form a. For example, the amino acid is selected from the group consisting of 46L, 53V, 425S, 443T, 474V, 619P and 670G (numbering as used in SEQ ID NO: 1). For example, the amino acid is selected from the group consisting of 425S, 443T, 474V, 619P and 670G (numbering as used in SEQ ID NO:1). For example, the amino acid is selected from the group consisting of 425S and 443T (numbering as used in SEQ ID NO: 1). For example, the amino acid is selected from the group consisting of 474V, 619P and 670G (numbering as used in SEQ ID NO:1). In an example, the PCSK9 form is the mature form. In an example, the PCSK9 form is the pro-form. In an example, the ligand also specifically binds to form a and/or a'. In an embodiment, the ligand specifically binds to an epitope of form f PCSK9, wherein the epitope comprises at least one amino acid that is not found in form a. In an embodiment, the ligand specifically binds to an epitope of form c PCSK9, wherein the epitope comprises at least one amino acid that is not found in form a. In an embodiment, the ligand specifically binds to an epitope of form r PCSK9, wherein the epitope comprises at least one amino acid that is not found in form a. In an embodiment, the ligand specifically binds to an epitope of form p PCSK9, wherein the epitope comprises at least one amino acid that is not found in form a. In an embodiment, the ligand specifically binds to an epitope of form m PCSK9, wherein the epitope comprises at least one amino acid that is not found in form a. In an embodiment, the ligand specifically binds to an epitope of form e PCSK9, wherein the epitope comprises at least one amino acid that is not found in form a. In an embodiment, the ligand specifically binds to an epitope of form h PCSK9, wherein the epitope comprises at least one amino acid that is not found in form a. In an embodiment, the ligand specifically binds to an epitope of form aj PCSK9, wherein the epitope comprises at least one amino acid that is not found in form a. In an embodiment, the ligand specifically binds to an epitope of form q PCSK9, wherein the epitope comprises at least one amino acid that is not found in form a.

In an embodiment, ligand binds specifically to the pro-domain of a human PCSK9 selected from the group consisting of forms f, c, r, p, m, e, h, aj and q. In an example, the ligand also specifically binds to the pro-domain of form a and/or a'. In an embodiment, the ligand specifically binds to the pro-domain of form f PCSK9, wherein the epitope comprises at least one amino acid that is not found in form a. In an embodiment, the ligand specifically binds to the pro-domain of form c PCSK9, wherein the epitope comprises at least one amino acid that is not found in form a. In an embodiment, the ligand specifically binds to the pro-domain of form r PCSK9, wherein the epitope comprises at least one amino acid that is not found in form a. In an embodiment, the ligand specifically binds to the pro-domain of form p PCSK9, wherein the epitope comprises at least one amino acid that is not found in form a. In an embodiment, the ligand specifically binds to the pro-domain of form m PCSK9, wherein the epitope comprises at least one amino acid that is not found in form a. In an embodiment, the ligand specifically binds to the pro-domain of form e PCSK9, wherein the epitope comprises at least one amino acid that is not found in form a. In an embodiment, the ligand specifically binds to the pro-domain of form h PCSK9, wherein the epitope comprises at least one amino acid that is not found in form a. In an embodiment, the ligand specifically binds to the pro-domain of form aj PCSK9, wherein the epitope comprises at least one amino acid that is not found in form a. In an embodiment, the ligand specifically binds to the pro-domain of form q PCSK9, wherein the epitope comprises at least one amino acid that is not found in form a.

In an embodiment, ligand binds specifically to the catalytic domain of a human PCSK9 selected from the group consisting of forms f, c, r, p, m, e, h, aj and q. In an example, the ligand also specifically binds to the catalytic domain of form a and/or a'. In an embodiment, the ligand specifically binds to the catalytic domain of form f PCSK9, wherein the epitope comprises at least one amino acid that is not found in form a. In an embodiment, the ligand specifically binds to the catalytic domain of form c PCSK9, wherein the epitope comprises at least one amino acid that is not found in form a. In an embodiment, the ligand specifically binds to the catalytic domain of form r PCSK9, wherein the epitope comprises at least one amino acid that is not found in form a. In an embodiment, the ligand specifically binds to the catalytic domain of form p PCSK9, wherein the epitope comprises at least one amino acid that is not found in form a. In an embodiment, the ligand specifically binds to the catalytic domain of form m PCSK9, wherein the epitope comprises at least one amino acid that is not found in form a. In an embodiment, the ligand specifically binds to the catalytic domain of form e PCSK9, wherein the epitope comprises at least one amino acid that is not found in form a. In an embodiment, the ligand specifically binds to the catalytic domain of form h PCSK9, wherein the epitope comprises at least one amino acid that is not found in form a. In an embodiment, the ligand specifically binds to the catalytic domain of form aj PCSK9, wherein the epitope comprises at least one amino acid that is not found in form a. In an embodiment, the ligand specifically binds to the catalytic domain of form q PCSK9, wherein the epitope comprises at least one amino acid that is not found in form a.

In an embodiment, ligand binds specifically to the C-terminal domain of a human PCSK9 selected from the group consisting of forms f, c, r, p, m, e, h, aj and q. In an example, the ligand also specifically binds to the C-terminal domain of form a and/or a'. In an embodiment, the ligand specifically binds to the C-terminal domain of form f PCSK9, wherein the epitope comprises at least one amino acid that is not found in form a. In an embodiment, the ligand specifically binds to the C-terminal domain of form c PCSK9, wherein the epitope comprises at least one amino acid that is not found in form a. In an embodiment, the ligand specifically binds to the C-terminal domain of form r PCSK9, wherein the epitope comprises at least one amino acid that is not found in form a. In an embodiment, the ligand specifically binds to the C-terminal domain of form p PCSK9, wherein the epitope comprises at least one amino acid that is not found in form a. In an embodiment, the ligand specifically binds to the C-terminal domain of form m PCSK9, wherein the epitope comprises at least one amino acid that is not found in form a. In an embodiment, the ligand specifically binds to the C-terminal domain of form e PCSK9, wherein the epitope comprises at least one amino acid that is not found in form a. In an embodiment, the ligand specifically binds to the C-terminal domain of form h PCSK9, wherein the epitope comprises at least one amino acid that is not found in form a. In an embodiment, the ligand specifically binds to the C-terminal domain of form aj PCSK9, wherein the epitope comprises at least one amino acid that is not found in form a. In an embodiment, the ligand specifically binds to the C-terminal domain of form q PCSK9, wherein the epitope comprises at least one amino acid that is not found in form a.

In an embodiment, ligand binds specifically to the substrate-binding groove of a human PCSK9 selected from the group consisting of forms f, c, r, p, m, e, h, aj and q (see Cunningham et al., Nat Struct Mol. Biol. 2007 May; 14 (5): 413-9. Epub 2007 Apr. 15, "Structural and biophysical studies of PCSK9 and its mutants linked to familial hypercholesterolemia", incorporated herein in its entirety by reference). In an example, the ligand also specifically binds to the substrate-binding groove of form a and/or a'. In an embodiment, the ligand specifically binds to the Substrate-binding groove of form f PCSK9, wherein the epitope comprises at least one amino acid that is not found in form a. In an embodiment, the ligand specifically binds to the Substrate-binding groove of form c PCSK9, wherein the epitope comprises at least one amino acid that is not found in form a. In an embodiment, the ligand specifically binds to the Substrate-binding groove of form r PCSK9, wherein the epitope comprises at least one amino acid that is not found in form a. In an embodiment, the ligand specifically binds to the Substrate-binding groove of form p PCSK9, wherein the epitope comprises at least one amino acid that is not found in form a. In an embodiment, the ligand specifically binds to the Substrate-binding groove of form m PCSK9, wherein the epitope comprises at least one amino acid that is not found in form a. In an embodiment, the ligand specifically binds to the Substrate-binding groove of form e PCSK9, wherein the epitope comprises at least one amino acid that is not found in form a. In an embodiment, the ligand specifically binds to the Substrate-binding groove of form h PCSK9, wherein the epitope comprises at least one amino acid that is not found in form a. In an embodiment, the ligand specifically binds to the Substrate-binding groove of form aj PCSK9, wherein the epitope comprises at least one amino acid that is not found in form a. In an embodiment, the ligand specifically binds to the Substrate-binding groove of form q PCSK9, wherein the epitope comprises at least one amino acid that is not found in form a.

Reference is made to US20120093818A1 (Amgen, Inc), the entire disclosure of which is incorporated herein. This patent application discloses relevant ligands for use in the present invention, as well as examples and methods of producing and testing ligands that can be used with reference to the present invention.

In an example, the ligand is or comprises an antibody disclosed in Table 2 of US20120093818A1 (Amgen, Inc) or is a PCSK9-binding derivative thereof.

In an embodiment, the PCSK9-binding ligand of the invention is selected from the antigen binding proteins disclosed in US20120093818A1 (Amgen, Inc), eg, in paragraphs [0009] to and [0058] to [0063] of US20120093818A1; all of these disclosures (including the sequences of such proteins) are incorporated herein by reference as though explicitly recited herein and for possible inclusion in one or more claims or for use in the present invention.

In this paragraph SEQ ID NOs are those as appearing in US20120093818A1 (Amgen, Inc) and these sequences are incorporated herein by reference as though explicitly recited herein and for possible inclusion in one or more claims or for use in the present invention. In some aspects, the ligand of the invention comprises an isolated antigen binding protein that binds PCSK9 comprising: A) one or more heavy chain complementary determining regions (CDRHs) selected from the group consisting of: (i) a CDRH1 from a CDRH1 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; (ii) a CDRH2 from a CDRH2 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; (iii) a CDRH3 from a CDRH3 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; and (iv) a CDRH of (i), (ii), and (iii) that contains one or more amino acid substitutions, deletions or insertions of no more than 4 amino acids; B) one or more light chain complementary determining regions (CDRLs) selected from the group consisting of: (i) a CDRL1 from a CDRL1 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; (ii) a CDRL2 from a CDRL2 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; (iii) a CDRL3 from a CDRL3 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; and (iv) a CDRL of (i), (ii) and (iii) that contains one or more amino acid substitutions, deletions or insertions of no more than 4 amino acids; or C) one or more heavy chain CDRHs of A) and one or more light chain CDRLs of B). In some embodiments, the isolated antigen binding protein comprises at least one CDRH of A) and at least one CDRL of B). In some embodiments, the isolated antigen binding protein comprises at least two CDRH of A) and at least two CDRL of B). In some embodiments, the isolated antigen binding protein comprises said CDRH1, CDRH2, CDRH3, CDRL1, CDRL2 and CDRL3. In some embodiments, the CDRH of A) is selected from at least one of the group consisting of: (i) a CDRH1 amino acid sequence selected from the CDRH1 in a sequence selected from the group consisting of SEQ ID NO: 67, 79, 89, and 49; (ii) a CDRH2 amino acid sequence selected from the CDRH2 in a sequence selected from the group consisting of SEQ ID NO: 67, 79, 89, and 49; (iii) a CDRH3 amino acid sequence selected from the CDRH3 in a sequence selected from the group consisting of SEQ ID NO: 67, 79, 89, and 49; and (iv) a CDRH of (i), (ii) and (iii) that contains one or more amino acid substitutions, deletions or insertions of no more than 2 amino acids. In addition, the CDRL of B) is selected from at least one of the group consisting of: (i) a CDRL1 amino acid sequence selected from the CDRL1 in a sequence selected from the group consisting of SEQ ID NO: 12, 35, 32, and 23; (ii) a CDRL2 amino acid sequence selected from the CDRL2 in a sequence selected from the group consisting of SEQ ID NO: 12, 35, 32, and 23; (iii) a CDRL3 amino acid sequence selected from the CDRL3 in a sequence selected from the group consisting of SEQ ID NO: 12, 35, 32, and 23; and (iv) a CDRL of (i), (ii) and (iii) that contains one or more amino acid substitutions, deletions or insertions of no more than 2 amino acids; or C) one or more heavy chain CDRHs of A) and one or more light chain CDRLs of B. In some embodiments, the CDRH of A) is selected from at least one of the group consisting of: (i) a CDRH1 amino acid sequence of the CDRH1 amino acid sequence in SEQ ID NO: 67; (ii) a CDRH2 amino acid sequence of the CDRH2 amino acid sequence in SEQ ID NO: 67; (iii) a CDRH3 amino acid sequence of the CDRH3 amino acid sequence in SEQ ID NO: 67; and (iv) a CDRH of (i), (ii) and (iii) that contains one or more amino acid substitutions, deletions or insertions of no more than 2 amino acids; said CDRL of B) is selected from at least one of the group consisting of: (i) a CDRL1 amino acid sequence of the CDRL1 amino acid sequence in SEQ ID NO: 12; (ii) a CDRL2 amino acid sequence of the CDRL2 amino acid sequence in SEQ ID NO: 12; (iii) a CDRL3 amino acid sequence of the CDRL3 amino acid sequence in SEQ ID NO: 12; and (iv) a CDRL of (i), (ii) and (iii) that contains one or more amino acid substitutions, deletions or insertions of no more than 2 amino acids; or C) one or more heavy chain CDRHs of A) and one or more light chain CDRLs of B). In some embodiments, the antigen binding protein comprises A) a CDRH1 of the CDRH1 sequence in SEQ ID NO: 67, a CDRH2 of the CDRH2 sequence in SEQ ID NO: 67, and a CDRH3 of the CDRH3 sequence in SEQ ID NO: 67, and B) a CDRL1 of the CDRL1 sequence in SEQ ID NO: 12, a CDRL2 of the CDRL2 sequence in SEQ ID NO: 12, and a CDRL3 of the CDRL3 sequence in SEQ ID NO: 12. In some embodiments, the antigen binding protein comprises a heavy chain variable region (VH) having at least 80% sequence identity with an amino acid sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or a light chain variable region (VL) having at least 80% sequence identity with an amino acid sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, the VH has at least 90% sequence identity with an amino acid sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or the VL has at least 90% sequence identity with an amino acid sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, the VH is selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or the VL is selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46.

In an example of any aspect of the invention, the PCSK9-targeting or binding ligand comprises or consists of AMG145 or 31H4, 16F12, 11F1, 8A3 or 21B12 disclosed in US20120093818A1 (Amgen, Inc) or an antibody comprising the variable domains of AMG145, 31H4, 16F12, 11F1, 8A3 or 21B12, the disclosures of which (including sequences) are incorporated herein by reference as though explicitly recited herein and for possible inclusion in one or more claims or for use in the present invention. Preferably, the PCSK9-targeting or binding ligand comprises or consists of AMG145.

In an example, the AMG145 or other ligand of the invention is glycosylated, eg, has human glycosylation (eg, produced by a CHO, Cos or Hek293 cell). In an example, the ligand of the invention is produced in CHO.

Reference is made to US20110065902A1 (Regeneron Pharmaceuticals, Inc), the entire disclosure of which is incorporated herein. This patent application discloses relevant ligands for use in the present invention, as well as examples and methods of producing and testing ligands and determining medical efficacy that can be used with reference to the present invention.

Reference is made to the following PCT applications, the entire disclosures of which are incorporated herein. These disclose relevant ligands for use in the present invention, as well as examples and methods of producing and testing ligands and determining medical efficacy that can be used with reference to the present invention.
WO2008057457
WO2008057458
WO2008057459
WO2008063382
WO2008133647
WO2009100297
WO2009100318
WO2011037791
WO2011053759
WO2011053783
WO2008125623
WO2011072263
WO2009055783
WO2010029513
WO2011111007
WO2010077854

Antibody ligands to PCSK9 are described in, for example, WO 2008/057457, WO 2008/057458, WO 2008/057459, WO 2008/063382, WO 2008/125623, and US 2008/0008697; each of which is incorporated by reference herein in its entirety.

In an example, the ligand is or comprises an antibody disclosed in the Examples of US20110065902A1 (eg, 316P or 300N) or is a PCSK9-binding derivative thereof. All of these disclosures (including the sequences of such proteins and corresponding nucleotide sequences) are incorporated herein by reference as though explicitly recited herein and for possible inclusion in one or more claims or for use in the present invention. In an embodiment, the ligand is or comprises the variable domains of antibody 316P or 300N disclosed in US20110065902A1 or is (or comprises) such antibody or a PCSK9-binding derivative thereof.

In an embodiment, the ligand is or comprises the variable domains of antibody alirocumab or SAR236553/REGN727 (Sanofi Aventis/Regeneron) or is (or comprises) such antibody or a PCSK9-binding derivative thereof. In an example, the alirocumab is glycosylated, eg, has human glycosylation (eg, produced by a CHO, Cos or Hek293 cell). Preferably, the ligand is alirocumab or SAR236553/REGN727.

In an embodiment, the ligand is or comprises the variable domains of antibody evolocumab or is (or comprises) such antibody or a PCSK9-binding derivative thereof. In an example, the antibody is glycosylated, eg, has human glycosylation (eg, produced by a CHO, Cos or Hek293 cell). Preferably, the ligand is evolocumab.

In an embodiment, the ligand is selected from evolocumab, 1D05-IgG2 (Merck & Co.), ALN-PCS02 (Alnylam), RN316 (Pfizer-Rinat) and alirocumab.

In an embodiment, the ligand is selected from the following (sequences and definitions as per US2011/0065902, incorporated herein by reference):—
1. An antibody or antigen-binding fragment thereof which specifically binds hPCSK9, wherein the antibody or antigen-binding fragment comprises the heavy and light chain CDRs of a HCVR/LCVR amino acid sequence pair having SEQ ID NOs: 218/226.
2. The antibody or antigen-binding fragment of concept 1 comprising heavy and light chain CDR amino acid sequences having SEQ ID NOs: 220, 222, 224, 228, 230 and 232.
3. The antibody or antigen-binding fragment of concept 2 comprising an HCVR having the amino acid sequence of SEQ ID NO: 218 and an LCVR having the amino acid sequence of SEQ ID NO: 226.
4. An antibody or antigen-binding fragment thereof which binds to the same epitope on hPCSK9 as an antibody comprising heavy and light chain CDR amino acid sequences having SEQ ID NOs: 220, 222, 224, 228, 230 and 232.
5. An antibody or antigen-binding fragment thereof which competes for binding to hPCSK9 with an antibody comprising heavy and light chain CDR amino acid sequences having SEQ ID NOs: 220, 222, 224, 228, 230 and 232.

In an embodiment, the ligand is selected from the following (sequences and definitions as per US2012/0093818, incorporated herein by reference):—
1. An isolated neutralizing antigen binding protein that binds to a PCSK9 protein comprising the amino acid sequence of SEQ ID NO: 1, wherein the neutralizing antigen binding protein decreases the LDLR lowering effect of PCSK9 on LDLR, wherein the antigen binding protein comprises a light chain comprising an amino acid sequence of SEQ ID NO: 46, and wherein the antigen binding protein comprises a heavy chain comprising an amino acid sequence of SEQ ID NO: 60.
2. The isolated neutralizing antigen binding protein of concept 2, wherein the antigen binding protein is a LDLR non-competitive neutralizing antigen binding protein.
3. The isolated neutralizing antigen binding protein of concept 2, wherein the antigen binding protein is a LDLR competitive neutralizing antigen binding protein.
4. An antigen binding protein that selectively binds to PCSK9, wherein said antigen binding protein binds to PCSK9 with a Kd that is less than 100 pM.
5. An antigen binding protein that binds to a PCSK 9 protein of SEQ ID NO: 303 in a first manner, wherein the antigen binding protein binds to a variant of PCSK9 in a second manner, wherein said PCSK9 variant has at least one point mutation at a position selected from the group consisting of: 207, 208, 185, 181, 439, 513, 538, 539, 132, 351, 390, 413, 582, 162, 164, 167, 123, 129, 311, 313, 337, 519, 521, and 554 of SEQ ID NO: 303, wherein the first manner comprises a first EC50, a first Bmax, or a first EC50 and a first Bmax, wherein the second manner comprises a second EC50, a second Bmax, or a second EC50 and a second Bmax, and wherein a value for the first manner is different from a value for the second manner, and wherein the antigen binding protein comprises a light chain comprising an amino acid sequence of SEQ ID NO: 46, and wherein the antigen binding protein comprises a heavy chain comprising an amino acid sequence of SEQ ID NO: 60.

6. The antigen binding protein of concept 6, wherein the first manner comprises a first Bmax, wherein the second manner comprises a second Bmax that is different from the first Bmax, and wherein said PCSK9 variant has at least one point mutation selected from the group consisting of: D162R, R164E, E167R, S123R, E129R, A311R, D313R, D337R, R519E, H521R, and Q554R.

7. The antigen binding protein of concept 6, wherein the antigen binding protein binds to PCSK9 at a location that overlaps with a location that LDLR binds to PCSK9.

8. A method of making an antigen binding protein that binds to a PCSK9 protein comprising the amino acid sequence of SEQ ID NO: 1, wherein the antigen binding protein decreases the LDLR lowering effect of PCSK9 on LDLR, said method comprising: providing a host cell comprising a nucleic acid sequence that encodes the antigen binding protein; and maintaining the host cell under conditions in which the antigen binding protein is expressed, wherein the antigen binding protein comprises a light chain comprising an amino acid sequence of SEQ ID NO: 46, and wherein the antigen binding protein comprises a heavy chain comprising an amino acid sequence of SEQ ID NO: 60.

9. A method for treating or preventing a condition associated with elevated serum cholesterol levels in a subject, said method comprising administering to a subject in need thereof an effective amount of an isolated neutralizing antigen binding protein simultaneously or sequentially with an agent that elevates the availability of LDLR protein, wherein the isolated antigen binding protein binds to a PCSK9 protein comprising the amino acid sequence of SEQ ID NO: 1, wherein the neutralizing antigen binding protein decreases the LDLR lowering effect of PCSK9 on LDLR, wherein the antigen binding protein comprises a light chain comprising an amino acid sequence of SEQ ID NO: 46, and wherein the antigen binding protein comprises a heavy chain comprising an amino acid sequence of SEQ ID NO: 60.

10. The method of concept 10, wherein the agent that elevates the availability of LDLR protein comprises a statin.

11. An antigen binding protein that binds to PCSK9, wherein when the antigen binding protein is bound to PCSK9, the antibody is positioned 8 angstroms or less from at least one of the following residues of PCSK9: S153, S188, I189, Q190, S191, D192, R194, E197, G198, R199, V200, D224, R237, D238, K243, S373, D374, S376, T377, F379, I154, T187, H193, E195, I196, M201, V202, C223, T228, S235, G236, A239, G244, M247, I369, S372, C375, or C378, wherein the antigen binding protein comprises a light chain comprising an amino acid sequence of SEQ ID NO: 46, and wherein the antigen binding protein comprises a heavy chain comprising an amino acid sequence of SEQ ID NO: 60.

The ligand can be used for the treatment, therapy, prophylaxis and/or diagnosis of one or more diseases or conditions or susceptibility thereto, wherein such diseases or conditions comprise those disclosed in US20120093818A1 (Amgen, Inc) and US20110065902A1 (Regeneron Pharmaceuticals, Inc), eg, a disease or condition disclosed in paragraphs [0375] to [0383] of US20120093818A1, which disclosure is incorporated herein by reference in its entirety for inclusion in one or more claims herein.

The ligand can be administered to a human characterised as described in US20120093818A1 (Amgen, Inc) or US20110065902A1.

The ligand can be administered in a form or combination disclosed in US20120093818A1 (Amgen, Inc) or US20110065902A1, which disclosure is incorporated herein by reference. For example, the ligand with a drug, excipient, diluent or carrier as described in US20120093818A1 (Amgen, Inc) or US20110065902A1 (eg, as disclose in paragraphs [0384] to [0412] of US20120093818A1), which disclosure is incorporated herein by reference, and the present invention also relates to the corresponding pharmaceutical compositions comprising the combination of a ligand of the invention and such a further agent.

The ligand can be used in a method of diagnosis as set out in US20120093818A1 (Amgen, Inc) or US20110065902A1, eg, in paragraphs [0413] to [0415] of US20120093818A1 which disclosure is incorporated herein by reference.

Diagnostic Applications

In some embodiments, the ligand of the invention is a diagnostic tool. The ligand can be used to assay the amount of PCSK9 present in a sample and/or subject. As will be appreciated by one of skill in the art, such ligands need not be neutralizing ligands. In some embodiments, the diagnostic ligand is not a neutralizing ligand. In some embodiments, the diagnostic ligand binds to a different epitope than a neutralizing ligand binds to. In some embodiments, the two ligands do not compete with one another.

In some embodiments, the ligands of the invention are used or provided in an assay kit and/or method for the detection of PCSK9 in mammalian tissues or cells in order to screen/diagnose for a disease or disorder associated with changes in levels of PCSK9. The kit comprises a ligand that binds PCSK9 and means for indicating the binding of the ligand with PCSK9, if present, and optionally PCSK9 protein levels. Various means for indicating the presence of a ligand can be used. For example, fluorophores, other molecular probes, or enzymes can be linked to the ligand and the presence of the ligand can be observed in a variety of ways. The method for screening for such disorders can involve the use of the kit, or simply the use of one of the disclosed ligands and the determination of whether the ligand binds to PCSK9 in a sample. As will be appreciated by one of skill in the art, high or elevated levels of PCSK9 will result in larger amounts of the ligand binding to PCSK9 in the sample. Thus, degree of ligand binding can be used to determine how much PCSK9 is in a sample. Subjects or samples with an amount of PCSK9 that is greater than a predetermined amount (e.g., an amount or range that a person without a PCSK9 related disorder would have) can be characterized as having a PCSK9 mediated disorder. In some embodiments, the invention provides a method wherein the ligand is administered to a subject taking a statin, in order to determine if the statin has increased the amount of PCSK9 in the subject.

In some embodiments, the ligand is a non-neutralizing ligand and is used to determine the amount of PCSK9 in a subject receiving an ABP and/or statin treatment.

In some embodiments, the ligand of the invention can specifically bind human PCSK9 (eg, one, two or more rare variant forms disclosed herein) and is characterized by at least one of: (i) capable of reducing serum total cholesterol at least about 25-35% and sustaining the reduction over at least a 24 day period relative to a predose level; (ii) capable of reducing serum LDL cholesterol at least about 65-80% and sustaining the reduction over at least a 24 day period relative to a predose level; (iii) capable of reducing serum LDL cholesterol at least about 40-70% and sustaining the reduction over at least a 60 or 90 day period relative to a predose level; (iv) capable of reducing serum triglyceride at least about 25-40% relative to predose level; (v) does not reduce serum HDL cholesterol or reduces serum HDL cholesterol no more than 5% relative to predose level. In some embodiments, an isolated nucleic acid molecule is provided and it encodes the ligand. In some embodiments an expression vector is provided and comprises the nucleic acid molecule. In some embodiments, a pharmaceutical composition is provided and it can comprise the ligand and a pharmaceutically acceptable carrier. In some embodiments, a method is provided for treating a disease or condition which is ameliorated, improved, inhibited or prevented with a PCSK9 antagonist ligand of the invention. The method can comprise administering a therapeutic amount of the pharmaceutical composition or ligand to a subject in need thereof. In some embodiments, the subject is a human subject suffering from hypercholesterolemia, hyperlipidemia, indicated for LDL apheresis, identified as heterozygous for Familial Hypercholesterolemia, statin intolerant. statin uncontrolled, at risk for developing hypercholesterolemia, dyslipidemia, cholestatic liver disease, nephrotic syndrome, hypothyroidism, obesity, atherosclerosis and cardiovascular diseases. In some embodiments, a method of providing a treatment or therapy is provided to a subject. In some embodiments, the method comprises reducing serum cholesterol at least about 40-70% over at least 60 to 90 days. In some embodiments, a method of receiving treatment or therapy is provided, the method can comprise receiving a ligand thereof at a frequency of once every 60 to 90 days.

In one aspect, the invention provides a ligand of the invention which is or comprises an human antibody or antigen-binding fragment of a human antibody that specifically binds and inhibits human proprotein convertase subtilisin/kexin type 9 (hPCSK9, eg, one, two or more rare variant forms disclosed herein and optionally form a and/or form a'), characterized by the ability to reduce serum LDL cholesterol in a human by 40-80% over a 24, 60 or 90 day period relative to predose levels, with little or no reduction in serum HDL cholesterol and/or with little or no measurable effect on liver function, as determined by ALT and AST measurements.

In one embodiment, the ligand of the invention comprises an antibody or antigen-binding fragment of an antibody that specifically binds hPCSK9 and is characterized by at least one of:
(i) capable of reducing serum total cholesterol at least about 25-35% and sustaining the reduction over at least a 24 day period relative to a predose level, preferably the reduction in serum total cholesterol is at least about 30-40%;
(ii) capable of reducing serum LDL cholesterol at least about 65-80% and sustaining the reduction over at least a 24 day period relative to a predose level;
(iii) capable of reducing serum triglyceride at least about 25-40% relative to predose level;
(iv) does not reduce serum HDL cholesterol or reduces serum HDL cholesterol no more than 5% relative to predose level.

See US2011/0065902 for definitions of these terms and optional features, the disclosure of which is incorporated herein by reference in its entirety.

In one embodiment, the invention comprises an antibody or antigen-binding fragment of an antibody that specifically binds hPCSK9 and is characterized by at least one of:
(i) capable of reducing serum LDL cholesterol at least about 40-70% and sustaining the reduction over at least a 60 or 90 day period relative to a predose level;
(ii) capable of reducing serum triglyceride at least about 25-40% relative to predose level;
(iii) does not reduce serum HDL cholesterol or reduces serum HDL cholesterol no more than 5% relative to predose level.

In one embodiment, the antibody or antigen-binding fragment is characterized as exhibiting an enhanced binding affinity (KD) for hPCSK9 at pH 5.5 relative to the KD at pH 7.4, as measured by plasmon surface resonance. In a specific embodiment, the antibody or fragment thereof exhibits at least a 20-fold, at least a 40-fold or at least a 50-fold enhanced affinity for PCSK9 at an acidic pH relative to a neutral pH, as measured by surface plasmon resonance.

In one embodiment, the antibody or antigen-binding fragment is characterized as not exhibiting an enhanced binding affinity for PCSK9 at an acidic pH relative to a neutral pH, as measured by surface plasmon resonance. In a specific embodiment, the antibody or fragment thereof exhibits a decreased binding affinity at an acidic pH.

In another embodiment, the antibody or antigen-binding fragment binds human, human GOF mutation D374Y, cynomolgus monkey, rhesus monkey, mouse, rat and hamster PCSK9.

In one embodiment, the antibody or antigen-binding fragment binds human and monkey PCSK9, but does not bind mouse, rat or hamster PCSK9.

In one embodiment, the invention comprises an antibody or antigen-binding fragment of an antibody comprising one or more of a heavy chain variable region (HCVR), light chain variable region (LCVR), HCDR1, HCDR2, HCDR3 disclosed in any of paragraphs [023]-[037] of US2011/0065902, the disclosures of which are incorporated herein by reference.

In a related embodiment, the invention comprises an antibody or antigen-binding fragment of an antibody which specifically binds hPCSK9, wherein the antibody or fragment comprises heavy and light chain CDR domains contained within heavy and light chain sequence pairs selected from the group consisting of SEQ ID NO (using the sequence numbering in US2011/0065902): 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744. In one embodiment, the CDR sequences are contained within HCVR and LCVR selected from the amino acid sequence pairs of SEQ ID NO: 50/58, 66/68, 70/72, 74/82, 90/92, 94/96, 122/130, 138/140, 142/144, 218/226, 234/236, 238/240, 242/250, 258/260, 262/264, 314/322, 330/332 and 334/336. In more specific embodiments, the CDR sequences are comprised within HCVR/LCVR sequences selected from SEQ ID NO: 90/92 or 218/226.

In an example, the invention features a pharmaceutical composition comprising a ligand of the invention, wherein the ligand comprises or consists of a recombinant human antibody or fragment thereof which specifically binds hPCSK9 and a pharmaceutically acceptable carrier. In one embodiment, the invention features a composition which is a combination of a ligand of the invention (eg, an antibody or antigen-binding fragment of an antibody), and a second therapeutic agent. The second therapeutic agent may be any agent that is advantageously combined with the ligand of the invention, for example, an agent capable of inducing a cellular depletion of cholesterol synthesis by inhibiting 3-hydroxy-3-methylglutaryl (HMG)-coenzyme A (CoA) reductase, such as, for example, cerovastatin, atorvastatin, simvastatin, pitavastin, rosuvastatin, fluvastatin, lovastatin, pravastatin, etc; capable of inhibiting cholesterol uptake and or bile acid re-absorption; capable of increasing lipoprotein catabolism (such as niacin); and/or activators of the LXR transcription factor that plays a role in cholesterol elimination such as 22-hydroxycholesterol.

In an example, the invention provides a method for inhibiting hPCSK9 activity using the anti-PCSK9 ligand of the invention (eg, an antibody or antigen-binding portion of the antibody of the invention), wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of PCSK9 activity. Specific populations treatable by the therapeutic methods of the invention include subjects indicated for LDL apheresis, subjects with PCSK9-activating mutations (gain of function mutations, "GOF"), subjects with heterozygous Familial Hypercholesterolemia (heFH); subjects with primary hypercholesterolemia who are statin intolerant or statin uncontrolled; and subjects at risk for developing hypercholesterolemia who may be preventably treated. Other indications include dyslipidemia associated with secondary causes such as Type 2 diabetes mellitus, cholestatic liver diseases (primary biliary cirrhosis), nephrotic syndrome, hypothyroidism, obesity; and the prevention and treatment of atherosclerosis and cardiovascular diseases.

In specific embodiments of the method of the invention, the ligand of the invention (eg, anti-hPCSK9 antibody or antibody fragment of the invention) is useful to reduce elevated total cholesterol, non-HDL cholesterol, LDL cholesterol, and/or apolipoprotein B (apolipoprotein B100).

The ligand (eg, antibody or antigen-binding fragment) of the invention may be used alone or in combination with a second agent, for example, an HMG-CoA reductase inhibitor and/or another lipid lowering drug.

Treatment Population

The invention provides therapeutic methods for treating a human patient in need of a composition or ligand of the invention. While modifications in lifestyle and conventional drug treatment are often successful in reducing cholesterol levels, not all patients are able to achieve the recommended target cholesterol levels with such approaches. Various conditions, such as familial hypercholesterolemia (FH), appear to be resistant to lowering of LDL-C levels in spite of aggressive use of conventional therapy. Homozygous and heterozygous familial hypercholesterolemia (hoFH, heFH) is a condition associated with premature atherosclerotic vascular disease. However, patients diagnosed with hoFH are largely unresponsive to conventional drug therapy and have limited treatment options. Specifically, treatment with statins, which reduce LDL-C by inhibiting cholesterol synthesis and upregulating the hepatic LDL receptor, may have little effect in patients whose LDL receptors are non-existent or defective. A mean LDL-C reduction of only less than about 20% has been recently reported in patients with genotype-confirmed hoFH treated with the maximal dose of statins. The addition of ezetimibe 10 mg/day to this regimen resulted in a total reduction of LDL-C levels of 27%, which is still far from optimal. Likewise, many patients are statin non-responsive, poorly controlled with statin therapy, or cannot tolerate statin therapy; in general, these patients are unable to achieve cholesterol control with alternative treatments. There is a large unmet medical need for new treatments that can address the short-comings of current treatment options.

Specific populations treatable by the therapeutic methods of the invention include patients indicated for LDL apheresis, subjects with PCSK9-activating (GOF) mutations, heterozygous Familial Hypercholesterolemia (heFH); subjects with primary hypercholesterolemia who are statin intolerant or statin uncontrolled; and subjects at risk for developing hypercholesterolemia who may be preventably treated.

Therapeutic Administration and Formulations

The invention provides therapeutic compositions comprising the anti-PCSK9 ligands, antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTINTM), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the ligand, eg, antibody, of the present invention is used for treating various conditions and diseases associated with PCSK9, including hypercholesterolemia, disorders associated with LDL and apolipoprotein B, and lipid metabolism disorders, and the like, in an adult patient, it is advantageous to intravenously administer the ligand or antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the pharmaceutical composition of the invention, thus the composition invention provides the ligand by e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

The invention provides therapeutic methods in which the ligand, eg, antibody or antibody fragment, of the invention is useful to treat hypercholesterolemia associated with a variety of conditions involving hPCSK9. The anti-PCSK9 ligands, eg, antibodies or antibody fragments, of the invention are particularly useful for the treatment of hypercholesterolemia and the like. Combination therapies may include the anti-PCSK9 ligand of the invention with, for example, one or more of any agent that (1) induces a cellular depletion of cholesterol synthesis by inhibiting 3-hydroxy-3-methylglutaryl (HMG)-coenzyme A (CoA) reductase, such as cerivastatin, atorvastatin, simvastatin, pitavastatin, rosuvastatin, fluvastatin, lovastatin, pravastatin; (2) inhibits cholesterol uptake and or bile acid re-absorption; (3) increase lipoprotein catabolism (such as niacin); and activators of the LXR transcription factor that plays a role in cholesterol elimination such as 22-hydroxycholesterol or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

Tailoring Antibodies to Rare PCSK9 Variant Profile

As outline above, the invention includes the possibility to tailor treatment of humans further by selecting antibody-based ligands with variable domains based on gene segments commonly found in humans of the ethnic populations where the variant PCSK9 forms are found to meet the selection criteria of the invention. An example is provided below for ligands comprising antibody VH domains derived from recombination of human VH3-23.

The inventor analysed the frequencies and distribution of various human VH3-23 alleles and realised the desirability of using ligands based on human VH3-23 alleles comprising SNP rs56069819. This SNP corresponds to a change from leucine at position 24 in the encoded protein sequence to a valine at that position (L24V change) and the SNP is at coordinate 106268889 on human chromosome 14.

FIG. 2 shows the cumulative allele frequency distribution across the 1000 Genomes Project database of human VH3-23 alleles comprising SNP rs56069819 (such alleles denoted "C" and the most frequent allele (which does not comprise this SNP) denoted "A"). The figure shows that VH3-23 alleles comprising SNP rs56069819 are present at a cumulative frequency of 11% across all human ethnic populations taken as a whole, whereas in certain specific human ethnic sub-populations (ASW, LWK, YRI, CEU and GBR) such alleles are present at an above-average cumulative frequency. Indicated in the figure are those human PCSK9 variant forms (marked "Variants") that are found in the various sub-populations with above-average occurrence of human VH3-23 alleles comprising SNP rs56069819. Table 7 shows the VH3-23 variants and the SNPs that they comprise, as well as their cumulative allele frequencies as found in the 1000 Genomes Project database.

Notably, human VH3-23 alleles comprising SNP rs56069819 were found in the CEU population at a frequency that is almost double the frequency of 11% for all populations. For the ASW and YRI populations the frequency was over a quarter of the population. Thus, the invention advantageously enables one to select a ligand comprising an antibody or antibody fragment, wherein the antibody or fragment comprises a VH domain derived from the recombination of a human VH gene segment, a human D gene segment and a human JH gene segment, the VH gene segment comprising a nucleotide sequence that comprises SNP rs56069819 (dbSNP numbering, build number as recited above).

In an example, one can tailor the treatment further by selecting such a ligand that specifically binds to a human PCSK9 selected from forms: f, c, m, e, h, p, q and aj, such forms being those appearing in human populations ASW, LWK, YRI, CEU and GBR.

In an example, the VH gene segment is VH3-23*04, which is a commonly found variant that comprises SNP rs56069819 in human populations ASW, LWK, YRI, CEU and GBR.

In an example, the ligand is for treating and/or preventing a PCSK9-mediated disease or condition in a human that expresses a human PCSK9 selected from forms: f, c, m, e, h, p, q and aj.

In an example, the ligand is for treating and/or preventing a PCSK9-mediated disease or condition in a human of ASW, LWK, YRI, CEU or GBR ancestry.

In an embodiment, the ligand is for treating and/or preventing a PCSK9-mediated disease or condition in a human of ASW ancestry, wherein the human expresses a PCSK9 selected from f, c, m, e, h, p and q or the human comprises a corresponding nucleotide or amino acid sequence as set out in Table 6. Optionally this ligand comprises a VH domain derived from recombination of human VH3-23*04.

In an embodiment, the ligand is for treating and/or preventing a PCSK9-mediated disease or condition in a human of LWK ancestry, wherein the human expresses a PCSK9 selected from f, c, m, e and h or the human comprises a corresponding nucleotide or amino acid sequence as set out in Table 6. Optionally this ligand comprises a VH domain derived from recombination of human VH3-23*04.

In an embodiment, the ligand is for treating and/or preventing a PCSK9-mediated disease or condition in a human of YRI ancestry, wherein the human expresses a PCSK9 selected from f, c, m, e and h or the human comprises a corresponding nucleotide or amino acid sequence as set out in Table 6. Optionally this ligand comprises a VH domain derived from recombination of human VH3-23*04.

In an embodiment, the ligand is for treating and/or preventing a PCSK9-mediated disease or condition in a human of CEU ancestry, wherein the human expresses a PCSK9 selected from f, c, p and aj or the human comprises a corresponding nucleotide or amino acid sequence as set out in Table 6. Optionally this ligand comprises a VH domain derived from recombination of human VH3-23*04.

In an embodiment, the ligand is for treating and/or preventing a PCSK9-mediated disease or condition in a human of GBR ancestry, wherein the human expresses a PCSK9 selected from f, c and p or the human comprises a corresponding nucleotide or amino acid sequence as set out in Table 6. Optionally this ligand comprises a VH domain derived from recombination of human VH3-23*04.

In an example, the ligand is alirocumab.

In other embodiments, as explained more fully above, the invention provides for ligands which are tailored to the human recipient's genotype and/or phenotype based on alternative human VH gene segments, or on Vκ, Vλ or constant region gene segments (see further Table 9 for representative variants).

For example, the ligand of the invention comprises or consists of an antibody that comprises a VH domain that is derived from the recombination of a human VH gene segment, a human D gene segment and a human JH gene segment, wherein the VH gene segment is selected from the group consisting of (i) IGHV1-18*01 and the genome of the human comprises a human IGHV1-18*01 nucleotide sequence or the human expresses antibodies comprising variable domains derived from the recombination of human IGHV1-18*01; or (ii) IGVH1-46*01 and the genome of the human comprises a human IGHV1-46*01 nucleotide sequence or the human expresses antibodies comprising variable domains derived from the recombination of human IGHV1-46*01.

For example, the ligand of the invention comprises or consists of an antibody that comprises a VL domain that is derived from the recombination of a human VL gene segment and a human JL gene segment, wherein the VL gene segment is selected from the group consisting of (i) IGKV4-1*01 and the genome of the human comprises a human IGKV4-1*01 nucleotide sequence or the human expresses antibodies comprising variable domains derived from the recombination of human IGKV4-1*01; (ii) IGLV2-14*01 and the genome of the human comprises a human IGLV2-14*01 nucleotide sequence or the human expresses antibodies comprising variable domains derived from the recombination of human IGLV2-14*01; or (iii) IGKV1-13*02 and the genome of the human comprises a human IGKV1-13*02 nucleotide sequence or the human expresses antibodies comprising variable domains derived from the recombination of human IGKV1-13*02.

For example, the inventor identified the possibility of addressing the rarer IGH-gamma-1 SNPs 204D (observed cumulative frequency of 0.296) and 206L (observed cumulative frequency of 0.283) individually or in combination. These residues are part of the CH3 domain, and as such they form part of antibody Fc regions. Thus, matching of these CH3 variations with the patient is especially beneficial for reasons as discussed above. Thus, in this example the ligand of the invention comprises or consists of an antibody that comprises a human gamma-1 heavy chain constant region that comprises an Asp corresponding to position 204 of SEQ ID NO: 42 or a Leu corresponding to position 206 of SEQ ID NO: 42 and wherein the genome of the human comprises a gamma-1 heavy chain constant region nucleotide sequence that encodes such an Asp or Leu or the human expresses antibodies comprising human gamma-1 constant regions comprising such an Asp or Leu. An example of such a ligand is alirocumab.

In another example, the inventor identified the possibility of addressing IGH-gamma-2 SNPs. This included consideration of Fc region variation—in this respect, the inventor focused on positions 161 and 257 which are in the Fc region. Thus, in this example the ligand of the invention comprises or consists of an antibody that comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44; and wherein the genome of the human comprises a gamma-2 heavy chain constant region nucleotide sequence that encodes such a selected amino acid or the human expresses antibodies comprising human gamma-2 constant regions comprising such a selected amino acid. An example of such a ligand is evolocumab or bococizumab.

In another example, the inventor addressed human kappa constant region variation. Thus, in this example the ligand of the invention comprises or consists of an antibody that comprises a human kappa light chain constant region that comprises a Val corresponding to position 84 of SEQ ID NO: 50 or a Cys corresponding to position 87 of SEQ ID NO: 50; and wherein the genome of the human comprises a kappa light chain constant region nucleotide sequence that encodes such a Val or Cys or the human expresses antibodies comprising human kappa light chain constant regions comprising such a Val or Cys. An example of such a ligand is alirocumab or bococizumab.

In another example, the inventor addressed human lambda constant region variation. Thus, in this example the ligand of the invention comprises or consists of an antibody that comprises a human IGLC2*01 light chain constant region; and wherein the genome of the human comprises a human IGLC2*01 nucleotide sequence or the human expresses antibodies comprising human light chain IGLC2*01 constant regions. An example of such a ligand is evolocumab.

Further exemplary ligands are in the paragraphs 1-17 as follows.

1. An antibody or antibody fragment for use in a method of
   (a) reducing cholesterol level or maintaining previously reduced cholesterol level in a human in need thereof, or
   (b) targeting PCSK9 in a human,
   wherein the antibody or fragment comprises a human gamma heavy chain constant region that comprises a first amino acid that is encoded by a human gamma heavy chain constant region gene segment SNP, and the antibody or fragment specifically binds a proprotein convertase subtilisin/kexin type 9 (PCSK9) amino acid sequence that comprises a C-terminal domain comprising a mutation I474V or E670G in SEQ ID NO: 1, wherein the human comprises a nucleotide sequence encoding said PCSK9 amino acid sequence and comprises a human gamma heavy chain constant region gene segment comprising said SNP, or the human expresses antibodies comprising human gamma constant regions comprising said first amino acid.
   In an embodiment of (b), the antibody or fragment treats or reduces cholesterol level or maintains previously reduced cholesterol level in the human.
   In an alternative, paragraph 1 provides:—
   An antibody or antibody fragment for use in a method of
   (a) reducing cholesterol level or maintaining previously reduced cholesterol level in a human in need thereof, or (b) targeting PCSK9 in a human,
   wherein the antibody or fragment comprises a human gamma-1 heavy chain constant region that comprises an Asp corresponding to position 204 of SEQ ID NO: 42 or a Leu corresponding to position 206 of SEQ ID NO: 42, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said amino acid sequence and comprises an IGHG1*01 human heavy chain constant region gene segment, or the human expresses antibodies comprising human gamma-1 constant regions comprising such an Asp and Leu.
   In an embodiment, said mutation is I474V. In another embodiment, said mutation is E670G.
   In an embodiment of (b), the antibody or fragment treats or reduces cholesterol level or maintains previously reduced cholesterol level in the human.

An example provides:—
An antibody or antibody fragment for use in a method of
   (a) reducing cholesterol level or maintaining previously reduced cholesterol level in a human in need thereof, or (b) targeting PCSK9 in a human,
   wherein the antibody or fragment comprises a human gamma-1 heavy chain constant region that comprises an Asp corresponding to position 204 of SEQ ID NO: 42 and a Leu corresponding to position 206 of SEQ ID NO: 42, and the antibody or fragment specifically binds a proprotein convertase subtilisin/kexin type 9 (PCSK9) amino acid sequence that comprises a C-terminal domain comprising a mutation I474V in SEQ ID NO: 1, wherein the human comprises a nucleotide sequence encoding said amino acid sequence and comprises an IGHG1*01 human heavy chain constant region gene segment. Optionally, the antibody or fragment comprises an IGHG1*01 human heavy chain constant region.
   In an embodiment of (b), the antibody or fragment treats or reduces cholesterol level or maintains previously reduced cholesterol level in the human.

Another example provides:—
An antibody or antibody fragment for use in a method of
   (a) reducing cholesterol level or maintaining previously reduced cholesterol level in a human in need thereof, or (b) targeting PCSK9 in a human,
   wherein the antibody or fragment comprises a human gamma-1 heavy chain constant region that comprises an Asp corresponding to position 204 of SEQ ID NO: 42 and a Leu corresponding to position 206 of SEQ ID NO: 42, and the antibody or fragment specifically binds a proprotein convertase subtilisin/kexin type 9 (PCSK9) amino acid sequence that comprises a C-terminal domain comprising a mutation E670G in SEQ ID NO: 1, wherein the human comprises a nucleotide sequence encoding said amino acid sequence and comprises an IGHG1*01 human heavy chain constant region gene segment. Optionally, the antibody or fragment comprises an IGHG1*01 human heavy chain constant region.
   In an embodiment of (b), the antibody or fragment treats or reduces cholesterol level or maintains previously reduced cholesterol level in the human.
   In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The antibody or antibody fragment of paragraph 1, wherein the antibody comprises a human gamma-1 heavy chain constant region that comprises an Asp corresponding to position 204 of SEQ ID NO: 42 and a Leu corresponding to position 206 of SEQ ID NO: 42.

3. The antibody or antibody fragment of paragraph 1 or 2, wherein the antibody comprises an IGHG1*01 human heavy chain constant region.

4. The antibody or antibody fragment of any one of paragraphs 1 to 3, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

5. The antibody or antibody fragment of any one of paragraphs 1 to 4, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

6. The antibody or antibody fragment of paragraph 5, wherein the step of determining comprises assaying a biological sample from the human for a nucleotide sequence encoding the PCSK9 that comprises the C-terminal domain comprising the mutation I474V or E670G in SEQ ID NO: 1.

7. The antibody or antibody fragment of paragraph 6, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.

8. The antibody or antibody fragment of paragraph 6 or 7, wherein the assaying comprises nucleic acid amplification and optionally one or more methods selected from sequencing, next generation sequencing, nucleic acid hybridization, and allele-specific amplification and/or wherein the assaying is performed in a multiplex format.

9. The antibody or antibody fragment of any one of paragraphs 1 to 8, wherein said antibody or antibody fragment is for administration to a human that is or has been further determined to be substantially resistant to statin treatment.

10. The antibody or antibody fragment of any one of paragraphs 1 to 9, wherein antibody or antibody fragment is for administration to a human that is receiving or has received statin treatment or has reduced responsiveness to statin treatment.

11. The antibody or antibody fragment of paragraph 9 or 10, wherein said antibody or antibody fragment is for administration to the human separately or simultaneously with said statin treatment.

12. The antibody or antibody fragment of any one of paragraphs 6 to 10, wherein said biological sample comprises serum, blood, faeces, tissue, a cell, urine and/or saliva of said human.

13. The antibody or antibody fragment of any one of paragraphs 1 to 12, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.

14. The antibody or antibody fragment of any one of paragraphs 1 to 13, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

15. The antibody or antibody fragment of any one of paragraphs 1 to 14, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

16. The antibody or antibody fragment of any one of paragraphs 1 to 15, wherein the nucleotide sequence is SEQ ID NO: 29 or 30.

17. The antibody or antibody fragment of any one of paragraphs 1 to 16, wherein said antibody or antibody fragment is for administration by intravenous or subcutaneous administration and/or is comprised in an injectable preparation.

Further exemplary methods are in the paragraphs 1-18 as follows.

1. A method of (a) reducing cholesterol level or maintaining previously reduced cholesterol level in a human in need thereof or (b) targeting PCSK9 in a human,
   the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment, or the human expresses antibodies comprising human gamma-1 heavy chain constant regions comprising such an Asp and Leu and (ii) a nucleotide sequence encoding said proprotein convertase subtilisin/kexin type 9 (PCSK9) that comprises a C-terminal domain comprising said mutation I474V or E670G in SEQ ID NO: 1.

In an embodiment, said mutation is I474V. In another embodiment, said mutation is E670G.

In an embodiment of (b), the antibody or fragment treats or reduces cholesterol level or maintains previously reduced cholesterol level in the human.

An example provides:—

A method of (a) reducing cholesterol level or maintaining previously reduced cholesterol level in a human in need thereof or (b) targeting PCSK9 in a human, the method comprising administering to said human an antibody or antibody fragment that specifically binds a proprotein convertase subtilisin/kexin type 9 (PCSK9) that comprises a C-terminal domain comprising a mutation I474 in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment and (ii) a nucleotide sequence encoding said proprotein convertase subtilisin/kexin type 9 (PCSK9) that comprises a C-terminal domain comprising said mutation I474V in SEQ ID NO: 1. Optionally, the antibody or fragment comprises a IGHG1*01 human heavy chain constant region.

In an embodiment of (b), the antibody or fragment treats or reduces cholesterol level or maintains previously reduced cholesterol level in the human.

Another example provides:—

A method of (a) reducing cholesterol level or maintaining previously reduced cholesterol level in a human in need thereof or (b) targeting PCSK9 in a human, the method comprising administering to said human an antibody or antibody fragment that specifically binds a proprotein convertase subtilisin/kexin type 9 (PCSK9) that comprises a C-terminal domain comprising a mutation E670G in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment and (ii) a nucleotide sequence encoding said proprotein convertase subtilisin/kexin type 9 (PCSK9) that comprises a C-terminal domain comprising said mutation E670G in SEQ ID NO: 1. Optionally, the antibody or fragment comprises an IGHG1*01 human heavy chain constant region.

In an embodiment of (b), the antibody or fragment treats or reduces cholesterol level or maintains previously reduced cholesterol level in the human.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The method of paragraph 1, comprising, before said administering, selecting a human comprising said nucleotide sequence of (ii), wherein the human is the human of paragraph 1.

3. The method of paragraph 1 or 2, wherein the antibody comprises a human gamma-1 heavy chain constant region that comprises an Asp corresponding to position 204 of SEQ ID NO: 42 and a Leu corresponding to position 206 of SEQ ID NO: 42.

4. The method of paragraph 1, 2 or 3, wherein the antibody comprises an IGHG1*01 human heavy chain constant region.

5. The method of any one of paragraphs 1 to 4, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

6. The method of any one of paragraphs 1 to 5, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

7. The method of paragraph 6, wherein the step of determining comprises assaying a biological sample from the human for a nucleotide sequence encoding the PCSK9 that comprises the C-terminal domain comprising the mutation I474V or E670G in SEQ ID NO: 1.

8. The method of paragraph 7, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and detecting the presence or absence of the complex, wherein detecting the presence of the complex determines that the human comprises the PCSK9 that comprises the C-terminal domain comprising the mutation I474V or E670G in SEQ ID NO: 1.

9. The method of paragraph 7 or 8, wherein the assaying comprises nucleic acid amplification and optionally one or more methods selected from sequencing, next generation sequencing, nucleic acid hybridization, and allele-specific amplification and/or wherein the assaying is performed in a multiplex format.

10. The method of any one of paragraphs 1 to 9, wherein said human is or has been further determined to be substantially resistant to statin treatment.

11. The method of any one of paragraphs 1 to 10, wherein said human is receiving or has received statin treatment or has reduced responsiveness to statin treatment.

12. The method of paragraph 10 or 11, wherein said antibody or antibody fragment is administered to the human separately or simultaneously with said statin treatment.

13. The method of any one of paragraphs 7 to 9, wherein said biological sample comprises serum, blood, faeces, tissue, a cell, urine and/or saliva of said human.

14. The method of any one of paragraphs 1 to 13, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.

15. The method of any one of paragraphs 1 to 14, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

16. The method of any one of paragraphs 1 to 15, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

17. The method of any one of paragraphs 1 to 16, wherein the nucleotide sequence is SEQ ID NO: 29 or 30.

18. The method of any one of paragraphs 1 to 17, wherein said antibody or antibody fragment is administered by intravenous or subcutaneous administration and/or is comprised in an injectable preparation.

Further exemplary ligands are in the paragraphs 1-17 as follows.

1. An antibody or antibody fragment for use in a method of (a) reducing cholesterol level or maintaining previously reduced cholesterol level in a human in need thereof or (b) targeting PCSK9 in a human,
    wherein the antibody comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44, and the antibody or fragment specifically binds a proprotein convertase subtilisin/kexin type 9 (PCSK9) amino acid sequence that comprises a C-terminal domain comprising a mutation I474V or E670G in SEQ ID NO: 1, wherein the human comprises a nucleotide sequence encoding said amino acid sequence and comprises an IGHG2*01 human heavy chain constant region gene segment, or the human expresses antibodies comprising human gamma-2 constant regions comprising such a Pro, Asn, Phe, Val and Ala.

In an embodiment, said mutation is I474V. In another embodiment, said mutation is E670G.

In an embodiment of (b), the antibody or fragment treats or reduces cholesterol level or maintains previously reduced cholesterol level in the human.

An example provides:—

An antibody or antibody fragment for use in a method of (a) reducing cholesterol level or maintaining previously reduced cholesterol level in a human in need thereof or (b) targeting PCSK9 in a human,
    wherein the antibody comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44, and the antibody or fragment specifically binds a proprotein convertase subtilisin/kexin type 9 (PCSK9) amino acid sequence that comprises a C-terminal domain comprising a mutation I474V in SEQ ID NO: 1, wherein the human comprises a nucleotide sequence encoding said amino acid sequence and comprises an IGHG2*01 human heavy chain constant region gene segment. Optionally, the antibody or fragment comprises an IGHG2*01 human heavy chain constant In an embodiment of (b), the antibody or fragment treats or reduces cholesterol level or maintains previously reduced cholesterol level in the human.region.

Another example provides:—

An antibody or antibody fragment for use in a method of (a) reducing cholesterol level or maintaining previously reduced cholesterol level in a human in need thereof or (b) targeting PCSK9 in a human,
    wherein the antibody comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44, and the antibody or fragment specifically binds a proprotein convertase subtilisin/kexin type 9 (PCSK9) amino acid sequence that comprises a C-terminal domain comprising a mutation E670G in SEQ ID NO: 1, wherein the human comprises a nucleotide sequence encoding said amino acid sequence and comprises an IGHG2*01 human heavy chain constant region gene segment. Optionally, the antibody or fragment comprises an IGHG2*01 human heavy chain constant region.

In an embodiment of (b), the antibody or fragment treats or reduces cholesterol level or maintains previously reduced cholesterol level in the human.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The antibody or antibody fragment of paragraph 1, wherein the antibody comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44.

3. The antibody or antibody fragment of paragraph 1 or 2, wherein the antibody comprises an IGHG2*01 human heavy chain constant region.

4. The antibody or antibody fragment of any one of paragraphs 1 to 3, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

5. The antibody or antibody fragment of any one of paragraphs 1 to 4, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

6. The antibody or antibody fragment of paragraph 5, wherein the step of determining comprises assaying a biological sample from the human for a nucleotide sequence encoding the PCSK9 that comprises the C-terminal domain comprising the mutation I474V or E670G in SEQ ID NO: 1.

7. The antibody or antibody fragment of paragraph 6, wherein the assaying comprises contacting the biological sample with
a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
detecting the presence or absence of the complex, wherein detecting the presence of the complex determines that the human comprises the PCSK9 that comprises the C-terminal domain comprising the mutation I474V or E670G in SEQ ID NO: 1.

8. The antibody or antibody fragment of paragraph 6 or 7, wherein the assaying comprises nucleic acid amplification and optionally one or more methods selected from sequencing, next generation sequencing, nucleic acid hybridization, and allele-specific amplification and/or wherein the assaying is performed in a multiplex format.

9. The antibody or antibody fragment of any one of paragraphs 1 to 8, wherein said antibody or antibody fragment is for administration to a human that is or has been further determined to be substantially resistant to statin treatment.

10. The antibody or antibody fragment of any one of paragraphs 1 to 9, wherein antibody or antibody fragment is for administration to a human that is receiving or has received statin treatment or has reduced responsiveness to statin treatment.

11. The antibody or antibody fragment of paragraph 9 or 10, wherein said antibody or antibody fragment is for administration to the human separately or simultaneously with said statin treatment.

12. The antibody or antibody fragment of any one of paragraphs 6 to 8, wherein said biological sample comprises serum, blood, faeces, tissue, a cell, urine and/or saliva of said human.

13. The antibody or antibody fragment of any one of paragraphs 1 to 12, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.

14. The antibody or antibody fragment of any one of paragraphs 1 to 13, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

15. The antibody or antibody fragment of any one of paragraphs 1 to 14, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

16. The antibody or antibody fragment of any one of paragraphs 1 to 15, wherein the nucleotide sequence is SEQ ID NO: 29 or 30.

17. The antibody or antibody fragment of any one of paragraphs 1 to 16, wherein said antibody or antibody fragment is for administration by intravenous or subcutaneous administration and/or is comprised in an injectable preparation.

Further exemplary methods are in the paragraphs 1-18 as follows.

1. A method of (a) reducing cholesterol level or maintaining previously reduced cholesterol level in a human in need thereof or (b) targeting PCSK9 in a human, the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment, or the human expresses antibodies comprising human gamma-2 heavy chain constant regions comprising such a Pro, Asn, Phe, Val and Ala and (ii) a nucleotide sequence encoding said proprotein convertase subtilisin/kexin type 9 (PCSK9) that comprises a C-terminal domain comprising said mutation I474V or E670G in SEQ ID NO: 1.

In an embodiment, said mutation is I474V. In another embodiment, said mutation is E670G. In an embodiment of (b), the antibody or fragment treats or reduces cholesterol level or maintains previously reduced cholesterol level in the human.

An example provides:—

A method of (a) reducing cholesterol level or maintaining previously reduced cholesterol level in a human in need thereof or (b) targeting PCSK9 in a human, the method comprising administering to said human an antibody or antibody fragment that specifically binds a proprotein convertase subtilisin/kexin type 9 (PCSK9) that comprises a C-terminal domain comprising a mutation I474 in SEQ ID NO: 1, wherein the antibody or fragment comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment and (ii) a nucleotide sequence encoding said proprotein convertase subtilisin/kexin type 9 (PCSK9) that comprises a C-terminal domain comprising said mutation I474V in SEQ ID NO: 1. Optionally, the antibody or fragment comprises an IGHG2*01 human heavy chain constant region. In an embodiment of (b), the antibody or fragment treats or reduces cholesterol level or maintains previously reduced cholesterol level in the human.

Another example provides:—

A method of (a) reducing cholesterol level or maintaining previously reduced cholesterol level in a human in need thereof or (b) targeting PCSK9 in a human, the method comprising administering to said human an antibody or antibody fragment that specifically binds a proprotein convertase subtilisin/kexin type 9 (PCSK9) that comprises a C-terminal domain comprising a mutation E670G in SEQ ID NO: 1, wherein the antibody or fragment comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment and (ii) a nucleotide sequence encoding said proprotein convertase subtilisin/kexin type 9 (PCSK9) that comprises a C-terminal domain comprising said mutation E670G in SEQ ID NO: 1. Optionally, the antibody or fragment comprises an IGHG2*01 human heavy chain constant region.

In an embodiment of (b), the antibody or fragment treats or reduces cholesterol level or maintains previously reduced cholesterol level in the human.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The method of paragraph 1, comprising, before said administering, selecting said human comprising said nucleotide sequence of (ii).

3. The method of paragraph 1 or 2, wherein the antibody comprises a human gamma-1 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44.

4. The method of paragraph 1, 2 or 3, wherein the antibody comprises an IGHG2*01 human heavy chain constant region.

5. The method of any one of paragraphs 1 to 4, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

6. The method of any one of paragraphs 1 to 5, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

7. The method of paragraph 6, wherein the step of determining comprises assaying a biological sample from the human for a nucleotide sequence encoding the PCSK9 that comprises the C-terminal domain comprising the mutation I474V or E670G in SEQ ID NO: 1.

8. The method of paragraph 7, wherein the assaying comprises contacting the biological sample with
  a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
  b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
  detecting the presence or absence of the complex, wherein detecting the presence of the complex determines that the human comprises the PCSK9 that comprises the C-terminal domain comprising the mutation I474V or E670G in SEQ ID NO: 1.

9. The method of paragraph 7 or 8, wherein the assaying comprises nucleic acid amplification and optionally one or more methods selected from sequencing, next generation sequencing, nucleic acid hybridization, and allele-specific amplification and/or wherein the assaying is performed in a multiplex format.

10. The method of any one of paragraphs 1 to 9, wherein said human is or has been further determined to be substantially resistant to statin treatment.

11. The method of any one of paragraphs 1 to 10, wherein said human is receiving or has received statin treatment or has reduced responsiveness to statin treatment.

12. The method of paragraph 10 or 11, wherein said antibody or antibody fragment is administered to the human separately or simultaneously with said statin treatment.

13. The method of paragraphs 7 to 9, wherein said biological sample comprises serum, blood, faeces, tissue, a cell, urine and/or saliva of said human.

14. The method of any one of paragraphs 1 to 13, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.

15. The method of any one of paragraphs 1 to 14, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

16. The method of any one of paragraphs 1 to 15, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

17. The method of any one of paragraphs 1 to 16, wherein the nucleotide sequence is SEQ ID NO: 29 or 30.

18. The method of any one of paragraphs 1 to 17, wherein said antibody or antibody fragment is administered by intravenous or subcutaneous administration and/or is comprised in an injectable preparation.

Further exemplary ligands are in the paragraphs 1-17 as follows.

1. An antibody or antibody fragment for use in a method of (a) reducing cholesterol level or maintaining previously reduced cholesterol level in a human in need thereof or (b) targeting PCSK9 in a human,
  wherein the antibody or fragment comprises a human kappa light chain constant region that comprises a Val corresponding to position 84 of SEQ ID NO: 50 or a Cys corresponding to position 87 of SEQ ID NO: 50, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said amino acid sequence and comprises an IGKC*01 human light chain constant region gene segment, or the human expresses antibodies comprising human kappa light chain constant regions comprising such an Val and Cys.

In an embodiment, said mutation is I474V. In another embodiment, said mutation is E670G.

In an embodiment of (b), the antibody or fragment treats or reduces cholesterol level or maintains previously reduced cholesterol level in the human.

An example provides:—

An antibody or antibody fragment for use in a method of (a) reducing cholesterol level or maintaining previously reduced cholesterol level in a human in need thereof or (b) targeting PCSK9 in a human,
  wherein the antibody or fragment comprises a human kappa light chain constant region that comprises a Val corresponding to position 84 of SEQ ID NO: 50 and a Cys corresponding to position 87 of SEQ ID NO: 50, and the antibody or fragment specifically binds a proprotein convertase subtilisin/kexin type 9 (PCSK9) amino acid sequence that comprises a C-terminal domain comprising a mutation I474V in SEQ ID NO: 1, wherein the human comprises a nucleotide sequence encoding said amino acid sequence and comprises an IGKC*01 human light chain constant region gene segment. Optionally, the antibody or fragment comprises an IGKC*01 human light chain constant region.

In an embodiment of (b), the antibody or fragment treats or reduces cholesterol level or maintains previously reduced cholesterol level in the human.

Another example provides:—

An antibody or antibody fragment for use in a method of (a) reducing cholesterol level or maintaining previously reduced cholesterol level in a human in need thereof or (b) targeting PCSK9 in a human,
wherein the antibody or fragment comprises a human kappa light chain constant region that comprises a Val corresponding to position 84 of SEQ ID NO: 50 and a Cys corresponding to position 87 of SEQ ID NO: 50, and the antibody or fragment specifically binds a proprotein convertase subtilisin/kexin type 9 (PCSK9) amino acid sequence that comprises a C-terminal domain comprising a mutation E670G in SEQ ID NO: 1, wherein the human comprises a nucleotide sequence encoding said amino acid sequence and comprises an IGKC*01 human light chain constant region gene segment. Optionally, the antibody or fragment comprises an IGKC*01 human light chain constant region.

In an embodiment of (b), the antibody or fragment treats or reduces cholesterol level or maintains previously reduced cholesterol level in the human.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human kappa light chain constant region that comprises a Val corresponding to position 84 of SEQ ID NO: 50 and a Cys corresponding to position 87 of SEQ ID NO: 50 and wherein said human comprises (i) an IGKC*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The antibody or antibody fragment of paragraph 1, wherein the antibody comprises a human kappa light chain constant region that comprises a Val corresponding to position 84 of SEQ ID NO: 50 or a Cys corresponding to position 87 of SEQ ID NO: 50.

3. The antibody or antibody fragment of paragraph 1 or 2, wherein the antibody comprises an IGKC*01 human kappa chain constant region.

4. The antibody or antibody fragment of any one of paragraphs 1 to 3, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

5. The antibody or antibody fragment of any one of paragraphs 1 to 4, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

6. The antibody or antibody fragment of paragraph 5, wherein the step of determining comprises assaying a biological sample from the human for a nucleotide sequence encoding the PCSK9 that comprises the C-terminal domain comprising the mutation I474V or E670G in SEQ ID NO: 1.

7. The antibody or antibody fragment of paragraph 6, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.

8. The antibody or antibody fragment of paragraph 6 or 7, wherein the assaying comprises nucleic acid amplification and optionally one or more methods selected from sequencing, next generation sequencing, nucleic acid hybridization, and allele-specific amplification and/or wherein the assaying is performed in a multiplex format.

9. The antibody or antibody fragment of any one of paragraphs 1 to 8, wherein said antibody or antibody fragment is for administration to a human that is or has been further determined to be substantially resistant to statin treatment.

10. The antibody or antibody fragment of any one of paragraphs 1 to 9, wherein antibody or antibody fragment is for administration to a human that is receiving or has received statin treatment or has reduced responsiveness to statin treatment.

11. The antibody or antibody fragment of paragraph 9 or 10, wherein said antibody or antibody fragment is for administration to the human separately or simultaneously with said statin treatment.

12. The antibody or antibody fragment of any one of paragraphs 6 to 10, wherein said biological sample comprises serum, blood, faeces, tissue, a cell, urine and/or saliva of said human.

13. The antibody or antibody fragment of any one of paragraphs 1 to 12, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.

14. The antibody or antibody fragment of any one of paragraphs 1 to 13, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

15. The antibody or antibody fragment of any one of paragraphs 1 to 14, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

16. The antibody or antibody fragment of any one of paragraphs 1 to 15, wherein the nucleotide sequence is SEQ ID NO: 29 or 30.

17. The antibody or antibody fragment of any one of paragraphs 1 to 16, wherein said antibody or antibody fragment is for administration by intravenous or subcutaneous administration and/or is comprised in an injectable preparation.

Further exemplary methods are in the paragraphs 1-18 as follows.

1. A method of (a) reducing cholesterol level or maintaining previously reduced cholesterol level in a human in need thereof or (b) targeting PCSK9 in a human,
   the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human kappa light chain constant region that comprises a Val corresponding to position 84 of SEQ ID NO: 50 or a Cys corresponding to position 87 of SEQ ID NO: 50 and wherein said human comprises (i) an IGKC*01 human light chain constant region gene segment, or the human expresses antibodies comprising human kappa light chain constant regions comprising such an Val and Cys and (ii) a nucleotide sequence encoding said proprotein convertase subtilisin/kexin type 9 (PCSK9) that comprises a C-terminal domain comprising said mutation I474V or E670G in SEQ ID NO: 1.
   In an embodiment, said mutation is I474V. In another embodiment, said mutation is E670G.
   In an embodiment of (b), the antibody or fragment treats or reduces cholesterol level or maintains previously reduced cholesterol level in the human.
   An example provides:—
   A method of (a) reducing cholesterol level or maintaining previously reduced cholesterol level in a human in need thereof or (b) targeting PCSK9 in a human,
   the method comprising administering to said human an antibody or antibody fragment that specifically binds a proprotein convertase subtilisin/kexin type 9 (PCSK9) that comprises a C-terminal domain comprising a mutation I474 in SEQ ID NO: 1, wherein the antibody or fragment comprises a human kappa light chain constant region that comprises a Val corresponding to position 84 of SEQ ID NO: 50 and a Cys corresponding to position 87 of SEQ ID NO: 50 and wherein said human comprises (i) an IGKC*01 human light chain constant region gene segment and (ii) a nucleotide sequence encoding said proprotein convertase subtilisin/kexin type 9 (PCSK9) that comprises a C-terminal domain comprising said mutation I474V in SEQ ID NO: 1. Optionally, the antibody or fragment comprises an IGKC*01 human light chain constant region.
   In an embodiment of (b), the antibody or fragment treats or reduces cholesterol level or maintains previously reduced cholesterol level in the human.
   Another example provides:—
   A method of (a) reducing cholesterol level or maintaining previously reduced cholesterol level in a human in need thereof or (b) targeting PCSK9 in a human,
   the method comprising administering to said human an antibody or antibody fragment that specifically binds a proprotein convertase subtilisin/kexin type 9 (PCSK9) that comprises a C-terminal domain comprising a mutation E670G in SEQ ID NO: 1, wherein the antibody or fragment comprises a human kappa light chain constant region that comprises a Val corresponding to position 84 of SEQ ID NO: 50 and a Cys corresponding to position 87 of SEQ ID NO: 50 and wherein said human comprises (i) an IGKC*01 human light chain constant region gene segment and (ii) a nucleotide sequence encoding said proprotein convertase subtilisin/kexin type 9 (PCSK9) that comprises a C-terminal domain comprising said mutation E670G in SEQ ID NO: 1. Optionally, the antibody or fragment comprises an IGKC*01 human light chain constant region.
   In an embodiment of (b), the antibody or fragment treats or reduces cholesterol level or maintains previously reduced cholesterol level in the human.
   In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human kappa light chain constant region that comprises a Val corresponding to position 84 of SEQ ID NO: 50 and a Cys corresponding to position 87 of SEQ ID NO: 50 and wherein said human comprises (i) an IGKC*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The method of paragraph 1, comprising, before said administering, selecting said human comprising said nucleotide sequence of (ii).

3. The method of paragraph 1 or 2, wherein the antibody comprises a human kappa light chain constant region that comprises a Val corresponding to position 84 of SEQ ID NO: 50 or a Cys corresponding to position 87 of SEQ ID NO: 50.

4. The method of paragraph 1, 2 or 3, wherein the antibody comprises an IGKC*01 human kappa chain constant region.

5. The method of any one of paragraphs 1 to 4, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

6. The method of any one of paragraphs 1 to 5, comprising the step of determining that the human comprises the nucleotide sequence that encodes a PCSK9 comprising a C-terminal domain comprising said mutation I474V or E670G and/or a proprotein convertase subtilisin/kexin type 9

(PCSK9) variant protein comprising said mutation I474V or E670G, optionally, wherein the determining step is performed before administration of the antibody to the human.
7. The method of paragraph 6, wherein the step of determining comprises assaying a biological sample from the human for a nucleotide sequence encoding the PCSK9 that comprises the C-terminal domain comprising the mutation I474V or E670G in SEQ ID NO: 1.
8. The method of paragraph 7, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.
9. The method of paragraph 7 or 8, wherein the assaying comprises nucleic acid amplification and optionally one or more methods selected from sequencing, next generation sequencing, nucleic acid hybridization, and allele-specific amplification and/or wherein the assaying is performed in a multiplex format.
10. The method of any one of paragraphs 1 to 9, wherein said human is or has been further determined to be substantially resistant to statin treatment.
11. The method of any one of paragraphs 1 to 10, wherein said human is receiving or has received statin treatment or has reduced responsiveness to statin treatment.
12. The method of paragraph 10 or 11, wherein said antibody or antibody fragment is administered to the human separately or simultaneously with said statin treatment.
13. The method of any one of paragraphs 7 to 9, wherein said biological sample comprises serum, blood, faeces, tissue, a cell, urine and/or saliva of said human.
14. The method of any one of paragraphs 1 to 13, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.
15. The method of any one of paragraphs 1 to 14, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
16. The method of any one of paragraphs 1 to 15, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
17. The method of any one of paragraphs 1 to 16, wherein the nucleotide sequence is SEQ ID NO: 29 or 30.
18. The method of any one of paragraphs 1 to 17, wherein said antibody or antibody fragment is administered by intravenous or subcutaneous administration and/or is comprised in an injectable preparation.

Further exemplary ligands are in the paragraphs 1-15 as follows.
1. An antibody or antibody fragment for use in a method of (a) reducing cholesterol level or maintaining previously reduced cholesterol level in a human in need thereof or (b) targeting PCSK9 in a human,
   wherein the antibody or fragment comprises a human IGLC2*01 lambda light chain constant region, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said amino acid sequence and comprises a human IGLC2*01 lambda light chain constant region gene segment, or the human expresses antibodies comprising human IGLC2*01 lambda light chain constant regions.
   In an embodiment, said mutation is I474V. In another embodiment, said mutation is E670G.
   In an embodiment of (b), the antibody or fragment treats or reduces cholesterol level or maintains previously reduced cholesterol level in the human.
   An example provides:—
   An antibody or antibody fragment for use in a method of (a) reducing cholesterol level or maintaining previously reduced cholesterol level in a human in need thereof or (b) targeting PCSK9 in a human,
   wherein the antibody or fragment comprises a human IGLC2*01 lambda light chain constant region, and the antibody or fragment specifically binds a proprotein convertase subtilisin/kexin type 9 (PCSK9) amino acid sequence that comprises a C-terminal domain comprising a mutation I474V in SEQ ID NO: 1, wherein the human comprises a nucleotide sequence encoding said amino acid sequence and comprises a human IGLC2*01 lambda light chain constant region gene segment. Optionally, the antibody or fragment comprises a human IGLC2*01 lambda light chain constant region.
   In an embodiment of (b), the antibody or fragment treats or reduces cholesterol level or maintains previously reduced cholesterol level in the human.
   Another example provides:—
   An antibody or antibody fragment for use in a method of (a) reducing cholesterol level or maintaining previously reduced cholesterol level in a human in need thereof or (b) targeting PCSK9 in a human, wherein the antibody or fragment comprises a human IGLC2*01 lambda light chain constant region, and the antibody or fragment specifically binds a proprotein convertase subtilisin/kexin type 9 (PCSK9) amino acid sequence that comprises a C-terminal domain comprising a mutation E670G in SEQ ID NO: 1, wherein the human comprises a nucleotide sequence encoding said amino acid sequence and comprises a human IGLC2*01 lambda light chain constant region gene segment. Optionally, the antibody or fragment comprises a human IGLC2*01 lambda light chain constant region.

In an embodiment of (b), the antibody or fragment treats or reduces cholesterol level or maintains previously reduced cholesterol level in the human.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human IGLC2*01 lambda light chain constant region and wherein said human comprises (i) an IGLC2*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The antibody or antibody fragment of paragraph 1, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

3. The antibody or antibody fragment of paragraphs 1 or 2, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

4. The antibody or antibody fragment of paragraph 3, wherein the step of determining comprises assaying a biological sample from the human for a nucleotide sequence encoding the PCSK9 that comprises the C-terminal domain comprising the mutation I474V or E670G in SEQ ID NO: 1.

5. The antibody or antibody fragment of paragraph 4, wherein the assaying comprises contacting the biological sample with a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and detecting the presence or absence of the complex, wherein detecting the presence of the complex determines that the human comprises the PCSK9 that comprises the C-terminal domain comprising the mutation I474V or E670G in SEQ ID NO: 1.

6. The antibody or antibody fragment of paragraph 4 or 5, wherein the assaying comprises nucleic acid amplification and optionally one or more methods selected from sequencing, next generation sequencing, nucleic acid hybridization, and allele-specific amplification and/or wherein the assaying is performed in a multiplex format.

7. The antibody or antibody fragment of any one of paragraphs 1 to 6, wherein said antibody or antibody fragment is for administration to a human that is or has been further determined to be substantially resistant to statin treatment.

8. The antibody or antibody fragment of any one of paragraphs 1 to 7, wherein antibody or antibody fragment is for administration to a human that is receiving or has received statin treatment or has reduced responsiveness to statin treatment.

9. The antibody or antibody fragment of paragraph 7 or 8, wherein said antibody or antibody fragment is for administration to the human separately or simultaneously with said statin treatment.

10. The antibody or antibody fragment of any one of paragraphs 4 to 8, wherein said biological sample comprises serum, blood, faeces, tissue, a cell, urine and/or saliva of said human.

11. The antibody or antibody fragment of any one of paragraphs 1 to 10, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.

12. The antibody or antibody fragment of any one of paragraphs 1 to 11, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

13. The antibody or antibody fragment of any one of paragraphs 1 to 12, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

14. The antibody or antibody fragment of any one of paragraphs 1 to 13, wherein the nucleotide sequence is SEQ ID NO: 29 or 30.
15. The antibody or antibody fragment of any one of paragraphs 1 to 14, wherein said antibody or antibody fragment is for administration by intravenous or subcutaneous administration and/or is comprised in an injectable preparation.

Further exemplary methods are in the paragraphs 1-16 as follows.
1. A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human IGLC2*01 lambda light chain constant region and wherein said human comprises (i) an IGLC2*01 human light chain constant region gene segment, or the human expresses antibodies comprising a human IGLC2*01 lambda light chain constant regions and (ii) a nucleotide sequence encoding said proprotein convertase subtilisin/kexin type 9 (PCSK9) that comprises a C-terminal domain comprising said mutation I474V or E670G in SEQ ID NO: 1.

In an embodiment, said mutation is I474V. In another embodiment, said mutation is E670G.

An example provides:—
A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 in SEQ ID NO: 1, wherein the antibody or fragment comprises a human IGLC2*01 lambda light chain constant region and wherein said human comprises (i) an IGLC2*01 human light chain constant region gene segment and (ii) a nucleotide sequence encoding said proprotein convertase subtilisin/kexin type 9 (PCSK9) that comprises a C-terminal domain comprising said mutation I474V in SEQ ID NO: 1. Optionally, the antibody or fragment comprises an IGLC2*01 human light chain constant region.

Another example provides:—
A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation E670G in SEQ ID NO: 1, wherein the antibody or fragment comprises a human IGLC2*01 lambda light chain constant region and wherein said human comprises (i) an IGLC2*01 human light chain constant region gene segment and (ii) a nucleotide sequence encoding said proprotein convertase subtilisin/kexin type 9 (PCSK9) that comprises a C-terminal domain comprising said mutation E670G in SEQ ID NO: 1. Optionally, the antibody or fragment comprises an IGLC2*01 human light chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human IGLC2*01 lambda light chain constant region and wherein said human comprises (i) an IGLC2*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1

2. The method of paragraph 1, comprising, before said administering, selecting said human comprising said nucleotide sequence of (ii).
3. The method of paragraph 1 or 2, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
4. The method of any one of paragraphs 1 to 3, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
5. The method of paragraph 4, wherein the step of determining comprises assaying a biological sample from the human for a nucleotide sequence encoding the PCSK9 that comprises the C-terminal domain comprising the mutation I474V or E670G in SEQ ID NO: 1.
6. The method of paragraph 5, wherein the assaying comprises contacting the biological sample with
    a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
    b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
    detecting the presence or absence of the complex, wherein detecting the presence of the complex determines that the human comprises the PCSK9 that comprises the C-terminal domain comprising the mutation I474V or E670G in SEQ ID NO: 1.
7. The method of paragraph 5 or 6, wherein the assaying comprises nucleic acid amplification and optionally one or more methods selected from sequencing, next generation sequencing, nucleic acid hybridization, and allele-specific amplification and/or wherein the assaying is performed in a multiplex format.
8. The method of any one of paragraphs 1 to 7, wherein said human is or has been further determined to be substantially resistant to statin treatment.
9. The method of any one of paragraphs 1 to 8, wherein said human is receiving or has received statin treatment or has reduced responsiveness to statin treatment.
10. The method of paragraph 8 or 9, wherein said antibody or antibody fragment is administered to the human separately or simultaneously with said statin treatment.
11. The method of any one of paragraphs 5 to 7, wherein said biological sample comprises serum, blood, faeces, tissue, a cell, urine and/or saliva of said human.
12. The method of any one of paragraphs 1 to 11, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.
13. The method of any one of paragraphs 1 to 12, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
14. The method of any one of paragraphs 1 to 13, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
15. The method of any one of paragraphs 1 to 14, wherein the nucleotide sequence is SEQ ID NO: 29 or 30.
16. The method of any one of paragraphs 1 to 15, wherein said antibody or antibody fragment is administered by intravenous or subcutaneous administration and/or is comprised in an injectable preparation.

Further exemplary ligands are in the paragraphs 1-15 as follows.
1. An antibody or antibody fragment for use in a method of (a) reducing cholesterol level or maintaining previously reduced cholesterol level in a human in need thereof or (b) targeting PCSK9 in a human, wherein the antibody or fragment comprises a human variable domain that is derived from the recombination of a human VH gene segment, a human D gene segment and a human JH gene segment, wherein the VH gene segment is as defined in any one of clauses 80 to 90, and the antibody or fragment specifically binds a proprotein convertase subtilisin/kexin type 9 (PCSK9) amino acid sequence that comprises a C-terminal domain comprising a mutation I474V or E670G in SEQ ID NO: 1, wherein the human comprises a nucleotide sequence encoding said amino acid sequence, and comprises said VH gene segment or expresses antibodies comprising VH domains that are derived from the recombination of said human VH gene segment, a human D gene segment and a human JH gene segment.
In an embodiment, said mutation is I474V. In another embodiment, said mutation is E670G.
In an embodiment of (b), the antibody or fragment treats or reduces cholesterol level or maintains previously reduced cholesterol level in the human.
2. The antibody or antibody fragment of paragraph 1, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
3. The antibody or antibody fragment of paragraphs 1 or 2, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
4. The antibody or antibody fragment of paragraph 3, wherein the step of determining comprises assaying a biological sample from the human for a nucleotide sequence encoding the PCSK9 that comprises the C-terminal domain comprising the mutation I474V or E670G in SEQ ID NO: 1.
5. The antibody or antibody fragment of paragraph 4, wherein the assaying comprises contacting the biological sample with
  a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
  b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
  detecting the presence or absence of the complex, wherein detecting the presence of the complex determines that the human comprises the PCSK9 that comprises the C-terminal domain comprising the mutation I474V or E670G in SEQ ID NO: 1.
6. The antibody or antibody fragment of paragraph 4 or 5, wherein the assaying comprises nucleic acid amplification and optionally one or more methods selected from sequencing, next generation sequencing, nucleic acid hybridization, and allele-specific amplification and/or wherein the assaying is performed in a multiplex format.
7. The antibody or antibody fragment of any one of paragraphs 1 to 6, wherein said antibody or antibody fragment is for administration to a human that is or has been further determined to be substantially resistant to statin treatment.
8. The antibody or antibody fragment of any one of paragraphs 1 to 7, wherein antibody or antibody fragment is for administration to a human that is receiving or has received statin treatment or has reduced responsiveness to statin treatment.
9. The antibody or antibody fragment of paragraph 7 or 8, wherein said antibody or antibody fragment is for administration to the human separately or simultaneously with said statin treatment.
10. The antibody or antibody fragment of any one of paragraphs 4 to 8, wherein said biological sample comprises serum, blood, faeces, tissue, a cell, urine and/or saliva of said human.
11. The antibody or antibody fragment of any one of paragraphs 1 to 10, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.
12. The antibody or antibody fragment of any one of paragraphs 1 to 11, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
13. The antibody or antibody fragment of any one of paragraphs 1 to 12, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
14. The antibody or antibody fragment of any one of paragraphs 1 to 13, wherein the nucleotide sequence is SEQ ID NO: 29 or 30.
15. The antibody or antibody fragment of any one of paragraphs 1 to 14, wherein said antibody or antibody fragment is for administration by intravenous or subcutaneous administration and/or is comprised in an injectable preparation.

Further exemplary methods are in the paragraphs 1-16 as follows.
1. A method of (a) reducing cholesterol level or maintaining previously reduced cholesterol level in a human in need thereof or (b) targeting PCSK9 in a human,
the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human variable domain that is derived from the recombination of a human VH gene segment, a human D gene segment and a human JH gene segment, wherein the VH gene segment is as defined in any one of clauses 80 to 90 and wherein said human comprises (i) comprises said VH gene segment or expresses antibodies comprising VH domains that are derived from the recombination of said human VH gene segment, a human D gene segment and a human JH gene segment and (ii) a nucleotide sequence encoding said proprotein convertase subtilisin/kexin type 9 (PCSK9) that comprises a C-terminal domain comprising said mutation I474V or E670G in SEQ ID NO: 1.

In an embodiment, said mutation is I474V. In another embodiment, said mutation is E670G.

In an embodiment of (b), the antibody or fragment treats or reduces cholesterol level or maintains previously reduced cholesterol level in the human.
2. The method of paragraph 1, comprising, before said administering, selecting said human comprising said nucleotide sequence of (ii).
3. The method of paragraph 1 or 2, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
4. The method of any one of paragraphs 1 to 3, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
5. The method of paragraph 4, wherein the step of determining comprises assaying a biological sample from the human for a nucleotide sequence encoding the PCSK9 that comprises the C-terminal domain comprising the mutation I474V or E670G in SEQ ID NO: 1.
6. The method of paragraph 5, wherein the assaying comprises contacting the biological sample with
a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
detecting the presence or absence of the complex, wherein detecting the presence of the complex determines that the human comprises the PCSK9 that comprises the C-terminal domain comprising the mutation I474V or E670G in SEQ ID NO: 1.

7. The method of paragraph 5 or 6, wherein the assaying comprises nucleic acid amplification and optionally one or more methods selected from sequencing, next generation sequencing, nucleic acid hybridization, and allele-specific amplification and/or wherein the assaying is performed in a multiplex format.
8. The method of any one of paragraphs 1 to 7, wherein said human is or has been further determined to be substantially resistant to statin treatment.
9. The method of any one of paragraphs 1 to 8, wherein said human is receiving or has received statin treatment or has reduced responsiveness to statin treatment.
10. The method of paragraph 8 or 9, wherein said antibody or antibody fragment is administered to the human separately or simultaneously with said statin treatment.
11. The method of any one of paragraphs 5 to 7, wherein said biological sample comprises serum, blood, faeces, tissue, a cell, urine and/or saliva of said human.
12. The method of any one of paragraphs 1 to 11, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.
13. The method of any one of paragraphs 1 to 12, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
14. The method of any one of paragraphs 1 to 13, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
15. The method of any one of paragraphs 1 to 14, wherein the nucleotide sequence is SEQ ID NO: 29 or 30.
16. The method of any one of paragraphs 1 to 15, wherein said antibody or antibody fragment is administered by intravenous or subcutaneous administration and/or is comprised in an injectable preparation.

Regimens

A: The invention further provides the following regimens, ligands and kits.
1. A method for treating a human PCSK9-mediated disease or condition in a human by targeting a rare variant human PCSK9, the method comprising administering to the human a ligand (eg, an antibody or fragment) that has been determined to specifically bind to said PCSK9 variant; wherein the human expresses said PCSK9 variant or the genome of the human comprises a nucleotide sequence encoding said PCSK9 variant; wherein said human is treated for said disease or condition.

In an alternative, clause 1 provides:—
A method for targeting a rare variant human PCSK9, the method comprising administering to the human a ligand (eg, an antibody or fragment) that has been determined to specifically bind to said PCSK9variant; wherein the human expresses said PCSK9 variant or the genome of the human comprises a nucleotide sequence encoding said PCSK9 variant. In an embodiment, said human is treated for said disease or condition.

The variant PCSK9 can, for example, be any rare variant as described herein.

For example, there is provided:
1a. A method for treating a PCSK9-mediated disease or condition in a human by targeting a PCSK9 that comprises a C-terminal domain amino acid polymorphism (compared to SEQ ID NO: 1), the method comprising administering to the human a ligand (eg, an antibody or fragment) that has been determined to specifically bind to a PCSK9 comprising a C-terminal domain comprising I474V or 670G (numbering according to SEQ ID NO: 1); wherein the human expresses said PCSK9 or the genome of the human comprises a nucleotide sequence encoding said PCSK9; wherein said human is treated for said disease or condition.

For example, there is provided:
1b. A method for targeting a PCSK9 that comprises a C-terminal domain amino acid polymorphism (compared to SEQ ID NO: 1), the method comprising administering to the human a ligand (eg, an antibody or fragment) that has been determined to specifically bind to a PCSK9 comprising a C-terminal domain comprising I474V or 670G (numbering according to SEQ ID NO: 1); wherein the human expresses said PCSK9 or the genome of the human comprises a nucleotide sequence encoding said PCSK9; optionally wherein said human is treated for said disease or condition.

In an embodiment, determination of said specific binding is by reference to binding assay data, eg, as determined using SPR or ELISA. Determination may, for example, be by reference to information in a printed publication, eg, with knowledge of data presented in the present or another patent application or in a journal article. Once armed with such knowledge (eg, in the absence of further testing of binding), the skilled person is able—by direction of the present invention—to treat a relevant human whose genotype or phenotype matches the binding specificity of the ligand.

The antibody or fragment can be according to any configuration, example, embodiment, aspect, clause or paragraph herein.

In an embodiment, the method comprises, before said administering, selecting a human comprising said nucleotide sequence encoding the PCSK9, wherein the human is said human in clause 1 (eg, 1a).
2. The method of clause 1, comprising before said administering the step of determining that the ligand specifically binds to said PCSK9, eg, using SPR or ELISA.
3. The method of clause 1 or 2, wherein the specific binding to said PCSK9 is binding with a dissociation constant (Kd) of 1 nM or less, eg, 100, 10 or 1 pM or less.
4. The method of any of clauses 1 to 3 (eg, clause 1a), wherein the condition is elevated LDL-cholesterol or is caused by elevated LDL-cholesterol.
5. The method of clause 4 (eg, when dependent from clause 1a), wherein the condition is selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
6. The method of any one of clauses 1 to 5 (eg, when dependent from clause 1a), wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

7. The method of any one of clauses 1 to 6 (eg, when dependent from clause 1a), comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

8. The method of clause 7, wherein the step of determining comprises assaying a biological sample from the human for a nucleotide sequence encoding the PCSK9 that comprises the C-terminal domain comprising the mutation I474V or E670G in SEQ ID NO: 1.

9. The method of clause 8, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.

10. The method of clause 8 or 9, wherein the assaying comprises nucleic acid amplification and optionally one or more methods selected from sequencing, next generation sequencing, nucleic acid hybridization, and allele-specific amplification and/or wherein the assaying is performed in a multiplex format.

11. The method of any one of clauses 1 to 10, wherein said human is or has been further determined to be substantially resistant to statin treatment.

12. The method of any one of clauses 1 to 11, wherein said human is receiving or has received statin treatment or has reduced responsiveness to statin treatment.

13. The method of clauses 11 or 12, wherein said antibody or antibody fragment is administered to the human separately or simultaneously with said statin treatment.

14. The method of any one of clauses 8 to 10, wherein said biological sample comprises serum, blood, faeces, tissue, a cell, urine and/or saliva of said human.

15. The method of any one of clauses 1 to 14, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.

16. The method of any one of clauses 1 to 15, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

17. The method of any one of clauses 1 to 16, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

18. The method of any one of clauses 1 to 17, wherein the nucleotide sequence is SEQ ID NO: 29 or 30.

19. The method of any one of clauses 1 to 18, wherein said antibody or antibody fragment is administered by intravenous or subcutaneous administration and/or is comprised in an injectable preparation.

20. A ligand (eg, an antibody or fragment) for use in the method of any one of clauses 1 to 19, wherein the ligand specifically binds the PCSK9.

21. A kit comprising the ligand of clause 20 and instructions for carrying out the method of any one of clauses 1 to 19.

B: The invention further provides the following regimens, ligands and kits.

1. A method of reducing cholesterol level or maintaining a previously reduced cholesterol level in a human in need thereof, the method comprising:—
   a. Carrying out an initial treatment of said human for an initial treatment period by administering an anti-human PCSK9 ligand (eg, an antibody or fragment) to said human, wherein (i) the ligand has been determined to specifically bind to a PCSK9 comprising a C-terminal domain comprising I474V or 670G (numbering according to SEQ ID NO: 1); (ii) the human expresses said PCSK9 or the genome of the human comprises a nucleotide sequence encoding said PCSK9 and (iii) the human has received or is receiving statin treatment to lower or maintain cholesterol level; wherein the initial treatment comprises the administration of a single or multiple doses of the ligand to the human;
   b. Determining to (i) terminate statin treatment (ii) keep the human off statin treatment; or (iii) reduce statin treatment after said initial treatment period; and
   c. Continuing to administer the ligand to said patient after said time period has expired, thereby reducing cholesterol level or maintaining a previously reduced cholesterol level in said human.

In an embodiment, determination of said specific binding is by reference to binding assay data, eg, as determined using SPR or ELISA. Determination may, for example, be by reference to information in a printed publication, eg, with knowledge of data presented in the present or another patent application or in a journal article. Once armed with such knowledge (eg, in the absence of further testing of binding), the skilled person is able—by direction of the present invention—to treat a relevant human whose genotype or phenotype matches the binding specificity of the ligand.

The antibody or fragment can be according to any configuration, example, embodiment, aspect, clause or paragraph herein.

A pharmaceutically-effective amount of said ligand is administered.

In an embodiment, the method comprises, before said administering, selecting a human comprising said nucleotide sequence encoding the PCSK9, wherein the human is said human recited in clause 1.

In an example, the initial treatment period is 7 days, 14 days, 21 days, 28 days, a month, two months, three months, four months, five months, six months, seven months, eight months, nine months or a year.

2. The method of clause 1, wherein the human has or is suffering from statin-associated memory loss or a statin-associated neurodegenerative condition, or has or is at increased risk of diabetes (eg, statin-associated diabetes).
3. The method of clause 1 or 2, comprising, before said initial treatment, the step of determining that the human has or is suffering from statin-associated memory loss or a statin-associated neurodegenerative condition, or has or is at increased risk of diabetes (eg, statin-associated diabetes).
4. The method of clause 2 or 3, comprising, after step (b) (eg, during step (c)) determining that the memory loss or said neurodegenerative condition has improved.
5. The method of any one of clauses 1 to 4, wherein said human is over 40 years of age (eg, 50 or over, 55 or over, 60 or over, 65 or over, or 70 or over).
6. The method of any one of clauses 1 to 5, wherein step (c) comprises determining to increase the doses of said ligand to be administered after said initial treatment period and administering said increased doses to said human.
7. The method of any one of clauses 1 to 6, wherein step (b) comprises determining that the human is intolerant or refactory to treatment by a statin.
8. The method of any one of clauses 1 to 7, wherein the initial treatment comprises the administration of a statin, fenofibrate (eg, Tricor™ or Lofibra™) or ezetimibe to the human in addition to the ligand.
9. The method of any one of clauses 1 to 8, wherein step (b) comprises terminating or reducing statin, fenofibrate (eg, Tricor™ or Lofibra™) or ezetimibe treatment during step (c).
10. The method of any one of clauses 1 to 9, comprising increasing (ie, increasing compared to the initial treatment dose) the ligand dose during step (c).
11. The method of any one of clauses 1 to 10, wherein the human has received high dose statin treatment prior to the initial treatment, and wherein step (c) comprises administering a lower (eg, a medium or low) dose statin treatment in addition to said ligand.

The skilled person is familiar with the meaning of high, medium and low dose treatments (and how to determine according to each patient, eg, the patient's body mass). For example, the statin is selected from rosuvastatin, atorvastatin and simvastatin.

For example daily statin doses are as follows:—Low 10 to 20 mg (eg, 10 mg); medium >20 and <60 mg (eg, 40 mg); high 60-100 mg (eg, 80 mg).

12. The method of any one of clauses 1 to 10, wherein the human has received medium dose statin treatment prior to the initial treatment, and wherein step (c) comprises administering a lower (eg, a low) dose statin treatment or no statin in addition to said ligand.
13. The method of any one of clauses 1 to 10, wherein the human has received low dose statin treatment prior to the initial treatment, and wherein step (c) comprises administering no statin in addition to said ligand.
14. The method of any one of clauses 1 to 13, comprising, before the initial treatment, the step of determining that the ligand specifically binds to said PCSK9, eg, using SPR or ELISA.
15. The method of any one of clauses 1 to 14, wherein the specific binding to said PCSK9 is binding with a dissociation constant (Kd) of 1 nM or less, eg, 100, 10 or 1 pM or less.
16. The method of any of clauses 1 to 15, wherein the human is at risk of or suffering from a condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
17. The method of clause 16, wherein step (c) treats or reduces the risk of said condition in the human.
18. The method of any one of clauses 1 to 17, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
19. The method of any one of clauses 1 to 18, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
20. The method of clause 19, wherein the step of determining comprises assaying a biological sample from the human for a nucleotide sequence encoding the PCSK9 that comprises the C-terminal domain comprising the mutation I474V or E670G in SEQ ID NO: 1.
21. The method of clause 20, wherein the assaying comprises contacting the biological sample with
    a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
    b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and detecting the presence or absence of the complex, wherein detecting the presence of the complex determines that the human comprises the PCSK9 that comprises the C-terminal domain comprising the mutation I474V or E670G in SEQ ID NO: 1.

22. The method of clause 20 or 21, wherein the assaying comprises nucleic acid amplification and optionally one or more methods selected from sequencing, next generation sequencing, nucleic acid hybridization, and allele-specific amplification and/or wherein the assaying is performed in a multiplex format.

23. The method of any one of clauses 1 to 22, wherein said human is or has been further determined to be substantially resistant to statin treatment.

24. The method of any one of clauses 20 to 22, wherein said biological sample comprises serum, blood, faeces, tissue, a cell, urine and/or saliva of said human.

25. The method of any one of clauses 1 to 24, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.

26. The method of any one of clauses 1 to 25, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

27. The method of any one of clauses 1 to 26, wherein the nucleotide sequence is SEQ ID NO: 29 or 30.

28. The method of any one of clauses 1 to 27, wherein said ligand (eg, antibody or antibody fragment) is administered by intravenous or subcutaneous administration and/or is comprised in an injectable preparation.

29. A ligand (eg, an antibody or fragment) for use in the method of any one of clauses 1 to 28, wherein the ligand specifically binds the PCSK9.

30. A kit comprising the ligand of clause 29 and instructions for carrying out the method of any one of clauses 1 to 28.

In an example of any aspect of the invention, the ligand (eg, antibody or fragment, eg, alirocumab, bocovizumab or evolocumab, or an antibody or fragment comprising the variable domains of 316P or 31H4) is administered to the human at a two-weekly dose of from 75 to 150 mg (eg, from 75 to 150 mg administered once or twice over a two-week period). In an example, the ligand is for such administration to the human.

Determination of Specific Binding of Ligands of the Invention to PCSK9 Variants

Method of SPR Determination of Binding

Binding of the antibodies to the PCSK9 variants was carried out by SPR using the ProteOn XPR36™ Array system (BioRad). An anti-human IgG surface (Jackson Labs 109-005-008) was created on a GLC Biosensor chip by primary amine coupling. Test antibodies were captured on this surface as ligands. The PCSK9 variants were used as analytes and passed over the captured antibodies at 256 nM, 64 nM, 16 nM, 4 nM and 1 nM. Binding curves were double referenced using a buffer injection (i.e. 0 nM) to remove baseline drift and injection artefacts. Regeneration of the capture surface was with 100 mM phosphoric acid which removed the captured antibody allowing another cycle of capture and binding. The binding sensorgrams generated were analysed using the 1:1 model inherent to the ProteOn XPR36 Array system analysis software. The assay was performed at 25° C. and using 1×HBS-EP (Teknova) as running buffer.

Data

Three antibodies were tested and the resulting binding data are presented below (Table 3). Antibodies 316P and 31H4 are antibodies disclosed in US20110065902A1 (the sequences of these antibodies and their variable domains are incorporated herein by reference for possible use in the present invention and possible inclusion in claims herein). Antibody 316P comprises heavy chain variable domains derived from recombination of human VH3-23*04 and JH2*01 (with a D), and light chain variable domains derived from recombination of human Vκ-4-1*01 and Jκ2*01.

Evolocumab comprises a human IGHG2*01 heavy chain and a human IGLC2*01 lambda light chain, a VH derived from recombination of human IGHV1-18*01 and IGHJ6*01 (with a D segment) and a Vλ derived from recombination of human IGLV2-14*01 and IGLJ2*01.

TABLE 3

SP Determination of Ligand Binding Specificity for PCSK9 Variants

| Variant/Antibody | ka (1/Ms) | kd (1/s) | KD (nM) |
|---|---|---|---|
| PCSK9 a | | | |
| 316P | 1.37E+06 | 2.75E−04 | 0.201 |
| 31H4 | 1.14E+06 | 6.38E−05 | 0.056 |
| Evolocumab | 1.14E+05 | 2.62E−05 | 0.229 |
| PCSK9 a' | | | |
| 316P | 1.50E+06 | 2.72E−04 | 0.181 |
| 31H4 | 1.23E+06 | 6.06E−05 | 0.049 |
| Evolocumab | 1.24E+05 | 2.29E−05 | 0.185 |
| PCSK9 c | | | |
| 316P | 1.49E+06 | 2.75E−04 | 0.184 |
| 31H4 | 1.22E+06 | 5.69E−05 | 0.047 |
| Evolocumab | 1.20E+05 | 2.20E−05 | 0.183 |
| PCSK9 r | | | |
| 316P | 1.40E+06 | 2.76E−04 | 0.197 |
| 31H4 | 1.15E+06 | 5.82E−05 | 0.051 |
| Evolocumab | 1.16E+05 | 2.67E−05 | 0.230 |
| PCSK9 f | | | |
| 316P | 1.39E+06 | 2.82E−04 | 0.203 |
| 31H4 | 1.13E+06 | 5.95E−05 | 0.053 |
| Evolocumab | 1.16E+05 | 2.66E−05 | 0.229 |
| PCSK9 p | | | |
| 316P | 1.39E+06 | 2.73E−04 | 0.196 |
| 31H4 | 1.14E+06 | 6.12E−05 | 0.054 |
| Evolocumab | 1.14E+05 | 2.50E−05 | 0.219 |

Results

The results showed that all antibodies tested bound to PCSK9 variants equally, with any binding variation seen being within experimental error for such a strong affinity interaction.

Thus, the invention determines that an antibody with the following profile can specifically bind one or more variants of the invention:—

1. An antibody (eg, 316P or alirocumab) that comprises heavy chain variable domains derived from recombination of human IGHV3-23*04 and IGHJH2*01 (with a D), and light chain variable domains derived from recombination of human IGKV4-1*01 and IGKJ2*01; or 2. An antibody (eg, evolocumab) that comprises human heavy chain variable domains derived from recombination of human IGHV1-18*01 and IGHJ6*01 (with a D segment) and light chain variable domains derived from recombination of human IGLV2-14*01 and IGLJ2*01.

Thus, according to the invention, the skilled person is hereby provided with the required determination of specific binding of the ligand to PCSK9 variants. Applications of this determination are set out above in the context of methods and other aspects of the invention.

REFERENCES

Horton et al, Trends Biochem Sci. 2007 February; 32(2):71-7. Epub 2007 Jan. 9, Molecular biology of PCSK9: its role in LDL metabolism.

Seidah and Prat, J Mol Med (Berl). 2007 July; 85(7):685-96. Epub 2007 Mar. 10, The proprotein convertases are potential targets in the treatment of dyslipidemia.

Benjannet et al, J Biol. Chem. 2004 Nov. 19; 279(47):48865-75. Epub 2004 Sep. 9, NARC-1/PCSK9 and its natural mutants: zymogen cleavage and effects on the low density lipoprotein (LDL) receptor and LDL cholesterol.

Lagace et al, J Clin Invest. 2006 November; 116(11):2995-3005, Secreted PCSK9 decreases the number of LDL receptors in hepatocytes and in livers of parabiotic mice.

Maxwell et al, Proc Natl Acad Sci USA. 2005 Feb. 8; 102(6): 2069-74. Epub 2005 Jan. 27, Overexpression of PCSK9 accelerates the degradation of the LDLR in a post-endoplasmic reticulum compartment.

Park et al, J Biol. Chem. 2004 Nov. 26; 279(48):50630-8. Epub 2004 Sep. 22, Post-transcriptional regulation of low density lipoprotein receptor protein by proprotein convertase subtilisin/kexin type 9a in mouse liver.

Rashid et al, Proc Natl Acad Sci USA. 2005 Apr. 12; 102(15): 5374-9. Epub 2005 Apr. 1, Decreased plasma cholesterol and hypersensitivity to statins in mice lacking Pcsk9.

Kotowski et al, Am J Hum Genet. 2006 March; 78(3):410-22. Epub 2006 Jan. 20, A spectrum of PCSK9 alleles contributes to plasma levels of low-density lipoprotein cholesterol.

Chen et al, J Am Coll Cardiol. 2005 May 17; 45(10):1611-9. Epub 2005 Apr. 21, A common PCSK9 haplotype, encompassing the E670G coding single nucleotide polymorphism, is a novel genetic marker for plasma low-density lipoprotein cholesterol levels and severity of coronary atherosclerosis.

Pisciotta et al, Atherosclerosis. 2006 June; 186(2):433-40. Epub 2005 Sep. 23, Additive effect of mutations in LDLR and PCSK9 genes on the phenotype of familial hypercholesterolemia.

Zhao et al, Am J Hum Genet. 2006 September; 79(3):514-23. Epub 2006 Jul. 18, Molecular characterization of loss-of-function mutations in PCSK9 and identification of a compound heterozygote.

Seidah et al, Proc Natl Acad Sci USA. 2003 Feb. 4; 100(3): 928-33. Epub 2003 Jan. 27, The secretory proprotein convertase neural apoptosis-regulated convertase 1 (NARC-1): liver regeneration and neuronal differentiation.

Example 2

IL4 Receptor Alpha (IL4Ra; CD124)

Interleukin-4 (IL-4, also known as B cell stimulating factor or BSF-1) was originally characterized by its ability to stimulate the proliferation of B cells in response to low concentrations of antibodies directed to surface immunoglobulin. IL-4 has been shown to possess a broad spectrum of biological activities, including growth stimulation of T cells, mast cells, granulocytes, megakaryocytes and erythrocytes. IL-4 induces the expression of class II major histocompatibility complex molecules in resting B cells, and enhances the secretion of IgE and IgG1 isotypes by stimulated B cells In an example, the invention provides a method of treating or reducing the risk of an IL4Ra-mediated disease or condition in a human in need thereof, the method comprising administering to said human a ligand (eg, an antibody or antibody fragment) that specifically binds a human IL4RA protein. The invention also provides a corresponding ligand.

The present invention provides anti-IL4Ra ligands; and IL4Ra-binding or targeting ligands as described herein. The ligands have a variety of utilities. Some of the ligands, for instance, are useful in specific binding assays, for genotyping or phenotyping humans, affinity purification of IL4Ra, in particular human IL4Ra or its ligands and in screening assays to identify other antagonists of IL4Ra activity. Some of the ligands of the invention are useful for inhibiting binding of IL4Ra to IL4, or inhibiting IL4Ra-mediated activities.

Anti-IL4Ra ligands (eg, antibodies and anti-sense RNA) have been developed based on targeting and neutralising so-called "wild-type" human IL4Ra, which is a commonly-occurring form (see, eg, SEQ ID NO: 67). While such therapies are useful for human patients harbouring this form of human IL4RA, the inventor considered it useful to investigate the possibility of targeting rarer—but still naturally-occurring—forms of IL4Ra amongst human populations. In this way, the inventor arrived at insight into the natural occurrences and distributions of rarer human IL4Ra forms that can serve as useful targets (at the protein or nucleic acid level) for human treatment, prophylaxis and diagnosis pertinent to diseases and conditions mediated or associated with IL4RA activity. This particularly provides for tailored therapies, prophylaxis and diagnosis in humans that are devoid of the common IL4Ra gene or protein.

The skilled person will know that SNPs or other changes that translate into amino acid variation can cause variability in activity and/or conformation of human targets to be addressed. This has spawned great interest in personalized medicine where genotyping and knowledge of protein and nucleotide variability is used to more effectively tailor medicines and diagnosis of patients. The invention, therefore, provides for tailored pharmaceuticals and testing that specifically addresses rarer IL4Ra polymorphic variant forms. Such forms or "alleles" (at the nucleotide level), comprise one or more changes at the nucleotide and amino acid levels from the corresponding common form nucleotide and amino acids sequences, ie, there are one or more non-synonymous changes at the nucleotide level that translate into one or more corresponding changes in the protein target in humans.

Furthermore, the inventor surprisingly realised that the rarer natural forms, although present in humans at much lower frequencies than the common form, nevertheless are represented in multiple and ethnically-diverse human populations and usually with many human examples per represented ethnic population. Thus, the inventor realised that targeting such rarer forms would provide for effective treatment, prophylaxis or diagnosis across many human ethnic populations, thereby extending the utility of the present invention.

With this realisation, the inventor realised that there is significant industrial and medical application for the invention in terms of guiding the choice of anti-IL4Ra ligand for administration to human patients for therapy and/or prophylaxis of IL4Ra-mediated or associated diseases or conditions. In this way, the patient receives drugs and ligands that are tailored to their needs—as determined by the patient's genetic or phenotypic makeup. Hand-in-hand with this, the invention provides for the genotyping and/or phenotyping of patients in connection with such treatment, thereby allowing a proper match of drug to patient. This increases the chances of medical efficacy, reduces the likelihood of inferior treatment using drugs or ligands that are not matched to the patient (eg, poor efficacy and/or side-effects) and avoids pharmaceutical mis-prescription and waste.

In developing this thinking, in this non-limiting example the present inventor decided to determine a set of human IL4Ra variants on the basis of the following criteria, these being criteria that the inventor realised would provide for useful medical drugs and diagnostics to tailored need in the human population. The inventor selected variants having at least 3 of the 4 following criteria:—

Naturally-occurring human IL4Ra variation having a cumulative human allele frequency of 35% or less;

Naturally-occurring human IL4Ra variation having a total human genotype frequency of about 50% or less;

Naturally-occurring human IL4Ra variation found in many different human ethnic populations (using the standard categorisation of the 1000 Genomes Project; see Table 2 below); and Naturally-occurring human IL4Ra variation found in many individuals distributed across such many different ethnic populations.

On the basis of these criteria, the inventor identified variants listed in Table 11 below. The inventor's selection included, as an additional or alternative consideration, selection for nucleotide variation that produced amino acid variation in corresponding IL4Ra forms (ie, non-synonymous variations), as opposed to silent variations that do not alter amino acid residues in the target protein.

In an example, the invention provides a method of treating or reducing the risk of an IL4Ra-mediated disease or condition in a human in need thereof, the method comprising administering to said human a ligand (eg, an antibody or antibody fragment) that specifically binds a human IL4RA protein that comprises a mutation selected from the group consisting of I75V, E400A, C431R, S503P, Q576R and S752A in SEQ ID NO: 67. As explained further below, these amino acid variations are found in naturally-occurring IL-4Ra variants in humans found in many populations. Said human comprises a nucleotide sequence encoding said IL4RA protein comprising said mutation selected from the group consisting of I75V, E400A, C431R, S503P, Q576R and S752A in SEQ ID NO: 67.

An example also provides a ligand (eg, an antibody or antibody fragment) for treating or reducing the risk of an IL4Ra-mediated disease or condition in a human in need thereof, the method comprising administering to said human said ligand, wherein the ligand specifically binds a human IL4RA protein that comprises a mutation selected from the group consisting of I75V, E400A, C431R, S503P, Q576R and S752A in SEQ ID NO: 67. Said human comprises a nucleotide sequence encoding said IL4RA protein comprising said mutation selected from the group consisting of I75V, E400A, C431R, S503P, Q576R and S752A in SEQ ID NO: 67.

In an example, the invention provides a method of targeting IL4Ra in a human, the method comprising administering to said human a ligand (eg, an antibody or antibody fragment) that specifically binds a human IL4RA protein that comprises a mutation selected from the group consisting of I75V, E400A, C431R, S503P, Q576R and S752A in SEQ ID NO: 67. Said human comprises a nucleotide sequence encoding said IL4RA protein comprising said mutation selected from the group consisting of I75V, E400A, C431R, S503P, Q576R and S752A in SEQ ID NO: 67. In an example, the human is suffering from or at risk of an IL4Ra-mediated disease or condition. In an example, the method treats or reduces the risk of an IL4Ra-mediated disease or condition in the human.

An example also provides a ligand (eg, an antibody or antibody fragment) for targeting IL4Ra in a human, the method comprising administering to said human said ligand, wherein the ligand specifically binds a human IL4RA protein that comprises a mutation selected from the group consisting of I75V, E400A, C431R, S503P, Q576R and S752A in SEQ ID NO: 67. Said human comprises a nucleotide sequence encoding said IL4RA protein comprising said mutation selected from the group consisting of I75V, E400A, C431R, S503P, Q576R and S752A in SEQ ID NO: 67. In an example, the human is suffering from or at risk of an IL4Ra-mediated disease or condition. In an example, the method treats or reduces the risk of an IL4Ra-mediated disease or condition in the human.

In an embodiment, (i) the antibody or fragment comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and wherein (ii) said human comprises a nucleotide sequence encoding said IL4RA protein comprising said mutation selected from the group consisting of I75V, E400A, C431R, S503P, Q576R and S752A in SEQ ID NO: 67.

Additionally or alternatively, in an embodiment, (i) the antibody or fragment comprises a human gamma-4 heavy chain constant region that comprises a Leu at position 189 shown in SEQ ID NO: 73 or an Arg at position 289 shown in SEQ ID NO: 73 and wherein said human comprises an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and wherein (ii) said human comprises a nucleotide sequence encoding said IL4RA protein comprising said mutation selected from the group consisting of I75V, E400A, C431R, S503P, Q576R and S752A in SEQ ID NO: 67.

The biological activities of IL-4 are mediated by specific cell surface receptors for IL-4. Human IL-4 receptor alpha (hIL-4Ra) is described in, for example, U.S. Pat. Nos. 5,599,905, 5,767,065, and 5,840,869. Antibodies to hIL-4R are described in U.S. Pat. No. 5,717,072.

Methods for using antibodies to hIL-4R are described in U.S. Pat. Nos. 5,714,146; 5,985,280; and 6,716,587.

The human IL-4Ra (aka IL-4Ra) subunit (Swiss Prot accession number P24394) is a 140 kDa type 1 membrane protein that binds human IL-4 with a high affinity (Andrews et al J. Biol. Chem. (2002) 277:46073-46078). The IL-4/IL-4Ra complex can dimerize with either the common gamma chain (γc, CD132) or the IL-13Ralpha1 (IL-13Rα1) subunit, via domains on IL-4, to create two different signalling complexes, commonly referred to as Type I and Type II receptors, respectively. Alternatively, IL-13 can bind IL-13Rα1 to form an IL-13/IL-13Rα1 complex that recruits the IL-4Ra subunit to form a Type II receptor complex. Thus, IL-4Ra mediates the biological activities of both IL-4 and IL-13 (reviewed by Gessner et al, Immunobiology, 201:285, 2000). In vitro studies have shown that IL-4 and IL-13 activate effector functions in a number of cell types, for example in T cells, B cells, eosinophils, mast cells, basophils, airway smooth muscle cells, respiratory epithelial cells, lung fibroblasts, and endothelial cells (reviewed by Steinke et al, Resp Res, 2:66, 2001, and by Willis-Karp, Immunol Rev, 202:175, 2004).

IL-4 by binding to its receptor (IL-4R) is essential for the development of airway inflammation present in asthma, through the induction of IgE synthesis in B cells and differentiation of T cells to a Th2 phenotype. Dupilumab is a monoclonal antibody designed for the treatment of atopic diseases. It binds to the alpha subunit of the interleukin-4 receptor. Through blockade of IL-4R alpha, dupilumab modulates signaling of both the IL-4 and IL-13 pathway, which have been implicated in the pathophysiology of allergic disease. Anti-IL4Ra ligands, antibodies and fragments according to the invention can, for example, be used for treating or reducing the risk of allergic disease.

In an example, the ligand, antibody or fragment is for treating or reducing the risk of (or treats or reduces the risk of) allergic asthma, eosinophilic asthma or atopic dermatitis, optionally wherein the antibody is dupilumab.

In addition to its role in asthma, IL-4Ra has been linked with a number of other pathologies, e.g. as follows (anti-IL4Ra ligands, antibodies and fragments according to the invention can, for example, be used for treating or reducing the risk of any one of these diseases or conditions):

Chronic Obstructive Pulmonary Disease (COPD) includes patient populations with varying degrees of chronic bronchitis, small airway disease and emphysema and is characterised by progressive irreversible lung function decline that responds poorly to current asthma based therapy. The underlying causes of COPD remain poorly understood. The "Dutch hypothesis" proposes that there is a common susceptibility to COPD and asthma and therefore, that similar mechanisms may contribute to the pathogenesis of both disorders (Sluiter et al., Eur Respir J,). Zheng et al (J Clin Invest, 106(9): 1081-93, 2000) have demonstrated that overexpression of IL-13 in the mouse lung caused emphysema, elevated mucus production and inflammation, reflecting aspects of human COPD. Furthermore, AHR, an IL-13 dependent response in murine models of allergic inflammation, has been shown to be predictive of lung function decline in smokers (Tashkin et al., Am J Respir Crit. Care Med, 153 (6 Pt 1):1802-11, 1996). A link has also been established between an IL-13 promoter polymorphism and susceptibility to develop COPD (Van Der Pouw Kraan et al., Genes Immun, 3(7): 436-9, 2002). The signs are therefore that IL-4/IL-13 pathway, and in particular IL-13, plays an important role in the pathogenesis of COPD.

In addition to asthma, the IL-4/11-13 pathway has been linked to other fibrotic conditions, like systemic sclerosis (Hasegawa et al., J Rheumatol, 24(2):328-32, 1997), pulmonary fibrosis (Hancock et al., Am J Respir Cell Mol Biol, 18(1): 60-5, 1998), parasite-induced liver fibrosis (Fallon et al., J Immunol, 164 (5): 2585-91, 2000; Chiaramonte et al., J Clin Invest, 104(6): 777-85, 1999; Chiaramonte Hepatology 34 (2):273-82, 2001), and cystic fibrosis (Hauber et al., J. Cyst Fibr, 2:189, 2003).

IL-4 and to some extent IL-13, are crucial for B cell mediated activities, such as B cell proliferation, immunoglobulin secretion, and expression of FcepsilonR. Clinical applications of an IL-4Ra inhibitor include for example, use in allergy therapy to suppress IgE synthesis (including for example atopic dermatitis and food allergy), use in transplantation therapy to prevent transplant rejection, as well as suppression of delayed-type hypersensitivity or contact hypersensitivity reactions.

Il-4R antagonists may also find use as adjuvants to allergy immunotherapy and as vaccine adjuvants.

IL-4Ra polymorphisms in the human population have been described (reviewed by Gessner et al, Immunobiology, 201: 285, 2000) and association with IgE levels or clinical atopy has been reported in some populations. For instance, V75R576 IL-4Rα is associated with allergic asthma and enhanced IL-4Rα function (Risma et al. J. Immunol. 169(3): 1604-1610, 2002).

Anti-IL4Ra ligands, antibodies and fragments according to the invention optionally neutralise IL-4Ra with high potency, for example as described in more detail in the Examples of EP2604628. Neutralisation means inhibition of a biological activity mediated by IL-4Ra. Ligands, antibodies and fragments according to the invention may neutralise one or more activities mediated by IL-4Ra. The inhibited biological activity is likely mediated by prevention of IL-4Ra forming a signalling complex with gamma chain (or IL-13Ra) and either of the associated soluble ligands, e.g. IL-4 or IL-13.

Neutralisation of IL-4 or IL-13 signalling through its IL-4Ra containing receptor complex may be measured by inhibition of IL-4 or IL-13 stimulated TF-1 cell proliferation.

The ligand, antibody or fragment according to the invention is, for example, dupilumab or any one disclosed in WO 08/054,606 (Regeneron), EP2604628 (Medimmune), WO 01/92340 (immnunex) or WO 05/047331 (Immunex), the disclosures of which (including the sequences, eg, VH, VL and heavy and light chain sequences) are incorporated herein by reference for potential inclusion in one or more claims herein. According to a further aspect of the ligand, antibody or fragment according to the invention is capable of binding human interleukin-4 receptor alpha (hIL-4Ra) and cynomolgus monkey interleukin-4 receptor alpha (cyIL-4Ra). Cynomolgus IL-4Ra cDNA sequence is shown as SEQ ID NO: 455 EP2604628. In a particular embodiment the antibody or fragment is a human antibody or fragment. The ligand, antibody or fragment according to the invention is an antibody or fragment, for example, that comprises a VH and/or VL of dupilumab, or comprises a heavy and/or light chain of dupilumab. In one embodiment, the ligand, antibody or fragment comprises a VH domain comprising SEQ ID NO: 69. In one embodiment, the ligand, antibody or fragment comprises a VL domain comprising SEQ ID NO: 70. In one embodiment, the ligand, antibody or fragment comprises a heavy chain comprising SEQ ID NO: 71. In one embodiment, the ligand, antibody or fragment comprises a light chain comprising SEQ ID NO: 72.

In a specific embodiment, the ligand, antibody or fragment of present invention comprises an Fc region, wherein the Fc region comprises at least one non-native amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241R. 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non-native amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

The ligand, antibody or fragment according to the invention is for treating or preventing or reducing the risk of (or treats or prevents or reduces the risk of), for example, any disease or condition disclosed in any of WO 08/054,606 (Regeneron), EP2604628 (Medimmune), WO 01/92340 (immunex) and WO 05/047331 (Immunex), the disclosures of which diseases and conditions are incorporated herein by reference for potential inclusion in one or more claims herein.

Further encompassed by the invention is the use of the ligand, antibody or fragment of an in the manufacture of a medicament for use to attenuate or inhibit an IL-4Ra-mediated disease or disorder in a human. IL-4Ra-mediated or related disorders which are treated by the ligand, antibody or fragment of the invention include, for example, arthritis (including septic arthritis), herpetiformis, chronic idiopathic urticaria, scleroderma, hypertrophic scarring, Whipple's Disease, benign prostate hyperplasia, lung disorders, such as mild, moderate or severe asthma, inflammatory disorders such as inflammatory bowel disease, allergic reactions, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, and nephrosis.

Particular conditions for which a ligand, antibody or fragment of the invention may be used in treatment or diagnosis include: asthma, COPD (eg, chronic bronchitis, small airway disease or emphysema), inflammatory bowel disease, a fibrotic condition (eg, systemic sclerosis, pulmonary fibrosis, parasite-induced liver fibrosis, or cystic fibrosis), allergy (for example atopic dermatitis, dust mite allergy, pet allergy or food allergy), transplation therapy to prevent transplant rejection, suppression of a delayed-type hypersensitivity or a contact hypersensitivity reaction, as an adjuvant to allergy immunotherapy or as a vaccine adjuvant.

Thus, a ligand, antibody or fragment of the invention is useful as a therapeutic agent in the treatment of a condition involving IL-4, IL-13 or IL-4Ra expression and/or activity. One embodiment, among others, is a method of treatment comprising administering an effective amount of a ligand, antibody or fragment of the invention to a patient in need thereof, wherein functional consequences of IL-4Ra activation are decreased. Another embodiment, among others, is a method of treatment comprising (i) identifying a patient demonstrating IL-4, IL-13 or IL-4Ra expression or activity, and (ii) administering an effective amount of a ligand, antibody or fragment of the invention to the patient, wherein a functional consequence of IL-4Ra activation are attenuated. An effective amount according to the invention is an amount that modulates (e.g. decreases) the functional consequences of IL-4Ra activation so as to modulate (e.g. decrease or lessen) the severity of at least one symptom of the particular disease or disorder being treated, but not necessarily cure the disease or disorder. Accordingly, one embodiment of the invention is a method of treating or reducing the severity of at least one symptom of any of the disorders referred to herein, comprising administering to a patient in need thereof an effective amount of one or more ligands, antibodies or fragments of the present invention alone or in a combined therapeutic regimen with another appropriate medicament known in the art or described herein such that the severity of at least one symptom of any of the disorders is reduced. Another embodiment of the invention, among others, is a method of antagonizing at least one effect of IL-4Ra comprising contacting with or administering an effective amount of one or more ligands, antibodies or fragments of the present invention such that said at least one effect of IL-4Ra is antagonized, e.g. the ability of IL-4Ra to form a complex (the precursor to active signalling) with IL-4.

A ligand, antibody or fragment of the invention can, in an example, be used in combination with another therapeutic agent for the treatment of cancer. Suitable agents to be used in combination include those disclosed in EP2604628 (eg, in paragaraph [0287]), which disclosure is incorporated herein by reference.

Tailoring Antibodies to Rarer IL4Ra Variant Profile

As outlined herein (for example, in the context of PCSK9 in Example 1), the invention includes the possibility to tailor treatment of humans further by selecting antibody-based ligands with variable domains and/or constant domains based on gene segments found in many humans of the ethnic populations where the variant TOI forms are found to meet the selection criteria of the invention. This also applies mutatis mutandis where the TOI is human IL4Ra, as in the present example. Thus, all disclosure herein relating to tailoring variable and/or constant domains apply to the present example, relating to IL4Ra and is combinable for use in one or more claims herein.

As described in Example 1, an example is provided for ligands comprising antibody VH domains derived from recombination of human IGHV gene segments comprising selected nucleotides at positions in the HCDR1 or FW3 where there is variability in humans (ie, where SNPs occur in humans).

Further information is provided in Table 4, which shows variation at these positions, as well as the variant distributions across the 1000 Genomes Project database relating to many human populations.

In other embodiments, as explained more fully above, the invention provides for ligands which are tailored to the human recipient's genotype and/or phenotype based on alternative human VH gene segments, or on Vκ, Vλ or constant region gene segments (see further Table 9 for representative variants).

In an example, following this guidance, the chosen ligand is dupilumab.

Further examples, therefore are:—

(i) wherein the ligand comprises a VH domain derived from the recombination of a human VH segment (eg, human VH3-23*04), a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40.

(ii) wherein the ligand comprises a VH domain derived from the recombination of human VH segment IGHV3-7*01, a human D gene segment and a human JH segment, and wherein said human comprises a IGHV3-7*01 VH gene segment or the human expresses VH domains derived from the recombination of human VH segment IGHV3-7*01, a human D gene segment and a human JH segment.

(iii) wherein the ligand comprises a Vκ domain derived from the recombination of human Vi segment IGKV1-12*01 and a human Jκ segment, and wherein said human comprises a IGKV1-12*01 Vκ gene segment or the human expresses Vκ domains derived from the recombination of human Vi segment IGKV1-12*01 and a human Jκ segment.

(iv) wherein the ligand comprises a Vκ domain derived from the recombination of a human Vi segment and a human Jκ segment, the human Vκ segment encoding (i) a CDR3 comprising a Pro at position 7 shown in SEQ ID NO: 36 and wherein said human comprises a Vκ gene segment encoding a CDR3 comprising a Pro at position 7 shown in SEQ ID NO: 36, or the human expresses Vκ domains that comprise a CDR3 comprising a Pro at position 7 shown in SEQ ID NO: 36; or (ii) a FW3 comprising a Ser at position 15 shown in SEQ ID NO: 38 and wherein said human comprises a Vκ gene segment encoding a FW3 comprising a Ser at position 15 shown in SEQ ID NO: 38 or the human expresses Vκ domains that comprise a FW3 comprising a Ser at position 15 shown in SEQ ID NO: 38.

(v) wherein the ligand comprises a human gamma-1 heavy chain constant region that comprises an Asp at position 204 shown in SEQ ID NO: 4 or a Leu at position 206 shown in SEQ ID NO: 4 and wherein said human comprises (i) an IGHG1*01 human heavy chain constant region gene segment, or the human expresses antibodies comprising human gamma-1 heavy chain constant regions comprising an Asp at position 204 shown in SEQ ID NO: 4 or a Leu at position 206 shown in SEQ ID NO: 4.

(vi) wherein the ligand comprises a human gamma-2 heavy chain constant region that comprises an amino acid selected from the group consisting of a Pro at position 72 shown in SEQ ID NO: 6, an Asn at position 75 shown in SEQ ID NO: 6, a Phe at position 76 shown in SEQ ID NO: 6, a Val at position 161 shown in SEQ ID NO: 6 and an Ala at position 257 shown in SEQ ID NO: 6 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 6, Asn at position 75 shown in SEQ ID NO: 6, Phe at position 76 shown in SEQ ID NO: 6, Val at position 161 shown in SEQ ID NO: 6 or Ala at position 257 shown in SEQ ID NO: 6.

(vii) wherein the ligand comprises a human kappa chain constant region that comprises a Val at position 84 shown in SEQ ID NO: 16 or a Cys at position 87 shown in SEQ ID NO: 16 and wherein said human comprises (i) an IGKC1*01 human heavy chain constant region gene segment, or the human expresses antibodies comprising human kappa chain constant regions comprising a Val corresponding to position 84 shown in SEQ ID NO: 16 or a Cys at position 87 shown in SEQ ID NO: 16 and (ii) a nucleotide sequence encoding said IL4RA protein comprising said Asp358Ala or Val385Ile in SEQ ID NO: 1.

(viii) wherein the ligand comprises a human IGLC1*01 lambda chain constant region and wherein said human comprises (i) a human IGLC1*01 lambda chain constant region gene segment, or the human expresses antibodies comprising human IGLC1*01 lambda chain constant regions.

(ix) wherein the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73.

For example, as per example (ix), the inventor identified the possibility of addressing IGH-gamma-4 variation and identified utility for variations 189L and 289R individually or in combination, since these residues are part of the CH3 domain, and as such they form part of antibody Fc regions. Thus, matching of these CH3 variations with the patient is especially beneficial for reasons as discussed above. Thus, in this example the ligand of the invention comprises or consists of an antibody that comprises a human gamma-4 heavy chain constant region that comprises a Leu corresponding to position 189 of SEQ ID NO: 73 or an Arg corresponding to position 289 of SEQ ID NO: 73 and wherein the genome of the human comprises a gamma-4 heavy chain constant region nucleotide sequence that encodes such a Leu and/or Arg or the human expresses antibodies comprising human gamma-4 constant regions comprising such a Leu and/or Arg. An example of such a ligand is dupilumab.

Determination of Specific Binding of Ligands of the Invention to IL4RA Variants

The specific binding of Ligands of the invention to IL4Ra variants can be performed using the SPR method described in Example 1.

Embodiments are provided as follows:—
Methods with VH Tailoring

1. A method of treating or reducing the risk of an IL4Ra-mediated disease or condition in a human in need thereof, the method comprising administering to said human a ligand (eg, an antibody or antibody fragment) that specifically binds a human IL4Ra protein that comprises a mutation selected from the group consisting of I75V, E400A, C431R, S503P, Q576R and S752A in SEQ ID NO: 67;
wherein (i) the ligand comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and
wherein (ii) said human comprises a nucleotide sequence encoding said IL4RA protein comprising said mutation selected from the group consisting of I75V, E400A, C431R, S503P, Q576R and S752A in SEQ ID NO: 67.

In an alternative, clause 1 provides:—
A method of targeting IL4Ra in a human, the method comprising administering to said human a ligand (eg, an antibody or antibody fragment) that specifically binds a human IL4Ra protein that comprises a mutation selected from the group consisting of I75V, E400A, C431R, S503P, Q576R and S752A in SEQ ID NO: 67;
wherein (i) the ligand comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and
wherein (ii) said human comprises a nucleotide sequence encoding said IL4RA protein comprising said mutation selected from the group consisting of I75V, E400A, C431R, S503P, Q576R and S752A in SEQ ID NO: 67.

In an example, the human is suffering from or at risk of an IL4Ra-mediated disease or condition. In an example, the method treats or reduces the risk of an IL4Ra-mediated disease or condition in the human.

In an example of the method or ligand of the invention, the IL4Ra comprises mutation I75V.

In an example of the method or ligand of the invention, the IL4Ra comprises mutation E400A.

In an example of the method or ligand of the invention, the IL4Ra comprises mutation C431R.

In an example of the method or ligand of the invention, the IL4Ra comprises mutation S503P.

In an example of the method or ligand of the invention, the IL4Ra comprises mutation Q576R.

In an example of the method or ligand of the invention, the IL4Ra comprises mutation S752A.

2. The method of clause 1, wherein the IL4Ra comprises mutations I75V and Q576R in SEQ ID NO: 67 and optionally the disease is asthma.

Q576R and I75V are associated with airway inflammation disease, eg, asthma. For example, see Clin Exp Allergy. 2003 August; 33 (8): 1111-7, "Polymorphisms in the interleukin-4 and interleukin-4 receptor alpha chain genes confer susceptibility to asthma and atopy in a Caucasian population", Beghé B et al (referring to I75V instead as I50V); J Asthma. 2010 April; 47 (3):238-44. doi: 10.3109/02770900903509099, "Association and gene-gene interactions of eight common single-nucleotide polymorphisms with pediatric asthma in middle china", Wu X et al; Clin Exp Allergy. 2004 October; 34(10): 1570-5, "Haplotypes of the interleukin-4 receptor alpha chain gene associate with susceptibility to and severity of atopic asthma", Hytinen A M et al, all incorporated herein by reference.

3. The method of clause 1 or 2, wherein the nucleotide sequence of (ii) comprises nucleotide mutation—3223T (dB SNP numbering).

This variation is associated with airway inflammation disease, eg, asthma.

4. The method of any preceding clause, wherein each said human VH gene segment comprises SEQ ID NO: 39.

5. The method of any preceding clause, wherein the VH gene segment comprised by said human is a germline VH gene segment.

6. The method of any preceding clause comprising, before said administering, selecting a human comprising said nucleotide sequence of (ii), wherein the human is the human of clause 1.

7. The method of any preceding clause, wherein the human has been determined to comprise the nucleotide sequence that encodes an IL4Ra protein comprising said mutation selected from the group consisting of I75V, E400A, C431R, S503P, Q576R and S752A in SEQ ID NO: 67 and/or an IL4Ra protein comprising said mutation selected from the group consisting of I75V, E400A, C431R, S503P, Q576R and S752A in SEQ ID NO: 67.

8. The method of any preceding clause, comprising the step of determining that the human comprises (a) the nucleotide sequence that encodes an IL4Ra protein comprising said mutation selected from the group consisting of I75V, E400A, C431R, S503P, Q576R and S752A in SEQ ID NO: 67 and/or (b) an IL4Ra protein comprising said mutation said mutation selected from the group consisting of I75V, E400A, C431R, S503P, Q576R and S752A in SEQ ID NO: 67, optionally, wherein the determining step is performed before administration of the antibody to the human.

9. The method of clause 8, wherein the step of determining comprises assaying a biological sample from the human for a nucleotide sequence encoding a IL4Ra protein comprising said mutation selected from the group consisting of I75V, E400A, C431R, S503P, Q576R and S752A in SEQ ID NO: 67.

10. The method of clause 9, wherein the assaying comprises contacting the biological sample with at least one oligonucleotide probe comprising a sequence of at least 10 contiguous nucleotides of a nucleotide sequence encoding an IL4Ra protein comprising said mutation selected from the group consisting of I75V, E400A, C431R, S503P, Q576R and S752A in SEQ ID NO: 67 or comprising an antisense sequence of said contiguous nucleotides, wherein said sequence of contiguous nucleotides comprises a nucleotide sequence encoding said mutation selected from the group consisting of I75V, E400A, C431R, S503P, Q576R and S752A in SEQ ID NO: 67, thereby forming a complex when at least one nucleotide sequence encoding the IL4Ra protein comprising said mutation selected from the group consisting of I75V, E400A, C431R, S503P, Q576R and S752A in SEQ ID NO: 67 is present; and detecting the presence or absence of the complex, wherein detecting the presence of the complex determines that the human comprises the IL4Ra protein comprising said mutation selected from the group consisting of I75V, E400A, C431R, S503P, Q576R and S752A in SEQ ID NO: 67.

11. The method of clause 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The method of clause 9 or 11, wherein said biological sample comprises serum, blood, faeces, tissue, a cell, urine and/or saliva of said human.

13. The method of any preceding clause, wherein said human is indicated as heterozygous for a nucleotide sequence encoding the IL4Ra protein comprising said mutation selected from the group consisting of I75V, E400A, C431R, S503P, Q576R and S752A in SEQ ID NO: 67, optionally, wherein said human is further indicated as comprising the nucleotide sequence of SEQ ID NO: 68, or said human is indicated as homozygous for a nucleotide sequence encoding the IL4Ra protein comprising said mutation selected from the group consisting of I75V, E400A, C431R, S503P, Q576R and S752A in SEQ ID NO: 67.

14. The method of any preceding clause, wherein said human is or has been further determined to be substantially resistant to an asthma treatment.

15. The method of any preceding clause, wherein said human is receiving or has received an asthma treatment or has reduced responsiveness to an asthma treatment.

16. The method of any preceding clause, wherein said disease or condition is an inflammatory disease or condition; an atopic disease or condition; a respiratory disease or condition; a disease or condition associated with elevated IgE; or a disease or condition associated with elevated IL-4 and/or IL-13 activity.

17. The method of any preceding clause, wherein said disease or condition is selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.

18. The method of any preceding clause, wherein said human has been diagnosed with at least one condition selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.

19. The method of any preceding clause, wherein said antibody or antibody fragment treats or reduces the risk in said human of at least one condition selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis 20. The method of any preceding clause, wherein the nucleotide sequence comprises one or more SNPs selected from the group consisting of rs1805010, rs1805011, rs1805012, rs1805015, rs1801275 and rs1805016.

21. The method of any preceding clause, wherein said antibody or antibody fragment is administered by inhaled, intravenous or subcutaneous administration and/or is comprised in an inhalable or injectable preparation.

22. The method of any preceding clause, wherein the VH domain comprises the amino acid sequence of SEQ ID NO: 69.

Ligands with VH Tailoring

1. A ligand (eg, an antibody or antibody fragment) for use in a method of treating or reducing the risk of an IL4Ra-mediated disease or condition (eg, asthma) in a human in need thereof, wherein the ligand specifically binds a human IL4RA protein that comprises a mutation selected from the group consisting of I75V, E400A, C431R, S503P, Q576R and S752A in SEQ ID NO: 67;
   wherein (i) the ligand comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and
   wherein (ii) said human comprises a nucleotide sequence encoding said IL4RA protein comprising said mutation selected from the group consisting of I75V, E400A, C431R, S503P, Q576R and S752A in SEQ ID NO: 67.

In an alternative, paragraph 1 provides:—
A ligand (eg, an antibody or antibody fragment) for use in a method of targeting IL4Ra in a human, wherein the ligand specifically binds a human IL4RA protein that comprises a mutation selected from the group consisting of I75V, E400A, C431R, S503P, Q576R and S752A in SEQ ID NO: 67;
   wherein (i) the ligand comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and
   wherein (ii) said human comprises a nucleotide sequence encoding said IL4RA protein comprising said mutation selected from the group consisting of I75V, E400A, C431R, S503P, Q576R and S752A in SEQ ID NO: 67.
   In an example, the human is suffering from or at risk of an IL4Ra-mediated disease or condition.
   In an example, the method treats or reduces the risk of an IL4Ra-mediated disease or condition in the human.

2. The ligand of paragraph 1, wherein the IL4Ra comprises mutations I75V and Q576R in SEQ ID NO: 67 and optionally the disease is asthma.

3. The ligand of paragraph 1 or 2, wherein the nucleotide sequence of (ii) comprises nucleotide mutation—3223T (dB SNP numbering).

4. The ligand of any preceding paragraph, wherein each said human VH gene segment comprises SEQ ID NO: 39.

5. The ligand of any preceding paragraph, wherein the VH gene segment comprised by said human is a germline VH gene segment.
6. The ligand of any preceding paragraph, said method comprising, before said administering, selecting a human comprising said nucleotide sequence of (ii), wherein the human is the human of paragraph 1.
7. The ligand of any preceding paragraph, wherein the human has been determined to comprise the nucleotide sequence that encodes an IL4Ra protein comprising said mutation selected from the group consisting of I75V, E400A, C431R, S503P, Q576R and S752A in SEQ ID NO: 67 and/or an IL4Ra protein comprising said mutation selected from the group consisting of I75V, E400A, C431R, S503P, Q576R and S752A in SEQ ID NO: 67.
8. The ligand of any preceding paragraph, said method comprising the step of determining that the human comprises (a) the nucleotide sequence that encodes an IL4Ra protein comprising said mutation selected from the group consisting of I75V, E400A, C431R, S503P, Q576R and S752A in SEQ ID NO: 67 and/or (b) an IL4Ra protein comprising said mutation said mutation selected from the group consisting of I75V, E400A, C431R, S503P, Q576R and S752A in SEQ ID NO: 67, optionally, wherein the determining step is performed before administration of the antibody to the human.
9. The ligand of paragraph 8, wherein the step of determining comprises assaying a biological sample from the human for a nucleotide sequence encoding a IL4Ra protein comprising said mutation selected from the group consisting of I75V, E400A, C431R, S503P, Q576R and S752A in SEQ ID NO: 67.
10. The ligand of paragraph 9, wherein the assaying comprises
    contacting the biological sample with at least one oligonucleotide probe comprising a sequence of at least 10 contiguous nucleotides of a nucleotide sequence encoding an IL4Ra protein comprising said mutation selected from the group consisting of I75V, E400A, C431R, S503P, Q576R and S752A in SEQ ID NO: 67 or comprising an antisense sequence of said contiguous nucleotides, wherein said sequence of contiguous nucleotides comprises a nucleotide sequence encoding said mutation selected from the group consisting of I75V, E400A, C431R, S503P, Q576R and S752A in SEQ ID NO: 67, thereby forming a complex when at least one nucleotide sequence encoding the IL4Ra protein comprising said mutation selected from the group consisting of I75V, E400A, C431R, S503P, Q576R and S752A in SEQ ID NO: 67 is present; and
    detecting the presence or absence of the complex, wherein detecting the presence of the complex determines that the human comprises the IL4Ra protein comprising said mutation selected from the group consisting of I75V, E400A, C431R, S503P, Q576R and S752A in SEQ ID NO: 67.
11. The ligand of paragraph 9, wherein the assaying comprises nucleic acid amplification and optionally one or more methods selected from sequencing, next generation sequencing, nucleic acid hybridization, and allele-specific amplification and/or wherein the assaying is performed in a multiplex format.
12. The ligand of paragraph 9 or 11, wherein said biological sample comprises serum, blood, faeces, tissue, a cell, urine and/or saliva of said human.
13. The ligand of any preceding paragraph, wherein said human is indicated as heterozygous for a nucleotide sequence encoding the IL4Ra protein comprising said mutation selected from the group consisting of I75V, E400A, C431R, S503P, Q576R and S752A in SEQ ID NO: 67, optionally, wherein said human is further indicated as comprising the nucleotide sequence of SEQ ID NO: 68, or said human is indicated as homozygous for a nucleotide sequence encoding the IL4Ra protein comprising said mutation selected from the group consisting of I75V, E400A, C431R, S503P, Q576R and S752A in SEQ ID NO: 67.
14. The ligand of any preceding paragraph, wherein said human is or has been further determined to be substantially resistant to an asthma treatment.
15. The ligand of any preceding paragraph, wherein said human is receiving or has received an asthma treatment or has reduced responsiveness to an asthma treatment.
16. The ligand of any preceding paragraph, wherein said disease or condition is an inflammatory disease or condition; an atopic disease or condition; a respiratory disease or condition; a disease or condition associated with elevated IgE; or a disease or condition associated with elevated IL-4 and/or IL-13 activity.
17. The ligand of any preceding paragraph, wherein said disease or condition is selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.
18. The ligand of any preceding paragraph, wherein said human has been diagnosed with at least one condition selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.
19. The ligand of any preceding paragraph, wherein said antibody or antibody fragment treats or reduces the risk in said human of at least one condition selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis
20. The ligand of any preceding paragraph, wherein the nucleotide sequence comprises one or more SNPs selected from the group consisting of rs1805010, rs1805011, rs1805012, rs1805015, rs1801275 and rs1805016.
21. The ligand of any preceding paragraph, wherein said antibody or antibody fragment is for inhaled, intravenous or subcutaneous administration and/or is comprised in an inhalable or injectable preparation.
22. The ligand of any preceding paragraph, wherein the VH domain comprises the amino acid sequence of SEQ ID NO: 69.

Methods with C Region Tailoring

1. A method of treating or reducing the risk of an IL4Ra-mediated disease or condition in a human in need thereof, the method comprising administering to said human a ligand (eg, an antibody or antibody fragment) that specifically binds a human IL4Ra protein that comprises a mutation selected from the group consisting of I75V, E400A, C431R, S503P, Q576R and S752A in SEQ ID NO: 67;
wherein the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and
wherein (ii) said human comprises a nucleotide sequence encoding said IL4RA protein comprising said mutation selected from the group consisting of I75V, E400A, C431R, S503P, Q576R and S752A in SEQ ID NO: 67.
In an alternative, clause 1 provides:—
A method of targeting IL4Ra in a human, the method comprising administering to said human a ligand (eg, an antibody or antibody fragment) that specifically binds a human IL4Ra protein that comprises a mutation selected from the group consisting of I75V, E400A, C431R, S503P, Q576R and S752A in SEQ ID NO: 67;
wherein the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and
wherein (ii) said human comprises a nucleotide sequence encoding said IL4RA protein comprising said mutation selected from the group consisting of I75V, E400A, C431R, S503P, Q576R and S752A in SEQ ID NO: 67.
In an example, the human is suffering from or at risk of an IL4Ra-mediated disease or condition.
In an example, the method treats or reduces the risk of an IL4Ra-mediated disease or condition in the human.
In an example of the method or ligand of the invention, the IL4Ra comprises mutation I75V.
In an example of the method or ligand of the invention, the IL4Ra comprises mutation E400A.
In an example of the method or ligand of the invention, the IL4Ra comprises mutation C431R.
In an example of the method or ligand of the invention, the IL4Ra comprises mutation S503P.
In an example of the method or ligand of the invention, the IL4Ra comprises mutation Q576R.
In an example of the method or ligand of the invention, the IL4Ra comprises mutation S752A.
2. The method of clause 1, wherein the IL4Ra comprises mutations I75V and Q576R in SEQ ID NO: 67 and optionally the disease is asthma.
3. The method of clause 1 or 2, wherein the nucleotide sequence of (ii) comprises nucleotide mutation—3223T (dB SNP numbering).
4. The method of any preceding clause, wherein said human gamma-4 heavy chain constant region that comprises SEQ ID NO: 73.
5. The method of any preceding clause, wherein the human expresses antibodies comprising human IGHG4*01 heavy chain constant regions.
6. The method of any preceding clause comprising, before said administering, selecting a human comprising said nucleotide sequence of (ii), wherein the human is the human of clause 1.
7. The method of any preceding clause, wherein the human has been determined to comprise the nucleotide sequence that encodes an IL4Ra protein comprising said mutation selected from the group consisting of I75V, E400A, C431R, S503P, Q576R and S752A in SEQ ID NO: 67 and/or an IL4Ra protein comprising said mutation selected from the group consisting of I75V, E400A, C431R, S503P, Q576R and S752A in SEQ ID NO: 67.
8. The method of any preceding clause, comprising the step of determining that the human comprises (a) the nucleotide sequence that encodes an IL4Ra protein comprising said mutation selected from the group consisting of I75V, E400A, C431R, S503P, Q576R and S752A in SEQ ID NO: 67 and/or (b) an IL4Ra protein comprising said mutation selected from the group consisting of I75V, E400A, C431R, S503P, Q576R and S752A in SEQ ID NO:

67, optionally, wherein the determining step is performed before administration of the antibody to the human.

9. The method of clause 8, wherein the step of determining comprises assaying a biological sample from the human for a nucleotide sequence encoding a IL4Ra protein comprising said mutation selected from the group consisting of I75V, E400A, C431R, S503P, Q576R and S752A in SEQ ID NO: 67.

10. The method of clause 9, wherein the assaying comprises contacting the biological sample with at least one oligonucleotide probe comprising a sequence of at least 10 contiguous nucleotides of a nucleotide sequence encoding an IL4Ra protein comprising said mutation selected from the group consisting of I75V, E400A, C431R, S503P, Q576R and S752A in SEQ ID NO: 67 or comprising an antisense sequence of said contiguous nucleotides, wherein said sequence of contiguous nucleotides comprises a nucleotide sequence encoding said mutation selected from the group consisting of I75V, E400A, C431R, S503P, Q576R and S752A in SEQ ID NO: 67, thereby forming a complex when at least one nucleotide sequence encoding the IL4Ra protein comprising said mutation selected from the group consisting of I75V, E400A, C431R, S503P, Q576R and S752A in SEQ ID NO: 67 is present; and detecting the presence or absence of the complex, wherein detecting the presence of the complex determines that the human comprises the IL4Ra protein comprising said mutation selected from the group consisting of I75V, E400A, C431R, S503P, Q576R and S752A in SEQ ID NO: 67.

11. The method of clause 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The method of clause 9 or 11, wherein said biological sample comprises serum, blood, faeces, tissue, a cell, urine and/or saliva of said human.

13. The method of any preceding clause, wherein said human is indicated as heterozygous for a nucleotide sequence encoding the IL4Ra protein comprising said mutation selected from the group consisting of I75V, E400A, C431R, S503P, Q576R and S752A in SEQ ID NO: 67, optionally, wherein said human is further indicated as comprising the nucleotide sequence of SEQ ID NO: 68, or said human is indicated as homozygous for a nucleotide sequence encoding the IL4Ra protein comprising said mutation selected from the group consisting of I75V, E400A, C431R, S503P, Q576R and S752A in SEQ ID NO: 67.

14. The method of any preceding clause, wherein said human is or has been further determined to be substantially resistant to an asthma treatment.

15. The method of any preceding clause, wherein said human is receiving or has received an asthma treatment or has reduced responsiveness to an asthma treatment.

16. The method of any preceding clause, wherein said disease or condition is an inflammatory disease or condition; an atopic disease or condition; a respiratory disease or condition; a disease or condition associated with elevated IgE; or a disease or condition associated with elevated IL-4 and/or IL-13 activity.

17. The method of any preceding clause, wherein said disease or condition is selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.

18. The method of any preceding clause, wherein said human has been diagnosed with at least one condition selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.

19. The method of any preceding clause, wherein said antibody or antibody fragment treats or reduces the risk in said human of at least one condition selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis 20. The method of any preceding clause, wherein the nucleotide sequence comprises one or more SNPs selected from the group consisting of rs1805010, rs1805011, rs1805012, rs1805015, rs1801275 and rs1805016.

21. The method of any preceding clause, wherein said antibody or antibody fragment is administered by inhaled, intravenous or subcutaneous administration and/or is comprised in an inhalable or injectable preparation.

Ligands with Constant Region Tailoring

1. A ligand (eg, an antibody or antibody fragment) for use in a method of treating or reducing the risk of an IL4Ra-mediated disease or condition (eg, asthma) in a human in need thereof, wherein the ligand specifically binds a human IL4RA protein that comprises a mutation selected from the group consisting of I75V, E400A, C431R, S503P, Q576R and S752A in SEQ ID NO: 67;
   wherein (i) the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and
   wherein (ii) said human comprises a nucleotide sequence encoding said IL4RA protein comprising said mutation selected from the group consisting of I75V, E400A, C431R, S503P, Q576R and S752A in SEQ ID NO: 67.

In an alternative, paragraph 1 provides:—

A ligand (eg, an antibody or antibody fragment) for use in a method of targeting IL4Ra in a human, wherein the ligand specifically binds a human IL4RA protein that comprises a mutation selected from the group consisting of I75V, E400A, C431R, S503P, Q576R and S752A in SEQ ID NO: 67;
   wherein (i) the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and
   wherein (ii) said human comprises a nucleotide sequence encoding said IL4RA protein comprising said mutation selected from the group consisting of I75V, E400A, C431R, S503P, Q576R and S752A in SEQ ID NO: 67.

In an example, the human is suffering from or at risk of an IL4Ra-mediated disease or condition.

In an example, the method treats or reduces the risk of an IL4Ra-mediated disease or condition in the human.

2. The ligand of paragraph 1, wherein the IL4Ra comprises mutations I75V and Q576R in SEQ ID NO: 67 and optionally the disease is asthma.

3. The ligand of paragraph 1 or 2, wherein the nucleotide sequence of (ii) comprises nucleotide mutation—3223T (dB SNP numbering).

4. The ligand of any preceding paragraph, wherein said human gamma-4 heavy chain constant region that comprises SEQ ID NO: 73.

5. The ligand of any preceding paragraph, wherein the human expresses antibodies comprising human IGHG4*01 heavy chain constant regions.

6. The ligand of any preceding paragraph, said method comprising, before said administering, selecting a human comprising said nucleotide sequence of (ii), wherein the human is the human of paragraph 1.

7. The ligand of any preceding paragraph, wherein the human has been determined to comprise the nucleotide sequence that encodes an IL4Ra protein comprising said mutation selected from the group consisting of I75V, E400A, C431R, S503P, Q576R and S752A in SEQ ID NO: 67 and/or an IL4Ra protein comprising said mutation selected from the group consisting of I75V, E400A, C431R, S503P, Q576R and S752A in SEQ ID NO: 67.

8. The ligand of any preceding paragraph, said method comprising the step of determining that the human comprises (a) the nucleotide sequence that encodes an IL4Ra protein comprising said mutation selected from the group consisting of I75V, E400A, C431R, S503P, Q576R and S752A in SEQ ID NO: 67 and/or (b) an IL4Ra protein comprising said mutation said mutation selected from the group consisting of I75V, E400A, C431R, S503P, Q576R and S752A in SEQ ID NO: 67, optionally, wherein the determining step is performed before administration of the antibody to the human.

9. The ligand of paragraph 8, wherein the step of determining comprises assaying a biological sample from the human for a nucleotide sequence encoding a IL4Ra protein comprising said mutation selected from the group consisting of I75V, E400A, C431R, S503P, Q576R and S752A in SEQ ID NO: 67.

10. The ligand of paragraph 9, wherein the assaying comprises
   contacting the biological sample with at least one oligonucleotide probe comprising a sequence of at least 10 contiguous nucleotides of a nucleotide sequence encoding an IL4Ra protein comprising said mutation selected from the group consisting of I75V, E400A, C431R, S503P, Q576R and S752A in SEQ ID NO: 67 or comprising an antisense sequence of said contiguous nucleotides, wherein said sequence of contiguous nucleotides comprises a nucleotide sequence encoding said mutation selected from the group consisting of I75V, E400A, C431R, S503P, Q576R and S752A in SEQ ID NO: 67, thereby forming a complex when at least one nucleotide sequence encoding the IL4Ra protein comprising said mutation selected from the group consisting of I75V, E400A, C431R, S503P, Q576R and S752A in SEQ ID NO: 67 is present; and
   detecting the presence or absence of the complex, wherein detecting the presence of the complex determines that the human comprises the IL4Ra protein comprising said mutation selected from the group consisting of I75V, E400A, C431R, S503P, Q576R and S752A in SEQ ID NO: 67.

11. The ligand of paragraph 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The ligand of paragraph 9 or 11, wherein said biological sample comprises serum, blood, faeces, tissue, a cell, urine and/or saliva of said human.
13. The ligand of any preceding paragraph, wherein said human is indicated as heterozygous for a nucleotide sequence encoding the IL4Ra protein comprising said mutation selected from the group consisting of I75V, E400A, C431R, S503P, Q576R and S752A in SEQ ID NO: 67, optionally, wherein said human is further indicated as comprising the nucleotide sequence of SEQ ID NO: 68, or said human is indicated as homozygous for a nucleotide sequence encoding the IL4Ra protein comprising said mutation selected from the group consisting of I75V, E400A, C431R, S503P, Q576R and S752A in SEQ ID NO: 67.
14. The ligand of any preceding paragraph, wherein said human is or has been further determined to be substantially resistant to an asthma treatment.
15. The ligand of any preceding paragraph, wherein said human is receiving or has received an asthma treatment or has reduced responsiveness to an asthma treatment.
16. The ligand of any preceding paragraph, wherein said disease or condition is an inflammatory disease or condition; an atopic disease or condition; a respiratory disease or condition; a disease or condition associated with elevated IgE; or a disease or condition associated with elevated IL-4 and/or IL-13 activity.
17. The ligand of any preceding paragraph, wherein said disease or condition is selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.
18. The ligand of any preceding paragraph, wherein said human has been diagnosed with at least one condition selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.
19. The ligand of any preceding paragraph, wherein said antibody or antibody fragment treats or reduces the risk in said human of at least one condition selected from the group consisting of an airway inflammatory disease or condition, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis
20. The ligand of any preceding paragraph, wherein the nucleotide sequence comprises one or more SNPs selected from the group consisting of rs1805010, rs1805011, rs1805012, rs1805015, rs1801275 and rs1805016.
21. The ligand of any preceding paragraph, wherein said antibody or antibody fragment is for inhaled, intravenous or subcutaneous administration and/or is comprised in an inhalable or injectable preparation.

In an example of any other example or embodiment, clause or paragraph relating to IL4Ra, the IL4Ra mutation is 75V and the human is of AFR or ASN ancestry, eg, the ancestry of the human is selected from ASW, LWK, CHS or JPT. All of these ancestries have greater than the average of 47% frequency for 75V.

In an example of any other example or embodiment, clause or paragraph relating to IL4Ra, the IL4Ra mutation is 400A and the human is of AFR ancestry, eg, the ancestry of the human is selected from ASW, LWK and YR1. All of these ancestries have greater than the average frequency for 400A.

In an example of any other example or embodiment, clause or paragraph relating to IL4Ra, the IL4Ra mutation is 431R and the human is of AFR or AMR ancestry, eg, the ancestry of the human is selected from YRI, CLM, MXL, PUR or CEU. All of these ancestries have greater than the average frequency for 431R.

In an example of any other example or embodiment, clause or paragraph relating to IL4Ra, the IL4Ra mutation is 752A and the human is of AFR ancestry, eg, the ancestry of the human is selected from ASW, LWK and YR1. All of these ancestries have 37-39% frequency, which is greater than the average frequency for 752A.

Frequencies are with reference to the 1000 Genomes database (version 20110521) here.

In an example of any other example or embodiment, clause or paragraph relating to IL4Ra, the IL4Ra mutation is 75V and the human is of AFR or ASN ancestry, eg, the ancestry of the human is selected from ASW, LWK, CHS or JPT. All of these ancestries have greater than the average of 47% frequency for 75V.

Example 3

Nav1.7 (SCN9A; ETHA; FEB3B; GEFSP7; NE-NA; NENA; PN1; SFNP)

Reference is made to J Clin Invest. 2007 December; 117 (12):3603-9, "Mutations in sodium-channel gene SCN9A cause a spectrum of human genetic pain disorders", Drenth J P & Waxman S G (incorporated herein by reference). Voltage-gated sodium channels play a critical role in the generation and conduction of action potentials and are thus important for electrical signalling by most excitable cells. Sodium channels are integral membrane proteins and are comprised of a large α subunit, which forms the voltage-sensitive and ion-selective pore, and smaller auxiliary β subunit(s) that can modulate the kinetics and voltage dependence of channel gating. To date, we know of 9 isoforms of the sodium-channel α subunit (Nav1.1-Nav1.9), each with a unique central and peripheral nervous system distribution. Four closely related sodium channels (Nav1.1, -1.2, -1.3, and -1.7) are encoded by a set of 4 genes (SCN1A, SCN2A, SCN3A, and SCN9A, respectively) located within a cluster on chromosome 2q24.3. Nav1.7 has a critical role in pain sensation. Furthermore, from KO studies and animal pain models, it would appear that Nav1.7 plays a major role in inflammatory pain.

Nav1.7 is located in peripheral neurons and plays an important role in action potential production in these cells. Recent genetic studies have identified Nav1.7 dysfunction in three different human pain disorders. Gain-of-function missense mutations in Nav1.7 have been shown to cause primary erythermalgia (PE) and paroxysmal extreme pain disorder (PEPD), while nonsense mutations in Nav1.7 result in loss of Nav1.7 function and a condition known as channelopathy-associated insensitivity to pain (CIP), a rare disorder in which affected individuals are unable to feel physical pain. Recent work has shown that different types of channelopathies (diseases caused by disturbed function of ion channel subunits or the proteins that regulate them), all involving the same Nav1.7 sodium channel, underlie these disorders.

Nav1.7 is encoded by SCN9A, a 113.5-kb gene comprising 26 exons (OMIM 603415) (FIG. 1A, Drenth & Waxman). The encoded sodium channel is composed of 1977 amino acids organized into 4 domains, each with 6 transmembrane segments, and is predominantly expressed in the dorsal root ganglion (DRG) neurons and sympathetic ganglion neurons (FIG. 1B, Drenth & Waxman). Immunohistochemical studies show that Nav1.7 is present at the distal ends of the wire-like projections of neurons known as neurites, close to the impulse trigger zone where neuronal firing is initiated. Interestingly, the large majority of DRG neurons that express Nav1.7 are pain sensing (nociceptive), suggesting a role for this sodium channel in the pathogenesis of pain.

Cell. 2014 Jun. 5; 157 (6):1393-404. doi: 10.1016/j.cell.2014.03.064. Epub 2014 May 22; "A monoclonal antibody that targets a NaV1.7 channel voltage sensor for pain and itch relief", Lee J H et al and 2011 (both incorporated herein by reference) describe the generation of a monoclonal antibody against human Nav1.7.

In an example, the invention provides a method of treating or reducing the risk of a Nav1.7-mediated disease or condition in a human in need thereof, the method comprising administering to said human a ligand (eg, an antibody or antibody fragment) that specifically binds a human Nav1.7 protein. The invention also provides a corresponding ligand.

The present invention provides anti-Nav1.7 ligands; and Nav1.7-binding or targeting ligands as described herein. The ligands have a variety of utilities. Some of the ligands, for instance, are useful in specific binding assays, for genotyping or phenotyping humans, affinity purification of Nav1.7, in particular human Nav1.7 or its ligands and in screening assays to identify other antagonists of Nav1.7 activity. Some of the ligands of the invention are useful for inhibiting Nav1.7-mediated activities.

Anti-Nav1.7 ligands (eg, antibodies and anti-sense RNA) have been developed based on targeting and neutralising so-called "wild-type" human Nav1.7, which is a commonly-occurring form (see, eg, SEQ ID NO: 75). While such therapies are useful for human patients harbouring this form of human NAV1.7, the inventor considered it useful to investigate the possibility of targeting rarer—but still naturally-occurring—forms of Nav1.7 amongst human populations. In this way, the inventor arrived at insight into the natural occurrences and distributions of rarer human Nav1.7 forms that can serve as useful targets (at the protein or nucleic acid level) for human treatment, prophylaxis and diagnosis pertinent to diseases and conditions mediated or associated with NAV1.7 activity. This particularly provides for tailored therapies, prophylaxis and diagnosis in humans that are devoid of the common Nav1.7 gene or protein.

The skilled person will know that SNPs or other changes that translate into amino acid variation can cause variability in activity and/or conformation of human targets to be addressed. This has spawned great interest in personalized medicine where genotyping and knowledge of protein and nucleotide variability is used to more effectively tailor medicines and diagnosis of patients. The invention, therefore, provides for tailored pharmaceuticals and testing that specifically addresses rarer Nav1.7 polymorphic variant forms. Such forms or "alleles" (at the nucleotide level), comprise one or more changes at the nucleotide and amino acid levels from the corresponding common form nucleotide and amino acids sequences, ie, there are one or more non-synonymous (aka "missense") changes at the nucleotide level that translate into one or more corresponding changes in the protein target in humans.

Furthermore, the inventor surprisingly realised that the rarer natural forms, although present in humans at much lower frequencies than the common form, nevertheless are represented in multiple and ethnically-diverse human populations and usually with many human examples per represented ethnic population. Thus, the inventor realised that targeting such rarer forms would provide for effective treatment, prophylaxis or diagnosis across many human ethnic populations, thereby extending the utility of the present invention.

With this realisation, the inventor saw that there is significant industrial and medical application for the invention in terms of guiding the choice of anti-Nav1.7 ligand for administration to human patients for therapy and/or prophylaxis of Nav1.7-mediated or associated diseases or conditions. In this way, the patient receives drugs and ligands that are tailored to their needs—as determined by the patient's genetic or phenotypic makeup. Hand-in-hand with this, the invention provides for the genotyping and/or phenotyping of patients in connection with such treatment, thereby allowing a proper match of drug to patient. This increases the chances of medical efficacy, reduces the likelihood of inferior treatment using drugs or ligands that are not matched to the patient (eg, poor efficacy and/or side-effects) and avoids pharmaceutical misprescription and waste.

In developing this thinking, in this non-limiting example the present inventor decided to determine a set of human Nav1.7 variants on the basis of the following criteria, these being criteria that the inventor realised would provide for useful medical drugs and diagnostics to tailored need in the human population. The inventor selected variants having at least 3 of the 4 following criteria:—

Naturally-occurring human Nav1.7 variation having a cumulative human allele frequency of 35% or less;

Naturally-occurring human Nav1.7 variation having a total human genotype frequency of about 50% or less;

Naturally-occurring human Nav1.7 variation found in many different human ethnic populations (using the standard categorisation of the 1000 Genomes Project; see Table 2 below); and Naturally-occurring human Nav1.7 variation found in many individuals distributed across such many different ethnic populations.

On the basis of these criteria, the inventor identified variants listed in Table 12 (see Further Variants) below. The inventor's selection included, as an additional or alternative consideration, selection for nucleotide variation that produced amino acid variation in corresponding Nav1.7 forms (ie, non-synonymous variations), as opposed to silent variations that do not alter amino acid residues in the target protein.

In an example, the invention provides a method of treating or reducing the risk of a Nav1.7-mediated disease or condition in a human in need thereof, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G. As explained further below, these amino acid variations are found in naturally-occurring Nav1.7 variants in humans found in many populations. Said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

For example, said amino acid is selected from the group consisting of any one of (a) to (e):— a) 136I, 216S, 241T, 395K, 848T, 858H, 858F, 863P and 1449V; or
b) 996C, 1298F, 1298D, 1299F, 1461T, 1462V, 1464I and 1627K; or
c) 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K) and 1689X (wherein X is an amino acid other than W); or
d) 395K, 1200L and 1235L; or
e) 422D, 490N, 943L, 1002L, 1161W and 1919G.

Amino acids (a)-(d) are discussed in Drenth & Waxman as being associated with pain conditions (either undesirable elevated or reduced pain). Thus, in one embodiment, the disease or condition is a pain disease or condition and the amino acid is selected from (a), (b), (c) or (d). Thus, in one embodiment, the disease or condition is an itching disease or condition and the amino acid is selected from (a), (b), (c) or (d). In an example, the disease is PE and the amino acid is selected from (a). In an example, the disease is PEPD and the amino acid is selected from (b). In an example, the disease is CIP and the amino acid is selected from (c) or (d). In an example, the disease or condition is a pain or itching disease or condition and the amino acid is selected from (e).

In one embodiment, the pain is inflammatory pain.

In one embodiment, the disease or condition is a channelopathy or associated with a channelopathy.

In one embodiment, the disease or condition is selected from the group consisting of primary erythermalgia (PE), paroxysmal extreme pain disorder (PEPD) and channelopathy-associated insensitivity to pain (CIP).

In an example, the ligand of the invention comprises an anti-human Nav1.7 binding site,
wherein the binding site is a human or humanized binding site, eg, the binding site comprises or consists of a human or humanized antibody variable domain or plurality of variable domains (eg, human VH/VL binding site(s)). Additionally or alternatively, the ligand comprises one or more human antibody constant regions (eg, a human antibody CH1, CH2, CH3 (or all of these) or Fc). In an example, the ligand is an antibody that comprises human or humanized variable regions and human constant regions (eg, bearing one or more mutations to enhance or dampen Fc function in a human patient).

An example provides a ligand (eg, an antibody or antibody fragment) for treating or reducing the risk of a Nav1.7-mediated disease or condition in a human in need thereof, the method comprising administering to said human said ligand, wherein the ligand specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G. Said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an example, the invention provides a method of targeting Nav1.7 in a human, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G. Said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G. In an example, the human is suffering from or at risk of a Nav1.7-mediated disease or condition. In an example, the method treats or reduces the risk of a Nav1.7-mediated disease or condition in the human.

An example also provides a ligand (eg, an antibody or antibody fragment) for targeting Nav1.7 in a human, the method comprising administering to said human said ligand, wherein the ligand specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G. Said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G. In an example, the human is suffering from or at risk of a Nav1.7-mediated disease or condition. In an example, the method treats or reduces the risk of a Nav1.7-mediated disease or condition in the human.

In an embodiment, (i) the antibody or fragment comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

Additionally or alternatively, in an embodiment, (i) the antibody or fragment comprises a human gamma-4 heavy chain constant region that comprises a Leu at position 189 shown in SEQ ID NO: 73 or an Arg at position 289 shown in SEQ ID NO: 73 and wherein said human comprises an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an example, the ligand, antibody or fragment is for treating or reducing the risk of (or treats or reduces the risk of) pain or itching, optionally wherein the antibody is a humanized mouse or Camelid (eg, llama or camel) antibody.

In a specific embodiment, the anti-Nav1.7 ligand, antibody or fragment also specifically binds to another Nay selected from Nav1.1-1.9, eg, it specifically binds to Nav1.8 or 1.9.

In a specific embodiment, the anti-Nav1.7 ligand, antibody or fragment of present invention comprises an Fc region, wherein the Fc region comprises at least one non-native amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241R, 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non-native amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

The ligand, antibody or fragment according to the invention is for treating or preventing or reducing the risk of (or treats or prevents or reduces the risk of), for example, any disease or condition disclosed in WO2011/051351, the disclosure of which diseases and conditions are incorporated herein by reference for potential inclusion in one or more claims herein. Guidance on obtaining and testing antibodies can also be found in that PCT application.

Further encompassed by the invention is the use of the ligand, antibody or fragment of an in the manufacture of a medicament for use to attenuate or inhibit an Nav1.7-mediated disease or disorder in a human. Nav1.7-mediated or related disorders which are treated by the ligand, antibody or fragment of the invention include, for example, a pain or itching disease or condition.

Thus, a ligand, antibody or fragment of the invention is useful as a therapeutic agent in the treatment of a condition involving Nav1.7 expression and/or activity. One embodiment, among others, is a method of treatment comprising administering an effective amount of a ligand, antibody or fragment of the invention to a patient in need thereof, wherein functional consequences of Nav1.7 activation are decreased. Another embodiment, among others, is a method of treatment comprising (i) identifying a patient demonstrating Nav1.7 expression or activity, and (ii) administering an effective amount of a ligand, antibody or fragment of the invention to the patient, wherein a functional consequence of Nav1.7 activation are attenuated. An effective amount according to the invention is an amount that modulates (e.g. decreases) the functional consequences of Nav1.7 activation so as to modulate (e.g. decrease or lessen) the severity of at least one symptom of the particular disease or disorder being treated, but not necessarily cure the disease or disorder. Accordingly, one embodiment of the invention is a method of treating or reducing the severity of at least one symptom of any of the disorders referred to herein, comprising administering to a patient in need thereof an effective amount of one or more ligands, antibodies or fragments of the present invention alone or in a combined therapeutic regimen with another appropriate medicament known in the art or described herein such that the severity of at least one symptom of any of the disorders is reduced. Another embodiment of the invention, among others, is a method of antagonizing at least one effect of Nav1.7 comprising contacting with or administering an effective amount of one or more ligands, antibodies or fragments of the present invention such that said at least one effect of Nav1.7 is antagonized, e.g. the ability of Nav1.7 to form an ion channel, such as a sodium channel.

Tailoring Antibodies to Rarer Nav1.7 Variant Profile

As outlined herein (for example, in the context of PCSK9 in Example 1), the invention includes the possibility to tailor treatment of humans further by selecting antibody-based ligands with variable domains and/or constant domains based on gene segments found in many humans of the ethnic populations where the variant TOI forms are found to meet the selection criteria of the invention. This also applies mutatis mutandis where the TOI is human Nav1.7, as in the present example. Thus, all disclosure herein relating to tailoring variable and/or constant domains apply to the present example, relating to Nav1.7 and is combinable for use in one or more claims herein.

As described in Example 1, an example is provided for ligands comprising antibody VH domains derived from recombination of human IGHV gene segments comprising selected nucleotides at positions in the HCDR1 or FW3 where there is variability in humans (ie, where SNPs occur in humans).

Further information is provided in Table 4, which shows variation at these positions, as well as the variant distributions across the 1000 Genomes Project database relating to many human populations.

In other embodiments, as explained more fully above, the invention provides for ligands which are tailored to the human recipient's genotype and/or phenotype based on alternative human VH gene segments, or on Vκ, Vλ or constant region gene segments (see further Table 9 for representative variants).

Further examples, therefore are:—
(i) wherein the ligand comprises a VH domain derived from the recombination of a human VH segment (eg, human VH3-23*04), a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40.
(ii) wherein the ligand comprises a VH domain derived from the recombination of human VH segment IGHV3-7*01, a human D gene segment and a human JH segment, and wherein said human comprises a IGHV3-7*01 VH gene segment or the human expresses VH domains derived from the recombination of human VH segment IGHV3-7*01, a human D gene segment and a human JH segment.
(iii) wherein the ligand comprises a Vκ domain derived from the recombination of human Vκ segment IGKV1-12*01 and a human Jκ segment, and wherein said human comprises a IGKV1-12*01 Vκ gene segment or the human expresses Vκ domains derived from the recombination of human Vκ segment IGKV1-12*01 and a human Jκ segment.

(iv) wherein the ligand comprises a Vκ domain derived from the recombination of a human Vi segment and a human Jκ segment, the human Vκ segment encoding (i) a CDR3 comprising a Pro at position 7 shown in SEQ ID NO: 36 and wherein said human comprises a Vκ gene segment encoding a CDR3 comprising a Pro at position 7 shown in SEQ ID NO: 36, or the human expresses Vi domains that comprise a CDR3 comprising a Pro at position 7 shown in SEQ ID NO: 36; or (ii) a FW3 comprising a Ser at position 15 shown in SEQ ID NO: 38 and wherein said human comprises a Vκ gene segment encoding a FW3 comprising a Ser at position 15 shown in SEQ ID NO: 38 or the human expresses Vκ domains that comprise a FW3 comprising a Ser at position 15 shown in SEQ ID NO: 38.

(v) wherein the ligand comprises a human gamma-1 heavy chain constant region that comprises an Asp at position 204 shown in SEQ ID NO: 4 or a Leu at position 206 shown in SEQ ID NO: 4 and wherein said human comprises (i) an IGHG1*01 human heavy chain constant region gene segment, or the human expresses antibodies comprising human gamma-1 heavy chain constant regions comprising an Asp at position 204 shown in SEQ ID NO: 4 or a Leu at position 206 shown in SEQ ID NO: 4.

(vi) wherein the ligand comprises a human gamma-2 heavy chain constant region that comprises an amino acid selected from the group consisting of a Pro at position 72 shown in SEQ ID NO: 6, an Asn at position 75 shown in SEQ ID NO: 6, a Phe at position 76 shown in SEQ ID NO: 6, a Val at position 161 shown in SEQ ID NO: 6 and an Ala at position 257 shown in SEQ ID NO: 6 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 6, Asn at position 75 shown in SEQ ID NO: 6, Phe at position 76 shown in SEQ ID NO: 6, Val at position 161 shown in SEQ ID NO: 6 or Ala at position 257 shown in SEQ ID NO: 6.

(vii) wherein the ligand comprises a human kappa chain constant region that comprises a Val at position 84 shown in SEQ ID NO: 16 or a Cys at position 87 shown in SEQ ID NO: 16 and wherein said human comprises (i) an IGKC1*01 human heavy chain constant region gene segment, or the human expresses antibodies comprising human kappa chain constant regions comprising a Val corresponding to position 84 shown in SEQ ID NO: 16 or a Cys at position 87 shown in SEQ ID NO: 16 and (ii) a nucleotide sequence encoding said Nav1.7 protein comprising said Asp358Ala or Val385Ile in SEQ ID NO: 1.

(viii) wherein the ligand comprises a human IGLC1*01 lambda chain constant region and wherein said human comprises (i) a human IGLC1*01 lambda chain constant region gene segment, or the human expresses antibodies comprising human IGLC1*01 lambda chain constant regions.

(ix) wherein the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73.

(x) wherein the ligand comprises a human gamma-3 heavy chain constant region encoded by a first human IGHG3 (eg, IGHG3*01) constant region gene segment and wherein said human comprises (i) said first constant region gene segment (eg, an IGHG3*01), or the human expresses antibodies comprising human gamma-3 heavy chain constant regions encoded by said first human IGHG3 (eg, IGHG3*01) constant region gene segment.

(xi) wherein the ligand comprises a human epsilon heavy chain constant region encoded by a first human epsilon heavy chain constant region gene segment and wherein said human comprises (i) said first constant region gene segment, or the human expresses antibodies comprising human epsilon heavy chain constant regions encoded by said first constant region gene segment.

(xii) wherein the ligand comprises a human mu heavy chain constant region encoded by a first human mu heavy chain constant region gene segment and wherein said human comprises (i) said first constant region gene segment, or the human expresses antibodies comprising human mu heavy chain constant regions encoded by said first constant region gene segment.

(xiii) wherein the ligand comprises a human alpha heavy chain constant region encoded by a first human alpha heavy chain constant region gene segment and wherein said human comprises (i) said first constant region gene segment, or the human expresses antibodies comprising human alpha heavy chain constant regions encoded by said first constant region gene segment.

(xiv) wherein the ligand comprises a human delta heavy chain constant region encoded by a first human delta heavy chain constant region gene segment and wherein said human comprises (i) said first constant region gene segment, or the human expresses antibodies comprising human delta heavy chain constant regions encoded by said first constant region gene segment.

(xv) wherein the ligand comprises a human kappa light chain constant region encoded by a first human kappa light chain constant region gene segment and wherein said human comprises (i) said first constant region gene segment, or the human expresses antibodies comprising human kappa light chain constant regions encoded by said first constant region gene segment.

(xvi) wherein the ligand comprises a human lambda light chain constant region encoded by a first human lambda light chain constant region gene segment and wherein said human comprises (i) said first constant region gene segment, or the human expresses antibodies comprising human lambda light chain constant regions encoded by said first constant region gene segment.

These examples, although written in the context of the present Nav1.7 example, are applicable to the invention as it relates to any other TOI herein and thus can be combined and used in claims herein relating to any TOI. In any of these example, the ligand is optionally an antibody, eg, a human or humanised antibody (eg, a humanised mouse, rat or Camelid antibody).

For ADCC efficacy for human constant regions is: IgG1≥IgG3>>IgG4≥IgG2

For CDC efficacy for human constant regions is: IgG3≥IgG1>>IgG2≈IgG4

Thus, it may be advantageous for Nav1.7 ligands, for the ligand to comprise a gamma-4 or gamma-2 constant region (eg, as per the examples above). For example, the gamma-4 is an IgG4PE (ie, a gamma-4 constant region with 228Pro and 235Glu). For example the gamma-2 is an IgG2Δa.

For example, as per example (ix), the inventor identified the possibility of addressing IGH-gamma-4 variation and identified utility for variations 189L and 289R individually or in combination, since these residues are part of the CH3 domain, and as such they form part of antibody Fc regions. Thus, matching of these CH3 variations with the patient is especially beneficial for reasons as discussed above. Thus, in this example the ligand of the invention comprises or consists of an antibody that comprises a human gamma-4 heavy chain constant region that comprises a Leu corresponding to position 189 of SEQ ID NO: 73 or an Arg corresponding to position 289 of SEQ ID NO: 73 and wherein the genome of the human comprises a gamma-4 heavy chain constant region nucleotide sequence that encodes such a Leu and/or Arg or the human expresses antibodies comprising human gamma-4 constant regions comprising such a Leu and/or Arg.

Determination of Specific Binding of Ligands of the Invention to NAV1.7 Variants The specific binding of ligands of the invention to Nav1.7 variants can be performed using the SPR method described in Example 1.

Embodiments are provided as follows: —

Methods with VH Tailoring

1. A method of treating or reducing the risk of a Nav1.7-mediated disease or condition in a human in need thereof, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;
    wherein (i) the ligand comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and
    wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an alternative, clause 1 provides:—

A method of targeting Nav1.7 in a human, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;
    wherein (i) the ligand comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and
    wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an example, the human is suffering from or at risk of a Nav1.7-mediated disease or condition. In an example, the method treats or reduces the risk of a Nav1.7-mediated disease or condition in the human.

2. The method of any preceding clause, wherein said amino acid is selected from the group consisting of any one of 136I, 216S, 241T, 395K, 848T, 858H, 858F, 863P and 1449V; optionally wherein said disease or condition is a pain disease or condition.

3. The method of any preceding clause, wherein said amino acid is selected from the group consisting of 996C, 1298F, 1298D, 1299F, 1461T, 1462V, 1464I and 1627K; optionally wherein said disease or condition is a pain disease or condition.

4. The method of any preceding clause, wherein said amino acid is selected from the group consisting of 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K) and 1689X (wherein X is an amino acid other than W); optionally wherein said disease or condition is a pain disease or condition.

5. The method of any preceding clause, wherein the VH gene segment comprised by said human is a germline VH gene segment.

6. The method of any preceding clause comprising, before said administering, selecting a human comprising said nucleotide sequence of (ii), wherein the human is the human of clause 1.

7. The method of any preceding clause, wherein the human has been determined to comprise the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

8. The method of any preceding clause, comprising the step of determining that the human comprises (a) the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or (b) an Nav1.7 protein comprising said mutation said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein the determining step is performed before administration of the antibody to the human.

9. The method of clause 8, wherein the step of determining comprises assaying a biological sample from the human for a nucleotide sequence encoding a Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

10. The method of clause 9, wherein the assaying comprises contacting the biological sample with at least one oligonucleotide probe comprising a sequence of at least 10 contiguous nucleotides of a nucleotide sequence encoding an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G or comprising an antisense sequence of said contiguous nucleotides, wherein said sequence of contiguous nucleotides comprises a nucleotide sequence encoding said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, thereby forming a complex when at least one nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G is present; and detecting the presence or absence of the complex, wherein detecting the presence of the complex determines that the human comprises the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

11. The method of clause 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The method of clause 9 or 11, wherein said biological sample comprises serum, blood, faeces, tissue, a cell, urine and/or saliva of said human.

13. The method of any preceding clause, wherein said human is indicated as heterozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein said human is further indicated as comprising the nucleotide sequence of SEQ ID NO: 76, or said human is indicated as homozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

14. The method of any preceding clause, wherein said human is or has been further determined to be substantially resistant to a pain or itching treatment.

15. The method of any preceding clause, wherein said human is receiving or has received a pain or itching treatment or has reduced responsiveness to a pain or itching treatment.

16. The method of any preceding clause, wherein said disease or condition is a pain or itching disease or condition.

17. The method of any preceding clause, wherein said disease or condition is a channelopathy or associated with a channelopathy; or is selected from the group consisting of primary erythermalgia (PE), paroxysmal extreme pain disorder (PEPD) and channelopathy-associated insensitivity to pain (CIP).

18. The method of any preceding clause, wherein said human has been diagnosed with at least one condition recited in claim 16 or 17.

19. The method of any preceding clause, wherein said antibody or antibody fragment treats or reduces the risk in said human of a condition recited in claim 16 or 17.

20. The method of any preceding clause, wherein the nucleotide sequence comprises one or more SNPs selected from the group consisting of rs6746030, rs3750904, rs58022607, rs4369876, rs13402180 and rs12478318.

21. The method of any preceding clause, wherein said ligand (eg, antibody or antibody fragment) is administered by inhaled, intravenous or subcutaneous administration and/or is comprised in an inhalable or injectable preparation.

22. The method of any preceding clause, wherein the VH domain comprises the amino acid sequence of SEQ ID NO: 69.

Ligands with VH Tailoring

1. A ligand (eg, an antibody or antibody fragment) for use in a method of treating or reducing the risk of a Nav1.7-mediated disease or condition (eg, asthma) in a human in need thereof, wherein the ligand specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;

wherein (i) the ligand comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an alternative, paragraph 1 provides:—

A ligand (eg, an antibody or antibody fragment) for use in a method of targeting Nav1.7 in a human, wherein the ligand specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;

wherein (i) the ligand comprises a VH domain derived from the recombination of a human VH segment, a human D gene segment and a human JH segment, the human VH segment encoding the framework 1 of SEQ ID NO: 40 and wherein said human comprises a VH gene segment encoding the framework 1 of SEQ ID NO: 40, or the human expresses VH domains that comprise the framework 1 of SEQ ID NO: 40; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an example, the human is suffering from or at risk of a Nav1.7-mediated disease or condition. In an example, the method treats or reduces the risk of a Nav1.7-mediated disease or condition in the human.

2. The ligand of any preceding clause, wherein said amino acid is selected from the group consisting of any one of 136I, 216S, 241T, 395K, 848T, 858H, 858F, 863P and 1449V; optionally wherein said disease or condition is a pain disease or condition.

3. The ligand of any preceding clause, wherein said amino acid is selected from the group consisting of 996C, 1298F, 1298D, 1299F, 1461T, 1462V, 1464I and 1627K; optionally wherein said disease or condition is a pain disease or condition.

4. The ligand of any preceding clause, wherein said amino acid is selected from the group consisting of 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K) and 1689X (wherein X is an amino acid other than W); optionally wherein said disease or condition is a pain disease or condition.

5. The ligand of any preceding clause, wherein the VH gene segment comprised by said human is a germline VH gene segment.

6. The ligand of any preceding clause said method comprising, before said administering, selecting a human comprising said nucleotide sequence of (ii), wherein the human is the human of clause 1.

7. The ligand of any preceding clause, wherein the human has been determined to comprise the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

8. The ligand of any preceding clause, said method comprising the step of determining that the human comprises (a) the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or (b) an Nav1.7 protein comprising said mutation said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein the determining step is performed before administration of the antibody to the human.

9. The ligand of clause 8, wherein the step of determining comprises assaying a biological sample from the human for a nucleotide sequence encoding a Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

10. The ligand of clause 9, wherein the assaying comprises contacting the biological sample with at least one oligonucleotide probe comprising a sequence of at least 10 contiguous nucleotides of a nucleotide sequence encoding an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G or comprising an antisense sequence of said contiguous nucleotides, wherein said sequence of contiguous nucleotides comprises a nucleotide sequence encoding said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, thereby forming a complex when at least one nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G is present; and detecting the presence or absence of the complex, wherein detecting the presence of the complex determines that the human comprises the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

11. The ligand of clause 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The ligand of clause 9 or 11, wherein said biological sample comprises serum, blood, faeces, tissue, a cell, urine and/or saliva of said human.

13. The ligand of any preceding clause, wherein said human is indicated as heterozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein said human is further indicated as comprising the nucleotide sequence of SEQ ID NO: 76, or said human is indicated as homozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.
14. The ligand of any preceding clause, wherein said human is or has been further determined to be substantially resistant to a pain or itching treatment.
15. The ligand of any preceding clause, wherein said human is receiving or has received a pain or itching treatment or has reduced responsiveness to a pain or itching treatment.
16. The ligand of any preceding clause, wherein said disease or condition is a pain or itching disease or condition.
17. The ligand of any preceding clause, wherein said disease or condition is a channelopathy or associated with a channelopathy; or is selected from the group consisting of primary erythermalgia (PE), paroxysmal extreme pain disorder (PEPD) and channelopathy-associated insensitivity to pain (CIP).
18. The ligand of any preceding clause, wherein said human has been diagnosed with at least one condition recited in claim 16 or 17.
19. The ligand of any preceding clause, wherein said antibody or antibody fragment treats or reduces the risk in said human of a condition recited in claim 16 or 17.
20. The ligand of any preceding clause, wherein the nucleotide sequence comprises one or more SNPs selected from the group consisting of rs6746030, rs3750904, rs58022607, rs4369876, rs13402180 and rs12478318.
21. The ligand of any preceding clause, wherein said ligand (eg, antibody or antibody fragment) is for inhaled, intravenous or subcutaneous administration and/or is comprised in an inhalable or injectable preparation.
22. The ligand of any preceding clause, wherein the VH domain comprises the amino acid sequence of SEQ ID NO: 69.

Methods with Gamma-4 Constant Region Tailoring

1. A method of treating or reducing the risk of a Nav1.7-mediated disease or condition in a human in need thereof, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;
   wherein (i) the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and
   wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an alternative, clause 1 provides:—
A method of targeting Nav1.7 in a human, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;
   wherein (i) the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and
   wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an example, the human is suffering from or at risk of a Nav1.7-mediated disease or condition. In an example, the method treats or reduces the risk of a Nav1.7-mediated disease or condition in the human.

2. The method of any preceding clause, wherein said amino acid is selected from the group consisting of any one of 136I, 216S, 241T, 395K, 848T, 858H, 858F, 863P and 1449V; optionally wherein said disease or condition is a pain disease or condition.

3. The method of any preceding clause, wherein said amino acid is selected from the group consisting of 996C, 1298F, 1298D, 1299F, 1461T, 1462V, 1464I and 1627K; optionally wherein said disease or condition is a pain disease or condition.
4. The method of any preceding clause, wherein said amino acid is selected from the group consisting of 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K) and 1689X (wherein X is an amino acid other than W); optionally wherein said disease or condition is a pain disease or condition.
5. The method of any preceding clause, wherein the constant region gene segment comprised by said human is a germline gene segment.
6. The method of any preceding clause comprising, before said administering, selecting a human comprising said nucleotide sequence of (ii), wherein the human is the human of clause 1.
7. The method of any preceding clause, wherein the human has been determined to comprise the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.
8. The method of any preceding clause, comprising the step of determining that the human comprises (a) the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or (b) an Nav1.7 protein comprising said mutation said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein the determining step is performed before administration of the antibody to the human.
9. The method of clause 8, wherein the step of determining comprises assaying a biological sample from the human for a nucleotide sequence encoding a Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.
10. The method of clause 9, wherein the assaying comprises contacting the biological sample with at least one oligonucleotide probe comprising a sequence of at least 10 contiguous nucleotides of a nucleotide sequence encoding an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G or comprising an antisense sequence of said contiguous nucleotides, wherein said sequence of contiguous nucleotides comprises a nucleotide sequence encoding said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, thereby forming a complex when at least one nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G is present; and detecting the presence or absence of the complex, wherein detecting the presence of the complex determines that the human comprises the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

11. The method of clause 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The method of clause 9 or 11, wherein said biological sample comprises serum, blood, faeces, tissue, a cell, urine and/or saliva of said human.

13. The method of any preceding clause, wherein said human is indicated as heterozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein said human is further indicated as comprising the nucleotide sequence of SEQ ID NO: 76, or said human is indicated as homozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

14. The method of any preceding clause, wherein said human is or has been further determined to be substantially resistant to a pain or itching treatment.

15. The method of any preceding clause, wherein said human is receiving or has received a pain or itching treatment or has reduced responsiveness to a pain or itching treatment.

16. The method of any preceding clause, wherein said disease or condition is a pain or itching disease or condition.

17. The method of any preceding clause, wherein said disease or condition is a channelopathy or associated with a channelopathy; or is selected from the group consisting of primary erythermalgia (PE), paroxysmal extreme pain disorder (PEPD) and channelopathy-associated insensitivity to pain (CIP).

18. The method of any preceding clause, wherein said human has been diagnosed with at least one condition recited in claim 16 or 17.

19. The method of any preceding clause, wherein said antibody or antibody fragment treats or reduces the risk in said human of a condition recited in claim 16 or 17.

20. The method of any preceding clause, wherein the nucleotide sequence comprises one or more SNPs selected from the group consisting of rs6746030, rs3750904, rs58022607, rs4369876, rs13402180 and rs12478318.

21. The method of any preceding clause, wherein said ligand (eg, antibody or antibody fragment) is administered by inhaled, intravenous or subcutaneous administration and/or is comprised in an inhalable or injectable preparation.

22. The method of any preceding clause, wherein the human gamma-4 heavy chain constant region of the ligand comprises the amino acid sequence of SEQ ID NO: 73 or an ADCC inactivated version thereof.

23. The method of any preceding clause, wherein the human gamma-4 heavy chain constant region comprises 228P and 235E.

Ligands with Gamma-4 Constant Region Tailoring

1. A ligand (eg, an antibody or antibody fragment) for use in a method of treating or reducing the risk of a Nav1.7-mediated disease or condition (eg, pain) in a human in need thereof, wherein the ligand specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;

wherein (i) the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;

In an alternative, paragraph 1 provides:—

A ligand (eg, an antibody or antibody fragment) for use in a method of targeting Nav1.7 in a human, wherein the ligand specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;

wherein (i) the ligand comprises a human gamma-4 heavy chain constant region that comprises a Leu at position 189 shown in SEQ ID NO: 73 or an Arg at position 289 shown in SEQ ID NO: 73 and wherein said human comprises (i) an IGHG4*01 human heavy chain constant region gene segment, or the human expresses antibodies comprising human gamma-4 heavy chain constant regions comprising a Leu at position 189 shown in SEQ ID NO: 73 or an Arg at position 289 shown in SEQ ID NO: 73; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an example, the human is suffering from or at risk of a Nav1.7-mediated disease or condition. In an example, the method treats or reduces the risk of a Nav1.7-mediated disease or condition in the human.

2. The ligand of any preceding clause, wherein said amino acid is selected from the group consisting of any one of 136I, 216S, 241T, 395K, 848T, 858H, 858F, 863P and 1449V; optionally wherein said disease or condition is a pain disease or condition.

3. The ligand of any preceding clause, wherein said amino acid is selected from the group consisting of 996C, 1298F, 1298D, 1299F, 1461T, 1462V, 1464I and 1627K; optionally wherein said disease or condition is a pain disease or condition.

4. The ligand of any preceding clause, wherein said amino acid is selected from the group consisting of 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K) and 1689X (wherein X is an amino acid other than W); optionally wherein said disease or condition is a pain disease or condition.

5. The ligand of any preceding clause, wherein the VH gene segment comprised by said human is a germline VH gene segment.

6. The ligand of any preceding clause said method comprising, before said administering, selecting a human comprising said nucleotide sequence of (ii), wherein the human is the human of clause 1.

7. The ligand of any preceding clause, wherein the human has been determined to comprise the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

8. The ligand of any preceding clause, said method comprising the step of determining that the human comprises (a) the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or (b) an Nav1.7 protein comprising said mutation said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein the determining step is performed before administration of the antibody to the human.

9. The ligand of clause 8, wherein the step of determining comprises assaying a biological sample from the human for a nucleotide sequence encoding a Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

10. The ligand of clause 9, wherein the assaying comprises contacting the biological sample with at least one oligonucleotide probe comprising a sequence of at least 10 contiguous nucleotides of a nucleotide sequence encoding an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G or comprising an antisense sequence of said contiguous nucleotides, wherein said sequence of contiguous nucleotides comprises a nucleotide sequence encoding said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, thereby forming a complex when at least one nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G is present; and detecting the presence or absence of the complex, wherein detecting the presence of the complex determines that the human comprises the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

11. The ligand of clause 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The ligand of clause 9 or 11, wherein said biological sample comprises serum, blood, faeces, tissue, a cell, urine and/or saliva of said human.

13. The ligand of any preceding clause, wherein said human is indicated as heterozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein said human is further indicated as comprising the nucleotide sequence of SEQ ID NO: 76, or said human is indicated as homozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

14. The ligand of any preceding clause, wherein said human is or has been further determined to be substantially resistant to a pain or itching treatment.

15. The ligand of any preceding clause, wherein said human is receiving or has received a pain or itching treatment or has reduced responsiveness to a pain or itching treatment.

16. The ligand of any preceding clause, wherein said disease or condition is a pain or itching disease or condition.

17. The ligand of any preceding clause, wherein said disease or condition is a channelopathy or associated with a channelopathy; or is selected from the group consisting of primary erythermalgia (PE), paroxysmal extreme pain disorder (PEPD) and channelopathy-associated insensitivity to pain (CIP).

18. The ligand of any preceding clause, wherein said human has been diagnosed with at least one condition recited in claim 16 or 17.

19. The ligand of any preceding clause, wherein said antibody or antibody fragment treats or reduces the risk in said human of a condition recited in claim 16 or 17.

20. The ligand of any preceding clause, wherein the nucleotide sequence comprises one or more SNPs selected from the group consisting of rs6746030, rs3750904, rs58022607, rs4369876, rs13402180 and rs12478318.

21. The ligand of any preceding clause, wherein said ligand (eg, antibody or antibody fragment) is for inhaled, intravenous or subcutaneous administration and/or is comprised in an inhalable or injectable preparation.

22. The ligand of any preceding clause, wherein the human gamma-4 heavy chain constant region of the ligand comprises the amino acid sequence of SEQ ID NO: 73 or an ADCC inactivated version thereof.

23. The ligand of any preceding clause, wherein the human gamma-4 heavy chain constant region comprises 228P and 235E.

Methods with Gamma-2 Constant Region Tailoring

1. A method of treating or reducing the risk of a Nav1.7-mediated disease or condition in a human in need thereof, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;

wherein (i) the ligand comprises a human gamma-2 heavy chain constant region that comprises an amino acid selected from the group consisting of a Pro at position 72 shown in SEQ ID NO: 6, an Asn at position 75 shown in SEQ ID NO: 6, a Phe at position 76 shown in SEQ ID NO: 6, a Val at position 161 shown in SEQ ID NO: 6 and an Ala at position 257 shown in SEQ ID NO: 6 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 6, Asn at position 75 shown in SEQ ID NO: 6, Phe at position 76 shown in SEQ ID NO: 6, Val at position 161 shown in SEQ ID NO: 6 or Ala at position 257 shown in SEQ ID NO: 6; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an alternative, clause 1 provides:—

A method of targeting Nav1.7 in a human, the method comprising administering to said human a ligand (eg, an antibody or antibody fragment) that specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;

wherein (i) the ligand comprises a human gamma-2 heavy chain constant region that comprises an amino acid selected from the group consisting of a Pro at position 72 shown in SEQ ID NO: 6, an Asn at position 75 shown in SEQ ID NO: 6, a Phe at position 76 shown in SEQ ID NO: 6, a Val at position 161 shown in SEQ ID NO: 6 and an Ala at position 257 shown in SEQ ID NO: 6 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 6, Asn at position 75 shown in SEQ ID NO: 6, Phe at position 76 shown in SEQ ID NO: 6, Val at position 161 shown in SEQ ID NO: 6 or Ala at position 257 shown in SEQ ID NO: 6; and wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an example, the human is suffering from or at risk of a Nav1.7-mediated disease or condition. In an example, the method treats or reduces the risk of a Nav1.7-mediated disease or condition in the human.

2. The method of any preceding clause, wherein said amino acid is selected from the group consisting of any one of 136I, 216S, 241T, 395K, 848T, 858H, 858F, 863P and 1449V; optionally wherein said disease or condition is a pain disease or condition.

3. The method of any preceding clause, wherein said amino acid is selected from the group consisting of 996C, 1298F, 1298D, 1299F, 1461T, 1462V, 1464I and 1627K; optionally wherein said disease or condition is a pain disease or condition.

4. The method of any preceding clause, wherein said amino acid is selected from the group consisting of 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K) and 1689X (wherein X is an amino acid other than W); optionally wherein said disease or condition is a pain disease or condition.

5. The method of any preceding clause, wherein the constant region gene segment comprised by said human is a germline gene segment.

6. The method of any preceding clause comprising, before said administering, selecting a human comprising said nucleotide sequence of (ii), wherein the human is the human of clause 1.

7. The method of any preceding clause, wherein the human has been determined to comprise the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

8. The method of any preceding clause, comprising the step of determining that the human comprises (a) the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or (b) an Nav1.7 protein comprising said mutation said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein the determining step is performed before administration of the antibody to the human.

9. The method of clause 8, wherein the step of determining comprises assaying a biological sample from the human for a nucleotide sequence encoding a Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

10. The method of clause 9, wherein the assaying comprises contacting the biological sample with at least one oligonucleotide probe comprising a sequence of at least 10 contiguous nucleotides of a nucleotide sequence encoding an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G or comprising an antisense sequence of said contiguous nucleotides, wherein said sequence of contiguous nucleotides comprises a nucleotide sequence encoding said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, thereby forming a complex when at least one nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G is present; and detecting the presence or absence of the complex, wherein detecting the presence of the complex determines that the human comprises the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

11. The method of clause 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The method of clause 9 or 11, wherein said biological sample comprises serum, blood, faeces, tissue, a cell, urine and/or saliva of said human.

13. The method of any preceding clause, wherein said human is indicated as heterozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein said human is further indicated as comprising the nucleotide sequence of SEQ ID NO: 76, or said human is indicated as homozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

14. The method of any preceding clause, wherein said human is or has been further determined to be substantially resistant to a pain or itching treatment.

15. The method of any preceding clause, wherein said human is receiving or has received a pain or itching treatment or has reduced responsiveness to a pain or itching treatment.

16. The method of any preceding clause, wherein said disease or condition is a pain or itching disease or condition.
17. The method of any preceding clause, wherein said disease or condition is a channelopathy or associated with a channelopathy; or is selected from the group consisting of primary erythermalgia (PE), paroxysmal extreme pain disorder (PEPD) and channelopathy-associated insensitivity to pain (CIP).
18. The method of any preceding clause, wherein said human has been diagnosed with at least one condition recited in claim 16 or 17.
19. The method of any preceding clause, wherein said antibody or antibody fragment treats or reduces the risk in said human of a condition recited in claim 16 or 17.
20. The method of any preceding clause, wherein the nucleotide sequence comprises one or more SNPs selected from the group consisting of rs6746030, rs3750904, rs58022607, rs4369876, rs13402180 and rs12478318.
21. The method of any preceding clause, wherein said ligand (eg, antibody or antibody fragment) is administered by inhaled, intravenous or subcutaneous administration and/or is comprised in an inhalable or injectable preparation.
22. The method of any preceding clause, wherein the human gamma-2 heavy chain constant region of the ligand comprises IGHG2*01 amino acid sequence or an ADCC inactivated version thereof.

Ligands with Gamma-2 Constant Region Tailoring

1. A ligand (eg, an antibody or antibody fragment) for use in a method of treating or reducing the risk of a Nav1.7-mediated disease or condition (eg, pain) in a human in need thereof, wherein the ligand specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;
   wherein (i) the ligand comprises a human gamma-2 heavy chain constant region that comprises an amino acid selected from the group consisting of a Pro at position 72 shown in SEQ ID NO: 6, an Asn at position 75 shown in SEQ ID NO: 6, a Phe at position 76 shown in SEQ ID NO: 6, a Val at position 161 shown in SEQ ID NO: 6 and an Ala at position 257 shown in SEQ ID NO: 6 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 6, Asn at position 75 shown in SEQ ID NO: 6, Phe at position 76 shown in SEQ ID NO: 6, Val at position 161 shown in SEQ ID NO: 6 or Ala at position 257 shown in SEQ ID NO: 6; and
   wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an alternative, paragraph 1 provides:—

A ligand (eg, an antibody or antibody fragment) for use in a method of targeting Nav1.7 in a human, wherein the ligand specifically binds a human Nav1.7 protein that comprises an amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G;
wherein (i) the ligand comprises a human gamma-2 heavy chain constant region that comprises an amino acid selected from the group consisting of a Pro at position 72 shown in SEQ ID NO: 6, an Asn at position 75 shown in SEQ ID NO: 6, a Phe at position 76 shown in SEQ ID NO: 6, a Val at position 161 shown in SEQ ID NO: 6 and an Ala at position 257 shown in SEQ ID NO: 6 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 6, Asn at position 75 shown in SEQ ID NO: 6, Phe at position 76 shown in SEQ ID NO: 6, Val at position 161 shown in SEQ ID NO: 6 or Ala at position 257 shown in SEQ ID NO: 6; and
wherein (ii) said human comprises a nucleotide sequence encoding said Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

In an example, the human is suffering from or at risk of a Nav1.7-mediated disease or condition. In an example, the method treats or reduces the risk of a Nav1.7-mediated disease or condition in the human.

2. The ligand of any preceding clause, wherein said amino acid is selected from the group consisting of any one of 136I, 216S, 241T, 395K, 848T, 858H, 858F, 863P and 1449V; optionally wherein said disease or condition is a pain disease or condition.
3. The ligand of any preceding clause, wherein said amino acid is selected from the group consisting of 996C, 1298F, 1298D, 1299F, 1461T, 1462V, 1464I and 1627K; optionally wherein said disease or condition is a pain disease or condition.
4. The ligand of any preceding clause, wherein said amino acid is selected from the group consisting of 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K) and 1689X (wherein X is an amino acid other than W); optionally wherein said disease or condition is a pain disease or condition.
5. The ligand of any preceding clause, wherein the VH gene segment comprised by said human is a germline VH gene segment.
6. The ligand of any preceding clause said method comprising, before said administering, selecting a human comprising said nucleotide sequence of (ii), wherein the human is the human of clause 1.
7. The ligand of any preceding clause, wherein the human has been determined to comprise the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.
8. The ligand of any preceding clause, said method comprising the step of determining that the human comprises (a) the nucleotide sequence that encodes an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G and/or (b) an Nav1.7 protein comprising said mutation said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein the determining step is performed before administration of the antibody to the human.
9. The ligand of clause 8, wherein the step of determining comprises assaying a biological sample from the human for a nucleotide sequence encoding a Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.
10. The ligand of clause 9, wherein the assaying comprises contacting the biological sample with at least one oligonucleotide probe comprising a sequence of at least 10 contiguous nucleotides of a nucleotide sequence encoding an Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G or comprising an antisense sequence of said contiguous nucleotides, wherein said sequence of contiguous nucleotides comprises a nucleotide sequence encoding said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, thereby forming a complex when at least one nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G is present; and detecting the presence or absence of the complex, wherein detecting the presence of the complex determines that the human comprises the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

11. The ligand of clause 9, wherein the assaying comprises nucleic acid amplification and optionally one or more methods selected from sequencing, next generation sequencing, nucleic acid hybridization, and allele-specific amplification and/or wherein the assaying is performed in a multiplex format.

12. The ligand of clause 9 or 11, wherein said biological sample comprises serum, blood, faeces, tissue, a cell, urine and/or saliva of said human.

13. The ligand of any preceding clause, wherein said human is indicated as heterozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G, optionally, wherein said human is further indicated as comprising the nucleotide sequence of SEQ ID NO: 76, or said human is indicated as homozygous for a nucleotide sequence encoding the Nav1.7 protein comprising said amino acid selected from the group consisting of 136I, 216S, 241T, 395K, 848T, 858H, 858F, 863P, 1449V, 996C, 1298F, 1298D, 1299F, 1461T, 1462V, 1464I, 1627K, 277X (wherein X is an amino acid other than R), 328X (wherein X is an amino acid other than Y), 395K, 459X (wherein X is an amino acid other than S), 693X (wherein X is an amino acid other than E), 767X (wherein X is an amino acid other than I), 830X (wherein X is an amino acid other than R), 897X (wherein X is an amino acid other than W), 1200L, 1235L, 1488X (wherein X is an amino acid other than R), 1659X (wherein X is an amino acid other than K), 1689X (wherein X is an amino acid other than W), 422D, 490N, 943L, 1002L, 1161W and 1919G.

14. The ligand of any preceding clause, wherein said human is or has been further determined to be substantially resistant to a pain or itching treatment.

15. The ligand of any preceding clause, wherein said human is receiving or has received a pain or itching treatment or has reduced responsiveness to a pain or itching treatment.

16. The ligand of any preceding clause, wherein said disease or condition is a pain or itching disease or condition.

17. The ligand of any preceding clause, wherein said disease or condition is a channelopathy or associated with a channelopathy; or is selected from the group consisting of primary erythermalgia (PE), paroxysmal extreme pain disorder (PEPD) and channelopathy-associated insensitivity to pain (CIP).

18. The ligand of any preceding clause, wherein said human has been diagnosed with at least one condition recited in claim 16 or 17.

19. The ligand of any preceding clause, wherein said antibody or antibody fragment treats or reduces the risk in said human of a condition recited in claim 16 or 17.

20. The ligand of any preceding clause, wherein the nucleotide sequence comprises one or more SNPs selected from the group consisting of rs6746030, rs3750904, rs58022607, rs4369876, rs13402180 and rs12478318.

21. The ligand of any preceding clause, wherein said ligand (eg, antibody or antibody fragment) is for inhaled, intravenous or subcutaneous administration and/or is comprised in an inhalable or injectable preparation.

22. The ligand of any preceding clause, wherein the human gamma-2 heavy chain constant region of the ligand comprises IGHG2*01 amino acid sequence or an ADCC inactivated version thereof.

TABLE 4

| 1000 GENOMES PROJECT HUMAN POPULATIONS Below is a summary of the ethnic populations as per the 1000 Genomes Project sequences. Population |
| --- |
| European ancestry |
| Utah residents (CEPH) with Northern and Western European ancestry (CEU) Toscani in Italia (TSI) British from England and Scotland (GBR) Finnish from Finland (FIN) Iberian populations in Spain (IBS) |

TABLE 4-continued

1000 GENOMES PROJECT HUMAN POPULATIONS
Below is a summary of the ethnic populations as per the 1000 Genomes Project sequences.
Population

East Asian ancestry

Han Chinese in Beijing China (CHB)
Japanese in Toyko, Japan (JPT)
Han Chinese South (CHS)
Chinese Dai in Xishuangbanna (CDX)
Kinh in Ho Chi Minh City, Vietnam (KHV)
Chinese in Denver, Colorado (CHD) (pilot 3 only)

West African ancestry

Yoruba in Ibadan, Nigeria (YRI)
Luhya in Webuye, Kenya (LWK)
Gambian in Western Division, The Gambia (GWD)
Malawian in Blantyre, Malawi (MAB)
West African Population (TBD)

Americas

African Ancestry in Southwest US (ASW)
African American in Jackson, MS (AJM)
African Caribbean in Barbados (ACB)
Mexican Ancestry in Los Angeles CA (MXL)
Puerto Rican in Puerto Rico (PUR)
Colombian in Medellin, Colombia (CLM)
Peruvian in Lima, Peru (PEL)

South Asian ancestry

Ahom in the State of Assam, India
Kayadtha in Calcutta, India
Reddy in Hyderabad, India
Maratha in Bombay, India
Punjabi in Lahore, Pakistan

TABLE 5

TOIs & Related Diseases, Conditions and Example Ligands

| Human TOI | Example Disease or Condition | Example Ligand |
| --- | --- | --- |
| Il-17a | Inflammatory Disease<br>Uveitis<br>Rheumatoid Arthritis<br>Psoriasis | AIN457<br>Ixekizumab |
| Angiotensin II Receptor Type 1 (AT$_1$) | Hypertension | LCZ696 |
| Neprilysin | Hypertension | LCZ696 |
| Metabotropic Glutamate Receptor 5 (Mglur5) | Fragile X Syndrome | AFQ056<br>Mavoglurant |
| A Histone Deacetylase | Cancer, Eg, Multiple Myeloma | LBH589<br>Panobinostat |
| Diacylglycerol acyltransferase-1 (DGAT-1) | Familial Chylomicronaemia Syndrome | LCQ908<br>Pradigastat |
| Smoothened (Smo) | Basal cell carcinoma<br>Solid tumour<br>Myelofibrosis<br>Medulloblastoma<br>Solid tumour | LDE225 |
| Smoothened (Smo) receptor | Basal cell carcinoma<br>Solid tumors | LEQ506 |
| ALK | Non small cell lung carcinoma (NSCLC) | LDK378 |
| phosphatidylinositol-3-kinase (PI3K)<br>mTOR<br>AKT | Cancer, e.g., solid tumour, breast cancer, Renal cell carcinoma (RCC), Endometrial cancer, Non-small cell lung cancer (NSCLC), prostate cancer, Glioblastoma multiforme (GBM)<br>CRPC<br>GIST<br>Myelofibrosis | BKM120 |
| mTOR<br>PI3K<br>AKT | Cancer, e.g., solid tumour, breast cancer, Renal cell carcinoma (RCC), Endometrial cancer, Non-small cell lung cancer (NSCLC), prostate cancer, Glioblastoma multiforme (GBM)<br>CRPC<br>GIST<br>Myelofibrosis | BEZ235 |
| PI3Kα<br>mTOR<br>PI3K | Cancer, e.g., solid tumour, breast cancer, Renal cell carcinoma (RCC), | BYL719 |

TABLE 5-continued

TOIs & Related Diseases, Conditions and Example Ligands

| Human TOI | Example Disease or Condition | Example Ligand |
|---|---|---|
| AKT | Endometrial cancer, Non-small cell lung cancer (NSCLC), prostate cancer, Glioblastoma multiforme (GBM) CRPC GIST Myelofibrosis | |
| Mitogen-activated ERK kinase 1 (MEK1) Mitogen-activated ERK kinase 2 (MEK2) | Cancer, e.g., solid tumour, melanoma, pancreatic, colon, lung or thyroid cancer Metastasis | MEK162 |
| protein kinase protein kinase C FLT-3 c-KIT | Acute myeloid leukemia (AML) Myelodysplastic syndrome (MDS) Aggressive systemic mastocytosis (ASM) | PKC412 Midostaurin |
| ActRIIB | Sporadic inclusion body myositis (sIBM) | BYM338 bimagrumab |
| CD19 | Cancer, e.g., Leukaemia, mast cell leukemia, Acute Lymphoblastic Leukemia, Chronic lymphocytic leukemia (CLL) or Hematological tumors | CTL019 (formerly CART-19) |
| 11β-hydroxylase | Cushing's syndrome | LCI699 |
| BRAF | Cancer, e.g., melanoma | LGX818 |
| Receptor Tyrosine Kinase FGFR | Cancer, e.g., solid tumour Breast Cancer Endometrial cancer Hepatocellular carcinoma Renal cell carcinoma (RCC) Bladder cancer multiple myeloma (MM), hepatocellular carcinoma endometrial cancer | TKI258 (formerly CHIR-258) Dovitinib |
| DAC enzyme | hematologic malignancy Multiple myeloma Myel\odysplastic syndrome (MDS) Myelofibrosis | LBH589 panobinostat |
| HSP90 | Cancer, e.g., Breast Cancer, gastric cancer or Non-small cell lung cancer (NSCLC) | AUY922 |
| FGFR | Cancer, e.g., solid tumour Breast Cancer Endometrial cancer Hepatocellular carcinoma Renal cell carcinoma (RCC) Bladder cancer multiple myeloma (MM), hepatocellular carcinoma endometrial cancer | BGJ398 |
| cIAP1 cIAP2 | Cancer, e.g., solid tumour Breast Cancer Endometrial cancer Hepatocellular | LCL161 |

TABLE 5-continued

TOIs & Related Diseases, Conditions and Example Ligands

| Human TOI | Example Disease or Condition | Example Ligand |
|---|---|---|
| | carcinoma<br>Renal cell carcinoma (RCC)<br>Bladder cancer<br>multiple myeloma (MM),<br>hepatocellular carcinoma<br>endometrial cancer | |
| Akt | Cancer, e.g., Solid tumour, gastric cancer (e.g., castration-resistant prostate cancer), prostate cancer, gastroesophageal junction cancer | GDC-0068<br>RG7440 |
| CD22 | Hematologic malignancies<br>Non-Hodgkin's lymphoma (e.g., relapsed or refractory follicular non-Hodgkin's lymphoma)<br>Diffuse large B-cell lymphoma (e.g., relapsed or refractory diffuse large B-cell lymphoma) | DCDT2980S<br>RG7593 |
| CD79b | Hematologic malignancies<br>Non-Hodgkin's lymphoma (e.g., relapsed or refractory follicular non-Hodgkin's lymphoma)<br>Diffuse large B-cell lymphoma (e.g., relapsed or refractory diffuse large B-cell lymphoma) | DCDS4501A<br>RG7596 |
| endothelin B receptor (ETBR) | Melanoma, e.g., metastatic or unresectable melanoma | DEDN6526A<br>RG7636 |
| HER3 | Cancer, e.g., metastatic epithelial tumour, metastatic squamous cell carcinoma of the head and neck cancer, metastatic colorectal cancer | MEHD7945A<br>RG7597 |
| EGFR | Cancer, e.g., metastatic epithelial tumour, metastatic squamous cell carcinoma of the head and neck cancer, metastatic colorectal cancer | MEHD7945A<br>RG7597<br>Necitumumab |
| MUC16 | Cancer, e.g., ovarian cancer (e.g., platinum-resistant ovarian cancer) | DMUC5754A<br>RG7458 |
| sodium-dependent phosphate transport protein 2b (NaPi2b) | Cancer, e.g., metastatic non-squamous non-small cell lung cancer, ovarian cancer (e.g., platinum-resistant ovarian cancer) | DNIB0600A<br>RG7599 |
| PDL1 (programmed death ligand 1) | Cancer, e.g., solid tumour<br>metastatic melanoma<br>non-small cell lung cancer | MPDL3280A<br>RG7446 |
| STEAP1 (six-transmembrane epithelial antigen of the prostate 1) | Cancer, e.g., prostate cancer (e.g., metastatic castration-resistant prostate cancer) | DSTP3086S<br>RG7450 |
| Bcl-2 | Cancer, e.g., leukaemia (e.g., chronic lymphocytic leukaemia), non-Hodgkin's lymphoma | GDC-0199<br>RG7601 |
| Checkpoint kinase 1 (ChK1) | Cancer, e.g., solid tumour, refractory solid tumour or lymphoma | GDC-0425<br>RG7602<br>GDC-0575<br>RG7741 |
| mitogen activated protein kinase kinase (MAPKK) | Cancer, e.g., solid tumour, melanoma (e.g., metastatic | GDC-0973<br>RG7421 |

TABLE 5-continued

TOIs & Related Diseases, Conditions and Example Ligands

| Human TOI | Example Disease or Condition | Example Ligand |
|---|---|---|
| MEK | melanoma) | Cobimetinib<br>GDC-0623<br>RG7420 |
| epidermal growth factor domain-like-7 (EGFL7) | Cancer, e.g., colorectal cancer (e.g., metastatic colorectal cancer), NSCLC | Parsatuzumab<br>MEGF0444A<br>RG7414 |
| phosphatidylinositol-3-kinase (PI3K) | Cancer, e.g., prostate cancer, renal cell carcinoma, endometrial cancer, breast cancer (e.g., HER2-negative metastatic breast cancer, metastatic hormone receptor-positive breast cancer), solid tumour | GDC-0032<br>RG7604<br>GDC-0084<br>RG7666<br>Pictilisib<br>GDC-0941<br>RG7321 |
| mTOR<br>TORC1<br>TORC2<br>PI3K | Cancer, e.g., prostate cancer, renal cell carcinoma, endometrial cancer, breast cancer (e.g., HER2-negative metastatic breast cancer, metastatic hormone receptor-positive breast cancer), solid tumour | GDC-0980<br>RG7422 |
| IL17 | Autoimmune disease<br>Ankylosing spondylitis;<br>Asthma; Multiple myeloma; Multiple sclerosis; Polymyalgia rheumatica; Psoriasis; Psoriatic arthritis; Rheumatoid arthritis; Uveitis | Secukinumab<br>ixekizumab |
| M1 prime segment of membrane IgE | Allergic Asthma | Quilizumab<br>MEMP1972A<br>RG7449 |
| IFN alpha | Autoimmune disease<br>Systemic lupus erythematosus | Rontalizumab |
| PCSK9 (proprotein convertase subtilisin/kexin type 9) | coronary heart disease (CHD) or high risk of CHD<br>hyperlipidaemia<br>hypercholesterolaemia<br>stroke<br>atherosclerosis<br>a cardiovascular disease or condition<br>a condition associated with elevated LDL | MPSK3169A<br>RG7652 |
| Vascular Endothelial Growth Factor-A (VEGF-A)<br>Placental Growth Factor (P1GF) | Diabetic Macular Edema (DME),<br>Branch Retinal Vein Occlusion (BRVO)<br>Wet age-related macular degeneration (Wet AMD) | EYLEA ®<br>Aflibercept<br>AVASTIN ™<br>LUCENTIS ™ |
| IL-6 receptor | Inflammatory disease, e.g., rheumatoid arthritis<br>Uveitis (e.g., non-infectious uveitis)<br>Ankylosing spondylitis;<br>Cancer | Sarilumab<br>REGN88 |
| PCSK9 (proprotein convertase subtilisin/kexin type 9) | coronary heart disease (CHD) or high risk of CHD<br>hyperlipidaemia<br>hypercholesterolaemia<br>stroke<br>atherosclerosis<br>a cardiovascular disease or condition<br>a condition associated with elevated LDL | Alirocumab<br>REGN727<br>LY3015014 |
| NGF | Osteoarthritis<br>Pain | Fasinumab<br>REGN475 |
| IL-4 receptor alpha<br>IL-13 receptor | Allergic asthma<br>eosinophilic asthma<br>Atopic dermatitis | Dupilumab<br>REGN668 |

TABLE 5-continued

TOIs & Related Diseases, Conditions and Example Ligands

| Human TOI | Example Disease or Condition | Example Ligand |
|---|---|---|
| delta-like ligand-4 (Dll4) | Cancer | Enoticumab REGN421 |
| angiopoietin-2 (Ang2) | Cancer | Nesvacumab REGN910 |
| GDF8 | Metabolic disorder cancer, obesity, diabetes, arthritis, multiple sclerosis, muscular dystrophy, amyotrophic lateral sclerosis, Parkinson's disease, osteoporosis, osteoarthritis, osteopenia, metabolic syndromes (including, but not limited to diabetes, obesity, nutritional disorders, organ atrophy, chronic obstructive pulmonary disease and anorexia) Disuse muscle atrophy cancer-related cachexia | REGN1033 LY2495655 |
| ERBB3 | Cancer | REGN1400 |
| angiopoietin -1 (Ang1) angiopoietin -1 (Ang2) | Cancer, e.g., ovarian cancer | AMG386 |
| VEGF receptor | Cancer | Motesanib |
| PDGF receptor | NSCLC | AMG 706 |
| Stem cell factor receptor | Breast cancer Thyroid cancer | |
| type 1 insulin-like growth factor receptor (IGF1R) | Cancer Breast cancer Pancreatic cancer | Ganitumab Linsitinib ASP7487 |
| hepatocyte growth factor (HGF) | Cancer Breast cancer Pancreatic cancer | Rilotumumab |
| HER3 | Cancer | AMG 888 |
| ErbB3 | Breast cancer Pancreatic cancer | U3-1287 |
| IL-17 receptor | Inflammatory disease Asthma Psoriasis | AMG 827 brodalumab |
| sclerostin | Bone-related condition postmenopausal osteoporosis fracture healing | AMG 785 CDP7851 |
| glucokinase | Diabetes | AMG 151 ARRY-403 |
| PCSK9 (proprotein convertase subtilisin/kexin type 9) | coronary heart disease (CHD) or high risk of CHD hyperlipidaemia hypercholesterolaemia stroke atherosclerosis a cardiovascular disease or condition a condition associated with elevated LDL | AMG 145 Evolocumab |
| VLA 2 Integrin α2β1 | Inflammatory bowel disease | SAR339658 |
| IL-4 IL-13 | Idiopathic pulmonary fibrosis | SAR156597 |
| lysophosphatidic acid receptor LPA-1 LPA-3 | Systemic sclerosis fibrosis | SAR100842 |
| Androgen receptor | Cancer, e.g., prostate cancer, breast cancer | MDV3100 enzalutamide |
| HER1 | Cancer, e.g., NSCLC | Erlotinib |
| EGFR | | ERBITUX ™ VECTIBIX ™ |
| VEGF receptor 1 VEGF receptor 2 VEGF receptor 3 | Cancer, e.g., colorectal cancer, breast cancer | ASP4130 tivozanib |
| JAK JAK1 JAK2 | Inflammatory disease, e.g., rheumatoid arthritis Diabetic nephropathy | ASP015K Baricitinib |

TABLE 5-continued

TOIs & Related Diseases, Conditions and Example Ligands

| Human TOI | Example Disease or Condition | Example Ligand |
|---|---|---|
| CD40 | Prevention of organ transplant rejection | ASP1240 |
| GnRH | Endometriosis Cancer, e.g., prostate cancer | ASP1707 degarelix |
| PDE9 | Lower unirary tract symptoms associated with benign prostatic hyperplasia | ASP4901 |
| TNF alpha | Inflammatory disease, e.g., rheumatoid arthritis, psoriasis, chrohn's disease, IBD | Certolizumab pegol |
| Programmed cell death protein 1 | Cancer Chronic myelocytic leukemia; Hepatitis C virus infection; Hepatocellular carcinoma; Hodgkins disease; Melanoma; Multiple myeloma; Non-Hodgkin lymphoma; Non-small-cell lung cancer; Renal cell carcinoma; Solid tumor; Stage IV melanoma | Nivolumab MK-3475 |
| Hepatocyte growth factor MET | Cancer Glioblastoma; Hepatocellular carcinoma; Metastatic colorectal cancer; Metastatic non small cell lung cancer; Metastatic stomach cancer; Non-small-cell lung cancer | onartuzumab |
| Angiopoietin ligand-1 Angiopoietin ligand-2 Tek tyrosine kinase receptor | Breast tumor; Cancer; Colorectal tumor; Fallopian tube cancer; Gastrointestinal tumor; Glioblastoma; Hepatocellular carcinoma; Metastatic esophageal cancer; Metastatic gastrointestinal cancer; Metastatic non small cell lung cancer; Metastatic ovary cancer; Metastatic renal cancer; Ovary tumor; Peritoneal tumor; Transitional cell carcinoma | trebananib |
| CD37 modulator Lymphocyte function antigen-3 receptor SLAM family member 7 | Cancer Multiple myeloma | elotuzumab |
| IL-2 IL-2 receptor alpha | Multiple sclerosis | daclizumab |
| EGFR | Cancer Metastatic non small cell lung cancer; Solid tumor | necitumumab |
| IL-5 | Asthma; Eosinophilic esophagitis | reslizumab |
| B-lymphocyte cell adhesion molecule CD22 | Cancer, e.g. Acute lymphoblastic leukemia; Follicle center lymphoma; Non-Hodgkin lymphoma; Systemic lupus erythematosus, hairy cell leukaemia | Inotuzumab inotuzumab ozogamicin epratuzumab moxetumomab moxetumomab pasudotox |
| IL1 beta | Acne vulgaris; Atherosclerosis; Behcets disease; Cardiovascular disease; Dermatomyositis; Insulin dependent diabetes; Multiple myeloma; Osteoarthritis; Paraproteinemia; Polymyositis; Pyoderma gangrenosum; Scleritis; Uveitis | gevokizumab |

TABLE 5-continued

TOIs & Related Diseases, Conditions and Example Ligands

| Human TOI | Example Disease or Condition | Example Ligand |
|---|---|---|
| CD20 | Cancer<br>Multiple sclerosis<br>follicular lymphoma (e.g., refractory or relapsed)<br>diffuse large B cell lymphoma (e.g., relapsed)<br>chronic lymphocytic leukaemia (e.g., first line therapy or relapsed) | Ocrelizumab<br>ofatumumab |
| IL-23 | Crohns disease;<br>Inflammatory disease;<br>Psoriasis | tildrakizumab |
| BAFF<br>Neutrokine alpha | Autoimmune disease<br>systemic lupus erythematosus<br>Multiple myeloma<br>vasculitis | Belimumab<br>Benlysta ™<br>Tabalumab |
| IL5 | Asthma | mepolizumab |
| IL6 | Inflammatory disease<br>rheumatoid arthritis | sirukumab |
| Lp-PLA2 | Atherosclerosis<br>diabetic macular oedema | darapladib |
| CCR9 chemokine receptor | Inflammatory disease<br>rheumatoid arthritis<br>Crohn's disease | Vercirnon |
| DOPA decarboxylase | Parkinson's Disease | Patrome |
| Her2<br>EGFR | Cancer, e.g., gastric cancer, breast cancer, head and neck squamous cell cancer, | Tyverb ™<br>Tykerb ™<br>lapatinib |
| ADP receptor | Cardiovascular disease or condition<br>Thrombosis, e.g., arterial thrombosis | Brilinta<br>Brilique |
| VEGFR<br>EGFR | Cancer, e.g.,<br>medullary thyroid cancer | Caprelsa |
| LABA<br>LAMA | Respiratory disease or condition, e.g., COPD | PT003 GFF |
| Factor Xa | thromboembolism | apixaban |
| Oxelumab | OX40 ligand<br>Asthma<br>Graft-versus-host disease | |
| Tremelimumab<br>Ticilimumab<br>ipilimumab | CTLA-4<br>CD152 | Cancer, e.g., melanoma<br>Autoimmune disease |
| MPDL3280A<br>MEDI4736 | PD-L1 | Cancer, e.g., solid tumour, kidney cancer, lung cancer, melanoma, NSCLC, multiple myeloma<br>Autoimmune disease |
| Nivolumab<br>AMP-514<br>AMP-224 | PD-1<br>LIGHT<br>TNF SF 14<br>CD40 ligand | Cancer, e.g., solid tumour, kidney cancer, lung cancer, melanoma, NSCLC, multiple myeloma<br>Autoimmune disease |
| JAK | Inflammatory disease, e.g., rheumatoid arthritis, psoriasis, chrohn's disease, IBD, ulcerative colitis, Psoriatic Arthritis | tofacitinib |
| Nerve Growth Factor | Pain<br>Osteoarthritis pain | tanezumab |
| Her1 receptor<br>Her2 receptor<br>Her4 receptor | Cancer, e.g., Non-Small Cell Lung Cancer | dacomitinib |
| c-MET<br>ALK | Cancer, e.g., Non-Small Cell Lung Cancer | crizotinib |
| Programmed cell death 1 receptor | Cancer, e.g., renal cell carcinoma | Nivolumab |
| SLAMF7<br>CD319 | Cancer, e.g., multiple myeloma | Elotuzumab |
| CD30 | Cancer, e.g., Hodgkin lymphoma, systemic anaplastic large cell lymphoma, T-cell lymphoma | Brentuximab<br>Brentuximab vedotin |

TABLE 5-continued

TOIs & Related Diseases, Conditions and Example Ligands

| Human TOI | Example Disease or Condition | Example Ligand |
|---|---|---|
| GPR40 | Diabetes, e.g., diabetes mellitus | Fasiglifam |
| DPP-4 | | trelagliptin |
| VEFGR-1 receptor | Cancer, e.g., non-squamous non-small cell lung cancer | Motesanib |
| VEFGR-2 receptor | | Motesanib diphosphate |
| VEFGR-3 receptor | | |
| PDGFR | | |
| cKit | | |
| amyloid β | Alzheimer's disease | Solanezumab |
| TNF alpha | Inflammatory disease, e.g., rheumatoid arthritis, psoriasis, chrohn's disease, IBD, ulcerative colitis, Psoriatic Arthritis | SIMPONI ™ HUMIRA ™ REMICADE ™ ENBREL ™ Adalimumab |
| IL-21 | Autoimmune disease or condition | Agonist or antagonist antibody specific for human IL-21 |
| | Inflammatory disease or condition | NNC0114-0005 |
| | Rheumatoid arthritis | NNC0114-0006 |
| | Crohn's disease | NN8828 |
| | IBD | ATR-107 |
| | Ulcerative colitis | Said or an anti-IL-21 antibody in combination with an agent selected from the group consisting of ipilimumab (e.g., to treat melanoma), an anti-PD1 antibody (e.g., to treat solid tumours), sunitinib (e.g., to treat renal cell carcinoma), rituximab (e.g., to treat Non-Hodgkin's lymphoma), sorafenib (e.g., to treat renal cell carcinoma), doxorubicin (e.g., to treat ovarian cancer) and cetuximab (e.g., to treat colorectal cancer). |
| | Systemic lupus erythematosus (SLE) | |
| | Graft versus host disease | |
| | Cancer | |
| | Metastatic melanoma | |
| | Renal cell carcinoma | |
| | Melanoma | |
| | Solid tumours | |
| | Acute myeloid leukaemia | |
| | Non-Hodgkin's lymphoma | |
| | Ovarian cancer | |
| | Colorectal cancer | |

TABLE 6

PCSK9 SEQUENCES

| FORM/ ALLELE | VERSION | SEQUENCE | SEQ ID NO: |
|---|---|---|---|

AMINO ACID SEQUENCES
*Italics* = signal sequence 1-30

`Courier` = pro peptide 31-152 lower case = catalytic domain 153-449
UPPER CASE = C-terminal domain 450-692
Underlined = residues changed from allele a in other sequences (aa residue number shown)

| a | Pro-Form with Signal Sequence | *MGTVSSRRSWWPLPLLLLLLLLLGPAGARA*`QEDEDGDYEELVLAL`<u>`R`</u>`SEEDGLA`<u>`E`</u>`APEHGTTATFHRCAKDP` `WRLPGTYVVVLKEETHLSQSERTARRLQAQAARRGYLTKILHVFHGLLPGFLVKMSGDLLELALKLPH` `VDYIEEDSSVFAQ`sipwnleritppryradeyqppdggslvevylldtsiqsdhreiegrvmvtdfenvpeedgtrfhrqaskcdshg thlagvvsgrdagvakgasmrslrvlncqgkgtvsgtliglefirksqlvqpvgplvvllplaggysrvlnaacqrlaragvvlvtaagnfrddacly spasapevitvgatnaqdqpvtlgtlgtnfgrcvdlfapgediigassdcstcfvsqsgtsqaaahvagiaammlsaepeltlaelrqrlihfsak | 1 |

TABLE 6-continued

PCSK9 SEQUENCES

| FORM/ALLELE | VERSION | SEQUENCE | SEQ ID NO: |
|---|---|---|---|
| | | 425 443 474<br>dvineawfpedqrvltpnlvaalppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>619 620<br>HKPPVLRPRGQPNQCVGHREASIHASCCHAPGLECKVKEHGIPAPQEQVTVACEEGWTLTGCSALPGTSHVLGAY<br><br>670<br>AVDNTCVVRSRDVSTTGSTSEEAVTAVAICCRSRHLAQASQELQ | |
| a | Pro-Form | QEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevylldtsiqsdhreiegrvmvtdfenvpeedgtrfhrqaskcdshg<br><br>thlagvvsgrdagvakgasmrslrvlncqgkgtvsgtligleﬁrksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>425 443 474<br>dvineawfpedqrvltpnlvaalppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>619 620<br>HKPPVLRPRGQPNQCVGHREASIHASCCHAPGLECKVKEHGIPAPQEQVTVACEEGWTLTGCSALPGTSHVLGAY<br><br>670<br>AVDNTCVVRSRDVSTTGSTSEEAVTAVAICCRSRHLAQASQELQ | 2 |
| a | Mature form | sipwnleritppryradeyqppdggslvevylldtsiqsdhreiegrvmvtdfenvpeedgtrfhrqaskcdshg<br><br>thlagvvsgrdagvakgasmrslrvlncqgkgtvsgtligleﬁrksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>425 443 474<br>dvineawfpedqrvltpnlvaalppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>619 620<br>HKPPVLRPRGQPNQCVGHREASIHASCCHAPGLECKVKEHGIPAPQEQVTVACEEGWTLTGCSALPGTSHVLGAY<br><br>670<br>AVDNTCVVRSRDVSTTGSTSEEAVTAVAICCRSRHLAQASQELQ | 3 |
| f | Pro-Form with Signal Sequence | 46 53<br>*MGTVSSRRSWWPLPLLLLLLLLLGPAGARA*QEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevylldtsiqsdhreiegrvmvtdfenvpeedgtrfhrqaskcdshg<br><br>thlagvvsgrdagvakgasmrslrvlncqgkgtvsgtligleﬁrksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak | 4 |

TABLE 6-continued

PCSK9 SEQUENCES

| FORM/ALLELE | VERSION | SEQUENCE | SEQ ID NO: |
|---|---|---|---|
| | | 425              443                              474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                                         619 620<br>HKPPVLRPRGQPNQCVGHREASIHASCCHAPGLECKVKEHGIPAPQEQVTVACEEGWTLTGCSALPGTSHVLGAY<br><br>                   670<br>AVDNTCVVRSRDVSTTGSTSEEAVTAVAICCRSRHLAQASQELQ | |
| f | Pro-Form | QEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>            425              443                              474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                                         619 620<br>HKPPVLRPRGQPNQCVGHREASIHASCCHAPGLECKVKEHGIPAPQEQVTVACEEGWTLTGCSALPGTSHVLGAY<br><br>                   670<br>AVDNTCVVRSRDVSTTGSTSEEAVTAVAICCRSRHLAQASQELQ | 5 |
| f, p, aj | Mature form | sipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>            425              443                              474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                                         619 620<br>HKPPVLRPRGQPNQCVGHREASIHASCCHAPGLECKVKEHGIPAPQEQVTVACEEGWTLTGCSALPGTSHVLGAY<br><br>                   670<br>AVDNTCVVRSRDVSTTGSTSEEAVTAVAICCRSRHLAQASQELQ | 6 |
| c | Pro-Form with Signal Sequence | *MGTVSSRRSWWPLPLLLLLLLLLGPAGARA*QEDEDGDYEELVLAL<u>R</u>SEEDGL<u>A</u>EAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak | 7 |

TABLE 6-continued

PCSK9 SEQUENCES

| FORM/ALLELE | VERSION | SEQUENCE | SEQ ID NO: |
|---|---|---|---|
| | |       425         443                     474<br>dv<u>i</u>neawfpedqrvltpnlvaa<u>l</u>ppsthGAGWQLFCRTVWSAHSGPTRMATA<u>I</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                              619 620<br>HKPPVLRPRGQPNQCVGHREASIHASCCHAPGLECKVKEHGIPAPQ<u>E</u>QVTVACEEGWTLTGCSALPGTSHVLGAY<br><br>                       670<br>AVDNTCVVRSRDVSTTGSTSE<u>G</u>AVTAVAICCRSRHLAQASQELQ | |
| c | Pro-Form | QEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>      425         443                     474<br>dv<u>i</u>neawfpedqrvltpnlvaa<u>l</u>ppsthGAGWQLFCRTVWSAHSGPTRMATA<u>I</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                              619 620<br>HKPPVLRPRGQPNQCVGHREASIHASCCHAPGLECKVKEHGIPAPQ<u>E</u>QVTVACEEGWTLTGCSALPGTSHVLGAY<br><br>                       670<br>AVDNTCVVRSRDVSTTGSTSE<u>G</u>AVTAVAICCRSRHLAQASQELQ | 8 |
| c, q | Mature form | sipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>      425         443                     474<br>dv<u>i</u>neawfpedqrvltpnlvaa<u>l</u>ppsthGAGWQLFCRTVWSAHSGPTRMATA<u>I</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                              619 620<br>HKPPVLRPRGQPNQCVGHREASIHASCCHAPGLECKVKEHGIPAPQ<u>E</u>QVTVACEEGWTLTGCSALPGTSHVLGAY<br><br>                       670<br>AVDNTCVVRSRDVSTTGSTSE<u>G</u>AVTAVAICCRSRHLAQASQELQ | 9 |
| r | Pro-Form with Signal Sequence |                                           46       53<br>*MGTVSSRRSSWWPLPLLLLLLLLLGPAGARA*QEDEDGDYEELVLALR<u>S</u>EEDGLA<u>E</u>APEHGTTATFHRCAKP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak | 10 |

TABLE 6-continued

PCSK9 SEQUENCES

| FORM/ALLELE | VERSION | SEQUENCE | SEQ ID NO: |
|---|---|---|---|
| | |      425       443             474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                      619 620<br>HKPPVLRPRGQPNQCVGHREASIHASCCHAPGLECKVKEHGIPAPQEQVTVACEEGWTLTGCSALPGTSHVLGAY<br><br>           670<br>AVDNTCVVRSRDVSTTGSTSEGAVTAVAICCRSRHLAQASQELQ | |
| r | Pro-Form | QEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>     425       443             474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                      619 620<br>HKPPVLRPRGQPNQCVGHREASIHASCCHAPGLECKVKEHGIPAPQEQVTVACEEGWTLTGCSALPGTSHVLGAY<br><br>            670<br>AVDNTCVVRSRDVSTTGSTSEGAVTAVAICCRSRHLAQASQELQ | 11 |
| r | Mature form | sipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>     425       443             474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                      619 620<br>HKPPVLRPRGQPNQCVGHREASIHASCCHAPGLECKVKEHGIPAPQEQVTVACEEGWTLTGCSALPGTSHVLGAY<br><br>            670<br>AVDNTCVVRSRDVSTTGSTSEGAVTAVAICCRSRHLAQASQELQ | 12 |
| p | Pro-Form with Signal Sequence |                                 46   53<br>MGTVSSRRSSWWPLPLLLLLLLLLLGPAGARAQEDEDGDYEELVLALRSEEDGLVEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnlerltppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak | 13 |

TABLE 6-continued

PCSK9 SEQUENCES

| FORM/ AL- LELE | VERSION | SEQUENCE | SEQ ID NO: |
|---|---|---|---|
| | | 425      443      474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                  619 620<br>HKPPVLRPRGQPNQCVGHREASIHASCCHAPGLECKVKEHGIPAPQEQVTVACEEGWTLTGCSALPGTSHVLGAY<br><br>         670<br>AVDNTCVVRSRDVSTTGSTSEEAVTAVAICCRSRHLAQASQELQ | |
| p | Pro-Form | QEDEDGDYEELVLALRSEEDGLVEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnlerltppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>425      443      474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                  619 620<br>HKPPVLRPRGQPNQCVGHREASIHASCCHAPGLECKVKEHGIPAPQEQVTVACEEGWTLTGCSALPGTSHVLGAY<br><br>         670<br>AVDNTCVVRSRDVSTTGSTSEEAVTAVAICCRSRHLAQASQELQ | 14 |
| m | Pro-Form with Signal Sequence |                                       46      53<br>MGTVSSRRSWWPLPLLLLLLLLLGPAGARAQEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnlerltppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>425      443      474<br>dvineawfpedqrvltpnlvatlppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                  619 620<br>HKPPVLRPRGQPNQCVGHREASIHASCCHAPGLECKVKEHGIPAPQEQVTVACEEGWTLTGCSALPGTSHVLGAY<br><br>         670<br>AVDNTCVVRSRDVSTTGSTSEEAVTAVAICCRSRHLAQASQELQ | 15 |
| m | Pro-Form | QEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnieritppryradeyqppdggsivevyiidtsiqsdhreiegrvmvtdfenvpeedgtrfhrqaskcdshg | 16 |

TABLE 6-continued

PCSK9 SEQUENCES

| FORM/ALLELE | VERSION | SEQUENCE | SEQ ID NO: |
|---|---|---|---|
| | | thlagvvsgrdagvakgasmrslrvlncqgkgtvsgtligleﬁrksqlvqpvgplvvllplaggysrvlnaacqrlaragvvlvtaagnfrddacly | |
| | | spasapevitvgatnaqdqpvtlgtlgtnfgrcvdlfapgediigassdcstcfvsqsgtsqaaahvagiaammlsaepeltlaelrqrlihfsak | |
| | |            425             443                    474<br>dvineawfpedqrvitpnivatippsthGAGWQLFCRTVWSAHSGPTRMATAIARCAPDEELLSCSSFSRSGKRRGERM | |
| | | EAQGGKLVCRAHNAFGGEGVYAIARCCLLPQANCSVHTAPPAEASMGTRVHCHQQGHVLTGCSSHWEVEDLGT | |
| | |                                       619 620<br>HKPPVLRPRGQPNQCVGHREASIHASCCHAPGLECKVKEHGIPAPQEQVTVACEEGWTLTGCSALPGTSHVLGAY | |
| | |                         670<br>AVDNTCVVRSRDVSTTGSTSEEAVTAVAICCRSRHLAQASQELQ | |
| m | Mature form | sipwnleritppryradeyqppdggslvevylldtsiqsdhreiegrvmvtdfenvpeedgtrfhrqaskcdshg | 17 |
| | | thlagvvsgrdagvakgasmrslrvlncqgkgtvsgtligleﬁrksqlvqpvgplvvllplaggysrvlnaacqrlaragvvlvtaagnfrddacly | |
| | | spasapevitvgatnaqdqpvtlgtlgtnfgrcvdlfapgediigassdcstcfvsqsgtsqaaahvagiaammlsaepeltlaelrqrlihfsak | |
| | |            425            443                    474<br>dvineawfpedqrvitpnivatippsthGAGWQLFCRTVWSAHSGPTRMATAIARCAPDEELLSCSSFSRSGKRRGERM | |
| | | EAQGGKLVCRAHNAFGGEGVYAIARCCLLPQANCSVHTAPPAEASMGTRVHCHQQGHVLTGCSSHWEVEDLGT | |
| | |                                       619 620<br>HKPPVLRPRGQPNQCVGHREASIHASCCHAPGLECKVKEHGIPAPQEQVTVACEEGWTLTGCSALPGTSHVLGAY | |
| | |                         670<br>AVDNTCVVRSRDVSTTGSTSEEAVTAVAICCRSRHLAQASQELQ | |
| e | Pro-Form with Signal Sequence | *MGTVSSRRSWWPLPLLLLLLLLLGPAGARA* QEDEDGDYEELVLALRSEEDGLAEAPEHGTTATFHRCAKDP | 18 |
| | | WRLPGTYVVVLKEETHLSQSERTARRLQAQAARRGYLTKILHVFHGLLPGFLVKMSGDLLELALKLPH | |
| | | VDYIEEDSSVFAQsipwnieritppryradeyqppdggsivevyiidtsiqsdhreiegrvmvtdfenvpeedgtrfhrqaskcdshg | |
| | | thlagvvsgrdagvakgasmrslrvlncqgkgtvsgtligleﬁrksqlvqpvgplvvllplaggysrvlnaacqrlaragvvlvtaagnfrddacly | |
| | | spasapevitvgatnaqdqpvtlgtlgtnfgrcvdlfapgediigassdcstcfvsqsgtsqaaahvagiaammlsaepeltlaelrqrlihfsak | |
| | |            425            443                    474<br>dviseawfpedqrvitpnlvaalppsthGAGWQLFCRTVWSAHSGPTRMATAVARCAPDEELLSCSSFSRSGKRRGERM | |
| | | EAQGGKLVCRAHNAFGGEGVYAIARCCLLPQANCSVHTAPPAEASMGTRVHCHQQGHVLTGCSSHWEVEDLGT | |
| | |                                       619 620<br>HKPPVLRPRGQPNQCVGHREASIHASCCHAPGLECKVKEHGIPAPQEQVTVACEEGWTLTGCSALPGTSHVLGAY | |
| | |                         670<br>AVDNTCVVRSRDVSTTGSTSEEAVTAVAICCRSRHLAQASQELQ | |
| e | Pro-Form | QEDEDGDYEELVLALRSEEDGLAEAPEHGTTATFHRCAKDP | 19 |
| | | WRLPGTYVVVLKEETHLSQSERTARRLQAQAARRGYLTKILHVFHGLLPGFLVKMSGDLLELALKLPH | |
| | | VDYIEEDSSVFAQsipwnleritppryradeyqppdggslvevylidtsiqsdhreiegrvmvtdfenvpeedgtrfhrqaskcdshg | |
| | | thlagvvsgrdagvakgasmrslrvlncqgkgtvsgtligleﬁrksqlvqpvgplvvllplaggysrvlnaacqrlaragvvlvtaagnfrddacly | |
| | | spasapevitvgatnaqdqpvtlgtlgtnfgrcvdlfapgediigassdcstcfvsqsgtsqaaahvagiaammlsaepeltlaelrqrlihfsak | |

TABLE 6-continued

PCSK9 SEQUENCES

| FORM/ ALLELE | VERSION | SEQUENCE | SEQ ID NO: |
|---|---|---|---|
| | | 425　　　　　　　443　　　　　　　　　　　474<br>dvi<u>s</u>eawfpedqrvltpnlvaa<u>l</u>ppsthGAGWQLFCRTVWSAHSGPTRMATA<u>V</u>ARCAPDEELLSCSSFSRGKRRGERM<br><br>EAQGGKLVCRAHNAFGGEGVYAIARCCLLPQANCSVHTAPPAEASMGTRVHCHQQGHVLTGCSSHWEVEDLGT<br><br>　　　　　　　　　　　　　　　　　　　　　　　　　　　　　619 620<br>HKPPVLRPRGQPNQCVGHREASIHASCCHAPGLECKVKEHGIPAPQ<u>E</u>QVTVACEEGWTLTGCSALPGTSHVLGAY<br><br>　　　　　670<br>AVDNTCVVRSRDVSTTGSTSE<u>E</u>AVTAVAICCRSRHLAQASQELQ | |
| e | Mature form | sipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>　　　　　　　425　　　　　　　443　　　　　　　　　　　474<br>dvi<u>s</u>eawfpedqrvltpnlvaa<u>l</u>ppsthGAGWQLFCRTVWSAHSGPTRMATA<u>V</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>　　　　　　　　　　　　　　　　　　　　　　　　　　　　　619 620<br>HKPPVLRPRGQPNQCVGHREASIHASCCHAPGLECKVKEHGIPAPQ<u>E</u>QVTVACEEGWTLTGCSALPGTSHVLGAY<br><br>　　　　　670<br>AVDNTCVVRSRDVSTTGSTSE<u>E</u>AVTAVAICCRSRHLAQASQELQ | 20 |
| h | Pro-Form with Signal Sequence | 　　　　　　　　　　　　　　　　　　　　　　　　46　　　53<br>*MGTVSSRRSWWPLPLLLLLLLLLLGPAGARA*QEDEDGDYEELVLAL<u>R</u>SEEDGL<u>AE</u>APEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevlldtsiqsdhreiegrvmvtdfenvpeedgtrfhqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>　　　　　　　425　　　　　　　443　　　　　　　　　　　474<br>dvi<u>n</u>eawfpedqrvitpnlvat<u>l</u>ppsthGAGWQLFCRTVWSAHSGPTRMATA<u>I</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>　　　　　　　　　　　　　　　　　　　　　　　　　　　　　619 620<br>HKPPVLRPRGQPNQCVGHREASIHASCCHAPGLECKVKEHGIPAPP<u>E</u>QVTVACEEGWTLTGCSALPGTSYVLGAY<br><br>　　　　　670<br>AVDNTCVVRSRDVSTTGSTSE<u>E</u>AVTAVAICCRSRHLAQASQELQ | 21 |
| h | Pro-Form | QEDEDGDYEELVLAL<u>R</u>SEEDGL<u>AE</u>APEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevlldtsiqsdhreiegrvmvtdfenvpeedgtrfhqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak | 22 |

TABLE 6-continued

PCSK9 SEQUENCES

| FORM/ALLELE | VERSION | SEQUENCE | SEQ ID NO: |
|---|---|---|---|
| | |             425            443                      474<br>dvineawfpedqrvltpnlvatippsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                              619 620<br>HKPPVLRPRGQPNQCVGHREASIHASCCHAPGLECKVKEHGIPAPPEQVTVACEEGWTLTGCSALPGTSHVLGAY<br><br>                  670<br>AVDNTCVVRSRDVSTTGSTSEEAVTAVAICCRSRHLAQASQELQ | |
| h | Mature form | sipwnleritppryradeyqppdggslvevylldtsiqsdhreiegrvmvtdfenvpeedgtrfhrqaskcdshg<br><br>thlagvvsgrdagvakgasmrslrvlncqgkgtvsgtligleflrksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>            425            443                      474<br>dvineawfpedqrvltpnlvatlppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                              619 620<br>HKPPVLRPRGQPNQCVGHREASIHASCCHAPGLECKVKEHGIPAPPEQVTVACEEGWTLTGCSALPGTSHVLGAY<br><br>                  670<br>AVDNTCVVRSRDVSTTGSTSEEAVTAVAICCRSRHLAQASQELQ | 23 |
| aj | Pro-Form with Signal Sequence |                                              46    53<br>*MGTVSSRRSWWPLPLLLLLLLLLGPAGARA*QEDEDGDYEELVLALLSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnleritppryradeyqppdggslvevylldtsiqsdhrelegrvmvtdfenvpeedgtrfhrqaskcdshg<br><br>thlagvvsgrdagvakgasmrslrvlncqgkgtvsgtligleflrksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>            425            443                      474<br>dvineawfpedqrvltpnlvaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                              619 620<br>HKPPVLRPRGQPNQCVGHREASIHASCCHAPGLECKVKEHGIPAPQEQVTVACEEGWTLTGCSALPGTSHVLGAY<br><br>                  570<br>AVDNTCVVRSRDVSTTGSTSEEAVTAVAICCRSRHLAQASQELQ | 24 |
| aj | Pro-Form | QEDEDGDYEELVLALLSEEDGLAEAPEHGTTATFHRCAKDP<br><br>WRLPGTYVVVLKEETHLSQSERTARRLQAQAARRGYLTKILHVFHGLLPGFLVKMSGDLLELAIKLPH<br><br>VDYIEEDSSVFAQsipwnleritppryradeyqppdggsivevylldtsiqsdhreiegrvmvtdfenvpeedgtrfhrqaskcdshg<br><br>thlagvvsgrdagvakgasmrslrvlncqgkgtvsgtligleflrksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak | 25 |

TABLE 6-continued

PCSK9 SEQUENCES

| FORM/ ALLELE | VERSION | SEQUENCE | SEQ ID NO: |
|---|---|---|---|
| | | 425 443 474<br>dvineawfpedqrvltpnivaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>619 620<br>HKPPVLRPRGQPNQCVGHREASIHASCCHAPGLECKVKEHGIPAPQEQVTVACEEGWTLTGCSALPGTSHVLGAY<br><br>570<br>AVDNTCVVRSRDVSTTGSTSEEAVTAVAICCRSRHLAQASQELQ | |
| q | Pro-Form with Signal Sequence | 46 53<br>*MGTVSSRRSWWPLPLLLLLLLLLGPAGARA*QEDEDGDYEELVLALRSEEDGLVEAPEHGTTATFHRCAKDP<br><br>WRLPGTYVVVLKEETHLSQSERTARRLQAQAARRGYLTKILHVFHGLLPGFLVKMSGDLLELAIKLPH<br><br>VDYIEEDSSVFAQsipwnleritppryradeyqppdggsivevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>425 443 474<br>dvineawfpedqrvltpnivaalppsthGAGWQLFCRTVWSAHSGPTRMATAVARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>619 620<br>HKPPVLRPRGQPNQCVGHREASIHASCCHAPGLECKVKEHGIPAPQEQVTVACEEGWTLTGCSALPGTSHVLGAY<br><br>570<br>AVDNTCVVRSRDVSTTGSTSEEAVTAVAICCRSRHLAQASQELQ | 26 |
| q | Pro-Form | QEDEDGDYEELVLALLSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSCFAQsipwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvlvtaagnfrddacly<br><br>spasapevitvgatnaqdqpvtlgtlgtnfgrcvdlfapgediigassdcstcfvsqsgtsqaaahvagiaammlsaepeltlaelrqrlihfsak<br><br>425 443 474<br>dvineawfpedqrvltpnfvaalppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>619 620<br>HKPPVLRPRGQPNQCVGHREASIHASCCHAPGLECKVKEHGIPAPQEQVTVACEEGWTLTGCSALPGTSHVLGAY<br><br>670<br>AVDNTCVVRSRDVSTTGSTSEGAVTAVAICCRSRHLAQASQELQ | 27 |

NUCLEOTIDE SEQUENCES
*Italics* = nucleotide sequence encoding signal sequence (nucleotides 1-90)

`Courier` = nucleotide sequence encoding propeptide (nucleotides 91-456)

TABLE 6-continued

PCSK9 SEQUENCES

| FORM/ALLELE | VERSION | SEQUENCE | SEQ ID NO: |
|---|---|---|---| lower case = nucleotide sequence encoding catalytic domain (nucleotides 457-1346)
UPPER CASE = nucleotide sequence encoding C-terminal domain (nucleotides 1347-2076)

| | | | |
|---|---|---|---|
| a | | ATGGGCACCGTCAGCTCCAGGCGGTCCTGGTGGCCGCTGCCACTGCTGCTGCTGCTGCTGCTCCTGGGTC | 28 |

R46L CGT to CTT
*CCGCGGGCGCCCGTGCG*caggaggacgaggacggcgactacgaggagctggtgctagccttgcGTTCCG A53V GCC to GTC
AGGAGGACGGCCTGGCCGAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCGACCTGCTGGAGCTGGCCTTGAAGTTGCCC

CATGTCGACTACATCGAGGAGGACTCCTCTGTCTTTGCCCAGagcatcccgtggaacctggagcggattacccctcca cggtaccgggcggatgaataccagcccccgacggaggcagcctggtggaggtgtatctcctagacaccagcatacagagtgaccaccgggaa atcgagggcagggtcatggtcaccgacttcgagaatgtgcccgaggaggacgggaccgcttccacagacaggccagcaagtgtgacagtcat ggcacccacctggcagggtggtcagcggccgggatgccggcgtggccaagggtgccagcatgcgcagcctgcgcgtgctcaactgccaaggg aagggcacggttagcggcaccctcataggcctggagttattcggaaaagccagctggtccagcctgtggggccactggtggtgctgctgcccct ggcgggtgggtacagccgcgtcctcaacgccgcctgccagcgcctggcgagggctggggtcgtgctggtcaccgctgccggcaacttccgggac gatgcctgcctctactccccagcctcagctcccgaggtcatcacagttggggccaccaatgcccaagaccagccggtgaccctggggactttggg gaccaactttggccgctgtgtggacctctttgccccaggggaggacatcattggtgcctccagcgactgcagcacctgctttgtgtcacagagtgg gacatcacaggctgctgcccacgtggctggcattgcagccatgatgctgtctgccgagccggagctcaccctggccgagttgaggcagagactg N425S AAT to AGT           A443T GCC to ACC
atccacttctctgccaaagatgtcatcaatgaggcctggttccctgaggaccagcgggtactgacccccaacctggtggccgccctgcccccccag cacccatGGGGCAGGTTGGCAGCTGTTTTGCAGGACTGTATGGTCAGCACACTCGGGGCCTACACGGATGGCC I474V ATC to GTC
ACAGCCATCGCCCGCTGCGCCCCAGATGAGGAGCTGCTGAGCTGCTCCAGTTTCTCCAGGAGTGGGAAGCGG

CGGGGCGAGCGCATGGAGGCCCAAGGGGGCAAGCTGGTCTGCCGGGCCCACAACGCTTTTGGGGGTGAGGG

TGTCTACGCCATTGCCAGGTGCTGCCTGCTACCCCAGGCCAACTGCAGCGTCCACACAGCTCCACCAGCTGAG

GCCAGCATGGGGACCCGTGTCCACTGCCACCAACAGGGCCACGTCCTCACAGGCTGCAGCTCCCACTGGGAG

GTGGAGGACCTTGGCACCCACAAGCCGCCTGTGCTGAGGCCACGAGGTCAGCCCAACCAGTGCGTGGGCCAC

AGGGAGGCCAGCATCCACGCTTCCTGCTGCCATGCCCCAGGTCTGGAATGCAAAGTCAAGGAGCATGGAA

Q619P CAG to CCG E620G GAG to GGG
TCCCGGCCCCTCAGGAGCAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTGTAGTCAGGAGCCGGGACGTCAGCA

E670G GAG to GGG
CTACAGGCAGCACCAGCGAAGAGGCCGTGACAGCCGTTGCCATCTGCTGCCGGAGCCGGCACCTGGCGCAGG

CCTCCCAGGAGCTCCAGTGAC

TABLE 6-continued

PCSK9 SEQUENCES

| FORM/ALLELE | VERSION | SEQUENCE | SEQ ID NO: |
|---|---|---|---|
| f | | ATGGGCACCGTCAGCTCCAGGCGGTCCTGGTGGCCGCTGCCACTGCTGCTGCTGCTGCTGCTCCTGGGTC<br><br>                                         R46L CGT to CTT<br>*CCGCGGGCGCCCGTGCG*CAGGAGGACGAGGACGGCGACTACGAGGAGCTGGTGCTAGCCTTG<u>C</u>GTTCCG<br><br>      A53V GCC to GTC<br>AGGAGGACGGCCTGG<u>CC</u>GAAGCACCCGAGCACGGAACCACAGCCACCTTCCACCGCTGCGCCAAGGAT<br><br>CCGTGGAGGTTGCCTGGCACCTACGTGGTGGTGCTGAAGGAGGAGACCCACCTCTCGCAGTCAGAGCG<br><br>CACTGCCCGCCGCCTGCAGGCCCAGGCTGCCCGCCGGGGATACCTCACCAAGATCCTGCATGTCTTCC<br><br>ATGGCCTTCTTCCTGGCTTCCTGGTGAAGATGAGTGGCGACCTGCTGGAGCTGGCCTTGAAGTTGCCC<br><br>CATGTCGACTACATCGAGGAGGACTCCTCTGTCTTTGCCCAGagcatcccgtggaacctggagcggattacccctcca<br><br>cggtaccgggcggatgaataccagcccccgacggaggcagcctggtggaggtgtatctcctagacaccagcatacagagtgaccaccgggaa<br><br>atcgagggcagggtcatggtcaccgacttcgagaatgtgcccgaggaggacgggacccgcttccacagacaggccagcaagtgtgacagtcat<br><br>ggcacccacctggcaggggtggtcagcggccgggatgccggcgtggccaagggtgccagcatgcgcagcctgcgcgtgctcaactgccaaggg<br><br>aagggcacggttagcggcaccctcataggcctggagtttattcggaaaagccagctggtccagcctgtggggccactggtggtgctgctgcccct<br><br>ggcgggtgggtacagccgcgtcctcaacgccgcctgccagcgcctggcgagggctggggtcgtgctggtcaccgctgccggcaacttccgggac<br><br>gatgcctgcctctactccccagcctcagctcccgaggtcatcacagttggggccaccaatgcccaagaccagccggtgaccctggggactttggg<br><br>gaccaactttggccgctgtgtggacctctttgccccaggggaggacatcattggtgcctccagcgactgcagcacctgctttgtgtcacagagtgg<br><br>gacatcacaggctgctgcccacgtggctggcattgcagccatgatgctgtctgccgagccggagctcaccctggccgagttgaggcagagactg<br><br>              N425S AAT to AGT               A443T GCC to ACC<br>atccacttctctgccaaagatgtcatc<u>aat</u>gaggcctggttccctgaggaccagcgggtactgacccccaacctggtggcc<u>gcc</u>ctgcccccag<br><br>cacccatGGGGCAGGTTGGCAGCTGTTTTGCAGGACTGTATGGTCAGCACACTCGGGGCCTACACGGATGGCC<br><br>  I474V ATC to GTC<br>ACAGCC<u>GTC</u>GCCCGCTGCGCCCCAGATGAGGAGCTGCTGAGCTGCTCCAGTTTCTCCAGGAGTGGGAAGCGG<br><br>CGGGGCGAGCGCATGGAGGCCCAAGGGGGCAAGCTGGTCTGCCGGGCCCACAACGCTTTTGGGGGTGAGGG<br><br>TGTCTACGCCATTGCCAGGTGCTGCCTGCTACCCCAGGCCAACTGCAGCGTCCACACAGCTCCACCAGCTGAG<br><br>GCCAGCATGGGGACCCGTGTCCACTGCCACCAACAGGGCCACGTCCTCACAGGCTGCAGCTCCCACTGGGAG<br><br>GTGGAGGACCTTGGCACCCACAAGCCGCCTGTGCTGAGGCCACGAGGTCAGCCCAACCAGTGCGTGGGCCAC<br><br>AGGGAGGCCAGCATCCACGCTTCCTGCTGCCATGCCCCAGGTCTGGAATGCAAAGTCAAGGAGCATGGAA<br><br>    Q619P CAG to CCG E620G GAG to GGG<br>TCCCGGCCCCT<u>CAGGAG</u>CAGGTGACCGTGGCCTGCGAGGAGGGCTGGACCCTGACTGGCTGCAGTGCCCTCC<br><br>CTGGGACCTCCCACGTCCTGGGGGCCTACGCCGTAGACAACACGTGTGTAGTCAGGAGCCGGGACGTCAGCA<br><br>      E670G GAG to GGG<br>CTACAGGCAGCACCAGCGAA<u>GAG</u>GCCGTGACAGCCGTTGCCATCTGCTGCCGGAGCCGGCACCTGGCGCAGG<br><br>CCTCCCAGGAGCTCCAGTGAC | 29 |

TABLE 6-continued

PCSK9 SEQUENCES

| FORM/ ALLELE | VERSION | SEQUENCE | SEQ ID NO: |
|---|---|---|---|
| | c | ATGGGCACCGTCAGCTCCAGGCGGTCCTGGTGGCCGCTGCCACTGCTGCTGCTGCTGCTGCTCCTGGGTC | 30 |

R46L CGT to CTT
*CCGCGGGCGCCCGTGCG*CAGGAGGACGAGGACGGCGACTACGAGGAGCTGGTGCTAGCCTTG<u>CGT</u>TCCG

A53V GCC to GTC
AGGAGGACGGCCTGG<u>GCC</u>GAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCGACCTGCTGGAGCTGGCCTTGAAGTTGCCC

CATGTCGACTACATCGAGGAGGACTCCTCTGTCTTTGCCCAGagcatcccgtggaacctggagcggattaccctcca cggtaccgggcggatgaataccagccccccgacggaggcagcctggtggaggtgtatctcctagacaccagcatacagagtgaccaccgggaa atcgagggcagggtcatggtcaccgacttcgagaatgtgcccgaggaggacgggacccgcttccacagacaggccagcaagtgtgacagtcat ggcacccacctggcaggggtggtcagcggccgggatgccggcgtggccaagggtgccagcatgcgcagcctgcgcgtgctcaactgccaaggg aagggcacggttagcggcacccctcataggcctggagtttattcggaaaagccagctggtccagcctgtggggccactggtggtgctgctgcccct ggcgggtgggtacagccgcgtcctcaacgccgcctgccagcgcctggcgagggctggggtcgtgctggtcaccgctgccggcaacttccgggac gatgcctgcctctactcccccagcctcagctcccgaggtcatcacagttggggccaccaatgcccaagaccagccggtgaccctggggactttggg gaccaactttggccgctgtgtggacctctttgccccaggggaggacatcattggtgcctccagcgactgcagcacctgctttgtgtcacagagtgg gacatcacaggctgctgcccacgtggctggcattgcagccatgatgctgtctgccgagccggagctcaccctggccgagttgaggcagagactg N425S AAT to AGT                                  A443T GCC to ACC
atccacttctctgccaaagatgtcatc<u>aat</u>gaggcctggttccctgaggaccagcgggtactgaccccaacctggtggcc<u>gcc</u>tgccccccag cacccatGGGGCAGGTTGGCAGCTGTTTTGCAGGACTGTATGGTCAGCACACTCGGGGCCTACACGGATGGCC I474V ATC to GTC
ACAGCC<u>ATC</u>GCCCGCTGCGCCCCAGATGAGGAGCTGCTGAGCTGCTCCAGTTTCTCCAGGAGTGGGAAGCGG

CGGGGCGAGCGCATGGAGGCCCAAGGGGGCAAGCTGGTCTGCCGGGCCCACAACGCTTTTGGGGGTGAGGG

TGTCTACGCCATTGCCAGGTGCTGCCTGCTACCCCAGGCCAACTGCAGCGTCCACACAGCTCCACCAGCTGAG

GCCAGCATGGGACCCGTGTCCACTGCCACCAACAGGGCCACGTCCTCACAGGCTGCAGCTCCCACTGGGAG

GTGGAGGACCTTGGCACCCACAAGCCGCCTGTGCTGAGGCCACGAGGTCAGCCCAACCAGTGCGTGGGCCAC

AGGGAGGCCAGCATCCACGCTTCCTGCTGCCATGCCCCAGGTCTGGAATGCAAAGTCAAGGAGCATGGAA

Q519P CAG to CCG E520G GAG to GGG
TCCCGGCCCCT<u>CAGGAG</u>CAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTGTAGTCAGGAGCCGGGACGTCAGCA

E570G GAG to GGG
CTACAGGCAGCACCAGCGAA<u>GGG</u>GCCGTGACAGCCGTTGCCATCTGCTGCCGGAGCCGGCACCTGGCGCAGG

CCTCCCAGGAGCTCCAGTGAC

| | r | ATGGGCACCGTCAGCTCCAGGCGGTCCTGGTGGCCGCTGCCACTGCTGCTGCTGCTGCTGCTCCTGGGTC | 31 |

R45L CGT to CTT
*CCGCGGGCGCCCGTGCG*CAGGAGGACGAGGACGGCGACTACGAGGAGCTGGTGCTAGCCTTG<u>CGT</u>TCCG

TABLE 6-continued

PCSK9 SEQUENCES

| FORM/ALLELE | VERSION | SEQUENCE | SEQ ID NO: |
|---|---|---|---|
| | | A53V GCC to GTC<br>AGGAGGACGGCCTG<u>GCC</u>GAAGCACCCGAGCACGGAACCACAGCCACCTTCCACCGCTGCGCCAAGGAT<br><br>CCGTGGAGGTTGCCTGGCACCTACGTGGTGGTGCTGAAGGAGGAGACCCACCTCTCGCAGTCAGAGCG<br><br>CACTGCCCGCCGCCTGCAGGCCCAGGCTGCCCGCCGGGGATACCTCACCAAGATCCTGCATGTCTTCC<br><br>ATGGCCTTCTTCCTGGCTTCCTGGTGAAGATGAGTGGCGACCTGCTGGAGCTGGCCTTGAAGTTGCCC<br><br>CATGTCGACTACATCGAGGAGGACTCCTCTGTCTTTGCCCAGagcatcccgtggaacctggagcggattaccccctcca<br><br>cggtaccgggcggatgaataccagcccccccgacggaggcagcctggtggaggtgtatctcctagacaccagcatacagagtgaccaccgggaa<br><br>atcgagggcagggtcatggtcaccgacttcgagaatgtgcccgaggaggacgggacccgcttccacagacaggccagcaagtgtgacagtcat<br><br>ggcacccacctggcaggggtggtcagcggccgggatgccggcgtggccaagggtgccagcatgcgcagcctgcgcgtgctcaactgccaaggg<br><br>aagggcacggttagcggcaccctcataggcctggagtttattcggaaaagccagctggtccagcctgtggggccactggtggtgctgctgccct<br><br>ggcgggtgggtacagccgcgtcctcaacgccgcctgccagcgcctggcgagggctggggtcgtgctggtcaccgctgccggcaacttccgggac<br><br>gatgcctgcctctactccccagcctcagctcccgaggtcatcacagttggggccaccaatgcccaagaccagccggtgaccctggggactttggg<br><br>gaccaactttggccgctgtgtggacctctttgccccaggggaggacatcattggtgcctccagcgactgcagcacctgctttgtgtcacagagtgg<br><br>gacatcacaggctgctgcccacgtggctggcattgcagccatgatgctgtctgccgagccggagctcaccctgccgagttgaggcgagagactg |  |
| | | N425S AAT to AGT        A443T GCC to ACC<br>atccacttctctgccaaagatgtcatc<u>aat</u>gaggcctggttccctgaggaccagcgggtactgaccccccaacctggtggcc<u>gcc</u>ctgcccccag<br><br>cacccatGGGGCAGGTTGGCAGCTGTTTTGCAGGACTGTATGGTCAGCACACTCGGGGCCTACACGGATGGCC<br><br>I474V ATC to GTC<br>ACAGCC<u>ATC</u>GCCCGCTGCGCCCCAGATGAGGAGCTGCTGAGCTGCTCCAGTTTCTCCAGGAGTGGGAAGCGG<br><br>CGGGGCGAGCGCATGGAGGCCCAAGGGGGCAAGCTGGTCTGCCGGGCCCACAACGCTTTTGGGGGTGAGGG<br><br>TGTCTACGCCATTGCCAGGTGCTGCCTGCTACCCCAGGCCAACTGCAGCGTCCACACAGCTCCACCAGCTGAG<br><br>GCCAGCATGGGGACCCGTGTCCACTGCCACCAACAGGGCCACGTCCTCACAGGCTGCAGCTCCCACTGGGAG<br><br>GTGGAGGACCTTGGCACCCACAAGCCGCCTGTGCTGAGGCCACGAGGTCAGCCCAACCAGTGCGTGGGCCAC<br><br>AGGGAGGCCAGCATCCACGCTTCCTGCTGCCATGCCCCAGGTCTGGAATGCAAAGTCAAGGAGCATGGAA<br><br>Q519P CAG to CCG E520G GAG to GGG<br>TCCCGGCCCCT<u>CAGGAG</u>CAGGTGACCGTGGCCTGCGAGGAGGGCTGGACCCTGACTGGCTGCAGTGCCCTCC<br><br>CTGGGACCTCCCACGTCCTGGGGGCCTACGCCGTAGACAACACGTGTGTAGTCAGGAGCCGGGACGTCAGCA<br><br>E570G GAG to GGG<br>CTACAGGCAGCACCAGCGAA<u>GGG</u>GCCGTGACAGCCGTTGCCATCTGCTGCCGGAGCCGGCACCTGGCGCAGG<br><br>CCTCCCAGGAGCTCCAGTGAC |  |
| p | | ATGGGCACCGTCAGCTCCAGGCGGTCCTGGTGGCCGCTGCCACTGCTGCTGCTGCTGCTGCTCCTGGGTC<br><br>                                                                       R46L CGT to CTT<br>*CCGCGGGCGCCCGTGCG* CAGGAGGACGAGGACGGCGACTACGAGGAGCTGGTGCTAGCCTTGC<u>GT</u>TCCG<br><br>A53V GCC to GTC<br>AGGAGGACGGCCTG<u>GT</u>CGAAGCACCCGAGCACGGAACCACAGCCACCTTCCACCGCTGCGCCAAGGAT<br><br>CCGTGGAGGTTGCCTGGCACCTACGTGGTGGTGCTGAAGGAGGAGACCCACCTCTCGCAGTCAGAGCG | 32 |

TABLE 6-continued

PCSK9 SEQUENCES

| FORM/ALLELE | VERSION | SEQUENCE | SEQ ID NO: |
|---|---|---|---|
| | | CACTGCCCGCCGCCTGCAGGCCCAGGCTGCCCGCCGGGGATACCTCACCAAGATCCTGCATGTCTTCC | |
| | | ATGGCCTTCTTCCTGGCTTCCTGGTGAAGATGAGTGGCGACCTGCTGGAGCTGGCCTTGAAGTTGCCC | |
| | | CATGTCGACTACATCGAGGAGGACTCCTCTGTCTTTGCCCAGagcatcccgtggaacctggagcggattacccctcca | |
| | | cggtaccgggcggatgaataccagccccccgacggaggcagcctggtggaggtgtatctcctagacaccagcatacagagtgaccaccgggaa | |
| | | atcgagggcagggtcatggtcaccgacttcgagaatgtgcccgaggaggacgggacccgcttccacagacaggccagcaagtgtgacagtcat | |
| | | ggcacccacctggcaggggtggtcagcggccgggatgccggcgtggccaagggtgccagcatgcgcagcctgcgcgtgctcaactgccaaggg | |
| | | aagggcacggttagcggcaccctcataggcctggagtttattcggaaaagccagctggtccagcctgtggggccactggtggtgctgctgcccct | |
| | | ggcgggtgggtacagccgcgtcctcaacgccgcctgccagcgcctggcgagggctggggtcgtgctggtcaccgctgccggcaacttccgggac | |
| | | gatgcctgcctctactcccagcctcagctcccgaggtcatcacagttggggccaccaatgcccaagaccagccggtgaccctggggactttggg | |
| | | gaccaactttggccgctgtgtggacctctttgccccaggggaggacatcattggtgcctccagcgactgcagcacctgctttgtgtcacagagtgg | |
| | | gacatcacaggctgctgcccacgtggctggcattgcagccatgatgctgtctgccgagccggagctcaccctggccgagttgaggcagagactg | |
| | |            N425S AAT to AGT             A443T GCC to ACC<br>atccacttctctgccaaagatgtcatc<u>aat</u>gaggcctggttccctgaggaccagcgggtactgaccccccaacctggtggcc<u>acc</u>ctgccccccag | |
| | | cacccat GGGGCAGGTTGGCAGCTGTTTTGCAGGACTGTATGGTCAGCACACTCGGGGCCTACACGGATGGCC | |
| | |   I474V ATC to GTC<br>ACAGCC<u>GTC</u>GCCCGCTGCGCCCCAGATGAGGAGCTGCTGAGCTGCTCCAGTTTCTCCAGGAGTGGGAAGCGG | |
| | | CGGGGCGAGCGCATGGAGGCCCAAGGGGGCAAGCTGGTCTGCCGGGCCCACAACGCTTTTGGGGGTGAGGG | |
| | | TGTCTACGCCATTGCCAGGTGCTGCCTGCTACCCCAGGCCAACTGCAGCGTCCACACAGCTCCACCAGCTGAG | |
| | | GCCAGCATGGGGACCCGTGTCCACTGCCACCAACAGGGCCACGTCCTCACAGGCTGCAGCTCCCACTGGGAG | |
| | | GTGGAGGACCTTGGCACCCACAAGCCGCCTGTGCTGAGGCCACGAGGTCAGCCCAACCAGTGCGTGGGCCAC | |
| | | AGGGAGGCCAGCATCCACGCTTCCTGCTGCCATGCCCCAGGTCTGGAATGCAAAGTCAAGGAGCATGGAA | |
| | |   Q619P CAG to CCG  E620G GAG to GGG<br>TCCCGGCCCCTC<u>AGGAG</u>CAGGTGACCGTGGCCTGCGAGGAGGGCTGGACCCTGACTGGCTGCAGTGCCCTCC | |
| | | CTGGGACCTCCCACGTCCTGGGGGCCTACGCCGTAGACAACACGTGTGTAGTCAGGAGCCGGGACGTCAGCA | |
| | |          E570G GAG to GGG<br>CTACAGGCAGCACCAGCGAA<u>GAG</u>GCCGTGACAGCCGTTGCCATCTGCTGCCGGAGCCGGCACCTGGCGCAGG | |
| | | CCTCCCAGGAGCTCCAGTGAC | |
| m | | ATGGGCACCGTCAGCTCCAGGCGGTCCTGGTGGCCGCTGCCACTGCTGCTGCTGCTGCTGCTCCTGGGTC | 33 |
| | |                                       R46L CGT to CTT<br>*CCGCGGGCGCCCGTGCG* CAGGAGGACGAGGACGGCGACTACGAGGAGCTGGTGCTAGCCTTG<u>CT</u>TTCCG | |
| | |   A53V GCC to GTC<br>AGGAGGACGGCCTGG<u>GTC</u>GAAGCACCCGAGCACGGAACCACAGCCACCTTCCACCGCTGCGCCAAGGAT | |
| | | CCGTGGAGGTTGCCTGGCACCTACGTGGTGGTGCTGAAGGAGGAGACCCACCTCTCGCAGTCAGAGCG | |
| | | CACTGCCCGCCGCCTGCAGGCCCAGGCTGCCCGCCGGGGATACCTCACCAAGATCCTGCATGTCTTCC | |
| | | ATGGCCTTCTTCCTGGCTTCCTGGTGAAGATGAGTGGCGACCTGCTGGAGCTGGCCTTGAAGTTGCCC | |
| | | CATGTCGACTACATCGAGGAGGACTCCTCTGTCTTTGCCCAGagcatcccgtggaacctggagcggattacccctcca | |

TABLE 6-continued

PCSK9 SEQUENCES

| FORM/ ALLELE | VERSION | SEQUENCE | SEQ ID NO: |
|---|---|---|---|
| | | cggtaccgggcggatgaataccagcccccgacggaggcagcctggtggaggtgtatctcctagacaccagcatacagagtgaccaccgggaa | |
| | | atcgagggcagggtcatggtcaccgacttcgagaatgtgcccgaggaggacgggacccgcttccacagacaggccagcaagtgtgacagtcat | |
| | | ggcacccacctggcaggggtggtcagcggccgggatgccggcgtggccaagggtgccagcatgcgcagcctgcgcgtgctcaactgccaaggg | |
| | | aagggcacggttagcggcaccctcataggcctggagtttattcggaaaagccagctggtccagcctgtggggccactggtggtgctgctgccct | |
| | | ggcgggtgggtacagccgcgtcctcaacgccgcctgccagcgcctggcgagggctggggtcgtgctggtcaccgctgccggcaacttccgggac | |
| | | gatgcctgcctctactcccagcctcagctcccgaggtcatcacagttggggccaccaatgcccaagaccagccggtgaccctggggactttggg | |
| | | gaccaactttggccgctgtgtggacctctttgccccaggggaggacatcattggtgcctccagcgactgcagcacctgctttgtgtcacagagtgg | |
| | | gacatcacaggctgctgcccacgtggctggcattgcagccatgatgctgtctgccgagccggagctcaccctggccgagttgaggcagagactg | |
| | | N425S AAT to AGT          A443T GCC to ACC<br>atccacttctctgccaaagatgtcatc<u>aat</u>gaggcctggttccctgaggacagcgggtactgacccccaacctggtggcc<u>acc</u>ctgcccccag | |
| | | cacccatGGGGCAGGTTGGCAGCTGTTTTGCAGGACTGTATGGTCAGCACACTCGGGGCCTACACGGATGGCC | |
| | | I474V ATC to GTC<br>ACAGCC<u>ATC</u>GCCCGCTGCGCCCCAGATGAGGAGCTGCTGAGCTGCTCCAGTTTCTCCAGGAGTGGGAAGCGG | |
| | | CGGGGCGAGCGCATGGAGGCCCAAGGGGGCAAGCTGGTCTGCCGGGCCCACAACGCTTTTGGGGGTGAGGG | |
| | | TGTCTACGCCATTGCCAGGTGCTGCCTGCTACCCCAGGCCAACTGCAGCGTCCACACAGCTCCACCAGCTGAG | |
| | | GCCAGCATGGGGACCCGTGTCCACTGCCACCAACAGGGCCACGTCCTCACAGGCTGCAGCTCCCACTGGGAG | |
| | | GTGGAGGACCTTGGCACCCACAAGCCGCCTGTGCTGAGGCCACGAGGTCAGCCCAACCAGTGCGTGGGCCAC | |
| | | AGGGAGGCCAGCATCCACGCTTCCTGCTGCCATGCCCCAGGTCTGGAATGCAAAGTCAAGGAGCATGGAA | |
| | | Q619P CAG to CCG E620G GAG to GGG<br>TCCCGGCCCCT<u>CAGGAG</u>CAGGTGACCGTGGCCTGCGAGGAGGGCTGGACCCTGACTGGCTGCAGTGCCCTCC | |
| | | CTGGGACCTCCCACGTCCTGGGGGCCTACGCCGTAGACAACACGTGTGTAGTCAGGAGCCGGGACGTCAGCA | |
| | | E670G GAG to GGG<br>CTACAGGCAGCACCAGCGAA<u>GAG</u>GCCGTGACAGCCGTTGCCATCTGCTGCCGGAGCCGGCACCTGGCGCAGG | |
| | | CCTCCCAGGAGCTCCAGTGAC | |
| e | | ATGGGCACCGTCAGCTCCAGGCGGTCCTGGTGGCCGCTGCCACTGCTGCTGCTGCTGCTGCTCCTGGGTC | 34 |
| | | R46L CGT to CTT<br>*CCGCGGGCGCCCGTGCG*CAGGAGGACGAGGACGGCGACTACGAGGAGCTGGTGCTAGCCTTG<u>C</u>G<u>T</u>TCCG | |
| | | A53V GCC to GTC<br>AGGAGGACGGCCTG<u>GCC</u>GAAGCACCCGAGCACGGAACCACAGCCACCTTCCACCGCTGCGCCAAGGAT | |
| | | CCGTGGAGGTTGCCTGGCACCTACGTGGTGGTGCTGAAGGAGGAGACCCACCTCTCGCAGTCAGAGCG | |
| | | CACTGCCCGCCGCCTGCAGGCCCAGGCTGCCCGCCGGGGATACCTCACCAAGATCCTGCATGTCTTCC | |
| | | ATGGCCTTCTTCCTGGCTTCCTGGTGAAGATGAGTGGCGACCTGCTGGAGCTGGCCTTGAAGTTGCCC | |
| | | CATGTCGACTACATCGAGGAGGACTCCTCTGTCTTTGCCCAGagcatcccgtggaacctggagcggattaccctcca | |
| | | cggtaccgggcggatgaataccagcccccgacggaggcagcctggtggaggtgtatctcctagacaccagcatacagagtgaccaccgggaa | |
| | | atcgagggcagggtcatggtcaccgacttcgagaatgtgcccgaggaggacgggacccgcttccacagacaggccagcaagtgtgacagtcat | |
| | | ggcacccacctggcaggggtggtcagcggccgggatgccggcgtggccaagggtgccagcatgcgcagcctgcgcgtgctcaactgccaaggg | |
| | | aagggcacggttagcggcaccctcataggcctggagtttattcggaaaagccagctggtccagcctgtggggccactggtggtgctgctgccct | |

TABLE 6-continued

PCSK9 SEQUENCES

| FORM/ ALLELE | VERSION | SEQUENCE | SEQ ID NO: |
|---|---|---|---|
| | | ggcgggtgggtacagccgcgtcctcaacgccgcctgccagcgcctggcgagggctggggtcgtgctggtcaccgctgccggcaacttccgggac | |
| | | gatgcctgcctctactccccagcctcagctcccgaggtcatcacagttggggccaccaatgcccaagaccagccggtgaccctggggactttggg | |
| | | gaccaactttggccgctgtgtggacctctttgccccaggggaggacatcattggtgcctccagcgactgcagcacctgctttgtgtcacagagtgg | |
| | | gacatcacaggctgctgcccacgtggctggcattgcagccatgatgctgtctgccgagccggagctcaccctggccgagttgaggcagagactg | |
| | |            N425S AAT to AGT                                   A443T GCC to ACC<br>atccacttctctgccaaagatgtcatc<u>agt</u>gaggcctggttccctgaggaccagcgggtactgaccccccaacctggtggcc<u>gcc</u>ctgcccccag | |
| | | cacccatGGGGCAGGTTGGCAGCTGTTTTGCAGGACTGTATGGTCAGCACACTCGGGGCCTACACGGATGGCC | |
| | |      I474V ATC to GTC<br>ACAGCC<u>GTC</u>GCCCGCTGCGCCCCAGATGAGGAGCTGCTGAGCTGCTCCAGTTTCTCCAGGAGTGGGAAGCGG | |
| | | CGGGGCGAGCGCATGGAGGCCCAAGGGGGCAAGCTGGTCTGCCGGGCCCACAACGCTTTTGGGGGTGAGGG | |
| | | TGTCTACGCCATTGCCAGGTGCTGCCTGCTACCCCAGGCCAACTGCAGCGTCCACACAGCTCCACCAGCTGAG | |
| | | GCCAGCATGGGGACCCGTGTCCACTGCCACCAACAGGGCCACGTCCTCACAGGCTGCAGCTCCCACTGGGAG | |
| | | GTGGAGGACCTTGGCACCCACAAGCCGCCTGTGCTGAGGCCACGAGGTCAGCCCAACCAGTGCGTGGGCCAC | |
| | | AGGGAGGCCAGCATCCACGCTTCCTGCTGCCATGCCCCAGGTCTGGAATGCAAAGTCAAGGAGCATGGAA | |
| | |      Q619P CAG to CCG E620G GAG to GGG<br>TCCCGGCCCCT<u>CAGGAG</u>CAGGTGACCGTGGCCTGCGAGGAGGGCTGGACCCTGACTGGCTGCAGTGCCCTCC | |
| | | CTGGGACCTCCCACGTCCTGGGGGCCTACGCCGTAGACAACACGTGTGTAGTCAGGAGCCGGGACGTCAGCA | |
| | |                E670G GAG to GGG<br>CTACAGGCAGCACCAGCGAA<u>GAG</u>GCCGTGACAGCCGTTGCCATCTGCTGCCGGAGCCGGCACCTGGCGCAGG | |
| | | CCTCCCAGGAGCTCCAGTGAC | |
| h | | ATGGGCACCGTCAGCTCCAGGCGGTCCTGGTGGCCGCTGCCACTGCTGCTGCTGCTGCTGCTCCTGGGTC | 35 |
| | |                                                         R46LCGT to CTT<br>*CCGCGGGCGCCCGTGCG*caggaggacgaggacggcgactacgaggagctggtgctagccttg<u>cgtt</u>ccg | |
| | |    A53V GCC to GTC<br>AGGAGGACGGCCTGG<u>GCC</u>GAAGCACCCGAGCACGGAACCACAGCCACCTTCCACCGCTGCGCCAAGGAT | |
| | | CCGTGGAGGTTGCCTGGCACCTACGTGGTGGTGCTGAAGGAGGAGACCCACCTCTCGCAGTCAGAGCG | |
| | | CACTGCCCGCCGCCTGCAGGCCCAGGCTGCCCGCCGGGGATACCTCACCAAGATCCTGCATGTCTTCC | |
| | | ATGGCCTTCTTCCTGGCTTCCTGGTGAAGATGAGTGGCGACCTGCTGGAGCTGGCCTTGAAGTTGCCC | |
| | | CATGTCGACTACATCGAGGAGGACTCCTCTGTCTTTGCCCAGagcatcccgtggaacctggagcggattacccctcca | |
| | | cggtaccgggcggatgaataccagcccccgacggaggcagcctggtggaggtgtatcctagacaccagcatacagagtgaccaccgggaa | |
| | | atcgagggcagggtcatggtcaccgacttcgagaatgtgcccgaggaggacgggaccccgcttccacagacaggccagcaagtgtgacagtcat | |
| | | ggcacccacctggcagggtggtcagcggccgggatgccggcgtggccaagggtgccagcatgcgcagcctgcgcgtgctcaactgccaaggg | |
| | | aagggcacggttagcggcaccctcataggcctggagtttattcggaaaagccagctggtccagcctgtggggccactggtggtgctgcccct | |
| | | ggcgggtgggtacagccgcgtcctcaacgccgcctgccagcgcctggcgagggctggggtcgtgctggtcaccgctgccggcaacttccgggac | |
| | | gatgcctgcctctactccccagcctcagctcccgaggtcatcacagttggggccaccaatgcccaagaccagccggtgaccctggggactttggg | |
| | | gaccaactttggccgctgtgtggacctctttgccccaggggaggacatcattggtgcctccagcgactgcagcacctgctttgtgtcacagagtgg | |
| | | gacatcacaggctgctgcccacgtggctggcattgcagccatgatgctgtctgccgagccggagctcaccctggccgagttgaggcagagactg | |

TABLE 6-continued

PCSK9 SEQUENCES

| FORM/ ALLELE | VERSION | SEQUENCE | SEQ ID NO: |
|---|---|---|---|
| | | N425S AAT to AGT          A443T GCC to ACC<br>atccacttctctgccaaagatgtcatc<u>aat</u>gaggcctggttccctgaggaccagcgggtactgacccccaacctggtggcc<u>acc</u>ctgcccccag<br><br>cacccatGGGGCAGGTTGGCAGCTGTTTTGCAGGACTGTATGGTCAGCACACTCGGGGCCTACACGGATGGCC<br><br>  I474V ATC to GTC<br>ACAGCC<u>ATC</u>GCCCGCTGCGCCCCAGATGAGGAGCTGCTGAGCTGCTCCAGTTTCTCCAGGAGTGGGAAGCGG<br><br>CGGGGCGAGCGCATGGAGGCCCAAGGGGGCAAGCTGGTCTGCCGGGCCCACAACGCTTTTGGGGGTGAGGG<br><br>TGTCTACGCCATTGCCAGGTGCTGCCTGCTACCCCAGGCCAACTGCAGCGTCCACACAGCTCCACCAGCTGAG<br><br>GCCAGCATGGGGACCCGTGTCCACTGCCACCAACAGGGCCACGTCCTCACAGGCTGCAGCTCCCACTGGGAG<br><br>GTGGAGGACCTTGGCACCCACAAGCCGCCTGTGCTGAGGCCACGAGGTCAGCCCAACCAGTGCGTGGGCCAC<br><br>AGGGAGGCCAGCATCCACGCTTCCTGCTGCCATGCCCCAGGTCTGGAATGCAAAGTCAAGGAGCATGGAA<br><br> Q519P CAG to CCG  E620G GAG to GGG<br>TCCCGGCCCCT<u>CCGGAG</u>CAGGTGACCGTGGCCTGCGAGGAGGGCTGGACCCTGACTGGCTGCAGTGCCCTCC<br><br>CTGGGACCTCCCACGTCCTGGGGGCCTACGCCGTAGACAACACGTGTGTAGTCAGGAGCCGGGACGTCAGCA<br><br>   E670G GAG to GGG<br>CTACAGGCAGCACCAGCGAA<u>GAGG</u>CCGTGACAGCCGTTGCCATCTGCTGCCGGAGCCGGCACCTGGCGCAGG<br><br>CCTCCCAGGAGCTCCAGTGAC | |
| aj | | ATGGGCACCGTCAGCTCCAGGCGGTCCTGGTGGCCGCTGCCACTGCTGCTGCTGCTGCTGCTCCTGGGTC<br><br>                          R46L CGT to CTT<br>*CCGCGGGCGCCCGTGCG*caggaggacgaggacggcgactacgaggagctggtgctagccttg<u>CTTT</u>CCG<br><br>  A53V GCC to GTC<br>AGGAGGACGGCCTGG<u>GCC</u>GAAGCACCCGAGCACGGAACCACAGCCACCTTCCACCGCTGCGCCAAGGAT<br><br>CCGTGGAGGTTGCCTGGCACCTACGTGGTGGTGCTGAAGGAGGAGACCCACCTCTCGCAGTCAGAGCG<br><br>CACTGCCCGCCGCCTGCAGGCCCAGGCTGCCCGCCGGGGATACCTCACCAAGATCCTGCATGTCTTCC<br><br>ATGGCCTTCTTCCTGGCTTCCTGGTGAAGATGAGTGGCGACCTGCTGGAGCTGGCCTTGAAGTTGCCC<br><br>CATGTCGACTACATCGAGGAGGACTCCTCTGTCTTTGCCCAGagcatcccgtggaacctggagcggattaccctcca<br><br>cggtaccgggcggatgaataccagccccccgacggaggcagcctggtggaggtgtatctcctagacaccagcatacagagtgaccaccgggaa<br><br>atcgagggcagggtcatggtcaccgacttcgagaatgtgcccgaggaggacgggacccgcttccacagacaggccagcaagtgtgacagtcat<br><br>ggcacccacctggcagggtggtcagcggccgggatgccggcgtggccaagggtgccagcatgcgcagcctgcgcgtgctcaactgccaaggg<br><br>aagggcacggttagcggcaccctcataggcctggagtttattcggaaaagccagctggtccagcctgtggggccactggtggtgctgctgccct<br><br>ggcgggtgggtacagccgcgtcctcaacgccgcctgccagcgcctggcgagggctggggtcgtgctggtcaccgctgccggcaacttccgggac<br><br>gatgcctgcctctactccccagcctcagctcccgaggtcatcacagttggggccaccaatgcccaagaccagccggtgacccctggggactttggg<br><br>gaccaactttggccgctgtgtggacctctttgccccaggggaggacatcattggtgcctccagcgactgcagcacctgctttgtgtcacagagtgg<br><br>gacatcacaggctgctgcccacgtggctggcattgcagccatgatgctgtctgccgagccggagctcacccttggccgagttgaggcagagactg<br><br>        N425S AAT to AGT          A443T GCC to ACC<br>atccacttctctgccaaagatgtcatc<u>aat</u>gaggcctggttccctgaggaccagcgggtactgacccccaacctggtggcc<u>gcc</u>ctgcccccag<br><br>cacccatGGGGCAGGTTGGCAGCTGTTTTGCAGGACTGTATGGTCAGCACACTCGGGGCCTACACGGATGGCC<br><br>  I474V ATC to GTC<br>ACAGCC<u>GTC</u>GCCCGCTGCGCCCCAGATGAGGAGCTGCTGAGCTGCTCCAGTTTCTCCAGGAGTGGGAAGCGG | 36 |

| FORM/ ALLELE | VERSION | SEQUENCE | SEQ ID NO: |
|---|---|---|---|
| | | CGGGGCGAGCGCATGGAGGCCCAAGGGGGCAAGCTGGTCTGCCGGGCCCACAACGCTTTTGGGGGTGAGGG | |
| | | TGTCTACGCCATTGCCAGGTGCTGCCTGCTACCCCAGGCCAACTGCAGCGTCCACACAGCTCCACCAGCTGAG | |
| | | GCCAGCATGGGGACCCGTGTCCACTGCCACCAACAGGGCCACGTCCTCACAGGCTGCAGCTCCCACTGGGAG | |
| | | GTGGAGGACCTTGGCACCCACAAGCCGCCTGTGCTGAGGCCACGAGGTCAGCCCAACCAGTGCGTGGGCCAC | |
| | | AGGGAGGCCAGCATCCACGCTTCCTGCTGCCATGCCCCAGGTCTGGAATGCAAAGTCAAGGAGCATGGAA | |
| | |   Q619P CAG to CCG E620G GAG to GGG<br>TCCCGGCCCCT<u>CAGGAG</u>CAGGTGACCGTGGCCTGCGAGGAGGGCTGGACCCTGACTGGCTGCAGTGCCCTCC | |
| | | CTGGGACCTCCCACGTCCTGGGGGCCTACGCCGTAGACAACACGTGTGTAGTCAGGAGCCGGGACGTCAGCA | |
| | |   E670G GAG to GGG<br>CTACAGGCAGCACCAGCGAA<u>GAG</u>GCCGTGACAGCCGTTGCCATCTGCTGCCGGAGCCGGCACCTGGCGCAGG | |
| | | CCTCCCAGGAGCTCCAGTGAC | |
| q | | ATGGGCACCGTCAGCTCCAGGCGGTCCTGGTGGCCGCTGCCACTGCTGCTGCTGCTGCTGCTCCTGGGTC | 37 |
| | |                                     R46L CGT to CTT<br>*CCGCGGGCGCCCGTGCG* CAGGAGGACGAGGACGGCGACTACGAGGAGCTGGTGCTAGCCTTG<u>C</u>GTTCCG | |
| | |   A53V GCC to GTC<br>AGGAGGACGGCCTGG<u>TC</u>GAAGCACCCGAGCACGGAACCACAGCCACCTTCCACCGCTGCGCCAAGGAT | |
| | | CCGTGGAGGTTGCCTGGCACCTACGTGGTGGTGCTGAAGGAGGAGACCCACCTCTCGCAGTCAGAGCG | |
| | | CACTGCCCGCCGCCTGCAGGCCCAGGCTGCCCGCCGGGGATACCTCACCAAGATCCTGCATGTCTTCC | |
| | | ATGGCCTTCTTCCTGGCTTCCTGGTGAAGATGAGTGGCGACCTGCTGGAGCTGGCCTTGAAGTTGCCC | |
| | | CATGTCGACTACATCGAGGAGGACTCCTCTGTCTTTGCCCAGagcatcccgtggaacctggagcggattaccctcca | |
| | | cggtaccgggcggatgaataccagccccccgacggaggcagcctggtggaggtgtatctcctagacaccagcatacagagtgaccaccgggaa | |
| | | atcgagggcagggtcatggtcaccgacttcgagaatgtgcccgaggaggacgggacccgcttccacagacaggccagcaagtgtgacagtcat | |
| | | ggcacccacctggcaggggtggtcagcggccgggatgccggcgtggccaagggtgccagcatgcgcagcctgcgcgtgctcaactgccaaggg | |
| | | aagggcacggttagcggcaccctcataggcctggagtttattcggaaaagccagctggtccagcctgtggggccactggtggtgctgctgcccct | |
| | | ggcgggtgggtacagccgcgtcctcaacgccgcctgccagcgcctggcgagggctggggtcgtgctggtcaccgctgccggcaacttccgggac | |
| | | gatgcctgcctctactcccagcctcagctcccgaggtcatcacagttggggccaccaatgcccaagaccagccggtgaccctggggactttggg | |
| | | gaccaactttggccgctgtgtggacctctttgccccaggggaggacatcattggtgcctccagcgactgcagcacctgctttgtgtcacagagtgg | |
| | | gacatcacaggctgctgcccacgtggctggcattgcagccatgatgctgtctgccgagccggagctcacctggccgagttgaggcagagactg | |
| | |         N425S AAT to AGT            A443T GCC to ACC<br>atccacttctctgccaaagatgtcatc<u>aat</u>gaggcctggttccctgaggaccagcgggtactgaccccccaacctggtggcc<u>gcc</u>ctgccccccag | |
| | | cacccatGGGGCAGGTTGGCAGCTGTTTTGCAGGACTGTATGGTCAGCACACTCGGGGCCTACACGGATGGCC | |
| | |   I474V ATC to GTC<br>ACAGCC<u>ATC</u>GCCCGCTGCGCCCCAGATGAGGAGCTGCTGAGCTGCTCCAGTTTCTCCAGGAGTGGGAAGCGG | |
| | | CGGGGCGAGCGCATGGAGGCCCAAGGGGGCAAGCTGGTCTGCCGGGCCCACAACGCTTTTGGGGGTGAGGG | |
| | | TGTCTACGCCATTGCCAGGTGCTGCCTGCTACCCCAGGCCAACTGCAGCGTCCACACAGCTCCACCAGCTGAG | |
| | | GCCAGCATGGGGACCCGTGTCCACTGCCACCAACAGGGCCACGTCCTCACAGGCTGCAGCTCCCACTGGGAG | |
| | | GTGGAGGACCTTGGCACCCACAAGCCGCCTGTGCTGAGGCCACGAGGTCAGCCCAACCAGTGCGTGGGCCAC | |

TABLE 6-continued

PCSK9 SEQUENCES

| FORM/ALLELE | VERSION | SEQUENCE | SEQ ID NO: |
|---|---|---|---|

AGGGAGGCCAGCATCCACGCTTCCTGCTGCCATGCCCCAGGTCTGGAATGCAAAGTCAAGGAGCATGGAA

Q619P CAG to CCG  E620G GAG to GGG
TCCCGGCCCCT<u>CAGGAG</u>CAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTGTAGTCAGGAGCCGGGACGTCAGCA

E670G GAG to GGG
CTACAGGCAGCACCAGCGAA<u>GAG</u>GCCGTGACAGCCGTTGCCATCTGCTGCCGGAGCCGGCACCTGGCGCAGG

CCTCCCAGGAGCTCCAGTGAC

TABLE 7

Human VH3-23 Variant Alleles

| VH3-23 haplotype | Cumulative allele frequency | SNPs | | | |
|---|---|---|---|---|---|
| a (=VH3 − 23 * 04) | 0.0983 | rs56069819 | | | |
| d | 0.0087 | rs56069819 | rs61750837 | rs61752504 | |
| e | 0.0046 | rs56069819 | rs1064090 | rs1055799 | |
| j | 0.0009 | rs56069819 | rs1055799 | | |
| u | 0.0005 | rs56069819 | rs1064091 | | |
| s | 0.0005 | rs56069819 | rs1064091 | rs61752504 | rs61750837 |
| r | 0.0005 | rs56069819 | rs1064090 | | |
| TOTAL: | 0.114 | | | | |

TABLE 8

Exemplary anti-PCSK9 antibodies and/or antibody fragments

| SEQ ID NOs comprising an anti-PCSK9 monoclonal antibody or fragment thereof | patent or patent Pblication |
|---|---|
| Light chain complementary determining regions (CDRL) SEQ ID NO: 5, 7, 9, 10, 12, 13, 14, 15, 16, 17, 18, 19, 20, 21, 22, 23, 24, 26, 28, 30, 31, 32, 33, 35, 36, 37, 38, 39, 40, 42, 44, 46, 270, 271, 272, 273, 275, 277, 286, 287, 288, 297, 299, 301, 405, 407, 409, 411, 413, 415, 417, 421, 425, 429, 433, 437, 441, 445, 449, 453, 457, 461, 465, 469, 473, 477, 481, 485; Heavy chain complementary determining regions (CDRH) SEQ ID NO: 47, 48, 49, 50, 51, 52, 53, 54, 55, 56, 57, 58, 60, 61, 62, 64, 65, 67, 69, 71, 72, 74, 76, 77, 78, 79, 80, 81, 83, 85, 87, 89, 91, 278, 289, 290, 291, 292, 298, 300, 302, 401, 404, 406, 408, 410, 412, 414, 416, 419, 423, 427, 431, 435, 439, 443, 447, 451, 455, 459, 463, 467, 471, 475, 479, 483; | US20120020975 A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 465; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 463; | US20120027765A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 465; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 463; | US8168762B2 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 222, 229, 238, 405, 407, 409, 411, 413, 415, 417; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 247, 256, 265, 404, 406, 408, 410, 412, 414, 416; | US20120020976A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 465, 485; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 459, 463, 483; | US20130085265A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 461, 465, 485; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 459, 463, 483; | US20130079501A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 158, 162, 395, 473, 477; CDRH SEQ ID NO: 47, 48, 49, 50, 51, 52, 53, | US20120213797A1 |

TABLE 8-continued

Exemplary anti-PCSK9 antibodies and/or antibody fragments

| SEQ ID NOs comprising an anti-PCSK9 monoclonal antibody or fragment thereof | patent or patent Pblication |
|---|---|
| 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 180, 175, 308, 368, 471, 475; CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416; | US20120251544A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 461, 465, 485; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 459, 463, 483; CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, | US20130052201A1 |
| | US20130058944A1 |
| 409, 411, 413, 415, 417, 461, 465, 485; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 459, 463, 483; CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416; | US20130079502A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416; | US20130245235A1 |

TABLE 9

Human variable & constant variants distributed over several human ethnic populations-useful for ligand tailoring

| Human Gene Segment Type | Example Human Allele[1] | Amino Acid Position & Variation | Nucleotide Variation[2] (NCBI dbSNP reference number)[3] | Variant Nucleotide Position | Human Populations[4] | No Individs[5] | Het Freq[6] | Hom Freq[7] (Het + Hom feq[8]) | Cum Freq[9] |
|---|---|---|---|---|---|---|---|---|---|
| IGHG1 | IGHG1*01 | 204D (CH3 variation) | GAT | 14:106208086 (forward strand) | A (European ancestry) | 153 | 0.400 | 0.096 (0.496) | 0.296 |
| | IGHG1*03 | 204E (CH3 variation) | GAG (rs1045853) | 14:106208086 (forward strand) | A (European ancestry) | 366 | 0.400 | 0.504 (0.904) | 0.704 |
| | IGHG1*01 (0.462) | 206L (CH3 variation) | CTG | 14:106208082 (forward strand) | A (European ancestry) | | 0.358 | 0.104 (0.538) | 0.283 |
| | IGHG1*03 | 206M (CH3 variation) | ATG (rs11621259) | 14:106208082 (forward strand) | A (European ancestry) | | 0.358 | 0.538 (0.896) | 0.717 |
| IGHG2 | IGHG2*01 | 72P (CH1 variation) | CCC | 14:106110914 (forward strand) | B | | 0.336 | 0.540 (0.876) | 0.708 |
| | IGHG2*02 | 72T (CH1 variation) | ACC (rs11627594) | 14:106110914 (forward strand) | B | | 0.336 | 0.124 (0.292) | 0.292 |
| | IGHG2*01 | 75N (CH1 variation) | AAC | 14:106110904 (forward strand) | A | | 0.007 | 0.993 | 0.997 |
| | IGHG2*04 | 75S (CH1 variation) | AGC (rs201590297) | 14:106110904 (forward strand) | A | | 0.007 | | 0.004 |
| | IGHG2*01 | 76F (CH1 variation) | TTC | | | | | | |
| | IGHG2*04 | 76L (CH1 variation) | TTG | | | | | | |
| | IGHG2*01 | 161V (CH2 variation) | GTG | 14:10611013 (forward strand) | B | | 0.342 | 0.539 (0.881) | 0.711 |
| | IGHG2*02 | 161M (CH2 variation) | ATG (rs8009156) | 14:10611013 (forward strand) | B | | 0.342 | 0.118 (0.46) | 0.289 |
| | IGHG2*01 | 257A (CH3 variation) | GCC | 14:106109752 (forward strand) | C | | 0.199 | 0.493 (0.692) | 0.592 |

TABLE 9-continued

Human variable & constant variants distributed over several human ethnic populations-useful for ligand tailoring

| Human Gene Segment Type | Example Human Allele[1] | Amino Acid Position & Variation | Nucleotide Variation[2] (NCBI dbSNP reference number)[3] | Variant Nucleotide Position | Human Populations[4] | No Individs[5] | Het Freq[6] | Hom Freq[7] (Het + Hom feq[8]) | Cum Freq[9] |
|---|---|---|---|---|---|---|---|---|---|
| | | | | | D | | 0.007 | 0.992 (0.999) | 0.995 |
| | IGHG2*06 | 257S (CH3 variation) | TCC (rs4983499) | 14:106109752 (forward strand) | C | | 0.199 | 0.308 (0.507) | 0.408 |
| | | | | | D | | 0.007 | 0.002 (0.009) | 0.005 |
| IGHG4 | IGHG4*01 | 189L (CH2 variation) | CTG | 14:105624992 (forward strand) | B | 1047 | 0.315 | 0.644 (0.959) | 0.801 |
| | IGHG4*02 | 189V (CH2 variation) | GTG (rs8015545) | 14:105624992 (forward strand) | B | 389 | 0.315 | 0.041 (0.356) | 0.199 |
| | IGHG4*01 | 289R (CH3 variation) | AGG | 14:105624594 (forward strand) | | | | | |
| | IGHG4*03 | 289K (CH3 variation) | AAG (rs77498506) | 14:105624594 (forward strand) | | | | | |

Table Footnotes:
1. IMGT notation (ww.imgt.org); refer to figures for other alleles comprising this variation.
2. SNP Underlined in Codon.
3. NCBI dbSNP Build 138 released on Apr. 25, 2013.
4. Human population used for representative variant frequency analysis.
Populations
A This population included 662 participants of European descent from the ClinSeq project, all of whom had undergone whole-exome sequencing using Agilent's 38 Mb or 50 Mb capture kit.
B 1000 Genomes database.
C ESP6500:African_American.
D ESP6500:European_American.
5. Number of individuals in representative population found to have the allele.
6. Heterozygous human genotype frequency, ie, cumulative frequency of all genotypes having one occurrence of the variant allele and one occurrence of another allele (heterozygous state), eg, ac genotype in the population.
7. Homozygous human genotype frequency, ie, cumulative frequency of two occurrences of the variant allele (homozygous state), eg, cc genotype in the population.
8. Total human genotype frequency, ie, total of heterozygous plus homozygous human genotype frequencies.
9. Cumulative human allele frequency of all occurrences of the variant allele in the population.

TABLE 10

FURTHER SEQUENCES

| SEQ ID NO: | Human Allele | Nucleotide/Amino Acid Sequence |
|---|---|---|
| | | HEAVY CHAIN ALLELES |
| 41 | IGHG1*01 (CH1 + Hinge + CH2 + CH3 + CH - S) | gcctccaccaagggcccatcggtcttcccctggcaccctcctccaaga gcacctctggg ggcacagcggccctgggctgcctggtcaaggactacttccccgaaccgg tgacggtgtcg tggaactcaggcgccctgaccagcggcgtgcacaccttcccggctgtcc tacagtcctca ggactctactccctcagcagcgtggtgaccgtgccctccagcagcttgg gcacccagacc tacatctgcaacgtgaatcacaagcccagcaacaccaaggtggacaaga aagttgagccc aaatcttgtgacaaaactcacacatgcccaccgtgcccagcacctgaac tcctgggggga ccgtcagtcttcctcttccccccaaaacccaaggacaccctcatgatct cccggacccct gaggtcacatgcgtggtggtggacgtgagccacgaagaccctgaggtca agttcaactgg tacgtggacggcgtggaggtgcataatgccaagacaaagccgcgggagg agcagtacaac agcacgtaccgggtggtcagcgtcctcaccgtcctgcaccaggactggc tgaatggcaag gagtacaagtgcaaggtctccaacaaagccctcccagcccccatcgaga aaaccatctcc aaagccaaagggcagccccgagaaccacaggtgtacaccctgccccat cccgggatgag |

TABLE 10-continued

FURTHER SEQUENCES

| SEQ ID NO: | Human Allele | Nucleotide/Amino Acid Sequence |
|---|---|---|
| | | ctgaccaagaaccaggtcagcctgacctgcctggtcaaaggcttctatc<br>ccagcgacatc<br>gccgtggagtgggagagcaatgggcagccggagaacaactacaagacca<br>cgcctcccgtg<br>ctggactccgacggctccttcttcctctacagcaagctcaccgtggaca<br>agagcaggtgg<br>cagcaggggaacgtcttctcatgctccgtgatgcatgaggctctgcaca<br>accactacacg<br>cagaagagcctctccctgtctccgggtaaa |
| 42 | | ASTKGPSVFPLAPSSKSTSGGTAALGCLVKDYFPEPVTVSWNSGALTSG<br>VHTFPAVLQSS<br>GLYSLSSVVTVPSSSLGTQTYICNVNHKPSNTKVDKKVEPKSCDKTHTC<br>PPCPAPELLGG<br>PSVFLFPPKPKDTLMISRTPEVTCVVVDVSHEDPEVKFNWYVDGVEVHN<br>AKTKPREEQYN<br>STYRVVSVLTVLHQDWLNGKEYKCKVSNKALPAPIEKTISKAKGQPREP<br>QVYTLPPSRDE<br>LTKNQVSLTCLVKGFYPSDIAVEWESNGQPENNYKTTPPVLDSDGSFFL<br>YSKLTVDKSRW<br>QQGNVFSCSVMHEALHNHYTQKSLSLSPGK<br>D = position 204<br>L = position 206 |
| 43 | IGHG2*01<br>(CH1 + Hinge +<br>CH2 + CH3 +<br>CH − S) | gcctccaccaagggcccatcggtcttccccctggcgccctgctccagga<br>gcacctccgag<br>agcacagccgccctgggctgcctggtcaaggactacttccccgaaccgg<br>tgacggtgtcg<br>tggaactcaggcgctctgaccagcggcgtgcacaccttcccagctgtcc<br>tacagtcctca<br>ggactctactccctcagcagcgtggtgaccgtgccctccagcaacttcg<br>gcacccagacc<br>tacacctgcaacgtagatcacaagcccagcaacaccaaggtggacaaga<br>cagttgagcgc<br>aaatgttgtgtcgagtgcccaccgtgcccagcaccacctgtggcaggac<br>cgtcagtcttc<br>ctcttccccccaaaacccaaggacaccctcatgatctcccggacccctg<br>aggtcacgtgc<br>gtggtggtggacgtgagccacgaagaccccgaggtccagttcaactggt<br>acgtggacggc<br>gtggaggtgcataatgccaagacaaagccacgggaggagcagttcaaca<br>gcacgttccgt<br>gtggtcagcgtcctcaccgttgtgcaccaggactggctgaacggcaagg<br>agtacaagtgc<br>aaggtctccaacaaaggcctcccagcccccatcgagaaaaccatctcca<br>aaaccaaaggg<br>cagccccgagaaccacaggtgtacaccctgcccccatcccgggaggaga<br>tgaccaagaac<br>caggtcagcctgacctgcctggtcaaaggcttctaccccagcgacatcg<br>ccgtggagtgg<br>gagagcaatgggcagccggagaacaactacaagaccacacctcccatgc<br>tggactccgac<br>ggctccttcttcctctacagcaagctcaccgtggacaagagcaggtggc<br>agcaggggaac<br>gtcttctcatgctccgtgatgcatgaggctctgcacaaccactacacgc<br>agaagagcctc<br>tccctgtctccgggtaaa |
| 44 | | ASTKGPSVFPLAPCSRSTSESTAALGCLVKDYFPEPVTVSWNSGALTSG<br>VHTFPAVLQSS<br>GLYSLSSVVTVPSSNFGTQTYTCNVDHKPSNTKVDKTVERKCCVECPPC<br>PAPPVAGPSVF<br>LFPPKPKDTLMISRTPEVTCVVVDVSHEDPEVQFNWYVDGVEVHNAKTK<br>PREEQFNSTFR<br>VVSVLTVVHQDWLNGKEYKCKVSNKGLPAPIEKTISKTKGQPREPQVYT<br>LPPSREEMTKN<br>QVSLTCLVKGFYPSDIAVEWESNGQPENNYKTTPPMLDSDGSFFLYSKL<br>TVDKSRWQQGN<br>VFSCSVMHEALHNHYTQKSLSLSPGK<br>P = position 72<br>N = position 75<br>F = position 76<br>V = position 161<br>A = position 257 |

| TABLE 10-continued | | |
|---|---|---|
| FURTHER SEQUENCES | | |
| SEQ ID NO: | Human Allele | Nucleotide/Amino Acid Sequence |
| 45 | IGHV1-18*01 | caggttcagctggtgcagtctggagctgaggtgaagaagcctggggcct cagtgaaggtc tcctgcaaggcttctggttacacctttaccagctatggtatcagctggg tgcgacaggcc cctggacaagggcttgagtggatgggatggatcagcgcttacaatggta acacaaactat gcacagaagctccagggcagagtcaccatgaccacagacacatccacga gcacagcctac atggagctgaggagcctgagatctgacgacacggccgtgtattactgtg cgagaga |
| 46 | | QVQLVQSGAEVKKPGASVKVSCKASGYTFTSYGISWVRQAP GQGLEWMGWISAYNGNTNYAQKLQGRVTMTTDTSTSTAYMELRSLRSDD TAVYYCAR |
| 47 | IGHV1-46*01 | caggtgcagctggtgcagtctggggctgaggtgaagaagcctggggcct cagtgaaggtt tcctgcaaggcatctggatacaccttcaccagctactatatgcactggg tgcgacaggcc cctggacaagggcttgagtggatgggaataatcaaccctagtggtggta gcacaagctac gcacagaagttccagggcagagtcaccatgaccagggacacgtccacga gcacagtctac atggagctgagcagcctgagatctgaggacacggccgtgtattactgtg cgagaga |
| 48 | | QVQLVQSGAEVKKPGASVKVSCKASGYTFTSYYMHWVRQAP GQGLEWMGIINPSGGSTSYAQKFQGRVTMTRDTSTSTVYMELSSLRSED TAVYYCAR |
| LIGHT CHAIN ALLELES | | |
| 49 | IGKC*01 | cgaactgtggctgcaccatctgtcttcatcttcccgccatctgatgagc agttgaaatct ggaactgcctctgttgtgtgcctgctgaataacttctatcccagagagg ccaaagtacag tggaaggtggataacgccctccaatcgggtaactcccaggagagtgtca cagagcaggac agcaaggacagcacctcacagcctcagcagcaccctgacgctgagcaaag cagactacgag aaacacaaagtctacgcctgcgaagtcacccatcagggcctgagctcgc ccgtcacaaag agcttcaacaggggagagtgt |
| 50 | | RTVAAPSVFIFPPSDEQLKSGTASVVCLLNNFYPREAKVQWKVDNALQS GNSQESVTEQD SKDSTYSLSSTLTLSKADYEKHKVYACEVTHQGLSSPVTKSFNRGEC V = position 84 C = position 87 |
| 51 | IGLC2*01 | ggtcagcccaaggctgccccctcggtcactctgttcccgccctcctctg aggagcttcaa gccaacaaggccacactggtgtgtctcataagtgacttctacccgggag ccgtgacagtg gcttggaaagcagatagcagccccgtcaaggcgggagtggagaccacca cacctccaaa caaagcaacaacaagtacgcggccagcagctatctgagcctgacgcctg agcagtggaag tcccacagaagctacagctgccaggtcacgcatgaagggagcaccgtgg agaagacagtg gcccctacagaatgttca |
| 52 | | GQPKAAPSVTLFPPSSEELQANKATLVCLISDFYPGAVTVAWKADSSPV KAGVETTTPSK QSNNKYAASSYLSLTPEQWKSHRSYSCQVTHEGSTVEKTVAPTECS |
| 53 | IGKV4-1*01 | atggtgttgcagacccaggtcttcatttctctgttgctctggatctctg gtgcctacggg gacatcgtgatgacccagtctccagactccctggctgtgtctctgggcg agagggccacc atcaactgcaagtccagccagagtgttttatacagctccaacaataaga actacttagct tggtaccagcagaaaccaggacagcctcctaagctgctcatttactggg catctacccgg |

TABLE 10-continued

FURTHER SEQUENCES

| SEQ ID NO: | Human Allele | Nucleotide/Amino Acid Sequence |
|---|---|---|
| | | gaatccggggtccctgaccgattcagtggcagcgggtctgggacagatt<br>tcactctcacc<br>atcagcagcctgcaggctgaagatgtggcagtttattactgtcagcaat<br>attatagtact<br>cctcc |
| 54 | | DIVMTQSPDSLAVSLGERATINCKSSQSVLYSSNNKNYLA<br>WYQQKPGQPPKLLIYWASTRESGVPDRFSGSGSGTDFTLTISSLQAEDV<br>AVYYCQQYYST<br>P |
| 55 | IGKV1-13*02 | atggacatgagggtccccgctcagctcctggggcttctgctgctctggc<br>tcccagcaggt<br>gccagatgtgccatccagttgacccagtctccatcctccctgtctgcat<br>ctgtaggagac<br>agagtcaccatcacttgccgggcaagtcagggcattagcagtgctttag<br>cctggtatcag<br>cagaaaccagggaaagctcctaagctcctgatctatgatgcctccagtt<br>tggaaagtggg<br>gtcccatcaaggttcagcggcagtggatctgggacagatttcactctca<br>ccatcagcagc<br>ctgcagcctgaagattttgcaacttattactgtcaacagtttaatagtt<br>accctcagtgc<br>cagatgtgccatccagttgacccagtctccatcctccctgtctgcatct<br>gtaggagacag<br>agtcaccatcacttgccgggcaagtcagggcattagcagtgctttagcc<br>tggtatcagca<br>gaaaccagggaaagctcctaagctcctgatctatgatgcctccagtttg<br>gaaagtgggt<br>cccatcaaggttcagcggcagtggatctgggacagatttcactctcacc<br>atcagcagcct<br>gcagcctgaagattttgcaacttattactgtcaacagtttaatagttac<br>cctca |
| 57 | IGKJ2*01 | tgtacacttttggccaggggaccaagctggagatcaaac |
| 58 | | YTFGQGTKLEIK |
| 59 | IGLJ2*01 | tgtggtattcggcggagggaccaagctgaccgtcctag |
| 60 | | VVFGGGTKLTVL |
| 61 | An IGHG1*01 Heavy Chain Constant Region | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br>EPKSCDKTHTCPPCPAPELLGGPS<br>VFLFPPKPKDTLMISRTPEVTCVVVDVSHEDPEVKFNWYVDGVEVHNAK<br>TKPREEQYNST<br>YRVVSVLTVLHQDWLNGKEYKCKVSNKALPAPIEKTISKAKGQPREPQV<br>YTLPPSRDELT<br>KNQVSLTCLVKGFYPSDIAVEWESNGQPENNYKTTPPVLDSDGSFFLYS<br>KLTVDKSRWQQGNVFSCSVMHEALHNHYTQKSLSLSPG |
| 62 | An IGKC*01 Kappa Light Chain Constant Region | RTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPV<br>TKSFNRGEC |
| 63 | An IGHG2*01 Heavy Chain Constant Region | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPPVAGPSVFLFPPKPKDTLMISRTPEVTCVVVDVSH<br>EDPEVQFNWYVDGVEVHNAKTKPREEQFNSTFRVVSVLTVVHQDWLNGK<br>EYKCKVSNKGLPAPIEKTISKTKGQPREPQVYTLPPSREEMTKNQVSLT<br>CLVKGFYPSDIAVEWESNGQPENNYKTTPPMLDSDGSFFLYSKLTVDKS<br>RWQQGNVFSCSVMHEALHNHYTQKSLSLSPGK |
| 64 | An IGLC2*01 Lambda Light Chain Constant Region | QPKAAPSVTLFPPSSEELQANKATLVCLISDFYPGAVTVAWKADSSPVK<br>AGVETTTPSKQSNNKYAASSYLSLTPEQWKSHRSYSCQVTHEGSTVEKT<br>VAPTECS |
| 65 | An IGHG2*01 Heavy Chain Constant Region | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPPVAGPSVFLFPPKPKDTLMISRTPEVTCVVVDVSH<br>EDPEVQFNWYVDGVEVHNAKTKPREEQFNSTFRVVSVLTVVHQDWLNGK<br>EYKCKVSNKGLPSSIEKTISKTKGQPREPQVYTLPPSREEMTKNQVSLT |

TABLE 10-continued

FURTHER SEQUENCES

| SEQ ID NO: | Human Allele | Nucleotide/Amino Acid Sequence |
|---|---|---|
| | | CLVKGFYPSDIAVEWESNGQPENNYKTTPPMLDSDGSFFLYSKLTVDKS<br>RWQQGNVFSCSVMHEALHNHYTQKSLSLSPGK |
| 66 | An IGKC*01 Kappa Light Chain Constant Region | RTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPV<br>TKSFNRGEC |

HUMAN IL4Ra SEQUENCES

| 67 | Amino Acid Sequence | MGWLCSGLLFPVSCLVLLQVASSGNMKVLQEPTCVSDYMSISTCEWKMNGPTNC<br>STELRLLYQLVFLLSEAHTCIPENNGGAGCVCHLLMDDVVSADNYTLDLWAGQQ<br>LLWKGSFKPSEHVKPRAPGNLTVHTNVSDTLLLTWSNPYPPDNYLYNHLTYAVN<br>IWSENDPADFRIYNVTYLEPSLRIAASTLKSGISYRARVRAWAQCYNTTWSEWS<br>PSTKWHNSYREPPFEQHLLLGVSVSCIVILAVCLLCYVSITKIKKEWWDQIPNPA<br>RSRLVAIIIQDAQGSQWEKRSRGQEPAKCPHWKNCLTKLLPCFLEHNMKRDEDP<br>HKAAKEMPFQGSGKSAWCPVEISKTVLWPESISVVRCVELFEAPVECEEEEEVE<br>EEKGSFCASPESSRDDFQEGREGIVARLTESLFLDLLGEENGGFCQQDMGESCL<br>LPPSGSTSAHMPWDEFPSAGPKEAPPWGKEQPLHLEPSPPASPTQSPDNLTCTE<br>TPLVIAGNPAYRSFSNSLSQSPCPRELGPDPLLARHLEEVEPEMPCVPQLSEPT<br>TVPQPEPETWEQILRRNVLQHGAAAAPVSAPTSGYQEFVHAVEQGGTQASAVVG<br>LGPPGEAGYKAFSSLLASSAVSPEKCGFGASSGEEGYKPFQDLIPGCPGDPAPV<br>PVPLFTFGLDREPPRSPQSSHLPSSSPEHLGLEPGEKVEDMPKPPLPQEQATDP<br>LVDSLGSGIVYSALTCHLCGHLKQCHGQEDGGQTPVMASPCCGCCCGDRSSPPT<br>TPLRAPDPSPGGVPLEASLCPASLAPSGISEKSKSSSSFHPAPGNAQSSSQTPK<br>IVNFVSVGPTYMRVS<br>I = position 75<br>E = position 400<br>C = position 431<br>S = position 503<br>Q = position 576<br>S = position 752 |
| 68 | Nucleotide Sequence | ATGGGGTGGCTTTGCTCTGGGCTCCTGTTCCCTGTGAGCTGCCTGGTCCTGCTG<br>CAGGTGGCAAGCTCTGGGAACATGAAGGTCTTGCAGGAGCCCACCTGCGTCTCC<br>GACTACATGAGCATCTCTACTTGCGAGTGGAAGATGAATGGTCCCACCAATTGC<br>AGCACCGAGCTCCGCCTGTTGTACCAGCTGGTTTTTCTGCTCTCCGAAGCCCAC<br>ACGTGTATCCCTGAGAACAACGGAGGCGCGGGGTGCGTGTGCCACCTGCTCATG<br>GATGACGTGGTCAGTGCGGATAACTATACACTGGACCTGTGGGCTGGGCAGCAG<br>CTGCTGTGGAAGGGCTCCTTCAAGCCCAGCGAGCATGTGAAACCCAGGGCCCCA<br>GGAAACCTGACAGTTCACACCAATGTCTCCGACACTCTGCTGCTGACCTGGAGC<br>AACCCGTATCCCCCTGACAATTACCTGTATAATCATCTCACCTATGCAGTCAAC<br>ATTTGGAGTGAAAACGACCCGGCAGATTTCAGAATCTATAACGTGACCTACCTA<br>GAACCCTCCCTCCGCATCGCAGCCAGCACCCTGAAGTCTGGGATTTCCTACAGG<br>GCACGGGTGAGGGCCTGGGCTCAGTGCTATAACACCACCTGGAGTGAGTGGAGC<br>CCCAGCACCAAGTGGCACAACTCCTACAGGGAGCCCTTCGAGCAGCACCTCCTG<br>CTGGGCGTCAGCGTTTCCTGCATTGTCATCCTGGCCGTCTGCCTGTTGTGCTAT<br>GTCAGCATCACCAAGATTAAGAAAGAATGGTGGGATCAGATTCCCAACCCAGCC<br>CGCAGCCGCCTCGTGGCTATAATAATCCAGGATGCTCAGGGGTCACAGTGGGAG<br>AAGCGGTCCCGAGGCCAGGAACCAGCCAAGTGCCCACACTGGAAGAATTGTCTT<br>ACCAAGCTCTTGCCCTGTTTTCTGGAGCACAACATGAAAAGGGATGAAGATCCT<br>CACAAGGCTGCCAAAGAGATGCCTTTCCAGGGCTCTGGAAAATCAGCATGGTGC<br>CCAGTGGAGATCAGCAAGACAGTCCTCTGGCCAGAGAGCATCAGCGTGGTCGA<br>TGTGTGGAGTTGTTTGAGGCCCCGGTGGAGTGTGAGGAGGAGGAGGAGGTAGAG<br>GAAGAAAAAGGGAGCTTCTGTGCATCGCCTGAGAGCAGCAGGGATGACTTCCAG<br>GAGGGAAGGGAGGGCATTGTGGCCCGGCTAACAGAGAGCCTGTTCCTGGACCTG<br>CTCGGAGAGGAGAATGGGGGCTTTTGCCAGCAGGACATGGGGGAGTCATGCCTT<br>CTTCCACCTTCGGGAAGTACGAGTGCTCACATGCCCTGGGATGAGTTCCCAAGT<br>GCAGGGCCCAAGGAGGCACCTCCCTGGGGCAAGGAGCAGCCTCTCCACCTGGAG<br>CCAAGTCCTCCTGCCAGCCCGACCCAGAGTCCAGACAACCTGACTTGCACAGAG<br>ACGCCCCTCGTCATCGCAGGCAACCCTGCTTACCGCAGCTTCAGCAACTCCCTG<br>AGCCAGTCACCGTGTCCCAGAGAGCTGGGTCCAGACCCACTGCTGGCCAGACAC<br>CTGGAGGAAGTAGAACCCGAGATGCCCTGTGTCCCCCAGCTCTCTGAGCCAACC<br>ACTGTGCCCCAACCTGAGCCAGAAACCTGGAGCAGATCCTCCGCCGAAATGTC<br>CTCCAGCATGGGGCAGCTGCAGCCCCCGTCTCGGCCCCCACCAGTGGCTATCAG<br>GAGTTTGTACATGCGGTGGAGCAGGGTGGCACCCAGGCCAGTGCGGTGGTGGGC<br>TTGGGTCCCCCAGGAGAGGCTGGTTACAAGGCCTTCTCAAGCCTGCTTGCCAGC<br>AGTGCTGTGTCCCCAGAGAAATGTGGGTTTGGGCTAGCAGTGGGGAAGAGGGG<br>TATAAGCCTTTCCAAGACCTCATTCCTGGCTGCCCTGGGGACCCTGCCCCAGTC<br>CCTGTCCCCTTGTTCACCTTTGGACTGGACAGGGAGCCACCTCGCAGTCCGCAG<br>AGCTCACATCTCCCAAGCAGCTCCCAGAGACACCTGGGTCTGGAGCCGGGGGAA<br>AAGGTAGAGGACATGCCAAAGCCCCCACTTCCCCAGGAGCAGGCCACAGACCCC<br>CTTGTGGACAGCCTGGGCAGTGGCATTGTCTACTCAGCCCTTACCTGCCACCTG<br>TGCGGCCACCTGAAACAGTGTCATGGCCAGGAGGATGGTGGCCAGACCCCTGTC<br>ATGGCCAGTCCTTGCTGTGGCTGCTGCTGTGGAGACAGGTCCTCGCCCCCTACA |

TABLE 10-continued

FURTHER SEQUENCES

| SEQ ID NO: | Human Allele | Nucleotide/Amino Acid Sequence |
|---|---|---|
| | | ACCCCCCTGAGGGCCCCAGACCCCTCTCCAGGTGGGGTTCCACTGGAGGCCAGT CTGTGTCCGGCCTCCCTGGCACCCTCGGGCATCTCAGAGAAGAGTAAATCCTCA TCATCCTTCCATCCTGCCCCTGGCAATGCTCAGAGCTCAAGCCAGACCCCCAAA ATCGTGAACTTTGTCTCCGTGGGACCCACATACATGAGGGTCTCTTAG |

ANTI-HUMAN IL4Ra ANTIBODY SEQUENCES

| 69 | VH | EVQLVESGGG LEQPGGSLRLSCAGSGFTFR DYAMTWVRQA PGKGLEWVSS ISGSGGNTYY ADSVKGRFTISRDNSKNTLY LQMNSLRAEDTAVYYCAKDR LSITIRPRYYGLDVWGQGTTVTVSS |
| 70 | VL | DIVMTQSPLSLPVTPGEPASISCRSSQSLLYSIGYNYLDWYLQKSGQSPQ LLIYLGSNRASGVPDRFSGSGSGTDFTLKISRVEAEDVGFYYCMQALQTP YTFGQGTKLEIK |
| 71 | HEAVY CHAIN | EVQLVESGGG LEQPGGSLRL SCAGSGFTFR DYAMTWVRQA PGKGLEWVSS ISGSGGNTYY ADSVKGRFTI SRDNSKNTLY LQMNSLRAED TAVYYCAKDR LSITIRPRYY GLDVWGQGTT VTVSSASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYGPP CPPCPAPEFL GGPSVFLFPP KPKDTLMISR TPEVTCVVVD VSQEDPEVQF NWYVDGVEVH NAKTKPREEQ FNSTYRVVSV LTVLHQDWLN GKEYKCKVSN KGLPSSIEKT ISKAKGQPRE PQVYTLPPSQ EEMTKNQVSL TCLVKGFYPS DIAVEWESNG QPENNYKTTP PVLDSDGSFF LYSRLTVDKS RWQEGNVFSC SVMHEALHNH YTQKSLSLSL G |
| 72 | LIGHT CHAIN | DIVMTQSPLSLPVTPGEPASISCRSSQSLLYSIGYNYLDWYLQKSGQSPQ LLIYLGSNRASGVPDRFSGSGSGTDFTLKISRVEAEDVGFYYCMQALQTP YTFGQGTKLEIKRTVAAPSVFIFPPSDEQLKSGTASVVCLLNNFYPREAK VQWKVDNALQSGNSQESVTEQDSKDSTYSLSSTLTLSKADYEKHKVYACE VTHQGLSSPVTKSF |

HUMAN IGHG4 SEQUENCES

| 73 | IGHG4*01 AMINO ACID SEQUENCE | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPSCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK<br>L = position 189<br>R = position 289 |
| 74 | IGHG4*01 NUCLEOTIDE SEQUENCE | GCTTCCACCAAGGGCCCATCGGTCTTCCCCCTGGCGCCCTGCTCCAGGA GCACCTCCGAGAGCACAGCCGCCCTGGGCTGCCTGGTCAAGGACTACTT CCCCGAACCGGTGACGGTGTCGTGGAACTCAGGCGCCCTGACCAGCGGC GTGCACACCTTCCCGGCTGTCCTACAGTCCTCAGGACTCTACTCCCTCA GCAGCGTGGTGACCGTGCCCTCCAGCAGCTTGGGCACGAAGACCTACAC CTGCAACGTAGATCACAAGCCCAGCAACACCAAGGTGGACAAGAGAGTT GAGTCCAAATATGGTCCCCCATGCCCATCATGCCCAGCACCTGAGTTCC TGGGGGGACCATCAGTCTTCCTGTTCCCCCCAAAACCCAAGGACACTCT CATGATCTCCCGGACCCCTGAGGTCACGTGCGTGGTGGTGGACGTGAGC CAGGAAGACCCCGAGGTCCAGTTCAACTGGTACGTGGATGGCGTGGAGG TGCATAATGCCAAGACAAAGCCGCGGGAGGAGCAGTTCAACAGCACGTA CCGTGTGGTCAGCGTCCTCACCGTCCTGCACCAGGACTGGCTGAACGGC AAGGAGTACAAGTGCAAGGTCTCCAACAAAGGCCTCCCGTCCTCCATCG AGAAAACCATCTCCAAAGCCAAAGGGCAGCCCCGAGAGCCACAGGTGTA CACCCTGCCCCCATCCCAGGAGGAGATGACCAAGAACCAGGTCAGCCTG ACCTGCCTGGTCAAAGGCTTCTACCCCAGCGACATCGCCGTGGAGTGGG AGAGCAATGGGCAGCCGGAGAACAACTACAAGACCACGCCTCCCGTGCT GGACTCCGACGGCTCCTTCTTCCTCTACAGCAGGCTCACCGTGGACAAG AGCAGGTGGCAGGAGGGGAATGTCTTCTCATGCTCCGTGATGCATGAGG CTCTGCACAACCACTACACACAGAAGAGCCTCTCCCTGTCTCTGGGTAA ATGA<br>C = position 565 (CTG encodes 189V)<br>G = position 866 (AGG encodes 289R) |

Nav1.7 SEQUENCES

| 75 | HUMAN Nav1.7 AMINO ACID SEQUENCE | MAMLPPPGPQSFVHFTKQSLALIEQRIAERKSKEPKEEKKDDDEEAPKPSSDLEAG KQLPFIYGDIPPGMVSEPLEDLDPYYADKKTFIVLNKGKTIFRFNATPALYMLSPFS PLRRISIKILVHSLFSMLIMCTILTNCIFMTMNNPPDWTKNVEYTFTGIYTFESLVKI |

TABLE 10-continued

FURTHER SEQUENCES

| SEQ ID NO: | Human Allele | Nucleotide/Amino Acid Sequence |
|---|---|---|
| | (ENST00000303354) | LARGFCVGEFTFLRDPWNWLDFVVIVFAYLTEFVNLGNVSALRTFRVLRALKTISVI<br>PGLKTIVGALIQSVKKLSDVMILTVFCLSVFALIGLQLFMGNLKHKCFRNSLENNET<br>LESIMNTLESEEDFRKYFYYLEGSKDALLCGFSTDSGQCPEGYTCVKIGRNPDYGYT<br>SFDTFSWAFLALFRLMTQDYWENLYQQTLRAAGKTYMIFFVVVIFLGSFYLINLIL<br>AVVAMAYEEQNQANIEEAKQKELEFQQMLDRLKKEQEEAEAIAAAAAEYTSIRRS<br>RIMGLSESSSETSKLSSKSAKERRNRRKKKNQKKLSSGEEKGDAEKLSKSESEDSIRR<br>KSFPHLGVEGHRRAHEKRLSTPNQSPLSIRGSLFSARRSSRTSLFSFKGRGRDIGSETE<br>FADDEHSIFGDNESRRGSLFVPHRPQERRSSNISQASRSPPMLPVNGKMHSAVD<br>CNGVVSLVDGRSALMLPNGQLLPEVIIDKATSDDSGTTNQIHKKRRCSSYLLSED<br>MLNDPNLRQRAMSRASILTNTVEELEESRQKCPPWWYRFAHKFLIWNCSPYWIK<br>FKKCIYFIVMDPFVDLAITICIVLNTLFMAMEHHPMTEEFKNVLAIGNLVFTGIFAA<br>EMVLKLIAMDPYEYFQVGWNIFDSLIVTLSLVELFLADVEGLSVLRSFRLLRVFKLA<br>KSWPTLNMLIKIIGNSVGALGNLTLVLAIIVFIFAVVGMQLFGKSYKECVCKINDDC<br>TLPRWHMNDFFHSFLIVFRVLCGEWIETMWDCMEVAGQAMCLIVYMMVMVI<br>GNLVVLNLFLALLLSSFSSDNLTAIEEDPDANNLQIAVTRIKKGINYVKQTLREFILKA<br>FSKKPKISREIRQAEDLNTKKENYISNHTLAEMSKGHNFLKEKDKISGFGSSVDKHL<br>MEDSDGQSFIHNPSLTVTVPIAPGESDLENMNAEELSSDSDSEYSKVRLNRSSSSE<br>CSTVDNPLPGEGEEAEAEPMNSDEPEACFTDGCVWRFSCCQVNIESGKGKIWW<br>NIRKTCYKIVEHSWFESFIVLMILLSS-<br>GALAFEDIYIERKKTIKIILEYADKIFTYIFILEM<br>LLKWIAYGYKTYFTNAWCWLDFLIVDVSLVTLVANTLGYSDLGPIKSLRTLRALRPL<br>RALSRFEGMRVVVNALIGAIPSIMNVLLVCLIFWLIFSIMGVNLFAGKFYECINTTD<br>GSRFPASQVPNRSECFALMNVSQNVRWKNLKVNFDNVGLGYLSLLQVATFKGW<br>TIIMYAAVDSVNVDKQPKYEYSLYMYIYFVVFIIFGSFFTLNLFIGVIIDNFNQQKKK<br>LGGQDIFMTEEQKKYYNAMKKLGSKKPQKPIPRPGNKIQGCIFDLVTNQAFDISI<br>MVLICLNMVTMMVEKEGQSQHMTEVLYWINVVFIILFTGECVLKLISLRHYYFTV<br>GWNIFDFVVVIISIVGMFLADLIETYFVSPTLFRVIRLARIGRILRLVKGAKGIRTLLFA<br>LMMSLPALFNIGLLLFLVMFIYAIFGMSNFAYVKKEDGINDMFNFETFGNSMICLF<br>QITTSAGWDGLLAPILNSKPPDCDPKKVHPGSSVEGDCGNPSVGIFYFVSYIIISFLV<br>VVNMYIAVILENFSVATEESTEPLSEDDFEMFYEVWEKFDPDATQFIEFSKLSDFA<br>AALDPPLLIAKPNKVQLIAMDLPMVSGDRIHCLDILFAFTKRVLGESGEMDSLRSQ<br>MEERFMSANPSKVSYEPITTTLKRKQEDVSATVIQRAYRRYRLRQNVKNISSIYIKD<br>GDRDDDLLNKKDMAFDNVNENSSPEKTDATSSTTSPPSYDSVTKPDKEKYEQDR<br>TEKEDKGKDSKESKK |
| 76 | HUMAN Nav1.7<br>NUCLEOTIDE<br>SEQUENCE<br>(ENST00000303354) | ATGGCAATGTTGCCTCCCCCAGGACCTCAGAGCTTTGTCCATTTCACAAAACA<br>GTCTCTTGCCCTCATTGAACAACGCATTGCTGAAAGAAAATCAAAGGAACCCA<br>AAGAAGAAAAGAAAGATGATGATGAAGAAGCCCCAAAGCCAAGCAGTGACT<br>TGGAAGCTGGCAAACAGCTGCCCTTCATCTATGGGGACATTCCTCCCGGCATG<br>GTGTCAGAGCCCCTGGAGGACTTGGACCCCTACTATGCAGACAAAAAGACTTT<br>CATAGTATTGAACAAAGGGAAAACAATCTTCCGTTTCAATGCCACACCTGCTTT<br>ATATATGCTTTCTCCTTTCAGTCCTCTAAGAAGAATATCTATTAAGATTTTAGTA<br>CACTCCTTATTCAGCATGCTCATCATGTGCACTATTCTGACAAACTGCATATTT<br>ATGACCATGAATAACCCACCGGACTGGACCAAAATGTCGAGTACACTTTTAC<br>TGGAATATATACTTTTGAATCACTTGTAAAAATCCTTGCAAGAGGCTTCTGTGT<br>AGGAGAATTCACTTTTCTTCGTGACCCGTGGAACTGGCTGGATTTTGTCGTCA<br>TTGTTTTTGCGTATTTAACAGAATTTGTAAACCTAGGCAATGTTTCAGCTCTTC<br>GAACTTTCAGAGTATTGAGAGCTTTGAAAACATATTTCTGTAATCCCAGGCCTG<br>AAGACAATTGTAGGGGCTTTGATCCAGTCAGTGAAGAAGCTTTCTGATGTCAT<br>GATCCTGACTGTGTTCTGTCTGAGTGTGTTTGCACTAATTGGACTACAGCTGTT<br>CATGGGAAACCTGAAGCATAAATGTTTTCGAAATTCACTTGAAAATAATGAAA<br>CATTAGAAAGCATAATGAATACCCTAGAGAGTGAAGAAGACTTTAGAAAATA<br>TTTTTATTACTTGGAAGGATCCAAAGATGCTCTCCTTTGTGGTTTCAGCACAGA<br>TTCAGGTCAGTGTCCAGAGGGGTACACCTGTGTGAAAATTGGCAGAAACCCT<br>GATTATGGCTACACGAGCTTTGACACTTTCAGCTGGGCCTTCTTAGCCTTGTTT<br>AGGCTAATGACCCAAGATTACTGGGAAAACCTTTACCAACAGACGCTGCGTG<br>CTGCTGGCAAAACCTACATGATCTTCTTTGTCGTAGTGATTTTCCTGGGCTCCT<br>TTTATCTAATAAACTTGATCCTGGCTGTGGTTGCCATGGCATATGAAGAACAG<br>AACCAGGCAAACATTGAAGAAGCTAAACAGAAAGAATTAGAATTTCAACAGA<br>TGTTAGACCGTCTTAAAAAAGAGCAAGAAGAAGCTGAGGCAATTGCAGCGGC<br>AGCGGCTGAATATACAAGTATTAGGAGAAGCAGAATTATGGGCCTCTCAGAG<br>AGTTCTTCTGAAACATCCAAACTGAGCTCTAAAAGTGCTAAAGAAAGAAGAAC<br>AGAAGAAAGAAAAGAATCAAAAGAAGCTCTCCAGTGAGAGGAAAGGGA<br>GATGCTGAGAAATTGTCGAAATCAGAATCAGAGGACAGCATCAGAAGAAAA<br>AGTTTCCACCTTGGTGTCGAAGGGCATAGGCGAGCACATGAAAAGAGGTTGT<br>CTACCCCCAATCAGTCACCACTCAGCATTCGTGGCTCCTTGTTTTCTGCAAGGC<br>GAAGCAGCAGAACAAGTCTTTTTAGTTTCAAAGGCAGAGGAAGAGATATAGG<br>ATCTGAGACTGAATTTGCCGATGATGAGCACAGCATTTTTGGAGACAATGAG<br>AGCAGAAGGGGCTCACTGTTTGTGCCCCACAGACCCCAGGAGCGACGCAGCA<br>GTAACATCAGCCAAGCCAGTAGGTCCCCACCAATGCTGCCGGTGAACGGGAA<br>AATGCACAGTGCTGTGGACTGCAACGGTGTGGTCTCCCTGGTTGATGGACGC<br>TCAGCCCTCATGCTCCCCAATGGACAGCTTCTGCCAGAGGTGATAATAGATAA<br>GGCAACTTCTGATGACAGCGGCACGACCAATCAAATACACAAGAAAAGGCGT<br>TGTAGTTCCTATCTCCTTTCAGAGGATATGCTGAATGATCCCAACCTCAGACAG<br>AGAGCAATGAGTAGAGCAAGCATATTAACAAACACTGTGGAAGAACTTGAAG |

TABLE 10-continued

FURTHER SEQUENCES

| SEQ ID NO: | Human Allele | Nucleotide/Amino Acid Sequence |
|---|---|---|
| | | AGTCCAGACAAAAATGTCCACCTTGGTGGTACAGATTTGCACACAAATTCTTG<br>ATCTGGAATTGCTCTCCATATTGGATAAAATTCAAAAAGTGTATCTATTTTATT<br>GTAATGGATCCTTTTGTAGATCTTGCAATTACCATTTGCATAGTTTTAAACACA<br>TTATTTATGGCTATGGAACACCCACCCAATGACTGAGGAATTCAAAAATGTACT<br>GCTATAGGAAATTTGGTCTTTACTGGAATCTTTGCAGCTGAAATGGTATTAAA<br>ACTGATTGCCATGGATCCATATGAGTATTTCCAAGTAGGCTGGAATATTTTTG<br>ACAGCCTTATTGTGACTTTAAGTTTAGTGGAGCTCTTTCTAGCAGATGTGGAA<br>GGATTGTCAGTTCTGCGATCATTCAGACTGCTCCGAGTCTTCAAGTTGGCAAA<br>ATCCTGGCCAACATTGAACATGCTGATTAAGATCATTGGTAACTCAGTAGGGG<br>CTCTAGGTAACCTCACCTTAGTGTTGGCCATCATCGTCTTCATTTTTGCTGTGG<br>TCGGCATGCAGCTCTTTGGTAAGAGCTACAAAGAATGTGTCTGCAAGATCAAT<br>GATGACTGTACGCTCCCACGGTGGCACATGAACGACTTCTTCCACTCCTTCCTG<br>ATTGTGTTCCGCGTGCTGTGTGGAGAGTGGATAGAGACCATGTGGGACTGTA<br>TGGAGGTCGCTGGTCAAGCTATGTGCCTTATTGTTTACATGATGGTCATGGTC<br>ATTGGAAACCTGGTGGTCCTAAACCTATTTCTGGCCTTATTATTGAGCTCATTT<br>AGTTCAGACAATCTTACAGCAATTGAAGAAGACCCTGATGCAAACAACCTCCA<br>GATTGCAGTGACTAGAATTAAAAAGGGAATAAATTATGTGAAACAAACCTTA<br>CGTGAATTTATTCTAAAAGCATTTTCCAAAAAGCCAAAGATTTCCAGGGAGAT<br>AAGACAAGCAGAAGATCTGAATACTAAGAAGGAAAACTATATTTCTAACCAT<br>ACACTTGCTGAAATGAGCAAAGGTCACAATTTCCTCAAGGAAAAAGATAAAA<br>TCAGTGGTTTTGGAAGCAGCGTGGACAAACACTTGATGGAAGACAGTGATGG<br>TCAATCATTTATTCACAATCCCAGCCTCACAGTGACAGTGCCAATTGCACCTGG<br>GGAATCCGATTTGGAAAATATGAATGCTGAGGAACTTAGCAGTGATTCGGAT<br>AGTGAATACAGCAAAGTGAGATTAAACCGGTCAAGCTCCTCAGAGTGCAGCA<br>CAGTTGATAACCCTTTGCCTGGAGAAGGAGAAGAAGCAGAGGCTGAACCTAT<br>GAATTCCGATGAGCCAGAGGCCTGTTTCACAGATGGTTGTGTATGGAGGTTCT<br>CATGCTGCCAAGTTAACATAGAGTCAGGGAAAGGAAAAATCTGGTGGAACAT<br>CAGGAAAACCTGCTACAAGATTGTTGAACACAGTTGGTTTGAAAAGCTTCATTG<br>TCCTCATGATCCTGCTCAGCAGTGGTGCCCTGGCTTTTGAAGATATTTATATTG<br>AAAGGAAAAAGACCATTAAGATTATCCTGGAGTATGCAGACAAGATCTTCACT<br>TACATCTTCATTCTGGAAATGCTTCTAAAATGGATAGCATATGGTTATAAAACA<br>TATTTCACCAATGCCTGGTGTTGGCTGGATTTCCTAATTGTTGATGTTTCTTTG<br>GTTACTTTAGTGGCAAACACTCTTGGCTACTCAGATCTTGGCCCCATTAAATCC<br>CTTCGGACACTGAGAGCTTTAAGACCTCTAAGAGCCTTATCTAGATTTGAAGG<br>AATGAGGGTCGTTGTGAATGCACTCATAGGAGCAATTCCTTCCATCATGAATG<br>TGCTACTTGTGTGTCTTATATTCTGGCTGATATTCAGCATCATGGGAGTAAATT<br>TGTTTGCTGGCAAGTTCTATGAGTGTATTAACACCACAGATGGGTCACGGTTT<br>CCTGCAAGTCAAGTTCCAAATCGTTCCGAATGTTTTGCCCTTATGAATGTTAGT<br>CAAAATGTGCGATGGAAAAACCTGAAAGTGAACTTTGATAATGTCGGACTTG<br>GTTACCTATCTCTGCTTCAAGTTGCAACTTTTAAGGGATGGACGATTATTATGT<br>ATGCAGCAGTGGATTCTGTTAATGTAGACAAGCAGCCCAAATATGAATATAGC<br>CTCTACATGTATATTTATTTTGTCGTCTTTATCATCTTTGGGTCATTCTTCACTTT<br>GAACTTGTTCATTGGTGTCATCATAGATAATTTCAACCAACAGAAAAAGAAGC<br>TTGGAGGTCAAGACATCTTTATGACAGAAGAACAGAAGAAATACTATAATGC<br>AATGAAAAAGCTGGGGTCCAAGAAGCCACAAAAGCCAATTCCTCGACCAGGG<br>AACAAAATCCAAGGATGTATATTTGACCTAGTGACAAATCAAGCCTTTGATAT<br>TAGTATCATGGTTCTTATCTGTCTCAACATGGTAACCATGATGGTAGAAAAGG<br>AGGGTCAAAGTCAACATATGACTGAAGTTTTATATTGGATAAATGTGGTTTTT<br>ATAATCCTTTTCACTGGAGAATGTGTGCTAAAACTGATCTCCCTCAGACACTAC<br>TACTTCACTGTAGGATGGAATATTTTTGATTTTGTGGTTGTGATTATCTCCATT<br>GTAGGTATGTTTCTAGCTGATTTGATTGAAACGTATTTTGTGTCCCCTACCCTG<br>TTCCGAGTGATCCGTCTTGCCAGGATTGGCCGAATCCTACGTCTAGTCAAAGG<br>AGCAAAGGGGATCCGCACGCTGCTCTTTGCTTTGATGATGTCCCTTCCTGCGT<br>TGTTTAACATCGGCCTCCTGCTCTTCCTGGTCATGTTCATCTACGCCATCTTTGG<br>AATGTCCAACTTTGCCTATGTTAAAAAGGAAGATGGAATTAATGACATGTTCA<br>ATTTTGAGACCTTTGGCAACAGTATGATTTGCCTGTTCCAAATTACAACCTCTG<br>CTGGCTGGGATGGATTGCTAGCACCTATTCTTAACAGTAAGCCACCCGACTGT<br>GACCCAAAAAAGTTCATCCTGGAAGTTCAGTTGAAGGAGACTGTGGTAACC<br>CATCTGTTGGAATATTCTACTTTGTTAGTTATATCATCATATCCTTCCTGGTTGT<br>GGTGAACATGTACATTGCAGTCATACTGGAGAATTTTAGTGTTGCCACTGAAG<br>AAAGTACTGAACCTCTGAGTGAGGATGACTTTGAGATGTTCTATGAGGTTTGG<br>GAGAAGTTTGATCCCGATGCGACCCAGTTTATAGAGTTCTCTAAACTCTCTGA<br>TTTTGCAGCTGCCCTGGATCCTCCTCTTCTCATAGCAAAACCCAACAAAGTCCA<br>GCTCATTGCCATGGATCTGCCCATGGTTAGTGGTGACCGGATCCATTGTCTTG<br>ACATCTTATTTGCTTTTACAAAGCGTGTTTTGGGTGAGAGTGGGGAGATGGAT<br>TCTCTTCGTTCACAGATGGAAGAAAGGTTCATGTCTGCAAATCCTTCCAAAGT<br>GTCCTATGAACCCATCACAACCACACTAAAACGGAAACAAGAGGATGTGTCT<br>GCTACTGTCATTCAGCGTGCTTATAGACGTTACCGCTTAAGGCAAAATGTCAA<br>AAATATATCAAGTATATACATAAAAGATGGAGACAGAGATGATGATTTACTCA<br>ATAAAAAAGATATGGCTTTTGATAATGTTAATGAGAACTCAAGTCCAGAAAAA<br>ACAGATGCCACTTCATCCACCACCTCTCCACCTTCATATGATAGTGTAACAAAG<br>CCAGACAAAGAGAAATATGAACAAGACAGAACAGAAAAGGAAGACAAAGGG<br>AAAGACAGCAAGGAAAGCAAAAAATAG |

TABLE 11

Human IL4Ra variants distributed over several human ethnic populations & having desired total human genotype frequency (a) Amino acid variability, population distributions and frequencies:

|  |  | Human Populations | No. Individs[1] | No. Unique Pops[2] | Het Freq[3] | Hom Freq[4] (Het + Hom freq[5]) | Cum Freq[6] |
|---|---|---|---|---|---|---|---|
| Most common | 75I |  | 835 |  | 0.462 | 0.302 (0.764) | 0.533 |
| Variant | 75V | ASW, CEU, CHB, CHS, CLM, FIN, GBR, IBS, JPT, LWK, MXL, PUR, TSI, YRI | 762 | 14 | 0.462 | 0.235 (0.697) | 0.467 |
| Most common | 400E |  | 988 |  | 0.256 | 0.648 (0.904) | 0.777 |
| Variant | 400A | ASW, CEU, CHB, CHS, CLM, FIN, GBR, IBS, JPT, LWK, MXL, PUR, TSI, YRI | 384 | 14 | 0.256 | 0.095 (0.351) | 0.223 |
| Most common | 431C |  | 1077 |  | 0.176 | 0.810 (0.986) | 0.898 |
| Variant | 431R | ASW, CEU, CHB, CHS, CLM, FIN, GBR, IBS, JPT, LWK, MXL, PUR, TSI, YRI | 207 | 14 | 0.176 | 0.014 (0.19) | 0.102 |
| Most common | 503S |  | 1010 |  | 0.269 | 0.656 (0.925) | 0.79 |
| Variant | 503P | ASW, CEU, CHB, CHS, CLM, FIN, GBR, IBS, JPT, LWK, MXL, PUR, TSI, YRI | 376 | 14 | 0.269 | 0.075 (0.344) | 0.21 |
| Most common | 576Q |  | 885 |  | 0.311 | 0.499 (0.81) | 0.655 |
| Variant | 576R | ASW, CEU, CHB, CHS, CLM, FIN, GBR, IBS, JPT, LWK, MXL, PUR, TSI, YRI | 547 | 14 | 0.311 | 0.190 (0.501) | 0.345 |
| Most common | 752S |  | 1059 |  | 0.176 | 0.794 (0.97) | 0.882 |
| Variant | 752A | ASW, CEU, CHB, CHS, CLM, FIN, GBR, IBS, JPT, LWK, MXL, PUR, TSI, YRI | 225 | 14 | 0.176 | 0.030 (0.206) | 0.118 |

Table Footnotes:
[1] Number of individuals in 1000 Genomes database (20110521) found to have the allele;
[2] Number of unique human ethnic populations in 1000 Genomes database in which the allele was found to occur;
[3] Heterozygous human genotype frequency, ie, cumulative frequency of all genotypes having one occurrence of the variant allele and one occurrence of another allele (heterozygous state), eg, ac genotype in 1000 Genomes database;
[4] Homozygous human genotype frequency, ie, cumulative frequency of two occurrences of the variant allele (homozygous state), eg, cc genotype in 1000 Genomes database; and
[5] Total human genotype frequency, ie, total of heterozygous plus homozygous human genotype frequencies.
[6] Cumulative human allele frequency of all occurrences of the variant allele in 1000 Genomes database.

(b) Nucleotide Sequence Variations of Selected Alleles

| Common Allele | A | A | T | T | A | T |
|---|---|---|---|---|---|---|
| Variant Allele | | | Nucleotide Position[1] | | | |
| | 16:27344882 | 16:27362551 | 16:27362643 | 16:27362859 | 16:27363079 | 16:27363606 |
| | | | Non-Synonymous Nucleotide Variation[2] | | | |
| | G | C | C | C | G | G |
| | | | Variant ID[3] | | | |
| | rs1805010 | rs1805011 | rs1805012 | rs1805015 | rs1801275 | rs1805016 |
| | | | Corresponding Amino Acid Variation | | | |
| | 75V | 400A | 431R | 503P | 576R | 752A |

Table Footnotes:
[1] Notation is chromosome number (all positions are on human chromosome 1):coordinate number (Ensembl release 73 - September 2013, Genome assembly: GRCh37 (GCA_000001405.13), (forward strand);
[2] Nucleotide change (compared to most common allele) giving rise to an amino acid change in the variant form (compared to most common allele); and
[3] NCBI dbSNP reference number (NCBI dbSNP Build 138 released on Apr 25, 2013).

TABLE 12

Human Nav1.7 (SCN9A) variants distributed over several human ethnic populations & having desired total human genotype frequency ( TABLE 12-continued Human Nav1.7 (SCN9A) variants distributed over several human ethnic populations & having desired total human genotype frequency

| | | | | | | |
|---|---|---|---|---|---|---|
| Variant | 693X | | | | | |
| Most common | 767I | | | | | |
| Variant | 767X | | | | | |
| Most common | 830R | | | | | |
| Variant | 830X | | | | | |
| Most common | 897W | | | | | |
| Variant | 897X | | | | | |
| Most common | 1200F | | | | | |
| Variant | 1200L | | | | | |
| Most common | 1235I | | | | | |
| Variant | 1235L | | | | | |
| Most common | 1488R | | | | | |
| Variant | 1488X | | | | | |
| Most common | 1659K | | | | | |
| Variant | 1659X | | | | | |
| Most common | 1689W | | | | | |
| Variant | 1689X | | | | | |

FURTHER VARIANTS

| | | | | | | |
|---|---|---|---|---|---|---|
| Most common | 422E | | 962 | | 0.442 | 0.439 (0.881) | 0.660 |
| Variant | 422D | ASW, CEU, CHB, CHS, CLM, FIN, GBR, IBS, JPT, LWK, MXL, PUR, TSI, YRI | 613 | 14 | 0.442 | 0.119 (0.561) | 0.340 |
| Most common | 490S | | 1086 | | 0.076 | 0.918 (0.994) | 0.957 |
| Variant | 490N | ASW, CEU, CHB, CHS, CLM, FIN, GBR, IBS, JPT, LWK, MXL, PUR, TSI, YRI | 89 | 14 | 0.076 | 0.005 (0.081) | 0.043 |
| Most common | 943M | | | | | | |
| Variant | 943L | ASW, CEU, CHB, CHS, CLM, FIN, GBR, IBS, JPT, LWK, MXL, PUR, TSI, YRI | | 14 | | | |
| Most common | 1161R | | 1076 | | 0.189 | 0.797 (0.986) | 0.891 |
| Variant | 1161W | ASW, CEU, CHB, CHS, CLM, FIN, GBR, IBS, JPT, LWK, MXL, PUR, TSI, YRI | 222 | 14 | 0.189 | 0.015 (0.204) | 0.109 |
| Most common | 1919D | | 1076 | | 0.109 | 0.876 (0.985) | 0.931 |
| Variant | 1919G | ASW, CEU, CHB, CHS, CLM, FIN, GBR, IBS, JPT, LWK, MXL, PUR, TSI, YRI | 135 | 14 | 0.109 | 0.015 (0.124) | 0.069 |

Table Footnotes:
[1] Number of individuals in 1000 Genomes database (20110521) found to have the allele;
[2] Number of unique human ethnic populations in 1000 Genomes database in which the allele was found to occur;
[3] Heterozygous human genotype frequency, ie, cumulative frequency of all genotypes having one occurrence of the variant allele and one occurrence of another allele (heterozygous state), eg, ac genotype in 1000 Genomes database;
[4]Homozygous human genotype frequency, ie, cumulative frequency of two occurrences of the variant allele (homozygous state), eg, cc genotype in 1000 Genomes database; and
[5]Total human genotype frequency, ie, total of heterozygous plus homozygous human genotype frequencies.
[6]Cumulative human allele frequency of all occurrences of the variant allele in 1000 Genomes database.
[7]See J Clin Invest. 2007 Dec; 117(12): 3603-9, “Mutations in sodium-channel gene SCN9A cause a spectrum of human genetic pain disorders”, Drenth JP & Waxman SG (incorporated herein by reference); amino acid position numbering is as per this reference.
[8]X here and elsewhere indicate change to an unknown amino acid (ie, a change from the most common amino acid at that position)
Amino acid positions are as per Ensembl, unless otherwise indicated.

TABLE 12-continued Human Nav1.7 (SCN9A) variants distributed over several human ethnic populations & having desired total human genotype frequency (b) Nucleotide Sequence Variations of Selected Alleles

| | | | | | | |
|---|---|---|---|---|---|---|
| Common Allele | G | T | C | C | T | T |
| Variant Allele | Nucleotide Position[1] | | | | | |
| | 2:166242648 | 2:166198883 | 2:166286469 | 2:166272746 | 2:166288485 | 2:166277030 |
| | Non-Synonymous Nucleotide Variation[2] | | | | | |
| | A | C | T | A | C | G |
| | Variant ID[3] | | | | | |
| | rs6746030 | rs3750904 | rs58022607 | rs4369876 | rs13402180 | rs12478318 |
| | Corresponding Amino Acid Variation | | | | | |
| | 1161W | 1919G | 490N | 1002L | 422D | 943L |

Table Footnotes:

[1]Notation is chromosome number (all positions are on human chromosome 1):coordinate number (Ensembl release 73 - September 2013, Genome assembly: GRCh37 (GCA_000001405.13), (forward strand);

[2]Nucleotide change (compared to most common allele) giving rise to an amino acid change in the variant form (compared to most common allele); and

[3]NCBI dbSNP reference number (NCBI dbSNP Build 138 released on Apr 25, 2013).

Example 4

Rarer IL6R Variants

The present invention provides anti-IL6R ligands; and IL6R-binding or targeting ligands as described herein. The ligands have a variety of utilities. Some of the ligands, for instance, are useful in specific binding assays, for genotyping or phenotyping humans, affinity purification of IL6R, in particular human IL6R or its ligands and in screening assays to identify other antagonists of IL6R activity. Some of the ligands of the invention are useful for inhibiting binding of IL6R to IL6 and/or gp130, or inhibiting IL6R-mediated activities.

Anti-IL6R ligands (eg, antibodies and anti-sense RNA) have been developed based on targeting and neutralising so-called "wild-type" human IL6R, which is a commonly-occurring form (see, eg, SEQ ID NO: 78). While such therapies are useful for human patients harbouring this form of human IL6R, the inventor considered it useful to investigate the possibility of targeting rarer—but still naturally-occurring—forms of IL6R amongst human populations. In this way, the inventor arrived at insight into the natural occurrences and distributions of rarer human IL6R forms that can serve as useful targets (at the protein or nucleic acid level) for human treatment, prophylaxis and diagnosis pertinent to diseases and conditions mediated or associated with IL6R activity. This particularly provides for tailored therapies, prophylaxis and diagnosis in humans that are devoid of the common IL6R gene or protein.

The skilled person will know that SNPs or other changes that translate into amino acid variation can cause variability in activity and/or conformation of human targets to be addressed. This has spawned great interest in personalized medicine where genotyping and knowledge of protein and nucleotide variability is used to more effectively tailor medicines and diagnosis of patients. The invention, therefore, provides for tailored pharmaceuticals and testing that specifically addresses rarer IL6R polymorphic variant forms. Such forms or "alleles" (at the nucleotide level), comprise one or more changes at the nucleotide and amino acid levels from the corresponding common form nucleotide and amino acids sequences, ie, there are one or more non-synonymous changes at the nucleotide level that translate into one or more corresponding changes in the protein target in humans.

Furthermore, the inventor surprisingly realised that the rarer natural forms, although present in humans at much lower frequencies than the common form, nevertheless are represented in multiple and ethnically-diverse human populations and usually with many human examples per represented ethnic population. Thus, the inventor realised that targeting such rarer forms would provide for effective treatment, prophylaxis or diagnosis across many human ethnic populations, thereby extending the utility of the present invention.

With this realisation, the inventor realised that there is significant industrial and medical application for the invention in terms of guiding the choice of anti-IL6R ligand for administration to human patients for therapy and/or prophylaxis of IL6R-mediated or associated diseases or conditions. In this way, the patient receives drugs and ligands that are tailored to their needs—as determined by the patient's genetic or phenotypic makeup. Hand-in-hand with this, the invention provides for the genotyping and/or phenotyping of patients in connection with such treatment, thereby allowing a proper match of drug to patient. This increases the chances of medical efficacy, reduces the likelihood of inferior treatment using drugs or ligands that are not matched to the patient (eg, poor efficacy and/or side-effects) and avoids pharmaceutical mis-prescription and waste.

In developing this thinking, in this non-limiting example the present inventor decided to determine a set of human IL6R variants on the basis of the following criteria, these being criteria that the inventor realised would provide for useful medical drugs and diagnostics to tailored need in the human population. The inventor selected variants having at least 3 of the 4 following criteria:—

Naturally-occurring human IL6R variation having a cumulative human allele frequency of 35% or less;

Naturally-occurring human IL6R variation having a total human genotype frequency of about 50% or less;

Naturally-occurring human IL6R variation found in many different human ethnic populations (using the standard categorisation of the 1000 Genomes Project; see Table 14 below); and Naturally-occurring human IL6R variation found in many individuals distributed across such many different ethnic populations.

On the basis of these criteria, the inventor identified the variants listed in Table 13 below. The inventor's selection included, as a consideration, selection for nucleotide variation that produced amino acid variation in corresponding IL6R forms (ie, non-synonymous variations), as opposed to silent variations that do not alter amino acid residues in the target protein.

TABLE 13

Human IL6R variants distributed over several human ethnic populations & having desired total human genotype frequency (a) Amino acid variability, population distributions and frequencies: Exon 9

|  |  | Human Populations | No. Individs[1] | No. Unique Pops[2] | Het Freq[3] | Hom Freq[4] (Het + Hom freq[5]) | Cum Freq[6] |
|---|---|---|---|---|---|---|---|
| Most common | 358D |  |  |  | 0.383 | 0.489 (0.872) | 0.680 |
| Variant | 358A | YRI, ASW, GBR, TSI, CLM, CHB, LWK, CHS, MXL, PUR, JPT, IBS, FIN, CEU (See note 7) | 557 | 14 | 0.383 | 0.128 (0.511) | 0.320 |
| Most common | 385V |  |  |  | 0.086 | 0.904 (0.99) | 0.947 |
| Variant | 385I | LWK, ASW, YRI, PUR (see note 8) | 105 | 4 | 0.086 | 0.010 (0.096) | 0.053 |

Table Footnotes:
[1]Number of individuals in 1000 Genomes database (20110521) found to have the allele;
[2]Number of unique human ethnic populations in 1000 Genomes database in which the allele was found to occur;
[3]Heterozygous human genotype frequency, ie, cumulative frequency of all genotypes having one occurrence of the variant allele and one occurrence of another allele (heterozygous state), eg, ac genotype in 1000 Genomes database;
[4]Homozygous human genotype frequency, ie, cumulative frequency of two occurrences of the variant allele (homozygous state), eg, cc genotype in 1000 Genomes database; and
[5]Total human genotype frequency, ie, total of heterozygous plus homozygous human genotype frequencies.
[6]Cumulative human allele frequency of all occurrences of the variant allele in 1000 Genomes database.
7. According to the 1000 Genomes database version 20130502, this variant is found in the following 26 human populations (KHV, GBR, CHB, CDX, CLM, MXL, CHS, JPT, GIH, PUR, ESN, FIN, ACB, BEB, YRI, ASW, ITU, PJL, TSI, PEL, MSL, LWK, STU, GWD, IBS, CEU) and in 1218 individuals with a cumulative frequency of 0.29.
8. According to the 1000 Genomes database version 20130502, this variant is found in the following 10 human populations (ASW, YRI, PEL, MSL, LWK, GWD, PUR, IBS, ESN, ACB) and in 267 individuals with a cumulative frequency of 0.06.

(b) Nucleotide Sequence Variations of Selected Alleles

| Common Allele | A | G |
|---|---|---|
| Variant Allele | Nucleotide Position[1] | |
|  | 1:154426970 | 1:154427050 |
|  | Non-Synonymous Nucleotide Variation[2] | |
|  | C | A |
|  | Variant ID[3] | |
|  | rs2228145 | rs28730736 |
|  | Corresponding Amino Acid Variation | |
|  | 358A | 385I |

Table Footnotes:
[1]Notation is chromosome number (all positions are on human chromosome 1):coordinate number (Ensembl release 73 - September 2013, Genome assembly: GRCh37 (GCA_000001405.13);
[2]Nucleotide change (compared to most common allele) giving rise to an amino acid change in the variant form (compared to most common allele); and
[3]NCBI dbSNP reference number (NCBI dbSNP Build 138 released on Apr 25, 2013).

Example 5

Tailoring Antibodies to Rarer IL6R Variant Profile

As outlined above, the invention includes the possibility to tailor treatment of humans further by selecting antibody-based ligands with variable and/or constant domains based on gene segments found in many humans of the ethnic populations where the variant IL6R forms are found to meet the selection criteria of the invention. An example is provided for ligands comprising antibody VH domains derived from recombination of human IGHV gene segments comprising selected nucleotides at positions in the HCDR1 or FW3 where there is variability in humans (ie, where SNPs occur in humans).

The inventor analysed human IGHV variation and used this to choose ligands based on human IGHV alleles comprising said selected nucleotides and for matching to human recipient genotypes and/or phenotypes. The inventor identified utility in using gene VH gene segments encoding (i) a CDR1 comprising a Phe at position 4 shown in SEQ ID NO: 109 and wherein said human comprises a VH gene segment encoding a CDR1 comprising a Phe at position 4 shown in SEQ ID NO: 109, or the human expresses VH domains that comprise a CDR1 comprising a Phe at position 4 shown in SEQ ID NO: 109; or (ii) a FW3 comprising a Thr at position 33 shown in SEQ ID NO: 111 and wherein said human comprises a VH gene segment encoding a FW3 comprising a Thr at position 33 shown in SEQ ID NO: 111 or the human expresses VH domains that comprise a FW3 comprising a Thr at position 33 shown in SEQ ID NO: 111. Further information is provided in Table 14, which shows variation at these positions, as well as the variant distributions across the 1000 Genomes Project database relating to many human populations.

In other embodiments, as explained more fully above, the invention provides for ligands which are tailored to the human recipient's genotype and/or phenotype based on alternative human VH gene segments, or on Vκ, Vλ or constant region gene segments (see further Table 16 for representative variants).

In an example, following this guidance, the chosen ligand can be sarilumab.

Further examples, therefore are:—
(i) wherein the ligand comprises a VH domain derived from the recombination of human VH segment IGHV3-7*01, a human D gene segment and a human JH segment, and wherein said human comprises a IGHV3-7*01 VH gene segment or the human expresses VH domains derived from the recombination of human VH segment IGHV3-7*01, a human D gene segment and a human JH segment.
(ii) wherein the ligand comprises a Vκ domain derived from the recombination of human Vκ segment IGKV1-12*01 and a human Jκ segment, and wherein said human comprises a IGKV1-12*01 Vκ gene segment or the human expresses Vκ domains derived from the recombination of human Vκ segment IGKV1-12*01 and a human Jκ segment.
(iii) wherein the ligand comprises a Vκ domain derived from the recombination of a human Vκ segment and a human Jκ segment, the human Vκ segment encoding (i) a CDR3 comprising a Pro at position 7 shown in SEQ ID NO: 113 and wherein said human comprises a Vκ gene segment encoding a CDR3 comprising a Pro at position 7 shown in SEQ ID NO: 113, or the human expresses Vκ domains that comprise a CDR3 comprising a Pro at position 7 shown in SEQ ID NO: 113; or (ii) a FW3 comprising a Ser at position 15 shown in SEQ ID NO: 115 and wherein said human comprises a Vκ gene segment encoding a FW3 comprising a Ser at position 15 shown in SEQ ID NO: 115 or the human expresses Vκ domains that comprise a FW3 comprising a Ser at position 15 shown in SEQ ID NO: 115.
(iv) wherein the ligand comprises a human gamma-1 heavy chain constant region that comprises an Asp at position 204 shown in SEQ ID NO: 81 or a Leu at position 206 shown in SEQ ID NO: 81 and wherein said human comprises (i) an IGHG1*01 human heavy chain constant region gene segment, or the human expresses antibodies comprising human gamma-1 heavy chain constant regions comprising an Asp at position 204 shown in SEQ ID NO: 81 or a Leu at position 206 shown in SEQ ID NO: 81.
(v) wherein the ligand comprises a human gamma-2 heavy chain constant region that comprises an amino acid selected from the group consisting of a Pro at position 72 shown in SEQ ID NO: 83, an Asn at position 75 shown in SEQ ID NO: 83, a Phe at position 76 shown in SEQ ID NO: 83, a Val at position 161 shown in SEQ ID NO: 83 and an Ala at position 257 shown in SEQ ID NO: 83 and wherein said human comprises (i) an IGHG2*01 human heavy chain constant region gene segment, or the human expresses antibodies comprising human gamma-2 heavy chain constant regions comprising said selected Pro at position 72 shown in SEQ ID NO: 83, Asn at position 75 shown in SEQ ID NO: 83, Phe at position 76 shown in SEQ ID NO: 83, Val at position 161 shown in SEQ ID NO: 83 or Ala at position 257 shown in SEQ ID NO: 83.
(vi) wherein the ligand comprises a human kappa chain constant region that comprises a Val at position 84 shown in SEQ ID NO: 93 or a Cys at position 87 shown in SEQ ID NO: 93 and wherein said human comprises (i) an IGKC1*01 human heavy chain constant region gene segment, or the human expresses antibodies comprising human kappa chain constant regions comprising a Val corresponding to position 84 shown in SEQ ID NO: 93 or a Cys at position 87 shown in SEQ ID NO: 93 and (ii) a nucleotide sequence encoding said IL6R protein comprising said Asp358Ala or Val385Ile in SEQ ID NO: 78.
(vii) wherein the ligand comprises a human IGLC1*01 lambda chain constant region and wherein said human comprises (i) a human IGLC1*01 lambda chain constant region gene segment, or the human expresses antibodies comprising human IGLC1*01 lambda chain constant regions.

For example, as per example (iv), the inventor identified the possibility of addressing the rarer IGH-gamma-1 SNPs 204D (observed cumulative frequency of 0.296) and 206L (observed cumulative frequency of 0.283) individually or in combination. These residues are part of the CH3 domain, and as such they form part of antibody Fc regions. Thus, matching of these CH3 variations with the patient is especially beneficial for reasons as discussed above. Thus, in this example the ligand of the invention comprises or consists of an antibody that comprises a human gamma-1 heavy chain constant region that comprises an Asp corresponding to position 204 of SEQ ID NO: 81 or a Leu corresponding to position 206 of SEQ ID NO: 81 and wherein the genome of the human comprises a gamma-1 heavy chain constant region nucleotide sequence that encodes such an Asp or Leu or the human expresses antibodies comprising human gamma-1 constant regions comprising such an Asp or Leu. An example of such a ligand is sarilumab.

In another example, as per example (v), the inventor identified the possibility of addressing IGH-gamma-2 SNPs. This included consideration of Fc region variation—in this respect, the inventor focused on positions 161 and 257 which are in the Fc region. Thus, in this example the ligand of the invention comprises or consists of an antibody that comprises a human gamma-2 heavy chain constant region that comprises an amino acid selected from the group consisting of a Pro corresponding to position 72 of SEQ ID NO: 83, an Asn corresponding to position 75 of SEQ ID NO: 83, a Phe corresponding to position 76 of SEQ ID NO: 83, a Val corresponding to position 161 of SEQ ID NO: 83 and an Ala corresponding to position 257 of SEQ ID NO: 83; and wherein the genome of the human comprises a gamma-2 heavy chain constant region nucleotide sequence that encodes such a selected amino acid or the human expresses antibodies comprising human gamma-2 constant regions comprising such a selected amino acid.

In another example, as per example (vi), the inventor addressed human kappa constant region variation. Thus, in this example the ligand of the invention comprises or consists of an antibody that comprises a human kappa light chain constant region that comprises a Val corresponding to position 84 of SEQ ID NO: 93 or a Cys corresponding to position 87 of SEQ ID NO: 93; and wherein the genome of the human comprises a kappa light chain constant region nucleotide sequence that encodes such a Val or Cys or the human expresses antibodies comprising human kappa light chain constant regions comprising such a Val or Cys. An example of such a ligand is sarilumab.

In another example, as per example (vii), the inventor addressed human lambda constant region variation. Thus, in this example the ligand of the invention comprises or consists of an antibody that comprises a human IGLC2*01 light chain constant region; and wherein the genome of the human comprises a human IGLC2*01 nucleotide sequence or the human expresses antibodies comprising human light chain IGLC2*01 constant regions.

Example 5

Determination of Specific Binding of Ligands of the Invention to IL6R Variants

The specific binding of ligands of the invention to IL6R variants can be performed using the following method.
Method of SPR Determination of Binding
Binding of the antibodies to the IL6R variants is carried out by SPR using the ProteOn XPR36™ Array system (BioRad). An anti-human IgG surface (Jackson Labs 109-005-008) was created on a GLC Biosensor chip by primary amine coupling. Test antibodies are captured on this surface as ligands. The IL6R variants are used as analytes and passed over the captured antibodies at 256 nM, 64 nM, 16 nM, 4 nM and 1 nM. Binding curves are double referenced using a buffer injection (i.e. 0 nM) to remove baseline drift and injection artefacts. Regeneration of the capture surface is with 100 mM phosphoric acid which removes the captured antibody allowing another cycle of capture and binding. The binding sensorgrams generated are analysed using the 1:1 model inherent to the ProteOn XPR36 Array system analysis software. The assay is performed at 25° C. and using 1×HBS-EP (Teknova) as running buffer.

REFERENCES

The references cited herein are incorporated by reference in their entirety
1. Ferreira et al (PLoS Genet. 2013 April; 9 (4):e1003444. doi: 10.1371/journal.pgen.1003444. Epub 2013 Apr. 4, "Functional IL6R 358Ala allele impairs classical IL-6 receptor signaling [sic] and influences risk of diverse inflammatory diseases";
2. Rantala A et al, Hum Immunol. 2011 January; 72 (1):63-8. doi: 10.1016/j.humimm.2010.10.010. Epub 2010 Oct. 15, "Association of IL-6 and IL-6R gene polymorphisms with susceptibility to respiratory tract infections in young Finnish men";
3. Zhang H Y et al, Oral Dis. 2014 January; 20 (1):69-75. doi: 10.1111/odi.12075. Epub 2013 Feb. 24, "The association of IL-6 and IL-6R gene polymorphisms with chronic periodontitis in a Chinese population";
4. J C Galicia et al, Genes and Immunity (2004) 5, 513-516. doi:10.1038/sj.gene.6364120 Published online 12 Aug. 2004, "Polymorphisms in the IL-6 receptor (IL-6R) gene: strong evidence that serum levels of soluble IL-6R are genetically influenced";
5. Esparza-Gordillo J et al, J Allergy Clin Immunol. 2013 August; 132 (2):371-7. doi: 10.1016/j.jaci.2013.01.057. Epub 2013 Apr. 9, "A functional IL-6 receptor (IL6R) variant is a risk factor for persistent atopic dermatitis".

TABLE 14

1000 GENOMES PROJECT HUMAN POPULATIONS
Below is a summary of the ethnic populations as per the
1000 Genomes Project sequences.

(a) 100 Genome Populations

| Population Code | Population Description | Super Population Code |
|---|---|---|
| CHB | Han Chinese in Bejing, China | ASN |
| JPT | Japanese in Tokyo, Japan | ASN |
| CHS | Southern Han Chinese | ASN |
| CDX | Chinese Dai in Xishuangbanna, China | ASN |
| KHV | Kinh in Ho Chi Minh City, Vietnam | ASN |
| CEU | Utah Residents (CEPH) with Northern and Western European ancestry | EUR |
| TSI | Toscani in Italia | EUR |
| FIN | Finnish in Finland | EUR |
| GBR | British in England and Scotland | EUR |
| IBS | Iberian population in Spain | EUR |
| YRI | Yoruba in Ibadan, Nigera | AFR |
| LWK | Luhya in Webuye, Kenya | AFR |
| GWD | Gambian in Western Divisons in The Gambia | AFR |
| MSL | Mende in Sierra Leone | AFR |
| ESN | Esan in Nigera | AFR |
| ASW | Americans of African Ancestry in SW USA | AFR |
| ACB | African Carribbeans in Barbados | AFR |
| MXL | Mexican Ancestry from Los Angeles USA | AMR |
| PUR | Puerto Ricans from Puerto Rico | AMR |
| CLM | Colombians from Medellin, Colombia | AMR |
| PEL | Peruvians from Lima, Peru | AMR |
| GIH | Gujarati Indian from Houston, Texas | SAN |
| PJL | Punjabi from Lahore, Pakistan | SAN |
| BEB | Bengali from Bangladesh | SAN |
| STU | Sri Lankan Tamil from the UK | SAN |
| ITU | Indian Telugu from the UK | SAN |

(b) Super Populations

AFR, African
AMR, Ad Mixed American
ASN, East Asian
EUR, European
SAN, South Asian (c) Population Ancestries
European ancestry Utah residents (CEPH) with Northern and
Western European ancestry (CEU)
Toscani in Italia (TSI)
British from England and Scotland (GBR)
Finnish from Finland (FIN)
Iberian populations in Spain (IBS)

East Asian ancestry

Han Chinese in Beijing, China (CHB)
Japanese in Toyko, Japan (JPT)

TABLE 14-continued

1000 GENOMES PROJECT HUMAN POPULATIONS
Below is a summary of the ethnic populations as per the 1000 Genomes Project sequences.

Han Chinese South (CHS)
Chinese Dai in Xishuangbanna (CDX)
Kinh in Ho Chi Minh City, Vietnam (KHV)
Chinese in Denver, Colorado (CHD) (pilot 3 only)

West African ancestry

Yoruba in Ibadan, Nigeria (YRI)
Luhya in Webuye, Kenya (LWK)
Gambian in Western Division, The Gambia (GWD)
Malawian in Blantyre, Malawi (MAB)
West African Population (TBD)

Americas

African Ancestry in Southwest US (ASW)
African American in Jackson, MS (AJM)
African Caribbean in Barbados (ACB)
Mexican Ancestry in Los Angeles, CA (MXL)
Puerto Rican in Puerto Rico (PUR)
Colombian in Medellin, Colombia (CLM)
Peruvian in Lima, Peru (PEL)

South Asian ancestry

Ahom in the State of Assam, India
Kayadtha in Calcutta, India
Reddy in Hyderabad, India
Maratha in Bombay, India
Punjabi in Lahore, Pakistan

TABLE 15

Exemplary anti-IL6R disclosures, eg of antibodies and/or antibody fragments, assays, treatments, formulations, kits, methods and indications, useful in any and all aspects of the invention Patent or patent application which is incorporated by reference in its entirety, and specifically, eg, with respect to the SEQ ID Nos. comprising an anti-IL6R monoclonal antibody or fragment thereof U.S. Pat. No. 8,568,721,
US20130157313A1,
US20130149310A1,
US20130122003A1,
U.S. Pat. No. 8,192,741,
U.S. Pat. No. 8,183,014,
US20120003697A1,
U.S. Pat. No. 8,080,248,
U.S. Pat. No. 8,043,617,
US20110171241A1,
US20100316636A1,
US20100316627A1,
U.S. Pat. No. 7,582,298

TABLE 16

Human antibody gene segment variants distributed over several human ethnic populations - useful for ligand tailoring

| Example Human Gene Segment Type | Example Human Allele[1] | Amino Acid Coordinate[2] & Variation | Nucleotide Variation[3] (NCBI dbSNP reference number)[4] | Variant Nucleotide Position | Human Populations[5] | No. Individs[6] | Het Freq[7] | Hom Freq[8] (Het + Hom freq[9]) | Cum Freq[10] |
|---|---|---|---|---|---|---|---|---|---|
| IGHV3-9 | IGHV3-9*01 | 30F (IMGT numbering) (Phe at position 4 in SEQ ID NO: 32) (CDR1 variation) | TTT | | | | | | |
| | IGHV3-9*02 | 30S (IMGT numbering) (CDR1 variation) | TCT | | | | | | |
| | IGHV3-9*01 | 110T (Thr at position 33 in SEQ ID NO: 34) (FW3 variation) | ACG | 14:106552310 (forward strand) | B | 1015 | 0.082 | 0.847 (0.929) | 0.888 |
| | IGHV3-9*03 | 110M (FW3 variation) | ATG (rs8020204) | 14:106552310 (forward strand) | B | 167 | 0.082 | 0.071 (0.153) | 0.112 |
| IGKV3-11 | IGKV3-11*01 | 115P (Pro at position 7 in SEQ ID NO: 36) (CDR3 variation) | CCT | 2:89326669 (forward strand) | B | 1090 | 0.064 | 0.934 (0.998) | 0.966 |
| | | 115H (CDR3 variation) | CAT (rs182958807) | 2:89326669 (forward strand) | B | 72 | 0.064 | 0.002 (0.066) | 0.034 |
| | IGKV3-11*01 | 87S (Ser at position 15 in SEQ ID NO: 38) (FW3 variation) | TCT | 2:89326754 (forward strand) | B | 1090 | 0.074 | 0.924 (0.998) | 0.961 |
| | | 87P (FW3 variation) | CCT (rs191612627) | 2:89326754 (forward strand) | B | 83 | 0.074 | 0.002 (0.076) | 0.039 |
| IGKC | IGKC*01 | 84V (Val at position 84 in SEQ ID NO: 16) | GTC | 2:89156948 (forward strand) | B | 454 | 0.345 | 0.071 (0.416) | 0.243 |
| | IGKC*04 | 84L | CTC (rs232230) | 2:89156948 (forward strand) | B | 1015 | 0.345 | 0.584 (0.929) | 0.757 |
| | IGKC*01 | 87C (Cys at position 87 in SEQ ID NO: 16) | TGC | 2:89156939 (forward strand) | | | | | |

TABLE 16-continued

Human antibody gene segment variants distributed over several human ethnic populations - useful for ligand tailoring

| Example Human Gene Segment Type | Example Human Allele[1] | Amino Acid Coordinate[2] & Variation | Nucleotide Variation[3] (NCBI dbSNP reference number)[4] | Variant Nucleotide Position | Human Populations[5] | No. Individs[6] | Het Freq[7] | Hom Freq[8] (Het + Hom freq[9]) | Cum Freq[10] |
|---|---|---|---|---|---|---|---|---|---|
| | IGKC*02 | 87G | G̲GC (rs200765148) | 2:89156939 (forward strand) | | | | | |
| IGHG1 | IGHG1*01 | 204D (CH3 variation) | GAT̲ | 14:106208086 (forward strand) | A (European ancestry) | 153 | 0.400 | 0.096 (0.496) | 0.296 |
| | IGHG1*03 | 204E (CH3 variation) | GAG̲ (rs1045853) | 14:106208086 (forward strand) | A (European ancestry) | 366 | 0.400 | 0.504 (0.904) | 0.704 |
| | IGHG1*01 | 206L (CH3 variation) | C̲TG | 14:106208082 (forward strand) | A (European ancestry) | | 0.358 | 0.104 (0.462) | 0.283 |
| | IGHG1*03 | 206M (CH3 variation) | A̲TG (rs11621259) | 14:106208082 (forward strand) | A (European ancestry) | | 0.358 | 0.538 (0.896) | 0.717 |
| IGHG2 | IGHG2*01 | 72P (CH1 variation) | C̲CC | 14:106110914 (forward strand) | B | | 0.336 | 0.540 (0.876) | 0.708 |
| | IGHG2*02 | 72T (CH1 variation) | A̲CC (rs11627594) | 14:106110914 (forward strand) | B | | 0.336 | 0.124 | 0.292 |
| | IGHG2*01 | 75N (CH1 variation) | AA̲C | 14:106110904 (forward strand) | A | | 0.007 | 0.993 | 0.997 |
| | IGHG2*04 | 75S (CH1 variation) | AG̲C (rs201590297) | 14:106110904 (forward strand) | A | | 0.007 | | 0.004 |
| | IGHG2*01 | 76F (CH1 variation) | TTC̲ | | | | | | |
| | IGHG2*04 | 76L (CH1 variation) | TTG̲ | | | | | | |
| | IGHG2*01 | 161V (CH2 variation) | G̲TG | 14:10611013 (forward strand) | B | | 0.342 | 0.539 (0.881) | 0.711 |
| | IGHG2*02 | 161M (CH2 variation) | A̲TG (rs8009156) | 14:10611013 (forward strand) | B | | 0.342 | 0.118 (0.46) | 0.289 |
| | IGHG2*01 | 257A (CH3 variation) | G̲CC | 14:106109752 (forward strand) | C | | 0.199 | 0.493 (0.692) | 0.592 |
| | | | | | D | | 0.007 | 0.992 (0.999) | 0.995 |
| | IGHG2*06 | 257S (CH3 variation) | T̲CC (rs4983499) | 14:106109752 (forward strand) | C | | 0.199 | 0.308 (0.507) | 0.408 |
| | | | | | D | | 0.007 | 0.002 (0.009) | 0.005 |

Table Footnotes:
[10]IMGT notation (ww.imgt.org); refer to figures for other alleles comprising this variation.
11. Numbering as indicated in Ensembl (available on the World Wide Web at ensembl.org) unless otherwise indicated
12. SNP Underlined in Codon.
13. NCBI dbSNP Build 138 released on Apr 25, 2013.
14. Human population used for representative variant frequency analysis.
Populations
A   This population included 662 participants of European descent from the ClinSeq project, all of whom had undergone whole-exome sequencing using Agilent's 38 Mb or 50 Mb capture kit.
B   1000 Genomes database.
C   ESP6500: African_American.
D   ESP6500: European_American.
15. Number of individuals in representative population found to have the allele.
16. Heterozygous human genotype frequency, ie, cumulative frequency of all genotypes having one occurrence of the variant allele and one occurrence of another allele (heterozygous state), eg, ac genotype in the population.
17. Homozygous human genotype frequency, ie, cumulative frequency of two occurrences of the variant allele (homozygous state), eg, cc genotype in the population.
18. Total human genotype frequency, ie, total of heterozygous plus homozygous human genotype frequencies.
19. Cumulative human allele frequency of all occurrences of the variant allele in the population.

TABLE 17

SEQUENCES

| SEQ ID NO: | Human Allele | Nucleotide/Amino Acid Sequence |
|---|---|---|
| 78 | IL-6R | MLAVGCALLAALLAAPGAALAPRRCPAQEVARGVLTSLPGDSVTLTCPGVEPED NATVHWVLRKPAAGSHPSRWAGMGRRLLLRSVQLHDSGNYSCYRAGRPAGTVHL |

TABLE 17-continued

SEQUENCES

| SEQ ID NO: | Human Allele | Nucleotide/Amino Acid Sequence |
|---|---|---|
| | | LVDVPPEEPQLSCFRKSPLSNVVCEWGPRSTPSLTTKAVLLVRKFQNSPAEDFQ<br>EPCQYSQESQKFSCQLAVPEGDSSFYIVSMCVASSVGSKFSKTQTFQGCGILQP<br>DPPANITVTAVARNPRWLSVTWQDPHSWNSSFYRLRFELRYRAERSKTFTTWMV<br>KDLQHHCVIHDAWSGLRHVVQLRAQEEFGQGEWSEWSPEAMGTPWTESRSPPAE<br>NEVSTPMQALTTNKDDDNILFRDSANATSLPVQ<u>D</u>SSSVPLPTFLVAGGSLAFGT<br>LLCIAI<u>V</u>LRFKKTWKLRALKEGKTSMHPPYSLGQLVPERPRPTPVLVPLISPPV<br>SPSSLGSDNTSSHNRPDARDPRSPYDISNTDYFFPR<br><u>D</u> = position 358<br><u>V</u> = position 385 |
| 79 | | ATGCTGGCCGTCGGCTGCGCGCTGCTGGCTGCCCTGCTGGCCGCGCCGGGAGCG<br>GCGCTGGCCCCAAGGC<br>GCTGCCCTGCGCAGGAGGTGGCGAGAGGCGTGCTGACCAGTCTGCCAGGAGACA<br>GCGTGACTCTGACCTG<br>CCCGGGGGTAGAGCCGGAAGACAATGCCACTGTTCACTGGGTGCTCAGGAAGCC<br>GGCTGCAGGCTCCCAC<br>CCCAGCAGATGGGCTGGCATGGGAAGGAGGCTGCTGCTGAGGTCGGTGCAGCTC<br>CACGACTCTGGAAACT<br>ATTCATGCTACCGGGCCGGCCGCCCAGCTGGGACTGTGCACTTGCTGGTGGATG<br>TTCCCCCCGAGGAGCC<br>CCAGCTCTCCTGCTTCCGGAAGAGCCCCCTCAGCAATGTTGTTTGTGAGTGGGG<br>TCCTCGGAGCACCCCA<br>TCCCTGACGACAAAGGCTGTGCTCTTGGTGAGGAAGTTTCAGAACAGTCCGGCC<br>GAAGACTTCCAGGAGC<br>CGTGCCAGTATTCCCAGGAGTCCCAGAAGTTCTCCTGCCAGTTAGCAGTCCCGG<br>AGGGAGACAGCTCTTT<br>CTACATAGTGTCCATGTGCGTCGCCAGTAGTGTCGGGAGCAAGTTCAGCAAAAC<br>TCAAACCTTTCAGGGT<br>TGTGGAATCTTGCAGCCTGATCCGCCTGCCAACATCACAGTCACTGCCGTGGCC<br>AGAAACCCCCGCTGGC<br>TCAGTGTCACCTGGCAAGACCCCCACTCCTGGAACTCATCTTTCTACAGACTAC<br>GGTTTGAGCTCAGATA<br>TCGGGCTGAACGGTCAAAGACATTCACAACATGGATGGTCAAGGACCTCCAGCA<br>TCACTGTGTCATCCAC<br>GACGCCTGGAGCGGCCTGAGGCACGTGGTGCAGCTTCGTGCCCAGGAGGAGTTC<br>GGGCAAGGCGAGTGGA<br>GCGAGTGGAGCCCGGAGGCCATGGGCACGCCTTGGACAGAATCCAGGAGTCCTC<br>CAGCTGAGAACGAGGT<br>GTCCACCCCCATGCAGGCACTTACTACTAATAAAGACGATGATAATATTCTCTT<br>CAGAGATTCTGCAAAT<br>GCGACAAGCCTCCCAGTGCAAGATTCTTCTTCAGTACCACTGCCCACATTCCTG<br>GTTGCTGGAGGGAGCC<br>TGGCCTTCGGAACGCTCCTCTGCATTGCCATTGTTCTGAGGTTCAAGAAGACGT<br>GGAAGCTGCGGGCTCT<br>GAAGGAAGGCAAGACAAGCATGCATCCGCCGTACTCTTTGGGGCAGCTGGTCCC<br>GGAGAGGCCTCGACCC<br>ACCCCAGTGCTTGTTCCTCTCATCTCCCCACCGGTGTCCCCCAGCAGCCTGGGG<br>TCTGACAATACCTCGA<br>GCCACAACCGACCAGATGCCAGGGACCCACGGAGCCCTTATGACATCAGCAATA<br>CAGACTACTTCTTCCC<br>CAGATAG |

HEAVY CHAIN ALLELES

| | | |
|---|---|---|
| 80 | IGHG1*01<br>(CH1 + Hinge +<br>CH2 + CH3 +<br>CH – S) | gcctccaccaagggcccatcggtcttccccctggcaccctcctccaagagcacctctggg<br>ggcacagcggccctgggctgcctggtcaaggactacttccccgaaccggtgacggtgtcg<br>tggaactcaggcgccctgaccagcggcgtgcacaccttcccggctgtcctacagtcctca<br>ggactctactccctcagcagcgtggtgaccgtgccctccagcagcttgggcacccagacc<br>tacatctgcaacgtgaatcacaagcccagcaacaccaaggtggacaagaaagttgagccc<br>aaatcttgtgacaaaactcacacatgcccaccgtgcccagcacctgaactcctggggggga<br>ccgtcagtcttcctcttccccccaaaacccaaggacaccctcatgatctcccggacccct<br>gaggtcacatgcgtggtggtggacgtgagccacgaagaccctgaggtcaagttcaactgg<br>tacgtggacggcgtggaggtgcataatgccaagacaaagccgcgggaggagcagtacaac<br>agcacgtaccgggtggtcagcgtcctcaccgtcctgcaccaggactggctgaatggcaag<br>gagtacaagtgcaaggtctccaacaaagcccctcccagccccatcgagaaaaccatctcc<br>aaagccaaagggcagccccgagaaccacaggtgtacaccctgcccccatcccgggatgag<br>ctgaccaagaaccaggtcagcctgacctgcctggtcaaaggcttctatcccagcgacatc<br>gccgtggagtgggagagcaatgggcagccggagaacaactacaagaccacgcctcccgtg<br>ctggactccgacggctccttcttcctctacagcaagctcaccgtggacaagagcaggtgg<br>cagcaggggaacgtcttctcatgctccgtgatgcatgaggctctgcacaaccactacacg<br>cagaagagcctctccctgtctccgggtaaa |
| 81 | | ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVHNAKTKPREEQYN |

TABLE 17-continued

SEQUENCES

| SEQ ID NO: | Human Allele | Nucleotide/Amino Acid Sequence |
|---|---|---|
| | | STYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK<br>D = position 204<br>L = position 206 |
| 82 | IGHG2*01<br>(CH1 + Hinge + CH2 + CH3 + CH - S) | gcctccaccaagggcccatcggtcttccccctggcgccctgctccaggagcacctccgagagcacagccgccctgggctgcctggtcaaggactacttccccgaaccggtgacggtgtcgtggaactcaggcgctctgaccagcggcgtgcacaccttcccagctgtcctacagtcctcaggactctactccctcagcagcgtggtgaccgtgccctccagcaacttcggcacccagacctacacctgcaacgtagatcacaagcccagcaacaccaaggtggacaagacagttgagcgcaaatgttgtgtcgagtgcccaccgtgcccagcaccacctgtggcaggaccgtcagtcttcctcttccccccaaaacccaaggacaccctcatgatctcccggacccctgaggtcacgtgcgtggtggtggacgtgagccacgaagaccccgaggtccagttcaactggtacgtggacggcgtggaggtgcataatgccaagacaaagccacgggaggagcagttcaacagcacgttccgtgtggtcagcgtcctcaccgttgtgcaccaggactggctgaacggcaaggagtacaagtgcaaggtctccaacaaaggcctcccagcccccatcgagaaaaccatctccaaaaccaaagggcagccccgagaaccacaggtgtacaccctgcccccatcccgggaggagatgaccaagaaccaggtcagcctgacctgcctggtcaaaggcttctaccccagcgacatcgccgtggagtgggagagcaatgggcagccggagaacaactacaagaccacacctcccatgctggactccgacggctccttcttcctctacagcaagctcaccgtggacaagagcaggtggcagcaggggaacgtcttctcatgctccgtgatgcatgaggctctgcacaaccactacacgcagaagagcctctccctgtctccgggtaaa |
| 83 | | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK<br>P = position 72<br>N = position 75<br>F = position 76<br>V = position 161<br>A = position 257 |
| 84 | IGHV3-9*01 | gaagtgcagctggtggagtctggggga ggcttggtacagcctggcaggtccctgagactctcctgtgcagcctctggattcacctttgatgattatgccatgcactgggtccggcaagctccagggaagggcctggagtgggtctcaggtattagtggaatagtggtagcataggctatgcggactctgtgaagggccgattcaccatctccagagacaacgccaagaactccctgtatctgcaaatgaacagtctgagagctgaggacacggccttgtattactgtgcaaaagata<br>t = nucleotide number 86<br>c = nucleotide number 272 |
| 85 | | EVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKD<br>F = position 30 (IMGT nomenclature)<br>T = position 110 (dbSNP nomenclature) |
| 86 | IGHV3-7*01 | gaggtgcagctggtggagtctggggga ggcttggtccagcctgggggggtccctgagactctcctgtgcagcctctggattcaccttt agtagctattggatgagctgggtccgccaggctccagggaaggggctggagtgggtggccaacataaagcaagatggaagtgagaaatactatgtggactctgtgaagggccgattcaccatctccagagacaacgccaagaactcactgtatctgcaaatgaacagcctgagagccgaggacacggctgtgtattactgtgcgagaga |
| 87 | | EVQLVESGGGLVQPGGSLRLSCAASGFTFSSYWMSWVRQAPGKGLEWVANIKQDGSEKYYVDSVKGRFTISRDNAKNSLYLQMNSLRAEDTAVYYCAR |
| 88 | IGHJ3*02 | T GAT GCT TTT GAT ATC TGG GGC CAA GGG ACA ATG GTC ACC GTC TCT TCA G |
| 89 | | D A F D I W G Q G T M V T V S S |
| 90 | IGHJ6*01 | AT TAC TAC TAC TAC TAC GGT ATG GAC GTC TGG GGG CAA GGG ACC ACG GTC ACC GTC TCC TCA G |
| 91 | | Y Y Y Y Y G M D V W G Q G T T V T V S S |

TABLE 17-continued

| SEQUENCES | | |
|---|---|---|
| SEQ ID NO: | Human Allele | Nucleotide/Amino Acid Sequence |

LIGHT CHAIN ALLELES

| | | |
|---|---|---|
| 92 | IGKC*01 | cgaactgtggctgcaccatctgtcttcatcttcccgccatctgatgagcagttgaaatct ggaactgcctctgttgtgtgcctgctgaataacttctatcccagagaggccaaagtacag tggaaggtggataacgccctccaatcgggtaactcccaggagagtgtcacagagcaggac agcaaggacagcacctacagcctcagcagcaccctgacgctgagcaaagcagactacgag aaacacaaagtctacgcctgcgaagtcacccatcagggcctgagctcgcccgtcacaaag agcttcaacaggggagagtgt |
| 93 | | RTVAAPSVFIFPPSDEQLKSGTASVVCLLNNFYPREAKVQWKVDNALQSGNSQESVTEQD SKDSTYSLSSTLTLSKADYEKHK<u>V</u>YA<u>C</u>EVTHQGLSSPVTKSFNRGEC <u>V</u> = position 84 <u>C</u> = position 87 |
| 94 | IGLC1*01 | cccaaggccaaccccacggtcactctgttcccgccctcctctgaggagctccaagccaac aaggccacactagtgtgtctgatcagtgacttctacccgggagctgtgacagtggcttgg aaggcagatggcagccccgtcaaggcgggagtggagaccaccaaaccctccaaacagagc aacaacaagtacgcggccagcagctacctgagcctgacgcccgagcagtggaagtcccac agaagctacagctgccaggtcacgcatgaagggagcaccgtggagaagacagtggccccta cagaatgttca |
| 95 | | PKANPTVTLFPPSSEELQANKATLVCLISDFYPGAVTVAWKADGSPVKAGVETT KPSKQSNNKYAASSYLSLTPEQWKSHRSYSCQVTHEGSTVEKTVAPTECS |
| 96 | IGKV1-12*01 | gacatccagatgacccagtctccatcttccgtgtctgcatctgtaggagacagagtcacc atcacttgtcgggcgagtcagggtattagcagctggttagcctggtatcagcagaaacca gggaaagcccctaagctcctgatctatgctgcatccagtttgcaaagtggggtcccatca aggttcagcggcagtggatctgggacagatttcactctcaccatcagcagcctgcagcct gaagattttgcaacttactattgtcaacaggctaacagtttccctcc |
| 97 | | DIQMTQSPSSVSASVGDRVTITCRASQGISSWLAWYQQKPGKAPKLLIYAASSLQSGVPS RFSGSGSGTDFTLTISSLQPEDFATYYCQQANSFP |
| 98 | IGKV3-11*01 | gaaattgtgttgacacagtctccagccaccctgtctttgtctccaggggaaagagccacc ctctcctgcagggccagtcagagtgttagcagctacttagcctggtaccaacagaaacct ggccaggctcccaggctcctcatctatgatgcatccaacagggccactggcatcccagcc aggttcagtggcagtgg<u>t</u>ctgggacagacttcactctcaccatcagcagcctagagcct gaagattttgcagtttattactgtcagcagcgtagcaactggc<u>c</u>tcc <u>t</u> = nucleotide number 199 <u>c</u> = nucleotide number 284 |
| 99 | | EIVLTQSPATLSLSPGERATLSCRASQSVSSYLAWYQQKPGQAPRLLIYDASNRATGIPA RFSGSG<u>S</u>GTDFTLTISSLEPEDFAVYYCQQRSNW<u>P</u> <u>S</u> = position 87 <u>P</u> = position 115 |
| 100 | IGKJ2*01 | tgtacacttttggccaggggaccaagctggagatcaaac |
| 101 | | YTFGQGTKLEIK |
| 102 | IGKJ4*01 | G CTC ACT TTC GGC GGA GGG ACC AAG GTG GAG ATC AAA C L  T   F   G   G   G   T   K   V   E   I   K |
| 104 | An IGHG1*01 Heavy Chain | EVQLVESGGG LVQPGRSLRL SCAASRFTFD DYAMHWVRQA PGKGLEWVSG ISWNSGRIGY ADSVKGRFTI SRDNAENSLF LQMNGLRAED TALYYCAKGR DSFDIWGQGT MVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVTYL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 105 | An IGKC*01 Kappa Light Chain | DIQMTQSPSS VSASVGDRVT ITCRASQGIS SWLAWYQQKP GKAPKLLIYG ASSLESGVPS RFSGSGSGTD FTLTISSLQP EDFASYYCQQ ANSFPYTFGQ GTKLEIKRTV AAPSVFIFPP |

TABLE 17-continued

SEQUENCES

| SEQ ID NO: | Human Allele | Nucleotide/Amino Acid Sequence |
|---|---|---|
| | | SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 106 | An IGHG1*01 Heavy Chain | EVQLVESGGGLVQPGGSLRLSCAASGFTFSPFAMSWVRQAPGKGLEWVAKISPG GSWTYY SDTVTGRFTISRDNAKNSLYLQMNSLRAEDTAVYYCARQLWGYYALDIWGQTT VTVSSA STKGPSVFPLAPSSKSTSGGTAALGCLVKDYFPEPVTVSWNSGALTSGVHTFPA VLQSSG LYSLSSVVTVPSSSLGTQTYICNVNHKPSNTKVDKKVEPKSCDKTHTCPPCPAP ELLGGP SVFLFPPKPKDTLMISRTPEVTCVVVDVSHEDPEVKFNWYVDGVEVHNAKTKPR EEQYNS TYRVVSVLTVLHQDWLNGKEYKCKVSNKALPAPIEKTISKAKGQPREPQVYTLP PSRDEL TKNQVSLTCLVKGFYPSDIAVEWESNGQPENNYKTTPPVLDSDGSFFLYSKLTV DKSRWQ QGNVFSCSVMHEALHNHYTQKSLSLSPGK |
| 107 | An IGKC*01 Kappa Light Chain | EIVLTQSPATLSLSPGERATLSCSASISVSYMYWYQQKPGQAPRLLIYDMSNLA SGIPAR FSGSGSGTDFTLTISSLEPEDFAVYYCMQWSGYPYTFGGGTKVEIKRTVAAPSV FIFPPS DEQLKSGTASVVCLLNNFYPREAKVQWKVDNALQSGNSQESVTEQDSKDSTYSL SSTLTL SKADYEKHKVYACEVTHQGLSSPVTKSFNRGEC |
| 108 | IGHV3-9*01 CDR1 (IMGT nomenclature) | ggattcacctttgatgattatgcc t = position 11 |
| 109 | | G F T F D D Y A F = position 4 |
| 110 | IGHV3-9*01 FW3 (IMGT nomenclature) | ggc tat gcg gac tct gtg aag ggc cga ttc acc atc tcc aga gac aac gcc aag aac tcc ctg tat ctg caa atg aac agt ctg aga gct gag gac acg gcc ttg tat tac tgt c = position 98 |
| 111 | | G Y A D S V K G R F T I S R D N A K N S L Y L Q M N S L R A E D T A L Y Y C T = position 33 |
| 112 | IGKV3-11*01 CDR3 (IMGT Nomenclature) | CAG CAG CGT AGC AAC TGG CCT CC C = nucleotide 20 |
| 113 | | QQRSNWP P = position 7 |
| 114 | IGKV3-11*01 FW3 (IMGT Nomenclature) | aacagggccactggcatcccagccaggttcagtggcagtgggtctgggacagacttcact ctcaccatcagcagcctagagcctgaagatttgcagtttattactgt T = nucleotide 43 |
| 115 | | NRATGIPARFSGSGSGTDFTLTISSLEPEDFAVYYC S = position 15 |

---

The invention claimed is:

1. A method of treating pain in a human in need thereof, the method comprising administering to said human an antibody or antibody fragment that specifically binds a human Nav1.7 protein that comprises a mutation selected from the group consisting of:

1161W, 1919G, 490N, 1002L, 422D and 943L in SEQ ID NO: 75;

wherein the antibody or antibody fragment comprises a human gamma-2 heavy chain constant region that comprises an amino acid selected from the group consisting of:

a Pro at position 72 shown in SEQ ID NO: 6; an Asn at position 75 shown in SEQ ID NO: 6; a Phe at position 76 shown in SEQ ID NO: 6; a Val at position 161 shown in SEQ ID NO: 6 and an Ala at position 257 shown in SEQ ID NO: 6; and wherein said human comprises (i) an IGHG2*01 human heavy chain constant region gene segment, or the human expresses antibodies comprising human gamma-2 heavy chain constant regions comprising said selected amino acid;

and wherein (ii) said human comprises a nucleotide sequence encoding said Nav1.7 protein comprising said selected mutation in SEQ ID NO: 75.

2. The method of claim 1, wherein said amino acid is 1161W.

3. A method of treating or reducing the risk of pain in a human in need thereof, the method comprising administering to said human an antibody or antibody fragment that specifically binds a human Nav1.7 protein encoded by a nucleotide sequence that comprises a SNP selected from the group consisting of:

rs6746030, rs3750904, rs58022607, rs4369876, rs13402180 and rs12478318;
wherein (i) the antibody or fragment comprises a human gamma-2 heavy chain constant region that comprises an amino acid selected from the group consisting of:
a Pro at position 72 shown in SEQ ID NO: 6; an Asn at position 75 shown in SEQ ID NO: 6; a Phe at position 76 shown in SEQ ID NO: 6; a Val at position 161 shown in SEQ ID NO: 6 and an Ala at position 257 shown in SEQ ID NO: 6; and
and (ii) said human comprises an IGHG2*01 human heavy chain constant region gene segment, or the human expresses antibodies comprising human gamma-2 heavy chain constant regions comprising said amino acid selected from the group consisting of:
a Pro at position 72 shown in SEQ ID NO: 6; an Asn at position 75 shown in SEQ ID NO: 6; a Phe at position 76 shown in SEQ ID NO: 6; a Val at position 161 shown in SEQ ID NO: 6 and an Ala at position 257 shown in SEQ ID NO: 6; and
wherein (iii) said human comprises a nucleotide sequence encoding a human Nav1.7 protein comprising said SNP selected from the group consisting of rs6746030, rs3750904, rs58022607, rs4369876, rs13402180 and rs12478318.

4. The method of claim 3, wherein the SNP is rs6746030.

5. The method of claim 1, wherein the constant region gene segment comprised by said human is a germline gene segment.

6. The method of claim 5, wherein the constant region gene segment comprised by said human is a germline gene segment.

7. The method of claim 1 comprising, before said administering, selecting a human comprising said nucleotide sequence of (ii), wherein the human is the human of claim 1.

8. The method of claim 3 comprising, before said administering, selecting a human comprising said nucleotide sequence of (ii), wherein the human is the human of claim 3.

9. The method of claim 1, wherein the human has been determined to comprise the nucleotide sequence that encodes a Nav1.7 protein comprising said amino acid.

10. The method of claim 1, comprising the step of determining that the human comprises (a) the nucleotide sequence that encodes a Nav1.7 protein comprising said amino acid, optionally wherein the determining step is performed before administration of the antibody to the human.

11. The method of claim 3, wherein the human has been determined to comprise the nucleotide sequence comprising said SNP.

12. The method of claim 3, comprising the step of determining that the human comprises (a) the nucleotide sequence comprising said SNP, optionally wherein the determining step is performed before administration of the antibody to the human.

13. The method of claim 12, wherein the step of determining comprises assaying a biological sample from the human for a nucleotide sequence comprising said SNP.

14. The method of claim 13, wherein the assaying comprises contacting the biological sample with at least one oligonucleotide probe comprising a sequence of at least 10 contiguous nucleotides of a nucleotide sequence encoding a Nav1.7 protein comprising said SNP, thereby forming a complex when at least one nucleotide sequence comprising said SNP is present; and
detecting the presence or absence of the complex, wherein detecting the presence of the complex determines that the human comprises the Nav1.7 nucleotide sequence comprising said SNP.

15. The method of claim 13, wherein the assaying comprises nucleic acid amplification and optionally one or more methods selected from sequencing, next generation sequencing, nucleic acid hybridization, and allele-specific amplification and/or wherein the assaying is performed in a multiplex format.

16. The method of claim 13, wherein said biological sample comprises serum, blood, faeces, tissue, a cell, urine and/or saliva of said human.

17. The method of claim 3, wherein said human is indicated as heterozygous for a nucleotide sequence encoding the Nav1.7 protein and comprising said SNP, optionally, wherein said human is further indicated as comprising the nucleotide sequence of SEQ ID NO: 76, or said human is indicated as homozygous for a nucleotide sequence encoding the Nav1.7 protein and comprising said SNP.

18. The method of claim 1, wherein said human is or has been further determined to be substantially resistant to a pain treatment.

19. The method of claim 1, wherein said human is receiving or has received a pain treatment or has reduced responsiveness to a pain treatment.

20. The method of claim 3, wherein said human is or has been further determined to be substantially resistant to a pain treatment.

21. The method of claim 3, wherein said human is receiving or has received a pain treatment or has reduced responsiveness to a pain treatment.

22. The method of claim 1, wherein said human has been diagnosed with pain.

23. The method of claim 3, wherein said human has been diagnosed with pain.

24. The method of claim 1, wherein the nucleotide sequence comprises one or more SNPs selected from the group consisting of rs6746030, rs3750904, rs58022607, rs4369876, rs13402180 and rs12478318.

25. The method of claim 1, wherein said antibody or fragment is administered by inhaled, intravenous or subcutaneous administration and/or is comprised in an inhalable or injectable preparation.

26. The method of claim 1, wherein the human gamma-2 heavy chain constant region of the antibody or fragment comprises IGHG2*01 amino acid sequence or an ADCC inactivated version thereof.

27. The method of claim 1, wherein said antibody or fragment is administered by inhaled, intravenous or subcutaneous administration and/or is comprised in an inhalable or injectable preparation.

28. The method of claim 3, wherein the human gamma-2 heavy chain constant region of the antibody or fragment comprises IGHG2*01 amino acid sequence or an ADCC inactivated version thereof.

* * * * *

UNITED STATES PATENT AND TRADEMARK OFFICE
CERTIFICATE OF CORRECTION

| | | |
|---|---|---|
| PATENT NO. | : 8,986,694 B1 | Page 1 of 1 |
| APPLICATION NO. | : 14/472698 | |
| DATED | : March 24, 2015 | |
| INVENTOR(S) | : Jasper Rupert Clube | |

It is certified that error appears in the above-identified patent and that said Letters Patent is hereby corrected as shown below:

Claims

Column 529, line 30, Claim 6 after claim should read -3-, instead of '5'

Column 529, line 41, Claim 9 after said should read -mutation-, instead of 'amino acid'

Column 529, line 44, Claim 10 after said should read -mutation-, instead of 'amino acid'

Signed and Sealed this
Eleventh Day of August, 2015

Michelle K. Lee
*Director of the United States Patent and Trademark Office*